United States Patent
Ghorbani et al.

(10) Patent No.: US 12,146,190 B2
(45) Date of Patent: Nov. 19, 2024

(54) OPTICAL SYSTEMS FOR NUCLEIC ACID SEQUENCING AND METHODS THEREOF

(71) Applicant: Element Biosciences, Inc., San Diego, CA (US)

(72) Inventors: Arash Ghorbani, Auburn, CA (US);
Russell Hudyma, Alamo, CA (US);
John Bailey, Escondido, CA (US);
Michael Previte, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/417,995

(22) Filed: Jan. 19, 2024

(65) Prior Publication Data

US 2024/0201088 A1 Jun. 20, 2024

Related U.S. Application Data

(63) Continuation of application No. PCT/US2022/037831, filed on Jul. 21, 2022.

(60) Provisional application No. 63/334,609, filed on Apr. 25, 2022, provisional application No. 63/334,613, filed on Apr. 25, 2022, provisional application No. 63/224,351, filed on Jul. 21, 2021.

(51) Int. Cl.
*C12Q 1/6874* (2018.01)
*C12Q 1/6869* (2018.01)
*G01N 21/64* (2006.01)

(52) U.S. Cl.
CPC .......... *C12Q 1/6874* (2013.01); *C12Q 1/6869* (2013.01); *G01N 21/6428* (2013.01); *G01N 21/6458* (2013.01); *G01N 2021/6439* (2013.01)

(58) Field of Classification Search
CPC ........... G01N 21/6428; G01N 21/6458; G01N 2021/6439; C12Q 1/6869
See application file for complete search history.

(56) References Cited

U.S. PATENT DOCUMENTS

| | | |
|---|---|---|
| 4,083,057 A | 4/1978 | Quinn |
| 5,428,441 A | 6/1995 | Ogino et al. |
| 5,512,131 A | 4/1996 | Kumar et al. |
| 5,547,839 A | 8/1996 | Dower et al. |
| 5,578,832 A | 11/1996 | Trulson et al. |
| 5,622,872 A | 4/1997 | Ribi |
| 5,834,758 A | 11/1998 | Trulson et al. |
| 6,115,192 A | 9/2000 | McDonald |
| 6,720,143 B2 | 4/2004 | Juncosa et al. |
| 6,829,051 B2 | 12/2004 | Abe et al. |
| 7,126,699 B1 | 10/2006 | Wihl et al. |
| 8,039,817 B2 | 10/2011 | Feng et al. |
| 8,071,962 B1 | 12/2011 | Feng et al. |
| 8,143,599 B2 | 3/2012 | Feng et al. |
| 8,242,463 B2 | 8/2012 | Feng et al. |
| 8,278,630 B1 | 10/2012 | Feng et al. |
| 8,399,196 B2 | 3/2013 | Hoser |
| 8,546,772 B2 | 10/2013 | Feng et al. |
| 8,586,947 B1 | 11/2013 | Feng et al. |
| 8,698,102 B2 | 4/2014 | Feng et al. |
| 8,895,249 B2 | 11/2014 | Shen et al. |
| 9,068,220 B2 | 6/2015 | Feng et al. |
| 9,193,998 B2 | 11/2015 | Khurana et al. |
| 9,217,178 B2 | 12/2015 | Fedurco et al. |
| 9,222,132 B2 | 12/2015 | Drmanac |
| 9,303,290 B2 | 4/2016 | Fedurco et al. |
| 9,365,898 B2 | 6/2016 | Feng et al. |
| 9,944,924 B2 | 4/2018 | Rigatti et al. |
| 9,970,055 B2 | 5/2018 | Fedurco et al. |
| 10,001,622 B2 | 6/2018 | Price et al. |
| 10,233,490 B2 | 3/2019 | Stapleton et al. |
| 10,406,519 B2 * | 9/2019 | Eltoukhy .............. B01L 3/5085 |
| 10,564,101 B1 | 2/2020 | Neron et al. |
| 10,634,487 B2 | 4/2020 | Zhao et al. |
| 10,655,176 B2 | 5/2020 | Stromberg et al. |
| 10,656,368 B1 | 5/2020 | Rosenberry et al. |
| 10,662,473 B2 | 5/2020 | Drmanac |
| 10,704,094 B1 | 7/2020 | Arslan et al. |
| 10,748,730 B2 | 8/2020 | Chuang et al. |
| 10,768,173 B1 | 9/2020 | Arslan et al. |
| 10,876,148 B2 | 12/2020 | Zhou et al. |
| 10,982,280 B2 | 4/2021 | Arslan et al. |

(Continued)

FOREIGN PATENT DOCUMENTS

| | | |
|---|---|---|
| CN | 102016546 A | 4/2011 |
| CN | 101460953 B | 5/2012 |

(Continued)

OTHER PUBLICATIONS

Chin Lan et al, Non-mechanical sub-pixel image shifter for acquiring super-digital resolution digital images, 2009, Optics Express 22993, Dec. 7, 2019. (Year: 2009).*

(Continued)

*Primary Examiner* — Narayan K Bhat
(74) *Attorney, Agent, or Firm* — WILSON SONSINI GOODRICH & ROSATI

(57) ABSTRACT

Fluorescence imaging system designs are described that provide larger fields-of-view, increased spatial resolution, improved modulation transfer and image quality, higher spatial sampling frequency, faster transitions between image capture when repositioning the fields-of-view, improved imaging system duty cycle and a more compact system, and thus enable higher throughput image acquisition and analysis for genomics and other imaging applications at a lower cost.

20 Claims, 69 Drawing Sheets

(56) References Cited

U.S. PATENT DOCUMENTS

| | | | |
|---|---|---|---|
| 10,996,453 B2 | 5/2021 | Newman et al. |
| 11,047,005 B2 | 6/2021 | Staker et al. |
| 11,053,540 B1 | 7/2021 | Chen et al. |
| 11,060,138 B1 * | 7/2021 | Chen | C12Q 1/6806 |
| 11,060,140 B2 | 7/2021 | Staker et al. |
| 11,198,121 B1 | 12/2021 | Guo et al. |
| 11,200,446 B1 | 12/2021 | Zhou et al. |
| 11,220,707 B1 | 1/2022 | Arslan et al. |
| 11,236,388 B1 | 2/2022 | Arslan et al. |
| 11,261,489 B2 | 3/2022 | Chen et al. |
| 11,287,422 B2 | 3/2022 | Previte et al. |
| 11,339,433 B2 | 5/2022 | Chen et al. |
| 11,365,444 B2 | 6/2022 | Chen et al. |
| 11,408,032 B2 * | 8/2022 | Chen | G06V 20/69 |
| 11,426,732 B2 | 8/2022 | Guo et al. |
| 11,427,855 B1 | 8/2022 | Arslan et al. |
| 11,459,608 B2 | 10/2022 | Chen et al. |
| 11,535,892 B1 | 12/2022 | Arslan et al. |
| 11,781,185 B2 | 10/2023 | Arslan et al. |
| 11,795,504 B2 | 10/2023 | Chen et al. |
| 2003/0170613 A1 | 9/2003 | Straus |
| 2003/0186227 A1 | 10/2003 | Balasubramanian et al. |
| 2004/0095573 A1 | 5/2004 | Tsai et al. |
| 2004/0248287 A1 | 12/2004 | Hu et al. |
| 2005/0073675 A1 | 4/2005 | Lo |
| 2006/0119865 A1 | 6/2006 | Hoyt et al. |
| 2007/0115457 A1 | 5/2007 | Matsuzawa et al. |
| 2008/0030721 A1 | 2/2008 | Kepler et al. |
| 2008/0274904 A1 | 11/2008 | Gormley et al. |
| 2008/0274905 A1 | 11/2008 | Greene |
| 2009/0047670 A1 | 2/2009 | Miller et al. |
| 2009/0103792 A1 | 4/2009 | Rahn et al. |
| 2009/0186775 A1 | 7/2009 | Nowak et al. |
| 2009/0272914 A1 | 11/2009 | Feng et al. |
| 2010/0099100 A1 | 4/2010 | Zaccarin et al. |
| 2010/0298171 A1 | 11/2010 | Shirazi et al. |
| 2010/0321786 A1 | 12/2010 | Rahn et al. |
| 2011/0165652 A1 | 7/2011 | Hardin et al. |
| 2011/0220775 A1 | 9/2011 | Triener et al. |
| 2012/0105858 A1 | 5/2012 | Popescu et al. |
| 2012/0148141 A1 | 6/2012 | Ozcan et al. |
| 2012/0214171 A1 | 8/2012 | Kotseroglou |
| 2012/0328177 A1 | 12/2012 | George et al. |
| 2013/0100272 A1 | 4/2013 | Price et al. |
| 2013/0235388 A1 | 9/2013 | Segale et al. |
| 2013/0260372 A1 | 10/2013 | Buermann et al. |
| 2013/0274119 A1 | 10/2013 | Knutson et al. |
| 2013/0280715 A1 | 10/2013 | Bornhop et al. |
| 2014/0139840 A1 | 5/2014 | Judkewitz et al. |
| 2015/0160450 A1 | 6/2015 | Ou et al. |
| 2015/0252416 A1 | 9/2015 | Feng et al. |
| 2016/0041095 A1 | 2/2016 | Rothberg et al. |
| 2016/0216208 A1 | 7/2016 | Kim et al. |
| 2016/0281150 A1 | 9/2016 | Rawlings et al. |
| 2016/0357173 A1 | 12/2016 | Foschini et al. |
| 2017/0153431 A1 | 6/2017 | Nguyen et al. |
| 2017/0315341 A1 | 11/2017 | Fuller et al. |
| 2017/0341075 A1 | 11/2017 | Sirkis et al. |
| 2018/0178215 A1 | 6/2018 | Fisher et al. |
| 2018/0209784 A1 | 7/2018 | Zhao et al. |
| 2018/0231465 A1 | 8/2018 | Rothberg et al. |
| 2018/0284010 A1 | 10/2018 | Scarcelli et al. |
| 2019/0049708 A1 | 2/2019 | Erlbacher et al. |
| 2019/0212266 A1 | 7/2019 | Baker |
| 2019/0219835 A1 | 7/2019 | Skinner et al. |
| 2019/0226992 A1 | 7/2019 | Guo |
| 2019/0276886 A1 | 9/2019 | Skinner et al. |
| 2019/0374944 A1 | 12/2019 | Lundquist et al. |
| 2020/0026090 A1 | 1/2020 | Hargis et al. |
| 2020/0129974 A1 | 4/2020 | Ren et al. |
| 2020/0139375 A1 | 5/2020 | Buermann et al. |
| 2020/0142170 A1 | 5/2020 | Cai |
| 2020/0149095 A1 | 5/2020 | Arslan et al. |
| 2020/0179921 A1 | 6/2020 | Arslan et al. |
| 2020/0182792 A1 | 6/2020 | Vaziri |
| 2020/0182866 A1 | 6/2020 | Arslan et al. |
| 2020/0192071 A1 | 6/2020 | Newman et al. |
| 2020/0218052 A1 | 7/2020 | Hong |
| 2020/0218053 A1 | 7/2020 | Zou et al. |
| 2020/0347443 A1 | 11/2020 | Arslan et al. |
| 2020/0370113 A1 | 11/2020 | Kellinger et al. |
| 2021/0040534 A1 | 2/2021 | Zhou et al. |
| 2021/0072234 A1 | 3/2021 | Arslan et al. |
| 2021/0121882 A1 | 4/2021 | Guo et al. |
| 2021/0123098 A1 | 4/2021 | Previte et al. |
| 2021/0123911 A1 | 4/2021 | Arslan et al. |
| 2021/0139884 A1 | 5/2021 | Kellinger et al. |
| 2021/0139981 A1 | 5/2021 | Arslan et al. |
| 2021/0223178 A1 | 7/2021 | Guo et al. |
| 2021/0223530 A1 | 7/2021 | Guo et al. |
| 2021/0223531 A1 | 7/2021 | Guo et al. |
| 2021/0247389 A1 | 8/2021 | Arslan et al. |
| 2021/0269793 A1 | 9/2021 | Kellinger et al. |
| 2021/0318295 A1 | 10/2021 | Arslan et al. |
| 2021/0332416 A1 | 10/2021 | Chen et al. |
| 2021/0332430 A1 | 10/2021 | Arslan et al. |
| 2021/0373000 A1 | 12/2021 | Arslan et al. |
| 2021/0387184 A1 | 12/2021 | Guo et al. |
| 2022/0136047 A1 | 5/2022 | Chen et al. |
| 2022/0251643 A1 | 8/2022 | Chen et al. |
| 2022/0251644 A1 | 8/2022 | Chen et al. |
| 2022/0267842 A1 | 8/2022 | Chen et al. |
| 2024/0200133 A1 | 6/2024 | Ghorbani et al. |

FOREIGN PATENT DOCUMENTS

| | | |
|---|---|---|
| CN | 104797925 A | 7/2015 |
| CN | 110248733 A | 9/2019 |
| CN | 110343612 A | 10/2019 |
| DE | 10014204 A1 | 10/2001 |
| EP | 4060321 A1 | 9/2022 |
| JP | 2007525571 A | 9/2007 |
| JP | 2015084717 A | 5/2015 |
| JP | 2018190083 A | 11/2018 |
| JP | 2019002933 A | 1/2019 |
| JP | 2019535247 A | 12/2019 |
| WO | WO-9508000 A2 | 3/1995 |
| WO | WO-0018957 A1 | 4/2000 |
| WO | WO-2005065814 A1 | 7/2005 |
| WO | WO-2009137435 A1 | 11/2009 |
| WO | WO-2010016937 A2 | 2/2010 |
| WO | WO-2011034620 A2 | 3/2011 |
| WO | WO-2014171898 A2 | 10/2014 |
| WO | WO-2015085268 A1 | 6/2015 |
| WO | WO-2018045109 A1 | 3/2018 |
| WO | WO-2018094091 A1 | 5/2018 |
| WO | WO-2018150471 A1 | 8/2018 |
| WO | WO-2019033062 A2 | 2/2019 |
| WO | WO-2019143561 A1 | 7/2019 |
| WO | WO-2019147584 A1 | 8/2019 |
| WO | WO-2019241305 A1 | 12/2019 |
| WO | WO-2020061237 A1 | 3/2020 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021081128 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022026891 A1 | 2/2022 |
| WO | WO-2022094332 A1 | 5/2022 |
| WO | WO-2022266470 A1 | 12/2022 |
| WO | WO-2023004014 A1 | 1/2023 |
| WO | WO-2022266462 A2 | 5/2023 |
| WO | WO-2023107719 A2 | 6/2023 |
| WO | WO-2023196924 A2 | 10/2023 |
| WO | WO-2023205707 A2 | 10/2023 |

(56) References Cited

OTHER PUBLICATIONS

Dover Motion (Microscope calculations: Field of View, Depth of Field, Numerical Aperture, YouTube tutorial Dover motion CTO, Kevin McCathy, DOF05 product Video dated, Aug. 9, 2019). https://dovermotion.com/applications-capabilities/automated-imaging/microscope-calculations/ (Year: 2019).

Feiner-Garcia et al., Advanced Optical Microscopy Techniques for the Investigation of Cell-Nanoparticle Interactions. Smart Nanoparticles for Biomedicine: Micro and Nano Technologies, pp. 219-236 (2018).

Lutz, Biological Imaging by Superresolution Light Microscopy. Comprehensive Biotechnology (Second Ed.) vol. 1: 579-589 (2011).

Nylk et al., Light-Sheet Fluorescence Microscopy with Structured Light. Neurophotonics and Biomedical Spectroscopy, pp. 477-501 (2019).

Oldenbourg et al., Methods in Molecular Medicine: Analysis of Microtubule Dynamics by Polarized Light. Methods Mol Med 137: 111-123 (2007).

PCT/US2022/037831 International Search Report and Written Opinion dated Dec. 13, 2022.

PCT/US2022/037831 Invitation to Pay Additional Fees mailed Oct. 13, 2022.

Guttenberg et al. Planar chip device for PCR and hybridization with surface acoustic wave pump. Lab on a Chip 5(3):308-317 (2005).

Palanisamy et al. Considerations of solid-phase DNA amplification. Bioconjug chem 21(4):690-695 (2010).

PCT/US2021/013696 International Search Report and Written Opinion dated Apr. 7, 2021.

Schlapak et al., Selective protein and DNA adsorption on PLL-PEG films modulated by ionic strength. Soft Matter. 5:613-621 (2009).

U.S. Appl. No. 17/151,020 Final Office Action dated Aug. 9, 2021.

U.S. Appl. No. 17/151,020 Non-Final Office Action dated Mar. 26, 2021.

U.S. Appl. No. 17/016,350 Final Office Action dated Apr. 20, 2021.

U.S. Appl. No. 17/016,350 Non-Final Office Action dated Jan. 6, 2021.

U.S. Appl. No. 17/016,353 Non-Final Office Action dated Jan. 13, 2021.

U.S. Appl. No. 17/372,362 Non-Final Office Action dated Apr. 4, 2022.

Zhang et al., Effects of polyethylene glycol on DNA adsorption and hybridization on gold nanoparticles and graphene oxide. Langmuir. 28(40):14330-14337 (2012).

Wong, T. et al. Pixel super resolution in serial time-encoded amplified microscopy. Lasers and Electro-Optics (CLEO), 2012 Conference (pp. 1-2) (May 6, 2012).

* cited by examiner

Imaging Area

Imaging 424 individual tiles

Imaging Area

Imaging < 40 individual tiles

OPTICAL SYSTEMS FOR NUCLEIC ACID SEQUENCING AND METHODS THEREOF

CROSS-REFERENCE

This application is a continuation of International Patent Application No. PCT/US2022/037831, filed Jul. 21, 2022, which claims the benefit of U.S. Provisional Application No. 63/224,351, filed Jul. 21, 2021, U.S. Provisional Application No. 63/334,613, filed Apr. 25, 2022, and U.S. Provisional Application No. 63/334,609, filed Apr. 25, 2022, each of which is incorporated herein by reference in its entirety.

BACKGROUND

In typical fluorescence-based genomic testing assays, e.g., genotyping or nucleic acid sequencing (using either real time, cyclic, or stepwise reaction schemes), dye molecules that are attached to nucleic acid molecules tethered on a substrate are excited using an excitation light source, a fluorescence photon signal is generated in one or more spatially-localized positions on the substrate, and the fluorescence is subsequently imaged through an optical system onto an image sensor. An analysis process is then used to analyze the images, find the positions of labeled molecules (or clonally amplified clusters of molecules) on the substrate, and quantify the fluorescence photon signal in terms of wavelength and spatial coordinates, which may then be correlated with the degree to which a specific chemical reaction, e.g., a hybridization event or base addition event, occurred in the specified locations on the substrate. Imaging-based methods provide large scale parallelism and multiplexing capabilities, which help to drive down the cost and accessibility of such technologies. However, detection errors that arise from, for example, overly dense packing of labeled molecules (or clonally-amplified clusters of molecules) within a small region of the substrate surface, or due to low contrast-to-noise ratio (CNR) in the image, may lead to errors in attributing the fluorescence signal to the correct molecules (or clonally amplified clusters of molecules).

SUMMARY

Aspects disclosed herein provide systems, comprising: a substrate comprising a curved surface, wherein said curved surface comprises at least one binding moiety configured to bind to an analyte; and an optical system comprising a light source, wherein said light source is configured to direct light to said curved surface and wherein said light is configured to probe a presence or absence of said analyte bound to said at least one binding moiety. In some embodiments, said analyte comprises a nucleic acid. In some embodiments, said at least one binding moiety comprises at least one nucleic acid configured to bind to said nucleic acid. In some embodiments, said curved surface is a component of a flow cell. In some embodiments, said systems further comprise a flow cell, wherein said flow cell comprises said curved surface. In some embodiments, the curved surface comprises a capillary of a flow cell. In some embodiments, said curved surface comprises a glass, a polymer, or a combination thereof. In some embodiments, said light source is configured to probe said curved surface in an epifluorescent configuration. In some embodiments, said light source is configured to probe said curved surface in a transmissive configuration. In some embodiments, said light source is a laser, a light emitting diode, a halogen lamp, or an incandescent lamp. In some embodiments, said light source is configured to generate said light with a wavelength of about 500 nanometers (nm) to 540 nm, 620 nm to 650 nm, or 460 nm to 500 nm. In some embodiments, said systems further comprise a second curved surface. In some embodiments, said systems further comprise a focal shifting assembly configured to move a focal field between said curved surface and said second curved surface. In some embodiments, said focal shifting assembly comprises at least one movable lens. In some embodiments, said at least one movable lens is disposed within a lens barrel. In some embodiments, said focal shifting assembly comprises at least one movable prism. In some embodiments, said curved surface and said second curved surface are different parts of a substantially cylindrical component of a flow cell. In some embodiments, said second curved surface comprises at least one second binding moiety configured to bind to a second analyte. In some embodiments, said optical system is movable with respect to said curved surface. In some embodiments, said optical system is rotatable around said curved surface. In some embodiments, said optical system is configured to image a plurality of binding moieties. In some embodiments, said curved surface has a deviation from flatness of 25 micrometers (μm). In some embodiments, said curved surface has a deviation from flatness greater than a focal depth of said optical system. In some embodiments, said systems further comprise a plurality of sub-optical systems, wherein said plurality of sub-optical systems are not parallel to one another. In some embodiments, each sub-optical system of said plurality of sub-optical systems are individually disposed perpendicular to a plurality of tangents of said curved surface. In some embodiments, said systems further comprise a stage, wherein said curved surface is disposed on said stage. In some embodiments, said stage comprises a tilt stage, a rotation stage, a translation stage, or any combination thereof. In some embodiments, said curved surface comprises a hydrophilic polymer coupled thereto. In some embodiments, said at least one binding moiety is coupled to said hydrophilic polymer. In some embodiments, said hydrophilic polymer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof. In some embodiments, said system has a numerical aperture of at most about 0.6. In some embodiments, said numerical aperture is at most about 0.25. In some embodiments, said systems further comprise an imaging sensor configured to collect said light subsequent to said directing to said curved surface. In some embodiments, said systems further comprise a heater configured to heat said surface. In some embodiments, said heater is an integrated heater. In some embodiments, said heater is an infrared heater.

Aspects disclosed herein provide systems, comprising: a flow cell; and an optical system comprising: a light source configured to direct a first light to said flow cell; a filter configured to (i) receive a second light from said flow cell and (ii) transmit a third light, wherein said third light comprises at least a portion of said second light and does not comprise said first light; and a sensor configured to receive said third light from said filter. In some embodiments, systems further comprise a focusing element assembly disposed between said light source and said filter, wherein said focusing element assembly is configured to focus said second light from said flow cell and said sensor. In some embodiments, said focusing element assembly comprises a first focusing element and a second focusing element, wherein said first focusing element is disposed between said filter and said second focusing element along an optical path between said light source and said sensor. In some embodiments, said focusing element assembly comprises a wedge block assembly, and wherein said first focusing element comprises a first wedge piece and said second focusing element comprises a second wedge piece. In some embodiments, said first wedge piece and said second wedge piece are comprised of fused silica. In some embodiments, said first wedge piece and said second wedge piece have a refractive index comprising about 1.5. In some embodiments, said systems further comprise a piezo drive coupled to said first wedge piece. In some embodiments, said systems further comprise a gap between said first wedge piece and said second wedge piece. In some embodiments, said systems further comprise a housing containing said flow cell. In some embodiments, said housing further contains said wedge block and said piezo drive in a wedge block-piezo drive assembly. In some embodiments, said wedge block-piezo drive assembly is disposed between said sensor and said flow cell. In some embodiments, said systems further comprise a stage. In some embodiments, said stage is a tilt stage, a rotation stage, a translation or a combination thereof. In some embodiments, said optical system further comprises an autofocus element configured for initial focus. In some embodiments, said systems further comprise a lens barrel. In some embodiments, said autofocus element is contained within said lens barrel. In some embodiments, said flow cell comprises one or more interior surfaces having a hydrophilic polymer layer coupled thereto. In some embodiments, said flow cell further comprises a plurality of biological polymers coupled to said hydrophilic polymer layer. In some embodiments, said flow cell comprises a first interior surface and a second interior surface, wherein said first interior surface is disposed between said sensor and said second interior surface. In some embodiments, said first interior surface and said second interior surface comprise biological polymers coupled thereto. In some embodiments, said hydrophilic polymer layer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof. In some embodiments, said filter comprises a multi-band filter. In some embodiments, said multi-band filter comprises a tri-band stopband filter. In some embodiments, said optical system further comprises an imaging optic disposed between said filter and said flow cell. In some embodiments, said imaging optic has a reduction comprising 1×. In some embodiments, said optical system has a field-of-view (FOV) comprising greater than 1 millimeter (mm)$^2$. In some embodiments, said optical system has a numerical aperture (NA) comprising less than 0.6. In some embodiments, said NA comprises about 0.25. In some embodiments, said sensor comprises a plurality of imaging sensors is configured to capture said FOV. In some embodiments, said light source comprises a plurality of light sources comprising: a first light source configured to emit said first light comprising a first wavelength range; a second light source configured to emit a second light comprising a second wavelength range; and a third light source configured to emit a third light comprising a third wavelength range, wherein said first wavelength range, said second wavelength range, and said third wavelength range are different wavelength ranges. In some embodiments, a first fluorophore excited by said first wavelength range of said first light source is different than a second fluorophore excited by said second wavelength range of said second light source. In some embodiments, a first fluorophore excited by said first wavelength range of said first light source is different than a second fluorophore excited by said second wavelength range of said second light source; and said second fluorophore excited by said second wavelength range of said second light source is different than a third fluorophore excited by said third wavelength range of said third light source. In some embodiments, a third fluorophore excited by said third wavelength range of said third light source is different than said first fluorophore excited by said first wavelength range of said first light source. In some embodiments, said first wavelength range of said first light source comprises between about 500 to about 540 nanometers (nm). In some embodiments, said second wavelength range of said second light source comprises between about 620 to about 640 nm. In some embodiments, said third wavelength range of the third light source comprises between about 460 to about 500 nm. In some embodiments, said flow cell comprises an interior surface comprising a plurality of discrete regions, wherein (i) a first discrete region of said plurality of discrete regions comprises a first set of nucleic acid molecules coupled to said interior surface at said first discrete region, and (ii) a second discrete region of said plurality of discrete regions comprises a second set of said nucleic acid molecules coupled to said interior surface at said second discrete region, wherein said first set of said nucleic acid molecules is different than said second set of said nucleic acid molecules. In some embodiments, said first set of said nucleic acid molecules comprises a first fluorophore coupled thereto, and said second set of said nucleic acid molecules comprises a second fluorophore coupled thereto, wherein said first fluorophore is different than said second fluorophore. In some embodiments, a third discrete region of said plurality of discrete regions comprises a third set of said nucleic acid molecules coupled to said interior surface at said third discrete region, and wherein said third set of said nucleic acid molecules is different than said first set and said second set of said nucleic acid molecules. In some embodiments, said third set of said nucleic acid molecules comprises a third fluorophore coupled thereto, wherein said third fluorophore is different than second first fluorophore and said second fluorophore. In some embodiments, a fourth discrete region of said plurality of discrete regions comprises a fourth set of nucleic acid molecules coupled to said interior surface at said forth discrete region, and wherein said fourth set of nucleic acid molecules comprise said first fluorophore and said third fluorophore, wherein said first fluorophore is different than said third fluorophore. In some embodiments, said light source comprises a light emitting diode (LED) light source. In some embodiments, the optical system further comprises a light delivery component. In some embodiments, said light delivery component comprises a waveguide, a light pipe, a fiber optic, or a combination thereof. In some embodiments, said light source comprises a solid-state light source. In some embodiments, said systems further comprise a heater. In some embodiments, said heater is an integrated heater. In some embodiments, said integrated heater is a transparent heater block integrated heater. In some embodiments, said heater is an infrared (IR) heater. In some embodiments, said optical system does not comprise a dichroic. In some embodiments, said optical system does not comprise a tube lens. In some embodiments, said optical system does not comprise a corrective optical element configured to move in and out of said optical path between said flow cell and said plurality of imaging sensor. In some embodiments, said optical system does not comprise a laser. In some embodiments, said optical system does not comprise any combination of a dichroic; a tube lens; a corrective optical element configured to move in and out of said optical path between said flow cell and said sensor; a laser. In some embodiments, said flow cell is disposed between said light source and said sensor.

Aspects disclosed herein provide systems, comprising: a light source configured to illuminate a sample; a sensor configured to obtain an image of said sample that is illuminated; and a focusing element assembly permanently disposed along an optical path between said light source and said sensor, wherein said focusing element assembly comprises: a housing; a first focusing element; and a second focusing element, wherein said first focusing element is configured to move relative to said second focusing element within said housing without moving said housing relative to said optical path. In some embodiments, said systems further comprise a plurality of said light source, wherein each light source of said plurality emits a light with a different wavelength. In some embodiments, said systems further comprise a plurality of said sensor, wherein each sensor of said plurality of said sensor is configured to obtain said image of said sample at different times. In some embodiments, said systems further comprise a filter disposed along said optical path between said light source and said sensor, wherein said filter is configured to receive a light from said sample and transmit another light to said sensor. In some embodiments, said filter comprises a multi-band filter. In some embodiments, said multi-band filter comprises a tri-band stopband filter. In some embodiments, said first lens is placed before said second lens in said optical path. In some embodiments, said first lens is placed after said second lens in said optical path. In some embodiments, said sample is coupled to one or more interior surfaces of a flow cell. In some embodiments, said sample is covalently coupled to said one or more interior surfaces of said flow cell. In some embodiments, said sample is coupled to two or more interior surfaces of a flow cell. In some embodiments, said sample is covalently coupled to said two or more interior surfaces of said flow cell. In some embodiments, said two or more interior surfaces of said flow cell comprise a first interior surface and a second interior surface, and wherein said first interior surface is disposed along said optical path between said light source and said second interior surface. In some embodiments, said one or more interior surfaces comprises a hydrophilic polymer layer coupled thereto. In some embodiments, said one or more interior surfaces comprises a hydrophilic polymer layer coupled thereto. In some embodiments, said sample comprises a plurality of biological polymers coupled to said hydrophilic polymer layer. In some embodiments, said hydrophilic polymer layer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, or dextran, or any combination thereof. In some embodiments, said system has a field-of-view (FOV) comprising greater than 1 millimeter (mm)$^2$. In some embodiments, said system has a numerical aperture (NA) comprising less than 0.6. In some embodiments, said NA comprises about 0.25. In some embodiments, said sensor comprises a plurality of imaging sensors that is configured to capture said FOV. In some embodiments, said focusing element assembly comprises a wedge block assembly, and wherein said first focusing element comprises a first wedge piece and said second focusing element comprises a second wedge piece. In some embodiments, said first wedge piece and said second wedge piece are comprised of fused silica. In some embodiments, said first wedge piece and said second wedge piece have a refractive index comprising about 1.5. In some embodiments, said systems further comprise a gap between said first focusing element and said second focusing element.

Aspects disclosed herein provide methods of imaging a sample, said method comprising: providing said system described herein; illuminating said sample with said light from said light source, wherein said sample is coupled to one or more interior surfaces of said flow cell; filtering said second light by said filter by receiving said second light from said sample coupled to said one or more interior surfaces of said flow cell and transmitting a third light to said sensor; and obtaining an image of said sample with said sensor. In some embodiments, said sample comprises biological polymers, wherein a first subset of said biological polymers is coupled to a first interior surface of said one or more interior surfaces of said flow cell, and a second subset of said biological polymers is coupled to a second interior surface of said one or more interior surfaces of said flow cell. In some embodiments, said obtaining said image of said sample with said sensor comprises imaging said first interior surface and said second interior surface of said flow cell.

Aspects disclosed herein provide methods of imaging a sample, said method comprising: providing said system disclosed herein; illuminating said sample by said light source; focusing a light emitted from said sample with said focusing element assembly; and receiving said light from (c) and obtaining an image of said sample by said sensor. In some embodiments, said sample comprises biological polymers, wherein a first subset of said biological polymers is coupled to a first interior surface of a flow cell, and a second subset of said biological polymers is coupled to a second interior surface of a flow cell. In some embodiments, said obtaining said image of said sample with said sensor comprises imaging the first interior surface and said second interior surface of said flow cell. In some embodiments, said first interior surface and said second interior surface comprise a hydrophilic polymer layer coupled thereto. In some embodiments, said obtaining said image of said sample by said sensor comprises imaging a field-of-view (FOV) of greater than 4 mm$^2$. In some embodiments, said methods further comprise sequencing said sample. In some embodiments, said sequencing comprises performing sequencing-by-binding or sequencing-by-synthesis. In some embodiments, said sequencing comprises: providing a detectable nucleotide conjugate comprising (i) a common core, (ii) a plurality of labels, and (iii) a plurality of nucleotides coupled to said common core; contacting a plurality of primed nucleic acid sequences of said sample with said detectable nucleotide conjugate under conditions that preclude phosphodiester bond formation between a nucleotide of said plurality of nucleotides and a complementary nucleotide of said plurality of primed nucleic acid sequences, wherein said nucleotide of said first plurality of nucleotides stably couples with said complementary nucleotide in a primed nucleic acid sequence of said plurality of primed nucleic acid sequences; detecting a signal from said plurality of labels of said detectable nucleotide conjugate, thereby identifying said complementary nucleotide of said primed nucleic acid sequence; and performing (a) to (c) with a different detectable nucleotide conjugate to detect a second signal, thereby identifying another complementary nucleotide in said primed nucleic acid sequence.

In an aspect, the present disclosure provides a system, comprising: a curved substrate, wherein the curved substrate comprises at least one binding moiety configured to bind to an analyte; and an optical system comprising a light source, wherein the light source is configured to direct light from the light source to the curved substrate and wherein the light is configured to probe a presence or absence of the analyte bound to the curved substrate.

In some embodiments, the analyte comprises a nucleic acid. In some embodiments, the at least one binding moiety comprises at least one nucleic acid configured to bind to the nucleic acid. In some embodiments, the curved substrate is a component of a flow cell. In some embodiments, the system further comprises a flow cell, wherein the flow cell comprises the curved substrate. In some embodiments, the curved substrate comprises a capillary of a flow cell. In some embodiments, the curved substrate comprises a glass, a polymer, or a combination thereof. In some embodiments, the light source is configured to probe the curved substrate in an epifluorescent configuration. In some embodiments, the light source is configured to probe the curved substrate in a transmissive configuration. In some embodiments, the light source is a laser, a light emitting diode, a halogen lamp, or an incandescent lamp. In some embodiments, the light source is configured to generate the light with a wavelength of about 500 nanometers (nm) to 540 nm, 620 nm to 650 nm, or 460 nm to 500 nm. In some embodiments, the system further comprises a second curved substrate. In some embodiments, the system further comprises a focal shifting assembly configured to move a focal field between the curved substrate and the second curved substrate. In some embodiments, the focal shifting assembly comprises at least one movable lens. In some embodiments, the at least one movable lens is disposed within a lens barrel. In some embodiments, the focal shifting assembly comprises at least one movable prism. In some embodiments, the curved substrate and the second curved substrate are different parts of a substantially cylindrical component of a flow cell. In some embodiments, the second curved substrate comprises at least one second binding moiety configured to bind to a second analyte. In some embodiments, the optical system is movable with respect to the curved substrate. In some embodiments, the optical system is rotatable around the curved substrate. In some embodiments, the optical system is configured to image a plurality of binding moieties. In some embodiments, the curved substrate has a deviation from flatness of 25 micrometers (µm). In some embodiments, the curved substrate has a deviation from flatness greater than a focal depth of the optical system. In some embodiments, the system further comprises a plurality of sub-optical systems, wherein the plurality of sub-optical systems are not parallel to one another. In some embodiments, each sub-optical system of the plurality of sub-optical systems are individually disposed perpendicular to a plurality of tangents of the curved substrate. In some embodiments, the system further comprises a stage, wherein the curved substrate is disposed on the stage. In some embodiments, the stage comprises a tilt stage, a rotation stage, a translation stage, or any combination thereof. In some embodiments, the curved substrate comprises a hydrophilic polymer coupled thereto. In some embodiments, the at least one binding moiety is coupled to the hydrophilic polymer. In some embodiments, the hydrophilic polymer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof. In some embodiments, the system has a numerical aperture of at most about 0.6. In some embodiments, the numerical aperture is at most about 0.25. In some embodiments, the system further comprises an imaging sensor configured to collect the light subsequent to the directing to the curved substrate. In some embodiments, the system further comprises a heater configured to heat the substrate. In some embodiments, the heater is an integrated heater. In some embodiments, the heater is an infrared heater.

In another aspect, the present disclosure provides a system, comprising: a curved substrate; and an optical system comprising a light source, wherein the light source is configured to direct light from the light source to the curved substrate.

In another aspect, the present disclosure provides a system, comprising: a substrate; and an optical system, wherein the optical system is configured to image an area of the substrate of at least about 5 square millimeters (mm$^2$).

In some embodiments, the optical system is configured to simultaneously image the area. In some embodiments, the optical system comprises a plurality of sub-optical systems. In some embodiments, the plurality of sub-optical systems are configured to image the area of the substrate in parallel. In some embodiments, the optical system comprises a light source configured to provide a light beam and a lens, wherein the lens is configured to focus the light beam from the light source onto a focal region of the substrate comprising the area. In some embodiments, a homogeneity of the light beam over the focal region is at least about 90%. In some embodiments, the area of the substrate is disposed as a hollow cylinder. In some embodiments, the substrate is at least a portion of a capillary flow cell. In some embodiments, the capillary flow cell comprises a solid core. In some embodiments, the system further comprises a stage, wherein the substrate is disposed on the stage. In some embodiments, the stage comprises a tilt stage, a rotation stage, a translation stage, or any combination thereof. In some embodiments, the substrate comprises a hydrophilic polymer coupled thereto. In some embodiments, the at least one binding moiety is coupled to the hydrophilic polymer. In some embodiments, the hydrophilic polymer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof. In some embodiments, the system has a numerical aperture of at most about 0.6. In some embodiments, the numerical aperture is at most about 0.25. In some embodiments, the system further comprises an imaging sensor configured to collect the light subsequent to the directing to the substrate. In some embodiments, the system further comprises a heater configured to heat the substrate. In some embodiments, the heater is an integrated heater. In some embodiments, the heater is an infrared heater. In some embodiments, the substrate is a curved substrate. In some embodiments, the curved substrate has a deviation from flatness of 25 micrometers (μm). In some embodiments, the curved substrate has a deviation from flatness greater than a focal depth of the optical system. In some embodiments, the optical system is configured to image the area of the substrate with a resolution of about 1 μm or less.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the inventive concepts are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A: illustration of imaging front and rear interior surfaces of a flow cell. FIG. 1B: illustration of imaging front and rear exterior surfaces of a substrate.

FIG. 2A: top isometric view. FIG. 2B: bottom isometric view.

FIG. 3A: top view. FIG. 3B: side view.

FIG. 6A: schematic illustration of a multichannel fluorescence imaging module comprising four detection channels.

FIG. 6B: detail view illustrating the angle of incidence (AOI) of a light beam on a dichroic reflector.

FIG. 9A illustrates the effect of folding angle on image quality degradation induced by the addition of 1 wave of PV spherical power to the last mirror. FIG. 9B illustrates the effect of folding angle on image quality degradation induced by the addition of 0.1 wave of PV spherical power to the last mirror.

FIG. 10A: transmission spectra for an example bandpass dichroic filter at angles of incidence of 40 degrees and 45 degrees, where the incident beam is linearly polarized and is p-polarized with respect to the plane of the dichroic filter. FIG. 10B: changing the orientation of the light source with respect to the dichroic filter, such that the incident beam is s-polarized with respect to the plane of the dichroic filter, results in a substantially sharper edge between the passband and the stopband.

FIG. 11A: first surface. FIG. 11B: second surface.

FIG. 12A: first surface. FIG. 12B: second surface.

FIG. 13A: first surface. FIG. 13B: second surface.

FIG. 14A: first surface. FIG. 14B: second surface.

FIG. 15A: first surface. FIG. 15B: second surface.

FIG. 16A: first surface. FIG. 16B: second surface.

FIG. 17A: plot of the Strehl ratios for imaging a second flow cell surface through a first flow cell surface as a function of the thickness of the intervening fluid layer (fluid channel height) for different objective lens and/or optical system numerical apertures. FIG. 17B: plot of the Strehl ratio as a function of numerical aperture for imaging a second flow cell surface through a first flow cell surface and an intervening layer of water having a thickness of 0.1 mm.

FIG. 36A shows the preparation of a one-piece glass flow cell. FIG. 36B shows the preparation of a two-piece glass flow cell. FIG. 36C shows the preparation of a three-piece glass flow cell.

FIG. 37A shows a one-piece glass flow cell design. FIG. 37B shows a two-piece glass flow cell design.

FIG. 37C shows a three-piece glass flow cell design.

FIG. 43A: side view of a multiplexed read-head in which individual microfluorimeters are configured to image a common surface, e.g., the interior surface of a flow cell. FIG. 43B: top view of a multiplexed read-head illustrating the imaging paths acquired by individual microfluorimeters of the multiplexed read-head.

FIG. 44A: side view of a multiplexed read-head in which a first subset of a plurality of individual microfluorimeters 4401 is configured to image a first surface, e.g., a first interior surface of a flow cell, and a second subset of the plurality of individual microfluorimeters is configured to image a second surface, e.g., a second interior surface of a flow cell. FIG. 44B: top view of the multiplexed read-head of FIG. 44A illustrating the imaging paths acquired by individual microfluorimeters 4401 of the multiplexed read-head.

FIG. 47A provides a non-limiting cut-away illustration of an optical system for imaging the surfaces of a flow cell, according to some embodiments herein. FIG. 47B provides a comparison of the optical system of FIG. 47A with IDEX instrument core.

FIG. 49A illustrates the optical system configured to focus on the back-interior surface of the flow cell. FIG. 49B illustrates the optical system configured to focus on the front-interior surface of the flow cell.

FIG. 51A shows a focusing lens assembly with a first lens and a second lens. FIG. 51B shows the same focus lens assembly with the relative movement of the second lens as compared with FIG. 51A.

FIG. 53A illustrates the optical axis of the center optical subsystem aligned with the z-axis. FIG. 53B illustrates the optical axis of the center optical subsystem rotated 90 degrees to align with the y-axis.

FIG. 54A illustrates the optical system configured to focus on the interior surface of the capillary flow cell closest to the light sources. FIG. 54B illustrates the optical system configured to focus on the interior surface of the capillary flow cell further from the light sources.

DETAILED DESCRIPTION

There is a need for fluorescence imaging methods and systems that provide increased optical resolution and improved image quality for genomics applications that lead to corresponding improvements in genomic testing accuracy. Disclosed herein are optical system designs for high-performance fluorescence imaging methods and systems that may provide any one or more of improved optical resolution (including high performance optical resolution), improved image quality, and higher throughput for fluorescence imaging-based genomics applications. The disclosed optical illumination and imaging system designs may provide any one or more of the following advantages: improved dichroic filter performance, increased uniformity of dichroic filter frequency response, improved excitation beam filtering, larger fields-of-view, increased spatial resolution, improved modulation transfer, contrast-to-noise ratio, and image quality, higher spatial sampling frequency, faster transitions between image capture when repositioning the sample plane to capture a series of images (e.g., of different fields-of-view), improved imaging system duty cycle, and higher throughput image acquisition and analysis.

Figure 45:
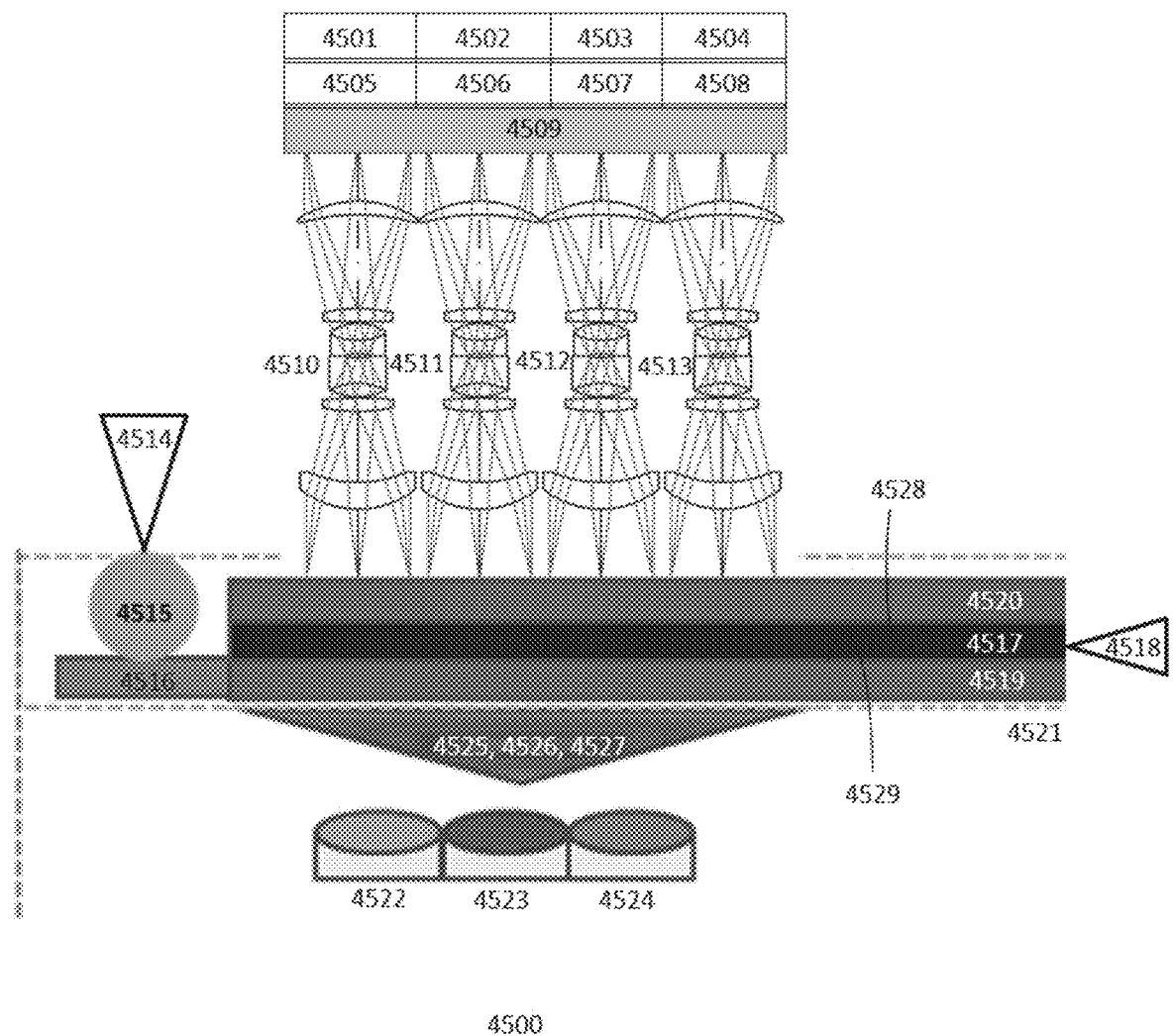
FIG. 45 illustrates a non-limiting example of an optical imaging system having multiple imaging sensors configured for transmission imaging a flow cell upon sequential illumination by multiple light sources, each light source emitting a different color, according to some embodiments herein. Liquid samples are introduced to the flow cell on a hydrophobic pad and flow through the flow cell by a pulling force.

Optical System: Described herein, in some embodiments, is an optical system 4500 as shown the non-limiting schematic of FIG. 45, that eliminates a need for dichroics, or corrective optics, such as a tube lens for dual-side imaging of a flow cell. The optical system 4500 disclosed herein may be used as components of systems designed for a variety of chemical analysis, biochemical analysis, nucleic acid analysis, cell analysis, or tissue analysis applications. As shown in FIG. 45, the optical system comprises multiple imaging sensors 4501-4504 are configured for imaging a flow cell 4521, in some embodiments. In some embodiments, an imaging sensor 4501-4504 may be a CCD imaging sensor. In some embodiments, the imaging sensor 4501-4504 may be a CMOS imaging sensor. In some embodiments, pixel shifters 4505-4508 are used to translate the object being imaged relative to a corresponding imaging sensor 4505-4508. In some embodiments the optical system comprises a multi-band bandpass filter 4509. In some embodiments, the multi-band bandpass filter is a multi-band fluorescence bandpass filter. In some embodiments, the multi-band bandpass filter is a ti-band fluorescence bandpass filter. In some embodiments, the tri-band fluorescence bandpass filter is referred to as a tri-band notch filter. In some embodiments, imaging optics 4510-4513 are positioned between the imaging sensors 4501-4504 and the flow cell 4521. In some embodiments, one imaging optic 4505-4508, also referred to as an imaging optic assembly, focuses light emitted from the flow cell 4521 to one of the imaging sensors, for e.g., 4501, 4502, 4503, or 4504. In some embodiments, the optical system comprises an integrated field flattening assembly. In some embodiments, the optical system comprises aberration correction. In some embodiments, the optical system lacks bandpass filters. In some embodiments, the optical system lacks cutoff filters. In some embodiments, the optical system lacks dichroic mirrors. In some embodiments, a liquid handling system 4514 dispenses a sample 4515 to the flow cell 4521. In some embodiments, the liquid handling system 4514 dispenses a liquid sample to a hydrophobic pad 4516 attached to the flow cell 4521. In some embodiments, the liquid handling system 4514 is a drop dispensing system. In some embodiments, the drop dispensing system 4514 delivers the sample 4515 as a droplet to the hydrophobic pad 4516 of the flow cell 4521. In some embodiments, the liquid sample 4515 is drawn into the interior 4517 of the flow cell 4521 by a pulling force. In some embodiments, the pulling force is initiated by a vacuum pump 4518. In some embodiments, the flow cell 4521 comprises an interior channel 4517 enclosed by a bottom plate 4519 and a top plate 4520. In some embodiments, the top plate 4520 and bottom plate 4519 are transparent. In some embodiments, the top plate comprises a front interior surface 4528. In some embodiments the bottom plate comprises a back interior surface 4529. In some embodiments, the sample, present in the interior channel 4517 of the flow cell 4521 is illuminated by a plurality of light sources 4522, 4523 or 4524. In some embodiments, each of the individual light sources 4522, 4523 and 4524 emit a different color or spectrum of light, 4525, 4526 and 4527 respectively. In some embodiments, the optical system 4500 comprises a heater.

In some embodiments, a notch filter refers to a band stop filter. In some embodiments, a notch filter refers to a band stop filter. In some embodiments, the notch of a filter refers to a band stop or stopband. In some embodiments, the notch of a filter refers to a band pass or passband. In some embodiments, a multiband notch filter refers to a multiband bandpass filter. In some embodiments, a multiband notch filter refers to a multiband band stop filter.

In some embodiments, an imaging optic 4510 of the optical system 4500 comprises a reduction of 1×. In some embodiments, the optical system has a field-of-view (FOV) of greater than 1 mm$^2$, greater than 2 mm$^2$, greater than 4 mm$^2$, greater than 10 mm$^2$, greater than 20 mm$^2$, greater than 36 mm$^2$, greater than 40 mm$^2$, greater than 60 mm$^2$, greater than 80 mm$^2$, or greater than 100 mm$^2$. In some embodiments, the optical system has a numerical aperture (NA) of less than 0.6. In some embodiments, the NA is between about 0.1 to about 0.50, about 0.20 to about 0.40, or about 0.30. In some embodiments, the NA is 0.25. In some embodiments, the NA is about 0.1, 0.15, 0.20, 0.25, 0.3, 0.35, 0.4, 0.45, 0.5, 0.55, or 0.60. In some embodiments, the plurality of imaging sensors is configured to capture the FOV. In some embodiments, a plurality of light sources comprise: a first light source 4522 configured to emit a first wavelength range 4525; a second light source 4523 configured to emit a second wavelength range 4526; and a third light source 4524 configured to emit a third wavelength range 4527. In some embodiments, a first fluorophore is excited by the first wavelength range 4525 of the first light source 4522. In some embodiments, a second fluorophore is excited by the second wavelength range 4526 of the second light source 4523. In some embodiments, a third fluorophore is excited by the third wavelength range 4527 of the third light source 4524. In some embodiments, a sample comprises a plurality of biological polymers. In some embodiments, the optical system 4500 does not comprise a dichroic. In some embodiments, the optical system 4500 does not comprise a tube lens.

Figure 46:
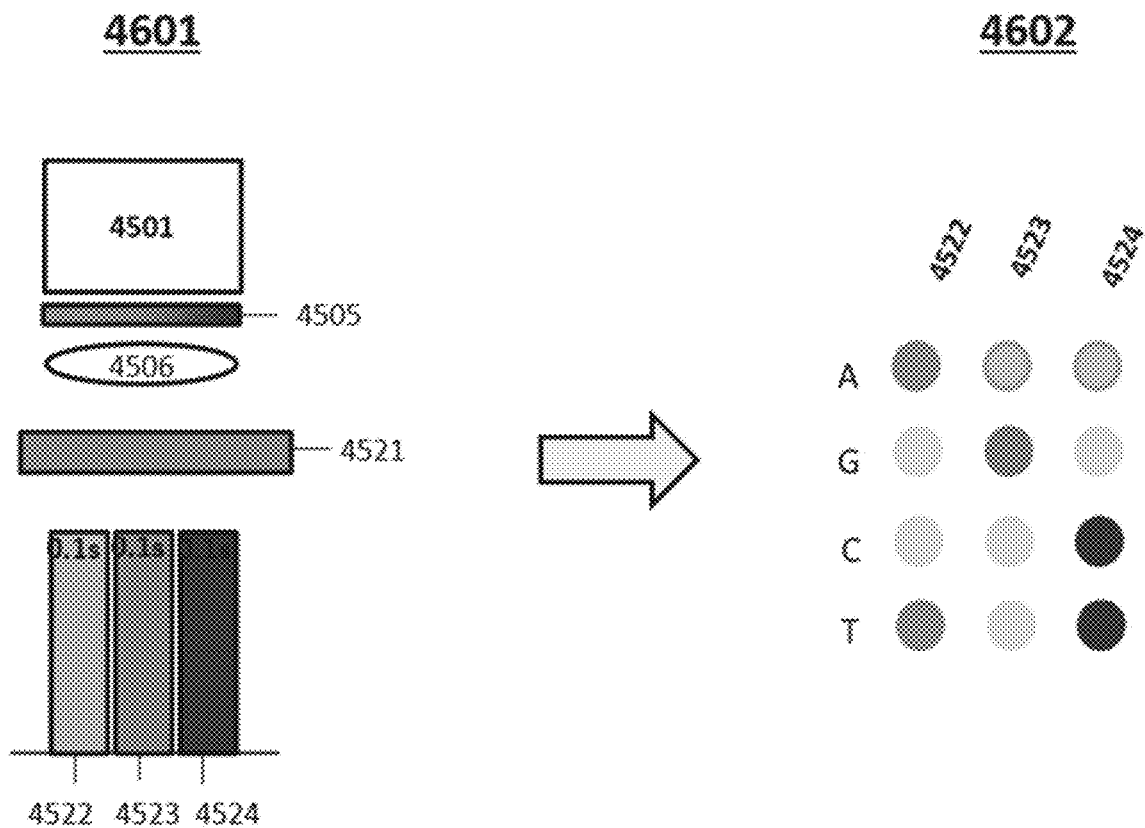
FIG. 46 provides a non-limiting schematic illustration of a method utilizing an optical system for imaging the surface of a flow cell for nucleic acid sequencing, according to some embodiments herein.

Described herein are various methods for a variety of chemical analysis, biochemical analysis, nucleic acid analysis, cell analysis, or tissue analysis application. FIG. 46 provides a schematic illustration of an imaging method 4601 utilizing the optical system 4500 shown in FIG. 45 for imaging a sample 4515 contained within the flow cell 4521, according to some embodiments herein. In some embodiments, the imaging method may be configured for nucleic acid sequencing. In some embodiments, the sample 4515 is contained within, or flows through, the interior channel 4517 of a flow cell 4521, as shown in FIG. 45. In some embodiments, the sample comprises a biological polymer. In some embodiments, the biological polymer comprises units. In some embodiments, a fluorophore is complementary to a unit of the biological polymer. In some embodiments, the fluorophore is attached to a nucleotide that is complementary to a unit of the biological polymer. In some embodiments, two or more detectably distinct fluorophores are attached to a nucleotide that is complementary to a unit of the biological polymer. In some embodiments, the biological polymer is a nucleic acid sequence. In some embodiments, the unit is a nucleotide complementary to the fluorophore labeled nucleotide. In some embodiments, the multiple light sources emit light, transmitting through the sample.

Described herein are various methods for sequencing a biological polymer (e.g., nucleic acid molecule). A non-limiting schematic illustration of the sequencing method and instrumentation 4601 and the base calling method 4602 is shown in FIG. 46. In some embodiments, the method comprises: illuminating a sample 4515 using an optical system 4500 comprising a first light source 4522 of a plurality of light sources, wherein the first light source 4522 emits a first wavelength range 4525 exciting a first fluorophore of the sample 4515 and acquiring a first image of the sample 4515, wherein the optical system 4500 comprises a plurality of imaging sensors 4501-4504, further wherein the sample 4515 is disposed in an optical path between the plurality of light sources 4522-4524 and the plurality of imaging sensors 4501-4504; illuminating the sample 4515 using a second light source 4523 of the plurality, wherein the second light source 4523 emits a second wavelength range 4526 exciting a second fluorophore of the sample 4515 and acquiring a second image the sample 4515; illuminating the sample 4515 using a third light source 4524 of the plurality, wherein the third light source 4524 emits a third wavelength range 4527 exciting a third fluorophore of the sample and acquiring a third image of the sample 4515; combining the first image, the second image, and the third image into a composite image; identifying the presence of a first nucleotide via a first signal emitted by the first fluorophore, wherein the first signal is extracted from a first region of interest (ROI) of the composite image; identifying the presence of a second nucleotide via a second signal emitted by the second fluorophore, wherein the second signal is extracted from a second ROI of the composite image; identifying the presence of a third nucleotide via a third signal emitted by the third fluorophore, wherein the third signal is extracted from a third ROI of the composite image; and identifying the presence of a fourth nucleotide via the first and third signals emitted by the first and third fluorophores, respectively, wherein the first and third signals are extracted from a fourth ROI of the composite image. In some embodiments, the optical system 4500 further comprises a flow cell 4521, wherein the flow cell 4521 is disposed in the optical path between the plurality of imaging sensors 4501-4504 and the plurality of light sources 4522-4524. In some embodiments, the optical system 4500 further comprises at least one pixel shifter 4505-4508. In some embodiments, the optical system 4500 further comprises a multi-band bandpass filter 4509 disposed in the optical path between the plurality of imaging sensors 4501-4504 and the flow cell 4521. In some embodiments, the method further comprises imaging optics 4510-4513 disposed in the optical path between the multi-band bandpass filter 4509 and the flow cell 4521. In some embodiments, the optical system 4500 has a reduction of 1×. In some embodiments, the optical system has a field-of-view (FOV) of greater than 1 mm², greater than 2 mm², greater than 4 mm², greater than 10 mm², greater than 20 mm², greater than 36 mm², greater than 40 mm², greater than 60 mm², greater than 80 mm², or greater than 100 mm². In some embodiments, the optical system has a numerical aperture (NA) of less than 0.6. In some embodiments, the NA is 0.25. In some embodiments, the FOV is captured by the plurality of image sensors 4501-4504.

In some embodiments, the sequencing is sequencing-by-avidity. Additional discussion of sequencing-by-avidity is included in U.S. Pat. No. 10,768,173 filed on Sep. 23, 2019, which is incorporated herein by reference in its entirety. In some embodiments, the first fluorophore is associated with a first nucleotide conjugate. In some embodiments, the second fluorophore is associated with a second nucleotide conjugate. In some embodiments, the third fluorophore is associated with a nucleotide conjugate. In some embodiments, the first fluorophore and the third fluorophore are associated with a fourth nucleotide conjugate. In some embodiments, the nucleotide conjugate may comprise a polymer-nucleotide conjugate. In some embodiments, the nucleotide conjugate may comprise a particle-nucleotide conjugate In some embodiments, fluorophores which may serve as a first fluorophore, a second fluorophore, and/or a third fluorophore include, but are not limited to fluorescein and fluorescein derivatives such as carboxyfluorescein, tetrachlorofluorescein, hexachlorofluorescein, carboxynaptho-fluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, Lissamine® rhodamine, Texas Red®, rhodamine B, rhodamine 6G, rhodamine 10, NHS-rhodamine, TMR-iodoacetamide, Lissamine® rhodamine B sulfonyl chloride, Lissamine® rhodamine B sulfonyl hydrazine, Texas Red® sulfonyl chloride, Texas Red® hydrazide, coumarin and coumarin derivatives such as AMCA, AMCA-NHS, AMCA-sulfo-NHS, AMCA-HPDP, DCIA, AMCE-hydrazide, BODIPY® and derivatives such as BODIPY® FL C3-SE, BODIPY® 530/550 C3, BODIPY® 530/550 C3-SE, BODIPY® 530/550 C3 hydrazide, BODIPY® 493/503 C3 hydrazide, BODIPY® FL C3 hydrazide, BODIPY® FL IA, BODIPY® 530/551 IA, Br-BODIPY® 493/503, Cascade Blue® and derivatives such as Cascade Blue® acetyl azide, Cascade Blue® cadaverine, Cascade Blue® ethylenediamine, Cascade Blue® hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy® 3, Cy® 5, lanthanide chelates and derivatives such as BCPDA, TBP, TMT, BHHCT, BCOT, Europium chelates, Terbium chelates, Alexa Fluor® dyes, DyLight® dyes, Atto dyes, LightCycler® Red dyes, CAL Flour® dyes, JOE® and derivatives thereof, Oregon Green® dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and comprise two indolenin, benzo-indolium, pyridium, thiozolium, and/or quinolinium groups separated by a polymethine bridge between two nitrogen atoms. Commercially available cyanine fluorophores include, for example, Cy®3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy®5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy®7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy®3.5, Cy®5.5 and Cy®7.5 are exceptions to this rule. In some embodiments, the reporter moiety can be a FRET pair, such that multiple classifications can be performed under a single excitation and imaging step. As used herein, FRET may comprise excitation exchange (Forster) transfers, or electron-exchange (Dexter) transfers.

Described herein are optical systems 4700 for imaging samples in a flow cell where no focusing step is included.

Figure 47A:
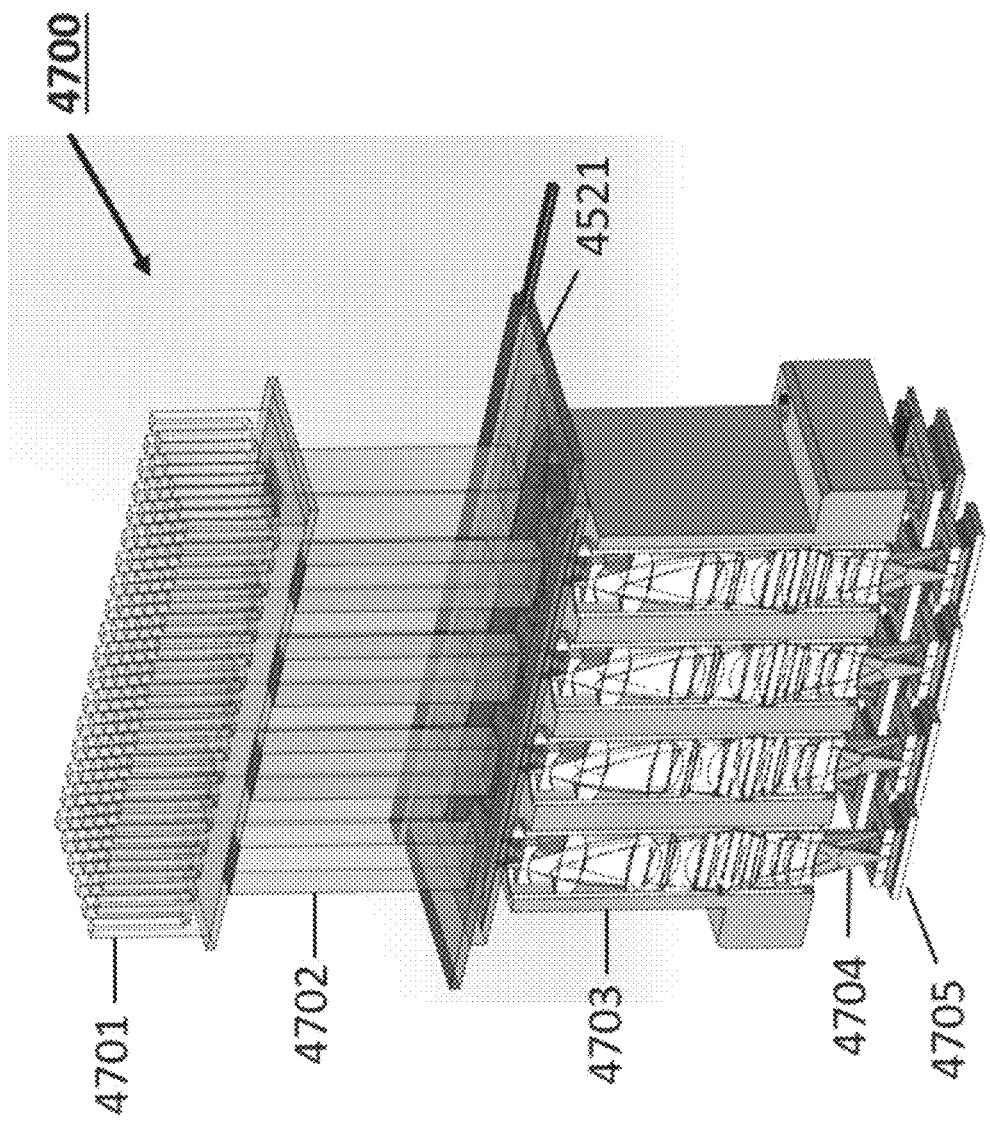
FIGS. 47A-47B provides optical systems according to various embodiments described herein.
Figure 47B:
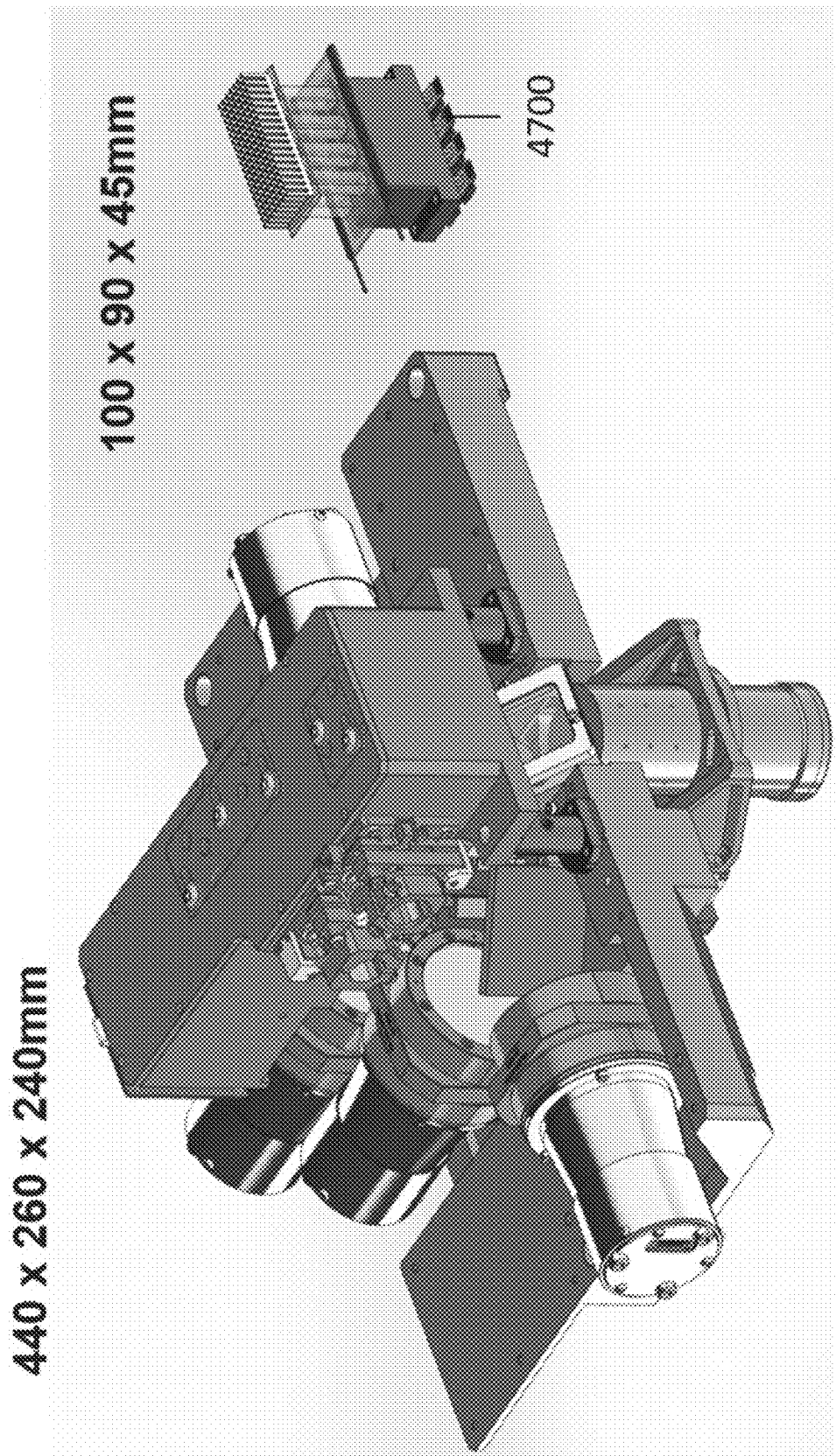
Figure 48A:
FIG. 48A provides a non-limiting example of a flow cell with 424 individual tiles, imaged by the IDEX instrument core shown in FIG. 47 B.
Figure 48A:
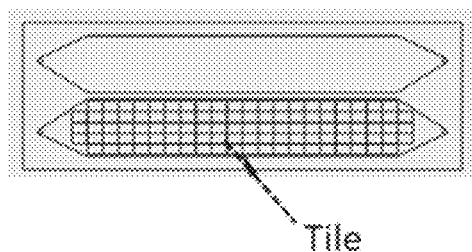
Figure 48B:
FIG. 48B provides a non-limiting example of a flow cell with <40 individual tiles, imaged by the optical system described herein (see FIGS. 45, 46, 47A-47B).
Figure 48B:
Figure 48B:
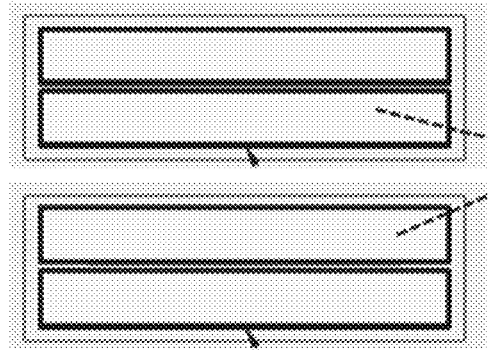

Described herein are optical systems 4700 for imaging samples in a flow cell for analysis of biological polymers (e.g., nucleic acid sequencing). In some embodiments, such systems 4700 as shown in FIGS. 47A-47B are more compact and higher throughput than previous optical systems. Table 1 and FIGS. 48A-48B provide a non-limiting example comparing sequencing cycle times for a standard flow cell and optical system versus the optical system as described herein. Table 1 provides cycle and run times and the respective calculations for a standard flow cell with 424 individual tiles (e.g., active area, region of interest, etc.) as shown in FIG. 48A, compared with a flow cell with <40 individual tiles optimized for imaging on the optical system described herein is shown in FIG. 48B. In some embodiments, one image is equivalent to one tile in area. In some embodiments, when the flow cell 4521, also shown in FIG. 48B, is imaged by the optical system, each tile is exposed to three sequential pulses of light from three separate LED light sources, where each LED light source emits a different wavelength. In some embodiments, each different wavelength is matched to the excitation spectra of a different fluorophore as described herein. In some embodiments, the imaging sensors of the optical system 4500 are synced with each excitation pulse to generate an image, wherein one image the entire area of one tile, and further wherein the pixels of the image each represent the amount of fluorescence emitted by the fluorophore. In some embodiments, 2 separate surfaces are imaged in one tile by the optical system 4500. In some embodiments, 8 total images having a total exposure time of 0.3 seconds are acquired by the optical system 4500, 4700 comprising 8 imaging modules (e.g., optical subsystems). In Table 1 the row titled "current" and highlighted in blue represent the total time, over 322 cycles, to be 36.17 hours for the standard flow cell shown in FIG. 48A when imaged with the IDEX optical system shown in FIG. 47B. In comparison, the rows titled "Sleq" show total times between 13.63 and 14.28 hours for the Sleq Cell (see FIG. 48B) when imaged with the optical system 4700 as shown in FIGS. 47A-47B. The bottom row of Table 1 displays a total time of 1.11 hours when only 25 cycles are performed. The decreased sequencing times demonstrate the advantage of a larger FOV allowed by the optical system 4700 as described herein.

an LED bank heat sink 4701, light pipe illuminators 4702, a flow cell 4521, sections of imaging optics 4703, one or more pixel shifters 4704, and a plurality of imaging sensors 4705. As shown in FIG. 47B, the optical system 4700 is smaller than a comparable instrument, such as the IDEX instrument core. Advantages of a smaller optical instrument include, but are not limited to reduced cabling requirements, reduction in the number of available failure modes, reduced heat exchange requirements, as well as a reduced benchtop footprint.

Figure 49A:
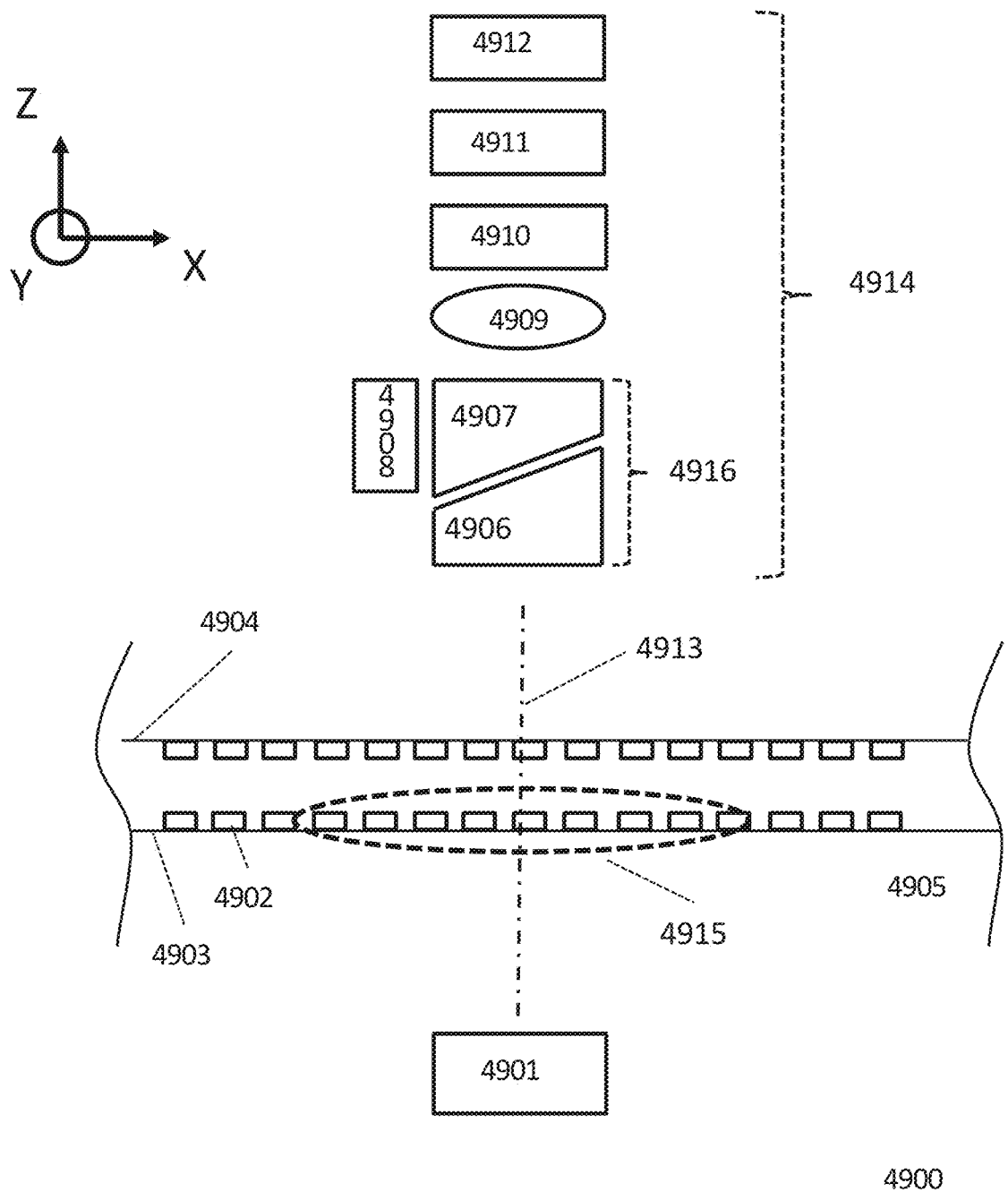
FIGS. 49A-49B provide a non-limiting cut-away illustration of an optical system configured for dual side imaging of a dual sided flow cell. The optical system as shown comprises a piezo driven wedge block for rapid focusing.
Figure 49B:
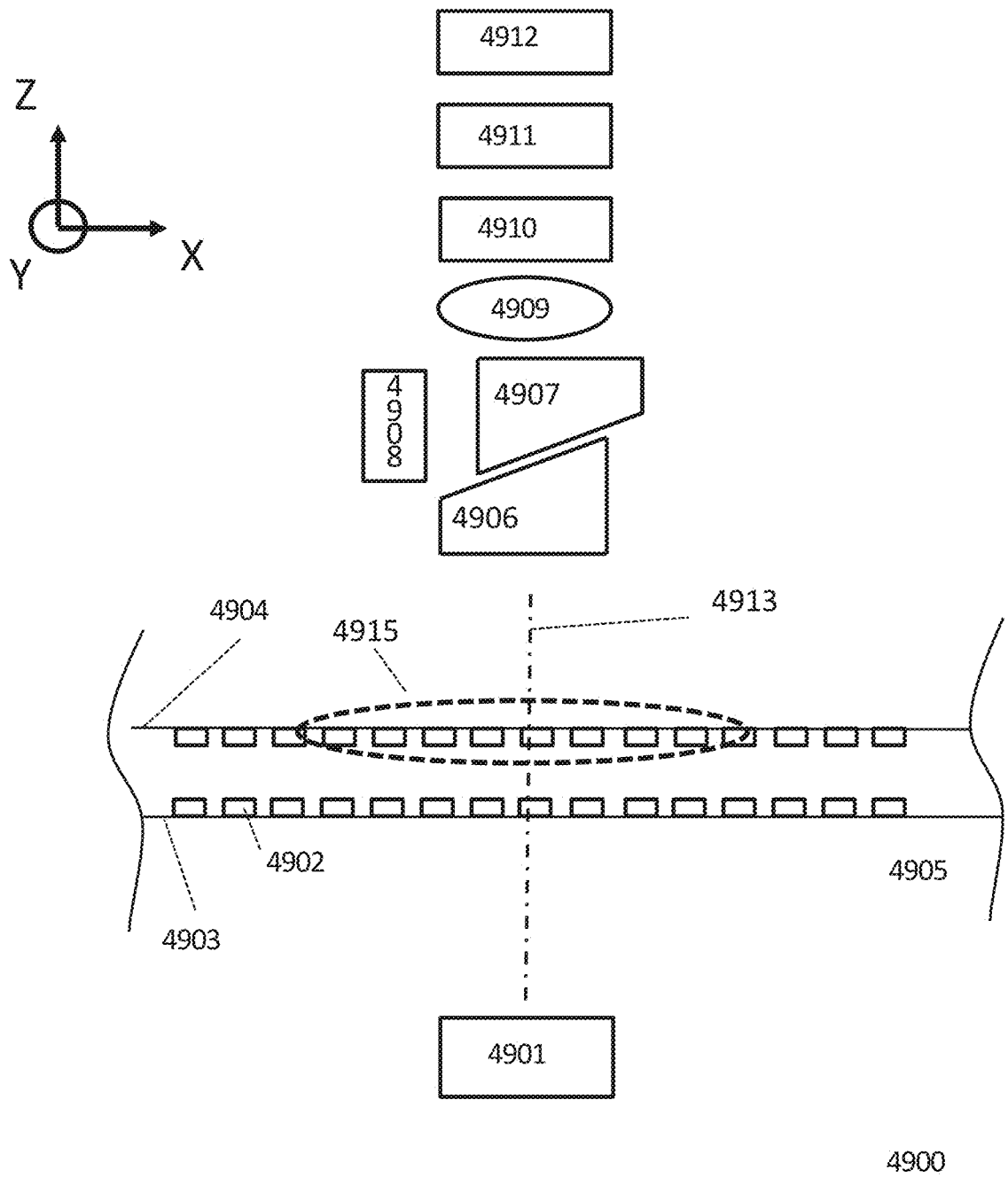

Described herein, in some embodiments, is an optical system 4900, as shown in the non-limiting schematic of FIGS. 49A-49B, configured for dual side imaging of a flow cell 4905. The optical system 4900 disclosed herein may be used in systems designed for a variety of chemical analysis, biochemical analysis, nucleic acid analysis, cell analysis, or tissue analysis applications. As shown in FIGS. 49A-49B, the optical system comprises an imaging sensor 4912 that may be configured for imaging a flow cell 4905. In some embodiments, the sample flow is coincident with the x-axis as shown in FIGS. 49A-49B. In some embodiments, there may be a plurality of imaging sensors 4912. The imaging sensor 4912 may be a CCD imaging sensor. In some embodiments, the imaging sensor 4912 may be a CMOS imaging sensor. In some embodiments, the optical system 4900 comprises a pixel shifter 4911. The pixel shifter 4911 may be configured to improve image resolution. In some embodiments, the pixel shifter 4911 translates the object being imaged relative to the imaging sensor 4912. In some embodiments the optical system comprises a filter 4910. In some embodiments, the filter 4910 is a multi-band filter. In some embodiments, the filter 4509 is a multi-band stopband filter. In some embodiments, the filter 4910 is a tri-band fluorescence stopband filter. In some embodiments, the tri-band fluorescence stopband filter is referred to as a tri-band notch filter. In some embodiments, the system comprises imaging optics 4909. In some embodiments, the imaging optics 4909 comprise an objective lens.

In some embodiments, the filter 4910 is positioned between the imaging sensor 4912 and the flow cell 4905. In some embodiments, the imaging optics 4909, also referred to as an imaging optic assembly, focuses light emitted from the flow cell 4909 to the imaging sensor 4912. In some embodiments, the optical system 4900 comprises an integrated field flattening assembly. In some embodiments, the

TABLE 1

Cycle and run times for the previous system versus the system according to some embodiments

| Flow cell Design | Width | Length | Total Tiles | Imaging Time per Tile (sec) | Imaging Time per Cycle (min) | Number of Cycles | Total Imaging Time (hrs) | Chemistry Time per Cycle (min) | Total Time (hrs) |
|---|---|---|---|---|---|---|---|---|---|
| Current | 35 | 640 | 424 | 0.6 | 4.24 | 322 | 22.75 | 2.5 | 36.17 |
| Sleq Cell | 7 | 64 | 8 | 0.3 | 0.04 | 322 | 0.21 | 2.5 | 13.63 |
| Sleq Cell | 7 | 64 | 16 | 0.3 | 0.08 | 322 | 0.43 | 2.5 | 13.85 |
| Sleq Cell | 7 | 64 | 32 | 0.3 | 0.16 | 322 | 0.86 | 2.5 | 14.28 |
| Sleq Cell | 7 | 64 | 32 | 0.3 | 0.16 | 25 | 0.07 | 2.5 | 1.11 |

FIG. 48A provides an illustration of an imaging area of a flow cell described herein with 424 individual tiles. FIG. 48B provides an illustration of an imaging area of a flow cell described herein with less than 40 tiles.

FIG. 47A provides a non-limiting cut-away illustration of an optical system for imaging the surfaces of a flow cell 4521. In some embodiments, the optical system comprises optical system comprises an aberration correction module. In some embodiments, the optical system comprises a wedge block 4916, configured for adjusting the pathlength of the optical system. In some embodiments, the wedge block 4916 comprises a first wedge piece 4907, a second wedge piece 4906, or a combination thereof. In some embodiments, the system comprises a piezo drive 4908 configured to move the position of the first wedge piece 4907 and the second wedge piece 4906 relative to each other, therefore adjusting the optical path length of the optical system. In some embodiments the flow cell 4905 is configured for dual sided imaging (DSI). In some embodiments, the flow cell 4905 comprises a front interior surface 4904, a back-interior surface 4905, or a combination thereof. In some embodiments the front interior surface 4904 and/or the back-interior surface 4903 comprise sample sites 4902. In some embodiments, the optical system comprises an optical axis 4913. In some embodiments, the optical system comprises an optimal imaging volume 4915. In certain aspects, the optimal imaging volume 4915 comprises the field-of-view (FOV), the area of illumination, the area of acquisition, the focal plane, the focal depth, the region and/or volume where sample sites 4902 emit a brightness at or above an acceptable level, or a combination thereof. Typically, in the art of microscopy, the brightness of objects in the center of the FOV may be maximum at the center and decrease toward the corners and/or edges.

In some embodiments, the optical system lacks bandpass filters. In some embodiments, the optical system lacks cutoff filters. In some embodiments, the optical system lacks dichroic mirrors.

Multivalent Molecules

The present disclosure provides a multivalent molecule comprising a core attached to at least one nucleotide-arm. In some embodiments, the at least one nucleotide-arm can comprise a core attachment moiety. In some embodiments, the at least one nucleotide-arm can comprise a spacer. In some embodiments, the at least one nucleotide-arm can comprise a linker. In some embodiments, the at least one nucleotide-arm can comprise a nucleotide unit. In some embodiments, the at least one nucleotide-arm can comprise a core attachment moiety, a spacer, a linker, and a nucleotide unit. In some embodiments, the core can comprise a bead, particle or nanoparticle. In some embodiments, the core can comprise an alkyl, alkenyl, or alkynyl core such as may be present in a branched polymer or dendrimer. In some embodiments the core can comprise a moiety that mediates conjugation of the core to the nucleotide-arm. In some embodiments, the core can be attached to a plurality of nucleotide-arms. In some cases, the core can be attached to between about 1 to about 50 nucleotide arms. In some cases, the core is attached to between about 2 to about 20 nucleotide-arms. In some cases, the core is attached to between about 2 to about 4 nucleotide-arms. In some cases, the core is attached to between about 4 to about 10 nucleotide-arms. In some cases, the core is attached to between about 10 to about 15 nucleotide-arms. In some cases, the core is attached to between about 15 to about 20 nucleotide-arms. FIGS. 1, 2 and 3 show the general architecture of multivalent molecules.

The present disclosure provides a multivalent molecule comprising a core attached to at least one biotinylated nucleotide-arm. In some embodiments, the at least one biotinylated nucleotide-arm can comprise a core attachment moiety. In some embodiments, the at least one biotinylated nucleotide-arm can comprise a spacer. In some embodiments, the at least one biotinylated nucleotide-arm can comprise a linker. In some embodiments, the at least one biotinylated nucleotide-arm can comprise a nucleotide unit. In some embodiments, the at least one biotinylated nucleotide-arm can comprise a core attachment moiety, a spacer, a linker, and a nucleotide unit. In some embodiments the core can comprise a streptavidin-type or avidin-type moiety, and the biotin unit of the biotinylated nucleotide-arm can mediate conjugation of the core to the biotinylated nucleotide-arm. A streptavidin-type or avidin-type core can be a tetrameric biotin-binding protein that can bind one, two, three or up to four biotinylated nucleotide-arms.

In some embodiments, the core can comprise a streptavidin-type or avidin-type moiety, including streptavidin or avidin protein, as well as any derivatives, analogs and other non-native forms of streptavidin or avidin that can bind to at least one biotin moiety. The streptavidin or avidin moiety can comprise native or recombinant forms, as well as mutant versions and derivatized molecules. Mutant versions of streptavidin and avidin can comprise any one or any combination of two or more of amino acid insertions, deletions, substitutions, or truncations. Mutant versions can also include fusion polypeptides. Many different forms of streptavidin and avidin are commercially-available.

The multivalent molecules can be configured using a streptavidin or avidin core having a high affinity for the biotin moiety on a biotinylated nucleotide-arm to reduce dissociation of the nucleotide-arms from the core. A mixture of multivalent molecules can be prepared, where the mixture contains two or more sub-populations of multivalent molecules and each sub-population contains multivalent molecules having one type of nucleotide units (e.g., dATP, dGTP, dCTP, dTTP or dUTP). Multivalent molecules that are configured to have high affinity between the core and nucleotide-arms can reduce undesirable dissociation of nucleotide-arms from the core, and exchange of nucleotide arms between different cores. Exchange of nucleotide arms during a sequencing reaction can lead to incorrect based calling and reduced sequencing accuracy. In some embodiments, multivalent molecules having increased stability (e.g., reduced dissociation of biotinylated nucleotide-arms) can comprise a dye labeled streptavidin, where the streptavidin subunits carry a Lys121Arg mutation which can exhibit reduced dissociation of a biotinylated nucleotide-arm from the streptavidin core.

The streptavidin moiety can comprise full-length or truncated forms having a high affinity for binding biotin. For example, the streptavidin moiety can exhibit a dissociation constant ($K_d$) of about $10^{-14}$ mol/L, or about $10^{-15}$ mol/L. In some embodiments, the streptavidin moiety can comprise any amino acid substitution mutation at a site that can be labeled with a dye. For example, the dye-labeling site can comprise lysine at position 121 which may overlap with a biotin binding site. In some embodiments, a dye attached to streptavidin at Lys121 may block or inhibit biotin binding to the dye-labeled streptavidin. A multivalent molecule comprising a dye labeled streptavidin carrying lysine at position 121 may exhibit dissociation of a biotinylated nucleotide-arm from the streptavidin core. A multivalent molecule having increased stability can comprise a dye labeled streptavidin carrying a Lys121Arg mutation which can exhibit reduced dissociation of a biotinylated nucleotide-arm from the streptavidin core.

In some embodiments, the streptavidin moiety can comprise any amino acid substitution that increases the affinity for binding biotin (e.g., increases the $K_d$ to about $10^{-16}$ mol/L), improves retention of biotin at temperatures up to about 60° C., or about 65° C., or about 70° C. or about 80° C., or a combination of increases the affinity for binding biotin and improves retention of biotin.

The avidin moiety can comprise full-length or truncated forms having a high affinity for binding biotin. For example, the avidin moiety can exhibit a dissociation constant ($K_d$) of about $10^{-14}$ mol/L, or about $10^{-15}$ mol/L. In some embodiments, the avidin can comprise substitutions of any one or any combination of the eight arginine residues (e.g., underlined and bolded in FIG. 22 or 23). The avidin can comprise partially de-glycosylated forms and non-glycosylated forms.

The avidin moiety can include derivatized forms, for example, N-acyl avidins, e.g., N-acetyl, N-phthalyl and N-succinyl avidin, and the commercially-available products including EXTRAVIDIN®, CAPTAVIDIN® (selective nitration of tyrosine residues at the four biotin-binding sites to generate avidin that reversibly binds biotin), NEUTRAVIDIN (having chemically de-glycosylated and include modified arginine residues), and NEUTRALITE AVIDIN (five of the eight arginine residues are replaced with neutral amino acids, two of the lysine residues are replaced with glutamic acid, and Asp17 is replaced with isoleucine). Amino acids having neutral non-polar side chains include alanine, glycine, isoleucine, leucine, methionine, phenylalanine, proline and valine. Amino acids having neutral polar side chains include asparagine, cysteine, glutamine, serine, threonine, tryptophan and tyrosine.

In some embodiments, the core can be labeled with a detectable reporter moiety. The core can be streptavidin or avidin which are homo-tetramers. Each subunit in the homo-tetramer can include at least one lysine residue which can be conjugated to a fluorophore. A labeling reaction can employ N-hydroxysuccinimide (NHS) ester-conjugated fluorophores. The maximum number of fluorophores that can be attached to a streptavidin or avidin subunit can be dictated by the number of lysine residues in the subunit.

When preparing labeled streptavidin or avidin cores, the labeling reaction can be optimized to achieve a predetermined degree of labeling (sometimes abbreviated as DoL). The degree of labeling can be expressed as a molar ratio in the form of label/protein. Dye-core conjugates with a lower degree of labeling will exhibit weaker fluorescent intensities. Dye-core conjugates with very high degree of labeling (e.g., DoL>6) may exhibit reduced fluorescence due to self-quenching from the conjugated fluorophore. In some embodiments, the predetermined degree of labeling for streptavidin or avidin cores may depend upon the dye. Fluorescent dyes include but are not limited to: CF®647, CF®680, CF®570 and CF®532 dyes from Biotium; AF®647, AF®680, AF®568 and AF®532 from Thermo Fisher Scientific; IFluor® 647, IFluor® 680, IFluor® 568 and IFlour® 532 from AATBio; DY648P1, DY679P1, DY585 and DY530 from Dyomics; and AFDy 647, IRFlour 680LT, AFDye 568 and AFDye 532 from Fluoroprobes. The predetermined degree of labeling can be about 1-10, or about 3-8, or about 3.5-7, or about 1.6-4.

Red fluorophores are brighter (higher intensity) than green dyes, which can cause color bleeding when imaging both red-labeled and green-labeled multivalent molecules on the same support (e.g., flow cell). The degree of labeling of a sub-population of multivalent molecules can be increased or decreased to achieve improved signal balance from a mixture of labeled multivalent molecules. For example, the degree of labeling of a sub-population of multivalent molecules labeled with a red fluorophore can be decreased compared to the degree of labeling of a sub-population of multivalent molecules labeled with a green fluorophore. In some embodiments, the degree of labeling of a sub-population of multivalent molecules labeled with a red fluorophore can be about 1-3, or about 2-3, or about 3-6. In some embodiments, the degree of labeling of a sub-population of multivalent molecules labeled with a green fluorophore can be about 4-7.

Solution fluorescence measurements can be used to determine the relative brightness of the labeled streptavidin or avidin cores. Alternatively, the degree of labeling can be determined by employing a functional assay (e.g., a flow cell trap assay) in which clonally-amplified template molecules immobilized on a flow cell are contacted with primers, polymerases and fluorescently-labeled multivalent molecules, under a condition suitable for binding the multivalent molecules to complexed polymerases without incorporating the nucleotide units into the primer, and signal intensity can be detected.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise the same type of nucleotide units. For example, a multivalent molecule can comprise a core (e.g., streptavidin or avidin core) attached to a plurality of nucleotide arms or biotinylated nucleotide arms, where all of the attached arms have a nucleotide unit selected from a group consisting of dATP, dGTP, dCTP, dTTP and dUTP.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise different types of nucleotide units. For example, a multivalent molecule can comprise a core (e.g., streptavidin or avidin core) attached to a plurality of nucleotide arms or biotinylated nucleotide arms, where at least a first attached arm can have a first nucleotide unit selected from a group consisting of dATP, dGTP, dCTP, dTTP and dUTP, and a second attached arm can have a second nucleotide unit selected from a group consisting of dATP, dGTP, dCTP, dTTP and dUTP, where the first and second nucleotide units are different.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise the same type of spacer For example, a multivalent molecule can comprise a core (e.g., streptavidin or avidin core) attached to a plurality of nucleotide arms or biotinylated nucleotide arms, where all of the attached arms have the same spacer.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise different types of spacers. For example, a multivalent molecule can comprise a core (e.g., streptavidin or avidin core) attached to a plurality of nucleotide arms or biotinylated nucleotide arms, where at least a first attached arm can have a first type of spacer, and a second attached arm can have a second type of spacer, where the first and second spacer units are different. In some embodiments, the first and second type of linker can be selected from any of the spacers described herein.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise the same type of linker. For example, a multivalent molecule can comprise a core (e.g., streptavidin or avidin core) attached to a plurality of nucleotide arms or biotinylated nucleotide arms, where all of the attached arms have the same linker. In some embodiments, the linker can be selected from any of the linkers described herein (e.g., FIGS. 5A (bottom) and 5B-F).

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise different types of linkers. For example, a multivalent molecule can comprise a core (e.g., streptavidin or avidin core) attached to a plurality of nucleotide arms or biotinylated nucleotide arms, where at least a first attached arm can have a first type of linker, and a second attached arm can have a second type of linker, where the first and second linker units are different. In some embodiments, the first and second type of linker can be selected from any of the linkers described herein (e.g., FIGS. 5A (bottom) and 5B-F).

The present disclosure provides compositions, systems, methods, and kits comprising a multivalent molecule. In some embodiments, the multivalent molecule can comprise a core attached to a plurality of e-arms. In some embodiments, the plurality of nucleotide-arms can comprise the same type of spacer and linker. For example, a multivalent molecule can comprise a core (e.g., streptavidin or avidin core) attached to a plurality of nucleotide arms or biotinylated nucleotide arms, where all of the attached arms have the same spacer and linker. In some embodiments, the spacer and linker can be selected from any of the spacers and linkers described herein.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise the same type of reactive group. For example, a multivalent molecule can comprise a core (e.g., streptavidin or avidin core) attached to a plurality of nucleotide arms or biotinylated nucleotide arms, where all of the attached arms have the same reactive group. In some embodiments, the reactive group can comprise an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group.

In some embodiments, the reactive group in the linker can be reactive with a chemical reagent. For example, the reactive groups alkyl, alkenyl, alkynyl and allyl can be reactive with tetrakis(triphenylphosphine)palladium(0) (Pd (PPh$_3$)$_4$) with piperidine, or with 2,3-Dichloro-5,6-dicyano-1,4-benzo-quinone (DDQ). The reactive groups aryl and benzyl can be reactive with H2 Pd/C. The reactive groups amine, amide, keto, isocyanate, phosphate, thio, disulfide can be reactive with phosphine or with a thiol group including beta-mercaptoethanol or dithiothritol (DTT). The reactive group carbonate can be reactive with potassium carbonate (K$_2$CO$_3$) in MeOH, with triethylamine in pyridine, or with Zn in acetic acid (AcOH). The reactive groups urea and silyl can be reactive with tetrabutylammonium fluoride, pyridine-HF, with ammonium fluoride, or with triethylamine trihydrofluoride.

In some embodiments, the nucleotide-arms can have the same type of reactive group in the linker where the reactive group can comprise an azide, azido or azidomethyl group. In some embodiments, the azide, azido or azidomethyl group in the linker can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP),bis-sulfo triphenyl phosphine (BS-TPP) or Tri(hydroxyproyl)phosphine (THPP).

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise different types of reactive groups in the linkers. For example, a multivalent molecule can comprise a core (e.g., streptavidin or avidin core) attached to a plurality of nucleotide arms or biotinylated nucleotide arms, where at least a first attached arm can have a first type of reactive group in a first linker unit, and a second attached arm can have a second type of reactive group in a second linker unit, where the first and second reactive groups are different.

In some embodiments, the first reactive group in the first linker unit, and the second reactive group in the second linker unit, can be selected in any combination from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, and silyl group.

In some embodiments, the first and second reactive groups can be reactive with a chemical agent. For example, the reactive groups alkyl, alkenyl, alkynyl and allyl can be reactive with tetrakis(triphenylphosphine)palladium(0) (Pd (PPh$_3$)$_4$) with piperidine, or with 2,3-Dichloro-5,6-dicyano-1,4-benzo-quinone (DDQ). The reactive groups aryl and benzyl can be reactive with H2 Pd/C. The reactive groups amine, amide, keto, isocyanate, phosphate, thio, disulfide can be reactive with phosphine or with a thiol group including beta-mercaptoethanol or dithiothritol (DTT). The reactive group carbonate can be reactive with potassium carbonate (K$_2$CO$_3$) in MeOH, with triethylamine in pyridine, or with Zn in acetic acid (AcOH). The reactive groups urea and silyl can be reactive with tetrabutylammonium fluoride, pyridine-HF, with ammonium fluoride, or with triethylamine trihydrofluoride.

In some embodiments, the nucleotide-arms can have the different types of reactive groups in the linkers where the reactive group can comprise an azide, azido or azidomethyl group. In some embodiments, the azide, azido or azidomethyl group in the linker can be reactive with a chemical agent. In some embodiments, the chemical agent can comprise a phosphine compound.

In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise a nucleotide unit with the same type of sugar 3'OH group. For example, a multivalent molecule can comprise a core (e.g., streptavidin or avidin core) attached to a plurality of nucleotide arms or biotinylated nucleotide arms, where all of the attached arms have a nucleotide unit having the same type of sugar 3'OH group.

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise a nucleotide unit with the same type of sugar 3' blocking group (e.g., chain terminating moiety For example, a multivalent molecule can comprise a core (e.g., streptavidin or avidin core) attached to a plurality of nucleotide arms or biotinylated nucleotide arms, where all of the attached arms can have a nucleotide unit having the same type of sugar 3' blocking group. In some embodiments, the sugar 3' blocking group can comprise an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the sugar 3' blocking group can comprise a 3'-O-alkyl hydroxylamino group, a 3'-phosphorothioate group, a 3'-O-malonyl group, or a 3'-O-benzyl group. In some embodiments, the sugar 3' blocking group can comprise an azide, azido or azidomethyl group.

In some embodiments, the sugar 3' blocking group can be reactive with a chemical reagent. For example, the sugar 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The sugar 3' blocking groups aryl and benzyl can be reactive with H2 Pd/C. The sugar 3' blocking groups amine, amide, keto, isocyanate, phosphate, thio, disulfide can be reactive with phosphine or with a thiol group including beta-mercaptoethanol or dithiothritol (DTT). The sugar 3' blocking group carbonate can be reactive with potassium carbonate (K$_2$CO$_3$) in MeOH, with triethylamine in pyridine, or with Zn in acetic acid (AcOH). The sugar 3' blocking groups urea and silyl can be reactive with tetrabutylammonium fluoride, pyridine-HF, with ammonium fluoride, or with triethylamine trihydrofluoride.

In some embodiments, the sugar 3' blocking group (e.g., azide, azido and azido methyl) can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise a nucleotide unit with different sugar 3' blocking groups. For example, a multivalent molecule can comprise a core (e.g., streptavidin or avidin core) attached to a plurality of nucleotide arms or biotinylated nucleotide arms, where at least a first attached arm can have a first nucleotide unit having a first 3' blocking group, and a second attached arm can have a second nucleotide unit having a second 3' blocking group, where the first and second 3' blocking groups are different.

In some embodiments, the first 3' blocking group in the first nucleotide unit, and the second 3' blocking group in the second nucleotide unit, can be selected in any combination from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the first 3' blocking group in the first nucleotide unit, and the second 3' blocking group in the second nucleotide unit, can be selected in any combination from a group consisting of an 3'-O-alkyl hydroxylamino group, a 3'-phosphorothioate group, a 3'-O-malonyl group, or a 3'-O-benzyl group. In some embodiments, the first 3' blocking group in the first nucleotide unit, and the second 3' blocking group in the second nucleotide unit, can be selected in any combination from a group consisting of an azide, azido or azidomethyl group.

In some embodiments, the first and second 3' blocking groups can be reactive with a chemical reagent. For example, the 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The 3' blocking groups aryl and benzyl can be reactive with H2 Pd/C. The 3' blocking groups amine, amide, keto, isocyanate, phosphate, thio, disulfide can be reactive with phosphine or with a thiol group including beta-mercaptoethanol or dithiothritol (DTT). The 3' blocking group carbonate can be reactive with potassium carbonate (K$_2$CO$_3$) in MeOH, with triethylamine in pyridine, or with Zn in acetic acid (AcOH). The 3' blocking groups urea and silyl can be reactive with tetrabutylammonium fluoride, pyridine-HF, with ammonium fluoride, or with triethylamine trihydrofluoride.

In some embodiments, the first and second 3' blocking groups (e.g., azide, azido and azido methyl) can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a multivalent molecule. In some embodiments, the multivalent molecule can comprise a core attached to a plurality of nucleotide-arms. In some embodiments, the plurality of nucleotide-arms can comprise a nucleotide unit with a first sugar 3' OH blocking groups. In some embodiments, the plurality of nucleotide-arms can comprise a nucleotide unit with a second 3' OH blocking group. In some cases, the first and second 3' OH blocking groups can be different. For example, a multivalent molecule can comprise a core (e.g., streptavidin or avidin core) attached to a plurality of nucleotide arms or biotinylated nucleotide arms, where (a) at least a first arm can comprise a first nucleotide unit having a sugar moiety which includes a 3'OH group, (b) at least second arm can comprise a second nucleotide unit having a first 3' blocking group, and (c) at least third arm can comprise a third nucleotide unit having a second blocking group, wherein the first and second 3' blocking groups are different from each other.

In some embodiments, the first 3' blocking group in the first nucleotide unit, and the second 3' blocking group in the second nucleotide unit, can be selected in any combination from a group consisting of an alkyl group, alkenyl group, alkynyl group, allyl group, aryl group, benzyl group, azide group, amine group, amide group, keto group, isocyanate group, phosphate group, thio group, disulfide group, carbonate group, urea group, or silyl group. In some embodiments, the first 3' blocking group in the first nucleotide unit, and the second 3' blocking group in the second nucleotide unit, can be selected in any combination from a group consisting of an 3'-O-alkyl hydroxylamino group, a 3'-phosphorothioate group, a 3'-O-malonyl group, or a 3'-O-benzyl group. In some embodiments, the first 3' blocking group in the first nucleotide unit, and the second 3' blocking group in the second nucleotide unit, can be selected in any combination from a group consisting of an azide, azido or azidomethyl group.

In some embodiments, the first and second 3' blocking groups can be reactive with a chemical reagent. For example, the 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The 3' blocking groups aryl and benzyl can be reactive with H2 Pd/C. The 3' blocking groups amine, amide, keto, isocyanate, phosphate, thio, disulfide can be reactive with phosphine or with a thiol group including beta-mercaptoethanol or dithiothritol (DTT). The 3' blocking group carbonate can be reactive with potassium carbonate (K$_2$CO$_3$) in MeOH, with triethylamine in pyridine, or with Zn in acetic acid (AcOH). The 3' blocking groups urea and silyl can be reactive with tetrabutylammonium fluoride, pyridine-HF, with ammonium fluoride, or with triethylamine trihydrofluoride.

In some embodiments, the first and second 3' blocking groups (e.g., azide, azido and azido methyl) can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri (hydroxyproyl)phosphine (THPP).

The present disclosure provides compositions, systems, methods, and kits comprising a multivalent molecule. In some embodiments, the multivalent molecule can have a core. In some embodiments, the core can be labeled with at least one detectable reporter moiety to form a labeled core. In some embodiments, a labeled core attached to two or more nucleotide-arms can comprise a labeled multivalent molecule. In some embodiments, a streptavidin or avidin core can be labeled with 1-6 or more reporter moieties. In some embodiments, the reporter moiety can comprise a fluorophore.

A mixture of multivalent molecules having different units in their nucleotide-arms, where distinction between the different multivalent molecules can be achieved. In some embodiments, the core of a first multivalent molecule can be labeled with a reporter moiety to distinguish it from a second labeled (or non-labeled) multivalent molecule. For example, a unit in a nucleotide-arm of the labeled first multivalent molecule can differ from a unit in a nucleotide-arm of a labeled second multivalent molecule. Any unit in the first multivalent molecule (e.g., spacer, linker, reactive group, nucleotide base, sugar 3'OH, 3' blocking group, or a combination thereof) can differ from a corresponding unit in the second multivalent molecule, where the first and second reporter moieties correspond to the differentiating unit. In some embodiments, the first and second reporter moieties can be spectrally distinguishable from each other.

In some embodiments, the core of a first multivalent molecule can be labeled with a first reporter moiety that corresponds to the base (e.g., dATP, dGTP, dCTP, dTTP or dUTP) in the attached nucleotide-arms, and the core of a second multivalent molecule can be labeled with a second reporter moiety that corresponds to the base (e.g., dATP, dGTP, dCTP, dTTP or dUTP) in the attached nucleotide-arms, where the base in the first multivalent molecule and the base in the second multivalent molecule are different. In some embodiments, the first and second reporter moieties are spectrally distinguishable from each other. In some embodiment, detection of the first reporter moiety indicates a binding event, an incorporation event, or a combination of binding and incorporation events of the first multivalent molecule having the first base, and detection of the second reporter moiety indicates a binding event, an incorporation event, or a combination of binding and incorporation events of the second multivalent molecule having the second base. The binding event can be a multivalent molecule binding to a complexed polymerase. The incorporation event can be a nucleotide unit incorporating into the terminal 3' end of an extendible primer in a complexed polymerase, where the nucleotide unit is part of a multivalent molecule.

Mixture of Multivalent Molecules

The present disclosure provides separate batches (sub-populations) of labeled multivalent molecules. In some embodiments, the separate batches of labeled multivalent molecules can be prepared using a different reporter moiety for each batch. In some embodiments, the different reporter moiety reporter moiety can correspond to a particular base in the nucleotide arms. A particular batch can be distinguishable from other batches based on the reporter moiety attached to the core. Two, three, four, five or more separate batches (sub-populations) can be mixed together to form a plurality of labeled multivalent molecules comprising two or more sub-populations of spectrally distinguishable multivalent molecules. In some embodiments, at least one batch of multivalent molecules in the mixture can be non-labeled (e.g., dark multivalent molecules).

The present disclosure provides compositions, systems, methods, and kits comprising a plurality of multivalent molecules which can comprise a mixture of at least two sub-populations of multivalent molecules labeled with different reporter moieties. In some embodiments, at least a first sub-population of multivalent molecules can be labeled with a first reporter moiety that corresponds to a first nucleotide unit on the nucleotide-arms. In some embodiments, at least a second sub-population of multivalent molecules can be labeled with a second reporter moiety that corresponds to a second nucleotide unit on the nucleotide-arms. In some cases, the first and second reporter moieties can differ from each other. In some embodiments, the plurality of multivalent molecules can further comprise at least a third sub-population of multivalent molecules which is labeled with a third reporter moiety, wherein the first, second and third reporter moieties can differ from each other. In some embodiments, the plurality of multivalent molecules can further comprise at least a fourth sub-population of multivalent molecules which is labeled with a fourth reporter moiety, wherein the first, second, third and fourth reporter moieties can differ from each other. In some embodiments, additional sub-populations (e.g., fifth, sixth, seventh, eighth, ninth, tenth or more) of labeled multivalent molecules can be added into the mixture. In some embodiments, the reporter moiety can be a fluorophore. In some embodiments, a first sub-population of multivalent molecules can be labeled with a first fluorophore and a second fluorophore of multivalent molecules can be labeled with a second fluorophore. In some cases, the first fluorophore and the second fluorophore can be different.

The present disclosure provides compositions, systems, methods, and kits comprising a plurality of multivalent molecules which can comprise a mixture of at least two sub-populations of multivalent molecules labeled with different reporter moieties. In some embodiments, at least a first sub-population of multivalent molecules can be labeled with a first reporter moiety that corresponds to a first nucleotide unit on the nucleotide-arms. In some embodiments, at least a second sub-population of multivalent molecules can be non-labeled (e.g., a dark multivalent molecule).

The present disclosure provides compositions, systems, methods, and kits comprising a plurality of multivalent molecules which comprises a mixture of at least three sub-populations of multivalent molecules labeled with different reporter moieties. In some embodiments, at least a first sub-population of multivalent molecules can be labeled with a first reporter moiety that corresponds to a first nucleotide unit on the nucleotide-arms. In some embodiments, at least a second sub-population of multivalent molecules can be labeled with a second reporter moiety that corresponds to a second nucleotide unit on the nucleotide-arms. In some embodiments, at least a third sub-population of multivalent molecules can be non-labeled (e.g., a dark multivalent molecule). In some embodiments, the first and second reporter moieties can differ from each other.

The present disclosure provides compositions, systems, methods, and kits comprising a plurality of multivalent molecules which comprises a mixture of at least four sub-populations of multivalent molecules labeled with different reporter moieties. In some embodiments, the mixture of multivalent molecules can have at least a first sub-population of multivalent molecules can be labeled with a first reporter moiety that corresponds to a first nucleotide unit on the nucleotide-arms. In some embodiments, the mixture of multivalent molecules can have at least a second sub-population of multivalent molecules can be labeled with a second reporter moiety that corresponds to a second nucleotide unit on the nucleotide-arms. In some embodiments, the mixture of multivalent molecules can have at least a third sub-population of multivalent molecules is labeled with a third reporter moiety. In some embodiments, the mixture of multivalent molecules can have at least a fourth sub-population of multivalent molecules can be non-labeled (e.g., a dark multivalent molecule). In some cases, the first, second and third reporter moieties can differ from each other.

An embodiment comprises: a mixture of four different types of multivalent molecules comprising (1) a first sub-population of multivalent molecules each comprising a dATP nucleotide unit and a core labeled with a first type of fluorophore, (2) a second sub-population of multivalent molecules each comprising a dGTP nucleotide unit and a core labeled with a second type of fluorophore, (3) a third sub-population of multivalent molecules each comprising a dCTP nucleotide unit and a core labeled with a third type of fluorophore, and (4) a fourth sub-population of multivalent molecules each comprising a dTTP nucleotide unit and a core labeled with a fourth type of fluorophore, where the first, second, third and fourth fluorophores can be spectrally distinguishable. In some embodiments, any one of the sub-populations of multivalent molecules can be non-labeled for use as "dark" multivalent molecules.

The present disclosure provides compositions, systems, methods, and kits comprising a plurality (e.g., a population) of multivalent molecules, wherein individual multivalent molecules in the plurality can comprise a core bound to at least one nucleotide-arm. In some embodiments, individual multivalent molecules in the plurality can comprise a core bound to 2-5 nucleotide-arms. In some embodiments, individual multivalent molecules in the plurality can comprise a streptavidin or avidin core bound to 2-5 biotinylated nucleotide-arms.

The present disclosure provides compositions, systems, methods, and kits comprising a plurality (e.g., a population) of multivalent molecules, wherein individual multivalent molecules in the plurality can comprise a core bound to at least one nucleotide-arm having one type of nucleotide unit comprising dATP, dGTP, dCTP, dTTP or dUTP. In some embodiments, individual multivalent molecules in the plurality can comprise a core bound to 2-5 nucleotide-arms, where the nucleotide-arms have one type of nucleotide unit comprising dATP, dGTP, dCTP, dTTP or dUTP. In some embodiments, individual multivalent molecules in the plurality can comprise a core bound to 2-5 biotinylated nucleotide-arms, where the biotinylated nucleotide-arms have one type of nucleotide unit comprising dATP, dGTP, dCTP, dTTP or dUTP.

The present disclosure provides compositions, systems, methods, and kits comprising a plurality of multivalent molecules comprising a mixture (sub-populations) of two or more different types of multivalent molecules. In some embodiments, the plurality of multivalent molecules can have at least a first multivalent molecule in the plurality. In some cases, the at least the first multivalent molecule can comprise a core bound to at least one nucleotide-arm having a first type of nucleotide selected from a group consisting of dATP, dGTP, dCTP, dTTP or dUTP.

In some embodiments, the plurality of multivalent molecules can have at least a second multivalent molecule. In some embodiments, the plurality of multivalent molecules can comprise at least a first multivalent molecule in the plurality and at least a second multivalent molecule. In some cases, the at least second multivalent molecule can comprise a core bound to at least one nucleotide-arm having a second type of nucleotide that differs from the first nucleotide in the first multivalent molecule. In some embodiments, the first multivalent molecule can comprise a core bound to 2-5 biotinylated nucleotide arms, where the biotinylated-arms can have a first type of nucleotide selected from a group consisting of dATP, dGTP, dCTP, dTTP or dUTP. In some embodiments, the second multivalent molecule can comprise a core bound to 2-5 biotinylated nucleotide arms, where the biotinylated-arms can have a second type of nucleotide selected from a group consisting of dATP, dGTP, dCTP, dTTP or dUTP, where the first and second type of nucleotides are different. In some embodiments, the mixture can comprise two, three, four, five, or more different types of multivalent molecules having nucleotides selected in any combination from a group consisting of dATP, dGTP, dCTP, dTTP or dUTP.

The present disclosure provides compositions, systems, methods, and kits comprising a plurality (e.g., a population) of multivalent molecules, wherein individual multivalent molecules in the plurality can comprise a core bound to at least one nucleotide-arm. In some embodiments, the at least one nucleotide arm that are bound to a core can have the same spacer. In some embodiments, individual multivalent molecules in the plurality can comprise a core bound to 2-5 nucleotide-arms. In some embodiments, individual multivalent molecules in the plurality can comprise a core bound to 2-5 biotinylated nucleotide-arms.

The present disclosure provides compositions, systems, methods, and kits comprising a plurality (e.g., a population) of multivalent molecules, wherein individual multivalent molecules in the plurality can comprise a core bound to at least one nucleotide-arm. In some embodiments, the at least one nucleotide-arm that are bound to a core can have the same linker. In some embodiments, individual multivalent molecules in the plurality can comprise a core bound to 2-5 nucleotide-arms. In some embodiments, individual multivalent molecules in the plurality can comprise a core bound to 2-5 biotinylated nucleotide-arms.

The present disclosure provides compositions, systems, methods, and kits comprising a plurality (e.g., a population) of multivalent molecules, wherein individual multivalent molecules in the plurality can comprise a core bound to at least one nucleotide-arm. In some embodiments, all of the nucleotide arms that are bound to a core can have the same spacer and linker. In some embodiments, individual multivalent molecules in the plurality can comprise a core bound to 2-5 nucleotide-arms. In some embodiments, individual multivalent molecules in the plurality can comprise a core bound to 2-5 biotinylated nucleotide-arms.

The present disclosure provides compositions, systems, methods, and kits comprising a plurality of multivalent molecules comprising a mixture (sub-populations) of two or more different types of multivalent molecules. In some embodiments, the plurality of multivalent molecules can comprise at least a first multivalent molecule in the plurality can comprise a core bound to at least one nucleotide-arm having a first type of spacer. In some embodiments, the plurality of multivalent molecules can comprise at least a second multivalent molecule can comprise a core bound to at least one nucleotide-arm having a second type of spacer. In some embodiments, the plurality of multivalent molecules can comprise a mixture of the at least the first multivalent molecule and the at least the second multivalent molecule. In some cases, the second type of spacer in the second multivalent molecule can differ from the first spacer in the first multivalent molecule. In some embodiments, the first multivalent molecule can comprise a core bound to 2-5 biotinylated nucleotide arms, where the biotinylated-arms can have a first type of spacer. In some embodiments, the second multivalent molecule can comprise a core bound to 2-5 biotinylated nucleotide arms, where the biotinylated-arms can have a second type of spacer, where the first and second type of spacers are different.

The present disclosure provides compositions, systems, methods, and kits comprising a plurality of multivalent molecules comprising a mixture (sub-populations) of two or more different types of multivalent molecules. In some embodiments, the plurality of multivalent molecules can comprise at least a first multivalent molecule in the plurality comprises a core bound to at least one nucleotide-arm having a first type of linker. In some embodiments, the plurality of multivalent molecules can comprise at least a second multivalent molecule comprises a core bound to at least one nucleotide-arm having a second type of linker. In some embodiments, the plurality of multivalent molecules can comprise a mixture of the at least the first multivalent molecule and the at least the second multivalent molecule. In some cases, the second type of linker in the second multivalent molecule can differ from the first linker in the first multivalent molecule. In some embodiments, the first multivalent molecule can comprise a core bound to 2-5 biotinylated nucleotide arms, where the biotinylated-arms can have a first type of linker. In some embodiments, the second multivalent molecule can comprise a core bound to 2-5 biotinylated nucleotide arms, where the biotinylated-arms can have a second type of linker, where the first and second type of spacers are different.

The present disclosure provides compositions, systems, methods, and kits comprising a plurality (e.g., a population) of multivalent molecules, wherein individual multivalent molecules in the plurality can comprise a core bound to at least one nucleotide-arm. In some embodiments, all of the nucleotide arms that are bound to a core can have the same reactive group in the linker. In some embodiments, individual multivalent molecules in the plurality can comprise a core bound to 2-5 nucleotide-arms. In some embodiments, individual multivalent molecules in the plurality can comprise a core bound to 2-5 biotinylated nucleotide-arms. In some embodiments, the reactive group can comprise alkyl, alkenyl, alkynyl, allyl, aryl, benzyl, azide, amine, amide, keto, isocyanate, phosphate, thio, disulfide, carbonate, urea, or silyl group. In some embodiments, the individual multivalent molecules can comprise a reactive group that can be reactive with a chemical agent. For example, the reactive groups alkyl, alkenyl, alkynyl and allyl are reactive with tetrakis(triphenylphosphine)palladium(0) ($Pd(PPh_3)_4$) with piperidine, or with 2,3-Dichloro-5,6-dicyano-1,4-benzo-quinone (DDQ). The reactive groups aryl and benzyl can be reactive with H2 Pd/C. The reactive groups amine, amide, keto, isocyanate, phosphate, thio, disulfide can be reactive with phosphine or with a thiol group including beta-mercaptoethanol or dithiothritol (DTT). The reactive group carbonate can be reactive with potassium carbonate ($K_2CO_3$) in MeOH, with triethylamine in pyridine, or with Zn in acetic acid (AcOH). The reactive groups urea and silyl can be reactive with tetrabutylammonium fluoride, pyridine-HF, with ammonium fluoride, or with triethylamine trihydrofluoride. In some embodiments, the reactive group can comprise an azide, azido or azidomethyl group. In some embodiments, the azide, azido or azidomethyl group in the linker can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems and kits comprising a plurality of multivalent molecules comprising a mixture (sub-populations) of two or more different types of multivalent molecules. In some embodiments, the plurality of multivalent molecules can have at least a first multivalent molecule (a first subpopulation) in the plurality. In some embodiments, the at least the first subpopulation can comprise a core bound to at least one nucleotide-arm having a first type of reactive group in the linker. In some embodiments, the plurality of multivalent molecules can have at least a second multivalent molecule (a second subpopulation) comprises a core bound to at least one nucleotide-arm having a second type of reactive group in the linker. In some cases, the first reactive group in the first type of linker in the first sub-population differ from the second reactive group in the second type of linker in the second sub-population. In some embodiments, the first multivalent molecule can comprise a core bound to 2-5 biotinylated nucleotide arms, where the biotinylated-arms can have a first type of reactive group in the linker. In some embodiments, the second multivalent molecule can comprise a core bound to 2-5 biotinylated nucleotide arms, where the biotinylated-arms can have a second type of reactive group in the linker, where the first reactive group differs from the second reactive group.

In some embodiments, the first and second reactive can be selected, in any combination, from a group consisting of alkyl, alkenyl, alkynyl, allyl, aryl, benzyl, azide, amine, amide, keto, isocyanate, phosphate, thio, disulfide, carbonate, urea, and silyl group. In some embodiments, the individual multivalent molecules can comprise a first or second reactive group that can be reactive with a chemical agent. For example, the reactive groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The reactive groups aryl and benzyl can be reactive with H2 Pd/C. The reactive groups amine, amide, keto, isocyanate, phosphate, thio, disulfide can be reactive with phosphine or with a thiol group including beta-mercaptoethanol or dithiothritol (DTT). The reactive group carbonate can be reactive with potassium carbonate (K$_2$CO$_3$) in MeOH, with triethylamine in pyridine, or with Zn in acetic acid (AcOH). The reactive groups urea and silyl can be reactive with tetrabutylammonium fluoride, pyridine-HF, with ammonium fluoride, or with triethylamine trihydrofluoride. In some embodiments, the first or second reactive can be selected, in any combination, from a group consisting of an azide, azido or azidomethyl group. In some embodiments, the azide, azido or azidomethyl reactive group in the linker can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a plurality (e.g., a population) of multivalent molecules, wherein individual multivalent molecules in the plurality can comprise a core bound to at least one nucleotide-arm, wherein all of the nucleotide arms that are bound to a core can have a nucleotide unit having the same sugar 3'OH group. In some embodiments, individual multivalent molecules in the plurality can comprise a core bound to 2-5 nucleotide-arms. In some embodiments, individual multivalent molecules in the plurality can comprise a core bound to 2-5 biotinylated nucleotide-arms.

The present disclosure provides compositions, systems, methods, and kits comprising a plurality (e.g., a population) of multivalent molecules, wherein individual multivalent molecules in the plurality can comprise a core bound to at least one nucleotide-arm, wherein all of the nucleotide arms that are bound to a core can have a nucleotide unit having the sugar 3'OH group substituted with the same 3' blocking group. In some embodiments, individual multivalent molecules in the plurality can comprise a core bound to 2-5 nucleotide-arms. In some embodiments, individual multivalent molecules in the plurality can comprise a core bound to 2-5 biotinylated nucleotide-arms. In some embodiments, the sugar 3'blocking group can comprise alkyl, alkenyl, alkynyl, allyl, aryl, benzyl, azide, amine, amide, keto, isocyanate, phosphate, thio, disulfide, carbonate, urea, or silyl group. In some embodiments, the individual multivalent molecules can comprise a 3' blocking group that can be reactive with a chemical agent. For example, the 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The 3' blocking groups aryl and benzyl can be reactive with H2 Pd/C. The 3' blocking groups amine, amide, keto, isocyanate, phosphate, thio, disulfide can be reactive with phosphine or with a thiol group including beta-mercaptoethanol or dithiothritol (DTT). The 3' blocking group carbonate can be reactive with potassium carbonate (K$_2$CO$_3$) in MeOH, with triethylamine in pyridine, or with Zn in acetic acid (AcOH). The 3' blocking groups urea and silyl can be reactive with tetrabutylammonium fluoride, pyridine-HF, with ammonium fluoride, or with triethylamine trihydrofluoride. In some embodiments, the 3' blocking group can comprise a 3'-O-alkyl hydroxylamino group, a 3'-phosphorothioate group, a 3'-O-malonyl group, or a 3'-O-benzyl group. In some embodiments, the 3' blocking group can comprise an azide, azido or azidomethyl group. In some embodiments, the azide, azido or azidomethyl 3' blocking group can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a plurality of multivalent molecules comprising a mixture (sub-populations) of two or more different types of multivalent molecules. In some embodiments, the plurality of multivalent molecules can comprise at least a first multivalent molecule in the plurality can comprise a core bound to at least one nucleotide-arm having a first nucleotide unit with a first type of sugar 3'OH blocking group (chain terminating moiety). In some embodiments, the plurality of multivalent molecules can comprise at least a second multivalent molecule comprises a core bound to at least one nucleotide-arm having a second nucleotide unit having a second type of sugar 3' blocking group (chain terminating moiety). In some embodiments, the plurality can comprise the first multivalent molecule and the second multivalent molecule. In some cases, the first 3' blocking group can differ from the second 3' blocking group. In some embodiments, the first multivalent molecule can comprise a core bound to 2-5 biotinylated nucleotide arms, where the biotinylated-arms can have a first type of 3' blocking group. In some embodiments, the second multivalent molecule can comprise a core bound to 2-5 biotinylated nucleotide arms, where the biotinylated-arms can have a second type of 3' blocking group, where the first 3' blocking group differs from the second 3' blocking group.

In some embodiments, the first and second 3' blocking group can be selected, in any combination, from a group consisting of alkyl, alkenyl, alkynyl, allyl, aryl, benzyl, azide, amine, amide, keto, isocyanate, phosphate, thio, disulfide, carbonate, urea, and silyl group. In some embodiments, the individual multivalent molecules can comprise a first or second 3' blocking group that can be reactive with a chemical agent. For example, the 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The 3' blocking groups aryl and benzyl can be reactive with H2 Pd/C. The 3' blocking groups amine, amide, keto, isocyanate, phosphate, thio, disulfide can be reactive with phosphine or with a thiol group including beta-mercaptoethanol or dithiothritol (DTT). The 3' blocking group carbonate can be reactive with potassium carbonate (K$_2$CO$_3$) in MeOH, with triethylamine in pyridine, or with Zn in acetic acid (AcOH). The 3' blocking groups urea and silyl can be reactive with tetrabutylammonium fluoride, pyridine-HF, with ammonium fluoride, or with triethylamine trihydrofluoride. In some embodiments, the first and second 3' blocking group can be selected, in any combination, from a group consisting of a 3'-O-alkyl hydroxylamino group, a 3'-phosphorothioate group, a 3'-O-malonyl group, and a 3'-O-benzyl group. In some embodiments, the first or second 3' blocking group can be selected, in any combination, from a group consisting of an azide, azido or azidomethyl group. In some embodiments, the azide, azido or azidomethyl 3' blocking group is reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a plurality of multivalent molecules comprising a mixture (sub-populations) of two or more different types of multivalent molecules. In some embodiments, the plurality of multivalent molecules can comprise at least a first multivalent molecule in the plurality can comprise a core bound to at least one nucleotide-arm having a first nucleotide unit with a sugar 3' OH group. In some embodiments, the plurality of multivalent molecules can comprise at least a second multivalent molecule comprising a core bound to at least one nucleotide-arm having a second nucleotide unit having a first type of sugar 3' blocking group. In some embodiments, the plurality of multivalent molecules can comprise the first multivalent molecule and the second multivalent molecule. In some embodiments, the first multivalent molecule can comprise a core bound to 2-5 biotinylated nucleotide arms, where the biotinylated-arms can have a sugar 3' OH group. In some embodiments, the second multivalent molecule can comprise a core bound to 2-5 biotinylated nucleotide arms, where the biotinylated-arms can have a first type of 3' blocking group.

In some embodiments, the first 3' blocking group can be selected, in any combination, from a group consisting of alkyl, alkenyl, alkynyl, allyl, aryl, benzyl, azide, amine, amide, keto, isocyanate, phosphate, thio, disulfide, carbonate, urea, and silyl group. In some embodiments, the individual multivalent molecules can comprise a first 3' blocking group that can bereactive with a chemical agent. For example, the 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The 3' blocking groups aryl and benzyl can be reactive with H2 Pd/C. The 3' blocking groups amine, amide, keto, isocyanate, phosphate, thio, disulfide can be reactive with phosphine or with a thiol group including beta-mercaptoethanol or dithiothritol (DTT). The 3' blocking group carbonate can be reactive with potassium carbonate (K$_2$CO$_3$) in MeOH, with triethylamine in pyridine, or with Zn in acetic acid (AcOH). The 3' blocking groups urea and silyl can be reactive with tetrabutylammonium fluoride, pyridine-HF, with ammonium fluoride, or with triethylamine trihydrofluoride. In some embodiments, the first 3' blocking group can be selected, in any combination, from a group consisting of a 3'-O-alkyl hydroxylamino group, a 3'-phosphorothioate group, a 3'-O-malonyl group, and a 3'-O-benzyl group. In some embodiments, the first 3' blocking group can be selected, in any combination, from a group consisting of an azide, azido or azidomethyl group. In some embodiments, the azide, azido or azidomethyl 3' blocking group can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

The present disclosure provides compositions, systems, methods, and kits comprising a plurality of multivalent molecules comprising a mixture (sub-populations) of three or more different types of multivalent molecules. In some embodiments, the plurality of multivalent molecules can comprise at least a first multivalent molecule. In some embodiments, the at least the first multivalent molecule can comprise a core bound to at least one nucleotide-arm having a first nucleotide unit with a sugar 3' OH group. In some embodiments, the plurality of multivalent molecules can comprise at least a second multivalent molecule. In some embodiments, the at least the second multivalent molecule can comprise a core bound to at least one nucleotide-arm having a second nucleotide unit having a first type of sugar 3' blocking group. In some embodiments, the plurality of multivalent molecules can comprise at least a third multivalent molecule. In some embodiments, the at least third multivalent molecule can comprise a core bound to at least one nucleotide-arm having a third nucleotide unit having a second type of sugar 3' blocking group. In some cases, the first and second 3' blocking groups are different. In some embodiments, the first multivalent molecule can comprise a core bound to 2-5 biotinylated nucleotide arms, where the biotinylated-arms can have a sugar 3' OH group. In some embodiments, the second multivalent molecule can comprise a core bound to 2-5 biotinylated nucleotide arms, where the biotinylated-arms can have a first type of 3' blocking group. In some embodiments, the third multivalent molecule can comprise a core bound to 2-5 biotinylated nucleotide arms, where the biotinylated-arms can have a second type of 3' blocking group.

In some embodiments, the first and second 3' blocking groups can be selected, in any combination, from a group consisting of alkyl, alkenyl, alkynyl, allyl, aryl, benzyl, azide, amine, amide, keto, isocyanate, phosphate, thio, disulfide, carbonate, urea, and silyl group. In some embodiments, the individual multivalent molecules can comprise a first or second 3' blocking group that can be reactive with a chemical agent. For example, the 3' blocking groups alkyl, alkenyl, alkynyl and allyl can be reactive with tetrakis(triphenylphosphine)palladium(0) (Pd(PPh$_3$)$_4$) with piperidine, or with 2,3-Dichloro-5,6-dicyano-1,4-benzo-quinone (DDQ). The 3' blocking groups aryl and benzyl can be reactive with H2 Pd/C. The 3' blocking groups amine, amide, keto, isocyanate, phosphate, thio, disulfide can be reactive with phosphine or with a thiol group including beta-mercaptoethanol or dithiothritol (DTT). The 3' blocking group carbonate can be reactive with potassium carbonate (K$_2$CO$_3$) in MeOH, with triethylamine in pyridine, or with Zn in acetic acid (AcOH). The 3' blocking groups urea and silyl can be reactive with tetrabutylammonium fluoride, pyridine-HF, with ammonium fluoride, or with triethylamine trihydrofluoride. In some embodiments, the first and second 3' blocking groups can be selected, in any combination, from a group consisting of a 3'-O-alkyl hydroxylamino group, a 3'-phosphorothioate group, a 3'-O-malonyl group, and a 3'-O-benzyl group. In some embodiments, the first and second 3' blocking groups can be selected, in any combination, from a group consisting of an azide, azido or azidomethyl group. In some embodiments, the azide, azido or azidomethyl 3' blocking group can be reactive with a chemical agent. In some embodiments, the chemical agent can comprise a phosphine compound. In some embodiments, the phosphine compound can comprise a derivatized tri-alkyl phosphine moiety or a derivatized tri-aryl phosphine moiety. In some embodiments, the phosphine compound can comprise Tris(2-carboxyethyl)phosphine (TCEP), bis-sulfo triphenyl phosphine (BS-TPP) or Tri(hydroxyproyl)phosphine (THPP).

Wedge-Block Assembly

Described herein are various embodiments of an optical system. In some embodiments, the optical system is an optical system configured for the fluorescent readout of samples. In some embodiments, the optical system comprises a wedge block assembly 4916 as shown in FIGS. 49A-49B. In certain aspects, the wedge block assembly 4916 comprises a first wedge piece 4907 and a second wedge piece 4906. In some embodiments, the wedge block assembly 4916 comprises an adjustable optical path length. In some embodiments, the first wedge piece 4907 is configured to move relative to the second wedge piece 4906. In some embodiments, the relative movement of the first wedge piece 4907 to the second wedge piece 4906 causes the optical path length of the wedge block assembly 4916 to change due to the change in the physical thickness wedge block assembly 4916 as shown in FIGS. 49A to 49B. In some embodiments, the wedge block assembly 4916 comprises a gap separating the first wedge piece 4907 from the second wedge piece 4906. In some embodiments, the gap maintains a constant distance, regardless of the relative position of the first wedge piece 4907 and the second wedge piece 4906. In some embodiments, the first wedge piece 4907 and the second wedge piece 4906 are comprised of fused silica. In some embodiments, the first wedge piece 4907 and the second wedge piece 4906 are comprised of fused silica having a refractive index of 1.5. In some embodiments, the first wedge piece 4907 is coupled to a piezo drive 4908. In some embodiments, the optical system comprises a housing. In some embodiments, the wedge block assembly 4916 and piezo drive 4908 are contained within the housing. In some embodiments, the wedge block assembly 4916 and piezo drive 4908 comprise a wedge block-piezo drive assembly. In some embodiments, the second wedge piece 4906 of the wedge block assembly 4916 contacts the housing. In some embodiments, the second wedge piece 4906 of the wedge block assembly 4916 contacts the flow cell 4905.

In some embodiments, the position of the first wedge piece 4907 relative to the second wedge piece 4906 determines the position of the focal plane along the optical axis 4913 (e.g., z axis). In some embodiments, the top wedge piece 4907 is aligned with the bottom wedge piece 4906, as illustrated in FIG. 49A. In such an embodiment, the physical distance of the wedge block assembly 4916 results in the focal plane aligning with the back-interior surface. In this case, the sample sites 4902 of the back-interior surface are in focus. In some embodiments, the piezo drive 4908 moves the top wedge piece 4907 to a position relative to the bottom wedge piece 4906, as illustrated in FIG. 49B, such that the physical thickness of the wedge block 4916 within the optical path is greater than in the aligned state illustrated in FIG. 49A. In such an embodiment, the focal plane is shifted to align with the front-interior surface. In this case, the sample sites 4902 of the front-interior surface are in focus.

Stage

Figure 50:
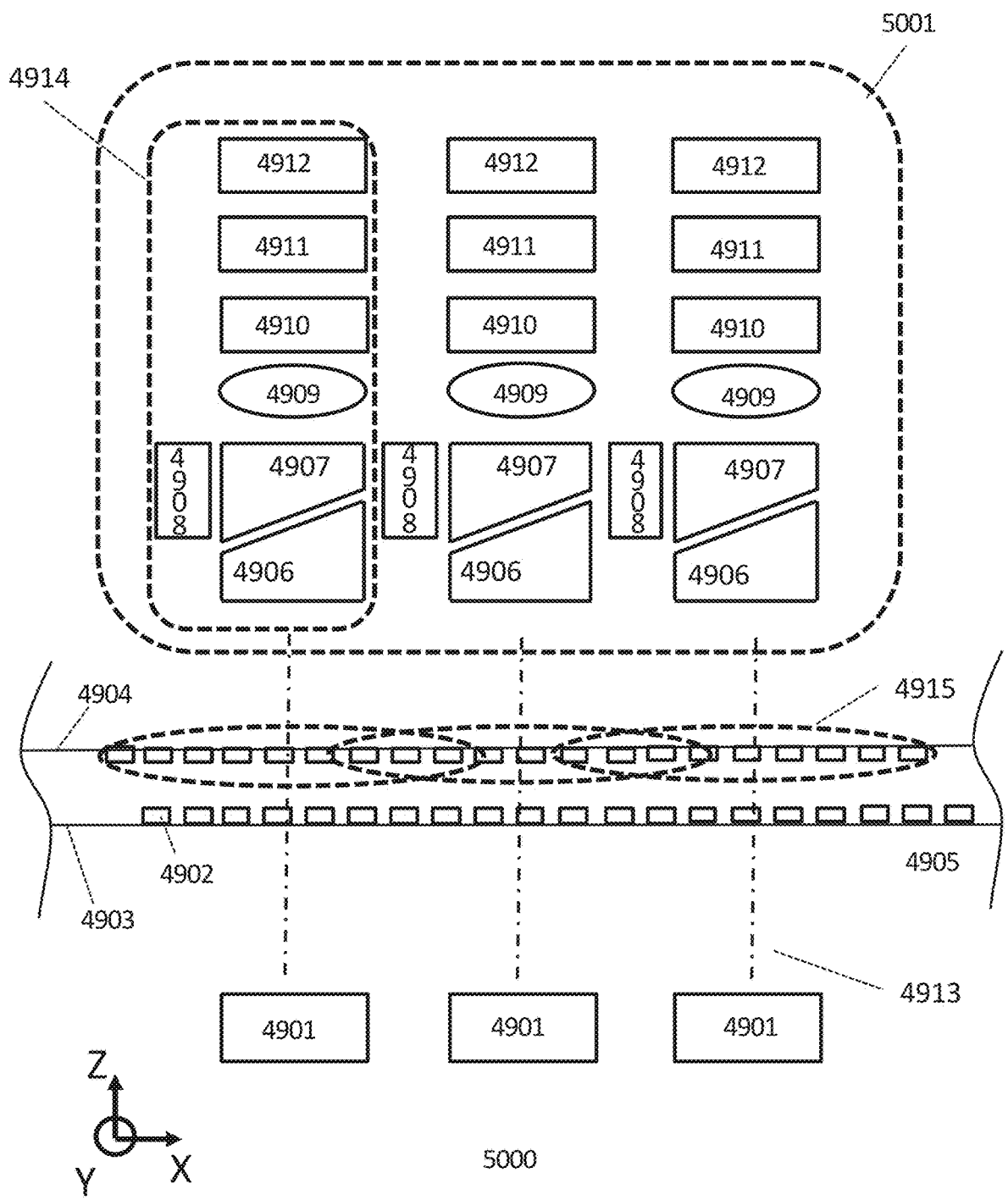
FIG. 50 provides a non-limiting cut-away illustration of an optical system configured for imaging a large area surface. The optical system comprises multiple optical subsystems, wherein the optimized FOV of each subsystem overlaps the FOV of each neighboring optical subsystem, thereby providing a large area FOV.
Figure 52:
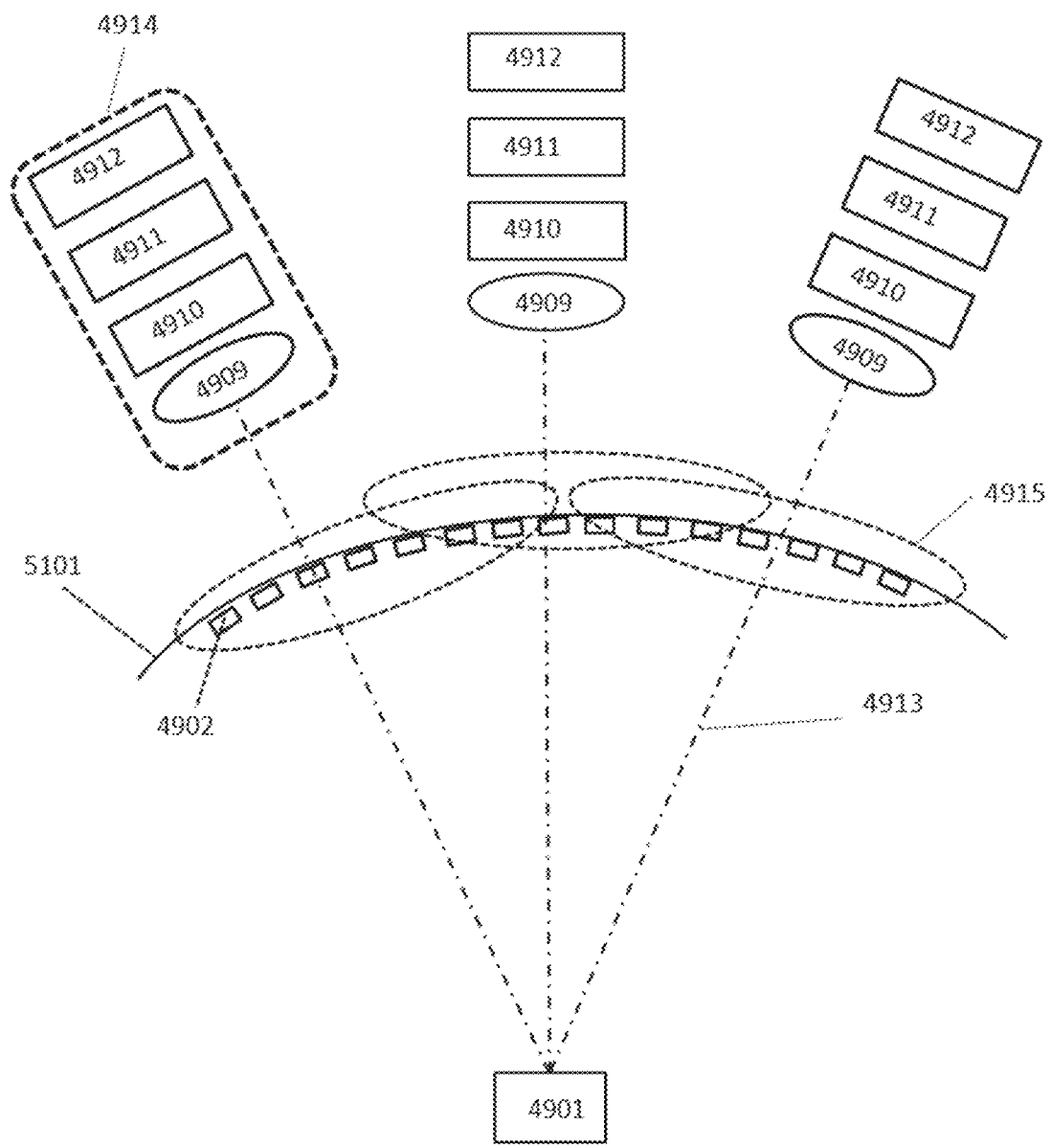
FIG. 52 provides a non-limiting cut-away illustration of an optical system configured for imaging a curved, large area surface. The optical system comprises multiple optical subsystems wherein each system is placed approximately orthogonal to the surface and wherein the FOV of each subsystem overlaps the FOV of each neighboring optical subsystem, thereby providing a system for imaging curved, large area surfaces.
Figure 53A:
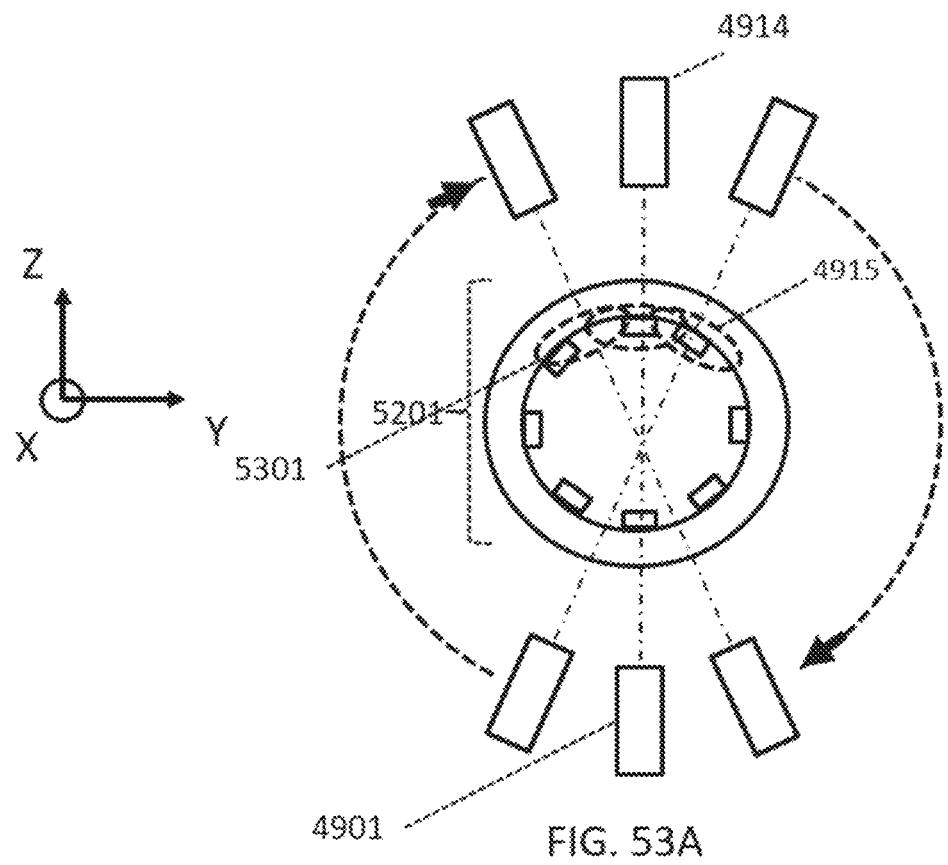
FIGS. 53A-53B provides a non-limiting cut away illustration of an optical system configured to image a capillary flow cell. In this example, the optical system configured to image curved, large area surfaces is rotated about the x-axis and translated along the x-axis to obtain images of the entire interior surface of the capillary flow cell.
Figure 53B:
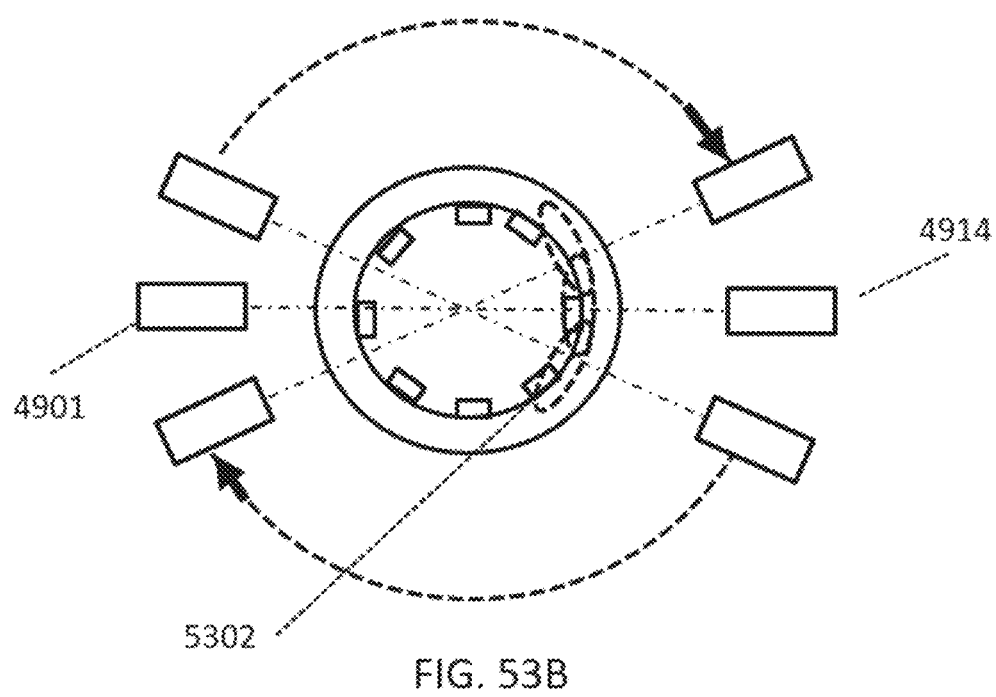

Described here are various embodiments of an optical system comprising a stage. The stage may be a tilt stage. The stage may be a tip-tilt stage. The stage may allow for rotation. The stage may be configured to translate in three different axes, simultaneously, wherein all axes are perpendicular to each other. The stage may be configured to translate in three different axes, simultaneously, wherein all axes are perpendicular to each other. The stage may be configured to translate in, and rotate about, three different axes, simultaneously, wherein all axes are perpendicular to each other. The stage may translate the plurality of optical subsystems 5001 relative to the flow cell 4905 as shown in FIG. 50. The stage may translate the flow cell 4905 relative to the plurality of optical subsystems 5001 as shown in FIG. 50. The stage may translate a single optical subsystem 4914. The stage may rotate the plurality of optical subsystems 5001 about the x-axis of the capillary flow cell 5201 as shown in FIG. 53A-53B. The stage may translate the plurality of optical subsystems 5001 along the x-axis, coincident to the long axis of the capillary flow cell 5201 as shown in FIG. 52A-53B.

Pixel Shifter

Described herein are various embodiments of an optical system comprising a pixel shifter 4911. In some embodiments, the pixel shifter 4911 enables sub-pixel resolution imaging. In certain aspects, the resolution of the optical system may be increased by use of the pixel shifter 4911 without increasing the actual optical system resolution. In some embodiments, the pixel shifter 4911, effectively multiplies the resolution of the imaging sensor 4912. In some embodiments, a piezoelectric actuator is configured for defined lateral pixel shifts coincident to the image plane (e.g., in the x-y plane). In some embodiments, a piezoelectric actuator is configured for pixel shifting in the optical axis 4913 (e.g., z-axis or z-axis containing planes). In some embodiments, tilt stage is configured for pixel shifts in X-Z or Y-Z or X-Y-Z. In some cases, the tilt stage is configured for pixel shifts in two dimensions. In some embodiments, the optical system comprising the pixel shifter is configured for imaging the ® sample objects. In some cases, the optical system comprising the pixel shifter is configured for imaging a 2D sample object.

In some embodiments, the 3D objects may comprise sample sites 4902. In some embodiments, sample sites 4902 are amplified nucleic acids. In some embodiments, a sample site may comprise a polony or multiple polonies. In some embodiments, a "polony" may refer to a polymermase colony. In some embodiments, a polony may refer to an isolated clonal amplification of a single nucleic acid. In some embodiments, the 3D object may comprise a non-biological material. In some embodiments, the 3D object may comprise an inorganic material. In some embodiments the 3D object may comprise a semiconductor. In some cases, a polony can be a nucleic acid library molecule which can be clonally amplified (e.g., in solution, on a support, etc.) to generate an amplicon. In some cases, the amplicon can serve as a template molecule for sequencing. A linear library molecule can be circularized to generate a circularized library molecule. In some cases, the circularized library molecule can be clonally amplified (e.g., in solution, on a support, etc.) to generate a concatemer. In some cases, the concatemer can serve as a nucleic acid template molecule. In some cases, the concatemer can be sequenced. In some cases, the concatemer can be a polony. In some cases, a polony comprises nucleotide strands.

The pixel-shifter 4911 may utilize polarization.

Autofocus Element

Described herein are various embodiments of an optical system comprising an autofocus element.

Figures 51A, 51B:
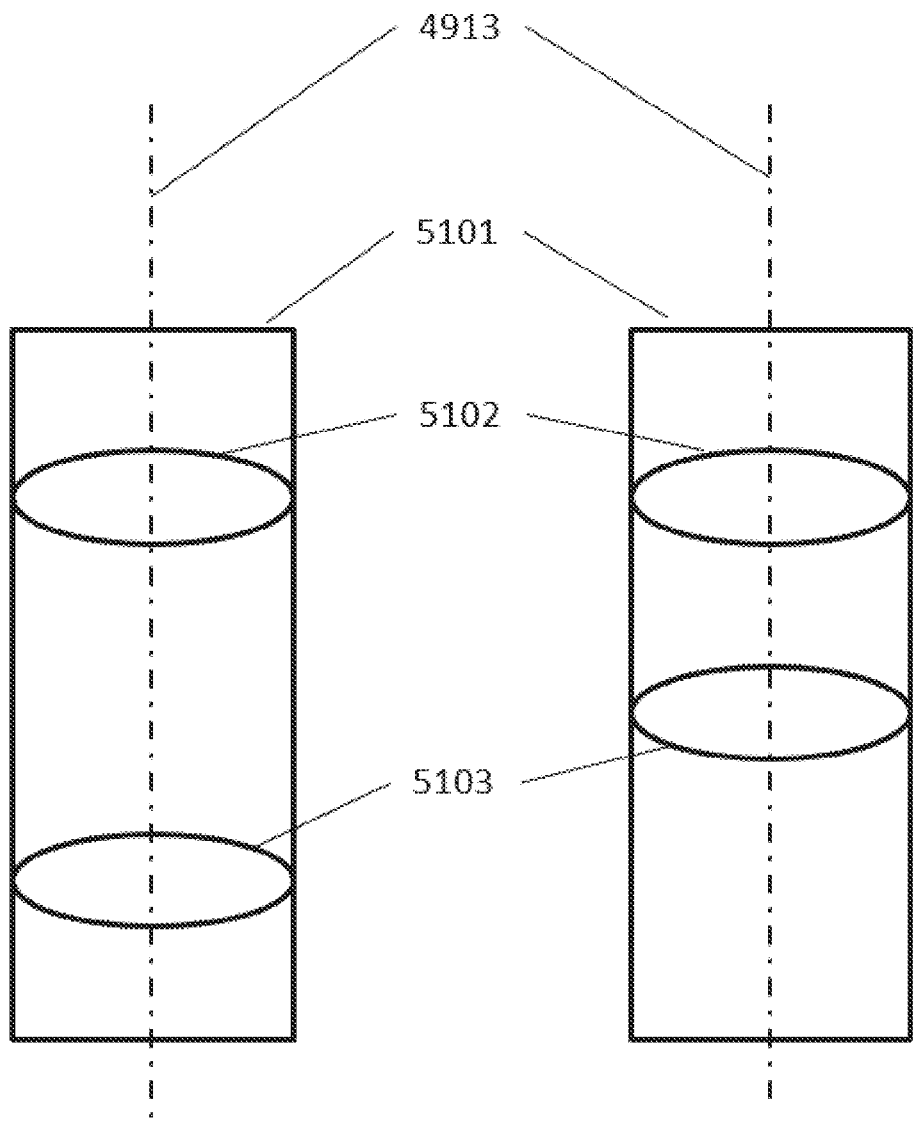
FIGS. 51A-51B provides a non-limiting cut-away illustration of a focusing lens assembly. The focusing lens assembly is configured to maintain a fixed position within the optical path (e.g. optical axis) and to allow for relative motion between at least a first lens and second lens contained within a lens housing of the focusing lens assembly.

FIGS. 51A-51B provides a non-limiting cut-away illustration of a focusing lens assembly. The focusing lens assembly is configured to maintain a fixed position within the optical pathway (e.g. optical axis) and to allow for relative motion between at least a first lens and second lens contained within a lens housing of the focusing lens assembly.

In some embodiments, the autofocus element is configured for initial focus. In some embodiments, the autofocus element is contained within a lens barrel. In some embodiments, the autofocus element is built into and/or integrated with the lens barrel. In some embodiments, the autofocus element is contained within the lens barrel of the lens assembly. In some embodiments, the autofocus element is configured to improve reliability, reduces mechanical footprint of the optical system. In some embodiments the autofocus element comprises the wedge block assembly, the piezo drive, the wedge block-piezo drive assembly, or a combination thereof.

Multiple Imaging Systems

Figure 38:
FIG. 38 illustrates visualization of cluster (e.g., polony) amplification in a capillary lumen.

In some embodiments, the optical system as seen in FIG. 50 comprises a plurality of optical subsystems 4914. In some embodiments, each optical subsystem 4914 of the plurality 5001 comprises an imaging sensor 4912, a pixel shifter 4911, a filter 4910, imaging optics 4909, a piezo driven— wedge block assembly, a light source 4901, or a combination thereof. In some embodiments, the imaging sensor 4912 is a cellphone-style camera. In some embodiments, the plurality of optical subsystems 5001 comprises an array of optical subsystems. In some embodiments, the array of optical subsystems may be configured for multiple focal depths, multiple wavelengths, or a combination thereof. In some embodiments, each optical subsystem 4914 of the plurality 5001 is configured for a focal depth, wherein the focal depths of at least two optical subsystems of the plurality are different. In some embodiments, each optical subsystem of the plurality is configured to detect a wavelength, wherein the wavelengths detected by at least two optical subsystems of the plurality are different. In some embodiments, an image sensor 4912 of each optical subsystem 4914 of the plurality 5001 comprise an array of image sensors 4912. In some embodiments, high resolution low-cost cameras are configured to provide imaging, with aberrations compensated by software. In some embodiments, the optical system comprises one optical subsystem 4914, wherein the optical subsystem 4914 comprises one optimal imaging volume as shown in FIGS. 49A-49B. In FIGS. 49A-49B the extent of the optimal imaging volume 4915 along the x axis is limited. Certain factors may affect the width of the optimal imaging volume in the xy plane (e.g., the focal plane). The xy plane, or focal plane, comprises a cross section of the optimal imaging volume and may comprise referred to as the area of illumination, area of acquisition, or a combination thereof. Surfaces comprising sample sites 4902 that extend beyond the optimal FOV are not optimally illuminated by the light source, not optimally captured by the imaging sensor, not optimally resolved by the optics, or a combination thereof. Such non-optimal regions of the surface exhibit non-uniform brightness and non-uniform resolution as may be observed in the edges and/or corners of the image in FIG. 38. In FIG. 38 the sample sites become dimmer and less resolved from the center to the edges and/or corners of the image. FIG. 50 illustrates an embodiment where the sample site 4902 covered surface extends beyond the optimal imaging volume 4915 of one optical subsystem 4916 and where overlapping optimal imaging volumes 4915 overlap to provide a composite optimal imaging volume.

In some embodiments, the optical system has an optimized FOV of 6 mm×6 mm. In some embodiments, the system has an optimized FOV of about 0.5 mm to about 9 mm. In some embodiments, the system has an optimized FOV of about 0.5 mm to about 1 mm, about 0.5 mm to about 3 mm, about 0.5 mm to about 6 mm, about 0.5 mm to about 9 mm, about 1 mm to about 3 mm, about 1 mm to about 6 mm, about 1 mm to about 9 mm, about 3 mm to about 6 mm, about 3 mm to about 9 mm, or about 6 mm to about 9 mm. In some embodiments, the system has an optimized FOV of about 0.5 mm, about 1 mm, about 3 mm, about 6 mm, or about 9 mm. In some embodiments, the system has an optimized FOV of at least about 0.5 mm, about 1 mm, about 3 mm, or about 6 mm. In some embodiments, the system has an optimized FOV of at most about 1 mm, about 3 mm, about 6 mm, or about 9 mm.

In some embodiments, the optical system has an optimized area of illumination, of 6 mm×6 mm. In some embodiments, the system has an optimized area of illumination, of about 0.5 mm to about 9 mm. In some embodiments, the system has an optimized area of illumination, of about 0.5 mm to about 1 mm, about 0.5 mm to about 3 mm, about 0.5 mm to about 6 mm, about 0.5 mm to about 9 mm, about 1 mm to about 3 mm, about 1 mm to about 6 mm, about 1 mm to about 9 mm, about 3 mm to about 6 mm, about 3 mm to about 9 mm, or about 6 mm to about 9 mm. In some embodiments, the system has an optimized area of illumination, of about 0.5 mm, about 1 mm, about 3 mm, about 6 mm, or about 9 mm. In some embodiments, the system has an optimized area of illumination, of at least about 0.5 mm, about 1 mm, about 3 mm, or about 6 mm. In some embodiments, the system has an optimized area of illumination, of at most about 1 mm, about 3 mm, about 6 mm, or about 9 mm.

In some embodiments, the optical system is configured for rapid imaging of the surface. In some embodiments, the optical system is configured for rapid imaging of the surface of the flow cell. In some embodiments, the optical system is configured for rapid imaging of a first surface and a second surface of the flow cell. In some embodiments, the entire active area (e.g., region of interest, ROI) of the surface 4903 or 4904 of the flow cell 4905 is imaged in 5 imaging steps. In some embodiments, the active area (e.g., region of interest) of the surface 4903 or 4904 is imaged in about 1 imaging step to about 10 imaging steps. In some embodiments, the active area (e.g., region of interest) of the surface is imaged in about 1 imaging step to about 2 imaging steps, about 1 imaging step to about 3 imaging steps, about 1 imaging step to about 4 imaging steps, about 1 imaging step to about 5 imaging steps, about 1 imaging step to about 6 imaging steps, about 1 imaging step to about 10 imaging steps, about 2 imaging steps to about 3 imaging steps, about 2 imaging steps to about 4 imaging steps, about 2 imaging steps to about 5 imaging steps, about 2 imaging steps to about 6 imaging steps, about 2 imaging steps to about 10 imaging steps, about 3 imaging steps to about 4 imaging steps, about 3 imaging steps to about 5 imaging steps, about 3 imaging steps to about 6 imaging steps, about 3 imaging steps to about 10 imaging steps, about 4 imaging steps to about 5 imaging steps, about 4 imaging steps to about 6 imaging steps, about 4 imaging steps to about 10 imaging steps, about 5 imaging steps to about 6 imaging steps, about 5 imaging steps to about 10 imaging steps, or about 6 imaging steps to about 10 imaging steps. In some embodiments, the active area (e.g., region of interest) of the surface is imaged in about 1 imaging step, about 2 imaging steps, about 3 imaging steps, about 4 imaging steps, about 5 imaging steps, about 6 imaging steps, or about 10 imaging steps. In some embodiments, the active area (e.g., region of interest) of the surface is imaged in at least about 1 imaging step, about 2 imaging steps, about 3 imaging steps, about 4 imaging steps, about 5 imaging steps, or about 6 imaging steps. In some embodiments, the active area (e.g., region of interest) of the surface is imaged in at most about 2 imaging steps, about 3 imaging steps, about 4 imaging steps, about 5 imaging steps, about 6 imaging steps, or about 10 imaging steps.

Optical System Method

Described herein are various methods for imaging a biological polymer, comprising: providing an optical system comprising: a plurality of optical subsystems, each optical subsystems of the plurality comprising: a light source configured to separately emit a first wavelength and a second wavelength, wherein said first wavelength is different from said second wavelength; a multiband filter configured to reject each of said first wavelength and said second wavelength; an imaging sensor configured to image one or more biological polymers disposed in an optical path between each light source and each imaging sensor; and bringing said one or more biological polymers into contact with a plurality of fluorophores under conditions sufficient to cause a first biological polymer of said one or more biological polymers to bind with a first fluorophore of said plurality of fluorophores and a second biological polymer of said one or more biological polymers to bind with a second fluorophore of said plurality of fluorophores, wherein said first fluorophore is different than said second fluorophore; imaging said first biological polymer with each imaging sensor, wherein said imaging comprises (i) illuminating said first biological polymer with said first wavelength, thereby exciting said first fluorophore, and (ii) acquiring a first image; and imaging said second biological polymer with each imaging sensor, wherein said imaging comprises (i) illuminating said second biological polymer with said second wavelength, thereby exciting said second fluorophore, and (ii) acquiring a second image, and wherein said one or more biological polymers are disposed on a curved surface, and wherein the optical axis of each optical subsystem of said plurality is orthogonal to said curved surface. In some embodiments, the method further comprises imaging a third biological polymer of said one or more biological polymers comprising (i) illuminating said third biological polymer with a third wavelength, exciting a third fluorophore of said plurality of fluorophores, and (ii) acquiring a third image. In some embodiments, the method further comprises combining said first image and said second image into a composite image. In some embodiments, the method further comprises identifying a unit of said first biological polymer bound by said first fluorophore comprising analyzing a first region of interest (ROI) of said composite image to detect a first signal emitted by said first fluorophore. In some embodiments, the method further comprises identifying a unit of said second biological polymer bound by said second fluorophore comprising analyzing a second ROI of said composite image to detect a second signal emitted by said second fluorophore. In some embodiments, the method further comprises identifying a first unit of said first biological polymer bound by said first fluorophore comprising analyzing a first ROI of said composite image to detect a first signal emitted by said first fluorophore; and identifying a second unit of said second biological polymer bound by said second fluorophore comprising analyzing a second ROI of said composite image to detect a second signal emitted by said first fluorophore. In some embodiments, the method further comprises combining said first image, said second image, and said third image into a composite image. In some embodiments, the method further comprises identifying a third unit of said third biological polymer bound by said third fluorophore comprising analyzing a third ROI of said composite image to detect a third signal emitted by said third fluorophore. In some embodiments, the method further comprises: identifying a first unit of said first biological polymer bound by said first fluorophore comprising analyzing a first region of interest (ROI) of said composite image to detect a first signal emitted by said first fluorophore; identifying a second unit of said second biological polymer bound by said second fluorophore comprising analyzing a second ROI of said composite image to detect a second signal emitted by said first fluorophore; identifying a third unit of said third biological polymer bound by said third fluorophore comprising analyzing a third ROI of said composite image to detect a third signal emitted by said third fluorophore; and identifying a third unit of said third biological polymer bound by said third fluorophore comprising analyzing a third ROI of said composite image to detect a third signal emitted by said third fluorophore.

Described herein are various methods of using the optical system as described herein for super resolution imaging. In some embodiments, the method comprises providing a surface further comprising at least one sample site comprising clonally-amplified, sample nucleic acid molecules immobilized to a plurality of attached oligonucleotide molecules, wherein said plurality of immobilized clonally amplified sample nucleic acid molecules are present at distance less than $\lambda/(2*NA)$, wherein $\lambda$ is the center wavelength of an excitation energy source and NA is the numerical aperture of an imaging system; applying a stochastic photo-switching chemistry to said clonally amplified sample nucleic acid molecules at the same time to cause said plurality of clonally amplified sample nucleic acid molecules to fluoresce in on and off events in up to four different colors by stochastic photo-switching; and detecting said on and off events in a color channel for each color in real-time as the on and off events are occurring for said plurality of clonally amplified sample nucleic acid molecules to determine an identify of a nucleotide of said clonally amplified sample nucleic acid molecule. The stochastic photo-switching may comprise use of dark states in an emissive fluorophore to randomly switch the fluorophores on and off. This may enable imaging individual fluorophores, which can then be localized to provide a super resolution image. In some cases, the stochastic photo-switching can comprise use of stimulated emission depletion (STED), stochastic optical reconstruction (STORM), or the like.

In some cases, the super resolution imaging may comprise imaging at a resolution of at most about 1,000, 950, 900, 850, 800, 750, 700, 650, 600, 550, 500, 450, 400, 350, 300, 250, 200, 150, 100, 50, or less nanometers. In some cases, the resolution of the super resolution imaging may be controlled by the numerical aperture of the system doing the imaging. In some cases, the resolution of the optical system may be sub-pixel resolution. Sub-pixel resolution may be imaging at a resolution higher than the resolution achievable given the size of the pixels used in imaging (e.g., by computer processing the image, etc.).

Light Source

In some embodiments, the light source 4901 as shown in FIGS. 49A-53B is a solid-state light source. In some embodiments, the solid-state light source is a light emitting diode (LED). In some embodiments, the light source 4901 is configured to emit a plurality of wavelengths. In some embodiments, the light source comprises a plurality of light sources. In some embodiments, each light source of the plurality is configured to emit a different wavelength of light. In some embodiments, the light source 4901 is configured to emit: a first wavelength of light at a first time; a second wavelength of light at a second time and a third wavelength of light at a third time. In some embodiments, the first wavelength of light at a first time, the second wavelength of light at the second time and the third wavelength of light at the third time are emitted in a sequence. In some embodiments, the plurality of light sources is configured to be delivered for timed pulse sequences in sequential colors. In some embodiments, the plurality of optical subsystems 5001 are configured to increase speed of detection. In some embodiments, the solid-state light source is not a laser. For some applications, the light source comprises a filter to narrow the spectrum of the light emitted by the light source. In some embodiments, the light source is referred to as the excitation source. In some embodiments, the light emitted by the light source is referred to as excitation light.

Light Delivery Component

In some embodiments, the optical system comprises a light delivery component. In some embodiments, the light delivery component is a waveguide. In some embodiments, the light delivery component is a light pipe 4702 as shown in FIG. 47. In some embodiments, the light delivery component is a fiber optic. In some embodiments, the light source delivers light to the flow cell by the light delivery component. In some embodiments, the light source delivers light to the flow cell by a light pipe. In some embodiments, the light delivery component is positioned between the light source 4901 and the flow cell 4905. In some embodiments, a second light delivery component is positioned between the flow cell and the image sensor.

Imaging Channels

The optical system as described herein may be configured for imaging one or more fluorophores. In some embodiments, the optical system is configured to distinctly image two, three, or more different fluorophores. In certain aspects, the optical system comprises one or more imaging channels. In some embodiments, a first imaging channel of the one or more imaging channels is configured to image a first fluorophore of the one or more fluorophores. In some embodiments, a second imaging channel of the one or more imaging channels is configured to image a second fluorophore of the one or more fluorophores. In some embodiments, a third imaging channel of the one or more imaging channels is configured to image a third fluorophore of the one or more fluorophores. In some embodiments, an imaging channel comprises at least one of a light source 4901, a filter 4910, an imaging sensor 4912, or a combination thereof.

Heater

Typically, assays require heating. In some instances, the flow cell 4905 further comprises a heater. In some embodiments, the heater is integrated with the flow cell. In some embodiments, the heater is integrated with a dual surface imaging flow cell 4905. In some embodiments, the heater is integrated with the capillary flow cell 5201. In some embodiments, the integrated heater is a transparent heater block integrated heater. In some embodiments, the heater is an IR heater.

In some embodiments, the transparent heater conforms to the surface of the flow cell. In some embodiments, the transparent heater conforms to and fully surrounds a flow cell with a non-rectangular cross section. In some embodiments, a transparent heater conforms to and fully surrounds a flow cell with a round cross section. In some embodiments, a transparent heater conforms to and fully surrounds a capillary flow cell 5201. In some embodiments, the transparent heater is transparent in all image channels of the one or more image channels of the optical system.

Flow Cell Shape

Typically, flow cell shape is limited by standard microscopy systems that require flat surfaces that can reside within the focal depth of the FOV of the microscope imaging system. Such limitations limit flow cell design at its interfaces, create gradients of pressure, temperature, viscosity, or a combination thereof. Such gradients may cause a propensity to form bubbles, differential reaction kinetics across the cell, or a combination thereof. Additionally, typical solutions to such problems require flow cell designs that may not be effectively imaged by standard microscopy systems. For optimal imaging performance of non-flat flow cell shapes infrared (IR) heating, conformable and transparent heaters, or a combination thereof, may be utilized to reduce gradients in binding, reaction kinetics or other assays factors. In some embodiments, the surface 5101 may be non-flat, or curved as illustrated in FIG. 52. The surface 5101 can include a concave (curving away from the optical system) or a convex curve (e.g., curving toward the optical system).

In some embodiments, the flow cell may comprise a capillary flow cell 5201 as illustrated in FIGS. 53A-53B and FIGS. 54A-54B. In FIGS. 53A-53B, the sample is flown through the capillary flow cell 5201, wherein the flow direction is along the x-axis. FIG. 53A illustrates a non-limiting example of a cross section of a capillary flow cell 5201, wherein sample sites 4902 are disposed on the interior surface of the capillary flow cell 5201. In some embodiments, a light source 4901 may be directed toward the capillary flow cell, wherein the light is focused, creating an optimized imaging volume 4915 containing sample sites 4902 disposed on the far side of the interior surface of the capillary flow cell. In some embodiments, a plurality of optical subsystems 5001, each comprising a light source 4901 are distributed around the capillary flow cell, such that the optimal imaging volumes 4915 overlap, enabling optimized imaging of sample sites disposed on an area larger than an area corresponding to one optimal imaging volume 4915. In some embodiments, the optical subsystems may be rotated about the x-axis of the capillary flow cell 5201 as illustrated in FIGS. 53A-53B, thus enabling the overlapping optimized imaging volumes 4915 to be scanned across the entire inside surface of the capillary flow cell 5201. Alternatively, the capillary flow cell 5201 may be rotated about the x-axis and the optical subsystems 4914 may be held in constant position while imaging.

Figure 54A:
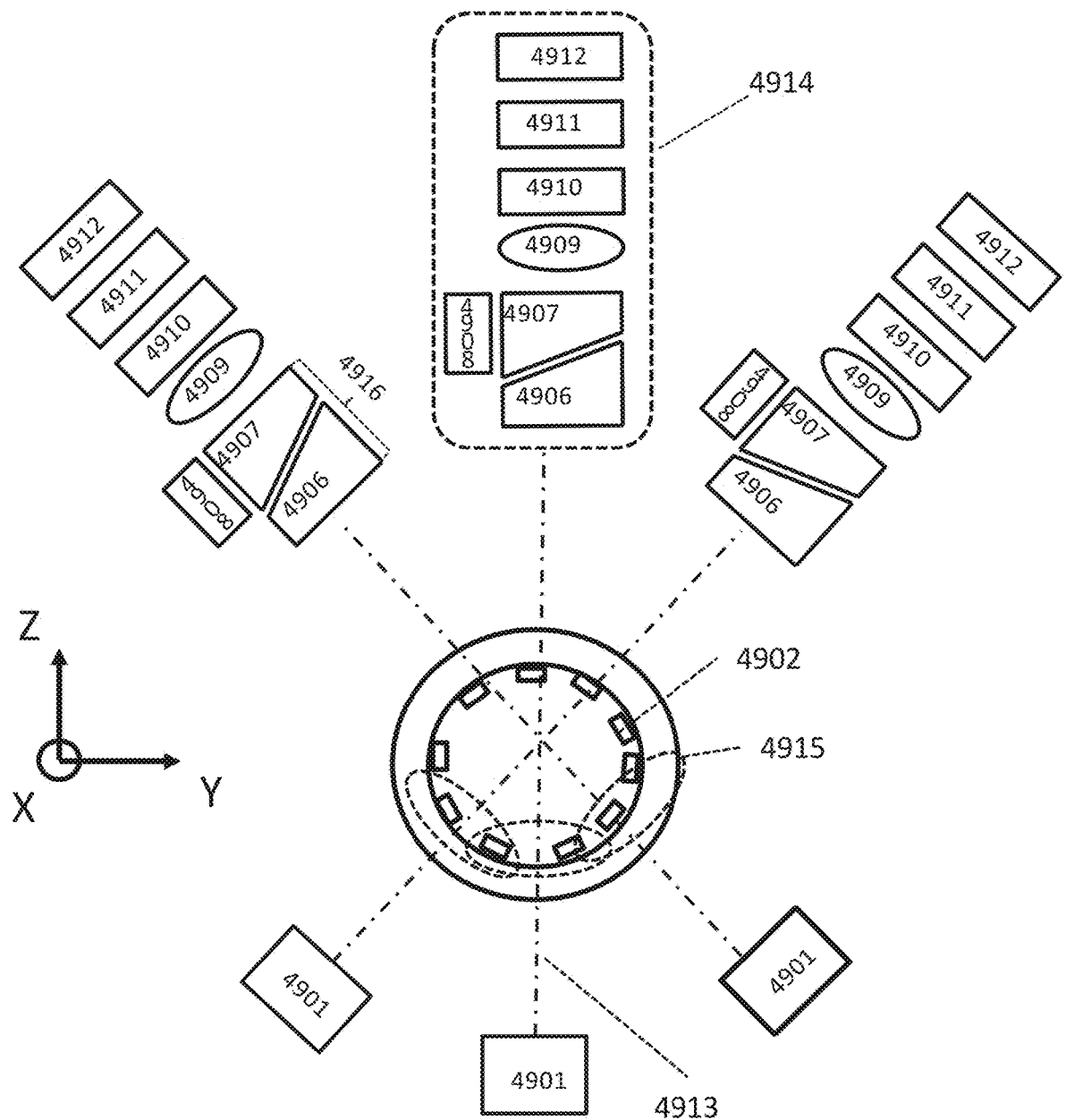
FIGS. 54A-54B provides a non-limiting cut away illustration of an optical system configured to image a capillary flow cell without the need for a stage to rotate the optical system about the x-axis. The optical system as shown comprises a piezo driven wedge block for rapid focusing.
Figure 54B:
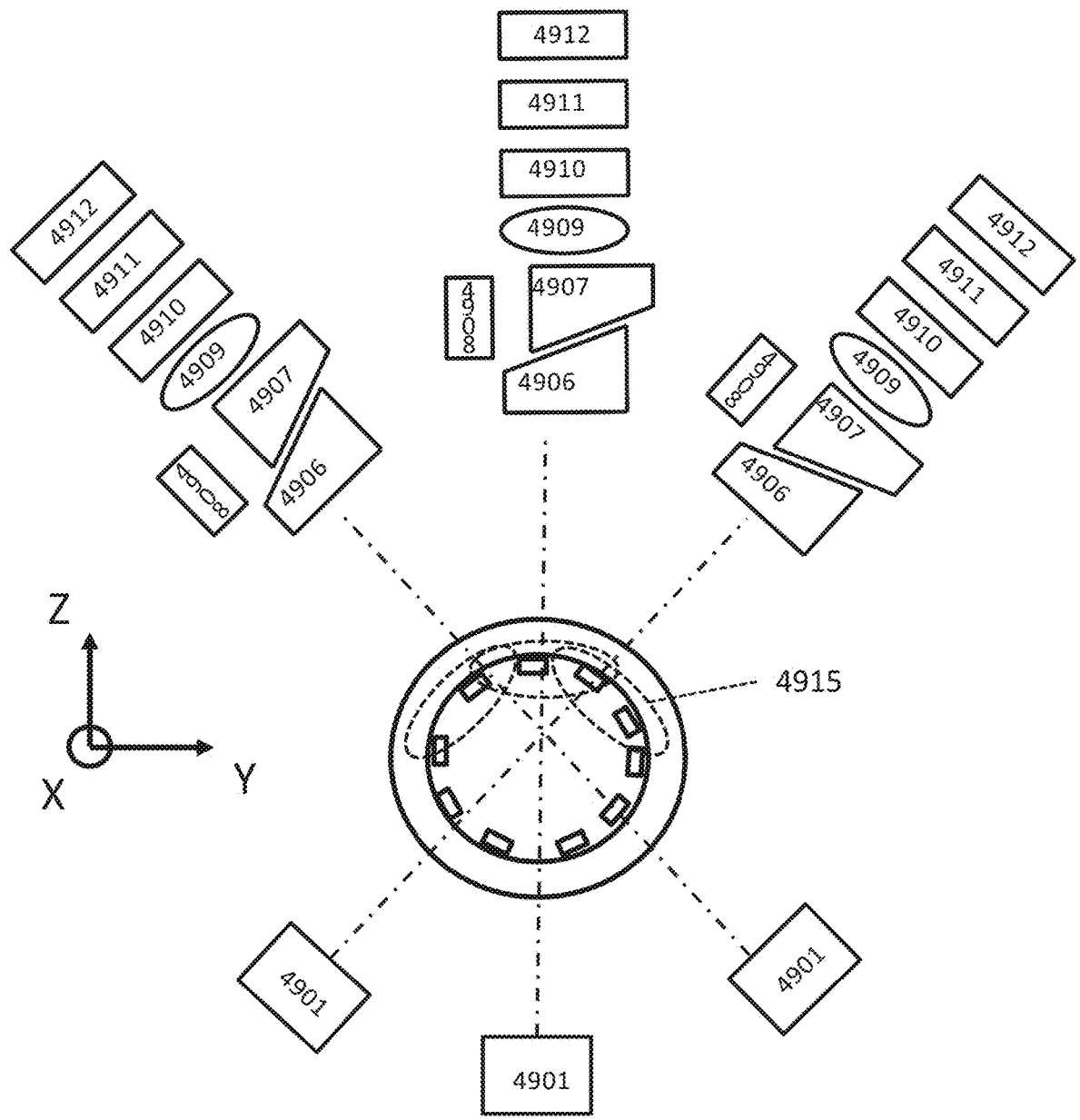

Another way to acquire images of sample sites 4902 disposed across the entire interior surface of the capillary flow cell 5201, with uniform image quality, is by incorporating a wedge block 4916 into each of the optical subsystems 4914, as illustrated in FIGS. 53A-53B. In certain aspects, multiple optical subsystems 4914 are disposed about the x-axis of the capillary flow cell. In such cases, the multiple optical subsystems 4914 may image a portion of interior surface of the capillary flow cell, larger than one optimal imaging volume 4915 of one optical subsystem 4914 via overlapping optimal imaging volumes 4915 as described herein. In certain aspects, as described herein, curved surfaces can also be properly imaged by placing the optical subsystems 4914 such that their corresponding optical axes 4913 are at least approximately orthogonal to the region of the surface to be imaged. In such cases, the plurality of optical subsystems 5001 can provide optimized images of curved, large area surfaces. In some embodiments, the wedge block assembly 4916 of each optical subsystem 4914 is adjusted to provide focus on half of the interior surface, closest to the light sources as illustrated in FIG. 54A. Alternatively, the wedge block assembly 4916 may be adjusted to focus on sample sites 4902 disposed on the opposite side of the interior surface of the capillary flow cell 5201 as illustrated in FIG. 54B. In such cases, there is no need to rotate the capillary flow cell 5201 or plurality of optical subsystems 5001 since refocusing and acquiring images, using the multiple optimal imaging volumes 4914 provides imaging coverage of the entire interior surface of the capillary flow cell. In some embodiments, the capillary flow cell is translated along the x-axis in order to provide images along the entire length of the capillary flow cell 5201. In some embodiments, the large area surface may comprise an area of at least about 5 square millimeters.

Aberration Correction

In some embodiments, aberration correction methods may be applied to allow for imaging through air bubbles that may appear within the flow cell. In some embodiments, non-flat flow cell surfaces enable right angle or off-axis illumination. In some embodiments, the optical system described herein may comprise magnetic positioning of various elements. In some embodiments, the optical system may be configured to image flow cells with round edges.

Integrated Field Flattener

Typically, the area of illumination and/or FOV of a standard fluorescence microscope imaging system is limited to the size of the single lens system and/or single imaging sensor present. Typically, the ability of a system to systematically capture brightness across the FOV may be referred to as field uniformity of the system. Non-uniformity of brightness and resolution across the FOV is, in some cases, observed from the center to the edge of the FOV. In some instances, illumination non-uniformity is caused by non-uniform field curvature effects of a lens the system, usually these are single lens systems. Systems, devices and methods designed to improve field uniformity are sometimes referred to as field flatteners or field flattening, respectively. The optical system described herein can comprise a field flattener. In some instances, the field flattener comprises a plurality of optical subsystems 5001 designed to provide overlapping coverage of the 'active area of the flow cell surface. Where one image of an individual optical subsystem 4914 of the plurality 5001 begins to become non-uniform (e.g., increased blurring, loss of intensity at corners and edges) the optimal imaging volume 4915 of a second optical subsystem 4914 may overlap. In some instances, the optimal imaging volume 4915 of a first optical subsystem overlaps with a second optical subsystem and a third optical subsystem.

In some embodiments, the surface 5101 of the flow cell comprising sample sites 4902 is not flat as shown in FIG. 52. In certain aspects, each optical subsystem 4914 of the plurality 5001 is positioned to match the contour of the active area of the flow cell as shown in FIG. 52

Optical System—Super-Resolution

For imaging very small sample site features present in high surface densities, such as nucleic acid polonies (e.g., spots comprising amplified target nucleic acids) super resolution imaging techniques as described herein may be used. In some embodiments, stochastic photo-switching techniques as described herein may be used to improve image resolution. Alternatively, structured illumination techniques as described herein may be used to improve image resolution in the optical system. In some cases, the super resolution imaging technique can comprise structured illumination.

In some instances, improvements in imaging performance, e.g., for dual-side (flow cell) imaging applications comprising the use of thick flow cell walls (e.g., wall (or coverslip) thickness>700 µm) and fluid channels (e.g., fluid channel height or thickness of 50-200 µm) may be achieved using novel objective lens designs that correct for optical aberration introduced by imaging surfaces on the opposite side of thick coverslips and/or fluid channels from the objective.

In some instances, improvements in imaging performance, e.g., for dual-side (flow cell) imaging applications comprising the use of thick flow cell walls (e.g., wall (or coverslip) thickness>700 µm) and fluid channels (e.g., fluid channel height or thickness of 50-200 µm) may be achieved even when using commercially-available, off-the-shelf objectives by using a novel tube lens design that, unlike the tube lens in a conventional microscope that simply forms an image at the intermediate image plane, corrects for the optical aberrations induced by the thick flow cell walls and/or intervening fluid layer in combination with the objective.

In some instances, improvements in imaging performance, e.g., for multichannel (e.g., two-color or four-color) imaging applications, may be achieved by using multiple tube lenses, one for each imaging channel, where each tube lens design has been optimized for the specific wavelength range used in that imaging channel.

In some instances, improvements in imaging performance, e.g., for dual-side (flow cell) imaging applications, may be achieved by using an electro-optical phase plate in combination with an objective lens to compensate for the optical aberrations induced by the layer of fluid separating the upper (near) and lower (far) interior surfaces of a flow cell. In some instances, this design approach may also compensate for vibrations introduced by, e.g., a motion-actuated compensator that is moved in or out of the optical path depending on which surface of the flow cell is being imaged.

Various multichannel fluorescence imaging module designs are disclosed that may include illumination and imaging optical paths comprising folded optical paths (e.g., comprising one or more beam splitters or beam combiners, such as dichroic beam splitters or combiners) that direct an excitation light beam to an objective lens, and direct emission light transmitted through the objective lens to a plurality of detection channels. Some particularly advantageous features of the fluorescence imaging modules described herein include specification of dichroic filter incidence angles that result in sharper and/or more uniform transitions between passband and stopband wavelength regions of the dichroic filters. Such filters may be included within the folded optics and may comprise dichroic beam splitters or combiners. Further advantageous features of the disclosed imaging optics designs may include the position and orientation of one or more excitation light sources and one or more detection optical paths with respect to the objective lens and to a dichroic filter that receives the excitation beam. The excitation beam may also be linearly-polarized and the orientation of the linear polarization may be such that s-polarized light is incident on the dichroic reflective surface of the dichroic filter. Such features may potentially improve excitation beam filtering and/or reduce wavefront error introduced into the emission light beam due to surface deformation of dichroic filters. The fluorescence imaging modules described herein may or may not include any of these features and may or may not include any of these advantages.

Also described herein are devices and systems configured to analyze large numbers of different nucleic acid sequences by imaging, e.g., arrays of immobilized nucleic acid molecules or amplified nucleic acid clusters formed on flow cell surfaces. The devices and systems described herein can also be useful in, e.g., performing sequencing for comparative genomics, tracking gene expression, performing micro RNA sequence analysis, epigenomics, aptamer and phage display library characterization, and for performing other sequencing applications. The devices and systems disclosed herein comprise various combinations of optical, mechanical, fluidic, thermal, electrical, and computing devices/aspects. The advantages conferred by the disclosed flow cell devices, cartridges, and systems include, but are not limited to: (i) reduced device and system manufacturing complexity and cost, (ii) significantly lower consumable costs (e.g., as compared to those for currently available nucleic acid sequencing systems), (iii) compatibility with typical flow cell surface functionalization methods, (iv) flexible flow control when combined with microfluidic components, e.g., syringe pumps and diaphragm valves, etc., and (v) flexible system throughput.

Disclosed herein are capillary flow-cell devices and capillary flow cell cartridges that are constructed from off-the-shelf, disposable, single lumen (e.g., single fluid flow channel) or multi-lumen capillaries that may also comprise fluidic adaptors, cartridge chassis, one or more integrated fluid flow control components, or any combination thereof. Also disclosed herein are capillary flow cell-based systems that may comprise one or more capillary flow cell devices (or microfluidic chips), one or more capillary flow cell cartridges (or microfluidic cartridges), fluid flow controller modules, temperature control modules, imaging modules, or any combination thereof.

The design features of some disclosed capillary flow cell devices, cartridges, and systems include, but are not limited to, (i) unitary flow channel construction, (ii) sealed, reliable, and repetitive switching between reagent flows that can be implemented with a simple load/unload mechanism such that fluidic interfaces between the system and capillaries are reliably sealed, thereby facilitating capillary replacement and system reuse, and enabling precise control of reaction conditions such as reagent concentration, pH, and temperature, (iii) replaceable single fluid flow channel devices or capillary flow cell cartridges comprising multiple flow channels that can be used interchangeably to provide flexible system throughput, and (iv) compatibility with a wide variety of detection methods such as fluorescence imaging.

Although the disclosed capillary flow cell devices and systems, capillary flow cell cartridges, capillary flow cell-based systems, microfluidic devices and cartridges, and microfluidic chip-based systems, are described primarily in the context of their use for nucleic acid sequencing applications, various aspects of the disclosed devices and systems may be applied not only to nucleic acid sequencing but also to any other type of chemical analysis, biochemical analysis, nucleic acid analysis, cell analysis, or tissue analysis application. It shall be understood that different aspects of the disclosed methods, devices, and systems can be appreciated individually, collectively, or in combination with each other. Although discussed herein primarily in the context of fluorescence imaging (including, e.g., fluorescence microscopy imaging, fluorescence confocal imaging, two-photon fluorescence, and the like), it will be understood by those of skill in the art that many of the disclosed optical design approaches and features are applicable to other imaging modes, e.g., bright-field imaging, dark-field imaging, phase contrast imaging, and the like.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term "about" a number refers to that number plus or minus 10% of that number. The term "about" when used in the context of a range refers to that range minus 10% of its lowest value and plus 10% of its greatest value.

As used herein, the phrases "imaging module", "imaging unit", "imaging system", "optical imaging module", "optical imaging unit", and "optical imaging system" are used interchangeably, and may comprise components or sub-systems of a larger system that may also include, e.g., fluidics modules, temperature control modules, translation stages, robotic fluid dispensing and/or microplate handling, processor or computers, instrument control software, data analysis and display software, etc.

As used herein, the term "detection channel" refers to an optical path (and/or the optical components therein) within an optical system that is configured to deliver an optical signal arising from a sample to a detector. In some instances, a detection channel may be configured for performing spectroscopic measurements, e.g., monitoring a fluorescence signal or other optical signal using a detector such as a photomultiplier. In some instances, a "detection channel" may be an "imaging channel", e.g., an optical path (and/or the optical components therein) within an optical system that is configured to capture and deliver an image to an image sensor.

As used herein, a "detectable label" may refer to any of a variety of detectable labels or tags known to those of skill in the art. Examples include, but are not limited to, chromophores, fluorophores, quantum dots, upconverting phosphors, luminescent or chemiluminescent molecules, radioisotopes, magnetic nanoparticles, mass tags, and the like. In some instances, a preferred label may comprise a fluorophore. Fluorescent moieties which may serve as fluorescent labels or fluorophores include, but are not limited to, fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, Lissamine® rhodamine, Texas Red®, rhodamine B, rhodamine 6G, rhodamine 10, NHS-rhodamine, TMR-iodoacetamide, Lissamine® rhodamine B sulfonyl chloride, Lissamine® rhodamine B sulfonyl hydrazine, Texas Red® sulfonyl chloride, Texas Red® hydrazide, coumarin and coumarin derivatives such as AMCA, AMCA-NHS, AMCA-sulfo-NHS, AMCA-HPDP, DCIA, AMCE-hydrazide, BODIPY® and derivatives such as BODIPY® FL C3-SE, BODIPY® 530/550 C3, BODIPY® 530/550 C3-SE, BODIPY® 530/550 C3 hydrazide, BODIPY® 493/503 C3 hydrazide, BODIPY® FL C3 hydrazide, BODIPY® FL IA, BODIPY® 530/551 IA, Br-BODIPY® 493/503, Cascade Blue® and derivatives such as Cascade Blue® acetyl azide, Cascade Blue® cadaverine, Cascade Blue® ethylenediamine, Cascade Blue® hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy® 3, Cy®5, lanthanide chelates and derivatives such as BCPDA, TBP, TMT, BHHCT, BCOT, Europium chelates, Terbium chelates, Alexa Fluor® dyes, DyLight® dyes, Atto dyes, LightCycler® Red dyes, CAL Flour® dyes, JOE® and derivatives thereof, Oregon Green® dyes, WellRED dyes, IRD dyes, phycoerythrin and phycobilin dyes, Malachite green, stilbene, DEG dyes, NR dyes, near-infrared dyes and others such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and comprise two indolenin, benzo-indolium, pyridium, thiozolium, and/or quinolinium groups separated by a polymethine bridge between two nitrogen atoms. Commercially available cyanine fluorophores include, for example, Cy®3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy®5 (which may comprise 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy®7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy®2 which is an oxazole derivative rather than indolenin, and the benzo-derivatized Cy®3.5, Cy®5.5 and Cy®7.5 are exceptions to this rule.

As used herein, the term "excitation wavelength" refers to the wavelength of light used to excite a fluorescent indicator (e.g., a fluorophore or dye molecule) and generate fluorescence. Although the excitation wavelength is typically specified as a single wavelength, e.g., 620 nm, it will be understood by those of skill in the art that this specification refers to a wavelength range or excitation filter bandpass that is centered on the specified wavelength. For example, in some instances, light of the specified excitation wavelength comprises light of the specified wavelength 2 nm, ±5 nm, ±10 nm, ±20 nm, ±40 nm, ±80 nm, or more. In some instances, the excitation wavelength used may or may not coincide with the absorption peak maximum of the fluorescent indicator.

As used herein, the term "emission wavelength" refers to the wavelength of light emitted by a fluorescent indicator (e.g., a fluorophore or dye molecule) upon excitation by light of an appropriate wavelength. Although the emission wavelength is typically specified as a single wavelength, e.g., 670 nm, it will be understood by those of skill in the art that this specification refers to a wavelength range or emission filter bandpass that is centered on the specified wavelength. In some instances, light of the specified emission wavelength comprises light of the specified wavelength ±2 nm, ±5 nm, ±10 nm, ±20 nm, ±40 nm, ±80 nm, or more. In some instances, the emission wavelength used may or may not coincide with the emission peak maximum of the fluorescent indicator.

As used herein, fluorescence is 'specific' if it arises from fluorophores that are annealed or otherwise tethered to the surface, such as fluorescently labeled nucleic acid sequences having a region of reverse complementarity to a corresponding segment of an oligonucleotide adapter on the surface and annealed to said corresponding segment. This fluorescence is contrasted with fluorescence arising from fluorophores not tethered to the surface through such an annealing process, or in some cases to background fluorescence of the surface.

As used herein, a "nucleic acid" (also referred to as a "nucleic acid molecule", a "polynucleotide", "oligonucleotide", ribonucleic acid (RNA), or deoxyribonucleic acid (DNA)) is a linear polymer of two or more nucleotides joined by covalent internucleosidic linkages, or variants or functional fragments thereof. In naturally occurring examples of nucleic acids, the internucleoside linkage is typically a phosphodiester bond. However, other examples optionally comprise other internucleoside linkages, such as phosphorothiolate linkages and may or may not comprise a phosphate group. Nucleic acids include double- and single-stranded DNA, as well as double- and single-stranded RNA, DNA/RNA hybrids, peptide-nucleic acids (PNAs), hybrids between PNAs and DNA or RNA, and may also include other types of nucleic acid modifications.

The term "nucleotide" as used herein refers to a molecule comprising an aromatic base, a sugar, and a phosphate. A "nucleotide moiety" as referred to here can be a nucleotide or a nucleoside that is modified, such as for example, a nucleotide moiety conjugated to a polymer core or linker (e.g., in a nucleotide conjugate, a polymer-nucleotide conjugate, or a particle-nucleotide conjugate). Canonical or non-canonical nucleotides are consistent with use of the term. The phosphate in some instances comprises a mono-phosphate, diphosphate, or triphosphate, or corresponding phosphate analog. In some embodiments, "nucleotide" refers to a nucleotide, nucleoside, or analog thereof. In some cases, the nucleotide is an N- or C-glycoside of a purine or pyrimidine base (e.g., a deoxyribonucleoside containing 2-deoxy-D-ribose or ribonucleoside containing D-ribose). Non-limiting examples of other nucleotide analogs include, but are not limited to, phosphorothioates, phosphoramidates, methyl phosphonates, chiral-methyl phosphonates, 2-O-methyl ribonucleotides, and the like.

The term "non-flat" as it relates to a surface described herein refers to a flatness of a surface that deviates from precise flatness of at least one dimension, which may be measured using flatness gauge or optical methods, such as reflectance or interferometry. In some cases, a non-flat surface can comprise one or more curved portions. In some cases, the curvature of the curved portions can be perceivable by the naked eye. In some cases, a non-flat surface can be a curved surface. For example, a curved surface described elsewhere herein may be a non-flat surface. A non-flat substrate can comprise features that deviate from flatness on a length scale comparable to the surface. For example, a non-flat surface can comprise one or more features that are at least about 1, 5, 10, 15, 20, 25, 30, 25, 40, 45, 50, 55, 60, or more percent of a dimension (e.g., length, width, thickness, etc.) of the non-flat surface. In some cases, a non-flat surface can comprise one or more features that are at most about 60, 55, 50, 45, 40, 35, 30, 25, 20, 15, 10, 5, 1, or less percent of a dimension of the non-flat surface. Examples of feature include, but are not limited to, curves (e.g., single curves, waveforms, etc.), triangular features, square features, other geometric features, or the like, or any combination thereof. A non-flat surface can have a change in the height of the surface (e.g., a deviation from flatness) of at least about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 300, 400, 500, or more percent of the length or width of the surface. For example, a semicircular portion of a cylinder of width of 5 millimeters can have a deviation from flatness of 100 percent. A non-flat surface can have a change in the height of the surface (e.g., a deviation from flatness) of at most about 500, 400, 300, 200, 175, 150, 125, 100, 95, 90, 85, 80, 75, 70, 65, 60, 55, 50, 45, 40, 35, 30, 25, 20, 15, 10, 9, 8, 7, 6, 5, 4, 3, 2, 1, or less percent of the length or width of the surface.

The term, "flat" or "flatness" as it relates to a surface described herein may refer to an average surface flatness or a deviation from planarity, which can be measured using mechanical gauges, or optical methods such as reflectance or interferometry. In some cases, a deviation from planarity may comprise an acute angle between tangential directions measured at two different points on the surface, e.g., separated by at least 1 angstrom, 1 nm, 1 um, 1 mm, 1 cm, or more, on the non-flat surface can be greater than 0.1 degrees, greater than 0.5 degrees, greater than 1 degree, greater than 2 degrees, greater than 5 degrees, greater than 10 degrees, 15 degrees, 20 degrees, or more, or within a range defined by any two of the foregoing.

In some cases, flatness may refer to a property of an object (e.g., a substrate) related to the degree to which the height of a surface of the object varies over the area of the object. For example, a flat object can have no or substantially no change in the height of a surface of the object over the length scale of the object. In another example, a non-flat object can have a change in the height of the surface of the object on the length scale of the object. In some cases, a non-flat surface can have a monotonically changing height (e.g., the height of the object changes in only one direction). For example, a semi-cylindrical object can have a monotonically changing height. In some cases, a non-flat surface can have a non-monotonically changing height. For example, a surface with a sinusoidal height profile can have a non-monotonically changing height.

The term "support" or "sample support structure" are used interchangeable herein to include any solid or semisolid article on which reagents such as nucleic acids can be immobilized. Nucleic acids may be immobilized on the solid support by any method including but not limited to physical adsorption, by ionic or covalent bond formation, or combinations thereof. A solid support may include a polymeric, a glass, or a metallic material. Non-limiting examples of solid supports include a membrane, a planar surface, a microtiter plate, a bead, a filter, a test strip, a slide, a cover slip, and a test tube, any solid phase material upon which an oligomer is synthesized, attached, ligated or otherwise immobilized. A support may comprise a "resin", "phase", "surface," "substrate," "coating," and/or "support." A support may comprise organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to comprise one or more wells, depressions or other containers, vessels, features or locations. A plurality of supports may be configured in an array at various locations. A support may be addressable (e.g., for robotic delivery of reagents), or by detection mechanisms including scanning by laser illumination and confocal or deflective light gathering. An amplification support (e.g., a bead) can be placed within or on another support (e.g., within a well of a second support). The support may be a flow cell, such as a nucleic acid sequencing flow cell. In some embodiments, the support may have a surface that is hydrophilic due to the polymeric material of the support.

Fluorescence imaging viewed as an information pipeline: A useful abstraction of the role that fluorescence imaging systems plays in typical genomic assay techniques (including nucleic acid sequencing applications) is as an information pipeline, where the photon signal enters at one end of the pipeline, e.g., the objective lens used for imaging, and location specific information regarding the fluorescence signal emerges at the other end of the pipeline, e.g., at the position of the image sensor. When more information is pumped through this pipeline, some content, inevitably, will be lost during this transfer process and never recovered. An example of this case is when too many labeled molecules (or clonally-amplified clusters of molecules) are present within a small region of a substrate surface to be clearly resolved in the image; at the position of the image sensor, it becomes difficult to differentiate photon signals arising from adjacent clusters of molecules, thus increasing the probability of attributing the signal to the wrong cluster and leading to detection errors. In some cases, the clusters are polonies.

Design of optical imaging modules: The goal of designing an optical imaging module is thus to maximize the flow of information content through this detection pipeline and to minimize detection errors. Several key design elements need to be addressed in the design process, including:

1) Matching the physical feature density on the substrate surface to be imaged with the overall image quality of the optical imaging system and the pixel sampling frequency of the image sensor used. A mismatch of these parameters may result in loss of information or sometimes even the generation of false information, e.g., spatial aliasing may arise when pixel sampling frequency is lower than twice the optical resolution limit.
2) Matching the size of the area to be imaged with the overall image quality of the optical imaging system and focus quality across the entire field-of-view.
3) Matching the optical collection efficiency, modulation transfer function, and image sensor performance characteristics of the optical system design with the fluorescence photon flux expected for the input excitation photon flux, dye efficiency (related to dye extinction coefficient and fluorescence quantum yield), while accounting for background signal and system noise characteristics.
4) Maximizing the separation of spectral content to reduce cross talk between fluorescence imaging channels.
5) Effective synchronization of image acquisition steps with repositioning of the sample or optics between image capture of different fields-of-view to minimize the down time (or maximize the duty cycle) of the imaging system and thus maximize the overall throughput of the image capture process.

This disclosure describes a systematic way to address each of the design elements outlined above and to create component level specifications for the imaging system.

Improved optical resolution and image quality to improve or maximize information transfer and throughput: One non-limiting design practice may be to start with the optical resolution required to distinguish two adjacent features as specified in terms of a number, X, of line pairs per mm (lp/mm) and translate it to a corresponding numerical aperture (NA) requirement. The numerical aperture requirement can then be used to assess the resulting impact on modulation transfer function and image contrast.

The standard modulation transfer function (MTF) describes the spatial frequency response for image contrast (modulation) transferred through an optical system; image contrast decreases as a function of spatial frequency and increases with increasing NA. This function limits the contrast/modulation that can be achieved for a given NA. Furthermore, wave front error can negatively impact the MTF, thus making it desirable to improve or optimize the optical system design using the true system MTF instead of that predicted by diffraction-limited optics. Note that, as used herein, MTF will refer to the total system MTF (including the complete optical path from coverslip to image sensor) although design practice may primarily consider the MTF of the objective lens.

In genomic testing applications, where the target to be imaged is an array of high density "spots" on a surface (either randomly distributed or patterned), one can determine the minimum modulation transfer value required by downstream analysis to resolve two adjacent spots and discriminate between four possible states (e.g., ON-OFF, ON-ON, OFF-ON and OFF-OFF). For example, assume that the spots are small enough to be approximated as point sources of light. Assuming that the detection task is to determine if the two adjacent spots separated by a distance, d, are ON or OFF (in other words, bright or dark), and that the contrast-to-noise ratio (CNR) for the fluorescence signals arising from the spots at the sample plane (or object plane) is $C_{sample}$, then under ideal conditions the CNR of the readout signal for the two adjacent spots at the image sensor plane, $C_{image}$, can be closely approximated as $C_{image} = C_{sample} * MTF(1/d)$, where $MTF(1/d)$ is the MTF value at spatial frequency=$(1/d)$.

In a typical design, the value of C may be at least 4 so that a simple threshold method can be used to avoid misclassification of fluorescence signals. Assuming a Gaussian distribution of fluorescence signal intensities around a mean value, at $C_{image}>4$, the expected error in correctly classifying fluorescence signals (e.g., as being ON or OFF) is <0.035%. The use of proprietary high CNR sequencing and surface chemistry, such as that described in U.S. patent application Ser. No. 16/363,842, allows one to achieve sample plane CNR ($C_{sample}$) values for clusters of clonally-amplified, labeled oligonucleotide molecules tethered to a substrate surface of greater than 12 (or even much higher) when measured for a sparse field (e.g., at a low surface density of clusters or spots) where the MTF has a value of close to 100%. Assuming a sample plane CNR value of $C_{sample}>12$ and targeting a classification error rate of <0.1% (thus, $C_{image}>4$), in some implementations the minimum value for $M(1/d)$ can be determined as $M(1/d)=4/12 \sim 33\%$. Thus, a modulation transfer function threshold of at least 33% may be used to retain the information content of the transferred image.

Design practice can relate the minimum separation distance of two features or spots, d, to the optical resolution requirement (specified as noted above in terms of X (lp/mm)) as $d=(1\ mm)/X$, e.g., d is the minimum separation distance between two features or spots which can be fully resolved by the optical system. In some designs disclosed herein, where the objective of the design analysis is to increase or maximize relevant information transfer, this design criterion can be relaxed to $d=(1\ mm)/X/A$, where $2>A>1$. For the same optical resolution of X lp/mm, the value of d, the minimum resolvable spot separation distance at the sample plane, is reduced, thereby enabling the use of higher feature densities.

Design practice determines the minimum spatial sampling frequency at the sample plane using the Nyquist criteria, where spatial sampling frequency $S \geq 2*X$ (and where X is the optical resolution of the imaging system specified in terms of X lp/mm as noted above). When the system spatial sampling frequency is close to the Nyquist criteria, as is often the case, imaging system resolution of greater than S results in aliasing as the higher frequency information resolved by the optical system cannot be sufficiently sampled by the image sensor.

In the some of the designs disclosed herein, an oversampling scheme based on the relationship $S=B*Y$ (where $B \geq 2$ and Y is the true optical system MTF limit) may be used to further improve the information transfer capacity of the imaging system. As indicated above, X (lp/mm) corresponds to a practical, non-zero (>33%) minimum modulation transfer value, whereas Y (lp/mm) is the limit of optical resolution so modulation at Y(lp/mm) is 0. Thus, in the disclosed designs, Y (lp/mm) may advantageously be significantly greater than X. For values of $B \geq 2$, the disclosed designs are oversampling for the sample object frequency X, e.g., $S \geq B*Y > 2*X$.

The above relationship can be used to determine the system magnification and may provide an upper bound for image sensor pixel size. The choice of image sensor pixel size is matched to the system optical quality as well to the spatial sampling frequency required to reduce aliasing. The lower bound of image sensor pixel size can be determined based on photon throughput, as relative noise contributions increase with smaller pixels.

Other design approaches are, however, also possible. For example, reducing the NA to less than 0.6 (e.g., 0.5 or less,) may provide increased depth of field. Such increased depth of field may enable dual surface imagining wherein two surfaces at different depths can be imaged at the same time with or without refocusing. As discussed above, reducing NA may reduce optical resolution. In some implementations, use of higher excitation beam power, e.g., 1 W or higher, may be employed to produce strong signal. An inherently high contrast sample (e.g., comprising a sample surface that exhibits strong foreground signal and dramatically reduced background signal, may also be used to facilitate acquisition of high contrast-to-noise ratio (CNR) images, e.g., having CNR values of >20, that provide for improved signal discrimination for base-calling in nucleic acid sequencing applications, etc. In some optical system designs disclosed herein, sample support structures such as flow cells having hydrophilic surfaces are used to reduce background noise.

In various implementations, a large field-of-view (FOV) is provided by the disclosed optical systems. For example, a FOV of greater than 2 or 3 mm may be provided with some optical imaging systems comprising, e.g., an objective lens and a tube lens. In some cases, the optical imaging system provides a reduced magnification, for example, a magnification of less than 10×. Such reduced magnification may in some implementations facilitate large FOV designs. Despite a reduced magnification, the optical resolution of such systems can still be sufficient as detector arrays having small pixel size or pitch may be used. In some implementations, image sensors comprising a pixel size that is smaller than twice the optical resolution provided by the optical imaging system (e.g., objective and tube lens) may be used to satisfy the Nyquist theorem.

Still other designs are also possible. In some optical designs configured to provide for dual surface imaging where two surfaces at different depths can be imaged at the same time, the optical imaging system (e.g., the objective lens and/or tube lens) is configured to reduce optical aberration for imaging said two surfaces (e.g., two planes) at those two respective depths more than at other locations (e.g., other planes) at other depths. Additionally, the optical imaging system may be configured to reduce aberration for imaging said two surfaces (e.g., two planes) at those two respective depths through a transmissive layer on said sample support structure (such as a layer of glass (e.g., a cover slip) and through a solution (e.g., an aqueous solution) comprising the sample or in contact with a sample on at least one of said two surfaces.

Multichannel fluorescence imaging modules and systems: In some instances, the imaging modules or systems disclosed herein may comprise fluorescence imaging modules or systems. In some instances, the fluorescence imaging systems disclosed herein may comprise a single fluorescence excitation light source (for providing excitation light at a single wavelength or within a single excitation wavelength range) and an optical path configured to deliver the excitation light to a sample (e.g., fluorescently-tagged nucleic acid molecules or clusters thereof disposed on a substrate surface). In some instances, the fluorescence imaging systems disclosed herein may comprise a single fluorescence emission imaging and detection channel, e.g., an optical path configured to collect fluorescence emitted by the sample and deliver an image of the sample (e.g., an image of a substrate surface on which fluorescently-tagged nucleic acid molecules or clusters thereof are disposed) to an image sensor or other photodetection device. In some instances, the fluorescence imaging systems may comprise two, three, four, or more than four fluorescence excitation light sources and/or optical paths configured to deliver excitation light at two, three, four, or more than four excitation wavelengths (or within two, three, four, or more than four excitation wavelength ranges). In some instances, the fluorescence imaging systems disclosed herein may comprise two, three, four, or more than four fluorescence emission imaging and detection channels configured to collect fluorescence emitted by the sample at two, three, four, or more than four emission wavelengths (or within two, three, four, or more than four emission wavelength ranges and deliver an image of the sample (e.g., an image of a substrate surface on which fluorescently-tagged nucleic acid molecules or clusters thereof are disposed) to two, three, four, or more than four image sensors or other photodetection devices.

Figure 1A:
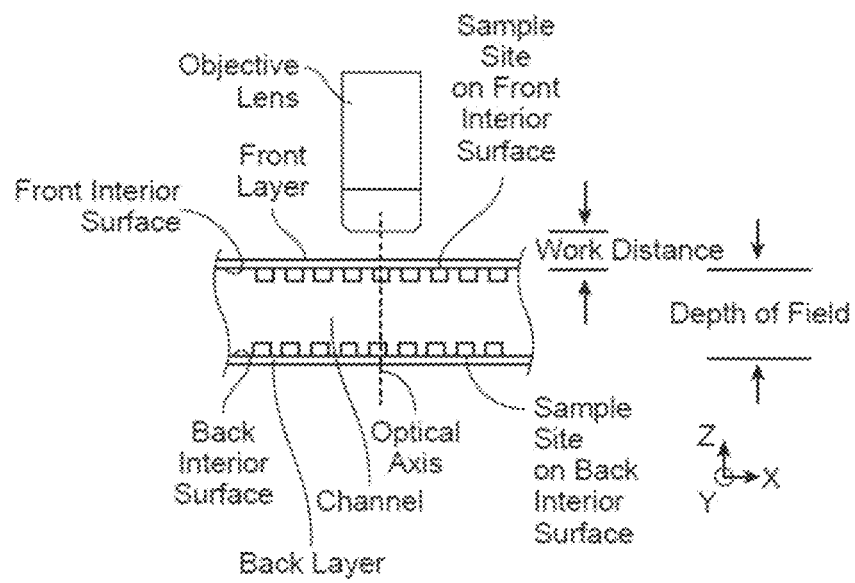
FIGS. 1A-1B schematically illustrate non-limiting examples of imaging dual surface support structures for presenting sample sites for imaging by the imaging systems disclosed herein.
Figure 1B:
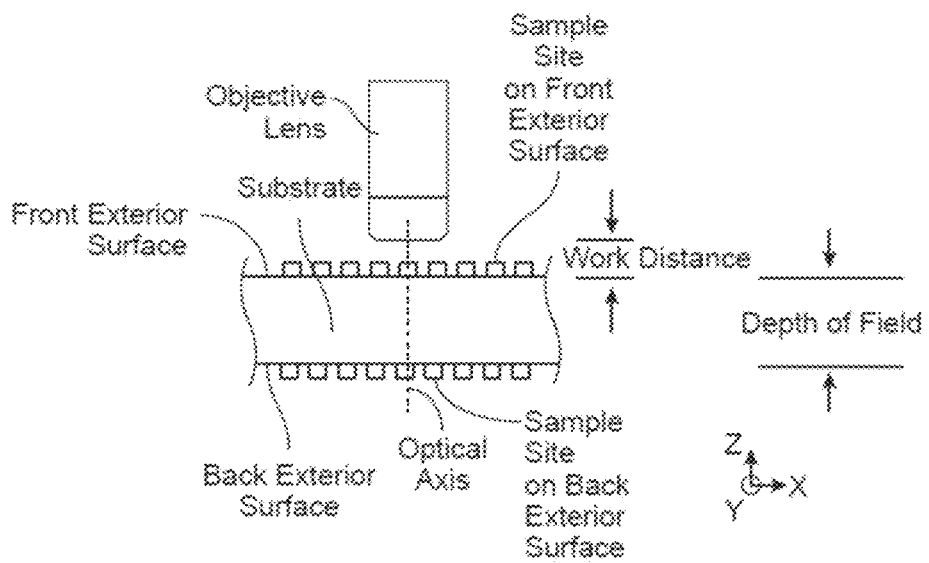

Dual surface imaging: In some instances, the imaging systems disclosed herein, including fluorescence imaging systems, may be configured to acquire high-resolution images of a single sample support structure or substrate surface. In some instances, the imaging systems disclosed herein, including fluorescence imaging systems, may be configured to acquire high-resolution images of two or more sample support structures or substrate surfaces, e.g., two or more surfaces of a flow cell. In some instances, the high-resolution images provided by the disclosed imaging systems may be used to monitor reactions occurring on the two or more surfaces of the flow cell (e.g., nucleic acid hybridization, amplification, and/or sequencing reactions) as various reagents flow through the flow cell or around a flow cell substrate. FIG. 1A and FIG. 1B provide schematic illustrations of such dual surface support structures. FIG. 1A shows a dual surface support structure such as a flow cell that includes an internal flow channel through which an analyte or reagent can be flowed. The flow channel may be formed between first and second, top and bottom, and/or front and back layers such as first and second, top and bottom, and/or front and back plates as shown. One or more of the plates may include a glass plate, such as a coverslip, or the like. In some implementations, the layer comprises borosilicate glass, quartz, or plastic. Interior surfaces of these top and bottom layers provide walls of the flow channel that assist in confining the flow of analyte or reagent through the flow channel of the flow cell. In some designs, these interior surfaces are planar. Similarly, the top and bottom layers may be planar. In some designs, at least one additional layer (not shown) is disposed between the top and bottom layers. This additional layer may have one or more pathways cut therein that assist in defining one or more flow channels and controlling the flow of the analyte or reagent within the flow channel. Additional discussion of sample support structures, e.g., flow cells, can be found below.

FIG. 1A schematically illustrates a plurality of fluorescing sample sites on the first and second, top and bottom, and/or front and back interior surfaces of the flow cell. In some implementations, reactions may occur at these sites to bind sample such that fluorescence is emitted from these sites (note that FIG. 1A is schematic and not drawn to scale; for example, the size and spacing of the fluorescing sample sites may be smaller than shown).

FIG. 1B shows another dual surface support structure having two surfaces containing fluorescing sample sites to be imaged. The sample support structure comprises a substrate having first and second, top and bottom, and/or front and back exterior surfaces. In some designs, these exterior surfaces are planar. In various implementations, the analyte or reagent is flowed across these first and second exterior surfaces. FIG. 1B schematically illustrates a plurality of fluorescing sample sites on the first and second, top and bottom, and/or front and back exterior surfaces of the sample support structure. In some implementations, reactions may occur at these sites to bind sample such that fluorescence is emitted from these sites (note that FIG. 1B is schematic and not drawn to scale; for example, the size and spacing of the fluorescing sample sites may be smaller than shown).

In some instances, the fluorescence imaging modules and systems described herein may be configured to image such fluorescing sample sites on first and second surfaces at different distances from the objective lens. In some designs, only one of the first or second surfaces is in focus at a time. Accordingly, in such designs, one of the surfaces is imaged at a first time, and the other surface is imaged at a second time. The focus of the fluorescence imaging module may be changed after imaging one of the surfaces in order to image the other surface with comparable optical resolution, as the images of the two surfaces are not simultaneously in focus. In some designs, an optical compensation element may be introduced into the optical path between the sample support structure and the image sensor in order to image one of the two surfaces. The depth of field in such fluorescence imaging configurations may not be sufficiently large to include both the first and second surfaces. In some implementations of the fluorescence imaging modules described herein, both the first and second surfaces may be imaged at the same time, e.g., simultaneously. For example, the fluorescence imaging module may have a depth of field that is sufficiently large to include both surfaces. In some instances, this increased depth of field may be provided by, for example, reducing the numerical aperture of the objective lens (or microscope objective) as will be discussed in more detail below.

As shown in FIGS. 1A and 1B, the imaging optics (e.g., an objective lens) may be positioned at a suitable distance (e.g., a distance corresponding to the working distance) from the first and second surfaces to form in-focus images of the first and second surfaces on an image sensor of a detection channel. As shown in the example of FIGS. 1A and 1B, the first surface may be between said objective lens and the second surface. For example, as illustrated, the objective lens is disposed above both the first and second surfaces, and the first surface is disposed above the second surface. The first and second surfaces, for example, are at different depths. The first and second surfaces are at different distances from any one or more of the fluorescence imaging module, the illumination and imaging module, imaging optics, or the objective lens. The first and second surfaces are separated from each other with the first surface spaced apart above the second surface. In the example shown, the first and second surfaces are planar surfaces and are separated from each other along a direction normal to said first and second planar surfaces. Also, in the example shown, said objective lens has an optical axis and said first and second surfaces are separated from each other along the direction of said optical axis. Similarly, the separation between the first and second surfaces may correspond to the longitudinal distance such as along the optical path of the excitation beam and/or along an optical axis through the fluorescence imaging module and/or the objective lens. Accordingly, these two surfaces may be separated by a distance from each other in the longitudinal (Z) direction, which may be along the direction of the central axis of the excitation beam and/or the optical axis of the objective lens and/or the fluorescence imaging module. This separation may correspond, for example, to a flow channel within a flow cell in some implementations.

In various designs, the objective lens (possibly in combination with another optical component, e.g., a tube lens) have a depth of field and/or depth of focus that is at least as large as the longitudinal separation (in the Z direction) between the first and second surfaces. The objective lens, alone or in combination with the additional optical component, may thus simultaneously form in-focus images of both the first and the second surface on an image sensor of one or more detection channels where these images have comparable optical resolution. In some implementations, the imaging module may or may not need to be re-focused to capture images of both the first and second surfaces with comparable optical resolution. In some implementations, compensation optics need not be moved into or out of an optical path of the imaging module to form in-focus images of the first and second surfaces. Similarly, in some implementations, one or more optical elements (e.g., lens elements) in the imaging module (e.g., the objective lens and/or a tube lens) need not be moved, for example, in the longitudinal direction along the first and/or second optical paths (e.g., along the optical axis of the imaging optics) to form in-focus images of the first surface in comparison to the location of said one or more optical element when used to form in-focus images of the second surface. In some implementations, however, the imaging module includes an autofocus system configured to provide both the first and second surface in focus at the same time. In various implementations, the sample is in focus to sufficiently resolve the sample sites, which are closely spaced together in lateral directions (e.g., the X and Y directions). Accordingly, in various implementations, no optical element enters an optical path between the sample support structure (e.g., between a translation stage that supports the sample support structure) and an image sensor (or photodetector array) in the at least one detection channel in order to form in-focus images of fluorescing sample sites on a first surface of the sample support structure and on a second surface of said sample support structure. Similarly, in various implementations, no optical compensation is used to form an in-focus image of fluorescing sample sites on a first surface of the sample support structure on the image sensor or photodetector array that is not identical to optical compensation used to form an in-focus image of fluorescing sample sites on a second surface of the sample support structure on the image sensor or photodetector array. Additionally, in certain implementations, no optical element in an optical path between the sample support structure (e.g., between a translation stage that supports the sample support structure) and an image sensor in the at least one detection channel is adjusted differently to form an in-focus image of fluorescing sample sites on a first surface of the sample support structure than to form an in-focus image of fluorescing sample sites on a second surface of the sample support structure. Similarly, in some various implementations, no optical element in an optical path between the sample support structure (e.g., between a translation stage that supports the sample support structure) and an image sensor in the at least one detection channel is moved a different amount or a different direction to form an in-focus image of fluorescing sample sites on the a first surface of the sample support structure on the image sensor than to form an in-focus image of fluorescing sample sites on a second surface of said sample support structure on the image sensor. Any combination of the features is possible. For example, in some implementations, in-focus images of the upper interior surface and the lower interior surface of the flow cell can be obtained without moving an optical compensator into or out of an optical path between the flow cell and the at least one image sensor and without moving one or more optical elements of the imaging system (e.g., the objective and/or tube lens) along the optical path (e.g., optical axis) therebetween. For example, in-focus images of the upper interior surface and the lower interior surface of the flow cell can be obtained without moving one or more optical elements of the tube lens into or out of the optical path, or without moving one or more optical elements of the tube lens along the optical path (e.g., optical axis) therebetween.

Any one or more of the fluorescence imaging module, the illumination optical path, the imaging optical path, the objective lens, or the tube lens may be designed to reduce or minimize optical aberration at two locations such as two planes corresponding to two surfaces on a flow cell or other sample support structure, for example, where fluorescing sample sites are located. Any one or more of the fluorescence imaging module, the illumination optical path, the imaging optical path, the objective lens, or the tube lens may be designed to reduce or minimize optical aberration at the selected locations or planes relative to other locations or planes, such as first and second surfaces containing fluorescing sample sites on a dual surface flow cell. For example, any one or more of the fluorescence imaging module, the illumination optical path, the imaging optical path, the objective lens, or the tube lens may be designed to reduce or minimize optical aberration at two depths or planes located at different distances from the objective lens as compared to the aberrations associated with other depths or planes at other distances from the objective lens. For example, optical aberration may be less for imaging the first and second surfaces than elsewhere in a region ranging from about 1 to about 10 mm from the objective lens. Additionally, any one or more of the fluorescence imaging module, the illumination optical path, the imaging optical path, the objective lens, or the tube lens may, in some instances, be configured to compensate for optical aberration induced by transmission of emission light through one or more portions of the sample support structure such as a layer that includes one of the surfaces on which sample adheres as well as possibly a solution that is in contact with the sample. This layer (e.g., a coverslip or the wall of a flow cell) may comprise, e.g., glass, quartz, plastic, or other transparent material having a refractive index and that introduces optical aberration.

Accordingly, the imaging performance may be substantially the same when imaging the first surface and second surface. For example, the optical transfer functions (OTF) and/or modulation transfer functions (MTF) may be substantially the same for imaging of the first and second surfaces. Either or both of these transfer functions may, for example, be within 20%, within 15%, within 10%, within 5%, within 2.5%, or within 1% of each other, or within any range formed by any of these values at one or more specified spatial frequencies or when averaged over a range of spatial frequencies. Accordingly, an imaging performance metric may be substantially the same for imaging the upper interior surface or the lower interior surface of the flow cell without moving an optical compensator into or out of an optical path between the flow cell and the at least one image sensor, and without moving one or more optical elements of the imaging system (e.g., the objective and/or tube lens) along the optical path (e.g., optical axis) therebetween. For example, an imaging performance metric may be substantially the same for imaging the upper interior surface or the lower interior surface of the flow cell without moving one or more optical elements of the tube lens into or out of the optical path or without moving one or more optical elements of the tube lens along the optical path therebetween. In some embodiments, the optical path is an optical axis. Additional discussion of MTF is included below and in U.S. Provisional Application No. 62/962,723 filed Jan. 17, 2020, which is incorporated herein by reference in its entirety.

It will be understood by those of skill in the art that the disclosed imaging modules or systems may, in some instances, be stand-alone optical systems designed for imaging a sample or substrate surface. In some instances, they may comprise one or more processors or computers. In some instances, they may comprise one or more software packages that provide instrument control functionality and/or image processing functionality. In some instances, in addition to optical components such as light sources (e.g., solid-state lasers, dye lasers, diode lasers, arc lamps, tungsten-halogen lamps, etc.), lenses, prisms, mirrors, dichroic reflectors, beam splitters, optical filters, optical bandpass filters, light guides, optical fibers, apertures, and image sensors (e.g., complementary metal oxide semiconductor (CMOS) image sensors and cameras, charge-coupled device (CCD) image sensors and cameras, etc.), they may also include mechanical and/or optomechanical components, such as X-Y translation stages, X—Y-Z translation stages, piezoelectric focusing mechanisms, electro-optical phase plates, and the like. In some instances, they may function as modules, components, sub-assemblies, or sub-systems of larger systems designed for, e.g., genomics applications (e.g., genetic testing and/or nucleic acid sequencing applications). For example, in some instances, they may function as modules, components, sub-assemblies, or sub-systems of larger systems that further comprise light-tight and/or other environmental control housings, temperature control modules, flow cells and cartridges, fluidics control modules, fluid dispensing robotics, cartridge- and/or microplate-handling (pick-and-place) robotics, one or more processors or computers, one or more local and/or cloud-based software packages (e.g., instrument/system control software packages, image processing software packages, data analysis software packages), data storage modules, data communication modules (e.g., Bluetooth, WiFi, intranet, or internet communication hardware and associated software), display modules, etc., or any combination thereof. These additional components of larger systems, e.g., systems designed for genomics applications, will be discussed in more detail below.

Figure 2A:
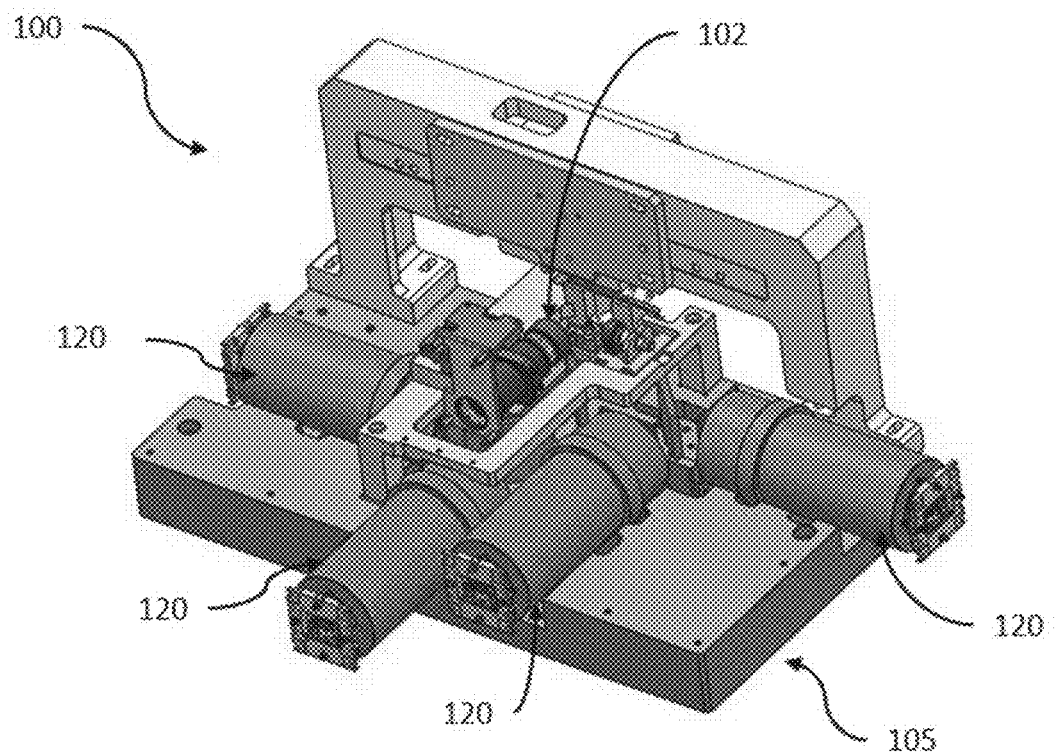
FIGS. 2A-2B illustrate a non-limiting example of a multi-channel fluorescence imaging module comprising a dichroic beam splitter for transmitting an excitation light beam to a sample, and for receiving and redirecting by reflection the resultant fluorescence emission to four detection channels configured for detection of fluorescence emission at four different respective wavelengths or wavelength bands.
Figure 2B:
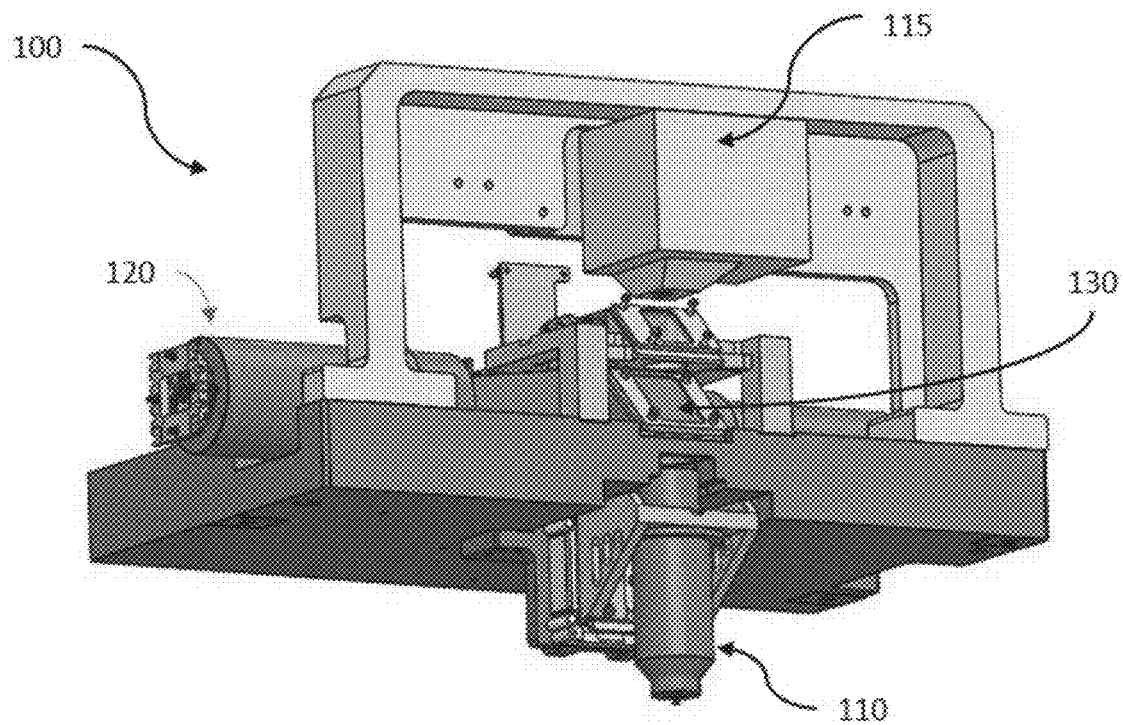

FIGS. 2A and 2B illustrate a non-limiting example of an illumination and imaging module 100 for multi-channel fluorescence imaging. The illumination and imaging module 100 includes an objective lens 110, an illumination source 115, a plurality of detection channels 120, and a first dichroic filter 130, which may comprise a dichroic reflector or beam splitter. An autofocus system, which may include an autofocus laser 102, for example, that projects a spot the size of which is monitored to determine when the imaging system is in-focus may be included in some designs. Some or all components of the illumination and imaging module 100 may be coupled to a baseplate 105.

The illumination or light source 115 may include any suitable light source configured to produce light of at least a desired excitation wavelength (discussed in more detail below). The light source may be a broadband source that emits light within one or more excitation wavelength ranges (or bands). The light source may be a narrowband source that emits light within one or more narrower wavelength ranges. In some instances, the light source may produce a single isolated wavelength (or line) corresponding to the desired excitation wavelength, or multiple isolated wavelengths (or lines). In some instances, the lines may have some very narrow bandwidth. Example light sources that may be suitable for use in the illumination source 115 include, but are not limited to, an incandescent filament, xenon arc lamp, mercury-vapor lamp, a light-emitting diode, a laser source such as a laser diode or a solid-state laser, or other types of light sources. As discussed below, in some designs, the light source may comprise a polarized light source such as a linearly polarized light source. In some implementations, the orientation of the light source is such that s-polarized light is incident on one or more surfaces of one or more optical components such as the dichroic reflective surface of one or more dichroic filters.

The illumination source 115 may further include one or more additional optical components such as lenses, filters, optical fibers, or any other suitable transmissive or reflective optics as appropriate to output an excitation light beam having suitable characteristics toward a first dichroic filter 130. For example, beam shaping optics may be included, for example, to receive light from a light emitter in the light source and produce a beam and/or provide a desired beam characteristic. Such optics may, for example, comprise a collimating lens configured to reduce the divergence of light and/or increase collimation and/or to collimate the light.

In some implementations, multiple light sources are included in the illumination and imaging module 100. In some such implementations, different light sources may produce light having different spectral characteristics, for example, to excite different fluorescence dyes. In some implementations, light produced by the different light sources may be directed to coincide and form an aggregate excitation light beam. This composite excitation light beam may be composed of excitation light beams from each of the light sources. The composite excitation light beam will have more optical power than the individual beams that overlap to form the composite beam. For example, in some implementations that include two light sources that produce two excitation light beams, the composite excitation light beam formed from the two individual excitation light beams may have optical power that is the sum of the optical power of the individual beams. Similarly, in some implementations, three, four, five or more light sources may be included, and these light sources may each output excitation light beams that together form a composite beam that has an optical power that is the sum of the optical power of the individual beams.

In some implementations, the light source 115 outputs a sufficiently large amount of light to produce sufficiently strong fluorescence emission. Stronger fluorescence emission can increase the signal-to-noise ratio (SNR) and the contrast-to-noise ratio (CNR) of images acquired by the fluorescence imaging module. In some implementations, the output of the light source and/or an excitation light beam derived therefrom (including a composite excitation light beam) may range in power from about 0.5 watts (W) to about 5.0 W, or more (as will be discussed in more detail below).

Referring again to FIGS. 2A and 2B, the first dichroic filter 130 is disposed with respect to the light source to receive light therefrom. The first dichroic filter may comprise a dichroic mirror, dichroic reflector, dichroic beam splitter, or dichroic beam combiner configured to transmit light in a first spectral region (or wavelength range) and reflect light having a second spectral region (or wavelength range). The first spectral region may include one or more spectral bands, e.g., one or more spectral bands in the ultraviolet and blue wavelength ranges. Similarly, a second spectral region may include one or more spectral bands, e.g., one or more spectral bands extending from the green to red and infrared wavelengths. Other spectral regions or wavelength ranges are also possible.

In some implementations, the first dichroic filter may be configured to transmit light from the light source to a sample support structure such as to a microscope slide, a capillary, a flow cell, a microfluidic chip, or other substrate or support structure. The sample support structure supports and positions the sample, e.g., a composition comprising a fluorescently-labeled nucleic acid molecule or complement thereof, with respect to the illumination and imaging module 100. Accordingly, a first optical path extends from the light source to the sample via the first dichroic filter. In various implementations, the sample support structure includes at least one surface on which the sample is disposed or to which the sample binds. In some instances, the sample may be disposed within or bound to different localized regions or sites on the at least one surface of the sample support structure.

In some instances, the support structure may include two surfaces located at different distances from objective lens 110 (e.g., at different positions or depths along the optical axis of objective lens 110) on which the sample is disposed. As discussed below, for example, a flow cell may comprise a fluid channel formed at least in part by first and second (e.g., upper and lower) interior surfaces, and the sample may be disposed at localized sites on the first interior surface, the second interior surface, or both interior surfaces. The first and second surface may be separated by the region corresponding to the fluid channel through which a solution flows, and thus be at different distances or depth with respect to objective lens 110 of the illumination and imaging module 100.

The objective lens 110 may be included in the first optical path between the first dichroic filter and the sample. This objective lens may be configured, for example, to have a focal length, working distance, and/or be positioned to focus light from the light source(s) onto the sample, e.g., onto a surface of the microscope slide, capillary, flow cell, microfluidic chip, or other substrate or support structure. Similarly, the objective lens 110 may be configured to have suitable focal length, working distance, and/or be positioned to collect light reflected, scattered, or emitted from the sample (e.g., fluorescence emission) and to form an image of the sample (e.g., a fluorescence image).

In some implementations, objective lens 110 may comprise a microscope objective such as an off-the-shelf objective. In some implementations, objective lens 110 may comprise a custom objective. An example of a custom objective lens and/or custom objective—tube lens combination is described below and in U.S. Provisional Application No. 62/962,723 filed on Jan. 17, 2020, which is incorporated herein by reference in its entirety. The objective lens 110 may be designed to reduce or minimize optical aberration at two locations such as two planes corresponding to two surfaces of a flow cell or other sample support structure. The objective lens 110 may be designed to reduce the optical aberration at the selected locations or planes, e.g., the first and second surfaces of a dual surface flow cell, relative to other locations or planes in the optical path. For example, the objective lens 110 may be designed to reduce the optical aberration at two depths or planes located at different distances from the objective lens as compared to the optical aberrations associated with other depths or planes at other distances from the objective. For example, in some instances, optical aberration may be less for imaging the first and second surfaces of a flow cell than that exhibited elsewhere in a region spanning from 1 to 10 mm from the front surface of the objective lens. Additionally, a custom objective lens 110 may in some instances be configured to compensate for optical aberration induced by transmission of fluorescence emission light through one or more portions of the sample support structure, such as a layer that includes one or more of the flow cell surfaces on which a sample is disposed, or a layer comprising a solution filling the fluid channel of a flow cell. These layers may comprise, e.g., glass, quartz, plastic, or other transparent material having a refractive index, and which may introduce optical aberration.

In some implementations, objective lens 110 may have a numerical aperture (NA) of 0.6 or more (as discussed in more detail below). Such a numerical aperture may provide for reduced depth of focus and/or depth of field, improved background discrimination, and increased imaging resolution.

In some implementations, objective lens 110 may have a numerical aperture (NA) of 0.6 or less (as discussed in more detail below). Such a numerical aperture may provide for increased depth of focus and/or depth of field. Such increased depth of focus and/or depth of field may increase the ability to image planes separated by a distance such as that that separates the first and second surfaces of a dual surface flow cell.

As discussed above, a flow cell may comprise, for example, first and second layers comprising first and second interior surfaces respectively that are separated by a fluid channel through which an analyte or reagent can flow. In some implementations, the objective lens 110 and/or illumination and imaging module 100 may be configured to provide a depth of field and/or depth of focus sufficiently large to image both the first and second interior surfaces of the flow cell, either sequentially by re-focusing the imaging module between imaging the first and second surfaces, or simultaneously by ensuring a sufficiently large depth of field and/or depth of focus, with comparable optical resolution. In some instances, the depth of field and/or depth of focus may be at least as large or larger than the distance separating the first and second surfaces of the flow cell to be imaged, such as the first and second interior surfaces of the flow cell. In some instances, the first and second surfaces, e.g., the first and second interior surfaces of a dual surface flow cell or other sample support structure, may be separated, for example, by a distance ranging from about 10 µm to about 700 µm, or more (as will be discussed in more detail below). In some instances, the depth of field and/or depth of focus may thus range from about 10 µm to about 700 µm, or more (as will be discussed in more detail below).

In some designs, compensation optics (e.g., an "optical compensator" or "compensator") may be moved into or out of an optical path in the imaging module, for example, an optical path by which light collected by the objective lens 110 is delivered to an image sensor, to enable the imaging module to image the first and second surfaces of the dual surface flow cell. The imaging module may be configured, for example, to image the first surface when the compensation optics is included in the optical path between the objective lens and an image sensor or photodetector array configured to capture an image of the first surface. In such a design, the imaging module may be configured to image the second surface when the compensation optics is removed from or not included in the optical path between the objective lens 110 and the image sensor or photodetector array configured to capture an image of the second surface. The need for an optical compensator may be more pronounced when using an objective lens 110 with a high numerical aperture (NA) value, e.g., for numerical aperture values of at least 0.6, least 0.65, at least 0.7, at least 0.75, at least 0.8, at least 0.85, at least 0.9, at least 0.95, at least 1.0, or higher. In some implementations, the optical compensation optics (e.g., an optical compensator or compensator) comprises a refractive optical element such as a lens, a plate of optically-transparent material such as glass, a plate of optically-transparent material such as glass, or in the case of polarized light beams, a quarter-wave plate or half-wave plate, etc. Other configurations may be employed to enable the first and second surfaces to be imaged at different times. For example, one or more lenses or optical elements may be configured to be translated in and out of, or along, an optical path between the objective lens 110 and the image sensor.

In certain designs, however, the objective lens 110 is configured to provide sufficiently large depth of focus and/or depth of field to enable the first and second surfaces to be imaged with comparable optical resolution without such compensation optics moving into and out of an optical path in the imaging module, such as an optical path between the objective lens and the image sensor or photodetector array. Similarly, in various designs, the objective lens 110 is configured to provide sufficiently large depth of focus and/or depth of field to enable the first and second surfaces to be imaged with comparable optical resolution without optics being moved, such as one or more lenses or other optical components being translated along an optical path in the imaging module, such as an optical path between the objective lens and the image sensor or photodetector array. Examples of such objective lenses will be described in more detail below.

In some implementations, the objective lens (or microscope objective) 110 may be configured to have reduced magnification. The objective lens 110 may be configured, for example, such that the fluorescence imaging module has a magnification of from less than 2× to less than 10× (as will be discussed in more detail below). Such reduced magnification may alter design constraints such that other design parameters can be achieved. For example, the objective lens 110 may also be configured such that the fluorescence imaging module has a large field-of-view (FOV) ranging, for example, from about 1.0 mm to about 5.0 mm (e.g., in diameter, width, length, or longest dimension) as will be discussed in more detail below.

In some implementations, the objective lens 110 may be configured to provide the fluorescence imaging module with a field-of-view as indicated above such that the FOV has diffraction-limited performance, e.g., less than 0.15 waves of aberration over at least 60%, 70%, 80%, 90%, or 95% of the field, as will be discussed in more detail below.

In some implementations, the objective lens 110 may be configured to provide the fluorescence imaging module with a field-of-view as indicated above such that the FOV has diffraction-limited performance, e.g., a Strehl ratio of greater than 0.8 over at least 60%, 70%, 80%, 90%, or 95% of the field, as will be discussed in more detail below.

Referring again to FIGS. 2A and 2B, the first dichroic beam splitter or beam combiner is disposed in the first optical path between the light source and the sample so as to illuminate the sample with one or more excitation beams. This first dichroic beam splitter or combiner is also in one or more second optical path(s) from the sample to the different optical channels used to detect the fluorescence emission. Accordingly, the first dichroic filter 130 couples the first optical path of the excitation beam emitted by the illumination source 115 and second optical path of the emission light emitted by a sample specimen to the various optical channels where the light is directed to respective image sensors or photodetector arrays for capturing images of the sample.

In various implementations, the first dichroic filter 130, e.g., first dichroic reflector or beam splitter or beam combiner, has a passband selected to transmit light from the illumination source 115 only within a specified wavelength band or possibly a plurality of wavelength bands that include the desired excitation wavelength or wavelengths. For example, the first dichroic beam splitter 130 includes a reflective surface comprising a dichroic reflector that has spectral transmissivity response that is, e.g., configured to transmit light having at least some of the wavelengths output by the light source that form part of the excitation beam. The spectral transmissivity response may be configured not to transmit (e.g., instead to reflect) light of one or more other wavelengths, for example, of one or more other fluorescence emission wavelengths. In some implementations, the spectral transmissivity response may also be configured not to transmit (e.g., instead to reflect) light of one or more other wavelengths output by the light source. Accordingly, the first dichroic filter 130 may be utilized to select which wavelength or wavelengths of light output by the light source reach the sample. Conversely, the dichroic reflector in the first dichroic beam splitter 130 has a spectral reflectivity response that reflects light having one or more wavelengths corresponding to the desired fluorescence emission from the sample and possible reflects light having one or more wavelengths output from the light source that is not intended to reach the sample. Accordingly, in some implementations, the dichroic reflector has a spectral transmissivity that includes one or more pass bands to transmit the light to be incident on the sample and one or more stop bands that reflects light outside the pass bands, for example, light at one or more emission wavelengths and possibly one or more wavelengths output by the light source that are not intended to reach the sample. Likewise, in some implementations the dichroic reflector has a spectral reflectivity that includes one or more spectral regions configured to reflect one or more emission wavelengths and possible one or more wavelengths output by the light source that are not intended to reach the sample and includes one or more regions that transmit light outside these reflection regions. The dichroic reflector included in the first dichroic filter 130 may comprise a reflective filter such as an interference filter (e.g., a quarter-wave stack) configured to provide the appropriate spectral transmission and reflection distributions. FIGS. 2A and 2B also show a dichroic filter 105, which may comprise for example a dichroic beam splitter or beam combiner, that may be used to direct the autofocus laser 102 though the objective and to the sample support structure.

Although the imaging module 100 shown in FIGS. 2A and 2B and discussed above is configured such that the excitation beam is transmitted by the first dichroic filter 130 to the objective lens 110, in some designs the illumination source 115 may be disposed with respect to the first dichroic filter 130 and/or the first dichroic filter is configured (e.g., oriented) such that the excitation beam is reflected by the first dichroic filter 130 to the objective lens 110. Similarly, in some such designs, the first dichroic filter 130 is configured to transmit fluorescence emission from the sample and possibly transmit light having one or more wavelengths output from the light source that is not intended to reach the sample. As will be discussed below, a design where the fluorescence emission is transmitted instead of reflected may potentially reduce wavefront error in the detected emission and/or possibly have other advantages. In either case, in various implementations the first dichroic reflector 130 is disposed in the second optical path so as to receive fluorescence emission from the sample, at least some of which continues on to the detection channels 120.

Figure 3A:
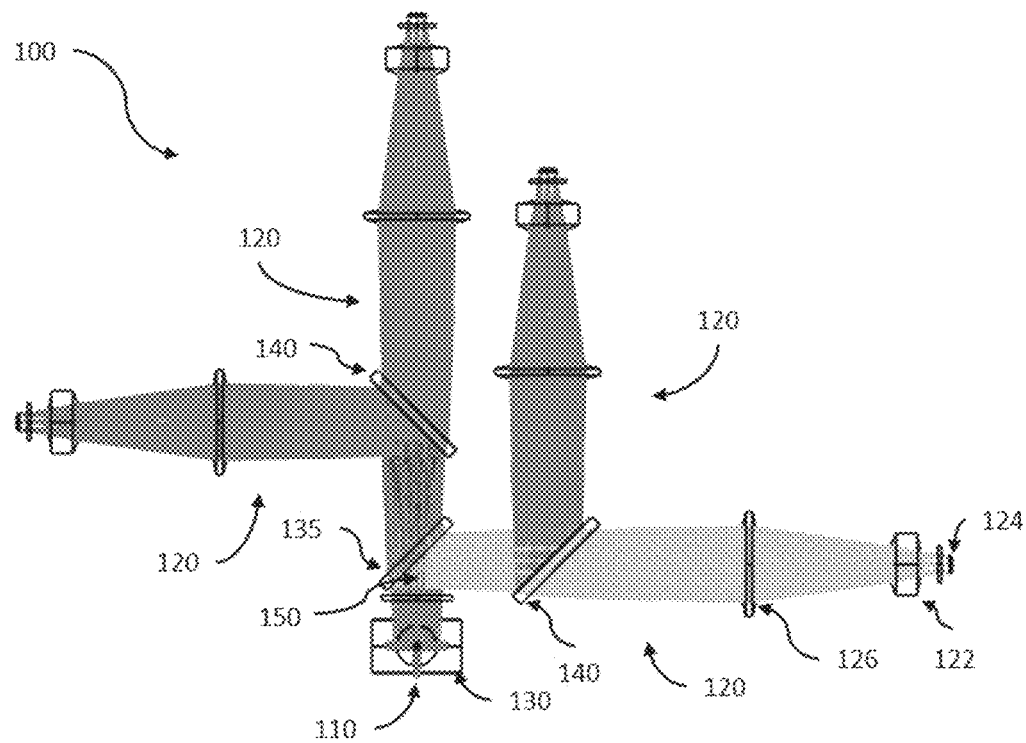
FIGS. 3A-3B illustrate the optical paths within the multi-channel fluorescence imaging module of FIGS. 2A and 2B comprising a dichroic beam splitter for transmitting an excitation light beam to a sample, and for receiving and redirecting by reflection a resultant fluorescence emission to four detection channels for detection of fluorescence emission at four different respective wavelengths or wavelength bands.
Figure 3B:
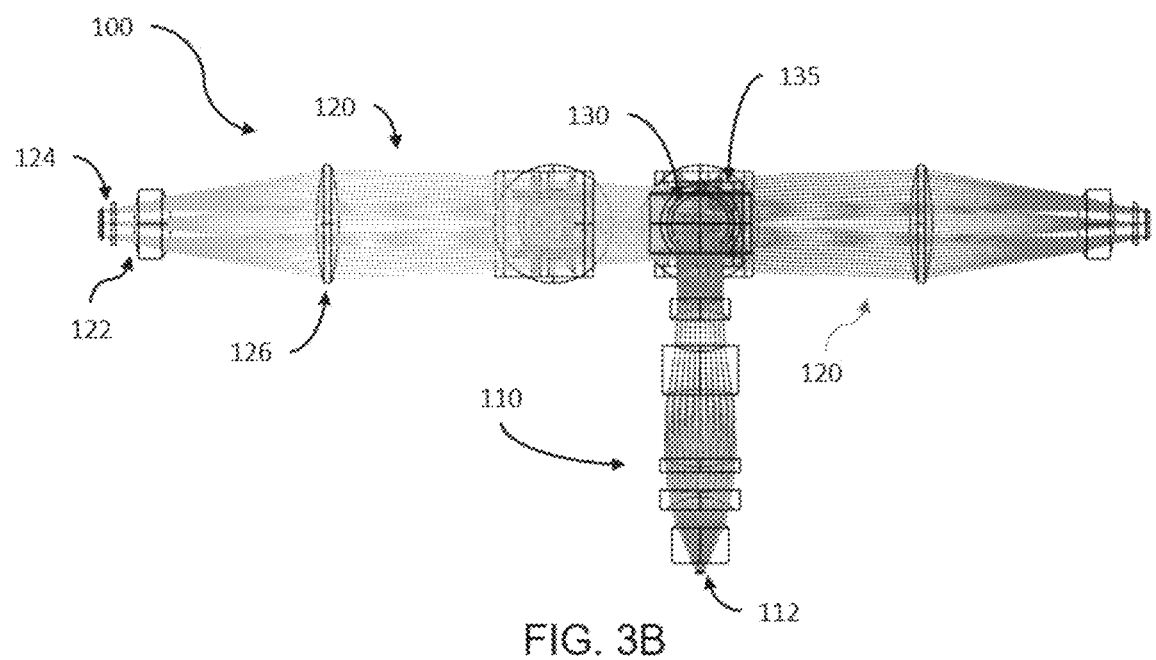

FIGS. 3A and 3B illustrate the optical paths within the multi-channel fluorescence imaging module of FIGS. 2A and 2B. In the example shown in FIG. 2A and FIG. 3A, the detection channels 120 are disposed to receive fluorescence emission from a sample specimen that is transmitted by the objective lens 110 and reflected by the first dichroic filter 130. As referred to above and described more below, in some designs the detection channels 120 may be disposed to receive the portion of the emission light that is transmitted, rather than reflected, by the first dichroic filter. In either case, the detection channels 120 may include optics for receiving at least a portion of the emission light. For example, the detection channels 120 may include one or more lenses, such as tube lenses, and may include one or more image sensors or detectors such as photodetector arrays (e.g., CCD or CMOS sensor arrays) for imaging or otherwise producing a signal based on the received light. The tube lenses may, for example, comprise one or more lens elements configured to form an image of the sample onto the sensor or photodetector array to capture an image thereof. Additional discussion of detection channels is included below and in U.S. Provisional Application No. 62/962,723, filed Jan. 17, 2020, which is incorporated herein by reference in its entirety. In some instances, improved optical resolution may be achieved using an image sensor having relatively high sensitivity, small pixels, and high pixel count, in conjunction with a suitable sampling scheme, which may include oversampling or undersampling.

FIGS. 3A and 3B are ray tracing diagrams illustrating optical paths of the illumination and imaging module 100 of FIGS. 2A and 2B. FIG. 3A corresponds to a top view of the illumination and imaging module 100. FIG. 3B corresponds to a side view of the illumination and imaging module 100. The illumination and imaging module 100 illustrated in these figures includes four detection channels 120. However, it will be understood that the disclosed illumination and imaging modules may equally be implemented in systems including more or fewer than four detection channels 120. For example, the multi-channel systems disclosed herein may be implemented with as few as one detection channel 120, or as many as two detection channels 120, three detection channels 120, four detection channels 120, five detection channels 120, six detection channels 120, seven detection channels 120, eight detection channels 120, or more than eight detection channels 120, without departing from the spirit or scope of the present disclosure.

The non-limiting example of imaging module 100 illustrated in FIGS. 3A and 3B includes four detection channels 120, a first dichroic filter 130 that reflects a beam 150 of emission light, a second dichroic filter (e.g., a dichroic beam splitter) 135 that splits the beam 150 into a transmitted portion and a reflected portion, and two channel-specific dichroic filters (e.g., dichroic beam splitters) 140 that further split the transmitted and reflected portions of the beam 150 among individual detection channels 120. The dichroic reflecting surface in the dichroic beam splitters 135 and 140 for splitting the beam 150 among detection channels are shown disposed at 45 degrees relative to a central beam axis of the beam 150 or an optical axis of the imaging module. However, as discussed below, an angle smaller than 45 degrees may be employed and may offer advantages such as sharper transitions from pass band to stop band.

The different detection channels 120 includes imaging devices 124, which may include an image sensor or photodetector array (e.g., a CCD or CMOS detector array). The different detection channels 120 further include optics 126 such as lenses (e.g., one or more tube lenses each comprising one or more lens elements) disposed to focus the portion of the emission light entering the detection channel 120 at a focal plane coincident with a plane of the photodetector array 124. The optics 126 (e.g., a tube lens) combined with the objective lens 110 are configured to form an image of the sample onto the photodetector array 124 to capture an image of the sample, for example, an image of a surface on the flow cell or other sample support structure after the sample has bound to that surface. Accordingly, such an image of the sample may comprise a plurality of fluorescent emitting spots or regions across a spatial extent of the sample support structure where the sample is emitting fluorescence light. The objective lens 110 together with the optics 126 (e.g., tube lens) may provide a field-of-view (FOV) that includes a portion of the sample or the entire sample. Similarly, the photodetector array 124 of the different detection channels

120 may be configured to capture images of a full field-of-view (FOV) provided by the objective lens and the tube lens, or a portion thereof. In some implementations, the photodetector array 124 of some or all detection channels 120 can detect the emission light emitted by a sample disposed on the sample support structure, e.g., a surface of the flow cell, or a portion thereof and record electronic data representing an image thereof. In some implementations, the photodetector array 124 of some or all detection channels 120 can detect features in the emission light emitted by a specimen without capturing and/or storing an image of the sample disposed on the flow cell surface and/or of the full field-of-view (FOV) provided by the objective lens and optics 126 and/or 122 (e.g., elements of a tube lens). In some implementations, the FOV of the disclosed imaging modules (e.g., that provided by the combination of objective lens 110 and optics 126 and/or 122) may range, for example, between about 1 mm and 5 mm (e.g., in diameter, width, length, or longest dimension) as will be discussed below. The FOV may be selected, for example, to provide a balance between magnification and resolution of the imaging module and/or based on one or more characteristics of the image sensors and/or objective lenses. For example, a relatively smaller FOV may be provided in conjunction with a smaller and faster imaging sensor to achieve high throughput.

Referring again to FIGS. 3A and 3B, in some implementations, the optics 126 in the detection channel (e.g., the tube lens) may be configured to reduce optical aberration in images acquired using optics 126 in combination with objective lens 110. In some implementations comprising multiple detection channels for imaging at different emission wavelengths, the optics 126 (e.g., the tube lens) for different detection channels have different designs to reduce aberration for the respective emission wavelengths at which that particular channel is configured to image. In some implementations, the optics 126 (e.g., the tube lens) may be configured to reduce aberrations when imaging a specific surface (e.g., a plane, object plane, etc.) on the sample support structure comprising fluorescing sample sites disposed thereon as compared to other locations (e.g., other planes in object space). Similarly, in some implementations, the optics 126 (e.g., the tube lens) may be configured to reduce aberrations when imaging first and second surfaces (e.g., first and second planes, first and second object planes, etc.) on a dual surface sample support structure (e.g., a dual surface flow cell) having fluorescing sample sites disposed thereon as compared to other locations (e.g., other planes in object space). For example, the optics 126 in the detection channel (e.g., tube lens) may be designed to reduce the aberration at two depths or planes located at different distances from the objective lens as compared to the aberrations associated with other depths or planes at other distances from the objective. For example, optical aberration may be less for imaging the first and second surfaces than elsewhere in a region from about 1 to about 10 mm from the objective lens. Additionally, custom optic 126 in the detection channel (e.g., a tube lens) may in some embodiments be configured to compensate for aberration induced by transmission of emission light through one or more portions of the sample support structure such as a layer that includes one of the surfaces on which the sample is disposed as well as possibly a solution adjacent to and in contact with the surface on which the sample is disposed. The layer comprising one of the surfaces on which the sample is disposed may comprise, e.g., glass, quartz, plastic, or other transparent material having a refractive index, and which introduces optical aberration. Custom optic 126 in the detection channel (e.g., the tube lens), for example, may in some implementations be configured to compensate for optical aberration induced by a sample support structure, e.g., a coverslip or flow cell wall, or other sample support structure components, as well as possibly a solution adjacent to and in contact with the surface on which the sample is disposed.

In some implementations, the optics 126 in the detection channel (e.g., a tube lens) are configured to have reduced magnification. The optics 126 in the detection channel (e.g., a tube lens) may be configured, for example, such that the fluorescence imaging module has a magnification of less than, for example, 10×, as will be discussed further below. Such reduced magnification may alter design constraints such that other design parameters can be achieved. For example, the optics 126 (e.g., a tube lens) may also be configured such that the fluorescence imaging module has a large field-of-view (FOV), for example, of at least 1.0 mm or larger (e.g., in diameter, width, length, or longest dimension), as will be discussed further below.

In some implementations, the optics 126 (e.g., a tube lens) may be configured to provide the fluorescence imaging module with a field-of-view as indicated above such that the FOV has less than 0.15 waves of aberration over at least 60%, 70%, 80%, 90%, or 95% of the field, as will be discussed further below.

Referring again to FIGS. 3A and 3B, in various implementations, a sample is located at or near a focal position 112 of the objective lens 110. As described above with reference to FIGS. 2A and 2B, a light source such as a laser source provides an excitation beam to the sample to induce fluorescence. At least a portion of fluorescence emission is collected by the objective lens 110 as emission light. The objective lens 110 transmits the emission light toward the first dichroic filter 130, which reflects some or all of the emission light as the beam 150 incident upon the second dichroic filter 135 and to the different detection channels, each comprising optics 126 that form an image of the sample (e.g., a plurality of fluorescing sample sites on a surface of a sample support structure) onto a photodetector array 124.

As discussed above, in some implementations, the sample support structure comprises a flow cell such as a dual surface flow cell having two surfaces (e.g., two interior surfaces, a first surface and a second surface, etc.) containing sample sites that emit fluorescent emission. These two surfaces may be separated by a distance from each other in the longitudinal (Z) direction along the direction of the central axis of the excitation beam and/or the optical axis of the objective lens. This separation may correspond, for example, to a flow channel within the flow cell. Analytes or reagents may be flowed through the flow channel and contact the first and second interior surfaces of the flow cell, which may thereby be contacted with a binding composition such that fluorescence emission is radiated from a plurality of sites on the first and second interior surfaces. The imaging optics (e.g., objective lens 110) may be positioned at a suitable distance (e.g., a distance corresponding to the working distance) from the sample to form in-focus images of the sample on one or more detector arrays 124. As discussed above, in various designs, the objective lens 110 (possibly in combination with the optics 126) may have a depth of field and/or depth of focus that is at least as large as the longitudinal separation between the first and second surfaces. The objective lens 110 and the optics 126 (of each detection channel) can thus simultaneously form images of both the first and the second flow cell surfaces on the photodetector array 124, and these images of the first and second surfaces are both in focus and have comparable optical resolution (or may be brought into focus with only minor refocusing of the objects to acquire images of the first and second surfaces that have comparable optical resolution). In various implementations, compensation optics need not be moved into or out of an optical path of the imaging module (e.g., into or out of the first and/or second optical paths) to form in-focus images of the first and second surfaces that are of comparable optical resolution. Similarly, in various implementations, one or more optical elements (e.g., lens elements) in the imaging module (e.g., the objective lens 110 or optics 126) need not be moved, for example, in the longitudinal direction along the first and/or second optical paths to form in-focus images of the first surface in comparison to the location of said one or more optical elements when used to form in-focus images of the second surface. In some implementations, the imaging module includes an autofocus system configured to quickly and sequentially refocus the imaging module on the first and/or second surface such that the images have comparable optical resolution. In some implementations, objective lens 110 and/or optics 126 are configured such that both the first and second flow cell surfaces are in focus simultaneously with comparable optical resolution without moving an optical compensator into or out of the first and/or second optical path, and without moving one or more lens elements (e.g., objective lens 110 and/or optics 126 (such as a tube lens) longitudinally along the first and/or second optics path. In some implementations, images of the first and/or second surfaces, acquired either sequentially (e.g., with refocusing between surfaces) or simultaneously (e.g., without refocusing between surfaces) using the novel objective lens and/or tube lens designs disclosed herein, may be further processed using a suitable image processing algorithm to enhance the effective optical resolution of the images such that the images of the first and second surfaces have comparable optical resolution. In various implementations, the sample plane is sufficiently in focus to resolve sample sites on the first and/or second flow cell surfaces, the sample sites being closely spaced in lateral directions (e.g., in the X and Y directions).

As discussed above, the dichroic filters may comprise interference filters that selectively transmit and reflect light of different wavelengths based on the principle of thin-film interference, using layers of optical coatings having different refractive indices and particular thickness. Accordingly, the spectral response (e.g., transmission and/or reflection spectra) of the dichroic filters implemented within multi-channel fluorescence imaging modules may be at least partially dependent upon the angle of incidence, or range of angles of incidence, at which the light of the excitation and/or emission beams are incident upon the dichroic filters. Such effects may be especially significant with respect to the dichroic filters of the detection optical path (e.g., the dichroic filters 135 and 140 of FIGS. 3A and 3B).

Figure 4:
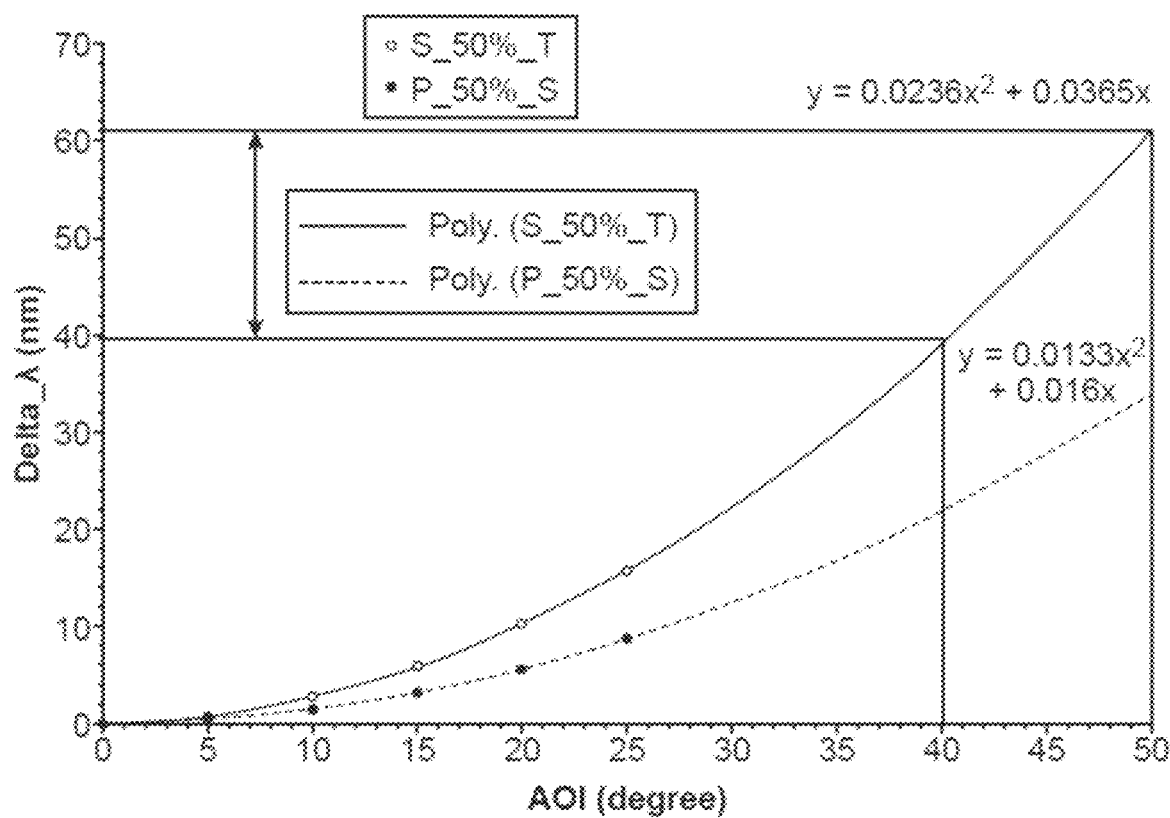
FIG. 4 is a graph illustrating a relationship between dichroic filter performance and beam angle of incidence.

FIG. 4 is a graph illustrating a relationship between dichroic filter performance and beam angle of incidence (AOI). Specifically, the graph of FIG. 4 illustrates the effect of angle of incidence on the transition width or spectral span of a dichroic filter, which corresponds to the range of wavelengths where the spectral response (e.g., transmission spectrum and/or reflection spectrum) transitions between the passband and stopband regions of a dichroic filter. Thus, a transmission edge (or reflection edge) having a relatively small spectral span (e.g., a small delta k value in the graph of FIG. 4) corresponds to a sharper transition between passband and stopband regions or the transmission and reflection regions (or conversely between reflection and transmission regions), while a transmission edge (or reflection edge) having a relatively large spectral span (e.g., a large delta_$\lambda$ value in the graph of FIG. 4) corresponds to a less sharp transition between passband and stopband regions. In various implementations, sharper transitions between passband and stopband regions are generally desirable. Moreover, it may also be desirable to have increased consistency or a relatively consistent transition width across all or most of the field-of-view and/or beam area.

Fluorescence imaging modules, in which the dichroic mirrors are disposed at 45 degrees relative to a central beam axis of the emission light or the optical axis of the optical paths (e.g., of the objective lens and/or tube lens), accordingly can have a transition width of roughly 50 nm for an example dichroic filter, as shown in FIG. 4. Because the emission light beam is not collimated and has some degree of divergence, fluorescence imaging modules may have a range of angles of incidence of approximately 5 degrees between opposing sides of the beam. Thus, as shown in FIG. 4, different portions of the beam of emission light may be incident upon a channel splitting dichroic filter at various angles of incidence between 40 degrees and 50 degrees. This range of relatively large angles of incidence corresponds to a range of transition widths between about 40 nm and about 62 nm. This range of relatively large angles of incidence thereby leads to an increase in transition width of the dichroic filter in the imaging module. Performance of multi-channel fluorescence imaging modules may thus be improved by providing smaller angles of incidence across the full beam, thereby making the transmission edge sharper and allowing better discrimination between different fluorescence emission bands.

Figure 5:
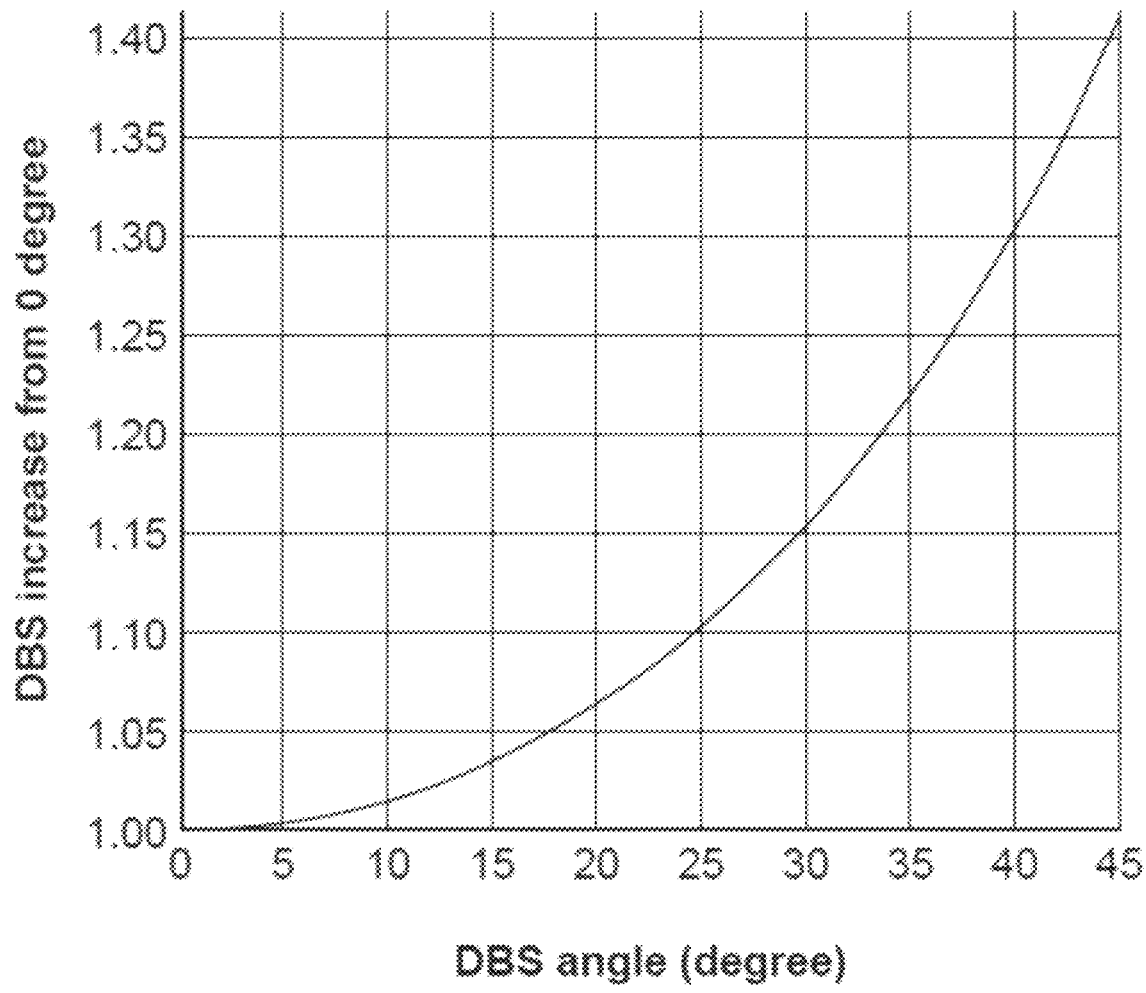
FIG. 5 is a graph illustrating a relationship between beam footprint size and beam angle of incidence on a dichroic filter.

FIG. 5 is a graph illustrating a relationship between beam footprint size (DBS) and beam angle of incidence (DBS angle) on a dichroic filter. In some instances, a smaller beam footprint may be desirable. For example, a small beam footprint allows smaller dichroic filters to be used to split a beam into different wavelength ranges. The use of smaller dichroic filters in turn reduces manufacturing costs and improves the ease of manufacturing suitably flat dichroic filters. As shown in FIG. 5, any angle of incidence greater than 0 degrees (e.g., perpendicular to the surface of the dichroic filter) results in an elliptical beam footprint having an area larger than the cross-sectional area of the beam. An angle of incidence of 45 degrees results in a large beam footprint on the dichroic reflector that is greater than 1.4 times the cross-sectional area of the beam when incident at zero degrees.

Figure 6A:
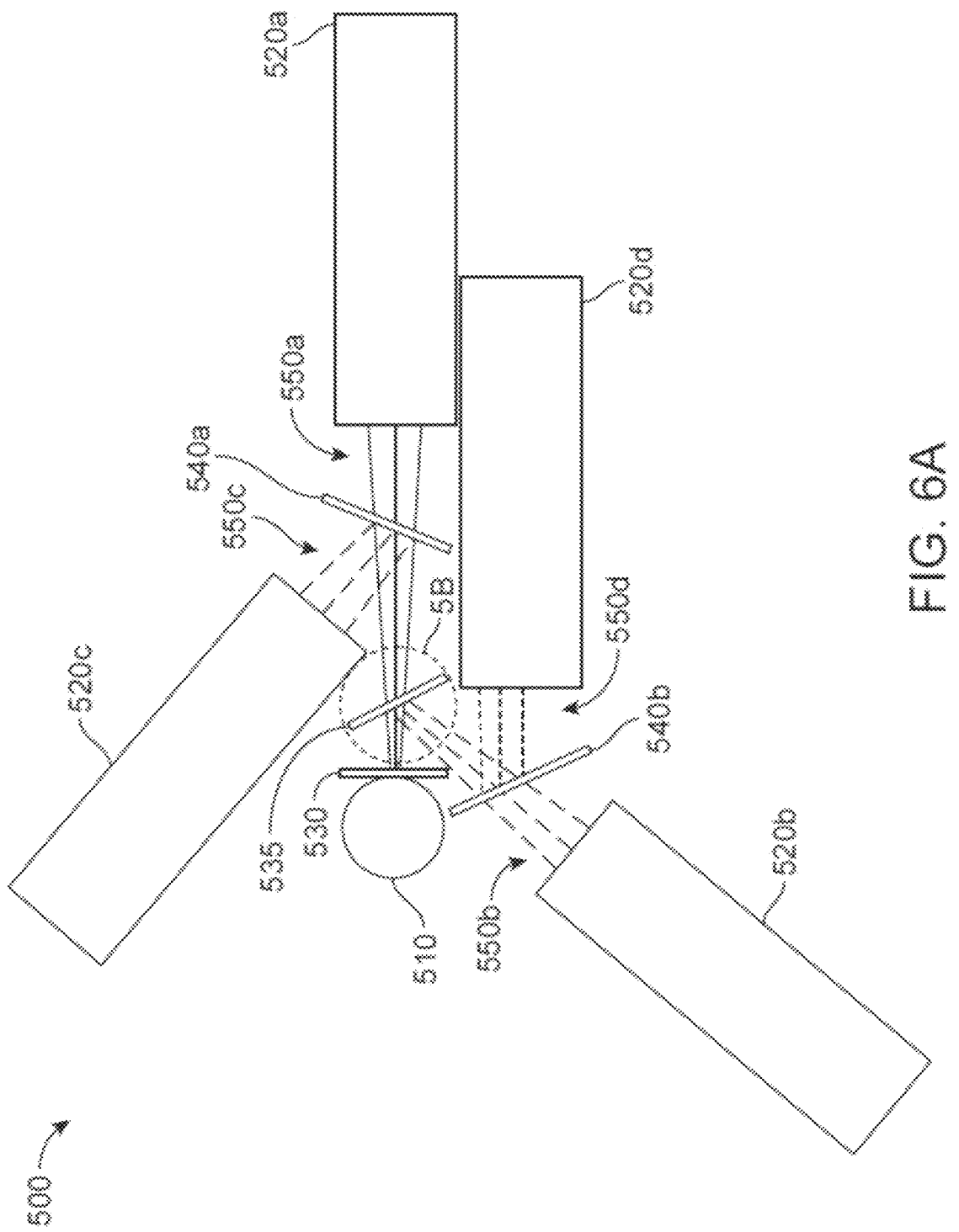
FIGS. 6A-6B schematically illustrate an example configuration of dichroic filters and detection channels of a multi-channel fluorescence imaging module wherein the dichroic filters have reflective surface tilted such that the angle between the incident beam (e.g., the central angle) and the reflective surface of the dichroic filter is less than 45.
Figure 6B:
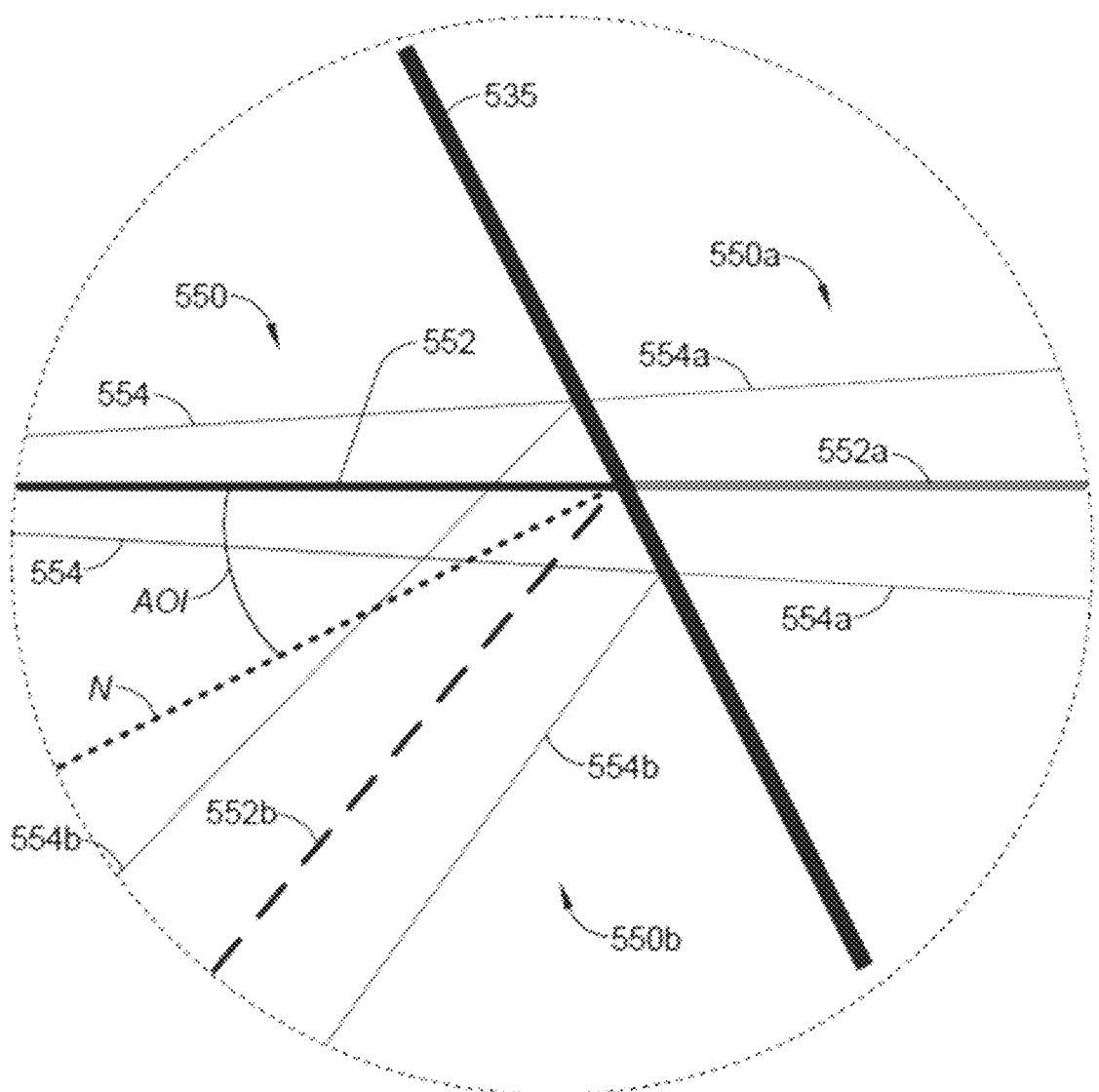

FIGS. 6A and 6B schematically illustrate a non-limiting example configuration of dichroic filters and detection channels in a multi-channel fluorescence imaging module where the dichroic mirrors are disposed at an angle of less than 45 degrees relative to a central beam axis of the emission light or the optical axis of the optical paths (e.g., of the objective lens and/or tube lens). FIG. 6A depicts an imaging module 500 including a plurality of detection channels 520a, 520b, 520c, 520d. FIG. 6B is a detailed view of the portion of the imaging module 500 within the circle 5B as shown in FIG. 6A. As will be described in greater detail, the configuration illustrated in FIGS. 6A and 6B includes a number of aspects that may result in significant improvements over conventional multi-channel fluorescence imaging module designs. In some instances, fluorescence imaging modules and systems of the present disclosure may, however, may be implemented with one or a subset of the features described with respect to FIGS. 6A and 6B without departing from the spirit or scope of the present disclosure.

The imaging module 500 depicted in FIG. 6A includes an objective lens 510 and four detection channels 520a, 520b, 520c, and 520d disposed to receive and/or image emission light transmitted by the objective lens 510. A first dichroic filter 530 is provided to couple the excitation and detection optical paths. In contrast to the design shown in FIGS. 2A and 2B, as well as in FIGS. 3A and 3B, the first dichroic filter 530 (e.g., a dichroic beam splitter or combiner) is configured to reflect light from the light source to the objective lens 510 and sample, and transmit fluorescence emission from the sample to the detection channels 520a, 520b, 520c, and 520d. A second dichroic filter 535 splits a beam of emission light among at least two detection channels 520a, 520b by transmitting a first portion 550a and reflecting a second portion 550b. Additional dichroic filters 540a, 540b are provided to further split the emission light. Dichroic filter 540a transmits at least a portion of the first portion 550a of the emission light and reflects a portion 550c to a third detection channel 520c. Dichroic filter 540b transmits at least a portion of the second portion 550b of the emission light and reflects a portion 550d to a fourth detection channel 520d. Although the imaging module 500 is depicted with four detection channels, in various embodiments the imaging module 500 may include more or fewer detection channels, with a correspondingly larger or smaller number of dichroic filters as appropriate to provide a portion of the emission light to each detection channel. For example, in some embodiments, the features of the imaging module 500 may be implemented with similar advantageous effects in an imaging module including only two detection channels 520a, 520b, and omitting additional dichroic filters 540a, 540b. In some implementations, only one detection channel may be included. Alternatively, three or more detection channels may be employed.

The detection channels 520a, 520b, 520c, 520d illustrated in FIG. 6A may include some or all of the same or similar components to those of the detection channels 120 illustrated in FIGS. 2A-3B. For example, different detection channel 520a, 520b, 520c, 520d may include one or more image sensors or photodetectors arrays, and may include transmissive and/or reflective optics such as one or more lenses (e.g., tube lenses) that focus the light received by the detection channel onto its respective image sensor or photodetector array.

The objective lens 510 is disposed to receive emission light emitted by fluorescence from a specimen. In particular, the first dichroic filter 530 is disposed to receive the emission light collected and transmitted by the objective lens 510. As discussed above and shown in FIG. 6A, in some designs, an illumination source (e.g., the illumination source 115 of FIGS. 2A and 2B) such as a laser source or the like is disposed to provide an excitation beam which is incident on the first dichroic filter 530 such that the first dichroic filter 530 reflects the excitation beam into the same objective lens 510 that transmits the emission light, for example, in an epifluorescence configuration. In some other designs, the illumination source may be directed to the specimen by other optical components along a different optical path that does not include the same objective lens 510. In such configurations, the first dichroic filter 530 may be omitted.

Similarly, as discussed above and shown in FIG. 6A, the detection optics (e.g., including the detection channels 520a, 520b, 520c, 520d and any optical components such as dichroic filters 535, 540a, 540b along the optical path between the objective lens 510 and the detection channels 520a, 520b, 520c, 520d) may be disposed on the transmission path of the first dichroic filter 530, rather than on the reflected path of the first dichroic filter 530. In one example implementations, the objective lens 510 and detection optics are disposed such that the objective lens 510 transmits the beam 550 of emission light directly toward the second dichroic filter 535. The wavefront quality of the emission light may be degraded somewhat by the presence of the first dichroic filter 530 along the path of the beam 550 of emission light (e.g., by imparting some wavefront error to the beam 550). However, the wavefront error introduced by a beam transmitted through a dichroic reflector of a dichroic beam splitter is generally significantly smaller than the wavefront error of a beam reflected from the dichroic reflecting surface of a dichroic beam splitter (e.g., an order of magnitude smaller). Thus, the wavefront quality and subsequent imaging quality of the emission light in a multi-channel fluorescence imaging module may be substantially improved by placing the detection optics along the transmitted beam path of the first dichroic filter 530 rather than along the reflected beam path.

Still referring to FIG. 6A, within the detection optics of the imaging module 500, dichroic filters 535, 540a, and 540b are provided to split the beam 550 of emission light among the detection channels 520a, 520b, 520c, 520d. For example, the dichroic filters 535, 540a, and 540b split the beam 550 on the basis of wavelength, such that a first wavelength or wavelength band of the emission light can be received by the first detection channel 520a, a second wavelength or wavelength band of the emission light can be received by the second detection channel 520b, a third wavelength or wavelength band of the emission light can be received by the third detection channel 520c, and a fourth wavelength or wavelength band of the emission light can be received by the fourth detection channel 520d. In some implementations, multiple separated wavelengths or wavelength bands can be received by the detection channel.

In contrast to the multi-channel fluorescence imaging module design shown in FIGS. 2A and 2B, as well as FIGS. 3A and 3B, the imaging module 500 has dichroic filters 535, 540a, and 540b disposed at angles of incidence of less than 45 degrees with respect to the central beam axis of the incident beams. As shown in FIG. 6B, the different beams 550, 550a, 550b have respective central beam axes 552, 552a, 552b. In various implementations, the central beam axes 552, 552a, 552b is at the center of a cross-section of the beam orthogonal to the propagation direction of the beam. These central beam axes 552, 552a, 552b may correspond to the optical axis of the objective lens and/or the optics within the separate channels, for example, the optical axes of the respective tube lenses. Additional rays 554, 554a, 554b of each beam 550, 550a, 550b are illustrated in FIG. 6B to indicate the diameter of each beam 550, 550a, 550b. Beam diameter may be defined, for example, as a full width at half maximum diameter, a D4σ (e.g., 4 times σ, where σ is the standard deviation of the horizontal or vertical marginal distribution of the beam respectively) or second-moment width, or any other suitable definition of beam diameter.

The central beam axis 552 of the beam 550 of emission light may serve as a reference point for defining the angle of incidence of the beam 550 on the second dichroic filter 535. Accordingly, the "angle of incidence" (AOI) of a beam 550 may be the angle between the central beam axis 552 of the incident beam 550 and a line N normal to the surface the beam is incident on, for example, the dichroic reflective surface. When the beam 550 of emission light is incident upon the dichroic reflective surface of the second dichroic filter 535 at an angle of incidence AOI, the second dichroic filter 535 transmits a first portion 550a of the emission light (e.g., the portion having wavelengths within the passband region of the second dichroic filter 535) and reflects a second portion 550b of the emission light (e.g., the portion having wavelengths within the stopband region of the second dichroic filter 535). The first portion 550a and the second portion 550b may each be similarly described in terms of a central beam axis 552a, 552b. As referred to above, the optical axis may alternatively or additionally be used.

In the example configuration of FIGS. 6A and 6B, the second dichroic filter 535 is disposed such that the central beam axis 552 of the beam 550 is incident at an angle of incidence of 30 degrees. Similarly, the additional dichroic filters 540a, 540b are disposed such that the central beam axes 552a, 552b of the first and second portions 550a, 550b of the beam 550 are also incident at angles of incidence of 30 degrees. However, in various implementations these angles of incidence may be other angles smaller than 45 degrees. In some instances, for example, the angles of incidence may range between about 20 degrees and about 45 degrees, as will be discussed further below. Moreover, the angles of incidence on each of the dichroic filters 535, 540a, 540b need not necessarily be the same. In some embodiments, some or all of the dichroic filters 535, 540a, 540b may be disposed such that their incident beams 550, 550a, 550b have different angles of incidence. As described above, the angle of incidence may be with respect to the optical axis of the optics within the imaging module, for example, the objective lens and/or the optics in the detection channels (e.g., the tube lenses) and the dichroic reflective surface in the respective dichroic beam splitter. The same ranges and values for the angle of incidence apply to the case when the optical axis is used to specify the AOI.

The beams 550, 550a, 550b of emission light in a fluorescence imaging module system are typically diverging beams. As noted above, the beams of emission light can have a beam divergence large enough that regions of the beam within the beam diameter are incident upon the dichroic filters at angles of incidence that differ by up to 5 degrees or more relative to the angle of incidence of the central beam axis and/or optical axis of the optics. In some designs, the objective lens 510 may be configured, for example, to have an f-number or numerical aperture selected to produce a smaller beam diameter for a given field-of-view of the microscope. In one example, the f-number or numerical aperture of the objective lens 510 may be selected such that the full diameter of the beams 550, 550a, 550b are incident upon dichroic filters 535, 540a, 540b at angles of incidence within, for example, 1 degree, 1.5 degrees, 2 degrees, 2.5 degrees, 3 degrees, 3.5 degrees, 4 degrees, 4.5 degrees, or 5 degrees of the angle of incidence of the central beam axes 552, 552a, 552b.

In some implementations, the focal length of the objective lens that is suitable for producing such a narrow beam diameter may be longer than those typically employed in fluorescence microscopes or imaging systems. For example, in some implementations, the focal length of the objective lens may range between 20 mm and 40 mm, as will be discussed further below. In one example, an objective lens 510 having a focal length of 36 mm may produce a beam 550 characterized by a divergence small enough that light across the full diameter of the beam 550 is incident upon the second dichroic filter 535 at angles within 2.5 degrees of the angle of incidence of the central beam axis.

Figure 7:
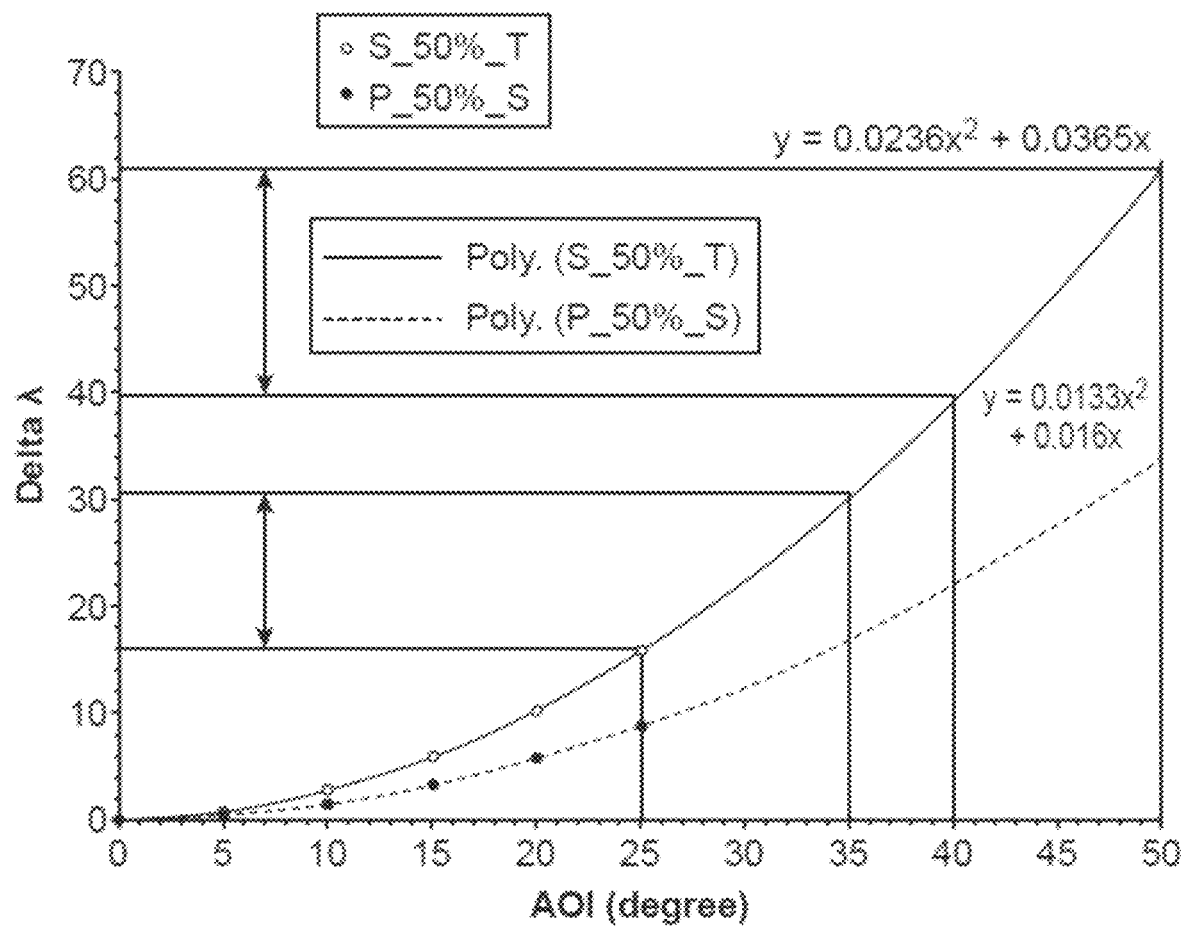
FIG. 7 provides a graph illustrating improved dichroic filter performance corresponding to the imaging module configuration illustrated in FIGS. 6A and 6B.
Figure 8:
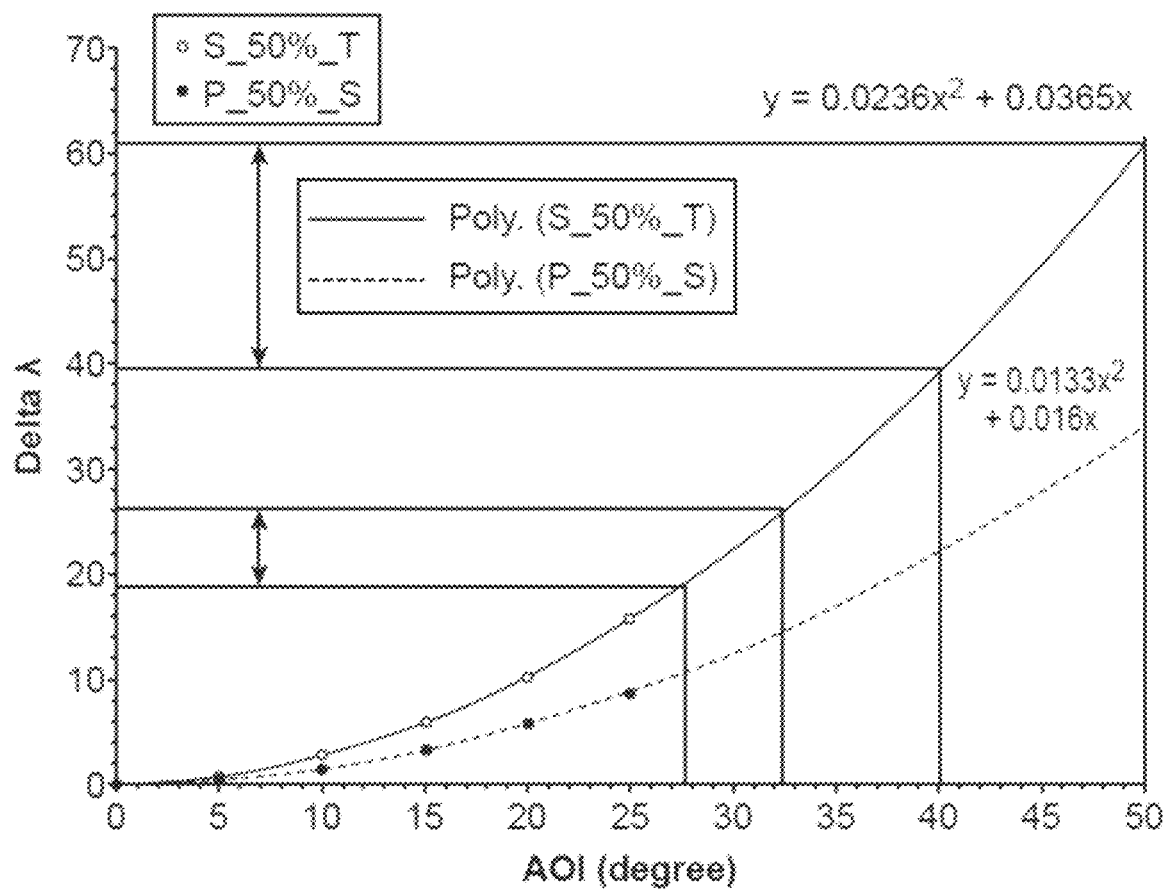
FIG. 8 provides a graph illustrating improved dichroic filter performance corresponding to the imaging module configuration illustrated in FIGS. 6A and 6B.

FIG. 7 and FIG. 8 provide graphs illustrating improved dichroic filter performance due to aspects of the imaging module configuration of FIGS. 6A and 6B (or any of the imaging module configurations disclosed herein). The graph in FIG. 7 is similar to that of FIG. 4 and illustrates the effect of angle of incidence on the transition width (e.g., the spectral span of the transmission edge) of a dichroic filter. FIG. 7 shows an example where the orientation of a dichroic filter (e.g., dichroic filters 535, 540a, and 540b) and the dichroic reflective surface therein is such that its incident beam has an angle of incidence of 30 degrees, rather than 45 degrees. FIG. 7 shows how this reduced angle of incidence significantly improves the sharpness and the uniformity of the transition width across the full beam diameter. For example, while an angle of incidence of 45 degrees at the central beam axis results in a range of transition widths between about 40 nm and about 62 nm, an angle of incidence of 30 degrees at the central beam axis results in a range of transition widths between about 16 nm and about 30 nm. In this example, the average transition width is reduced from about 51 nm to about 23 nm, indicating a sharper transition between passband and stopband. Moreover, the variation in transition widths across the beam diameter is reduced by nearly 40% from a 22 nm range to a 14 nm range, indicating a more uniform sharpness of the transition over the area of the beam.

FIG. 8 illustrates additional advantages that may be realized by selecting the appropriate f-number or numerical aperture for the objective lens to reduce beam divergence in any of the imaging module configurations disclosed herein. In some implementations, a longer focal length is used. In the example of FIG. 8, the objective lens 510 has a focal length of 36 mm, which with the appropriate numerical aperture (e.g., less than 5), reduces the range of angles of incidence within the beam 550 from 30 degrees±5 degrees to 30 degrees±2.5 degrees. With this design, the range of transition widths may be reduced to between about 19 nm and about 26 nm. When compared to the improved system of FIG. 7, although the average transition width is substantially the same (e.g., a spectral span of roughly 23 nm), the variation in transition widths across the beam diameter is further reduced to a 7 nm range, representing a reduction of nearly 70% relative to the range of transition widths illustrated in FIG. 4.

Referring again to FIG. 5, the reduction in angle of incidence from 45 degrees to 30 degrees at the central beam axis is further advantageous because it reduces the beam spot size on the dichroic filter. As shown in FIG. 5, an angle of incidence of 45 degrees results in a beam footprint on the dichroic filter having an area greater than 1.4 times the cross-sectional area of the beam. However, an angle of incidence of 30 degrees results in a beam footprint on the dichroic filter having an area only about 1.15 times the cross-sectional area of the beam. Thus, reducing the angle of incidence at the dichroic filters 535, 540a, 540b from 45 degrees to 30 degrees results in a reduction of about 18% in the area of the beam footprint on the dichroic filters 535, 540a, 540b. This reduction in beam footprint area allows smaller dichroic filters to be used.

Figure 9A:
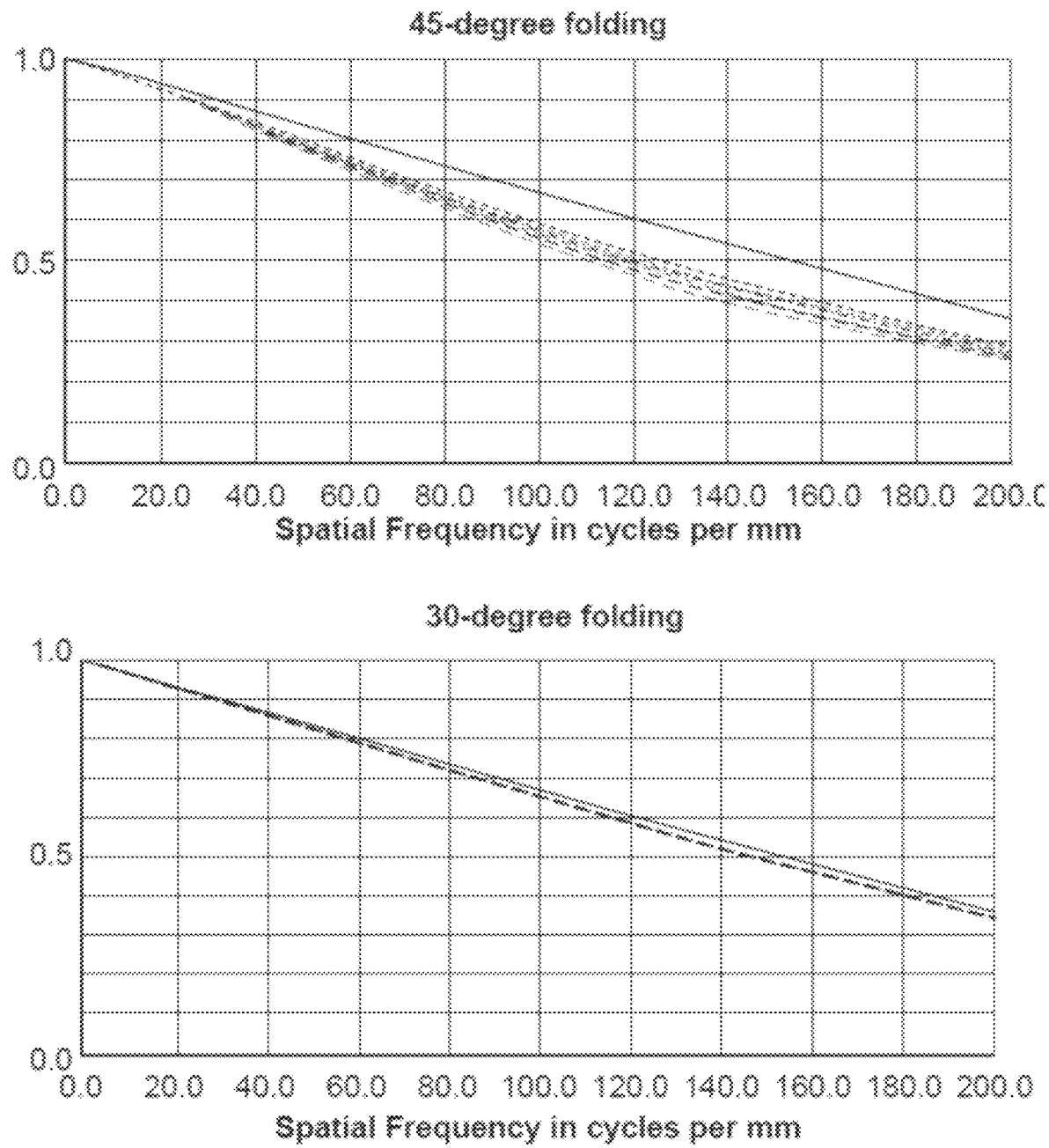
FIGS. 9A-9B provide graphs illustrating reduced surface deformation resulting from the imaging module configuration of FIGS. 6A and 6B.
Figure 9B:
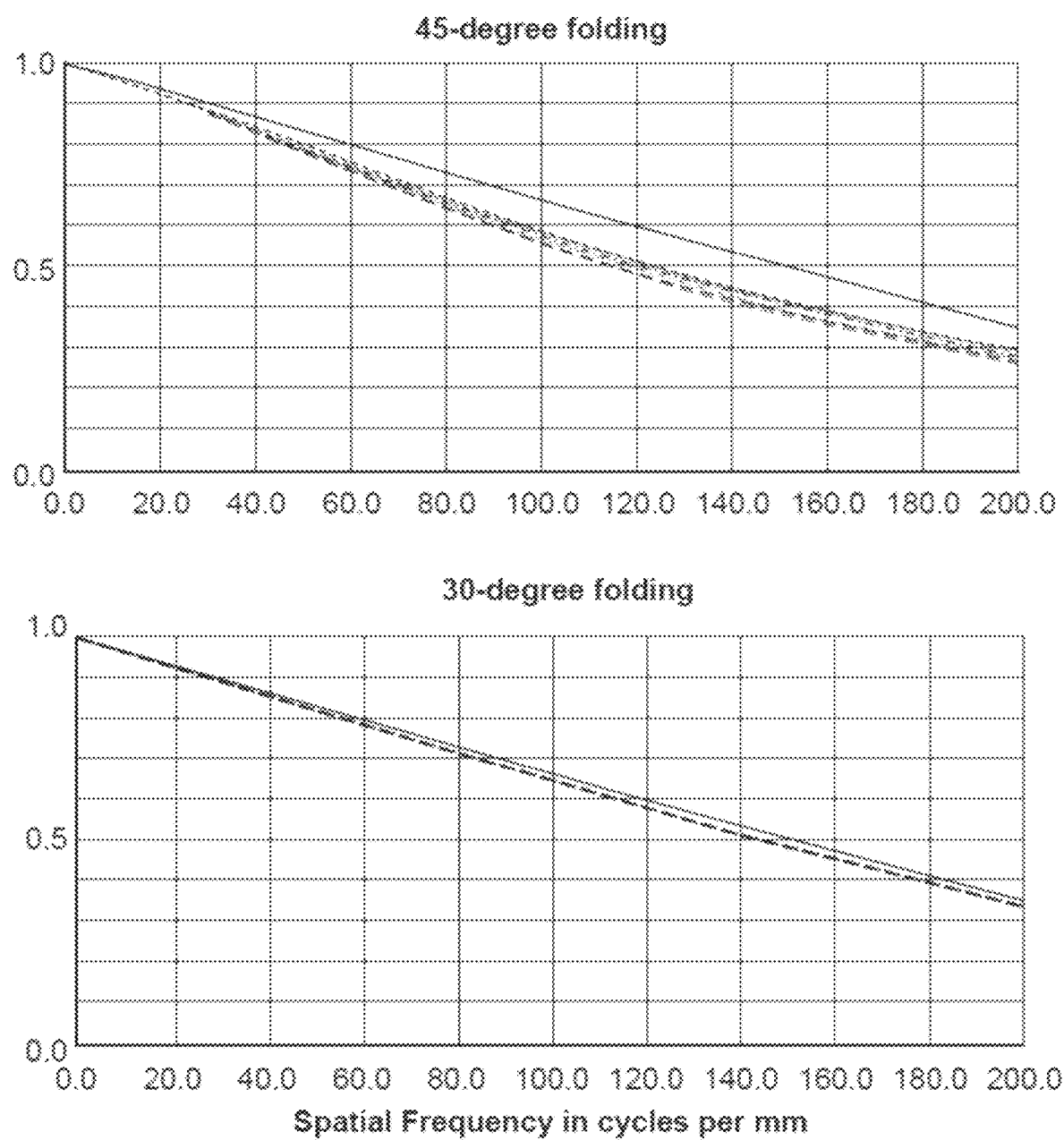

Referring now jointly to FIGS. 9A-B, the reduction in angle of incidence from 45 degrees to 30 degrees may also provide improved performance with regard to surface deformation caused by the dichroic filters in any of the imaging module configurations disclosed herein, as indicated by improvements in the modulation transfer function. In general, the amount of surface deformation increases with larger area optical elements. If a larger area on the dichroic filter is employed, a larger amount of surface deformation is encountered, thereby introducing more wavefront error into the beam. FIG. 9A illustrates the effect of folding angle on image quality degradation induced by the addition of 1 wave of peak-to-valley (PV) spherical power to the last mirror. FIG. 9B illustrates the effect of folding angle on image quality degradation induced by the addition of 0.1 wave of PV spherical power to the last mirror. As shown in FIGS. 9A and 9B, the reduction in angle of incidence to 30 degrees significantly reduces the effect of surface deformation to achieve close to diffraction-limited performance of the detection optics.

In some implementations of the disclosed imaging modules, the polarization state of the excitation beam may be utilized to further improve the performance of the multi-channel fluorescence imaging modules disclosed herein. Referring back to FIGS. 2A, 2B, and 6A, for example, some implementations of the multi-channel fluorescence imaging modules disclosed herein have an epifluorescence configuration in which a first dichroic filter 130 or 530 merges the optical paths of the excitation beam and the beam of emission light such that both the excitation and emission light are transmitted through the objective lens 110, 510. As discussed above, the illumination source 115 may include a light source such as a laser or other source which provides the light that forms the excitation beam. In some designs, the light source comprises a linearly polarized light source and the excitation beam may be linearly polarized. In some designs, polarization optics are included to polarize the light and/or rotate the polarization of the light. For example, a polarizer such as a linear polarizer may be included in an optical path of the excitation beam to polarize the excitation beam. Retarders such as half wave retarders or a plurality of quarter wave retarders or retarders having other amounts of retardance may be included to rotate the linear polarization in some designs.

The linearly polarized excitation beam, when it is incident upon any dichroic filter or other planar interface, may be p-polarized (e.g., having an electric field component parallel to the plane of incidence), s-polarized (e.g., having an electric field component normal to the plane of incidence), or may have a combination of p-polarization and s-polarization states within the beam. The p- or s-polarization state of the excitation beam may be selected and/or changed by selecting the orientation of the illumination source 115 and/or one or more components thereof with respect to the first dichroic filter 130, 530 and/or with respect to any other surfaces with which the excitation beam will interact. In some implementations where the light source outputs linearly polarized light, the light source can be configured to provide s-polarized light. For example, the light source may comprise an emitter such as a solid-state laser or a laser diode that may be rotated about its optical axis or the central axis of the beam to orient the linearly polarized light output therefrom. Alternatively, or in addition, retarders may be employed to rotate the linear polarization about the optical axis or the central axis of the beam. As discussed above, in some implementations, for example when the light source does not output polarized light, a polarizer disposed in the optical path of the excitation beam can polarize the excitation beam. In some designs, for example, a linear polarizer is disposed in the optical path of the excitation beam. This polarizer may be rotated to provide the proper orientation of the linear polarization to provide s-polarized light.

In some designs, the linear polarization is rotated about the optical axis or the central axis of the beam such that s-polarization is incident on the dichroic reflector of the dichroic beam splitter. When s-polarized light is incident on the dichroic reflector of the dichroic beam splitter the transition between the pass band and the stop band is sharper as opposed to when p-polarized light is incident on the dichroic reflector of the dichroic beam splitter.

Figure 10A:
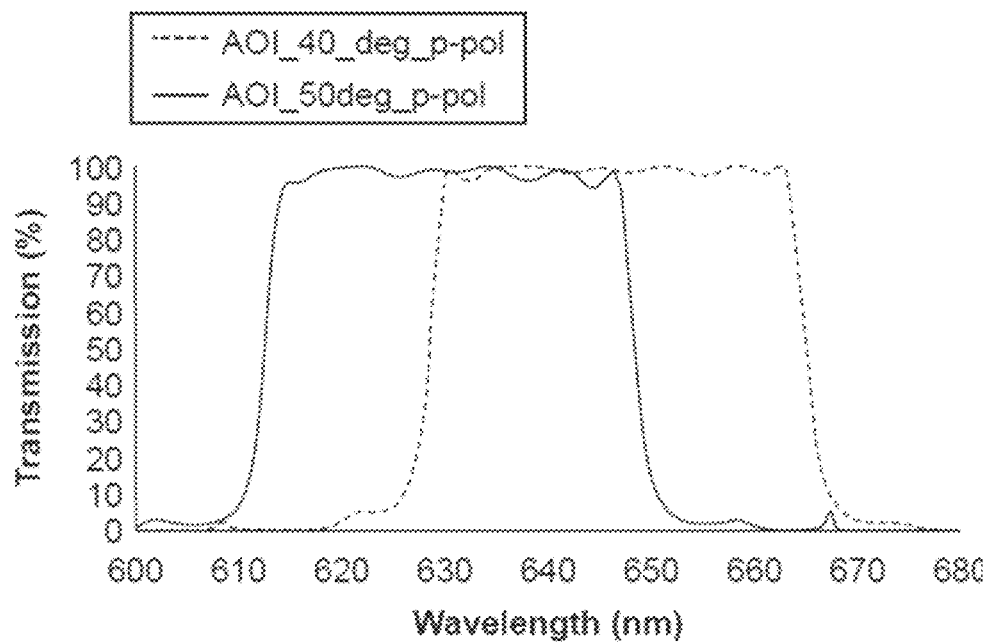
FIGS. 10A-10B provide graphs illustrating improved excitation filter performance (e.g. sharper transitions between pass bands and surrounding stop bands) resulting from use of s-polarization of the excitation beam.
Figure 10B:
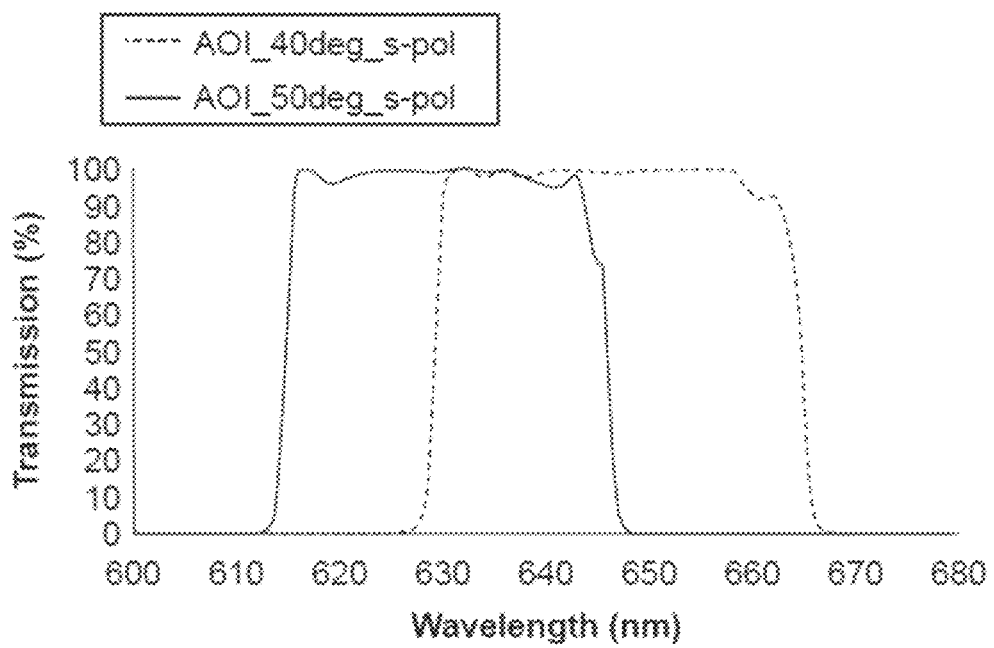

As shown in FIGS. 10A and 10B, use of the p- or s-polarization state of the excitation beam may significantly affect the narrowband performance of any excitation filters such as the first dichroic filter 130, 530. FIG. 10A illustrates a transmission spectrum between 610 nm and 670 nm for an example bandpass dichroic filter at angles of incidence of 40 degrees and 45 degrees, where the incident beam is linearly polarized and is p-polarized with respect to the plane of the dichroic filter. As shown in FIG. 10B, changing the orientation of the light source with respect to the dichroic filter, such that the incident beam is s-polarized with respect to the plane of the dichroic filter, results in a substantially sharper edge between the passband and the stopband of the dichroic filter. Thus, the illumination and imaging modules 100, 500 disclosed herein may advantageously have an illumination source 115 oriented relative to the first dichroic filter 130, 530 such that the excitation beam is s-polarized with respect to the plane of the first dichroic filter 130, 530. As discussed above, in some implementations, a polarizer such as a linear polarizer may be used to polarize the excitation beam. This polarizer may be rotated to provide an orientation of the linearly polarized light corresponding to s-polarized light. Also as discussed above, in some implementations, other approaches to rotating the linearly polarized light may be used. For example, optical retarders such as half wave retarders or multiple quarter wave retarders may be used to rotate the polarization direction. Other arrangements are also possible.

As discussed elsewhere herein, reducing the numerical aperture (NA) of the fluorescence imaging module and/or of the objective lens may increase the depth of field to enable the comparable imaging of the two surfaces. FIGS. 11A-16B, show how the MTF is more similar at first and second surfaces separated by 1 mm of glass for lower numerical apertures than for larger numerical apertures.

Figure 11A:
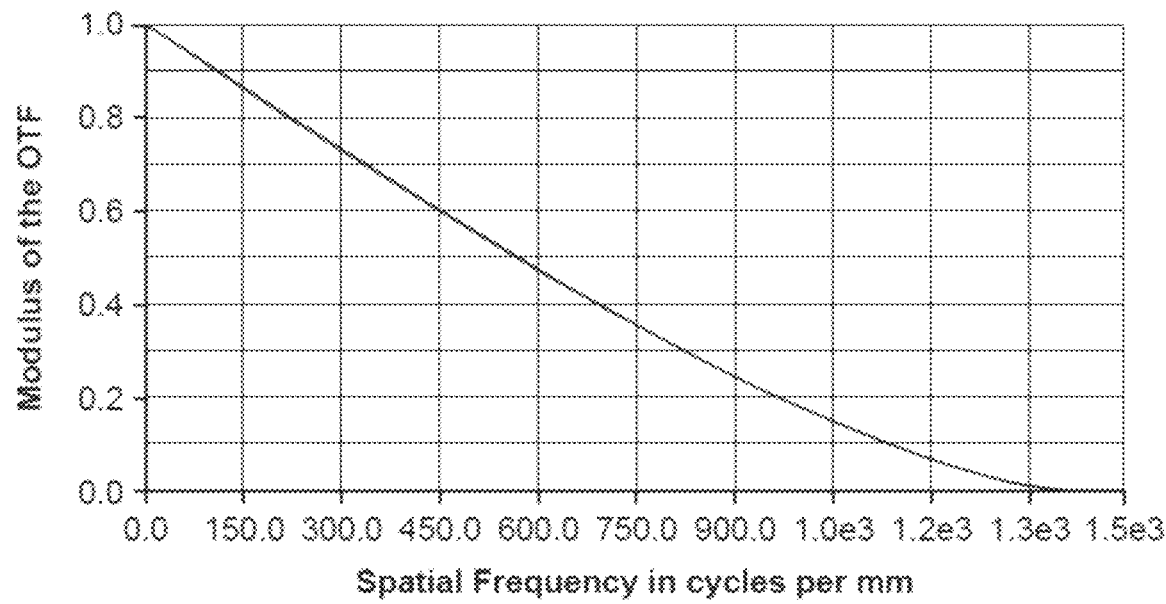
FIGS. 11A-11B illustrate the modulation transfer function (MTF) of an example dual surface imaging system disclosed herein having a numerical aperture (NA) of 0.3.
Figure 11B:
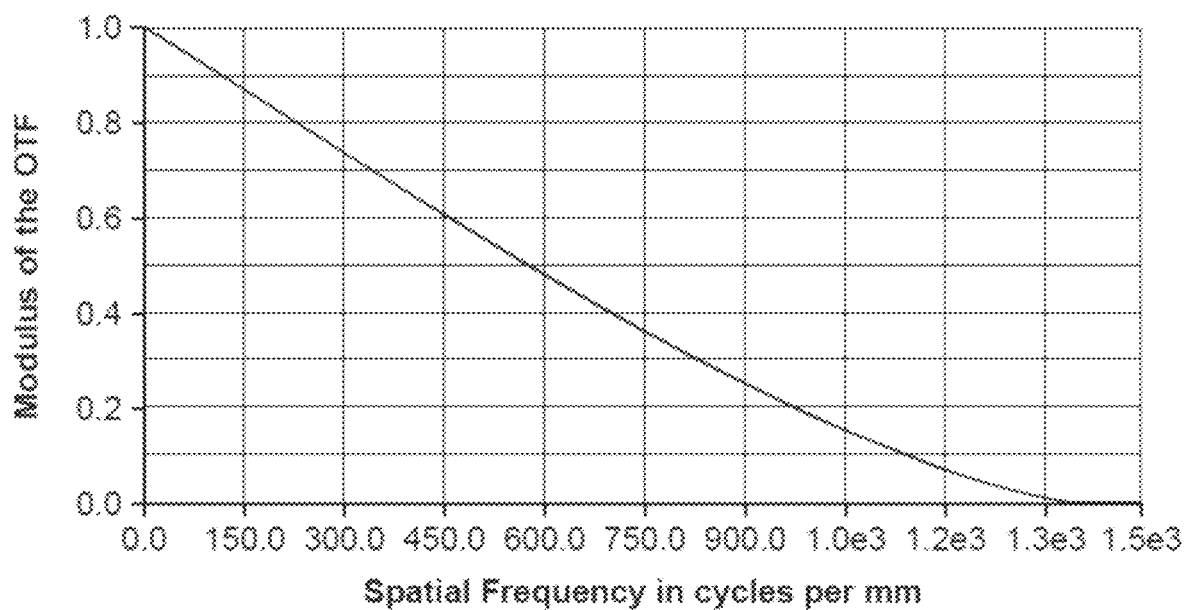

FIGS. 11A and 11B show the MTF at first (FIG. 11A) and second (FIG. 11B) surfaces for an NA of 0.3.

Figure 12A:
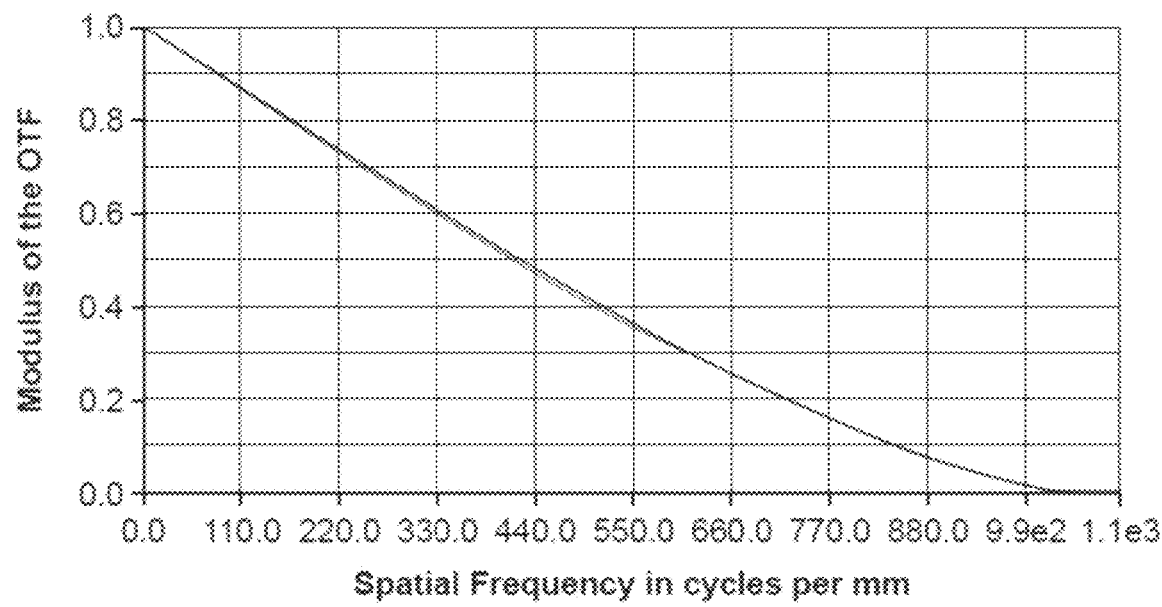
FIGS. 12A-12B illustrate the MTF of an example dual surface imaging system disclosed herein having an NA of 0.4.
Figure 12B:
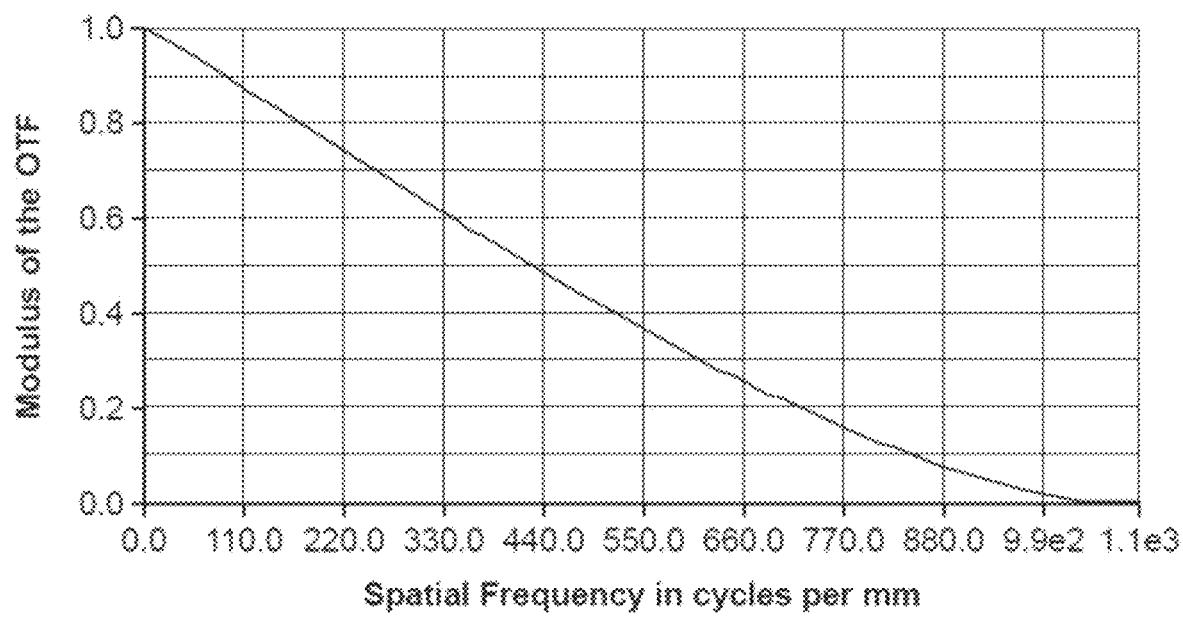

FIGS. 12A and 12B show the MTF at first (FIG. 12A) and second (FIG. 12B) surfaces for an NA of 0.4.

Figure 13A:
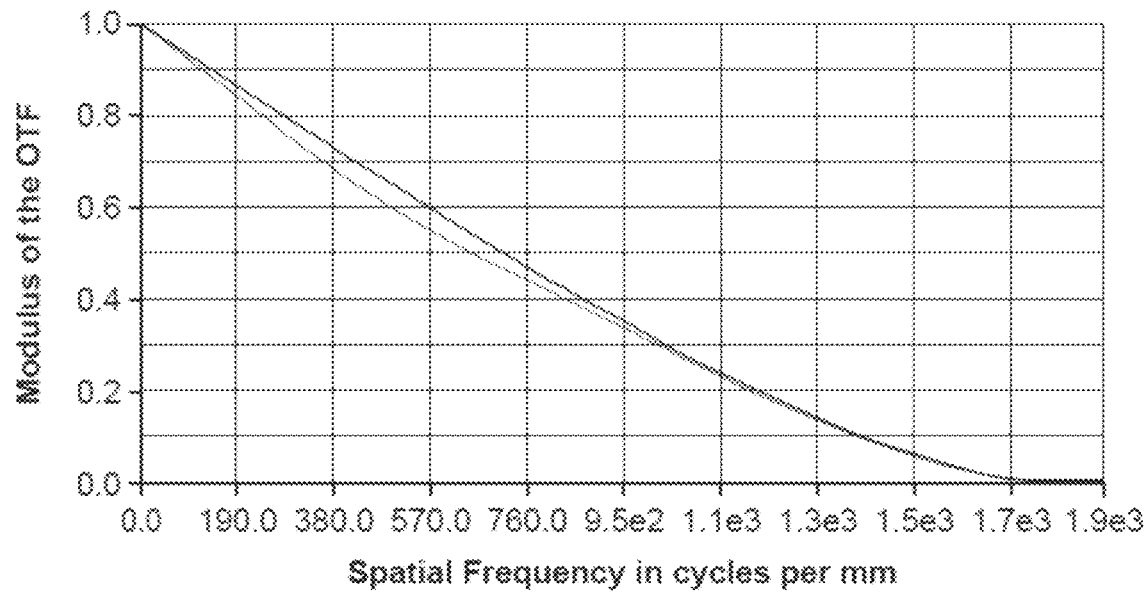
FIGS. 13A-13B illustrate the MTF of an example dual surface imaging system disclosed herein having an NA of 0.5.
Figure 13B:
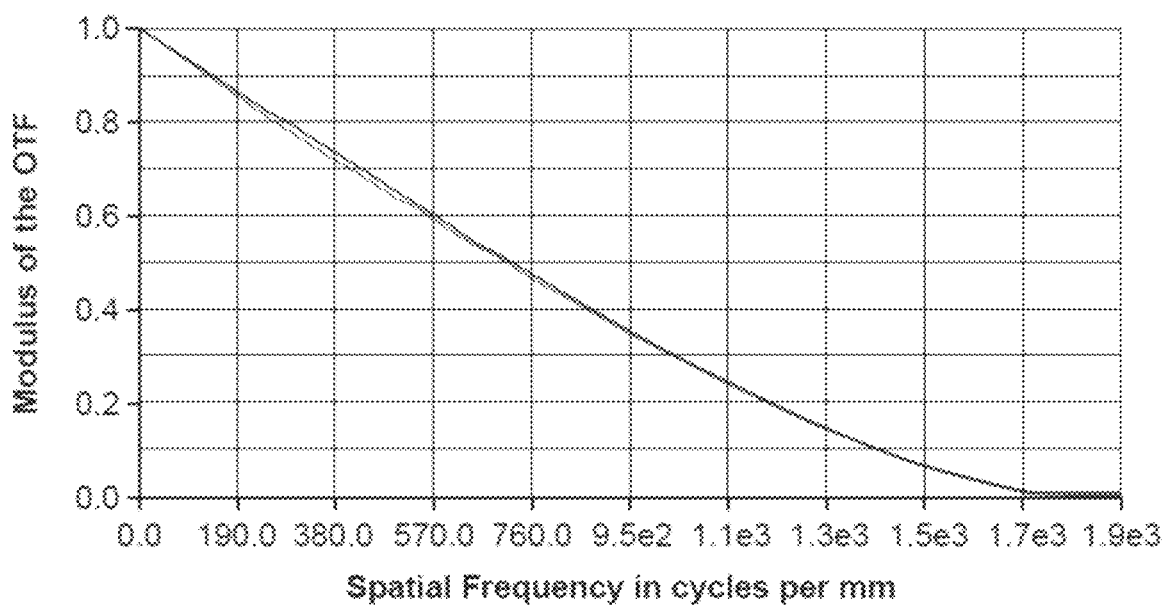

FIGS. 13A and 13B show the MTF at first (FIG. 13A) and second (FIG. 13B) surfaces for an NA of 0.5.

Figure 14A:
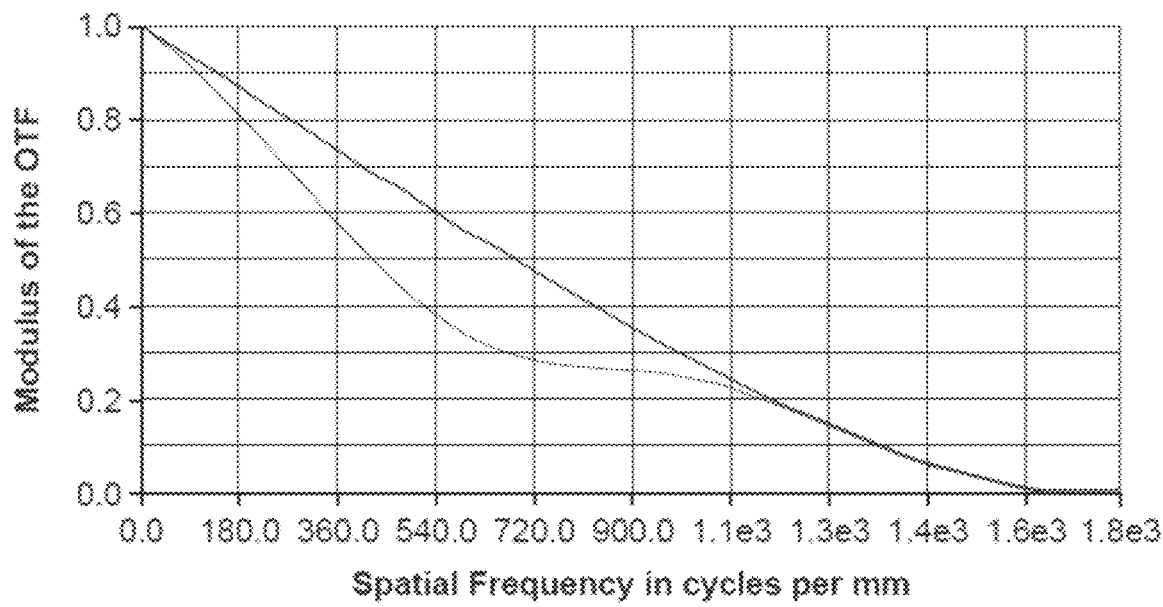
FIGS. 14A-14B illustrate the MTF of an example dual surface imaging system disclosed herein having an NA of 0.6.
Figure 14B:
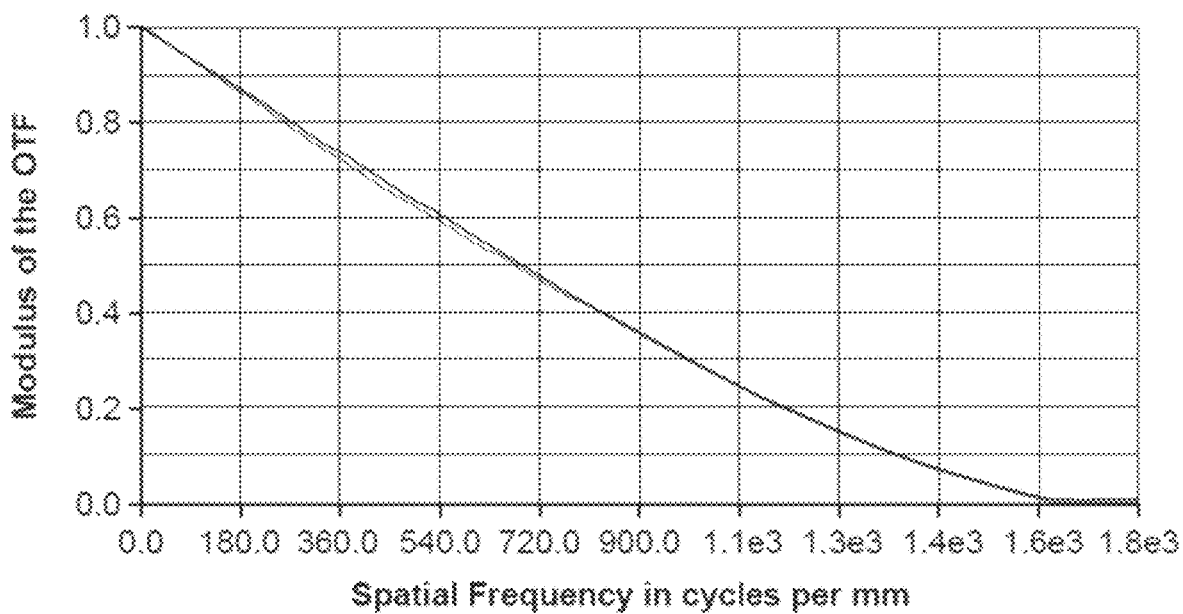

FIGS. 14A and 14B show the MTF at first (FIG. 14A) and second (FIG. 14B) surfaces for an NA of 0.6.

Figure 15A:
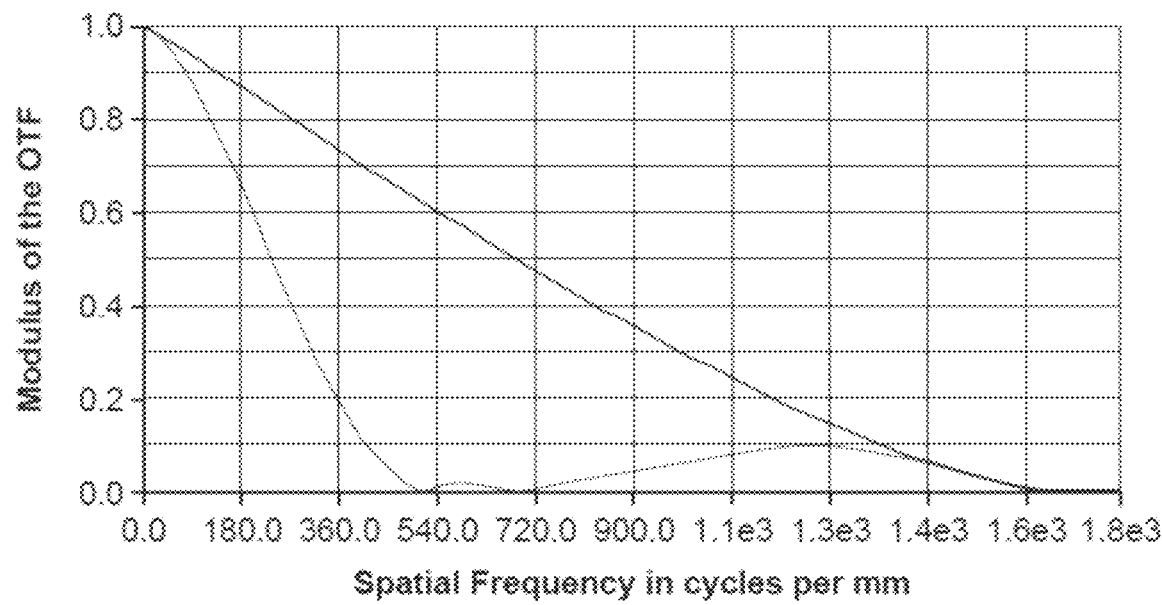
FIGS. 15A-15B illustrate the MTF of an example dual surface imaging system disclosed herein having an NA of 0.7.
Figure 15B:
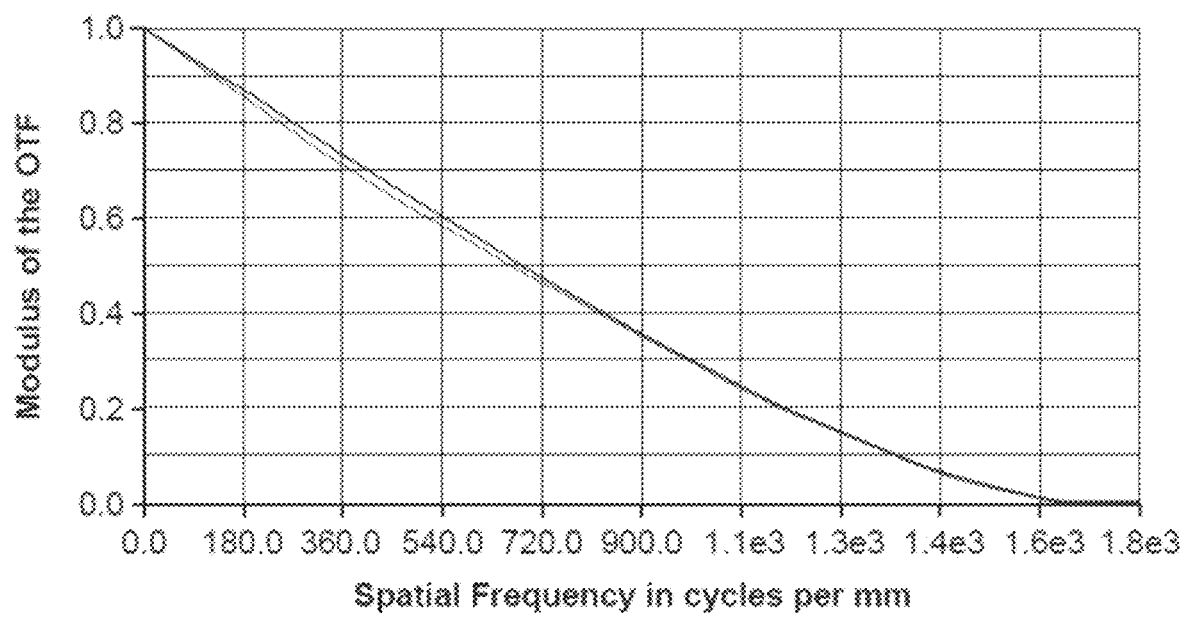

FIGS. 15A and 15B show the MTF at first (FIG. 15A) and second (FIG. 15B) surfaces for an NA of 0.7.

Figure 16A:
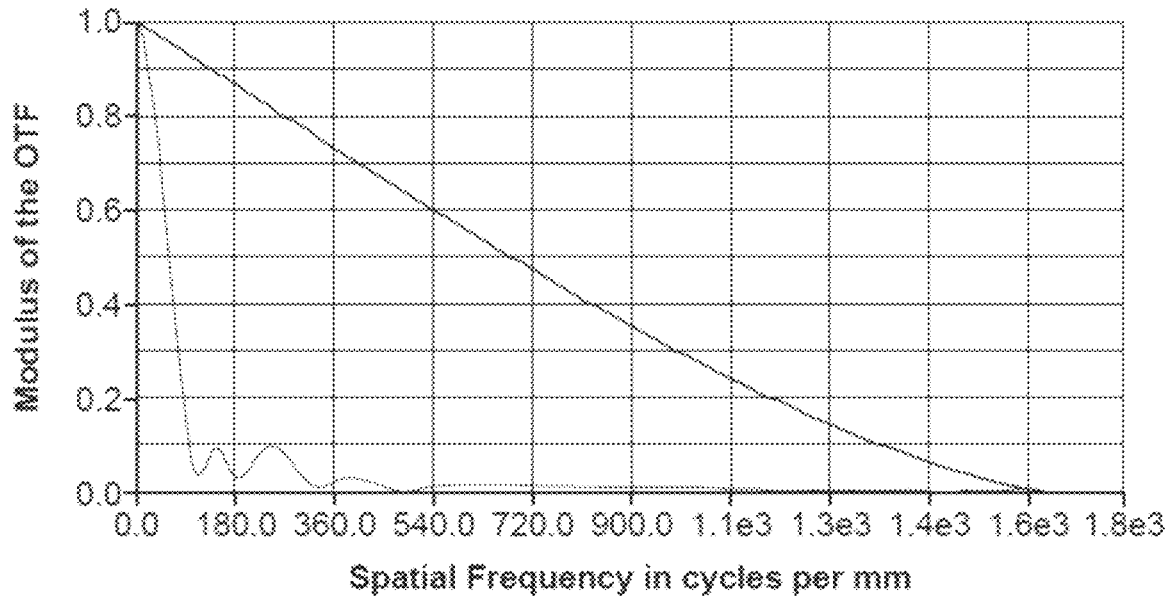
FIGS. 16A-16B illustrate the MTF of an example dual surface imaging system disclosed herein having an NA of 0.8.
Figure 16B:
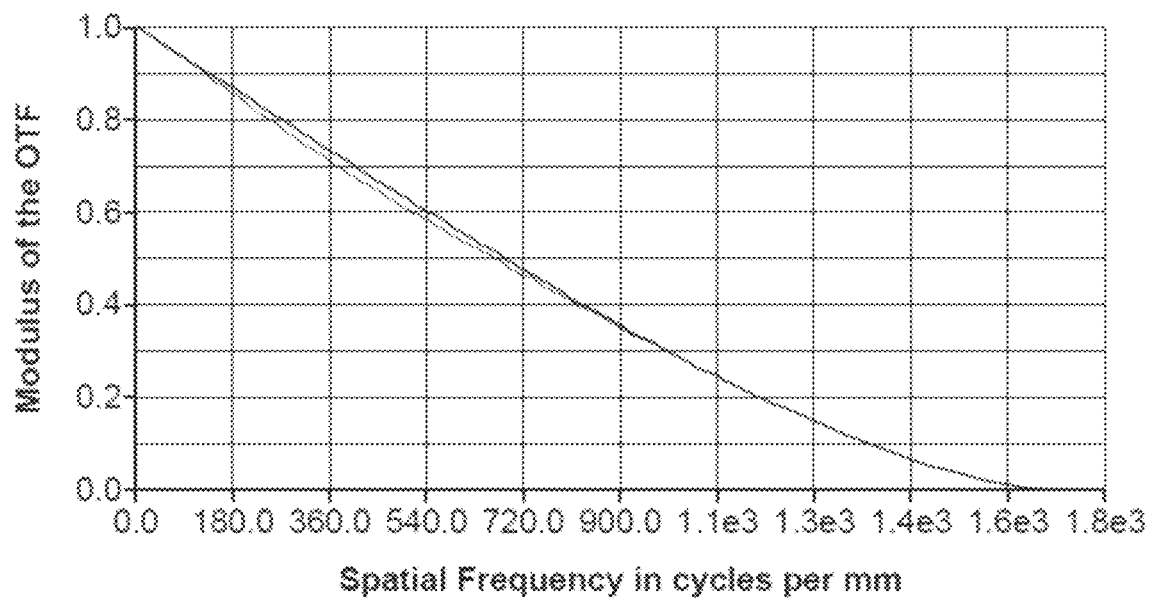

FIGS. 16A and 16B show the MTF at first (FIG. 16A) and second (FIG. 16B) surfaces for an NA of 0.8. The first and second surfaces in each of these figures correspond to, e.g., the top and bottom surfaces of a flow cell.

Figure 17A:
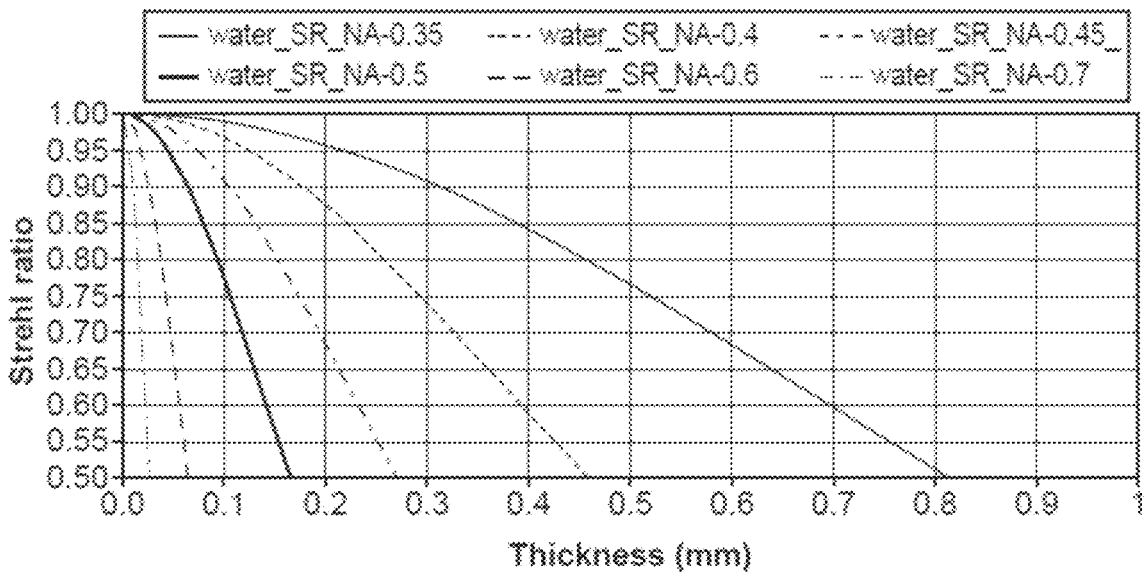
FIGS. 17A-17B provide plots of the calculated Strehl ratio for imaging a second flow cell surface through a first flow cell surface.
Figure 17B:
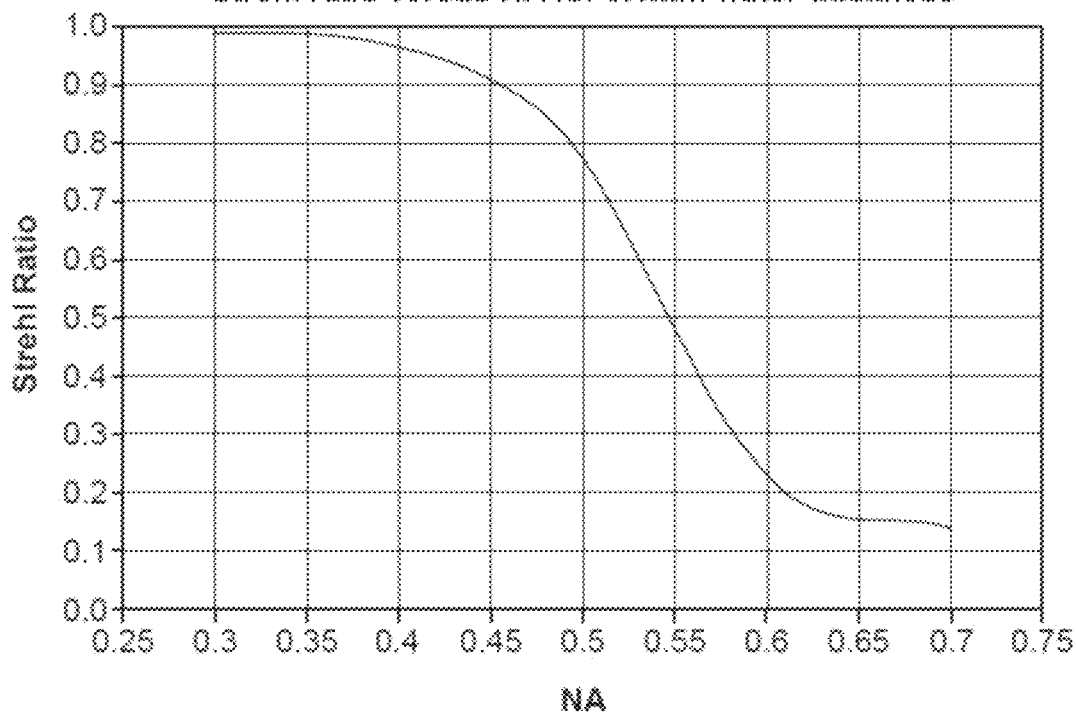

FIGS. 17A-B provide plots of the calculated Strehl ratio (e.g., the ratio of peak light intensity focused or collected by the optical system versus that focused or collected by an ideal optical system and point light source) for imaging a second flow cell surface through a first flow cell surface. FIG. 17A shows a plot of the Strehl ratios for imaging a second flow cell surface through a first flow cell surface as a function of the thickness of the intervening fluid layer (fluid channel height) for different objective lens and/or optical system numerical apertures. As shown, the Strehl ratio decreases with increasing separation between the first and second surfaces. One of the surfaces can thus have deteriorated image quality with increasing separation between the two surfaces. The decrease in second surface imaging performance with increased separation distance between the two surfaces is reduced for imaging systems having smaller numerical apertures as compared to those having larger numerical apertures. FIG. 17B shows a plot of the Strehl ratio as a function of numerical aperture for imaging a second flow cell surface through a first flow cell surface and an intervening layer of water having a thickness of 0.1 mm. The loss of imaging performance at higher numerical apertures may be attributed to the increased optical aberration induced by the fluid for the second surface imaging. With increasing NA, the increased optical aberration introduced by the fluid for the second surface imaging degrades the image quality significantly. In general, however, reducing the numerical aperture of the optical system reduces the achievable resolution. This loss of image quality can be at least partially offset by providing an increased sample plane (or object plane) contrast-to-noise ratio, for example, by using chemistries for nucleic acid sequencing applications that enhance the fluorescence emission for labeled nucleic acid clusters and/or that reduce background fluorescence emission. In some instances, for example, sample support structures comprising hydrophilic substrate materials and/or hydrophilic coatings may be employed. In some cases, such hydrophilic substrates and/or hydrophilic coatings may reduce background noise. Additional discussion of sample support structures, hydrophilic surfaces and coatings, and methods for enhancing contrast-to-noise ratios, e.g., for nucleic acid sequencing applications, can be found below.

In some implementations, any one or more of the fluorescence imaging system, the illumination and imaging module 100, the imaging optics (e.g., optics 126), the objective lens, and/or the tube lens is configured to have reduced magnification, such as a magnification of less than 10×, as will be discussed further below. Such reduced magnification may adjust design constraints such that other design parameters can be achieved. For example, any one or more of the fluorescence microscope, illumination and imaging module 100, the imaging optics (e.g., optics 126), the objective lens or the tube lens may also be configured such that the fluorescence imaging module has a large field-of-view (FOV), for example, a field-of-view of at least 3.0 mm or larger (e.g., in diameter, width, height, or longest dimension), as will be discussed further below. Any one or more of the fluorescence imaging system, the illumination and imaging module 100, the imaging optics (e.g., optics 126), the objective lens and/or the tube lens may be configured to provide the fluorescence microscope with such a field-of-view such that the FOV has less than, e.g., 0.1 waves of aberration over at least 80% of field. Similarly, any one or more of the fluorescence imaging system, illumination and imaging module 100, the imaging optics (e.g., optics 126), the objective lens and/or the tube lens may be configured such that the fluorescence imaging module has such a FOV and is diffraction limited or is diffraction limited over such an FOV.

As discussed above, in various implementations, a large field-of-view (FOV) is provided by the disclosed optical systems. In some implementations, obtaining an increased FOV is facilitated in part by the use of larger image sensors or photodetector arrays. The photodetector array, for example, may have an active area with a diagonal of at least 15 mm or larger, as will be discussed further below. As discussed above, in some implementations the disclosed optical imaging systems provide a reduced magnification, for example, of less than 10× which may facilitate large FOV designs. Despite the reduced magnification, the optical resolution of the imaging module may still be sufficient as detector arrays having small pixel size or pitch may be used.

The pixel size and/or pitch may, for example, be about 5 µm or less, as will be discussed in more detail below. In some implementations, the pixel size is smaller than twice the optical resolution provided by the optical imaging system (e.g., objective and tube lens) to satisfy the Nyquist theorem. Accordingly, the pixel dimension and/or pitch for the image sensor(s) may be such that a spatial sampling frequency for the imaging module is at least twice an optical resolution of the imaging module. For example, the spatial sampling frequency for the photodetector array may be is at least 2 times, at least 2.5 times, at least 3 times, at least 4 times, or at least 5 times the optical resolution of the fluorescence imaging module (e.g., the illumination and imaging module, the objective and tube lens, the object lens and optics 126 in the detection channel, the imaging optics between the sample support structure or stage configured to support the sample support stage and the photodetector array) or any spatial sampling frequency in a range between any of these values.

Although a wide range of features are discussed herein with respect to fluorescence imaging modules, any of the features and designs described herein may be applied to other types of optical imaging systems including without limitation bright-field and dark-field imaging, and may apply to luminescence or phosphorescence imaging.

Figure 18:
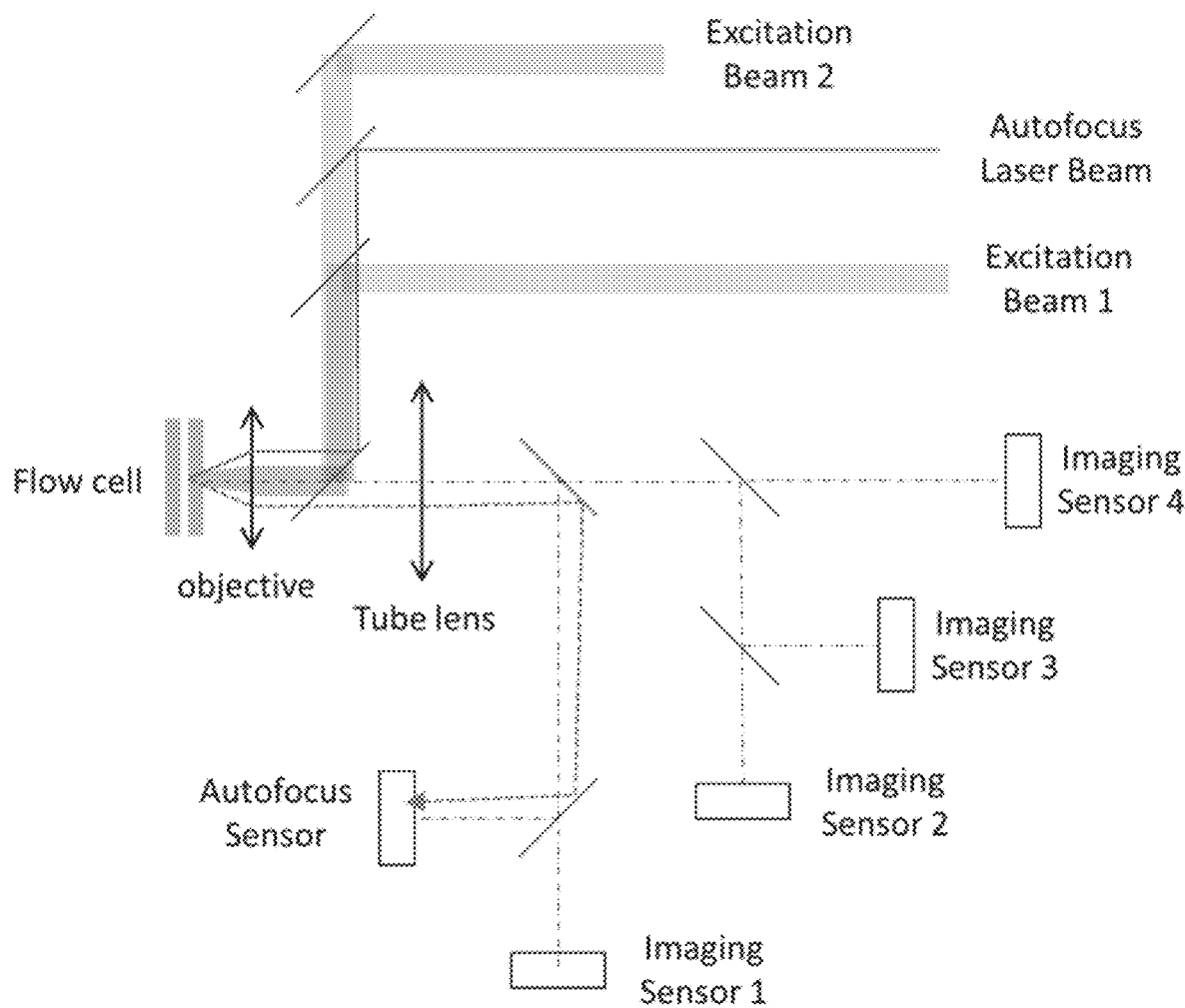
FIG. 18 provides a schematic illustration of a dual-wavelength excitation/four channel emission fluorescence imaging system of the present disclosure.

Dual wavelength excitation four channel imaging system: FIG. 18 illustrates a dual excitation wavelength/four channel imaging system for dual-side imaging applications that includes an objective and tube lens combination that is scanned in a direction perpendicular to the optical axis to provide for large area imaging, e.g., by tiling several images to create a composite image having a total field-of-view (FOV) that is much larger than that for each individual image. The system comprises two excitation light sources, e.g., lasers or laser diodes, operating at different wavelengths and an autofocus laser. The two excitation light beams and autofocus laser beam are combined using a series of mirrors and/or dichroic reflectors and delivered to an upper or lower interior surface of the flow cell through the objective. Fluorescence that is emitted by labeled oligonucleotides (or other biomolecules) tethered to one of the flow cell surfaces is collected by the objective, transmitted through the tube lens, and directed to one of four imaging sensors according to the wavelength of the emitted light by a series of intermediate dichroic reflectors. Autofocus laser light that has been reflected from the flow cell surface is collected by the objective, transmitted through the tube lens, and directed to an autofocus sensor by a series of intermediate dichroic reflectors. The system allows accurate focus to be maintained (e.g., by adjusting the relative distance between the flow cell surface and the objective using a precision linear actuator, translation stage, or microscope turret-mounted focus adjustment mechanism, to reduce or minimize the reflected light spot size on the autofocus image sensor) while the objective/tube lens combination is scanned in a direction perpendicular to the optical axis of the objective. Dual wavelength excitation used in combination with four channel (e.g. four wavelength) imaging capability provides for high-throughput imaging of the upper (near) and lower (far) interior surfaces of the flow cell.

Multiplexed Optical Read-Heads:

In some instances, miniaturized versions of any of the imaging modules described herein may be assembled to create a multiplexed read-head that may be translated in one or more directions horizontally relative to a sample surface, e.g., an interior surface of a flow cell, to image several sections of the surface simultaneously. A non-limiting example of a multiplexed read-head has recently been described in U.S. Published Patent Application No. 2020/0139375 A1.

In some instances, for example, a miniaturized imaging module may comprise a "microfluorometer" comprising an illumination or excitation light source such as an LED or laser diode (or the tip of an optical fiber connected to an external light source), one or more lenses for collimating or focusing the illumination or excitation light, one or more dichroic reflectors, one or more optical filters, one or more mirrors, beam-splitters, prisms, apertures, etc., one or more objectives, one or more custom tube lenses for enabling dual surface imaging with minimal focus adjustment as described elsewhere herein, one or more image sensors, or any combination thereof, as described elsewhere herein. In some instances, a miniaturized imaging module (e.g., a "microfluorometer") may further comprise an autofocus mechanism, a microprocessor, power and data transfer connectors, a light-tight housing, etc. The resulting miniaturized imaging module may thus comprise an integrated imaging package or unit having a small form factor. In some instances, the shortest dimension (e.g., width or diameter) of the miniaturized imaging module may be less than 5 cm, less than 4.5 cm, less than 4 cm, less than 3.5 cm, less than 3 cm, less than 2.5 cm, less than 2 cm, less than 1.8 cm, less than 1.6 cm, less than 1.4 cm, less than 1.2 cm, less than 1 cm, less than 0.8 cm, or less than 0.6 cm. In some instances, the longest dimension (e.g., height or length) of the miniaturized imaging module may be less than 16 cm, less than 14 cm, less than 12 cm, less than 10 cm, less than 9 cm, less than 8 cm, less than 7 cm, less than 5 cm, less than 5 cm, less than 4.5 cm, less than 4 cm, less than 3.5 cm, less than 3 cm, less than 2.5 cm, less than 2 cm, less than 1.8 cm, less than 1.6 cm, less than 1.4 cm, less than 1.2 cm, or less than 1 cm. In some instances, one or more individual miniaturized imaging modules within the multiplexed read-head may comprise an autofocus mechanism.

In some instances, multiplexed read-heads as described herein may comprise an assembly of 2, 3, 4, 5, 6, 7, 8, 9, 10, 11, 12, or more than 12 miniaturized imaging modules or microfluorometers held in fixed position relative to each other. In some instances, the optical design specifications and performance properties of the individual miniaturized imaging modules or microfluorometers, e.g, for numerical aperture, field-of-view, depth-of-field, image resolution, etc., may be the same as described elsewhere herein for other versions of the disclosed imaging modules. In some instances, the plurality of individual miniaturized imaging modules may be arranged in a linear arrangement comprising one, two, three, four, or more than four rows and/or columns. In some instances, the plurality of individual miniaturized imaging modules may be arranged in, e.g., a hexagonal close pack arrangement. In some instances, the plurality of individual miniaturized imaging modules may be arranged in a circular or spiral arrangement, a randomly distributed arrangement, or in any other arrangement known to those of skill in the art.

Figure 43A:
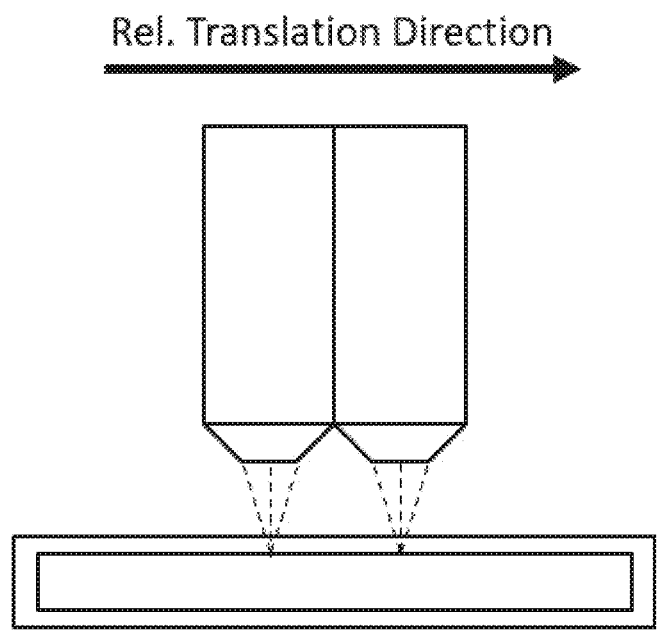
FIGS. 43A-43B provide non-limiting schematic illustrations of a multiplexed read-head as disclosed herein.
Figure 43B:
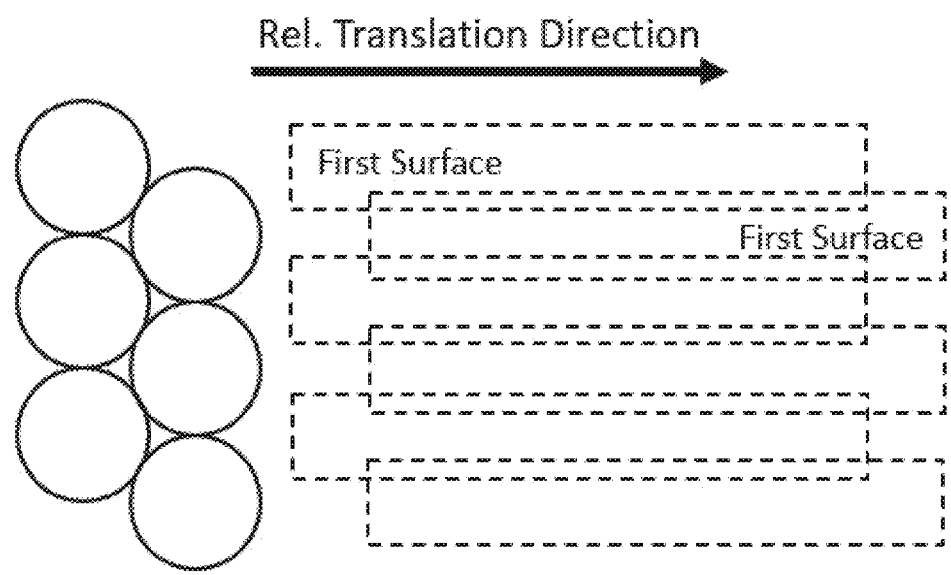

FIGS. 43A-B provide non-limiting schematic illustrations of a multiplexed read-head as disclosed herein. FIG. 43A shows a side view of a multiplexed read-head in which two rows of individual microfluorometers (seen from the end on) having common optical design specifications, e.g., numerical aperture, field-of-view, working distance, etc., are configured to image a common surface, e.g., a first interior surface of a flow cell. FIG. 43B shows a top view of the same multiplexed read-head illustrating the overlapping imaging paths acquired by individual microfluorometers of the multiplexed read-head as the read-head is translated relative to the flow cell (or vice versa). In some instances, the individual fields-of-view for the individual microfluorometers may overlap, as indicated in FIG. 43B. In some instances, they may not overlap. In some instances, the multiplexed-read head may be designed such that it aligns with and images predetermined features, e.g., individual fluid channels, within a flow cell.

Figure 44A:
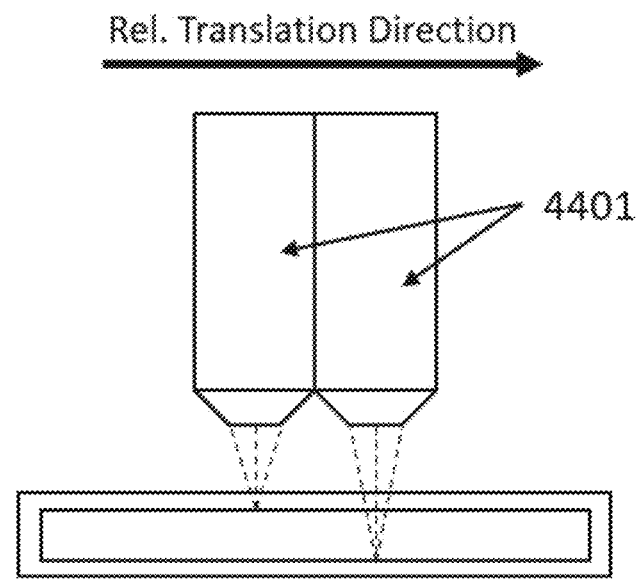
FIGS. 44A-44B provide non-limiting schematic illustrations of a multiplexed read-head as disclosed herein.
Figure 44B:
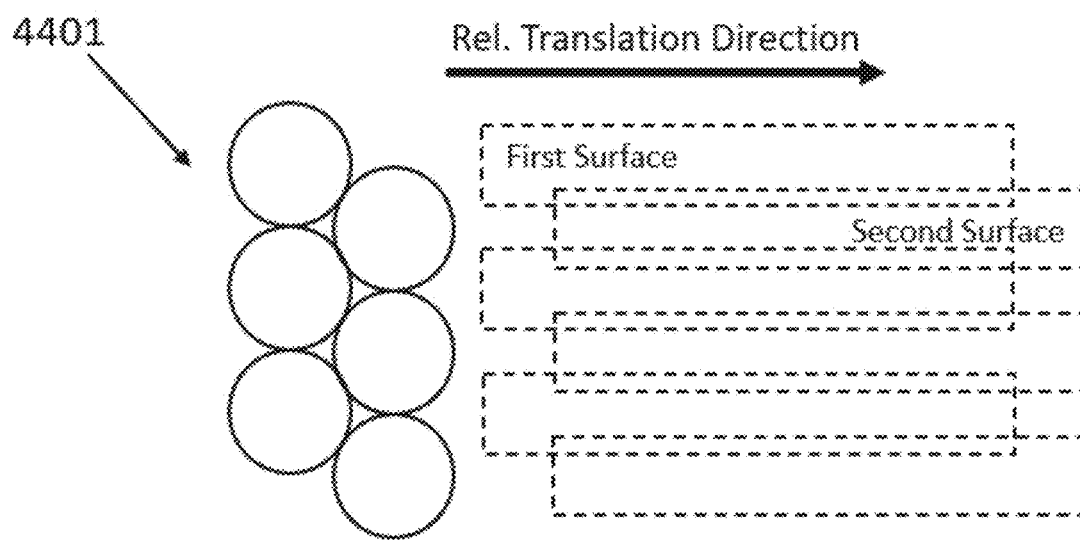

FIGS. 44A-B provide non-limiting schematic illustrations of a multiplexed read-head where a first subset of the plurality of individual miniaturized imaging modules is configured to image a first sample plane, e.g., a first interior surface of a flow cell, and a second subset of the plurality is configured to simultaneously image a second sample plane, e.g., a second interior surface of a flow cell. FIG. 44A shows a side view of the multiplexed read-head in which the first subset of individual microfluorimeters is configured to image, e.g., the first or upper interior surface of a flow cell, and the second subset is configured to image a second surface, e.g., the second or lower interior surface of a flow cell. FIG. 44B shows a top view of the multiplexed read-head of FIG. 44A illustrating the imaging paths acquired by individual microfluorimeters of the multiplexed read-head. Again, in some instances, the individual fields-of-view for the individual microfluorometers in a given subset may overlap. In some instances, they may not overlap. In some instances, the multiplexed-read head may be designed such that the individual miniaturized imaging modules of the first and second subsets align with and image predetermined features, e.g., individual fluid channels, within a flow cell.

Improved or optimized objective and or tube lens for use with thicker coverslips: Existing design practice includes the design of objective lenses and/or use of commonly available off-the-shelf microscope objectives to optimize image quality when images are acquired through thin (e.g., <200 µm thick) microscope coverslips. When used to image on both sides of a fluidic channel or flow cell, the extra height of the gap between the two surfaces (e.g., the height of the fluid channel; typically, about 50 µm to 200 µm) introduces optical aberration in images captured for the non-optimal side of the fluidic channel, thereby causing lower optical resolution. This is primarily because the additional gap height is significant compared to the optimal coverslip thickness (typical fluid channel or gap heights of 50-200 µm vs. coverslip thicknesses of <200 µm). Another common design practice is to utilize an additional "compensator" lens in the optical path when imaging is to be performed on the non-optimal side of the fluid channel or flow cell. This "compensator" lens and the mechanism required to move it in or out of the optical path so that either side of the flow cell may be imaged further increases system complexity and imaging system down time, and potentially degrades image quality due to vibration, etc.

In the present disclosure, the imaging system is designed for compatibility with flow cell consumables that comprise a thicker coverslip or flow cell wall (thickness >700 µm). The objective lens design may be improved or optimized for a coverslip that is equal to the true cover slip thickness plus half of the effective gap thickness (e.g., 700 µm+12*fluid channel (gap) height). This design significantly reduces the effect of gap height on image quality for the two surfaces of the fluid channel and balances the optical quality for images of the two surfaces, as the gap height is small relative to the total coverslip thickness and thus its impact on optical quality is reduced.

Additional advantages of using a thicker coverslip include improved control of thickness tolerance error during manufacturing, and a reduced likelihood that the coverslip undergoes deformation due to thermal and mounting-induced stress. Coverslip thickness error and deformation adversely impact imaging quality for both the top surface and the bottom surface of a flow cell.

To further improve the dual surface imaging quality for sequencing applications, our optical system design places a strong emphasis on improving or optimizing MTF (e.g., through improving or optimizing the objective lens and/or tube lens design) in the mid- to high-spatial frequency range that is most suitable for imaging and resolving small spots or clusters.

Improved or optimized tube lens design for use in combination with commercially available, off-the-shelf objectives: For low-cost sequencer design, the use of a commercially available, off-the-shelf objective lens may be preferred due to its relatively low price. However, as noted above, low-cost, off-the-shelf objectives are mostly optimized for use with thin coverslips of about 170 μm in thickness. In some instances, the disclosed optical systems may utilize a tube lens design that compensates for a thicker flow cell coverslip while enabling high image quality for both interior surfaces of a flow cell in dual-surface imaging applications. In some instances, the tube lens designs disclosed herein enable high quality imaging for both interior surfaces of a flow cell without moving an optical compensator into or out of the optical path between the flow cell and an image sensor, without moving one or more optical elements or components of the tube lens along the optical path, and without moving one or more optical elements or components of the tube lens into or out of the optical path.

Figure 19:
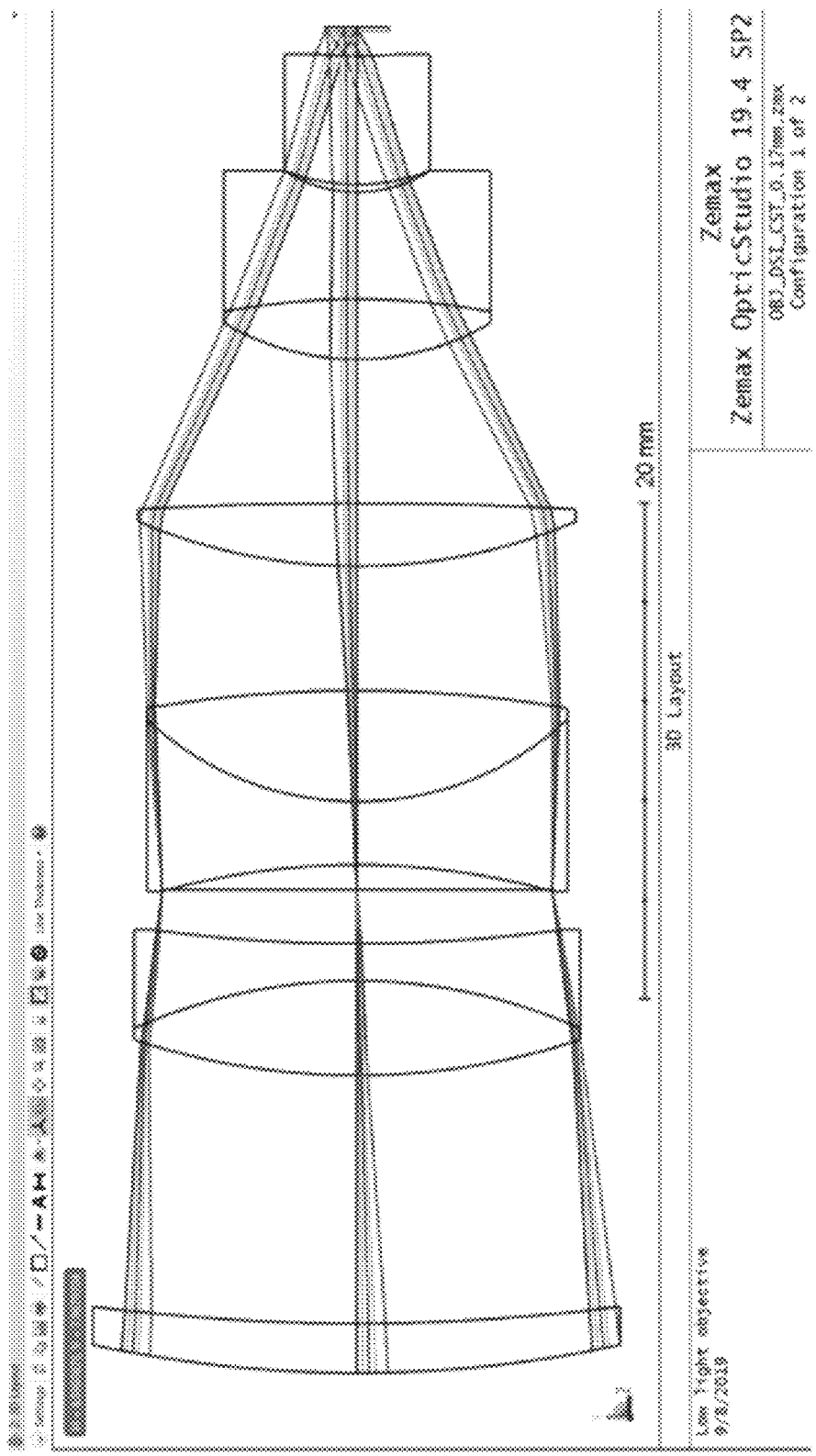
FIG. 19 provides an optical ray tracing diagram for an objective lens design that has been designed for imaging a surface on the opposite side of a 0.17 mm thick coverslip.
Figure 20:
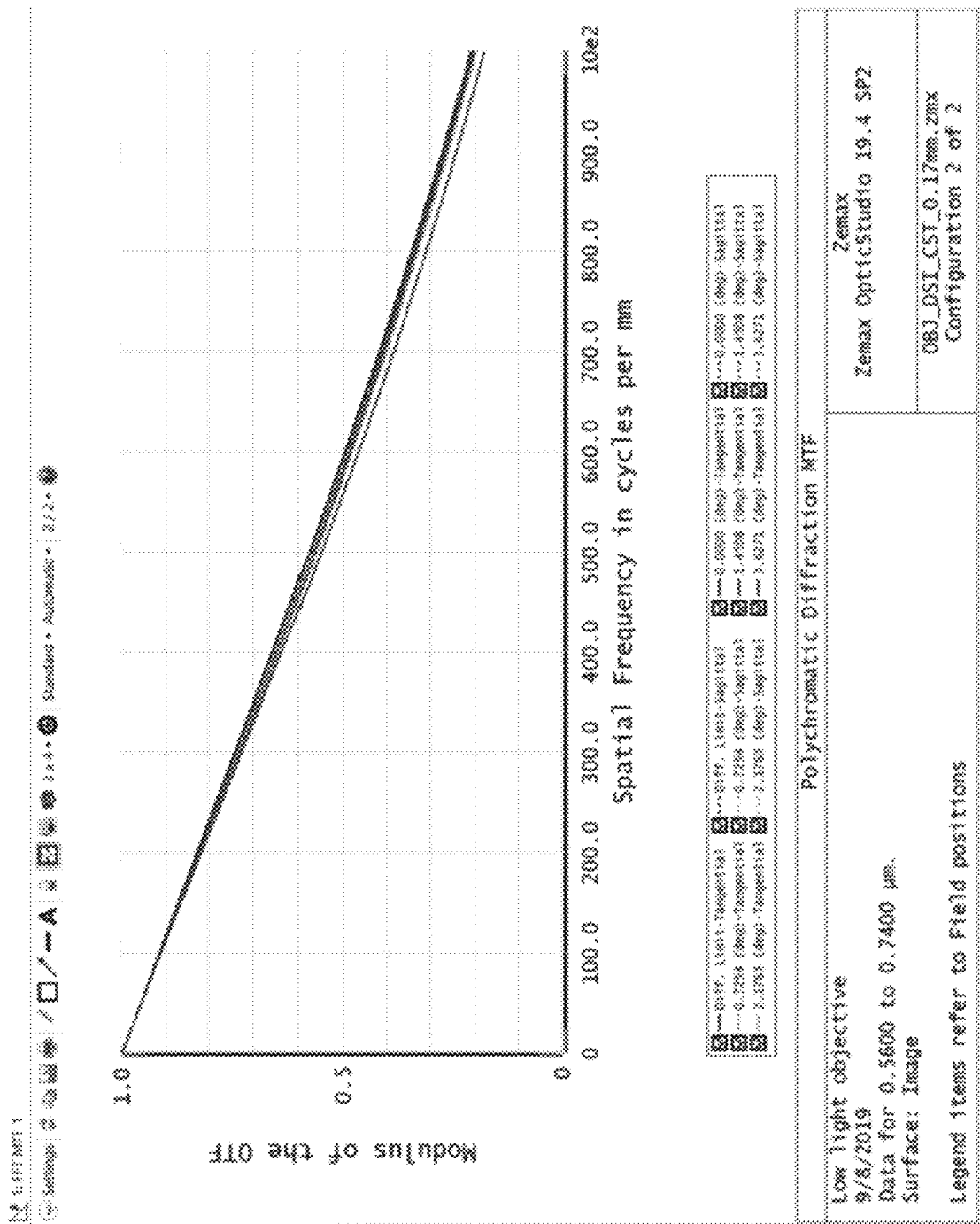
FIG. 20 provides a plot of the modulation transfer function for the objective lens illustrated in FIG. 19 as a function of spatial frequency when used to image a surface on the opposite side of a 0.17 mm thick coverslip.

FIG. 19 provides an optical ray tracing diagram for a low light objective lens design that has been improved or optimized for imaging a surface on the opposite side of a 0.17 mm thick coverslip. The plot of modulation transfer function for this objective, shown in FIG. 20, indicates near-diffraction limited imaging performance when used with the designed-for 0.17 mm thick coverslip.

Figure 21:
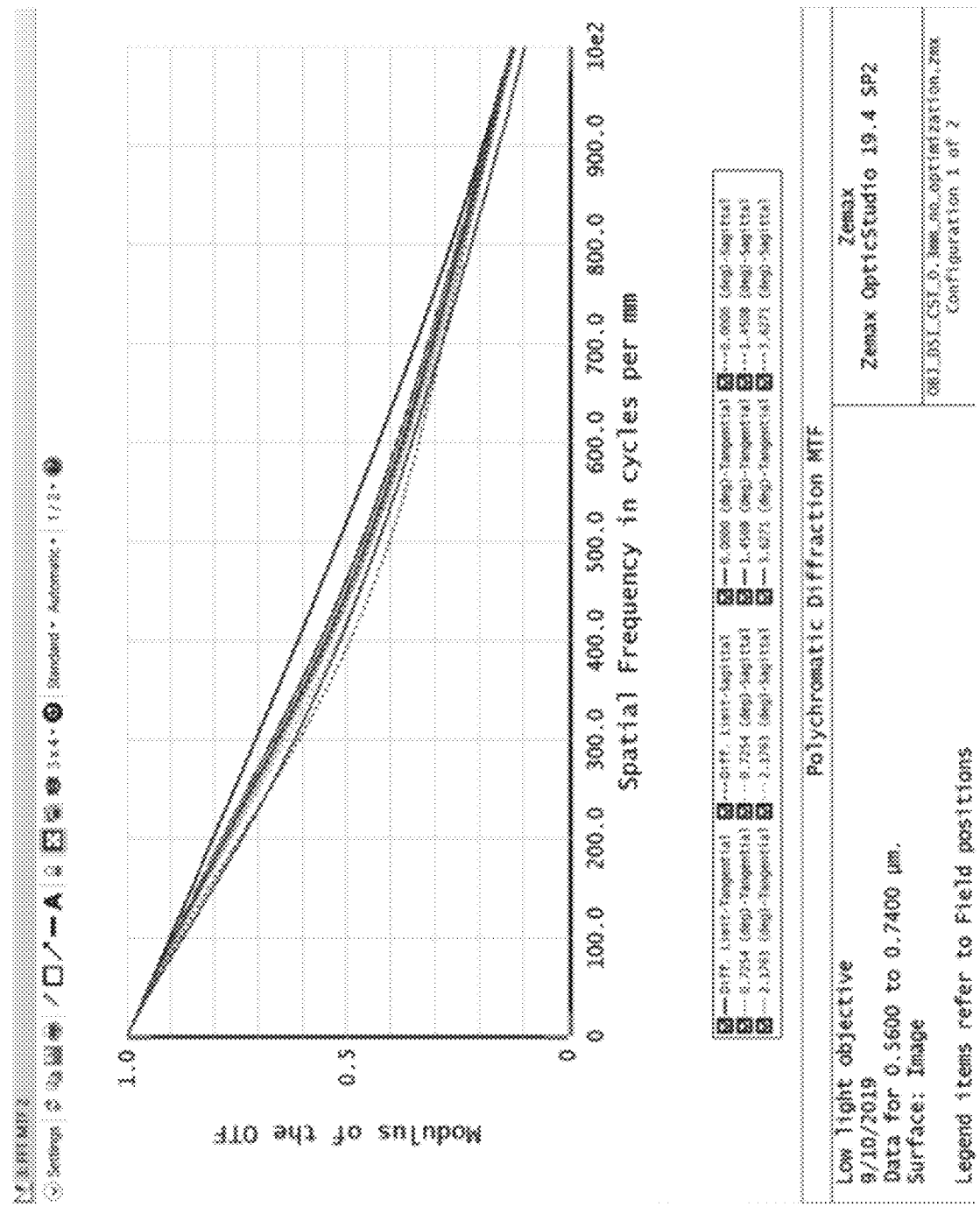
FIG. 21 provides a plot of the modulation transfer function for the objective lens illustrated in FIG. 19 as a function of spatial frequency when used to image a surface on the opposite side of a 0.3 mm thick coverslip.

FIG. 21 provides a plot of the modulation transfer function for the same objective lens illustrated in FIG. 19 as a function of spatial frequency when used to image a surface on the opposite side of a 0.3 mm thick coverslip. The relatively minor deviations of MTF value over the spatial frequency range of about 100 to about 800 lines/mm (or cycles/mm) indicates that the image quality obtained even when using a 0.3 mm thick coverslip is still reasonable.

Figure 22:
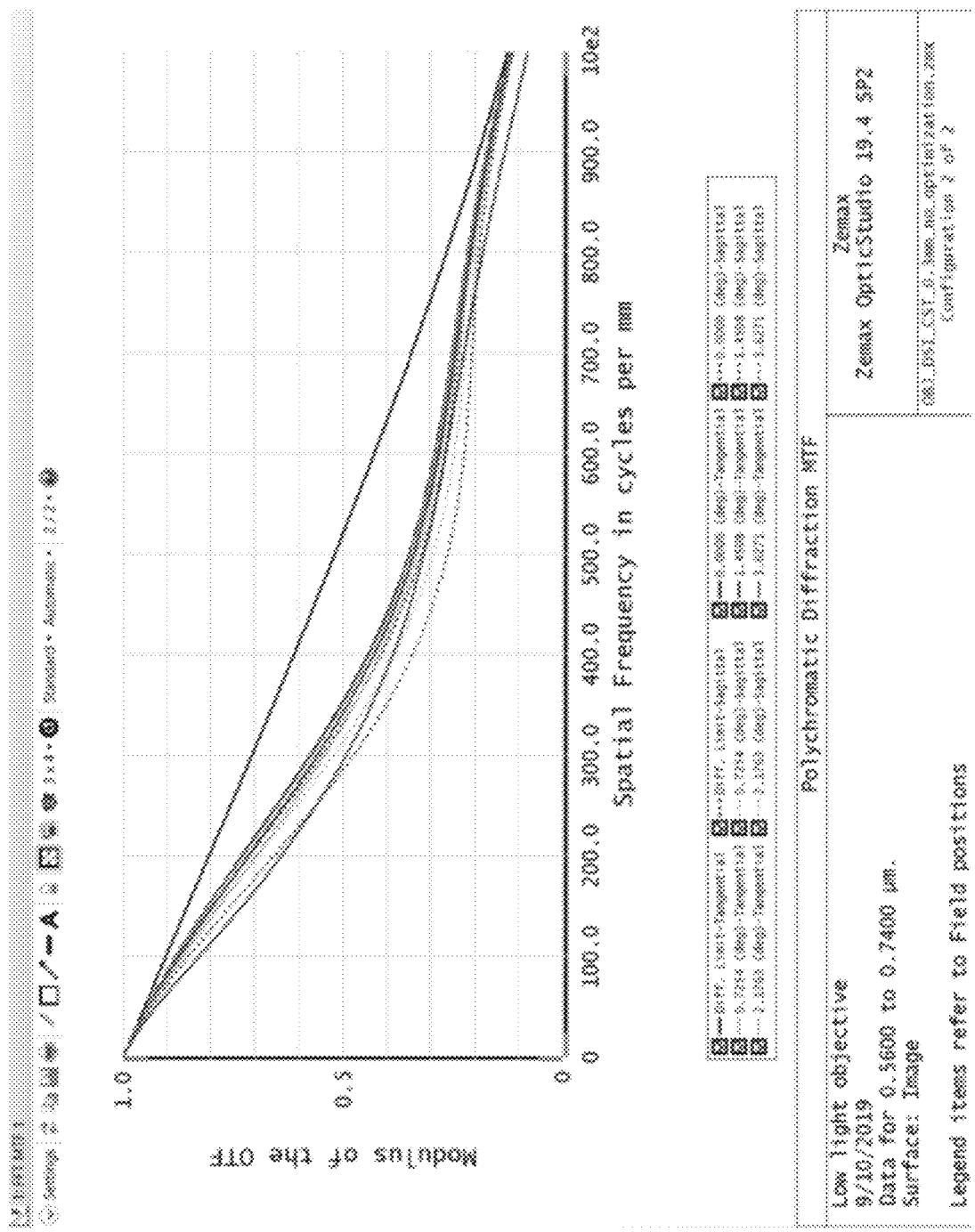
FIG. 22 provides a plot of the modulation transfer function for the objective lens illustrated in FIG. 19 as a function of spatial frequency when used to image a surface that is separated from that on the opposite side of a 0.3 mm thick coverslip by a 0.1 mm thick layer of aqueous fluid.

FIG. 22 provides a plot of the modulation transfer function for the same objective lens illustrated in FIG. 19 as a function of spatial frequency when used to image a surface that is separated from that on the opposite side of a 0.3 mm thick coverslip by a 0.1 mm thick layer of aqueous fluid (e.g., under the kind of conditions encountered for dual-side imaging of a flow cell when imaging the far surface). As can be seen in the plot of FIG. 22, imaging performance is degraded, as indicated by the deviations of the MTF curves from those for the an ideal, diffraction-limited case over the spatial frequency range of about 50 lp/mm to about 900 lp/mm.

Figure 23:
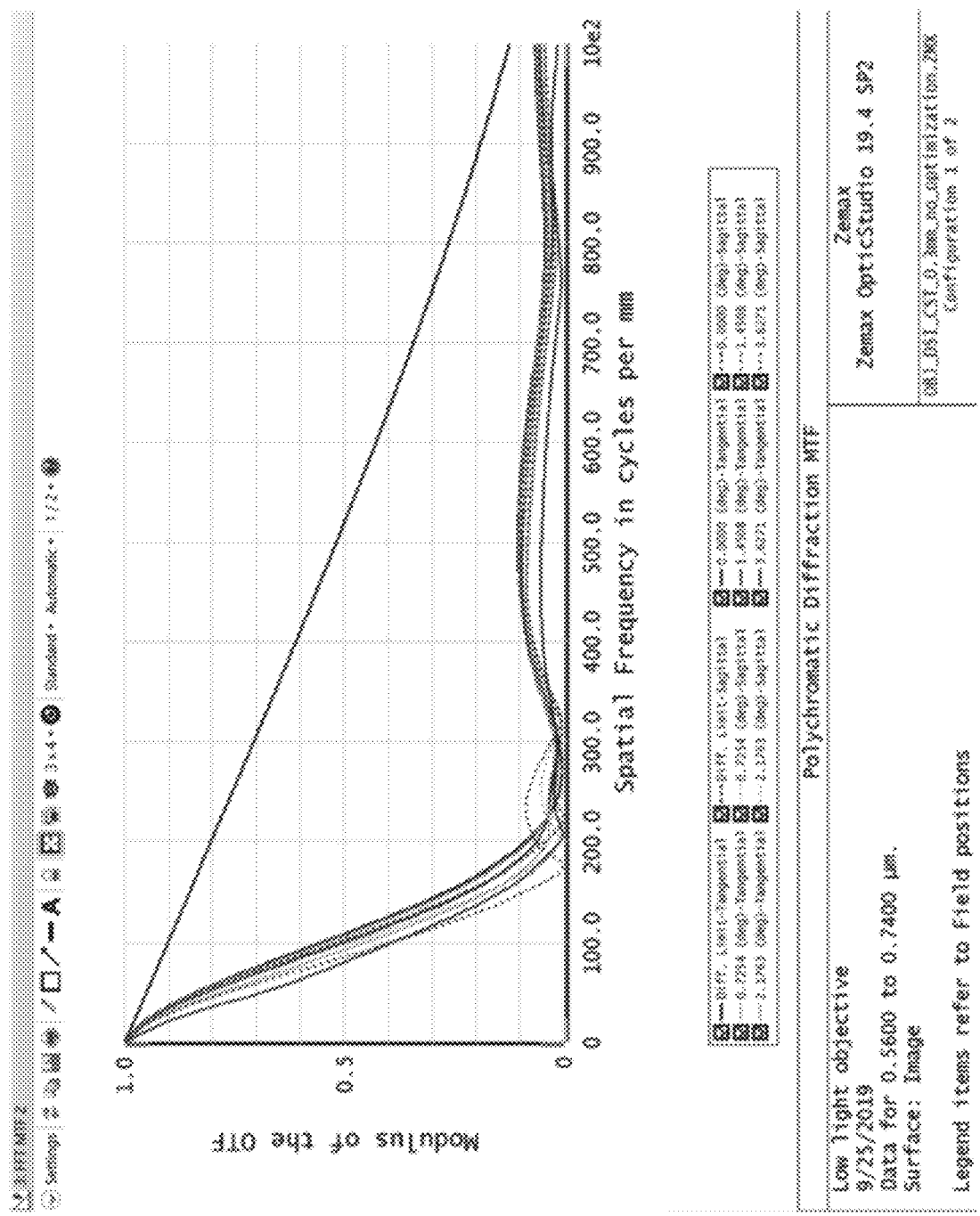
FIG. 23 provides a plot of the modulation transfer function for the objective lens illustrated in FIG. 19 as a function of spatial frequency when used to image a surface on the opposite side of a 1.0 mm thick coverslip.
Figure 24:
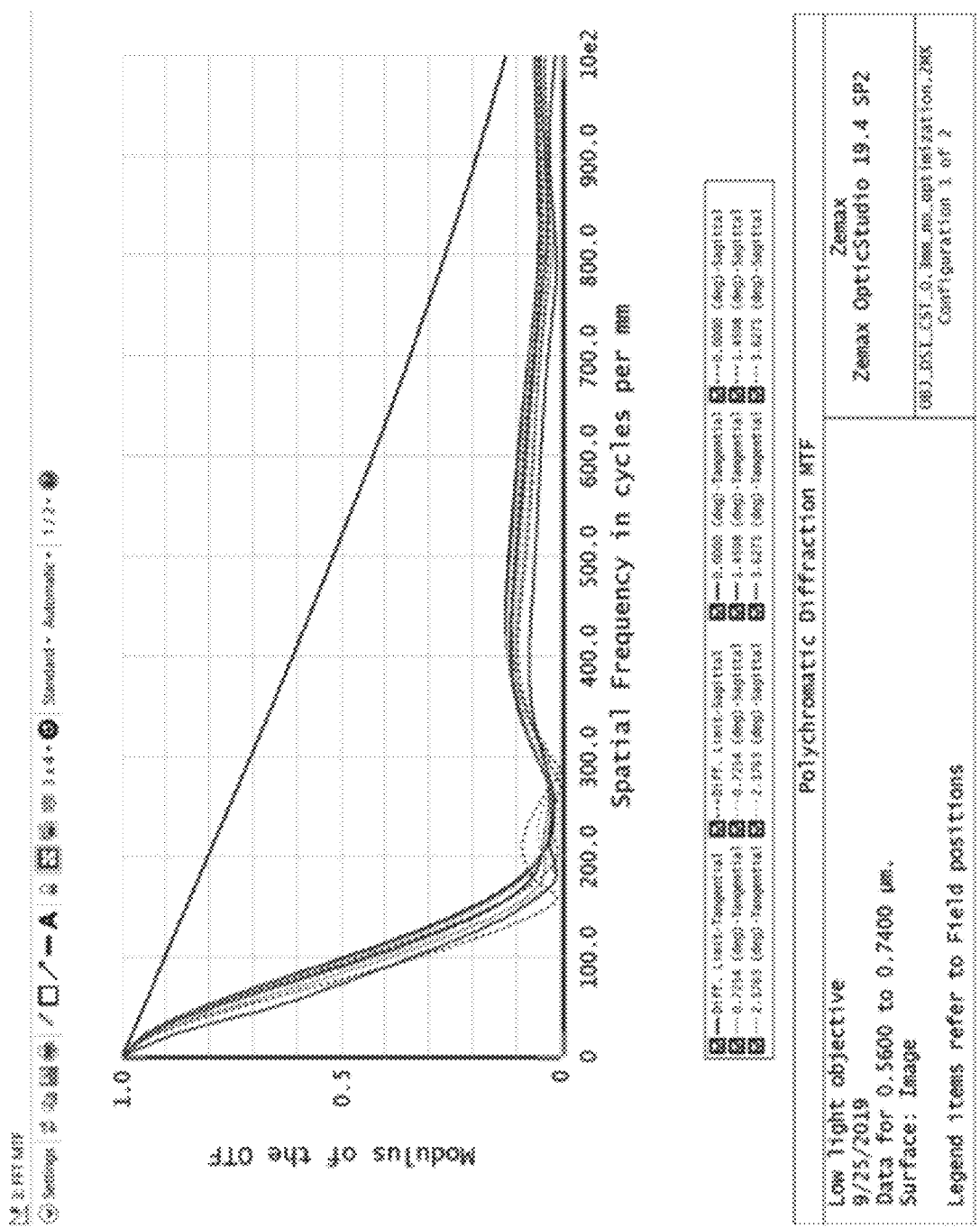
FIG. 24 provides a plot of the modulation transfer function for the objective lens illustrated in FIG. 19 as a function of spatial frequency when used to image a surface that is separated from that on the opposite side of a 1.0 mm thick coverslip by a 0.1 mm thick layer of aqueous fluid.

FIG. 23 and FIG. 24 provide plots of the modulation transfer function as a function of spatial frequency for the upper (or near) interior surface (FIG. 23) and lower (or far) interior surface (FIG. 24) of a flow cell when imaged using the objective lens illustrated in FIG. 19 through a 1.0 mm thick coverslip, and when the upper and lower interior surfaces are separated by a 0.1 mm thick layer of aqueous fluid. As can be seen, imaging performance is significantly degraded for both surfaces.

Figure 25:
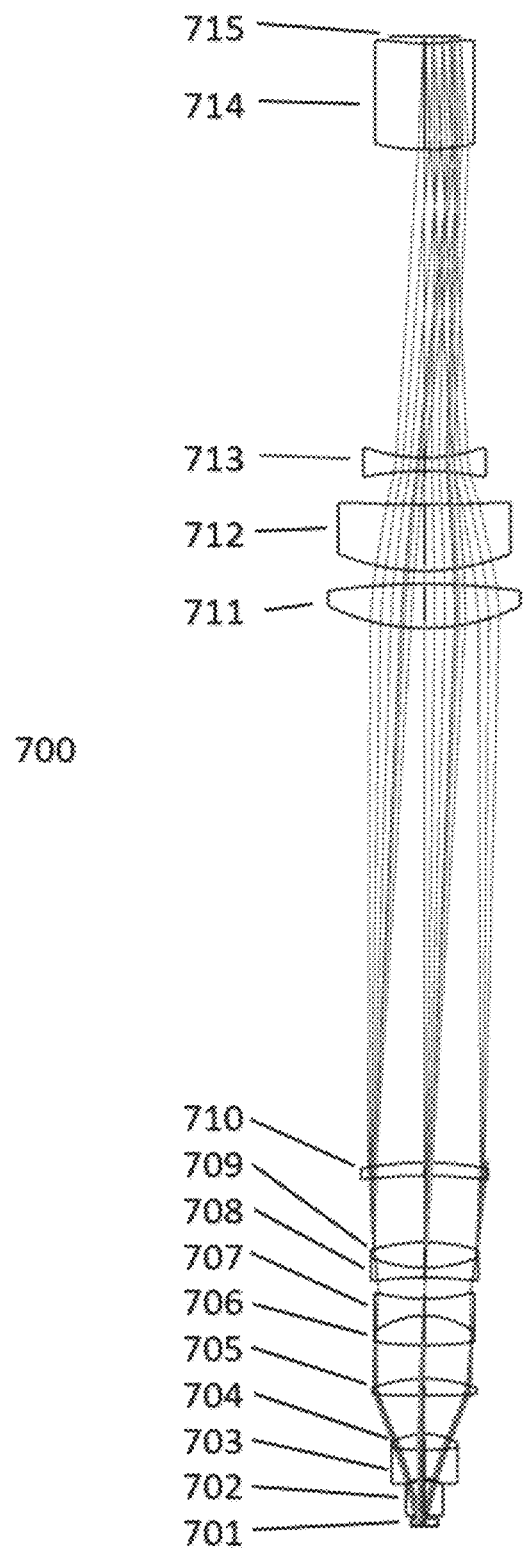
FIG. 25 provides a ray tracing diagram for a tube lens design which, if used in conjunction with the objective lens illustrated in FIG. 19, provides for improved dual-side imaging through a 1 mm thick coverslip.

FIG. 25 provides a ray tracing diagram for a tube lens design which, if used in conjunction with the objective lens illustrated in FIG. 19, provides for improved dual-side imaging through a 1 mm thick coverslip. The optical design 700 comprising a compound objective (lens elements 702, 703, 704, 705, 706, 707, 708, 709, and 710) and a tube lens (lens elements 711, 712, 713, and 714) is improved or optimized for use with flow cells comprising a thick coverslip (or wall), e.g., greater than 700 μm thick, and a fluid channel thickness of at least 50 μm, and transfers the image of an interior surface from the flow cell 701 to the image sensor 715 with dramatically improved optical image quality and higher CNR.

In some instances, the tube lens (or tube lens assembly) may comprise at least two optical lens elements, at least three optical lens elements, at least four optical lens elements, at least five optical lens elements, at least six optical lens elements, at least seven optical lens elements, at least eight optical lens elements, at least nine optical lens elements, at least ten optical lens elements, or more, where the number of optical lens elements, the surface geometry of each element, and the order in which they are placed in the assembly is improved or optimized to correct for optical aberrations induced by the thick wall of the flow cell, and in some instances, allows one to use a commercially-available, off-the-shelf objective while still maintaining high-quality, dual-side imaging capability.

In some instances, as illustrated in FIG. 25, the tube lens assembly may comprise, in order, a first asymmetric convex-convex lens 711, a second convex-plano lens 712, a third asymmetric concave-concave lens 713, and a fourth asymmetric convex-concave lens 714.

Figure 26:
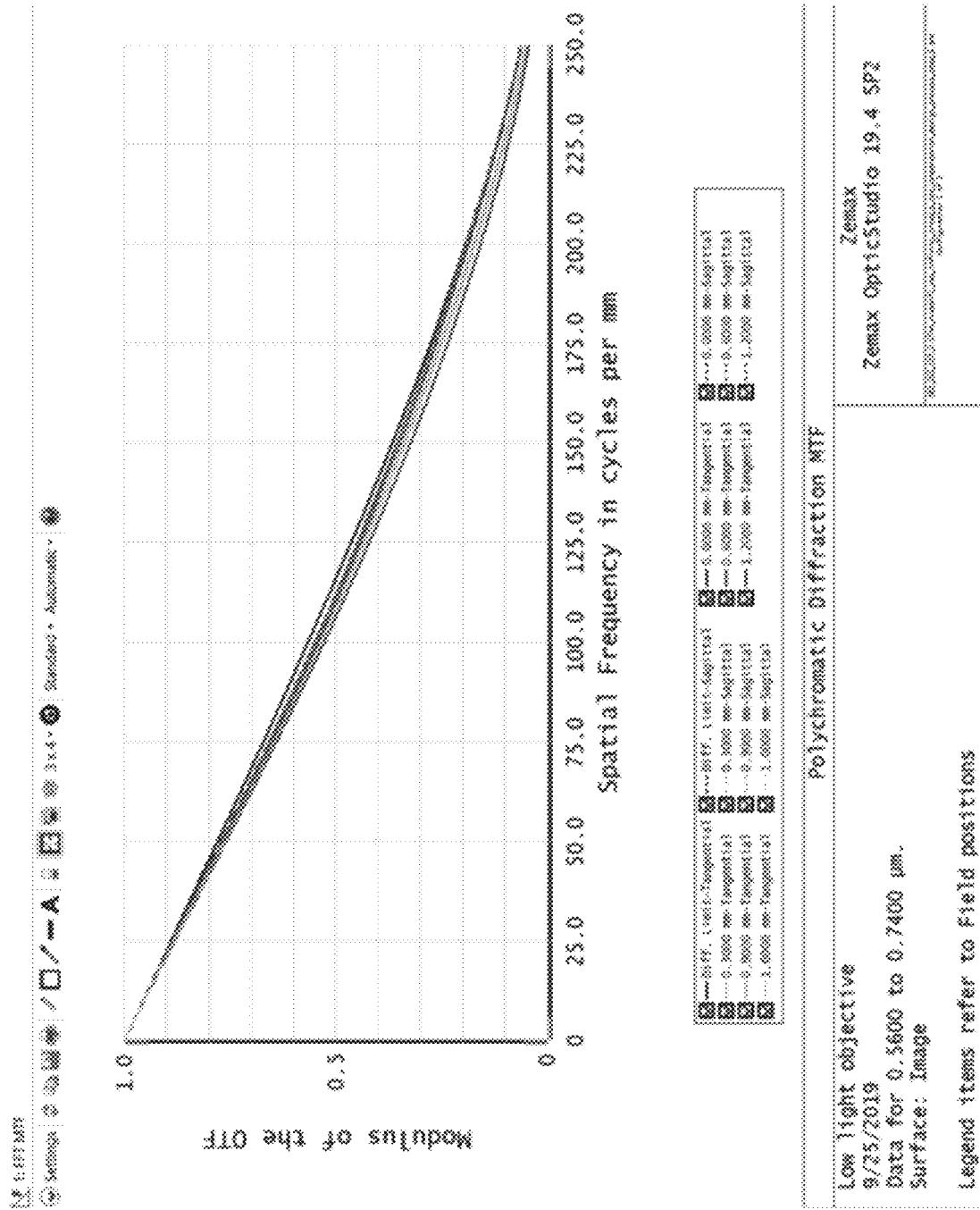
FIG. 26 provides a plot of the modulation transfer function for the combination of objective lens and tube lens illustrated in FIG. 25 as a function of spatial frequency when used to image a surface on the opposite side of a 1.0 mm thick coverslip.
Figure 27:
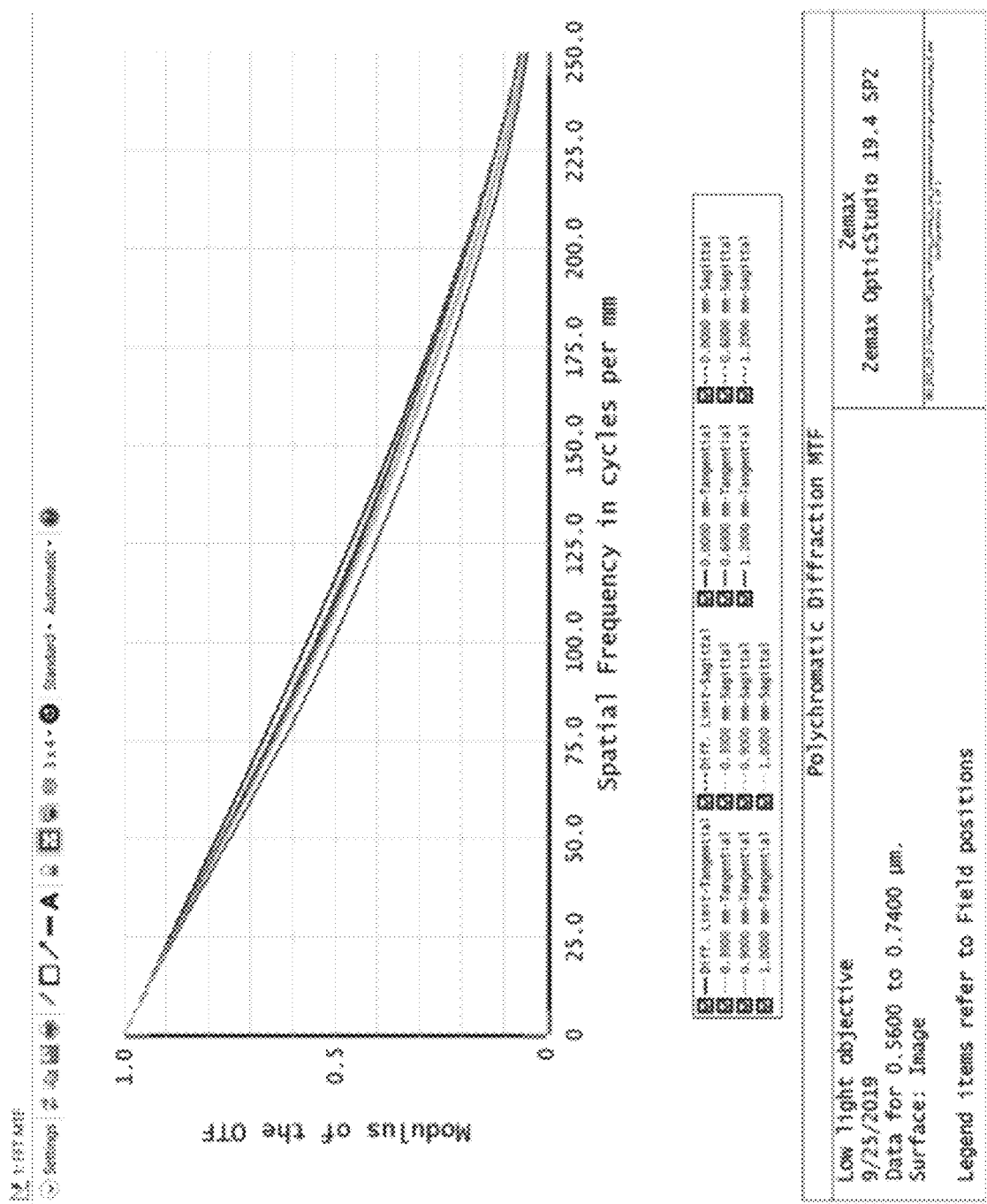
FIG. 27 provides a plot of the modulation transfer function for the combination of objective lens and tube lens illustrated in FIG. 25 as a function of spatial frequency when used to image a surface that is separated from that on the opposite side of a 1.0 mm thick coverslip by a 0.1 mm thick layer of aqueous fluid.

FIG. 26 and FIG. 27 provide plots of the modulation transfer function as a function of spatial frequency for the upper (or near) interior surface (FIG. 26) and lower (or far) interior surface (FIG. 27) of a flow cell when imaged using the objective lens (corrected for a 0.17 mm coverslip) and tube lens combination illustrated in FIG. 25 through a 1.0 mm thick coverslip, and when the upper and lower interior surfaces are separated by a 0.1 mm thick layer of aqueous fluid. As can be seen, the imaging performance achieved is nearly that expected for a diffraction-limited optical design.

Figure 28:
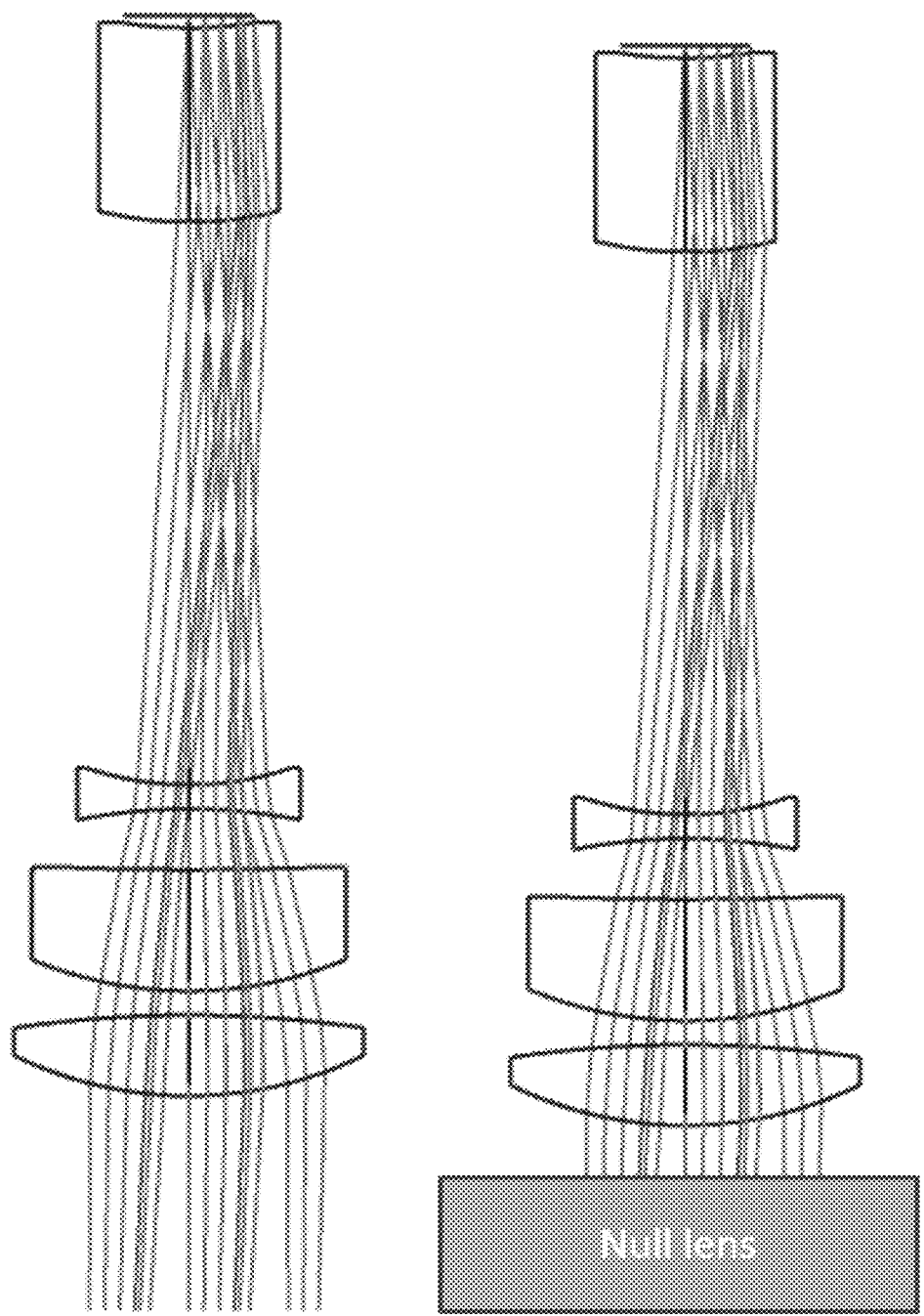
FIG. 28 provides ray tracing diagrams for tube lens design (left) of the present disclosure that has been optimized to provide high-quality, dual-side imaging performance. Because the tube lens is no longer infinity-corrected, an appropriately designed null lens (right) may be used in combination with the tube lens to compensate for the non-infinity-corrected tube lens for manufacturing and testing purposes.

FIG. 28 provides ray tracing diagrams for tube lens design (left) of the present disclosure that has been improved or optimized to provide high-quality, dual-side imaging performance. Because the tube lens is no longer infinity-corrected, an appropriately designed null lens (right) may be used in combination with the tube lens to compensate for the non-infinity-corrected tube lens for manufacturing and testing purposes.

Imaging channel-specific tube lens adaptation or optimization: In imaging system design, it is possible to improve or optimize both the objective lens and the tube lens in the same wavelength region for all imaging channels. Typically, the same objective lens is shared by all imaging channels (see, for example, FIG. 18), and each imaging channel either uses the same tube lens or has a tube lens that shares the same design.

In some instances, the imaging systems disclosed herein may further comprise a tube lens for each imaging channel where the tube lens has been independently improved or optimized for the specific imaging channel to improve image quality, e.g., to reduce or minimize distortion and field curvature, and improve depth-of-field (DOF) performance for each channel. Because the wavelength range (or bandpass) for each specific imaging channel is much narrower than the combined wavelength range for all channels, the wavelength- or channel-specific adaptation or optimization of the tube lens used in the disclosed systems results in significant improvements in imaging quality and performance. This channel-specific adaptation or optimization results in improved image quality for both the top and bottom surfaces of the flow cell in dual-side imaging applications.

Dual-side imaging w/o fluid present inflow cell: For optimal imaging performance of both top and bottom interior surfaces of a flow cell, a motion-actuated compensator is typically required to correct for optical aberrations induced by the fluid in the flow cell (typically comprising a fluid layer thickness of about 50-200 µm). In some instances of the disclosed optical system designs, the top interior surface of the flow cell may be imaged with fluid present in the flow cell. Once the sequencing chemistry cycle has been completed, the fluid may be extracted from the flow cell for imaging of the bottom interior surface. Thus, in some instances, even without the use of a compensator, the image quality for the bottom surface is maintained.

Compensation for optical aberration and or vibration using electro-optical phase plates: In some instances, dual-surface image quality may be improved without requiring the removal of the fluid from the flow cell by using an electro-optical phase plate (or other corrective lens) in combination with the objective to cancel the optical aberrations induced by the presence of the fluid. In some instances, the use of an electro-optical phase plate (or lens) may be used to remove the effects of vibration arising from the mechanical motion of a motion-actuated compensator and may provide faster image acquisition times and sequencing cycle times for genomic sequencing applications.

Improved contrast-to-noise ratio (CNR), field-of-view (FOV), spectral separation, and timing design to increase or maximize information transfer and throughput: Another way to increase or maximize information transfer in imaging systems designed for genomics applications is to increase the size of the field-of-view (FOV) and reduce the time required to image a specific FOV. With typical large NA optical imaging systems, it may be common to acquire images for fields-of-view that are on the order of 1 $mm^2$ in area, where in the presently disclosed imaging system designs large FOV objectives with long working distances are specified to enable imaging of areas of 2 $mm^2$ or larger.

In some cases, the disclosed imaging systems are designed for use in combination with proprietary low-binding substrate surfaces and DNA amplification processes that reduce fluorescence background arising from a variety of confounding signals including, but are not limited to, nonspecific adsorption of fluorescent dyes to substrate surfaces, nonspecific nucleic acid amplification products (e.g., nucleic acid amplification products that arise the substrate surface in areas between the spots or features corresponding to clonally-amplified clusters of nucleic acid molecules (e.g., specifically amplified colonies), nonspecific nucleic acid amplification products that may arise within the amplified colonies, phased and pre-phased nucleic acid strands, etc. The use of low-binding substrate surfaces and DNA amplification processes that reduce fluorescence background in combination with the disclosed optical imaging systems may significantly cut down on the time required to image each FOV.

The presently disclosed system designs may further reduce the required imaging time through imaging sequence improvement or optimization where multiple channels of fluorescence images are acquired simultaneously or with overlapping timing, and where spectral separation of the fluorescence signals is designed to reduce cross-talks between fluorescence detection channels and between the excitation light and the fluorescence signal(s).

The presently disclosed system designs may further reduce the required imaging time through improvement or optimization of scanning motion sequence. In the typical approach, an X-Y translation stage is used to move the target FOV into position underneath the objective, an autofocus step is performed where optimal focal position is determined and the objective is moved in the Z direction to the determined focal position, and an image is acquired. A sequence of fluorescence images is acquired by cycling through a series of target FOV positions. From an information transfer duty cycle perspective, information is only transferred during the fluorescence image acquisition portion of the cycle. In the presently disclosed imaging system designs, a single-step motion in which all axes (X-Y-Z) are repositioned simultaneously is performed, and the autofocus step is used to check focal position error. The additional Z motion is only commanded if the focal position error (e.g., the difference between the focal plane position and the sample plane position) exceeds a certain limit (e.g., a specified error threshold). Coupled with high speed X-Y motion, this approach increases the duty cycle of the system, and thus increases the imaging throughput per unit time.

Furthermore, by matching the optical collection efficiency, modulation transfer function, and image sensor performance characteristics of the design with the fluorescence photon flux expected for the input excitation photon flux, dye efficiency (related to dye extinction coefficient and fluorescence quantum yield), while accounting for background signal and system noise characteristics, the time required to acquire high quality (high contrast-to-noise ratio (CNR) images) may be reduced or minimized.

The combination of efficient image acquisition and improved or optimized translation stage step and settle times leads to fast imaging times (e.g., the overall time required per field-of-view) and higher throughput imaging system performance.

Along with the large FOV and fast image acquisition duty cycle, the disclosed designs may comprise also specifying image plane flatness, chromatic focus performance between fluorescence detection channels, sensor flatness, image distortion, and focus quality specifications.

Chromatic focus performance is further improved by individually aligning the image sensors for different fluorescence detection channels such that the best focal plane for each detection channel overlaps. The design goal is to ensure that images across more than 90 percent of the field-of-view are acquired within +100 nm (or less) relative to the best focal plane for each channel, thus increasing or maximizing the transfer of individual spot intensity signals. In some instances, the disclosed designs further ensure that images across 99 percent of the field-of-view are acquired within +150 nm (or less) relative to the best focal plane for each channel, and that images across more the entire field-of-view are acquired within +200 nm (or less) relative to the best focal plane for each imaging channel.

Illumination optical path design: Another factor for improving signal-to-noise ratio (SNR), contrast-to-noise ratio (CNR), and/or increasing throughput is to increase illumination power density to the sample. In some instances, the disclosed imaging systems may comprise an illumination path design that utilizes a high-power laser or laser diode coupled with a liquid light guide. The liquid light guide removes optical speckle that is intrinsic to coherent light sources such as lasers and laser diodes. Furthermore, the coupling optics are designed in such a way as to underfill the entrance aperture of the liquid light guide. The underfilling of the liquid light guide entrance aperture reduces the effective numerical aperture of the illumination beam entering the objective lens, and thus improves light delivery efficiency through the objective onto the sample plane. With this design innovation, one can achieve illumination power densities up to 3× that for conventional designs over a large field-of-view (FOV).

By utilizing the angle-dependent discrimination of s- and p-polarization, in some instances, the illumination beam polarization may be orientated to reduce the amount of back-scattered and back-reflected illumination light that reaches the imaging sensors.

Structured illumination systems: In some instances, the disclosed imaging modules and systems may comprise a structured illumination optical design to increase the effective spatial resolution of the imaging system and thus enable the use of higher surface densities of clonally-amplified target nucleic acid sequences (clusters) on flow cell surfaces for improved sequencing throughput.

Structured illumination microscopy (SIM) utilizes spatially structured (e.g., periodic) patterns of light for illumination of the sample plane and relies on the generation of interference patterns known as Moiré fringes. Several images are acquired under slightly different illumination conditions, e.g., by shifting and/or rotating the pattern of the structured illumination, to create the Moiré fringes. Mathematical deconvolution of the resulting interference signal allows reconstruction of a super-resolution image having up to about a two-fold improvement in spatial resolution over that achieved using diffraction-limited imaging optics [Lutz (2011), "Biological Imaging by Superresolution Light Microscopy", *Comprehensive Biotechnology (Second Ed.)*, vol. 1, pages 579-589, Elsevier; Feiner-Gracia, et al. (2018), "15—Advanced Optical Microscopy Techniques for the Investigation of Cell-Nanoparticle Interactions", *Smart Nanoparticles for Biomedicine: Micro andNano Technologies*, pages 219-236, Elsevier; Nylk, et al. (2019), "Light-Sheet Fluorescence Microscopy With Structured Light", *Neurophotonics and Biomedical Spectroscopy*, pages 477-501, Elsevier]. An example of structured illumination microscopy imaging systems has recently been described in Hong, U.S. Patent Application Publication No. 2020/0218052.

Figure 41:
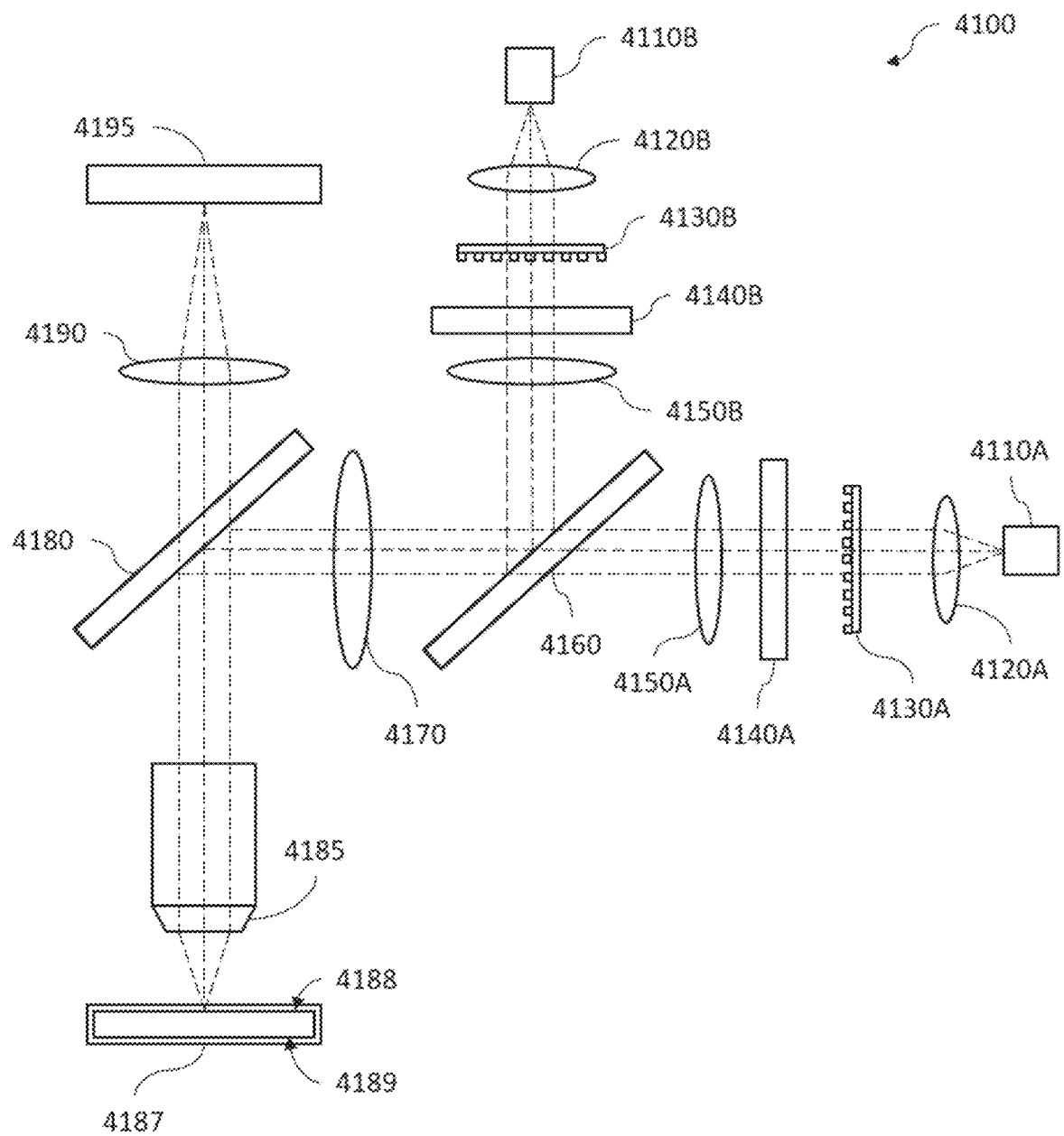
FIG. 41 provides a non-limiting example of a schematic for a structured illumination system as disclosed herein.

FIG. 41 provides a non-limiting schematic illustration of an imaging system 4100 comprising a branched structured illumination optical design as disclosed herein. The first branch (or arm) of the illumination optical path of system 4100 comprises, e.g., a light source (light emitter) 4110A, an optical collimator 4120A to collimate light emitted by light source 4110A, a diffraction grating 4130A in a first orientation with respect to the optical axis, a rotating window 4140A, and a lens 4150A. The second branch of the illumination optical path of system 4100 comprises, e.g., a light source 4110B, an optical collimator 4120B to collimate light emitted by light source 4110B, a diffraction grating 4130B in a second orientation with respect to the optical axis, a rotating window 4140B, and a lens 4150B. The diffraction gratings 4130A and 4130B enable projection of patterns of light fringes on the sample plane.

In some instances, the light sources 4110A and 4110B may be incoherent light sources (e.g., comprising one or more light emitting diodes (LEDs)) or coherent light sources (e.g., comprising one or more lasers or laser diodes). In some instances, the light sources 4110A and 4110B may comprise an optical fiber coupled to, e.g., an LED, laser, or laser diode that outputs a light beam that is then collimated by the respective collimator lenses 4120A and 4120B. In some instances, light sources 4110A and 4110B may output light of the same wavelength. In some instances, light sources 4110A and 4110B may output light of different wavelengths. Either of light sources 4110A and 4110B may be configured to output light of any wavelength and/or wavelength range described elsewhere herein. During imaging, light sources 4110A and 4110B may be switched on or off using, for example, a high-speed shutter (not shown) positioned in the optical path or by pulsing the light sources at a predetermined frequency.

In the example shown in FIG. 41, the first illumination arm of system 4100 includes a fixed vertical grating 4130A used to project a grating pattern (e.g., a vertical light fringe pattern) in a first orientation onto the sample plane, e.g., a first interior surface 4188 of a flow cell 4187, and the second illumination arm includes a fixed horizontal grating 4130B to project a grating pattern (e.g., a horizontal light fringe pattern) in a second orientation onto the sample plane 4188. Advantageously, the diffraction gratings of imaging system 4100 do not need to be mechanically rotated or translated during imaging in this non-limiting example, which may provide improved imaging speed, system reliability, and system repeatability. In some instances, diffraction gratings 4130A and/or 4130B may be rotatable about their respective optical axes such that the angle between the light fringe patterns projected on the sample plane is adjustable.

As illustrated in FIG. 41, in some instances, diffraction gratings 4130A and 4130B may be transmissive diffraction gratings that comprise a plurality of diffracting elements (e.g., parallel slits or grooves) formed in a glass substrate or other suitable surface. In some instances, the gratings may be implemented as phase gratings that provide a periodic variation of the refractive index of the grating material. In some instances, the groove or feature spacing may be chosen to diffract light at suitable angles and/or be tuned to the minimum resolvable feature size of the imaged samples for operation of imaging system 4100. In other instances, the diffraction gratings may be reflective diffraction gratings.

In the example illustrated in FIG. 41, the orientations of the vertical and horizontal light fringe patterns are offset by about 90 degrees. In other instances, other orientations of the diffraction gratings may be used to create an offset of about 90 degrees. For example, the diffraction gratings may be oriented such that they project light fringe patterns that are offset ±45 degrees from the x or y axes of sample plane (e.g., first interior flow cell surface) 4188. The configuration of imaging system 4100 illustrated in FIG. 41 may be particularly advantageous in the case of a sample support surface (e.g., an interior surface 4188 of a flow cell 4187) comprising regularly patterned features laid out on a rectangular grid, as enhancement of image resolution using the structured illumination approach can be achieved using only two perpendicular grating orientations (e.g., the vertical grating orientation and horizontal grating orientation).

Diffraction gratings 4130A and 4130B, in the example of system 4100, may be configured to diffract the input illumination light beams into a series of intensity maxima due to constructive interference according to the relationship:

$$m = \text{order number} = d\sin(\theta)/\lambda$$

where d=the distance between slits or grooves in the diffraction grating, θ=the angle of incidence of the illumination light relative to a normal to the surface of the diffraction grating, k=the wavelength of the illumination light, and m=an integer value corresponding to an intensity maxima of the diffracted light, e.g., m=0, ±1, ±2, etc. In some instances, a specific order of the diffracted illumination light, e.g., the first order (m=±1) light may be projected on the sample plane, e.g., interior flow cell surface 4188. In some instances, for example, vertical grating 4130A may diffract a collimated light beam into first order diffracted beams (±1 orders) which are focused onto the sample plane in a first orientation, and horizontal grating 4130B may diffract a collimated light beam into first order diffracted beams which are focused onto the sample plane in a second orientation. In some instances, the zeroth order beam and/or all other higher order beams (e.g., m=±2 or higher) may be blocked, e.g., filtered out of the illumination pattern projected onto the sample plane 4188, using, for example, a beam blocking element (not shown) such as an order filter that may be inserted into the optical paths following the diffraction gratings.

Each branch of the structured illumination system in the example of 4100 includes an optical phase modulator or phase shifter 4140A and 4140B to phase shift the diffracted light transmitted or reflected by each of the diffraction gratings 4130A and 4130B. During structured imaging, the optical phase of each diffracted beam may be shifted by some fraction (e.g., ½, ½, ¼, etc.) of the pitch (X) of each fringe of the structured pattern. In the example of FIG. 41, phase modulators 4140A and 4140B may be implemented, e.g., as rotating optical phase plates actuated by rotary actuators or other actuator mechanisms to rotate and modulate the optical path-length of each diffracted beam. For example, optical phase plate 4140A may be rotated about the vertical axis to shift the image projected by vertical grating 4130A on sample plane 4188 left or right, and optical phase plate 4140B may rotate about the horizontal axis to shift the image projected by horizontal grating 4130B on sample plane 4188 in the perpendicular direction.

In other implementations, other types of phase modulators that change the optical path length of the diffracted light (e.g., optical wedges mounted on linear translation stages, etc.) may be used. Additionally, although optical phase modulators 4140A and 4140B are illustrated as being placed after diffraction gratings 4130A and 4130B, in other implementations they may be placed at other positions in the illumination optical path. In some instances, a single optical phase modulator may be operated in two different directions to produce different light fringe patterns, or the position of a single optical phase modulator may be adjusted using a single motion to simultaneously adjust the path lengths of both arms of the illumination optical path.

In the example illustrated in FIG. 41, optical component 4160 may be used to combine light from the two illumination optical paths. Optical component 4160 may comprise, for example, a partially-silvered mirror, a dichroic mirror (depending on the wavelengths of light output by light sources 4110A and 4110B), a mirror comprising a pattern of holes or a patterned reflective coating such that light from the two arms of the illumination system are combined in a lossless or nearly lossless manner (e.g., without significant loss of optical power other than a small amount of absorption by the reflective coating), a polarizing beam splitter (in the case that light sources 4110A and 4110B are configured to produce polarized light), and the like. Optical component 4160 may be located such that the desired diffracted orders of light reflected or transmitted by each of the diffraction gratings are spatially resolved, and the unwanted orders of light are blocked. In some instances, optical component 4160 may pass the first order light output by the first illumination light path and reflect the first order light output by the second illumination light path. In some instances, the structured illumination pattern on the sample surface 4188 may be switched from a vertical orientation (e.g., using diffraction grating 4130A) to a horizontal orientation (e.g., using diffraction grating 4130B) by turning each light source on or off, or by opening and closing an optical shutter in the optical path for the light source. In other instances, the structured illumination pattern may be switched by using an optical switch to change the illumination optical path used to illuminate the sample plane.

Referring again to FIG. 41, a lens 4170, a semi-reflective mirror or dichroic mirror 4180, and an objective 4185 may be used to focus the structured illumination light onto sample surface 4188 (e.g., the first interior surface of a flow cell 4187). Light that is emitted by, reflected by, or scattered by the sample surface 4188 is then collected by objective 4185, transmitted through mirror 4180, and imaged by image sensor or camera 4195. As noted, mirror 4180 may be a dichroic mirror to reflect structured illumination light received from each branch of the illumination optical path into objective 4185 for projection onto sample plane 4188, and to pass through light emitted by the sample plane 4188 (e.g., fluorescent light, which is emitted at different wavelengths than the excitation light) for imaging onto image sensor 4195.

In some instances, system 4100 may optionally comprise a custom tube lens 4190 as described elsewhere herein such that the focus of the imaging system may be shifted from the first interior surface 4188 to the second interior surface 4189 of the flow cell 4187 to enable dual surface imaging with minimal adjustment. In some instances, lens 4170 may comprise a custom tube lens as described elsewhere herein such that the focus of the illumination optical path may be shifted from the first interior surface 4188 to the second interior surface 4189 of the flow cell 4187 to enable dual surface imaging with minimal adjustment. In some instances, lens 4170 may be implemented to articulate along the optical axis to adjust the focus of the structured illumination pattern on the sample plane. In some instances, system 4100 may comprise an autofocus mechanism (not shown) to adjust focus of the illumination light and/or the focus of the image at the plane of image sensor 4195. In some instances, the system 4100 illustrated in FIG. 41 may provide a high optical efficiency due to the absence of a polarizer in the optical path. The use of unpolarized light may or may not have a significant impact on illumination pattern contrast depending on the numerical aperture of objective 4185.

For the sake of simplicity, some optical components of imaging system 4100 may have been omitted from FIG. 41 and the foregoing discussion. Although system 4100 is illustrated in this non-limiting example as a single channel detection system, in other instances, it may be implemented as a multi-channel detection system (e.g., using two different image sensors and appropriate optics as well as light sources that emit at two different wavelengths). Furthermore, although the illumination optical path of system 4100 is illustrated in this non-limiting example as comprising two branches, in some instances it may be implemented as comprising, e.g., three branches, four branches, or more than four branches, each of which comprises a diffraction grating at a fixed or adjustable relative orientation to each other.

In some instances, alternative illumination path optical designs may be used to create structured illumination. For example, in some instances, a single large, rotating optical phase modulator may be positioned after optical component 4160 and used in place of optical phase modulators 4140A and 4140B to modulate the phases of both diffracted beams output by the vertical and horizontal diffraction gratings 4130A and 4130B. In some instances, instead of being parallel with respect to the optical axis of one of the diffraction gratings, the axis of rotation for the single rotating optical compensator may be offset by 45 degrees (or another angular offset) from the optical axis of each of the vertical and horizontal diffraction gratings to allow for phase shifting along both illumination directions. In some instances, the single rotating optical phase modulator may be replaced by, e.g., a wedged optical component rotating about the nominal beam axis.

In another alternative illumination optical path design, diffraction gratings 4130A and 4130B may be mounted on respective linear motion stages so that they may be translated to change the optical path length (and thus the phase) of light reflected or transmitted by diffraction gratings 4130A and 4130B. The axis of motion of the linear motion stages may be perpendicular or otherwise offset from the orientation of their respective diffraction grating to provide translation of the diffraction grating's fringe pattern along sample plane 4188. Suitable translation stages may comprise, e.g., crossed roller bearing stages, a linear motor, a high-accuracy linear encoder, and/or other linear actuator technologies to provide precise linear translation of the diffraction gratings.

Figure 42:
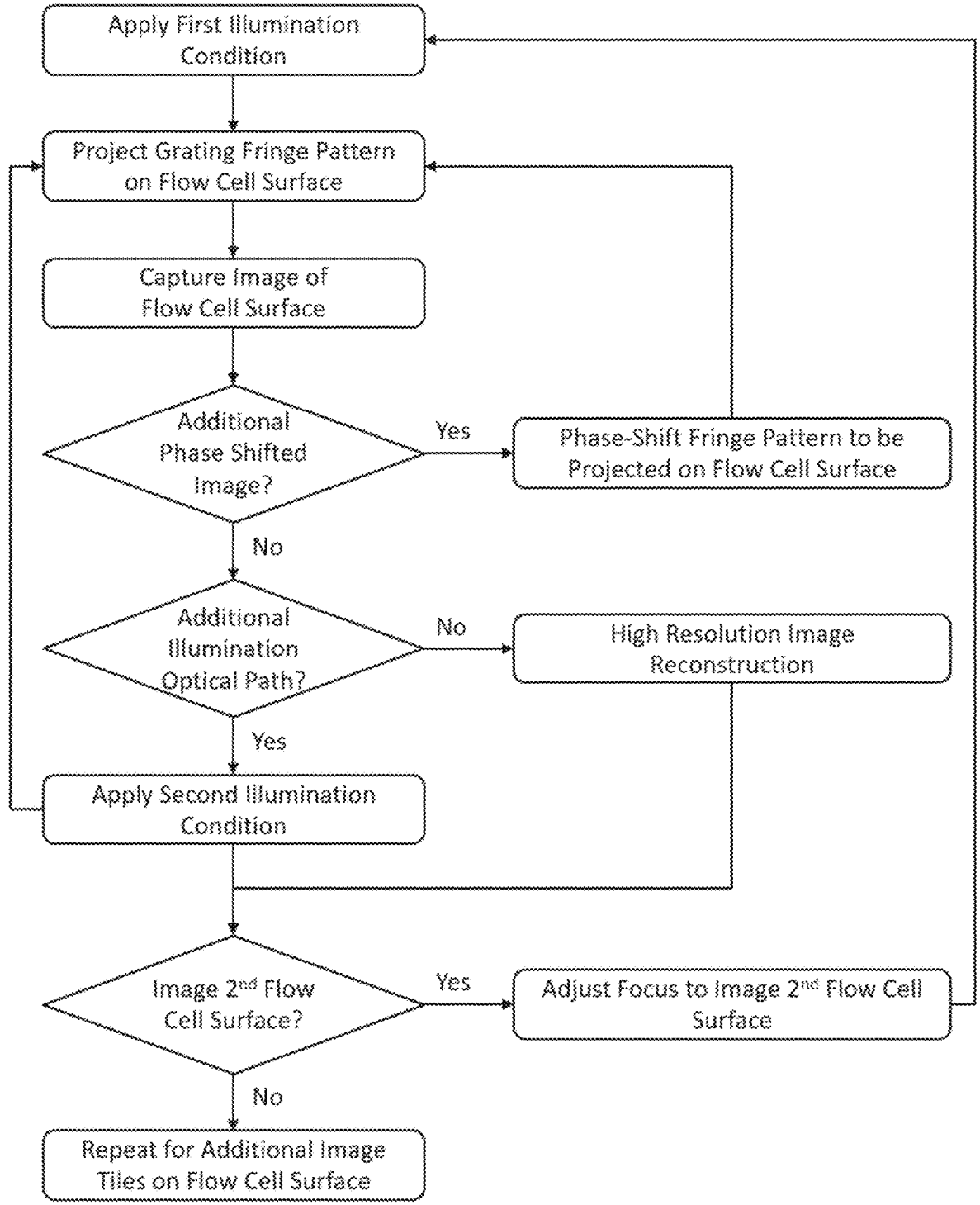
FIG. 42 provides a non-limiting example of a flow chart for acquiring and processing structured illumination images of a flow cell surface as disclosed herein.

FIG. 42 provides a non-limiting example of a workflow for acquiring and processing images using structured illumination to enhance the spatial resolution of the imaging system. In some instances, the workflow illustrated in FIG. 42 may be performed to image an entire sample plane (e.g., an interior surface of a flow cell by image tiling) or to image a single area of a larger sample plane. The vertical 4130A and horizontal 4130B diffraction gratings of the system 4100 illustrated in FIG. 41 may be used to project illumination light fringe patterns onto the sample plane that have different known orientations and/or different known phase shifts. For example, the imaging system 4100 may use vertical grating 4130A and horizontal grating 4130B to generate the horizontal and vertical illumination patterns respectively, while optical phase modulators 4140A and 4140B may be set to three different positions to produce the three phase shifts shown for each orientation.

During operation, a first illumination condition (e.g., a specific orientation of the diffraction grating and phase shift setting) may be used to project a grating light fringe pattern on the sample plane, e.g., flow cell surface. Following capture of an image using the first illumination condition, one or more additional images acquired using one or more phase shifted illumination patterns (e.g., 1, 2, 3, 4, 5, 6, or more than 6 additional images acquired using 1, 2, 3, 4, 5, 6, or more than 6 phase shifted illumination patterns) may be acquired. If the imaging system comprises a second branch of the illumination optical path, the image acquisition process may be repeated using a second illumination condition as a starting point (e.g., a second specific orientation of the diffraction grating and phase shift setting), and the image acquisition process may be repeated. In some instances, images may be acquired for at least three different orientations of the diffraction grating (e.g., spaced apart by 60 degrees relative to each other) using at least 5 different phase shifted light fringe patterns. If no more images are to be acquired using different orientations of the diffraction grating or phase shifted illumination light fringe patterns, an image reconstruction algorithm may be used to process the acquired images and produce a reconstructed super-resolution image. In some instances, images may be acquired for at least 1, 2, 3, 4, 5, 6, or more than 6 different orientations of the diffraction grating using at least 1, 2, 3, 4, 5, 6, or more than 6 different phase-shifted light fringe patterns at each orientation.

A potential disadvantage of acquiring multiple images for use in reconstructing single, super-resolution images is the time required to adjust the orientation and/or relative phase shift of the projected light fringe patterns and the exposure time required for acquiring each image, as well as the downstream image processing. Therefore, optical designs that minimize the time required to change diffraction grating orientation and relative phase, along with highly efficient image reconstruction algorithms, are to be preferred. In some instances, fewer images may be required to reconstruct super-resolution images of, e.g., flow cell surfaces comprising discrete, fluorescently labeled clusters of amplified target nucleic acid sequences tethered to the low-nonspecific binding surfaces described elsewhere herein than may ordinarily be required for reconstructing higher resolution images of conventional samples, e.g., stained tissue samples.

Referring again to FIG. 42, the afore-mentioned cycle may be repeated for different areas of a given flow cell surface, e.g., in the case that the images will be tiled to create a higher resolution image of the entire flow cell surface. In some instances, the afore-mentioned cycle may be repeated after adjusting the focus of the imaging system if, e.g., a second flow cell surface is to be imaged.

Other super-resolution imaging techniques: In some instances, the disclosed imaging systems may comprise the use of an alternative super-resolution imaging technique, e.g., photoactivation localization microscopy (PALM), fluorescence photoactivation localization microscopy (FPALM), and/or stochastic optical reconstruction microscopy (STORM) [see, for example, Lutz, et al. (2011), "Biological Imaging by Superresolution Light Microscopy", *Comprehensive Biotechnology (Second Ed.)*, vol. 1, pages 579-589, Elsevier), which are based on statistical curve fitting of the intensity distribution observed in images of a single molecule's point spread function (PSF) to a Gaussian distribution function. The Gaussian distribution function is then used to define location of the molecule in the sample plane with much higher precision than allowed by the classical resolution limit. The same approach may be used to image, e.g., small dispersed subsets of fluorescently labeled molecules such as clonally amplified clusters of target nucleic acid sequences tethered to a low non-specific binding surface on a sample support or the interior surface of a flow cell.

The spatial accuracy or resolution achieved using these methods depends upon the number of photons collected from the molecule before it is photobleached and upon the background noise level [Lutz, et al. (2011), ibid]. In the case that background noise is negligible and collection of at least 10,000 photons per molecule is possible, position accuracies of 1-2 nm have been demonstrated. In some instances, e.g., using the sequencing-by-avidity approach described elsewhere herein, nucleotide conjugates comprising a plurality of fluorescent labels (e.g., 1, 2, 3, 4, 5, 6, 7, 8, 9, 10, or more than 10 labels per conjugate) to ensure a high photon count, optionally used in combination with the low non-specific binding surfaces disclosed elsewhere herein to ensure very low background signals, may facilitate the use of these super-resolution imaging techniques for genetic testing and sequencing applications. Spatial accuracy or resolution decreases with decreasing numbers of photons collected, however, even in the case that only moderate numbers of photons are collected, position location accuracy or resolution of 20 nm is possible. In some cases, an improvement of 10-fold or better in lateral spatial resolution may be achieved. In some cases, an image resolution of better than 500 nm, 400 nm, 300 nm, 200 nm, 175 nm, 150 nm, 125 nm, 100 nm, 75 nm, 50 nm, 25 nm, or 10 nm may be achieved.

The second principle fundamental to this class of imaging is that small numbers of spatially separated fluorescent molecules within the sample are imaged at any given time.

In some instances, the ability to control fluorescence emission of small, dispersed subsets of fluorescent molecules in the sample plane is key to facilitating super-resolution imaging. In the case of fluorescence photoactivation localization microscopy (FPALM) and photoactivation localization microscopy (PALM), for example, the use of photoactivatable green fluorescent proteins (PA-GFP) as a label has allowed for controlled induction of fluorescent subsets in a sample using short pulses of 405 nm light to photo convert the PA-GFP from a dark, nonfluorescent state to a 488 nm excitable fluorescent state, thereby resulting in spatially separated subsets of fluorescent molecules that can be imaged [Lutz, et al. (2011), ibid]. In the case of stochastic optical reconstruction microscopy (STORM), the photo-switching properties of, for example, the cyanine dye pairs Cy®5-Cy®3 may be used in a similar fashion to enable the stochastic induction of Cy®5 fluorescence from a small subset of the molecules in the sample at any given time, e.g., small subsets of molecules that are spatially separated by at least several resolution units. In some instances, e.g., when combined with the sequencing-by-avidity approach described elsewhere herein, nucleotide conjugates may comprise a photoactivatable green fluorescent protein (PA-GFP) or a subdomain or portion thereof. In some instances, the nucleotide conjugates may comprise a mixture of conjugates in which a first portion is labeled with, e.g., Cy®3 labels, and a second portion is labeled with, e.g., Cy®5 labels. In some instances, the nucleotide conjugates may comprise a mixture of, e.g., Cy®3 and Cy®5 labels within the same conjugate.

The super-resolved image is reconstructed from the sum of the Gaussian fits from all molecules or features (e.g., labeled nucleic acid clusters) imaged in a time stack of acquired images [Lutz, et al. (2011), ibid], where the intensity corresponds to the positional uncertainty of the location of each molecule or subset of molecules. Unique to this kind of data set is the ability to render the image with different localization precisions or resolutions. In some instances, an imaging module comprising a total internal reflectance fluorescence (TIRF) optical imaging design may be advantageous in implementing the use of these super-resolution imaging techniques as the evanescent wave used for excitation of fluorescence is restricted in the axial dimension to less than 200 nm from the sample support or flow cell surface and thus suppresses background fluorescence signal. In some instances, the imaging system may comprise a higher numerical aperture objective than utilized in other imaging module designs disclosed herein. The use of higher numerical aperture objectives may facilitate implementation of evanescent wave excitation and highly efficient capture of photons from the fluorescent probes. In some instances, wide-field imaging using single-photon-sensitive EM-CCD cameras or other types of image sensors may enable simultaneous imaging of many molecules or subsets of molecules (e.g., nucleic acid sequence clusters) per frame, thereby improving the throughput of image acquisition.

In some instances, the data acquisition time required to acquire enough images for adequate feature definition and resolution may be shortened by improvements in the sensitivity and speed of the imaging system, through the use of the sequencing-by-avidity reagents and low non-specific binding surfaced disclosed herein to increase signal while reducing or eliminating background, and the use of improved image reconstruction algorithms.

Assessing image quality: For any of the embodiments of the optical imaging designs disclosed herein, imaging performance or imaging quality may be assessed using any of a variety of performance metrics known to those of skill in the art. Examples include, but are not limited to, measurements of modulation transfer function (MTF) at one or more specified spatial frequencies, defocus, spherical aberration, chromatic aberration, coma, astigmatism, field curvature, image distortion, contrast-to-noise ratio (CNR), or any combination thereof.

In some instances, the disclosed optical designs for dual-side imaging (e.g., the disclosed objective lens designs, tube lens designs, the use of an electro-optical phase plate in combination with an objective, etc., alone or in combination) may yield significant improvements for image quality for both the upper (near) and lower (far) interior surfaces of a flow cell, such that the difference in an imaging performance metric for imaging the upper interior surface and the lower interior surface of the flow cell is less than 20%, less than 15%, less than 10%, less than 5%, less than 4%, less than 3%, less than 2%, or less than 1% for any of the imaging performance metrics listed above, either individually or in combination.

In some instances, the disclosed optical designs for dual-side imaging (e.g., comprising the disclosed tube lens designs, the use of an electro-optical phase plate in combination with an objective, etc.) may yield significant improvements for image quality such that an image quality performance metric for dual-side imaging provides for an at least 1%, at least 2%, at least 3%, at least 4%, at least 5%, at least 10%, at least 15%, at least 20%, at least 25%, or at least 30% improvement in the imaging performance metric for dual-side imaging compared to that for a conventional system comprising, e.g., an objective lens, a motion-actuated compensator (that is moved out of or into the optical path when imaging the near or far interior surfaces of a flow cell), and an image sensor for any of the imaging performance metrics listed above, either individually or in combination. In some instances, fluorescence imaging systems comprising one or more of the disclosed tube lens designs provides for an at least equivalent or better improvement in an imaging performance metric for dual-side imaging compared to that for a conventional system comprising an objective lens, a motion-actuated compensator, and an image sensor. In some instances, fluorescence imaging systems comprising one or more of the disclosed tube lens designs provides for an at least 5%, 10%, 15%, 20%, 25%, 30%, 35%, 40%, 45%, or 50% improvement in an imaging performance metric for dual-side imaging compared to that for a conventional system comprising an objective lens, a motion-actuated compensator, and an image sensor.

Imaging Module Specifications:

Excitation light wavelength(s): In any of the disclosed optical imaging module designs, the light source(s) of the disclosed imaging modules may produce visible light, such as green light and/or red light. In some instances, the light source(s), alone or in combination with one or more optical components, e.g., excitation optical filters and/or dichroic beam splitters, may produce excitation light at about 350 nm, 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the excitation wavelength may have any value within this range, e.g., about 620 nm.

Excitation light bandwidths: In any of the disclosed optical imaging module designs, the light source(s), alone or in combination with one or more optical components, e.g., excitation optical filters and/or dichroic beam splitters, may produce light at the specified excitation wavelength within a bandwidth of ±2 nm, 5 nm, 10 nm, 20 nm, 40 nm, 80 nm, or greater. Those of skill in the art will recognize that the excitation bandwidths may have any value within this range, e.g., about +18 nm.

Light source power output: In any of the disclosed optical imaging module designs, the output of the light source(s) and/or an excitation light beam derived therefrom (including a composite excitation light beam) may range in power from about 0.5 Watts to about 5.0 Watts, or more (as will be discussed in more detail below). In some instances, the output of the light source and/or the power of an excitation light beam derived therefrom may be at least 0.5 Watts, at least 0.6 Watts, at least 0.7 Watts, at least 0.8 Watts, at least 1 Watts, at least 1.1 Watts, at least 1.2 Watts, at least 1.3 Watts, at least 1.4 Watts, at least 1.5 Watts, at least 1.6 Watts, at least 1.8 Watts, at least 2.0 Watts, at least 2.2 Watts, at least 2.4 Watts, at least 2.6 Watts, at least 2.8 Watts, at least 3.0 Watts, at least 3.5 Watts, at least 4.0 Watts, at least 4.5 Watts, or at least 5.0 Watts. In some implementations, the output of the light source and/or the power of an excitation light beam derived therefrom (including a composite excitation light beam) may be at most 5.0 Watts, at most 4.5 Watts, at most 4.0 Watts, at most 3.5 Watts, at most 3.0 Watts, at most 2.8 Watts, at most 2.6 Watts, at most 2.4 Watts, at most 2.2 Watts, at most 2.0 Watts, at most 1.8 Watts, at most 1.6 Watts, at most 1.5 Watts, at most 1.4 Watts, at most 1.3 Watts, at most 1.2 Watts, at most 1.1 Watts, at most 1 Watts, at most 0.8 Watts, at most 0.7 Watts, at most 0.6 Watts, or at most 0.5 Watts. Any of the lower and upper values described in this paragraph may be combined to form a range included within the present disclosure, for example, in some instances the output of the light source and/or the power of an excitation light beam derived therefrom (including a composite excitation light beam) may range from about 0.8 Watts to about 2.4 Watts. Those of skill in the art will recognize that the output of the light source and/or the power of an excitation light beam derived therefrom (including a composite excitation light beam) may have any value within this range, e.g., about 1.28 Watts.

Light source output power and CNR: In some implementations of the disclosed optical imaging module designs, the output power of the light source(s) and/or the power of excitation light beam(s) derived therefrom (including a composite excitation light beam) is sufficient, in combination with an appropriate sample, to provide for a contrast-to-noise ratio (CNR) in images acquired by the illumination and imaging module of at least 5, at least 10, at least 15, at least 20, at least 21, at least 22, at least 23, at least 24, at least 25, at least 30, at least 35, at least 40, or at least 50 or more, or any CNR within any range formed by any of these values.

Fluorescence emission bands: In some instances, the disclosed fluorescence optical imaging modules may be configured to detect fluorescence emission produced by any of a variety of fluorophores known to those of skill in the art. Examples of suitable fluorescence dyes for use in, e.g., genotyping and nucleic acid sequencing applications (e.g., by conjugation to nucleotides, oligonucleotides, or proteins) include, but are not limited to, fluorescein, rhodamine, coumarin, cyanine, and derivatives thereof, including the cyanine derivatives cyanine dye-3 (Cy®3), cyanine dye-5 (Cy®5), cyanine dye-7 (Cy®7), etc.

Fluorescence emission wavelengths: In any of the disclosed optical imaging module designs, the detection channel or imaging channel of the disclosed optical systems may include one or more optical components, e.g., emission optical filters and/or dichroic beam splitters, configured to collect emission light at about 350 nanometer (nm), 375 nm, 400 nm, 425 nm, 450 nm, 475 nm, 500 nm, 525 nm, 550 m, 575 nm, 600 nm, 625 nm, 650 nm, 675 nm, 700 nm, 725 nm, 750 nm, 775 nm, 800 nm, 825 nm, 850 nm, 875 nm, or 900 nm. Those of skill in the art will recognize that the emission wavelength may have any value within this range, e.g., about 825 nm.

Fluorescence emission light bandwidths: In any of the disclosed optical imaging module designs, the detection channel or imaging channel may comprise one or more optical components, e.g., emission optical filters and/or dichroic beam splitters, configured to collect light at the specified emission wavelength within a bandwidth of ±2 nm, ±5 nm, ±10 nm, ±20 nm, ±40 nm, ±80 nm, or greater. Those of skill in the art will recognize that the excitation bandwidths may have any value within this range, e.g., about ±18 nm.

Numerical aperture: In some instances, the numerical aperture of the objective lens and/or optical imaging module (e.g., comprising an objective lens and/or tube lens) in any of the disclosed optical system designs may range from about 0.1 to about 1.4. In some instances, the numerical aperture may be at least 0.1, at least 0.2, at least 0.3, at least 0.4, at least 0.5, at least 0.6, at least 0.7, at least 0.8, at least 0.9, at least 1.0, at least 1.1, at least 1.2, at least 1.3, or at least 1.4. In some instances, the numerical aperture may be at most 1.4, at most 1.3, at most 1.2, at most 1.1, at most 1.0, at most 0.9, at most 0.8, at most 0.7, at most 0.6, at most 0.5, at most 0.4, at most 0.3, at most 0.2, or at most 0.1. Any of the lower and upper values described in this paragraph may be combined to form a range included within the present disclosure, for example, in some instances the numerical aperture may range from about 0.1 to about 0.6. Those of skill in the art will recognize that the numerical aperture may have any value within this range, e.g., about 0.55.

Optical resolution: In some instances, depending on the numerical aperture of the objective lens and/or optical system (e.g., comprising an objective lens and/or tube lens), the minimum resolvable spot (or feature) separation distance at the sample plane achieved by any of the disclosed optical system designs may range from about 0.5 μm to about 2 μm. In some instances, the minimum resolvable spot separation distance at the sample plane may be at least 0.5 μm, at least 0.6 μm, at least 0.7 μm, at least 0.8 μm, at least 0.9 μm, at least 1.0 μm, at least 1.2 μm, at least 1.4 μm, at least 1.6 μm, at least 1.8 μm, or at least 1.0 μm. In some instances, the minimum resolvable spot separation distance may be at most 2.0 μm, at most 1.8 μm, at most 1.6 μm, at most 1.4 μm, at most 1.2 μm, at most 1.0 μm, at most 0.9 μm, at most 0.8 μm, at most 0.7 μm, at most 0.6 μm, or at most 0.5 μm. Any of the lower and upper values described in this paragraph may be combined to form a range included within the present disclosure, for example, in some instances the minimum resolvable spot separation distance may range from about 0.8 μm to about 1.6 μm. Those of skill in the art will recognize that the minimum resolvable spot separation distance may have any value within this range, e.g., about 0.95 μm.

Optical resolution of first and second surfaces at different depths: In some instances, the use of the novel objective lens and/or tube lens designs disclosed herein, in any of the optical modules or systems disclosed herein, may confer comparable optical resolution for first and second surfaces (e.g. the upper and lower interior surfaces of a flow cell) with or without the need to refocus between acquiring the images of the first and second surfaces. In some instances, the optical resolution of the images thus obtained of the first and second surfaces may be with 20%, 18%, 16%, 14%, 12%, 10%, 8%, 6%, 4%, 2%, or 1% of each other, or within any value within this range.

Magnification: In some instances, the magnification of the objective lens and/or tube lens, and/or optical system (e.g., comprising an objective lens and/or tube lens) in any of the disclosed optical configurations may range from about 2× to about 20×. In some instances, the optical system magnification may be at least 2×, at least 3×, at least 4×, at least 5×, at least 6×, at least 7×, at least 8×, at least 9×, at least 10×, at least 15×, or at least 20×. In some instances, the optical system magnification may be at most 20×, at most 15×, at most 10×, at most 9×, at most 8×, at most 7×, at most 6×, at most 5×, at most 4×, at most 3×, or at most 2×. Any of the lower and upper values described in this paragraph may be combined to form a range included within the present disclosure, for example, in some instances the optical system magnification may range from about 3× to about 10×. Those of skill in the art will recognize that the optical system magnification may have any value within this range, e.g., about 7.5×.

Objective lens focal length: In some implementations of the disclosed optical designs, the focal length of the objective lens may range between 20 mm and 40 mm. In some instances, the focal length of the objective lens may be at least 20 mm, at least 25 mm, at least 30 mm, at least 35 mm, or at least 40 mm. In some instances, the focal length of the objective lens may be at most 40 mm, at most 35 mm, at most 30 mm, at most 25 mm, or at most 20 mm. Any of the lower and upper values described in this paragraph may be combined to form a range included within the present disclosure, for example, in some instances the focal length of the objective lens may range from 25 mm to 35 mm. Those of skill in the art will recognize that the focal length of the objective lens may have any value within the range of values specified above, e.g., about 37 mm.

Objective lens working distance: In some implementations of the disclosed optical designs, the working distance of the objective lens may range between about 100 µm and 30 mm. In some instances, the working distance may be at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 4 mm, at least 6 mm, at least 8 mm, at least 10 mm, at least 15 mm, at least 20 mm, at least 25 mm, or at least 30 mm. In some instances, the working distance may be at most 30 mm, at most 25 mm, at most 20 mm, at most 15 mm, at most 10 mm, at most 8 mm, at most 6 mm, at most 4 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm. Any of the lower and upper values described in this paragraph may be combined to form a range included within the present disclosure, for example, in some instances the working distance of the objective lens may range from 500 µm to 2 mm. Those of skill in the art will recognize that the working distance of the objective lens may have any value within the range of values specified above, e.g., about 1.25 mm.

Objectives optimized for imaging through thick coverslips: In some instances of the disclosed optical designs, the design of the objective lens may be improved or optimized for a different coverslip of flow cell thickness. For example, in some instances the objective lens may be designed for optimal optical performance for a coverslip that is from about 200 µm to about 1,000 µm thick. In some instances, the objective lens may be designed for optimal performance with a coverslip that is at least 200 µm, at least 300 µm, at least 400 µm, at least 500 µm, at least 600 µm, at least 700 µm, at least 800 µm, at least 900 µm, or at least 1,000 µm thick. In some instances, the objective lens may be designed for optimal performance with a coverslip that is at most 1,000 µm, at most 900 µm, at most 800 µm, at most 700 µm, at most 600 µm, at most 500 µm, at most 400 µm, at most 300 µm, or at most 200 µm thick. Any of the lower and upper values described in this paragraph may be combined to form a range included within the present disclosure, for example, in some instances the objective lens may be designed for optimal optical performance for a coverslip that may range from about 300 µm to about 900 µm. Those of skill in the art will recognize that the objective lens may be designed for optimal optical performance for a coverslip that may have any value within this range, e.g., about 725 µm.

Depth of field and depth of focus: In some instances, the depth of field and/or depth of focus for any of the disclosed imaging module (e.g., comprising an objective lens and/or tube lens) designs may range from about 10 µm to about 800 µm, or more. In some instances, the depth of field and/or depth of focus may be at least 10 µm, at least 20 µm, at least 30 µm, at least 40 µm, at least 50 µm, at least 75 µm, at least 100 µm, at least 125 µm, at least 150 µm, at least 175 µm, at least 200 µm, at least 250 µm, at least 300 µm, at least 300 µm, at least 400 µm, at least 500 µm, at least 600 µm, at least 700 µm, or at least 800 µm, or more. In some instances, the depth of field and/or depth of focus be at most 800 µm, at most 700 µm, at most 600 µm, at most 500 µm, at most 400 µm, at most 300 µm, at most 250 µm, at most 200 µm, at most 175 µm, at most 150 µm, at most 125 µm, at most 100 µm, at most 75 µm, at most 50 µm, at most 40 µm, at most 30 µm, at most 20 µm, at most 10 µm, or less. Any of the lower and upper values described in this paragraph may be combined to form a range included within the present disclosure, for example, in some instances the depth of field and/or depth of focus may range from about 100 µm to about 175 µm. Those of skill in the art will recognize that the depth of field and/or depth of focus may have any value within the range of values specified above, e.g., about 132 µm.

Field-of-view (FOV): In some implementations, the FOV of any of the disclosed imaging module designs (e.g., that provided by a combination of objective lens and detection channel optics (such as a tube lens)) may range, for example, between about 1 mm and 5 mm (e.g., in diameter, width, length, or longest dimension). In some instances, the FOV may be at least 1.0 mm, at least 1.5 mm, at least 2.0 mm, at least 2.5 mm, at least 3.0 mm, at least 3.5 mm, at least 4.0 mm, at least 4.5 mm, or at least 5.0 mm (e.g., in diameter, width, length, or longest dimension). In some instances, the FOV may be at most 5.0 mm, at most 4.5 mm, at most 4.0 mm, at most 3.5 mm, at most 3.0 mm, at most 2.5 mm, at most 2.0 mm, at most 1.5 mm, or at most 1.0 mm (e.g., in diameter, width, length, or longest dimension). Any of the lower and upper values described in this paragraph may be combined to form a range included within the present disclosure, for example, in some instances the FOV may range from about 1.5 mm to about 3.5 mm (e.g., in diameter, width, length, or longest dimension). Those of skill in the art will recognize that the FOV may have any value within the range of values specified above, e.g., about 3.2 mm (e.g., in diameter, width, length, or longest dimension).

Field-of-view (FOV) area: In some instances of the disclosed optical system designs, the area of the field-of-view may range from about 2 mm$^2$ to about 5 mm$^2$. In some instances, the field-of-view may be at least 2 mm$^2$, at least 3 mm$^2$, at least 4 mm$^2$, or at least 5 mm$^2$ in area. In some instances, the field-of-view may be at most 5 mm$^2$, at most 4 mm$^2$, at most 3 mm$^2$, or at most 2 mm$^2$ in area. Any of the lower and upper values described in this paragraph may be combined to form a range included within the present disclosure, for example, in some instances the field-of-view may range from about 3 mm$^2$ to about 4 mm$^2$ in area. Those of skill in the art will recognize that the area of the field-of-view may have any value within this range, e.g., 2.75 mm$^2$.

Optimization of objective lens and or tube lens MTF: In some instances, the design of the objective lens and/or at least one tube lens in the disclosed imaging modules and systems is configured to optimize the modulation transfer function in the mid to high spatial frequency range. For example, in some instances, the design of the objective lens and/or at least one tube lens in the disclosed imaging modules and systems is configured to optimize the modulation transfer function in the spatial frequency range from 500 cycles per mm to 900 cycles per mm, from 700 cycles per mm to 1100 cycles per mm, from 800 cycles per mm to 1200 cycles per mm, or from 600 cycles per mm to 1000 cycles per mm in the sample plane.

Optical aberration and diffraction-limited imaging performance: In some implementations of any of the optical imaging module designs disclosed herein, the objective lens and/or tube lens may be configured to provide the imaging module with a field-of-view as indicated above such that the FOV has less than 0.15 waves of aberration over at least 60%, 70%, 80%, 90%, or 95% of the field. In some implementations, the objective lens and/or tube lens may be configured to provide the imaging module with a field-of-view as indicated above such that the FOV has less than 0.1 waves of aberration over at least 60%, 70%, 80%, 90%, or 95% of the field.

In some implementations, the objective lens and/or tube lens may be configured to provide the imaging module with a field-of-view as indicated above such that the FOV has less than 0.075 waves of aberration over at least 60%, 70%, 80%, 90%, or 95% of the field. In some implementations, the objective lens and/or tube lens may be configured to provide the imaging module with a field-of-view as indicated above such that the FOV is diffraction-limited over at least 60%, 70%, 80%, 90%, or 95% of the field.

Angle of incidence of light beams on dichroic reflectors, beam splitter, and beam combiners: In some instances of the disclosed optical designs, the angles of incidence for a light beam incident on a dichroic reflector, beam splitter, or beam combiner may range between about 20 degrees and about 45 degrees. In some instances, the angles of incidence may be at least 20 degrees, at least 25 degrees, at least 30 degrees, at least 35 degrees, at least 40 degrees, or at least 45 degrees. In some instances, the angles of incidence may be at most 45 degrees, at most 40 degrees, at most 35 degrees, at most 30 degrees, at most 25 degrees, or at most 20 degrees. Any of the lower and upper values described in this paragraph may be combined to form a range included within the present disclosure, for example, in some instances the angles of incidence may range from about 25 degrees to about 40 degrees. Those of skill in the art will recognize that the angles of incidence may have any value within the range of values specified above, e.g., about 43 degrees.

Image sensor (photodetector array) size: In some instances, the disclosed optical systems may comprise image sensor(s) having an active area with a diagonal ranging from about 10 mm to about 30 mm, or larger. In some instances, the image sensors may have an active area with a diagonal of at least 10 mm, at least 12 mm, at least 14 mm, at least 16 mm, at least 18 mm, at least 20 mm, at least 22 mm, at least 24 mm, at least 26 mm, at least 28 mm, or at least 30 mm. In some instances, the image sensors may have an active area with a diagonal of at most 30 mm, at most 28 mm, at most 26 mm, at most 24 mm, at most 22 mm, at most 20 mm, at most 18 mm, at most 16 mm, at most 14 mm, at most 12 mm, or at most 10 mm. Any of the lower and upper values described in this paragraph may be combined to form a range included within the present disclosure, for example, in some instances the image sensor(s) may have an active area with a diagonal ranging from about 12 mm to about 24 mm. Those of skill in the art will recognize that the image sensor(s) may have an active area with a diagonal having any value within the range of values specified above, e.g., about 28.5 mm.

Image sensor pixel size and pitch: In some instances, the pixel size and/or pitch selected for the image sensor(s) used in the disclosed optical system designs may range in at least one dimension from about 1 μm to about 10 m. In some instances, the pixel size and/or pitch may be at least 1 μm, at least 2 μm, at least 3 μm, at least 4 μm, at least 5 μm, at least 6 μm, at least 7 μm, at least 8 μm, at least 9 μm, or at least 10 μm. In some instances, the pixel size and/or pitch may be at most 10 m, at most 9 μm, at most 8 μm, at most 7 μm, at most 6 μm, at most 5 μm, at most 4 μm, at most 3 μm, at most 2 μm, or at most 1 μm. Any of the lower and upper values described in this paragraph may be combined to form a range included within the present disclosure, for example, in some instances the pixel size and/or pitch may range from about 3 μm to about 9 μm. Those of skill in the art will recognize that the pixel size and/or pitch may have any value within this range, e.g., about 1.4 μm.

Oversampling: In some instances of the disclosed optical designs, a spatial oversampling scheme is utilized wherein the spatial sampling frequency is at least 2×, 2.5×, 3×, 3.5×, 4×, 4.5×, 5×, 6×, 7×, 8×, 9×, or 10× the optical resolution X(lp/mm).

Maximum translation stage velocity: In some instances of the disclosed optical imaging modules, the maximum translation stage velocity on any one axis may range from about 1 mm/sec to about 5 mm/sec. In some instances, the maximum translation stage velocity may be at least 1 mm/sec, at least 2 mm/sec, at least 3 mm/sec, at least 4 mm/sec, or at least 5 mm/sec. In some instances, the maximum translation stage velocity may be at most 5 mm/sec, at most 4 mm/sec, at most 3 mm/sec, at most 2 mm/sec, or at most 1 mm/sec. Any of the lower and upper values described in this paragraph may be combined to form a range included within the present disclosure, for example, in some instances the maximum translation stage velocity may range from about 2 mm/sec to about 4 mm/sec. Those of skill in the art will recognize that the maximum translation stage velocity may have any value within this range, e.g., about 2.6 mm/sec.

Maximum translation stage acceleration: In some instances of the disclosed optical imaging modules, the maximum acceleration on any one axis of motion may range from about 2 mm/sec² to about 10 mm/sec². In some instances, the maximum acceleration may be at least 2 mm/sec², at least 3 mm/sec², at least 4 mm/sec², at least 5 mm/sec², at least 6 mm/sec², at least 7 mm/sec², at least 8 mm/sec², at least 9 mm/sec², or at least 10 mm/sec². In some instances, the maximum acceleration may be at most 10 mm/sec², at most 9 mm/sec², at most 8 mm/sec², at most 7 mm/sec², at most 6 mm/sec², at most 5 mm/sec², at most 4 mm/sec², at most 3 mm/sec², or at most 2 mm/sec². Any of the lower and upper values described in this paragraph may be combined to form a range included within the present disclosure, for example, in some instances the maximum acceleration may range from about 2 mm/sec² to about 8 mm/sec². Those of skill in the art will recognize that the maximum acceleration may have any value within this range, e.g., about 3.7 mm/sec².

Translation stage positioning repeatability: In some instances of the disclosed optical imaging modules, the repeatability of positioning for any one axis may range from about 0.1 µm to about 2 µm. In some instances, the repeatability of positioning may be at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, at least 1.0 µm, at least 1.2 µm, at least 1.4 µm, at least 1.6 µm, at least 1.8 µm, or at least 2.0 µm. In some instances, the repeatability of positioning may be at most 2.0 µm, at most 1.8 µm, at most 1.6 µm, at most 1.4 µm, at most 1.2 µm, at most 1.0 µm, at most 0.9 µm, at most 0.8 µm, at most 0.7 µm, at most 0.6 µm, at most 0.5 µm, at most 0.4 µm, at most 0.3 µm, at most 0.2 µm, or at most 0.1 µm. Any of the lower and upper values described in this paragraph may be combined to form a range included within the present disclosure, for example, in some instances the repeatability of positioning may range from about 0.3 µm to about 1.2 µm. Those of skill in the art will recognize that the repeatability of positioning may have any value within this range, e.g., about 0.47 µm.

FOV repositioning time: In some instances of the disclosed optical imaging modules, the maximum time required to reposition the sample plane (field-of-view) relative to the optics, or vice versa, may range from about 0.1 sec to about 0.5 sec. In some instances, the maximum repositioning time (e.g., the scan stage step and settle time) may be at least 0.1 sec, at least 0.2 sec, at least 0.3 sec, at least 0.4 sec, or at least 0.5 sec. In some instances, the maximum repositioning time may be at most 0.5 sec, at most 0.4 sec, at most 0.3 sec, at most 0.2 sec, or at most 0.1 sec. Any of the lower and upper values described in this paragraph may be combined to form a range included within the present disclosure, for example, in some instances the maximum repositioning time may range from about 0.2 sec to about 0.4 sec. Those of skill in the art will recognize that the maximum repositioning time may have any value within this range, e.g., about 0.45 sec.

Error threshold for autofocus correction: In some instances of the disclosed optical imaging modules, the specified error threshold for triggering an autofocus correction may range from about 50 nm to about 200 nm. In some instances, the error threshold may be at least 50 nm, at least 75 nm, at least 100 nm, at least 125 nm, at least 150 nm, at least 175 nm, or at least 200 nm. In some instances, the error threshold may be at most 200 nm, at most 175 nm, at most 150 nm, at most 125 nm, at most 100 nm, at most 75 nm, or at most 50 nm. Any of the lower and upper values described in this paragraph may be combined to form a range included within the present disclosure, for example, in some instances the error threshold may range from about 75 nm to about 150 nm. Those of skill in the art will recognize that the error threshold may have any value within this range, e.g., about 105 nm.

Image acquisition time: In some instances of the disclosed optical imaging modules, the image acquisition time may range from about 0.001 sec to about 1 sec. In some instances, the image acquisition time may be at least 0.001 sec, at least 0.01 sec, at least 0.1 sec, or at least 1 sec. in some instances, the image acquisition time may be at most 1 sec, at most 0.1 sec, at most 0.01 sec, or at most 0.001 sec. Any of the lower and upper values described in this paragraph may be combined to form a range included within the present disclosure, for example, in some instances the image acquisition time may range from about 0.01 sec to about 0.1 sec. Those of skill in the art will recognize that the image acquisition time may have any value within this range, e.g., about 0.250 seconds.

Imaging time per FOV: In some instances, the imaging times may range from about 0.5 seconds to about 3 seconds per field-of-view. In some instances, the imaging time may be at least 0.5 seconds, at least 1 second, at least 1.5 seconds, at least 2 seconds, at least 2.5 seconds, or at least 3 seconds per FOV. In some instances, the imaging time may be at most 3 seconds, at most 2.5 seconds, at most 2 seconds, at most 1.5 seconds, at most 1 second, or at most 0.5 seconds per FOV. Any of the lower and upper values described in this paragraph may be combined to form a range included within the present disclosure, for example, in some instances the imaging time may range from about 1 second to about 2.5 seconds. Those of skill in the art will recognize that the imaging time may have any value within this range, e.g., about 1.85 seconds.

Flatness of field: In some instances, images across 80%, 90%, 95%, 98%, 99%, or 100% percent of the field-of-view are acquired within ±200 nm, ±175 nm, ±150 nm, ±125 nm, ±100 nm, ±75 nm, or ±50 nm relative to the best focal plane for each fluorescence (or other imaging mode) detection channel.

Figure 39:
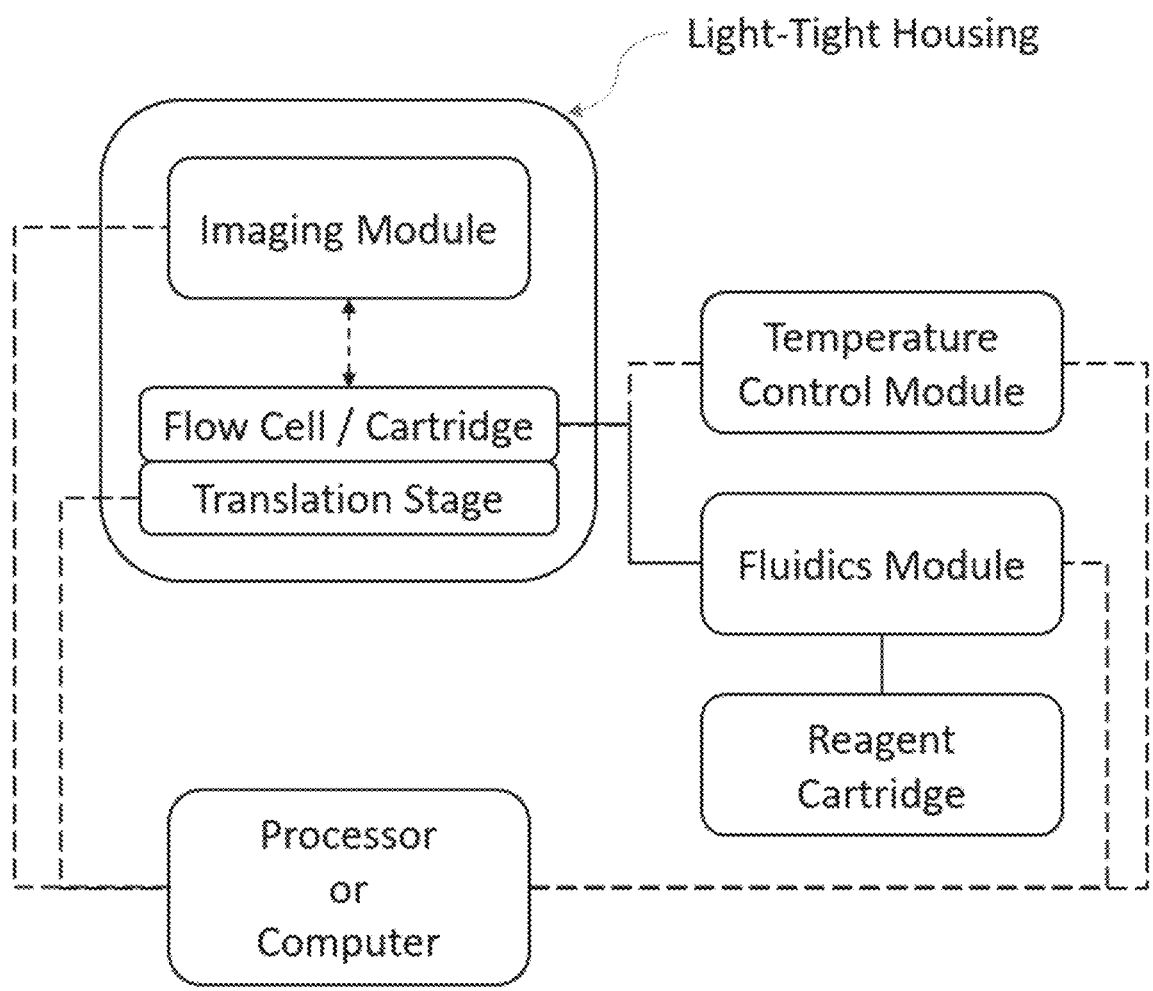
FIG. 39 provides a non-limiting example of a block diagram for a sequencing system as disclosed herein.

Systems and system components for genomics and other applications: As noted above, in some implementations, the disclosed optical imaging modules may function as modules, components, sub-assemblies, or sub-systems of larger systems configured for performing, e.g., genomics applications (e.g., genetic testing and/or nucleic acid sequencing applications) or other chemical analysis, biochemical analysis, nucleic acid analysis, cell analysis or tissue analysis applications. FIG. 39 provides a non-limiting example of a block diagram for, e.g., a sequencing system as disclosed herein. In addition to one, two, three, four, or more than four imaging modules as disclosed herein (each of which may comprise one or more illumination optical paths and/or one or more detection optical paths (e.g., one or more detection channels configured for imaging fluorescence emission within a specified wavelength range onto an image sensor)), such systems may comprise one or more X-Y translation stages, one or more X-Y-Z translation stages, flow cells or cartridges, fluidics systems and fluid flow control modules, reagent cartridges, temperature control modules, fluid dispensing robotics, cartridge- and/or microplate-handling (pick-and-place) robotics, light-tight housings and/or environmental control chambers, one or more processors or computers, data storage modules, data communication modules (e.g., Bluetooth, WiFi, intranet, or internet communication hardware and associated software), display modules, one or more local and/or cloud-based software packages (e.g., instrument/system control software packages, image processing software packages, data analysis software packages), etc., or any combination thereof.

Translation stages: In some implementations of the imaging and analysis systems (e.g., nucleic acid sequencing systems) disclosed herein, the system may comprise one or more (e.g., one, two, three, four, or more than four) high precision X-Y (or in some cases, X-Y-Z) translation stage(s) for re-positioning one or more sample support structure(s) (e.g., flow cell(s)) in relation to the one or more imaging modules, for example, in order to tile one or more images, each corresponding to a field-of-view of the imaging module, to reconstruct composite image(s) of an entire flow cell surface. In some implementations of the imaging systems and genomics analysis systems (e.g., nucleic acid sequencing systems) disclosed herein, the system may comprise one or more (e.g., one, two, three, four, or more than four) high precision X-Y (or in some cases, X-Y-Z) translation stage(s) for re-positioning the one or more imaging modules in relation to one or more sample support structure(s) (e.g., flow cell(s)), for example, in order to tile one or more images, each corresponding to a field-of-view of the imaging module, to reconstruct composite image(s) of an entire flow cell surface.

Suitable translation stages are commercially available from a variety of vendors, for example, Parker Hannifin. Precision translation stage systems typically comprise a combination of several components including, but not limited to, linear actuators, optical encoders, servo and/or stepper motors, and motor controllers or drive units. High precision and repeatability of stage movement is required for the systems and methods disclosed herein in order to ensure accurate and reproducible positioning and imaging of, e.g., fluorescence signals when interspersing repeated steps of reagent delivery and optical detection.

Consequently, the systems disclosed herein may comprise specifying the precision with which the translation stage is configured to position a sample support structure in relation to the illumination and/or imaging optics (or vice versa). In one aspect of the present disclosure, the precision of the one or more translation stages is between about 0.1 µm and about 10 µm. In other aspects, the precision of the translation stage is about 10 µm or less, about 9 µm or less, about 8 µm or less, about 7 µm or less, about 6 µm or less, about 5 µm or less, about 4 µm or less, about 3 µm or less, about 2 µm or less, about 1 µm or less, about 0.9 µm or less, about 0.8 µm or less, about 0.7 µm or less, about 0.6 µm or less, about 0.5 µm or less, about 0.4 µm or less, about 0.3 µm or less, about 0.2 µm or less, or about 0.1 µm or less. Those of skill in the art will appreciate that, in some instances, the positioning precision of the translation stage may fall within any range bounded by any of two of these values (e.g. from about 0.5 µm to about 1.5 µm). In some instances, the positioning precision of the translation stage may have any value within the range of values included in this paragraph, e.g., about 0.12 µm.

Flow cells, microfluidic devices, and cartridges: The flow cell devices and flow cell cartridges disclosed herein may be used as components of systems designed for a variety of chemical analysis, biochemical analysis, nucleic acid analysis, cell analysis, or tissue analysis application. In general, such systems may comprise one or more one or more of the disclosed single capillary flow cell devices, multiple capillary flow cell devices, capillary flow cell cartridges, and/or microfluidic devices and cartridges described herein. Additional description of the disclosed flow cell devices and cartridges may be found in PCT Patent Application Publication WO 2020/118255, which is incorporated herein by reference in its entirety.

In some instances, the systems disclosed herein may comprise 1, 2, 3, 4, 5, 6, 7, 8, 9, 10, or more than 10 single capillary flow cell devices, multiple capillary flow cell devices, capillary flow cell cartridges, and/or microfluidic devices and cartridges. In some instances, the single capillary flow cell devices, multiple capillary flow cell devices, and/or microfluidic devices and cartridges may be fixed components of the disclosed systems. In some instances, the single capillary flow cell devices, multiple capillary flow cell devices, and/or microfluidic devices and cartridges may be removable, exchangeable components of the disclosed systems. In some instances, the single capillary flow cell devices, multiple capillary flow cell devices, and/or microfluidic devices and cartridges may be disposable or consumable components of the disclosed systems.

In some implementations, the disclosed single capillary flow cell devices (or single capillary flow cell cartridges) comprise a single capillary, e.g., a glass or fused-silica capillary, the lumen of which forms a fluid flow path through which reagents or solutions may flow, and the interior surface of which may form a sample support structure to which samples of interest are bound or tethered. In some implementations, the multi-capillary capillary flow cell devices (or multi-capillary flow cell cartridges) disclosed herein may comprise 2, 3, 4, 5, 6, 7, 8, 9, 10, 11, 12, 13, 14, 15, 16, 17, 18, 19, 20, or more than 20 capillaries configured for performing an analysis technique that further comprises imaging as a detection method.

In some instances, one or more capillaries may be packaged within a chassis to form a cartridge that facilitates ease-of-handling, incorporates adapters or connectors for making external fluid connections, and may optionally include additional integrated functionality such as reagent reservoirs, waste reservoirs, valves (e.g., microvalves), pumps (e.g., micropumps), etc., or any combination thereof.

Figure 29:
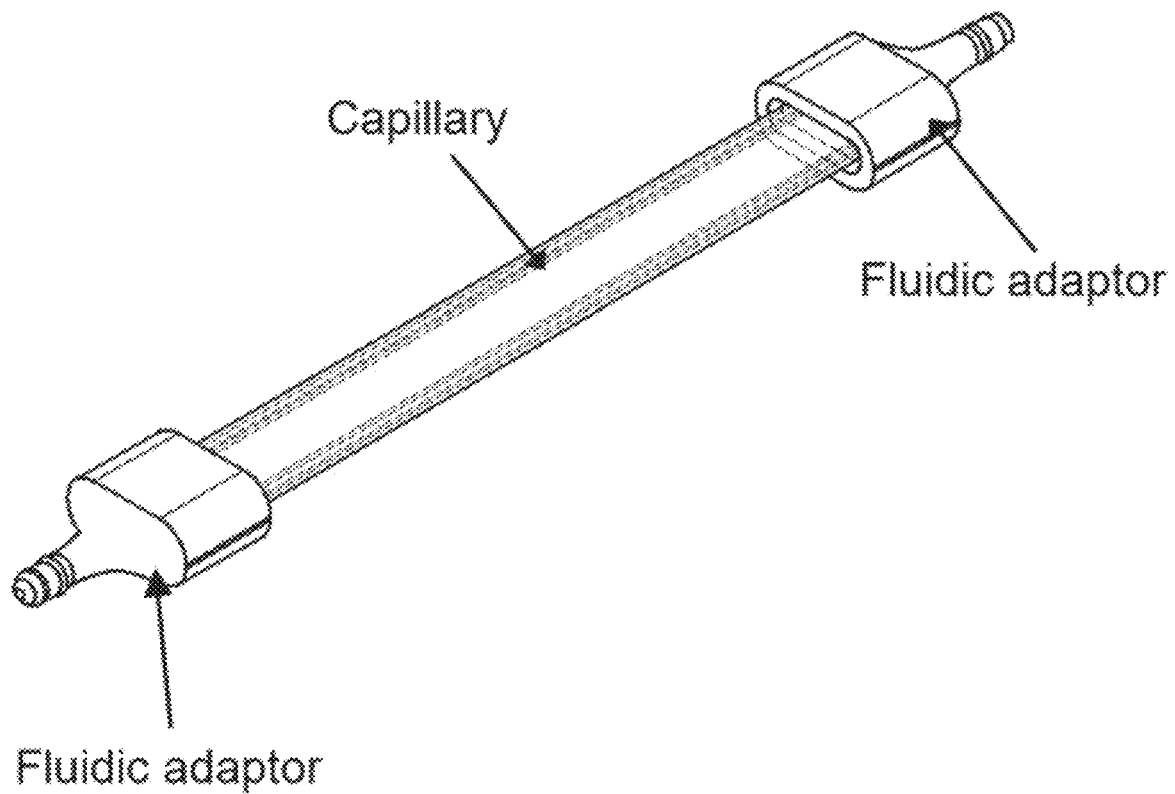
FIG. 29 illustrates one non-limiting example of a single capillary flow cell having 2 fluidic adaptors.

FIG. 29 illustrates one non-limiting example of a single glass capillary flow cell device that comprises two fluidic adaptors—one affixed to each end of the piece of glass capillary—that are designed to mate with standard OD fluidic tubing to provide for convenient, interchangeable fluid connections with an external fluid flow control system. The fluidic adaptors can be attached to the capillary using any of a variety of techniques known to those of skill in the art including, but not limited to, press fit, adhesive bonding, solvent bonding, laser welding, etc., or any combination thereof.

In general, the capillaries used in the disclosed capillary flow cell devices and capillary flow cell cartridges will have at least one internal, axially-aligned fluid flow channel (or "lumen") that runs the full length of the capillary. In some instances, the capillary may have two, three, four, five, or more than five internal, axially-aligned fluid flow channels (or "lumen").

A number specified cross-sectional geometries for suitable capillaries (or the lumen thereof) are consistent with the disclosure herein including, but not limited to, circular, elliptical, square, rectangular, triangular, rounded square, rounded rectangular, or rounded triangular cross-sectional geometries. In some instances, the capillary (or lumen thereof) may have any specified cross-sectional dimension or set of dimensions. For example, in some instances the largest cross-sectional dimension of the capillary lumen (e.g. the diameter if the lumen is circular in shape, or the diagonal if the lumen is square or rectangular in shape) may range from about 10 µm to about 10 mm. In some aspects, the largest cross-sectional dimension of the capillary lumen may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the largest cross-sectional dimension of the capillary lumen may be at most 10 mm, at most 9 mm, at most 8 mm, at most 7 mm, at most 6 mm, at most 5 mm, at most 4 mm, at most 3 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the present disclosure, for example, in some instances the largest cross-sectional dimension of the capillary lumen may range from about 100 µm to about 500 µm. Those of skill in the art will recognize that the largest cross-sectional dimension of the capillary lumen may have any value within this range, e.g., about 124 µm.

In some instances, e.g., wherein the lumen of the one or more capillaries in a flow cell device or cartridge has a square or rectangular cross-section, the distance between a first interior surface (e.g., a top or upper surface) and a second interior surface (e.g., a bottom or lower surface) that defines the gap height or thickness of a fluid flow channel may range from about 10 µm to about 500 µm. In some instances, the gap height may be at least 10 µm, at least 20 µm, at least 30 µm, at least 40 µm, at least 50 µm, at least 60 µm, at least 70 µm, at least 80 µm, at least 90 µm, at least 100 µm, at least 125 µm, at least 150 µm, at least 175 µm, at least 200 µm, at least 225 µm, at least 250 µm, at least 275 µm, at least 300 µm, at least 325 µm, at least 350 µm, at least 375 µm, at least 400 µm, at least 425 µm, at least 450 µm, at least 475 µm, or at least 500 µm. In some instances, the gap height may be at most 500 µm, at most 475 µm, at most 450 µm, at most 425 µm, at most 400 µm, at most 375 µm, at most 350 µm, at most 325 µm, at most 300 µm, at most 275 µm, at most 250 µm, at most 225 µm, at most 200 µm, at most 175 µm, at most 150 µm, at most 125 µm, at most 100 µm, at most 90 µm, at most 80 µm, at most 70 µm, at most 60 µm, at most 50 µm, at most 40 µm, at most 30 µm, at most 20 µm, or most 10 µm. Any of the lower and upper values described in this paragraph may be combined to form a range included within the present disclosure, for example, in some instances the gap height may range from about 40 µm to about 125 µm. Those of skill in the art will recognize that the gap height may have any value within the range of values in this paragraph, e.g., about 122 µm.

In some instances, the length of the one or more capillaries used to fabricate the disclosed capillary flow cell devices or flow cell cartridges may range from about 5 mm to about 5 cm or greater. In some instances, the length of the one or more capillaries may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, or at least 5 cm. In some instances, the length of the one or more capillaries may be at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the one or more capillaries may range from about 1.5 cm to about 2.5 cm. Those of skill in the art will recognize that the length of the one or more capillaries may have any value within this range, e.g., about 1.85 cm. In some instances, devices or cartridges may comprise a plurality of two or more capillaries that are the same length. In some instances, devices or cartridges may comprise a plurality of two or more capillaries that are of different lengths.

The capillaries used for constructing the disclosed capillary flow cell devices or capillary flow cell cartridges may be fabricated from any of a variety of materials known to those of skill in the art including, but not limited to, glass (e.g., borosilicate glass, soda lime glass, etc.), fused silica (quartz), polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives, or any combination thereof. PEI is somewhere between polycarbonate and PEEK in terms of both cost and chemical compatibility. FFKM is also known as Kalrez.

The one or more materials used to fabricate the capillaries are often optically transparent to facilitate use with spectroscopic or imaging-based detection techniques. In some instances, the entire capillary will be optically transparent. Alternatively, in some instances, only a portion of the capillary (e.g., an optically transparent "window") will be optically transparent.

The capillaries used for constructing the disclosed capillary flow cell devices and capillary flow cell cartridges may be fabricated using any of a variety of techniques known to those of skill in the art, where the choice of fabrication technique is often dependent on the choice of material used, and vice versa. Examples of suitable capillary fabrication techniques include, but are not limited to, extrusion, drawing, precision computer numerical control (CNC) machining and boring, laser photoablation, and the like.

In some implementations, the capillaries used in the disclosed capillary flow cell devices and cartridges may be off-the-shelf commercial products. Examples of commercial vendors that provide precision capillary tubing include Accu-Glass (St. Louis, MO; precision glass capillary tubing), Polymicro Technologies (Phoenix, AZ; precision glass and fused-silica capillary tubing), Friedrich & Dimmock, Inc. (Millville, NJ; custom precision glass capillary tubing), and Drummond Scientific (Broomall, PA; OEM glass and plastic capillary tubing).

The fluidic adapters that are attached to the capillaries of the capillary flow cell devices and cartridges disclosed herein, and other components of the capillary flow cell devices or cartridges, may be fabricated using any of a variety of suitable techniques (e.g., extrusion molding, injection molding, compression molding, precision CNC machining, etc.) and materials (e.g., glass, fused-silica, ceramic, metal, polydimethylsiloxane, polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), etc.), where again the choice of fabrication technique is often dependent on the choice of material used, and vice versa.

Figure 30:
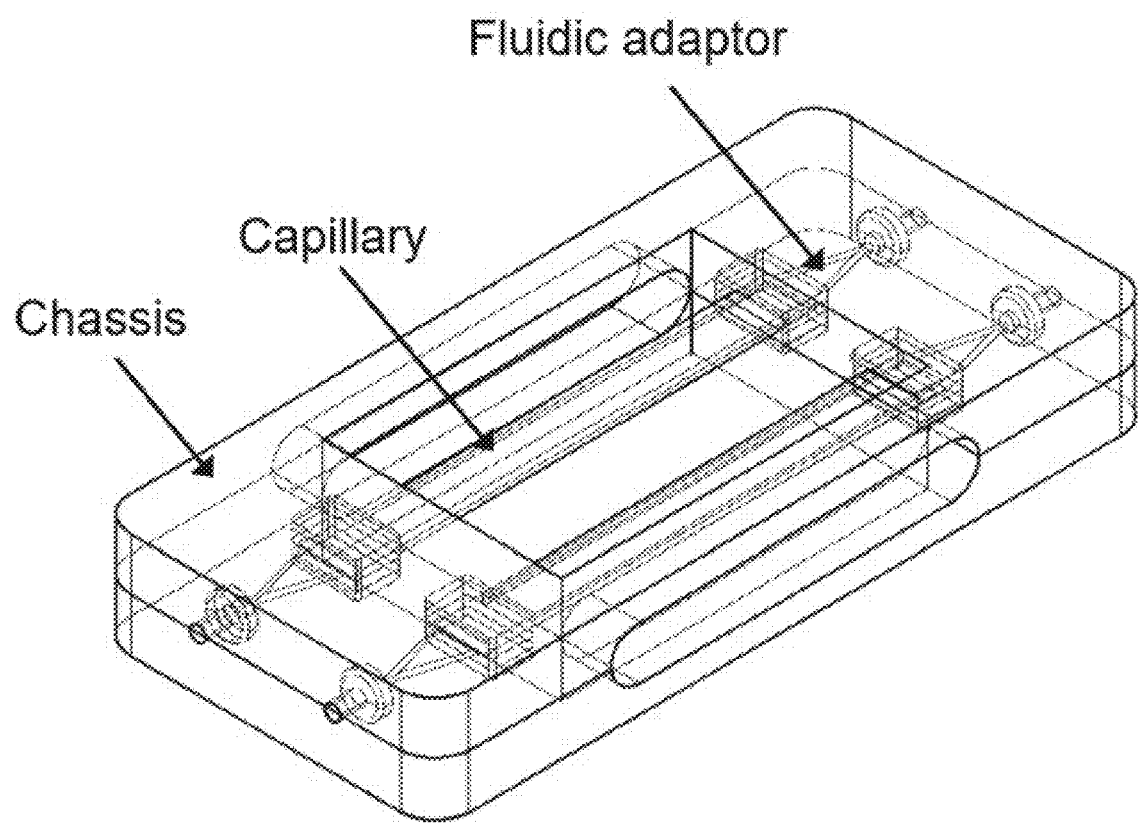
FIG. 30 illustrates one non-limiting example of a flow cell cartridge comprising a chassis, fluidic adapters, and optionally other components, that is designed to hold two capillaries.

FIG. 30 provides a non-limiting example of capillary flow cell cartridge that comprises two glass capillaries, fluidic adaptors (two per capillary in this example), and a cartridge chassis that mates with the capillaries and/or fluidic adapters such that the capillaries are held in a fixed orientation relative to the cartridge. In some instances, the fluidic adaptors may be integrated with the cartridge chassis. In some instances, the cartridge may comprise additional adapters that mate with the capillaries and/or capillary fluidic adapters. As noted elsewhere herein, in some instances, the cartridge may comprise additional functional components. In some instances, the capillaries are permanently mounted in the cartridge. In some instances, the cartridge chassis is designed to allow one or more capillaries of the flow cell cartridge to be interchangeably removed and replaced. For example, in some instances, the cartridge chassis may comprise a hinged "clamshell" configuration which allows it to be opened so that one or more capillaries may be removed and replaced. In some instances, the cartridge chassis is configured to mount on, for example, the stage of a fluorescence microscope or within a cartridge holder of a fluorescence imaging module or instrument system of the present disclosure.

In some instances, the disclosed flow cell devices may comprise microfluidic devices (or "microfluidic chips") and cartridges, where the microfluidic devices are fabricated by forming fluid channels in one or more layers of a suitable material and comprise one or more fluid channels (e.g., "analysis" channels) configured for performing an analysis technique that further comprises imaging as a detection method. In some implementations, the microfluidic devices or cartridges disclosed herein may comprise 1, 2, 3, 4, 5, 6, 7, 8, 9, 10, 11, 12, 13, 14, 15, 16, 17, 18, 19, 20, or more than 20 fluid channels (e.g., "analysis" fluid channels) configured for performing an analysis technique that further comprises imaging as a detection method. In some instances, the disclosed microfluidic devices may further comprise additional fluid channels (e.g., for dilution or mixing of reagents), reagent reservoirs, waste reservoirs, adapters for making external fluid connections, and the like, to provide integrated "lab-on-a-chip" functionality within the device.

A non-limiting example of microfluidic flow cell cartridge comprises a chip having two or more parallel glass channels formed on the chip, fluidic adaptors coupled to the chip, and a cartridge chassis that mates with the chip and/or fluidic adapters such that the chip is posited in a fixed orientation relative to the cartridge. In some instances, the fluidic adaptors may be integrated with the cartridge chassis. In some instances, the cartridge may comprise additional adapters that mate with the chip and/or fluidic adapters. In some instances, the chip is permanently mounted in the cartridge. In some instances, the cartridge chassis is designed to allow one or more chips of the flow cell cartridge to be interchangeably removed and replaced. For example, in some instances, the cartridge chassis may comprise a hinged "clamshell" configuration which allows it to be opened so that one or more chips may be removed and replaced. In some instances, the cartridge chassis is configured to mount on, for example, the stage of a microscope system or within a cartridge holder of an imaging system. Even though only one chip is described in the non-limiting example, it is understood that more than one chip can be used in the microfluidic flow cell cartridge. The flow cell cartridges of the present disclosure may comprise a single microfluidic chip or a plurality of microfluidic chips. In some instances, the flow cell cartridges of the present disclosure may comprise 2, 3, 4, 5, 6, 7, 8, 9, 10, 11, 12, 13, 14, 15, 16, 17, 18, 19, 20, or more than 20 microfluidic chips. The packaging of one or more microfluidic devices within a cartridge may facilitate ease-of-handling and correct positioning of the device within the optical imaging system.

The fluid channels within the disclosed microfluidic devices and cartridges may have an of a variety of cross-sectional geometries including, but not limited to, circular, elliptical, square, rectangular, triangular, rounded square, rounded rectangular, or rounded triangular cross-sectional geometries. In some instances, the fluid channels may have any specified cross-sectional dimension or set of dimensions. For example, in some instances, the height (e.g., gap height), width, or largest cross-sectional dimension of the fluid channels (e.g., the diagonal if the fluid channel has a square, rounded square, rectangular, or rounded rectangular cross-section) may range from about 10 µm to about 10 mm. In some aspects, the height (e.g., gap height), width, or largest cross-sectional dimension of the fluid channels may be at least 10 µm, at least 25 µm, at least 50 µm, at least 75 µm, at least 100 µm, at least 200 µm, at least 300 µm, at least 400 µm, at least 500 µm, at least 600 µm, at least 700 µm, at least 800 µm, at least 900 µm, at least 1 mm, at least 2 mm, at least 3 mm, at least 4 mm, at least 5 mm, at least 6 mm, at least 7 mm, at least 8 mm, at least 9 mm, or at least 10 mm. In some aspects, the height (e.g., gap height), width, or largest cross-sectional dimension of the fluid channels may be at most 10 mm, at most 9 mm, at most 8 mm, at most 7 mm, at most 6 mm, at most 5 mm, at most 4 mm, at most 3 mm, at most 2 mm, at most 1 mm, at most 900 µm, at most 800 µm, at most 700 µm, at most 600 µm, at most 500 µm, at most 400 µm, at most 300 µm, at most 200 µm, at most 100 µm, at most 75 µm, at most 50 µm, at most 25 µm, or at most 10 µm. Any of the lower and upper values described in this paragraph may be combined to form a range included within the present disclosure, for example, in some instances the height (e.g., gap height), width, or largest cross-sectional dimension of the fluid channels may range from about 20 µm to about 200 µm. Those of skill in the art will recognize that the height (e.g., gap height), width, or largest cross-sectional dimension of the fluid channels may have any value within this range, e.g., about 122 µm.

In some instances, the length of the fluid channels in the disclosed microfluidic devices and cartridges may range from about 5 mm to about 10 cm or greater. In some instances, the length of the fluid channels may be less than 5 mm, at least 5 mm, at least 1 cm, at least 1.5 cm, at least 2 cm, at least 2.5 cm, at least 3 cm, at least 3.5 cm, at least 4 cm, at least 4.5 cm, at least 5 cm, at least 6 cm, at least 7 cm, at least 8 cm, at least 9 cm, or at least 10 cm. In some instances, the length of the fluid channels may be at most 10 cm, at most 9 cm, at most 8 cm, at most 7 cm, at most 6 cm, at most 5 cm, at most 4.5 cm, at most 4 cm, at most 3.5 cm, at most 3 cm, at most 2.5 cm, at most 2 cm, at most 1.5 cm, at most 1 cm, or at most 5 mm. Any of the lower and upper values described in this paragraph may be combined to form a range included within the present disclosure, for example, in some instances the length of the fluid channels may range from about 1.5 cm to about 2.5 cm. Those of skill in the art will recognize that the length of the fluid channels may have any value within this range, e.g., about 1.35 cm. In some instances, the microfluidic devices or cartridges may comprise a plurality of fluid channels that are the same length. In some instances, the microfluidic devices or cartridges may comprise a plurality of fluid channels that are of different lengths.

The disclosed microfluidic devices will comprise at least one layer of material having one or more fluid channels formed therein. In some instances, the microfluidic chip may include two layers bonded together to form one or more fluid channels. In some instances, the microfluidic chip may include three or more layers bonded together to form one or more fluid channels. In some instances, the microfluidic fluid channels may have an open top. In some instances, the microfluidic fluid channels may be fabricated within one layer, e.g., the top surface of a bottom layer, and sealed by bonding the top surface of the bottom layer to the bottom surface of a top layer of material. In some instances, the microfluidic channels may be fabricated within one layer, e.g., as patterned channels the depth of which extends through the full thickness of the layer, which is then sandwiched between and bonded to two non-patterned layers to seal the fluid channels. In some instances, the microfluidic channels are fabricated by the removal of a sacrificial layer on the surface of a substrate. This method does not require the bulk substrate (e.g., a glass or silicon wafer) to be etched away. Instead, the fluid channels are located on the surface of the substrate. In some instances, the microfluidic channels may be fabricated in or on the surface of a substrate and then sealed by deposition of a conformal film or layer on the surface of the substrate to create sub-surface or buried fluid channels in the chip.

The microfluidic chips can be manufactured using a combination of microfabrication processes. Because the devices are microfabricated, substrate materials will typically be selected based upon their compatibility with known microfabrication techniques, e.g., photolithography, wet chemical etching, laser ablation, laser irradiation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electromagnetic (e.g. light) or electric fields.

The disclosed microfluidic chips may be fabricated from any of a variety of materials known to those of skill in the art including, but not limited to, glass (e.g., borosilicate glass, soda lime glass, etc.), fused-silica (quartz), silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) (as more chemically inert alternatives), or any combination thereof. In some preferred instances, the substrate material(s) may include silica-based substrates, such as borosilicate glass, and quartz, as well as other substrate materials.

The disclosed microfluidic devices may be fabricated using any of a variety of techniques known to those of skill in the art, where the choice of fabrication technique is often dependent on the choice of material used, and vice versa. The microfluidic channels on the chip can be constructed using techniques suitable for forming micro-structures or micro-patterns on the surface of a substrate. In some instances, the fluid channels are formed by laser irradiation. In some instances, the microfluidic channels are formed by focused femtosecond laser radiation. In some instances, the microfluidic channels are formed by photolithography and etching including, but not limited to, chemical etching, plasma etching, or deep reactive ion etching. In some instances, the microfluidic channels are formed using laser etching. In some instances, the microfluidic channels are formed using a direct-write lithography technique. Examples of direct-write lithography include electron beam direct-write and focused ion beam milling.

In additional preferred instances, the substrate material(s) may comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates may be readily patterned or micromachined using available microfabrication techniques, such as those described above. In some instances, microfluidic chips may be fabricated from polymeric materials, e.g., from microfabricated masters, using well known molding techniques, such as injection molding, embossing, stamping, or by polymerizing the polymeric precursor material within a mold (see, e.g., U.S. Pat. No. 5,512,131). In some instances, such polymeric substrate materials are preferred for their ease of manufacture, low cost, and disposability, as well as their general inertness to most extreme reaction conditions. As with flow cell devices fabricated from other materials, e.g., glass, flow cell devices fabricated from these polymeric materials may include treated surfaces, e.g., derivatized or coated surfaces, to enhance their utility in the microfluidic system, as will be discussed in more detail below.

The fluid channels and/or fluid chambers of the microfluidic devices are typically fabricated into the upper surface of a first substrate as microscale channels (e.g., grooves, indentations, etc.) using the above described microfabrication techniques. The first substrate comprises a top side having a first planar surface and a bottom side. In the microfluidic devices prepared in accordance with the methods described herein, the plurality of fluid channels (e.g., grooves and/or indentations) are formed on the first planar surface. In some instances, the fluid channels (e.g., grooves and/or indentations) formed in the first planar surface (prior to bonding to a second substrate) have a bottom and side walls, with the top remaining open. In some instances, the fluid channels (e.g., grooves and/or indentations) formed in the first planar surface (prior to bonding to a second substrate) have a bottom and side walls and the top remaining closed. In some instances, the fluid channels (e.g., grooves and/or indentations) formed in the first planar surfaces (prior to bonding to a second substrate) have only side walls and no top or bottom surface (e.g., the fluid channels span the full thickness of the first substrate.

Fluid channels and chambers may be sealed by placing the first planar surface of the first substrate in contact with, and bonding to, the planar surface of a second substrate to form the channels and/or chambers (e.g., the interior portion) of the device at the interface of these two components. In some instances, after the first substrate is bonded to a second substrate, the structure may further be placed in contact with and bonded to a third substrate. In some instances, the third substrate may be placed in contact with the side of the first substrate that is not in contact with the second substrate. In some instances, the first substrate is placed between the second substrate and the third substrate. In some instances, the second substrate and the third substrate can cover and/or seal the grooves, indentations, or apertures formed on the first substrate to form the channels and/or chambers (e.g., the interior portion) of the device at the interface of these components.

The device can have openings that are oriented such that they are in fluid communication with at least one of the fluid channels and/or fluid chambers formed in the interior portion of the device, thereby forming fluid inlets and/or fluid outlets. In some instances, the openings are formed on the first substrate. In some instances, the openings are formed on the first and the second substrate. In some instances, the openings are formed on the first, the second, and the third substrate. In some instances, the openings are positioned at the top side of the device. In some instances, the openings are positioned at the bottom side of the device. In some instances, the openings are positioned at the first and/or the second ends of the device, and the channels run along the direction from the first end to the second end.

Conditions under which substrates may be bonded together are generally widely understood by those of skill in the art, and such bonding of substrates is generally carried out by any of a variety of methods, the choice of which may vary depending upon the nature of the substrate materials used. For example, thermal bonding of substrates may be applied to a number of substrate materials including, e.g., glass or silica-based substrates, as well as some polymer based-substrates. Such thermal bonding techniques typically comprise mating the substrate surfaces that are to be bonded under conditions of elevated temperature and, in some cases, application of external pressure. The precise temperatures and pressures utilized will generally vary depending upon the nature of the substrate materials used.

For example, for silica-based substrate materials, e.g., glass (borosilicate glass, Pyrex™, soda lime glass, etc.), fused-silica (quartz), and the like, thermal bonding of substrates is typically carried out at temperatures ranging from about 500° C. to about 1400° C., and preferably, from about 500° C. to about 1200° C. For example, soda lime glass is typically bonded at temperatures of around 550° C., whereas borosilicate glass is typically thermally bonded at or near 800° C. Quartz substrates, on the other hand, are typically thermally bonded at temperatures at or near 1200° C. These bonding temperatures are typically achieved by placing the substrates to be bonded into high temperature annealing ovens.

Polymeric substrates that are thermally bonded, on the other hand, will typically utilize lower temperatures and/or pressures than silica-based substrates, in order to prevent excessive melting of the substrates and/or distortion, e.g., flattening of the interior portion of the device (e.g., the fluid channels or chambers). Generally, such elevated temperatures for bonding polymeric substrates will vary from about 80° C. to about 200° C., depending upon the polymeric material used, and will preferably be between about 90° C. and about 150° C. Because of the significantly reduced temperatures required for bonding polymeric substrates, such bonding may typically be carried out without the need for the high temperature ovens used in the bonding of silica-based substrates. This allows incorporation of a heat source within a single integrated bonding system, as described in greater detail below.

Adhesives may also be used to bond substrates together according to well-known methods, which typically comprise applying a layer of adhesive between the substrates that are to be bonded and pressing them together until the adhesive sets. A variety of adhesives may be used in accordance with these methods, including, e.g., UV curable adhesives, that are commercially available. Alternative methods may also be used to bond substrates together in accordance with the present disclosure, including e.g., acoustic or ultrasonic welding and/or solvent welding of polymeric parts.

Typically, a number of the described microfluidic chips or devices will be manufactured at the same time, e.g., using "wafer-scale" fabrication. For example, polymeric substrates may be stamped or molded in large separable sheets which can then be mated and bonded together. Individual devices or bonded substrates may then be separated from the larger sheet by cutting or dicing. Similarly, for silica-based substrates, individual devices can be fabricated from larger substrate wafers or plates, allowing higher throughput of the manufacturing process. Specifically, a plurality of fluid channel structures can be fabricated on a first substrate wafer or plate, which is then overlaid with and bonded to a second substrate wafer or plate, and optionally further overlaid with and bonded to a third substrate wafer or plate. The individual devices are then segmented from the larger substrates using known methods, such as sawing, scribing and breaking, and the like.

As noted above, the top or second substrate is overlaid upon the bottom or first substrate to seal the various channels and chambers. In carrying out the bonding process according to the methods of the present disclosure, the bonding of the first and second substrates may be carried out using vacuum and/or pressure to maintain the two substrate surfaces in optimal contact. In particular, the bottom substrate may be maintained in optimal contact with the top substrate by, e.g., mating the planar surface of the bottom substrate with the planar surface of the top substrate and applying a vacuum through holes that are disposed through the top substrate. Typically, application of a vacuum to holes in the top substrate is carried out by placing the top substrate on a vacuum chuck, which typically comprises a mounting table or surface, having an integrated vacuum source. In the case of silica-based substrates, the bonded substrates are subjected to elevated temperatures in order to create an initial bond, so that the bonded substrates may then be transferred to the annealing oven, without any shifting relative to each other.

Alternate bonding systems for incorporation with the apparatus described herein include, e.g., adhesive dispensing systems, for applying adhesive layers between the two planar surfaces of the substrates. This may be done by applying the adhesive layer prior to mating the substrates, or by placing an amount of the adhesive at one edge of the adjoining substrates and allowing the wicking action of the two mated substrates to draw the adhesive across the space between the two substrates.

In certain instances, the overall bonding system can include automatable systems for placing the top and bottom substrates on the mounting surface and aligning them for subsequent bonding. Typically, such systems include translation systems for moving either the mounting surface or one or more of the top and bottom substrates relative to each other. For example, robotic systems may be used to lift, translate and place each of the top and bottom substrates upon the mounting table, and within the alignment structures, in turn. Following the bonding process, such systems also can remove the finished product from the mounting surface and transfer these mated substrates to a subsequent operation, e.g., a separation or dicing operation, an annealing oven for silica-based substrates, etc., prior to placing additional substrates thereon for bonding.

In some instances, the manufacturing of the microfluidic chip includes the layering or laminating of two or more layers of substrate, e.g., patterned and non-patterned polymeric sheets, in order to produce the chip. For example, in microfluidic devices, the microfluidic features of the device are typically produced by laser irradiation, etching, or otherwise fabricating features into the surface of a first layer. A second layer is then laminated or bonded to the surface of the first to seal these features and provide the fluidic elements of the device, e.g., the fluid channels.

As noted above, in some instances one or more capillary flow cell devices or microfluidic chips may be mounted in a cartridge chassis to form a capillary flow cell cartridge or microfluidic cartridge. In some instances, the capillary flow cell cartridge or microfluidic cartridge may further comprise additional components that are integrated with the cartridge to provide enhanced performance for specific applications. Examples of additional components that may be integrated into the cartridge include, but are not limited to, adapters or connectors for making fluidic connections to other components of the system, fluid flow control components (e.g., miniature valves, miniature pumps, mixing manifolds, etc.), temperature control components (e.g., resistive heating elements, metal plates that serve as heat sources or sinks, piezoelectric (Peltier) devices for heating or cooling, temperature sensors), or optical components (e.g., optical lenses, windows, filters, mirrors, prisms, fiber optics, and/or light-emitting diodes (LEDs) or other miniature light sources that may collectively be used to facilitate spectroscopic measurements and/or imaging of one or more capillary or fluid flow channels.

The fluidic adaptors, cartridge chassis, and other cartridge components may be attached to the capillaries, capillary flow cell device(s), microfluidic chip(s) (or fluid channels within the chip) using any of a variety of techniques known to those of skill in the art including, but not limited to, press fit, adhesive bonding, solvent bonding, laser welding, etc., or any combination thereof. In some instances, the inlet(s) and/or outlet(s) of the microfluidic channels in the microfluidic chip are apertures on the top surface of the chip, and the fluidic adaptors can be attached or coupled to the inlet(s) and/or outlet(s) of the microfluidic channels within the chip. In some instances, the cartridge may comprise additional adapters (e.g., in addition to the fluidic adapters) that mate with the chip and/or fluidic adapters and help to position the chip within the cartridge. These adapters may be constructed using the same fabrication techniques and materials as those outlined above for the fluidic adapters.

The cartridge chassis (or "housing") may be fabricated from metal and/or polymer materials such as aluminum, anodized aluminum, polycarbonate (PC), acrylic (PMMA), or Ultem (PEI), while other materials are also consistent with the present disclosure. A housing may be fabricated using CNC machining and/or molding techniques, and designed so that one, two, or more than two capillaries or microfluidic chips are constrained by the chassis in a fixed orientation to create one or more independent flow channels. The capillaries or chips may be mounted in the chassis using, e.g., a compression fit design, or by mating with compressible adapters made of silicone or a fluoroelastomer. In some instances, two or more components of the cartridge chassis (e.g., an upper half and a lower half) are assembled using, e.g., screws, clips, clamps, or other fasteners so that the two halves are separable. In some instances, two or more components of the cartridge chassis are assembled using, e.g., adhesives, solvent bonding, or laser welding so that the two or more components are permanently attached.

Flow cell surface coatings: In some instances, one or more interior surfaces of the capillary lumens or microfluidic channels in the disclosed flow cell devices may be coated using any of a variety of surface modification techniques or polymer coatings known to those of skill in the art. In some instances, the coatings may be formulated to increase or maximize the number of available binding sites (e.g., tethered oligonucleotide adapter/primer sequences) on the one or more interior surfaces to increase or maximize a foreground signal, e.g., a fluorescence signal arising from labeled nucleic acid molecules hybridized to tethered oligonucleotide adapter/primer sequences. In some instances, the coatings may be formulated to decrease or minimize non-specific binding of fluorophores and other small molecules, or labeled or unlabeled nucleotides, proteins, enzymes, antibodies, oligonucleotides, or nucleic acid molecules (e.g., DNA, RNA, etc.), in order to decrease or minimize a background signal, e.g., background fluorescence arising from the nonspecific binding of labeled biomolecules or from autofluorescence of a sample support structure. The combination of increased foreground signal and reduced background signal that may be achieved in some instances through the use of the disclosed coatings may thus provide improved signal-to-noise ratio (SNR) in spectroscopic measurements or improved contrast-to-noise ratio (CNR) in imaging methods.

As will be discussed in more detail below, the disclosed hydrophilic, polymer-coated flow cell devices, optionally used in combination with the improved hybridization and/or amplification protocols, yield solid-phase bioassay reactions that exhibit: (i) negligible non-specific binding of protein and other reaction components (thus reducing or minimizing substrate background), (ii) negligible non-specific nucleic acid amplification product, and (iii) provide tunable nucleic acid amplification reactions. Although described herein primarily in the context of nucleic acid hybridization, amplification, and sequencing assays, it will be understood by those of skill in the art that the disclosed low-binding supports may be used in any of a variety of other bioassay formats including, but not limited to, sandwich immunoassays, enzyme-linked immunosorbent assays (ELISAs), etc.

In a preferred aspect, one or more layers of a coating material may be applied to the interior flow cell device surfaces, where the number of layers and/or the material composition of each layer is chosen to adjust one or more surface properties of the interior flow cell device surfaces, as noted in U.S. patent application Ser. No. 16/363,842, the disclosure of which is incorporated by reference in its entirety. Examples of surface properties that may be adjusted include, but are not limited to, surface hydrophilicity/hydrophobicity, overall coating thickness, the surface density of chemically-reactive functional groups, the surface density of grafted linker molecules or oligonucleotide adapters/primers, etc. In some preferred applications, one or more surface properties of the capillary or channel lumen are adjusted to, for example, (i) provide for very low non-specific binding of proteins, oligonucleotides, fluorophores, and other molecular components of chemical or biological analysis applications, including solid-phase nucleic acid amplification and/or sequencing applications, (ii) provide for improved solid-phase nucleic acid hybridization specificity and efficiency, and (iii) provide for improved solid-phase nucleic acid amplification rate, specificity, and efficiency.

Any of a variety of molecules known to those of skill in the art including, but not limited to, silanes, amino acids, peptides, nucleotides, oligonucleotides, other monomers or polymers, or combinations thereof may be used in creating the one or more chemically-modified layers on the interior flow cell device surfaces, where the choice of components used may be varied to alter one or more properties of the support surface, e.g., the surface density of functional groups and/or tethered oligonucleotide primers, the hydrophilicity/hydrophobicity of the support surface, or the three three-dimensional nature (e.g., "thickness") of the support surface.

The attachment chemistry used to graft a first chemically-modified layer to an interior surface of the flow cell (capillary or channel) will generally be dependent on both the material from which the flow cell device is fabricated and the chemical nature of the layer. In some instances, the first layer may be covalently attached to the interior flow cell device surfaces. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the support surface. For example, glass or silicon surfaces may be acid-washed using a Piranha solution (a mixture of sulfuric acid ($H_2SO_4$) and hydrogen peroxide ($H_2O_2$)) and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (e.g., comprising a free amino functional group), maleimide-PEG silane, biotin-PEG silane, and the like.

Examples of preferred polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface and/or to cross-link the layers to each other include, but are not limited to, biotin-streptavidin interactions (or variations thereof), His tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

In some instances, the number of layers of polymer or other chemical layers on the interior flow cell device surfaces may range from 1 to about 10, or greater than 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, the one or more layers may all comprise the same material. In some instances, each layer may comprise a different material. In some instances, a plurality of layers may comprise a plurality of materials.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a 'power of 2' number of branches, such as 2, 4, 8, 16, 32, 64, or 128 branches.

In some instances, the resulting functional end groups distal from the surface following the deposition of one or more layers, e.g., polymer layers can include, but are not limited to, biotin, methoxy ether, carboxylate, amine, NHS ester, maleimide, and bis-silane.

Linear, branched, or multi-branched polymers used to create one or more layers of any of the multi-layered surfaces disclosed herein may have a molecular weight of at least 500 Daltons, at least 1,000 Daltons, at least 1,500 Daltons, at least 2,000 Daltons, at least 2,500 Daltons, at least 3,000 Daltons, at least 3,500 Daltons, at least 4,000 Daltons, at least 4,500 Daltons, at least 5,000 Daltons, at least 7,500 Daltons, at least 10,000 Daltons, at least 12,500 Daltons, at least 15,000 Daltons, at least 17,500 Daltons, at least 20,000 Daltons, at least 25,000 Daltons, at least 30,000 Daltons, at least 35,000 Daltons, at least 40,000 Daltons, at least 45,000 Daltons, or at least 50,000 Daltons. In some instances, the linear, branched, or multi-branched polymers used to create one or more layers of any of the multi-layered surfaces disclosed herein may have a molecular weight of at most 50,000 Daltons, at most 45,000 Daltons, at most 40,000 Daltons, at most 35,000 Daltons, at most 30,000 Daltons, at most 25,000 Daltons, at most 20,000 Daltons, at most 17,500 Daltons, at most 15,000 Daltons, at most 12,500 Daltons, at most 10,000 Daltons, at most 7,500 Daltons, at most 5,000 Daltons, at most 4,500 Daltons, at most 4,000 Daltons, at most 3,500 Daltons, at most 3,000 Daltons, at most 2,500 Daltons, at most 2,000 Daltons, at most 1,500 Daltons, at most 1,000 Daltons, or at most 500 Daltons. Any of the lower and upper values described in this paragraph may be combined to form a range included within the present disclosure, for example, in some instances the molecular weight of linear, branched, or multi-branched polymers used to create one or more layers of any of the multi-layered surfaces disclosed herein may range from about 1,500 Daltons to about 20,000 Daltons. Those of skill in the art will recognize that the molecular weight of linear, branched, or multi-branched polymers used to create one or more layers of any of the multi-layered surfaces disclosed herein may have any value within this range, e.g., about 1,260 Daltons.

In some instances, two or more layers may be covalently coupled to each other or internally cross-linked to improve the stability of the resulting surface. In some instances, e.g., wherein at least one layer of a multi-layered surface comprises a branched polymer, the number of covalent bonds between a branched polymer molecule of the layer being deposited and molecules of the previous layer may range from about one covalent linkage per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32, or more than 32 covalent linkages per molecule. In some instances, the number of covalent bonds between a branched polymer molecule of the new layer and molecules of the previous layer may be at most 32, at most 30, at most 28, at most 26, at most 24, at most 22, at most 20, at most 18, at most 16, at most 14, at most 12, at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of covalent bonds between a branched polymer molecule of the new layer and molecules of the previous layer may range from about 4 to about 16. Those of skill in the art will recognize that the number of covalent bonds between a branched polymer molecule of the new layer and molecules of the previous layer may have any value within this range, e.g., about 11 in some instances, or an average number of about 4.6 in other instances.

Any reactive functional groups that remain following the coupling of a material layer to the interior flow cell device surfaces may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

In order to scale binding site surface density, e.g., oligonucleotide adapter/primer surface density, and add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase adapter/primer loading density on the surface significantly. Traditional PEG coating approaches use monolayer primer deposition, which has been tested and reported for single molecule sequencing applications but do not yield high copy numbers for nucleic acid amplification applications. As described herein, "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, polyacrylamide, polyester, dextran, poly-lysine, and copolymers of poly-lysine and PEG. In some instances, the different layers may be cross-linked to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high adapter/primer density materials may be constructed in solution and subsequently layered onto the surface in multiple steps.

In some cases, PEG multilayers include PEG (8 arm, 16 arm, 8 arm) on PEG-amine-APTES. Similar concentrations were observed for 3-layer multi-arm PEG (8 arm, 16 arm, 8 arm) and (8 arm, 64 arm, 8 arm) on PEG-amine-APTES exposed to 8 uM primer, and 3-layer multi-arm PEG (8 arm, 8 arm, 8 arm) using star-shape PEG-amine to replace 16 arm and 64 arm. PEG multilayers having comparable first, second and third PEG layers are also contemplated.

In some instances, the resultant surface density of binding sites on the interior flow cell device surfaces, e.g., oligonucleotide adapter/primer surface densities, may range from about 100 primer molecules per $\mu m^2$ to about 1,000,000 primer molecules per $\mu m^2$. In some instances, the surface density of binding sites may be at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of binding sites may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, or at most 100 molecules per $\mu m^2$. Any of the lower and upper values described in this paragraph may be combined to form a range included within the present disclosure, for example, in some instances the surface density of binding sites may range from about 10,000 molecules per $\mu m^2$ to about 100,000 molecules per $\mu m^2$. Those of skill in the art will recognize that the surface density of binding sites may have any value within this range, e.g., about 3,800 molecules per $\mu m^2$ in some instances, or about 455,000 molecules per $\mu m^2$ in other instances. In some instances, as will be discussed further below for nucleic acid sequencing applications, the surface density of template library nucleic acid sequences (e.g., sample DNA molecules) initially hybridized to adapter or primer sequences tethered to the interior flow cell device surfaces may be less than or equal to that indicated for the surface density of binding sites. In some instances, as will also be discussed further below, the surface density of clonally-amplified template library nucleic acid sequences hybridized to adapter or primer sequences on the interior flow cell device surfaces may span the same range or a different range as that indicated for the surface density of tethered oligonucleotide adapters or primers.

Local surface densities of binding sites on the interior flow cell device surfaces as listed above do not preclude variation in density across a surface, such that a surface may comprise a region having a binding site density of, for example, 500,000/um$^2$, while also comprising at least a second region having a substantially different local surface density.

In some instances, capture probes, e.g., oligonucleotide primers with different base sequences and base modifications (or other biomolecules, e.g., enzymes or antibodies) may be tethered to one or more layers of the resulting surface at various surface densities. In some instances, for example, both surface functional group density and the capture probe concentration used for coupling may be varied to target a certain capture probe surface density range. Additionally, capture probe surface density may be controlled by diluting capture probes with other "inert" molecules that carry the same reactive functional group for coupling to the surface. For example, amine-labeled oligonucleotide probes can be diluted with amine-labeled polyethylene glycol in a reaction with an NHS-ester coated surface to reduce the final primer density. In the case of oligonucleotide adapters/primers, probe sequences with different lengths of linker between the hybridization region and the surface attachment functional group may also be applied to vary surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure or estimate the capture probe surface density, fluorescently labeled capture probes may be tethered to the surface and a fluorescence reading then compared with that for a calibration solution comprising a known concentration of the fluorophore.

In some instances, the degree of hydrophilicity (or "wettability" with aqueous solutions) of the disclosed support surfaces, e.g., interior flow cell device surfaces, may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surface(s) disclosed herein may range from about 0 degrees to about 50 degrees. In some instances, the water contact angle for the hydrophilic, low-binding support surface(s) disclosed herein may no more than 50 degrees, 45 degrees, 40 degrees, 35 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than any value within this range, e.g., no more than 40 degrees. Those of skill in the art will realize that a given hydrophilic, low-binding support surface of the present disclosure may exhibit a water contact angle having a value of anywhere within this range, e.g., about 27 degrees. In some instances, the disclosed low nonspecific binding surfaces have a water contact angle of less than 45 degrees. In some instances, the disclosed low nonspecific binding surfaces have a water contact angle of less than 35 degrees.

As noted, the hydrophilic coated interior flow cell device surfaces of the present disclosure exhibit reduce non-specific binding of proteins, nucleic acids, fluorophores, and other components of biological and biochemical assay methods. The degree of non-specific binding exhibited by a given support surface, e.g., an interior flow cell device surface, may be assessed either qualitatively or quantitatively. For example, in some instances, exposure of the surface to fluorescent dyes (e.g., cyanine dye 3 (Cy®3), cyanine dye 5 (Cy®5), etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

In some instances, the degree of non-specific binding exhibited by the disclosed low nonspecific binding support surfaces may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of nonspecific binding exhibited by a given support surface formulation may thus be assessed in terms of the number of non-specifically bound protein molecules (or other molecules) per unit area. In some instances, the low nonspecific binding supports of the present disclosure may exhibit nonspecific protein binding (or nonspecific binding of other specified molecules, e.g., cyanine dye 3 (Cy®3) of less than 0.001 molecule per μm$^2$, less than 0.01 molecule per μm$^2$, less than 0.1 molecule per μm$^2$, less than 0.25 molecule per μm$^2$, less than 0.5 molecule per μm$^2$, less than 1 molecule per μm², less than 10 molecules per μm², less than 100 molecules per μm², or less than 1,000 molecules per μm². Those of skill in the art will realize that a given support surface of the present disclosure may exhibit nonspecific binding falling anywhere within this range, for example, of less than 86 molecules per μm². For example, some modified surfaces disclosed herein exhibit nonspecific protein binding of less than 0.5 molecule/μm² following contact with a 1 uM solution of Cy®3 labeled streptavidin (GE Amersham) in phosphate buffered saline (PBS) buffer for 15 minutes, followed by 3 rinses with deionized water. Some modified surfaces disclosed herein exhibit nonspecific binding of Cy®3 dye molecules of less than 0.25 molecules per μm2. In independent nonspecific binding assays, 1 μM labeled Cy®3 SA (ThermoFisher), 1 uM Cy®5 SA dye (ThermoFisher), 10 uM Aminoallyl-dUTP-ATTO-647N (Jena Biosciences), 10 uM Aminoallyl-dUTP-ATTO-Rho11 (Jena Biosciences), 10 uM Aminoallyl-dUTP-ATTO-Rho11 (Jena Biosciences), 10 uM 7-Propargylamino-7-deaza-dGTP-Cy®5 (Jena Biosciences, and 10 uM 7-Propargylamino-7-deaza-dGTP-Cy®3 (Jena Biosciences) were incubated on the low nonspecific binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon (GE Healthcare Lifesciences, Pittsburgh, PA) instrument using the Cy®3, AF®555, or Cy®5 filter sets (according to dye test performed) as specified by the manufacturer at a PMT gain setting of 800 and resolution of 50-100 μm. For higher resolution imaging, images were collected on an Olympus IX83 microscope (Olympus Corp., Center Valley, PA) with a total internal reflectance fluorescence (TIRF) objective (20×, 0.75 NA or 100×, 1.5 NA, Olympus), an sCMOS Andor camera (Zyla 4.2. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per μm².

In some instances, the coated flow cell device surfaces disclosed herein may exhibit a ratio of specific to nonspecific binding of a fluorophore such as Cy®3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

In some instances, one or more surface modification and/or polymer layers may be applied to the interior flow cell device surfaces using a technique such as chemical vapor deposition (CVD). In some instances, one or more surface modification and/or polymer layers may be applied to the interior flow cell device surfaces by flowing one or more appropriate chemical coupling or coating reagents through the capillaries or fluid channels prior to use for their intended application. In some instances, one or more coating reagents may be added to a buffer used, e.g., a nucleic acid hybridization, amplification reaction, and/or sequencing reaction buffer to provide for dynamic coating of the interior flow cell device surfaces.

In some instances, the chemical modification layers may be applied uniformly across the surface of the substrate or support structure. Alternatively, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. Alternatively or in combination, the substrate surface may be patterned using, e.g., contact printing and/or ink-jet printing techniques.

In some instances, an ordered array or random pattern of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions, or any intermediate number of discrete regions spanned by the range herein.

In some instances, fluorescence images of the disclosed low nonspecific binding surfaces when used, e.g., in nucleic acid hybridization or amplification applications to create clusters of hybridized or clonally-amplified nucleic acid molecules (e.g., "discrete regions" that have been directly or indirectly labeled with a fluorophore) exhibit contrast-to-noise ratios (CNRs) of at least 5, 10, 20, 30, 40, 50, 60, 70, 80, 90, 100, 110, 120, 130, 140, 150, 160, 170, 180, 190, 20, 210, 220, 230, 240, 250, or greater than 250 when the nucleic acid molecules are labeled with Cy®3 and the images are acquired using an Olympus IX83 inverted fluorescence microscope equipped with a 20×, 0.75 NA objective, a 532 nm light source, a bandpass and dichroic mirror filter set adapted or optimized for 532 nm long-pass excitation and Cy®3 fluorescence emission filter, a Semrock 532 nm dichroic reflector, and a camera (Andor sCMOS, Zyla 4.2) where the excitation light intensity is adjusted to avoid signal saturation, and the surface is immersed in a buffer (e.g., 25 mM ACES, pH 7.4 buffer) while the image is acquired. As used herein, contrast-to-noise ratio (CNR) is calculated as:

$$CNR=(S-B)/\text{Noise}$$

where S=foreground signal (e.g., the fluorescence signal as measured in the image that arises from a labeled nucleic acid colony or cluster on a sample support surface), B=background signal (where $B=B_{inter}+B_{intra}$), $B_{inter}$=background signal measured at a location on the sample support surface that is between labeled nucleic acid colonies or clusters, $B_{intra}$=background signal measured at the location of a nucleic acid colony or cluster (determined, e.g., by contacting the sample support surface with a labeled, non-complementary oligonucleotide and measuring the resulting fluorescence), and Noise=the signal noise. The contrast-to-noise ratio (CNR) of images of sequencing surfaces, for example, provides a key metric in assessing nucleic acid amplification specificity and non-specific binding on the support. While signal-to-noise ratio (SNR) is often considered to be a benchmark of overall signal quality, it can be shown that improved CNR can provide a significant advantage over SNR as a benchmark for signal quality in imaging applications that require rapid image capture (e.g., nucleic acid sequencing applications for which cycle times can be minimized). Further description of low nonspecific binding surfaces can be found in U.S. Pat. Nos. 10,876,148, 10,704,094 and 10,982,280 which are incorporated herein by reference in their entirety.

In some instances, polymer-coated sample support structures, e.g., interior flow cell device surfaces comprising the disclosed hydrophilic polymer coatings, may exhibit improved stability to repetitive exposure to solvents, changes in temperature, changes in pH, or long-term storage.

Fluidics systems and fluid flow control modules: in some implementations, the disclosed imaging and/or analysis systems may provide fluid flow control capability for delivering samples or reagents to the one or more flow cell devices or flow cell cartridges (e.g., single capillary flow cell device or microfluidic channel flow cell device) connected to the system. Reagents and buffers may be stored in bottles, reagent and buffer cartridges, or other suitable containers that are connected to the flow cell inlets by tubing and valve manifolds. The disclosed systems may also include processed sample and waste reservoirs in the form of bottles, cartridges, or other suitable containers for collecting fluids downstream of the capillary flow cell devices or capillary flow cell cartridges. In some embodiments, the fluid flow (or "fluidics") control module may provide programmable switching of flow between different sources, e.g. sample or reagent reservoirs or bottles located in the instrument, and the inlet(s) to a central region (e.g., a capillary flow cell or microfluidic device, or a large fluid chamber such as a large fluid chamber within a microfluidic device). In some instances, the fluid flow control module may provide programmable switching of flow between outlet(s) from the central region (e.g., a capillary flow cell or microfluidic device) and different collection points, e.g., processed sample reservoirs, waste reservoirs, etc., connected to the system. In some instances, samples, reagents, and/or buffers may be stored within reservoirs that are integrated into the flow cell cartridge or microfluidic cartridge itself. In some instances, processed samples, spent reagents, and/or used buffers may be stored within reservoirs that are integrated into the flow cell cartridge or microfluidic device cartridge itself.

In some implementations, one or more fluid flow control modules may be configured to control the delivery of fluids to one or more capillary flow cells, capillary flow cell cartridges, microfluidic devices, microfluidic cartridges, or any combination thereof. In some instances, the one or more fluidics controllers may be configured to control volumetric flow rates for one or more fluids or reagents, linear flow velocities for one or more fluids or reagents, mixing ratios for one or more fluids or reagents, or any combination thereof. Control of fluid flow through the disclosed systems will typically be performed using pumps (or other fluid actuation mechanisms) and valves (e.g., programmable pumps and valves). Examples of suitable pumps include, but are not limited to, syringe pumps, programmable syringe pumps, peristaltic pumps, diaphragm pumps, and the like. Examples of suitable valves include, but are not limited to, check valves, electromechanical two-way or three-way valves, pneumatic two-way and three-way valves, and the like. In some instances, fluid flow through the system may be controlled by applying positive pneumatic pressure to one or more inlets of the reagent and buffer containers, or to inlets incorporated into flow cell cartridge(s) (e.g., capillary flow cell or microfluidic cartridges). In some embodiments, fluid flow through the system may be controlled by drawing a vacuum at one or more outlets of waste reservoir(s), or at one or more outlets incorporated into flow cell cartridge(s) (e.g., capillary flow cell or microfluidic cartridges).

In some instances, different modes of fluid flow control are utilized at different points in an assay or analysis procedure, e.g. forward flow (relative to the inlet and outlet for a given capillary flow cell device), reverse flow, oscillating or pulsatile flow, or combinations thereof. In some applications, oscillating or pulsatile flow may be applied, for example, during assay wash/rinse steps to facilitate complete and efficient exchange of fluids within the one or more flow cell devices or flow cell cartridges (e.g., capillary flow cell devices or cartridges, and microfluidic devices or cartridges).

Similarly, in some cases different fluid flow rates may be utilized at different locations within a flow cell device or at different points in the assay or analysis process workflow, for example, in some instances, the volumetric flow rate may vary from −100 ml/sec to +100 ml/sec. In some embodiment, the absolute value of the volumetric flow rate may be at least 0.001 ml/sec, at least 0.01 ml/sec, at least 0.1 ml/sec, at least 1 ml/sec, at least 10 ml/sec, or at least 100 ml/sec. In some embodiments, the absolute value of the volumetric flow rate may be at most 100 ml/sec, at most 10 ml/sec, at most 1 ml/sec, at most 0.1 ml/sec, at most 0.01 ml/sec, or at most 0.001 ml/sec. The volumetric flow rate at a given location with the flow cell device or at a given point in time may have any value within this range, e.g. a forward flow rate of 2.5 ml/sec, a reverse flow rate of −0.05 ml/sec, or a value of 0 ml/sec (e.g., stopped flow).

In some implementations, the fluidics system may be designed to minimize the consumption of key reagents (e.g., expensive reagents) required for performing, e.g., genomic analysis applications. For example, in some implementations the disclosed fluidics systems may comprise a first reservoir housing a first reagent or solution, a second reservoir housing a second reagent or solution, and a central region, e.g., a central capillary flow cell or microfluidic device, where an outlet from the first reservoir and an outlet from the second reservoir are fluidically coupled to an inlet of the central capillary flow cell or microfluidic device through at least one valve such that the volume of the first reagent or solution flowing per unit time from the outlet of the first reservoir to the inlet of the central capillary flow cell or microfluidic device is less than the volume of the second reagent or solution flowing per unit time from the outlet of the second reservoir to the inlet of the central region. In some implementations, the first reservoir and second reservoir may be integrated into a capillary flow cell cartridge or microfluidic cartridge. In some instances, the at least one valve may also be integrated into the capillary flow cell cartridge or microfluidic cartridge.

In some instances, the first reservoir is fluidically coupled to the central capillary flow cell or microfluidic device through a first valve, and the second reservoir is fluidically coupled to the central capillary flow cell or microfluidic device through a second valve. In some instances, the first and/or second valves may be, e.g., a diaphragm valve, pinch valve, gate valve, or other suitable valve. In some instances, the first reservoir is positioned in close proximity to the inlet of the central capillary flow cell or microfluidic device to reduce dead volume for delivery of the first reagent solution. In some instances, the first reservoir is placed in closer proximity to the inlet of the central capillary flow cell or microfluidic device than is the second reservoir. In some instances, the first reservoir is positioned in close proximity to the second valve so as to reduce the dead volume for delivery of the first reagent relative to that for delivery of a plurality of "second" reagents (e.g., two, three, four, five, or six or more "second" reagents) from a plurality of "second" reservoirs (e.g., two, three, four, five, or six or more "second" reservoirs).

The first and second reservoirs described above may be used to house the same or different reagents or solutions. In some instances, the first reagent that is housed in the first reservoir is different from the second reagent that is housed in the second reservoir, and the second reagent comprises at least one reagent that is used in common by a plurality of reactions occurring in the central a central capillary flow cell or microfluidic device. In some instances, e.g., in fluidics systems configured for performing nucleic acid sequencing chemistry within the central capillary flow cell or microfluidic device, the first reagent comprises at least one reagent selected from the group consisting of a polymerase, nucleotide, and a nucleotide analog. In some instances, the second reagent comprises a low-cost reagent, e.g., a solvent.

In some instances, the interior volume of the central region, e.g., a central capillary flow cell cartridge, or microfluidic device comprising one or more fluid channels or fluid chambers, can be adjusted based on the specific application to be performed, e.g., nucleic acid sequencing. In some embodiments, the central region comprises an interior volume suitable for sequencing a eukaryotic genome. In some embodiments, the central region comprises an interior volume suitable for sequencing a prokaryotic genome. In some embodiments, the central region comprises an interior volume suitable for sequencing a viral genome. In some embodiments, the central region comprises an interior volume suitable for sequencing a transcriptome. For example, in some embodiments, the interior volume of the central region may comprise a volume of less than 0.05 µl, between 0.05 µl and 0.1 µl, between 0.05 µl and 0.2 µl, between 0.05 µl and 0.5 µl, between 0.05 µl and 0.8 µl, between 0.05 µl and 1 µl, between 0.05 µl and 1.2 µl, between 0.05 µl and 1.5 µl, between 0.1 µl and 1.5 µl, between 0.2 µl and 1.5 µl, between 0.5 µl and 1.5 µl, between 0.8 µl and 1.5 µl, between 1 µl and 1.5 µl, between 1.2 µl and 1.5 µl, or greater than 1.5 µl, or a range defined by any two of the foregoing. In some embodiments, the interior volume of the central region may comprise a volume of less than 0.5 µl, between 0.5 µl and 1 µl, between 0.5 µl and 2 µl, between 0.5 µl and 5 µl, between 0.5 µl and 8 µl, between 0.5 µl and 10 µl, between 0.5 µl and 12 µl, between 0.5 µl and 15 µl, between 1 µl and 15 µl, between 2 µl and 15 µl, between 5 µl and 15 µl, between 8 µl and 15 µl, between 10 µl and 15 µl, between 12 µl and 15 µl, or greater than 15 µl, or a range defined by any two of the foregoing. In some embodiments, the interior volume of the central region may comprise a volume of less than 5 µl, between 5 µl and 10 µl, between 5 µl and 20 µl, between 5 µl and 500 µl, between 5 µl and 80 µl, between 5 µl and 100 µl, between 5 µl and 120 µl, between 5 µl and 150 µl, between 10 µl and 150 µl, between 20 µl and 150 µl, between 50 µl and 150 µl, between 80 µl and 150 µl, between 100 µl and 150 µl, between 120 µl and 150 µl, or greater than 150 µl, or a range defined by any two of the foregoing. In some embodiments, the interior volume of the central region may comprise a volume of less than 50 µl, between 50 µl and 100 µl, between 50 µl and 200 µl, between 50 µl and 500 µl, between 50 µl and 800 µl, between 50 µl and 1000 µl, between 50 µl and 1200 µl, between 50 µl and 1500 µl, between 100 µl and 1500 µl, between 200 µl and 1500 µl, between 500 µl and 1500 µl, between 800 µl and 1500 µl, between 1000 µl and 1500 µl, between 1200 µl and 1500 µl, or greater than 1500 µl, or a range defined by any two of the foregoing. In some embodiments, the interior volume of the central region may comprise a volume of less than 500 µl, between 500 µl and 1000 µl, between 500 µl and 2000 µl, between 500 µl and 5 ml, between 500 µl and 8 ml, between 500 µl and 10 ml, between 500 µl and 12 ml, between 500 µl and 15 ml, between 1 ml and 15 ml, between 2 ml and 15 ml, between 5 ml and 15 ml, between 8 ml and 15 ml, between 10 ml and 15 ml, between 12 ml and 15 ml, or greater than 15 ml, or a range defined by any two of the foregoing. In some embodiments, the interior volume of the central region may comprise a volume of less than 5 ml, between 5 ml and 10 ml, between 5 ml and 20 ml, between 5 ml and 50 ml, between 5 ml and 80 ml, between 5 ml and 100 ml, between 5 ml and 120 ml, between 5 ml and 150 ml, between 10 ml and 150 ml, between 20 ml and 150 ml, between 50 ml and 150 ml, between 80 ml and 150 ml, between 100 ml and 150 ml, between 120 ml and 150 ml, or greater than 150 ml, or a range defined by any two of the foregoing. In some embodiments, the systems described herein comprise an array or collection of flow cell devices or systems comprising multiple discrete capillaries, microfluidic channels, fluid channels, chambers, or lumenal regions, wherein the combined interior volume is, comprises, or includes one or more of the values within a range disclosed herein.

In some instances, the ratio of volumetric flow rate for the delivery of the first reagent to the central capillary flow cell or microfluidic device to that for delivery of the second reagent to the central capillary flow cell or microfluidic device may be less than 1:20, less than 1:16, least than 1:12, less than 1:10, less than 1:8, less than 1:6, or less than 1:2. In some instances, the ratio of volumetric flow rate for the delivery of the first reagent to the central capillary flow cell or microfluidic device to that for delivery of the second reagent to the central capillary flow cell or microfluidic device may have any value with the range spanned by these values, e.g., less than 1:15.

As noted, the flow cell devices and/or fluidics systems disclosed herein may be configured to achieve a more efficient use of the reagents than that achieved by, e.g., other sequencing devices and systems, particularly for the costly reagents used in a variety of sequencing chemistry steps. In some instances, the first reagent comprises a reagent that is more expensive than the second reagent. In some instances, the first reagent comprises a reaction-specific reagent and the second reagent comprises a nonspecific reagent common to all reactions performed in the central capillary flow cell or microfluidic device region, and wherein the reaction specific reagent is more expensive than the nonspecific reagent.

In some instances, utilization of the flow cell devices and/or fluidic systems disclosed herein may convey advantages in terms of reduced consumption of costly reagents. In some instances, for example, utilization of the flow cell devices and/or fluidic systems disclosed herein may results in at least a 5%, at least a 7.5%, at least a 10%, at least a 12.5%, at least a 15%, at least a 17.5%, at least a 20%, at least a 22.5%, at least a 25%, at least a 30%, at least a 35%, at least a 40%, at least a 45%, or at least a 50% reduction in reagent consumption compared to the reagent consumption encountered when operating, e.g., current commercially-available nucleic acid sequencing systems.

Figure 31:
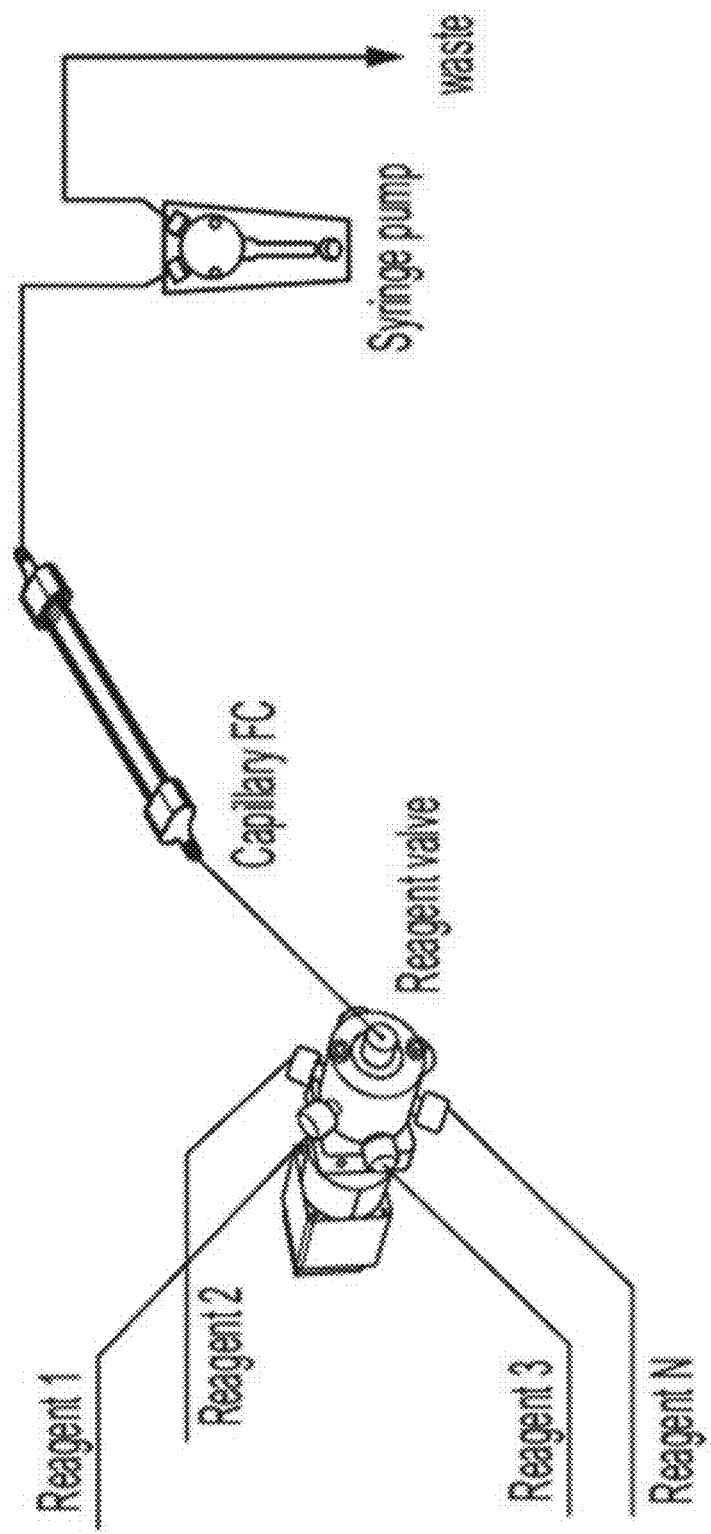
FIG. 31 illustrates one non-limiting example of a system comprising a single capillary flow cell connected to various fluid flow control components, where the single capillary is compatible with mounting on a microscope stage or in a custom imaging instrument for use in various imaging applications.

FIG. 31 illustrates a non-limiting example of a simple fluidics system comprising a single capillary flow cell connected to various fluid flow control components, where the single capillary is optically accessible and compatible with mounting on a microscope stage or in a custom imaging instrument for use in various imaging applications. A plurality of reagent reservoirs is fluidically-coupled with the inlet end of the single capillary flow cell device, where the reagent flowing through the capillary at any given point in time is controlled by a programmable rotary valve that allows the user to control the timing and duration of reagent flow. In this non-limiting example, fluid flow is controlled by a programmable syringe pump that provides precise control and timing of volumetric fluid flow and fluid flow velocity.

Figure 32:
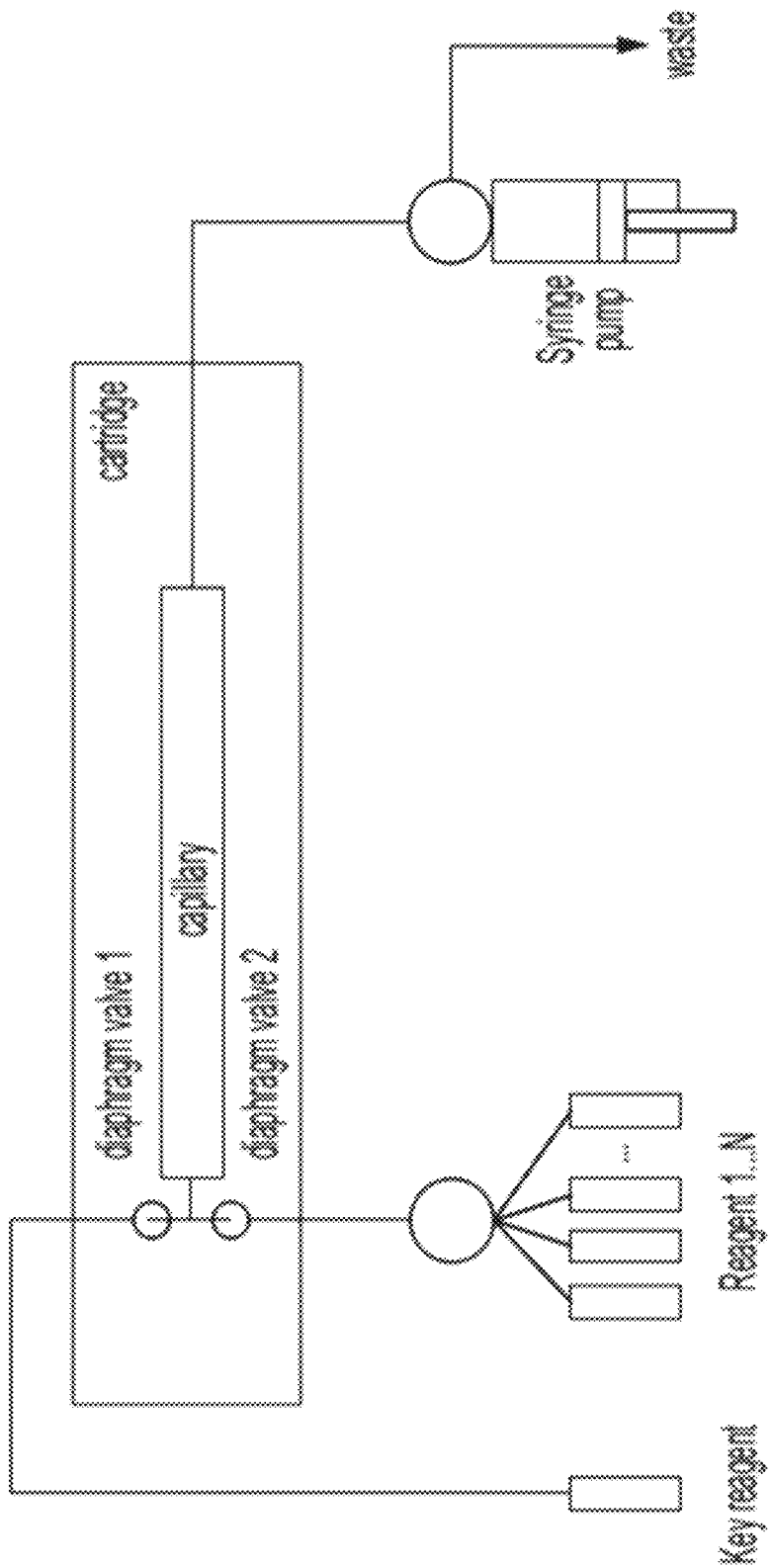
FIG. 32 illustrates one non-limiting example of a system that comprises a capillary flow cell cartridge having integrated diaphragm valves to reduce or minimize dead volume and conserve certain key reagents.

FIG. 32 illustrates a non-limiting example of a fluidics system that comprises a capillary flow cell cartridge having integrated diaphragm valves to reduce or minimize dead volume and conserve certain key reagents. The integration of miniature diaphragm valves into the cartridge allows the valve to be positioned in close proximity to the inlet of the capillary, thereby reducing or minimizing dead volume within the device and reducing the consumption of costly reagents. The integration of valves and other fluid control components within the capillary flow cell cartridge also allows greater fluid flow control functionality to be incorporated into the cartridge design.

Figure 33:
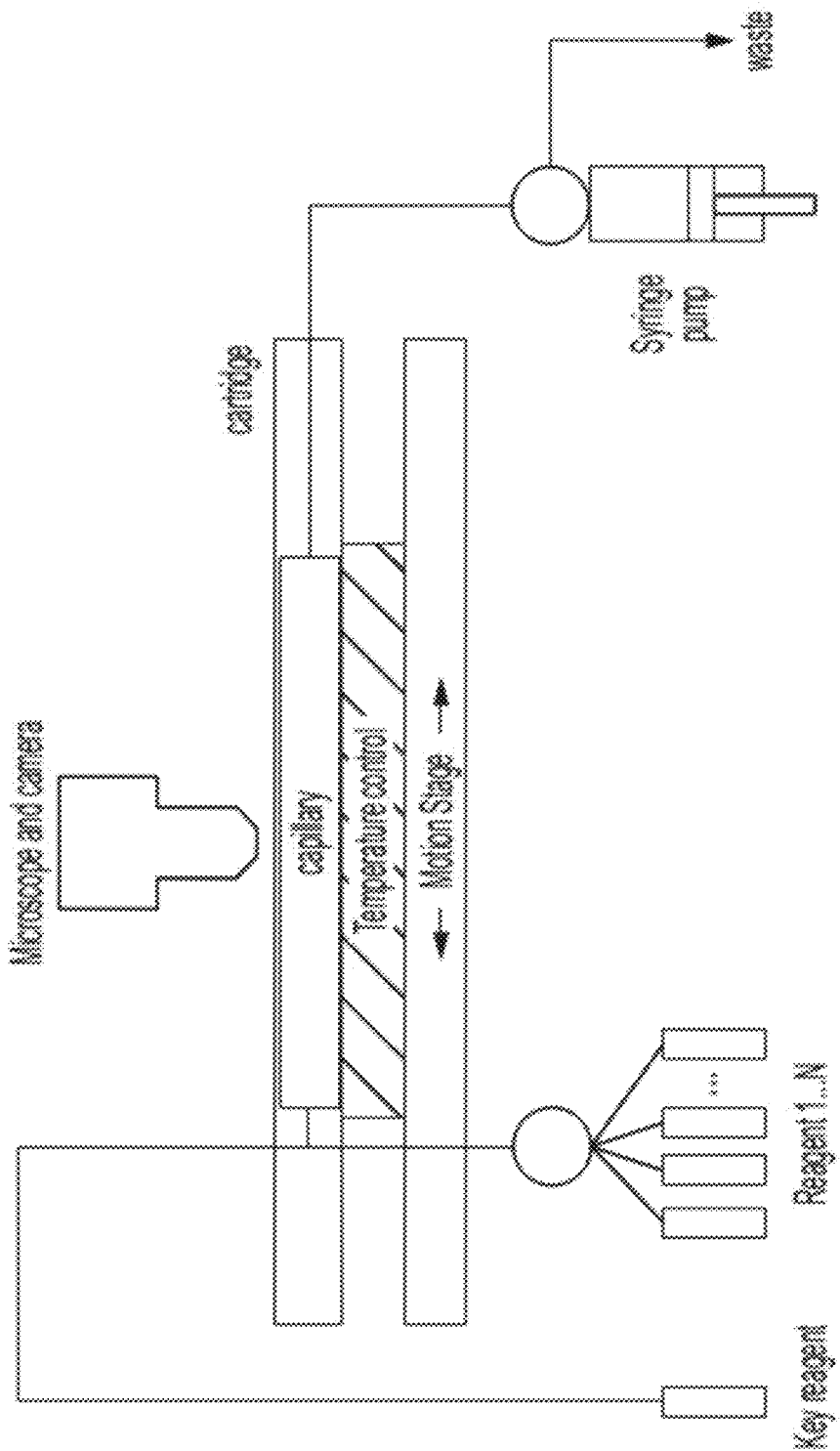
FIG. 33 illustrates one non-limiting example of a system that comprises a capillary flow cell, a microscope setup, and a temperature control mechanism.

FIG. 33 illustrates a non-limiting example of a capillary flow cell cartridge-based fluidics system used in combination with a microscope setup, where the cartridge incorporates or mates with a temperature control component such as a metal plate that makes contact with the capillaries within the cartridge and serves as a heat source/sink. The microscope setup may comprise an illumination system (e.g., including a laser, LED, or halogen lamp, etc., as a light source), an objective lens, an imaging system (e.g., a CMOS or CCD camera), and a translation stage to move the cartridge relative to the optical system, which allows, e.g., fluorescence and/or bright field images to be acquired for different regions of the capillary flow cells as the stage is moved.

Temperature control modules: In some implementations the disclosed systems will include temperature control functionality for the purpose of facilitating the accuracy and reproducibility of assay or analysis results. Examples of temperature control components that may be incorporated into the instrument system (or capillary flow cell cartridge) design include, but are not limited to, resistive heating elements, infrared light sources, Peltier heating or cooling devices, heat sinks, thermistors, thermocouples, and the like. In some instances, the temperature control module (or "temperature controller") may provide for a programmable temperature change at a specified, adjustable time prior to performing specific assay or analysis steps. In some instances, the temperature controller may provide for programmable changes in temperature over specified time intervals. In some embodiments, the temperature controller may further provide for cycling of temperatures between two or more set temperatures with specified frequency and ramp rates so that thermal cycling for amplification reactions may be performed.

Figure 34:
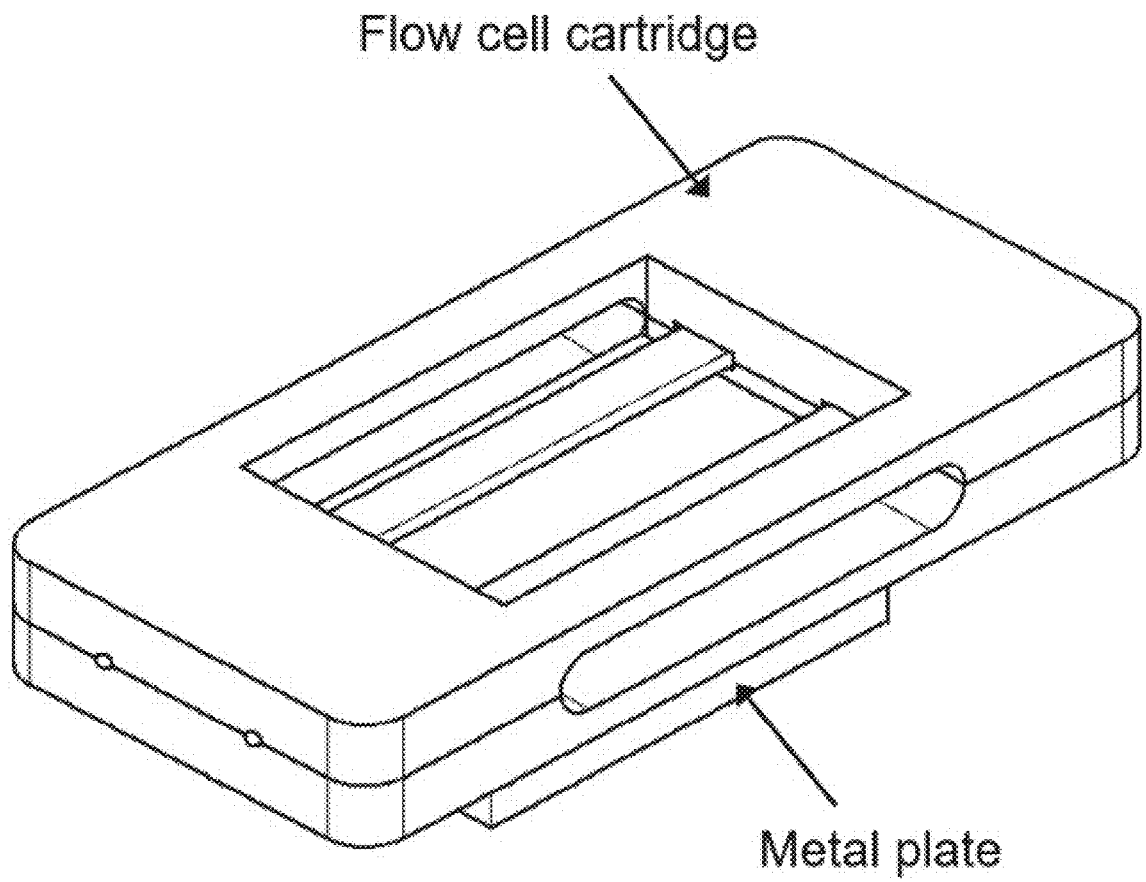
FIG. 34 illustrates one non-limiting example for temperature control of the capillary flow cells through the use of a metal plate that is placed in contact with the flow cell cartridge.

FIG. 34 illustrates one non-limiting example for temperature control of the flow cells (e.g., capillary flow cells or microfluidic device-based flow cells) through the use of a metal plate that is placed in contact with the flow cell cartridge. In some instances, the metal plate may be integrated with the cartridge chassis. In some instances, the metal plate may be temperature controlled using a Peltier or resistive heater.

Figure 35:
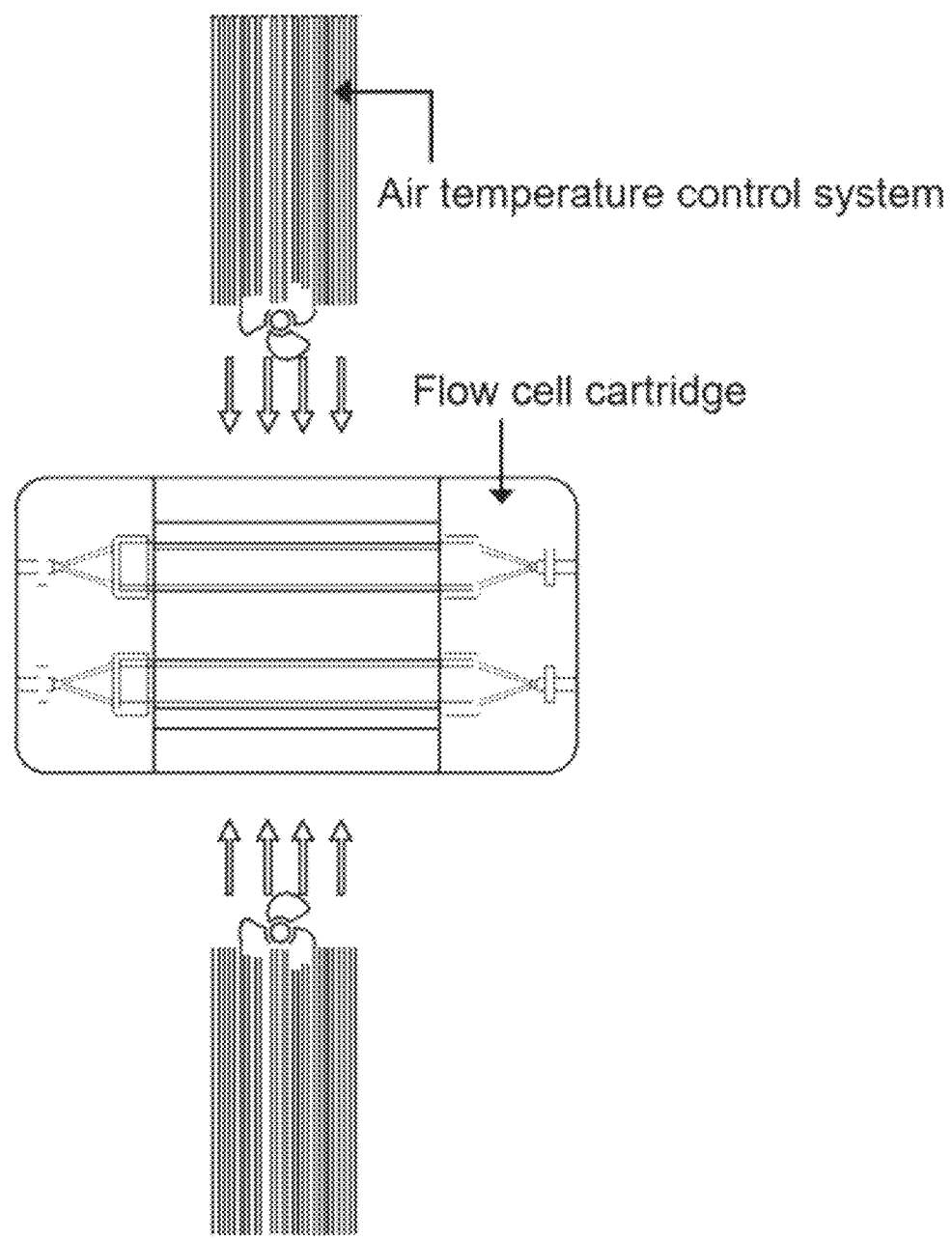
FIG. 35 illustrates one non-limiting approach for temperature control of the capillary flow cells that comprises a non-contact thermal control mechanism.

FIG. 35 illustrates one non-limiting approach for temperature control of the flow cells (e.g., capillary or microfluidic channel flow cells) that comprises a non-contact thermal control mechanism. In this approach, a stream of temperature-controlled air is directed through the flow cell cartridge (e.g., towards a single capillary flow cell device or a microfluidic channel flow cell device) using an air temperature control system. The air temperature control system comprises a heat exchanger, e.g., a resistive heater coil, fins attached to a Peltier device, etc., that is capable of heating and/or cooling the air and holding it at a constant, user-specified temperature. The air temperature control system also comprises an air delivery device, such as a fan, that directs the stream of heated or cooled air to the capillary flow cell cartridge. In some instances, the air temperature control system may be set to a constant temperature T1 so that the air stream, and consequently the flow cell or cartridge (e.g., capillary flow cell or microfluidic channel flow cell) is kept at a constant temperature T2, which in some cases may differ from the set temperature T1 depending on the environment temperature, air flow rate, etc. In some instances, two or more such air temperature control systems may be installed around the capillary flow cell device or flow cell cartridge so that the capillary or cartridge may be rapidly cycled between several different temperatures by controlling which one of the air temperature control systems is active at a given time. In another approach, the temperature setting of the air temperature control system may be varied so the temperature of the capillary flow cell or cartridge may be changed accordingly.

Fluid dispensing robotics: In some implementations, the disclosed systems may comprise an automated, programmable fluid-dispensing (or liquid-dispensing) system for use in dispensing reagents or other solutions into, e.g., microplates, capillary flow cell devices and cartridges, microfluidic devices and cartridges, etc. Suitable automated, programmable fluid-dispensing systems are commercially available from a number of vendors, e.g. Beckman Coulter, Perkin Elmer, Tecan, Velocity 11, and many others. In a preferred aspect of the disclosed systems, the fluid-dispensing system further comprises a multichannel dispense head, e.g. a 4 channel, 8 channel, 16 channel, 96 channel, or 384 channel dispense head, for simultaneous delivery of programmable volumes of liquid (e.g. ranging from about 1 microliter to several milliliters) to multiple wells or locations on a flow cell cartridge or microfluidic cartridge.

Cartridge- and or microplate-handling (pick-and-place) robotics: In some implementations, the disclosed system may comprise a cartridge- and/or microplate-handling robotic system for automated replacement and positioning of microplates, capillary flow cell cartridges, or microfluidic device cartridges in relation to the optical imaging system, or for optionally moving microplates, capillary flow cell cartridges, or microfluidic device cartridges between the optical imaging system and a fluid-dispensing system. Suitable automated, programmable microplate-handling robotic systems are commercially available from a number of vendors, including Beckman Coulter, Perkin Elemer, Tecan, Velocity 11, and many others. In a preferred aspect of the disclosed systems, an automated microplate-handling robotic system is configured to move collections of microwell plates comprising samples and/or reagents to and from, e.g., refrigerated storage units.

Spectroscopy or imaging modules: As indicated above, in some implementations the disclosed analysis systems will include optical imaging capabilities and may also include other spectroscopic measurement capabilities. For example, the disclosed imaging modules may be configured to operate in any of a variety of imaging modes known to those of skill in the art including, but not limited to, bright-field, dark-field, fluorescence, luminescence, or phosphorescence imaging. In some instances, the one or more capillary flow cells or microfluidic devices of a fluidics sub-system comprise a window that allows at least a section of one or more capillaries or one or more fluid channels in each flow cell or microfluidic device to be illuminated and imaged.

In some embodiments, single wavelength excitation and emission fluorescence imaging may be performed. In some embodiments, dual wavelength excitation and emission (or multi-wavelength excitation or emission) fluorescence imaging may be performed. In some instances, the imaging module is configured to acquire video images. The choice of imaging mode may impact the design of the flow cells devices or cartridges in that all or a portion of the capillaries or cartridge can be optically transparent over the spectral range of interest. In some instances, a plurality of capillaries within a capillary flow cell cartridge may be imaged in their entirety within a single image. In some instances, only a single capillary or a subset of capillaries within a capillary flow cell cartridge, or portions thereof, may be imaged within a single image. In some instances, a series of images may be "tiled" to create a single high-resolution image of one, two, several, or the entire plurality of capillaries within a cartridge. In some instances, a plurality of fluid channels within a microfluidic chip may be imaged in their entirety within a single image. In some instances, only a single fluid channel or a subset of fluid channels within a microfluidic chip, or portions thereof, may be imaged within a single image. In some instances, a series of images may be "tiled" to create a single high-resolution image of one, two, several, or the entire plurality of fluid channels within a cartridge.

A spectroscopy or imaging module may comprise, e.g., a microscope equipped with a CMOS of CCD camera. In some instances, the spectroscopy or imaging module may comprise, e.g., a custom instrument such as one of the imaging modules described herein that is configured to perform a specific spectroscopic or imaging technique of interest. In general, the hardware associated with the spectroscopy or imaging module may include light sources, detectors, and other optical components, as well as processors or computers.

Light sources: Any of a variety of light sources may be used to provide the imaging or excitation light, including but not limited to, tungsten lamps, tungsten-halogen lamps, arc lamps, lasers, light emitting diodes (LEDs), or laser diodes. In some instances, a combination of one or more light sources, and additional optical components, e.g. lenses, filters, apertures, diaphragms, mirrors, and the like, may be configured as an illumination system (or sub-system).

Detectors: Any of a variety of image sensors may be used for imaging purposes, including but not limited to, photodiode arrays, charge-coupled device (CCD) cameras, or complementary metal-oxide-semiconductor (CMOS) image sensors. As used herein, "imaging sensors" may be one-dimensional (linear) or two-dimensional array sensors. In many instances, a combination of one or more image sensors, and additional optical components, e.g. lenses, filters, apertures, diaphragms, mirrors, and the like, may be configured as an imaging system (or sub-system). In some instances, e.g., where spectroscopic measurements are performed by the system rather than imaging, suitable detectors may include, but are not limited to, photodiodes, avalanche photodiodes, and photomultipliers.

Other optical components: The hardware components of the spectroscopic measurement or imaging module may also include a variety of optical components for steering, shaping, filtering, or focusing light beams through the system. Examples of suitable optical components include, but are not limited to, lenses, mirrors, prisms, apertures, diffraction gratings, colored glass filters, long-pass filters, short-pass filters, bandpass filters, narrowband interference filters, broadband interference filters, dichroic reflectors, optical fibers, optical waveguides, and the like. In some instances, as noted above, the spectroscopic measurement or imaging module may further comprise one or more translation stages or other motion control mechanisms for the purpose of moving capillary flow cell devices and cartridges relative to the illumination and/or detection/imaging sub-systems, or vice versa.

Total internal reflection: In some instances, the optical module or sub-system may be designed to use all or a portion of an optically transparent wall of the capillaries or microfluidic channels in flow cell devices and cartridges as a waveguide for delivering excitation light to the capillary or channel lumen(s) via total internal reflection. When incident excitation light strikes the surface of the capillary or channel lumen at an angle with respect to a normal to the surface that is larger than the critical angle (determined by the relative refractive indices of the capillary or channel wall material and the aqueous buffer within the capillary or channel), total internal reflection occurs at the surface and the light propagates through the capillary or channel wall along the length of the capillary or channel. Total internal reflection generates an evanescent wave at the lumen surface which penetrates the lumen interior for extremely short distances, and which may be used to selectively excite fluorophores at the surface, e.g., labeled nucleotides that have been incorporated by a polymerase into a growing oligonucleotide through a solid-phase primer extension reaction.

Light-tight housings and environmental control chambers: In some implementations, the disclosed systems may comprise a light-tight housing to prevent stray ambient light from creating glare and obscuring, e.g., relatively faint fluorescence signals. In some implementations, the disclosed systems may comprise an environmental control chamber that enables the system to operate under a tightly controlled temperature, humidity level, etc.

Processors and computers: In some instances, the disclosed systems may comprise one or more processors or computers. The processor may be a hardware processor such as a central processing unit (CPU), a graphic processing unit (GPU), a general-purpose processing unit, or a computing platform. The processor may be comprised of any of a variety of suitable integrated circuits, microprocessors, logic devices, field-programmable gate arrays (FPGAs) and the like. In some instances, the processor may be a single core or multi core processor, or a plurality of processors may be configured for parallel processing. Although the disclosure is described with reference to a processor, other types of integrated circuits and logic devices are also applicable.

The processor may have any suitable data operation capability. For example, the processor may perform 512 bit, 256 bit, 128 bit, 64 bit, 32 bit, or 16 bit data operations. The processor or CPU can execute a sequence of machine-readable instructions, which can be embodied in a program or software. The instructions may be stored in a memory location. The instructions can be directed to the CPU, which can subsequently program or otherwise configure the CPU to implement, e.g., the system control methods of the present disclosure. Examples of operations performed by the CPU can include fetch, decode, execute, and write back.

Some processors may comprise a processing unit of a computer system. The computer system may enable cloud-based data storage and/or computing. In some instances, the computer system may be operatively coupled to a computer network ("network") with the aid of a communication interface. The network may be the internet, an intranet and/or extranet, an intranet and/or extranet that is in communication with the internet, or a local area network (LAN). The network in some cases is a telecommunication and/or data network. The network may include one or more computer servers, which may enable distributed computing, such as cloud-based computing.

The computer system may also include computer memory or memory locations (e.g., random-access memory, read-only memory, flash memory), electronic storage units (e.g., hard disk), communication interfaces (e.g., network adapters) for communicating with one or more other systems, and peripheral devices, such as cache, other memory units, data storage units and/or electronic display adapters. In some instances, the communication interface may allow the computer to be in communication with one or more additional devices. The computer may be able to receive input data from the coupled devices for analysis. Memory units, storage units, communication interfaces, and peripheral devices may be in communication with the processor or CPU through a communication bus (solid lines), such as may be incorporated into a motherboard. A memory or storage unit may be a data storage unit (or data repository) for storing data. The memory or storage units may store files, such as drivers, libraries and saved programs. The memory or storage units may store user data, e.g., user preferences and user programs.

The system control, image processing, and/or data analysis methods as described herein can be implemented by way of machine-executable code stored in an electronic storage location of the computer system, such as, for example, in the memory or electronic storage unit. The machine-executable or machine-readable code can be provided in the form of software. During use, the code can be executed by the processor. In some cases, the code can be retrieved from the storage unit and stored in memory for ready access by the processor. In some situations, the electronic storage unit can be precluded, and machine-executable instructions are stored in memory.

In some instances, the code may be pre-compiled and configured for use with a machine having a processor adapted to execute the code. In some instances, the code may be compiled during runtime. The code can be supplied in a programming language that can be selected to enable the code to execute in a pre-compiled or as-compiled fashion.

Some aspects of the systems and methods provided herein can be embodied in software. Various aspects of the technology may be thought of as "products" or "articles of manufacture" typically in the form of machine (or processor) executable code and/or associated data that is carried on or embodied in a type of machine-readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

In some instances, the system control, image processing, and/or data analysis methods of the present disclosure may be implemented by way of one or more algorithms. An algorithm may be implemented by way of software upon execution by the central processing unit.

System control software: In some instances, the system may comprise a computer (or processor) and a computer-readable medium that includes code for providing a user interface as well as manual, semi-automated, or fully-automated control of all system functions, e.g., control of the fluid flow control module(s), the temperature control module(s), and/or the spectroscopy or imaging module(s), as well as other data analysis and display options. The system computer or processor may be an integrated component of the system (e.g. a microprocessor or mother board embedded within the instrument) or may be a stand-alone module, for example, a main frame computer, a personal computer, or a laptop computer. Examples of fluid flow control functions provided by the system control software include, but are not limited to, volumetric fluid flow rates, fluid flow velocities, the timing and duration for sample and reagent addition, buffer addition, and rinse steps. Examples of temperature control functions provided by the system control software include, but are not limited to, specifying temperature set point(s) and control of the timing, duration, and ramp rates for temperature changes. Examples of spectroscopic measurement or imaging control functions provided by the system control software include, but are not limited to, autofocus capability, control of illumination or excitation light exposure times and intensities, control of image acquisition rate, exposure time, and data storage options.

Image processing software: In some instances, the system may further comprise a computer (or processor) and computer-readable medium that includes code for providing image processing and analysis capability. Examples of image processing and analysis capability that may be provided by the software include, but are not limited to, manual, semi-automated, or fully-automated image exposure adjustment (e.g. white balance, contrast adjustment, signal-averaging and other noise reduction capability, etc.), automated edge detection and object identification (e.g., for identifying clonally-amplified clusters of fluorescently-labeled oligonucleotides on the lumen surface of capillary flow cell devices), automated statistical analysis (e.g., for determining the number of clonally-amplified clusters of oligonucleotides identified per unit area of the capillary lumen surface, or for automated nucleotide base-calling in nucleic acid sequencing applications), and manual measurement capabilities (e.g. for measuring distances between clusters or other objects, etc.). Optionally, instrument control and image processing/analysis software may be written as separate software modules. In some embodiments, instrument control and image processing/analysis software may be incorporated into an integrated package.

Any of a variety of image processing methods known to those of skill in the art may be used for image processing/pre-processing. Examples include, but are not limited to, Canny edge detection methods, Canny-Deriche edge detection methods, first-order gradient edge detection methods (e.g., the Sobel operator), second order differential edge detection methods, phase congruency (phase coherence)

edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), and mathematical analysis algorithms (e.g., Fourier transform, fast Fourier transform, wavelet analysis, auto-correlation, etc.), or any combination thereof.

Nucleic acid sequencing systems & applications: Nucleic acid sequencing provides one non-limiting example of an application for the disclosed flow cell devices (e.g., capillary flow cell devices or cartridges and microfluidic devices and cartridges) and imaging systems. Many "second generation" and "third generation" sequencing technologies utilize a massively parallel, cyclic array approach to perform sequencing-by-nucleotide incorporation, in which accurate decoding of a single-stranded template oligonucleotide sequence tethered to a solid support relies on successfully classifying signals that arise from the stepwise addition of A, G, C, and T nucleotides by a polymerase to a complementary oligonucleotide strand. These methods typically require the oligonucleotide template to be modified with a known adapter sequence of fixed length, affixed to a solid support (e.g., the lumen surface(s) of the disclosed capillary flow cell devices or microfluidic chips) in a random or patterned array by hybridization to surface-tethered capture probes (also referred to herein as "adapters" or "primers" tethered to the interior flow cell surfaces) of known sequence that are complementary to that of the adapter sequence, and then probed through a cyclic series of single base addition primer extension reactions that use, e.g., fluorescently-labeled nucleotides to identify the sequence of bases in the template oligonucleotides. These processes thus require the use of miniaturized fluidics systems that offer precise, reproducible control of the timing of reagent introduction to the flow cell in which the sequencing reactions are performed, and small volumes to reduce or minimize the consumption of costly reagents.

Existing commercially-available NGS flow cells are constructed from layers of glass that have been etched, lapped, and/or processed by other methods to meet the tight dimensional tolerances required for imaging, cooling, and/or other requirements. When flow cells are used as consumables, the costly manufacturing processes required for their fabrication result in costs per sequencing run that are too high to make sequencing routinely accessible to scientists and medical professionals in the research and clinical fields.

This disclosure provides an example of a low-cost flow cell architecture that includes low cost glass or polymer capillaries or microfluidic channels, fluidics adapters, and cartridge chassis. Utilizing glass or polymer capillaries that are extruded in their final cross-sectional geometry may eliminate the need for multiple high-precision and costly glass manufacturing processes. Robustly constraining the orientation of the capillaries or microfluidic channels and providing convenient fluidic connections using molded plastic and/or elastomeric components further reduces cost. Laser bonding the components of the polymer cartridge chassis provides a fast and efficient sealing of the capillary or the microfluidic channels and structurally stabilizing the capillaries or channels and flow cell cartridge without requiring the use of fasteners or adhesives.

The disclosed devices and systems may be configured to perform nucleic acid sequencing using any of a variety of "sequencing-by-nucleotide incorporation", "sequencing-by-nucleotide binding", "sequencing-by-nucleotide base-pairing", and "sequencing-by-avidity" sequencing biochemistries. The improvements in flow cell device design disclosed herein, e.g., comprising hydrophilic coated surfaces that maximize foreground signals for, e.g., fluorescently-labeled nucleic acid clusters disposed thereon, while minimizing background signal may give rise to improvements in CNR for images used for base-calling purposes, in combination with improvements in optical imaging system design for fast dual-surface flow cell imaging (comprising simultaneous or near-simultaneous imaging of the interior flow cell surfaces) achieved through improved objective lens and/or tube lens designs that provide for larger depth of field and larger fields-of-view, and reduced reagent consumption (achieved through improved flow cell design) may give rise to dramatic improvements in base-calling accuracy, shortened imaging cycle times, shortened overall sequencing reaction cycle times, and higher throughput nucleic acid sequencing at reduced cost per base.

Figure 40:
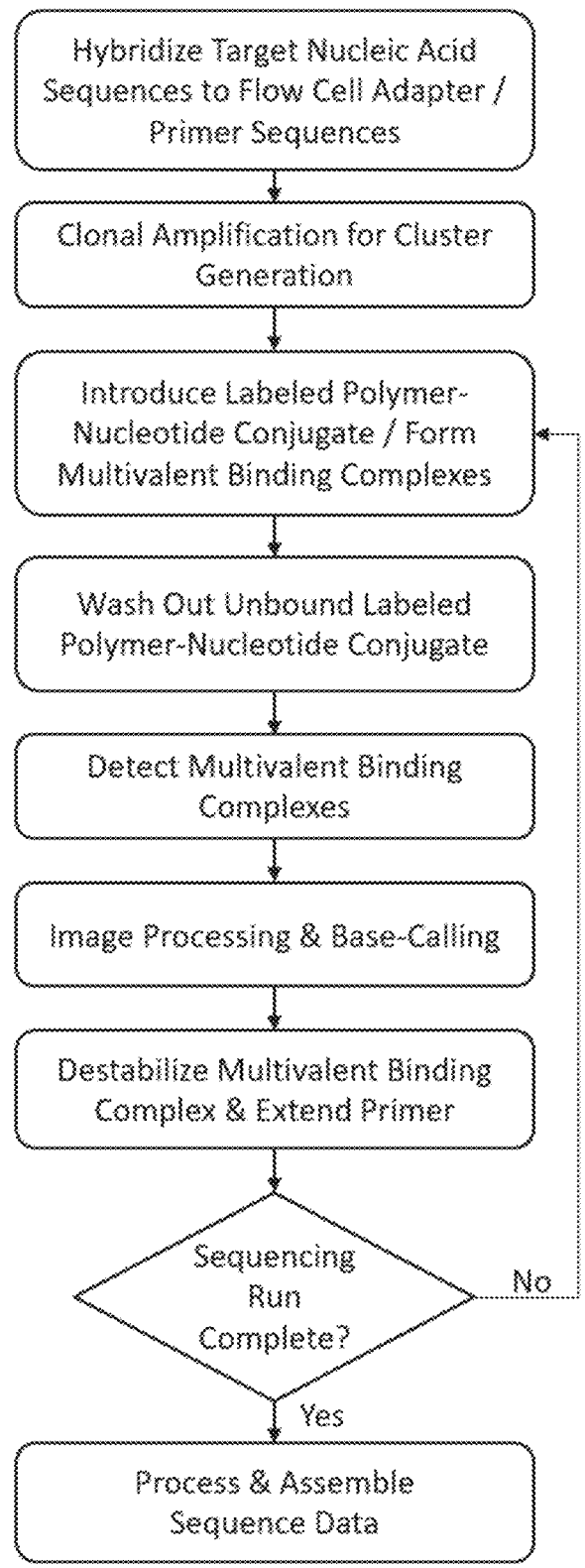
FIG. 40 provides a non-limiting example of a flow chart for a sequencing method as disclosed herein.

The systems disclosed herein may be configured to implement any of a variety of different sequencing methodologies using a variety of different sequencing chemistries. For example, FIG. 40 provides a non-limiting example of a flow chart for implementing a sequencing-by-avidity method. A nucleotide conjugate may be used to form a multivalent binding complex with a plurality of primed target nucleic acid sequences tethered to a support surface, e.g., one or more interior surfaces of a flow cell, such that the multivalent binding complex exhibits a significantly longer persistence time than afforded by the binding interactions between single nucleotides and single primed target nucleic acid sequences. In general, such a sequencing-by-avidity approach will comprise one or more of the following steps: hybridization of target nucleic acid sequences to adapter/primer sequences tethered to the support surface; clonal amplification to create clusters of amplified target sequences on the support surface; contacting the support surface with a nucleotide conjugate comprising a plurality of nucleotide moieties conjugated to a polymer core, wherein the nucleotide conjugate may further comprise one or more detectable labels, e.g., fluorophores, to create a stable, multivalent binding complex; washing out of any excess, unbound nucleotide conjugate; detection of multivalent binding complexes, e.g., by fluorescence imaging of the support surface; identification of a nucleotide in the target nucleic acid sequence (base-calling); destabilization of the multivalent binding complex, e.g., by changing the ionic strength, ionic composition, and/or pH of the buffer; rinsing of the flow cell; and performing a primer extension reaction to add a nucleotide comprising the complementary base for the nucleotide that was identified. The cycle may be repeated to identify additional nucleotide bases in the sequence, followed by processing and assembly of the sequence data. In some instances, data processing may comprise calculation of sequencing performance metrics, such as a Q-score, in real-time as the sequencing run is performed or as part of a post-run data processing step.

In some instances, the disclosed hydrophilic, polymer coated flow cell devices used in combination with the optical imaging systems disclosed herein may confer one or more of the following additional advantages for a nucleic acid sequencing system: (i) decreased fluidic wash times (due to reduced non-specific binding, and thus faster sequencing cycle times), (ii) decreased imaging times (and thus faster turnaround times for assay readout and sequencing cycles), (iii) decreased overall work flow time requirements (due to decreased cycle times), (iv) decreased detection instrumentation costs (due to the improvements in CNR), (v) improved readout (base-calling) accuracy (due to improvements in CNR), (vi) improved reagent stability and decreased reagent usage requirements (and thus reduced reagents costs), and (vii) fewer run-time failures due to nucleic acid amplification failures.

The methods, devices, and systems disclosed herein for performing nucleic acid sequencing are suitable for a variety of sequencing applications and for sequencing nucleic acid molecules derived from any of a variety of samples and sources. Nucleic acids, in some instances, may be extracted from any of a variety of biological samples, e.g., blood samples, saliva samples, urine samples, cell samples, tissue samples, and the like. For example, the disclosed devices and systems may be used for the analysis of nucleic acid molecules derived from any of a variety of different cell, tissue, or sample types known to those of skill in the art. For example, nucleic acids may be extracted from cells, or tissue samples comprising one or more types of cells, derived from eukaryotes (such as animals, plants, fungi, protista), archaebacteria, or eubacteria. In some cases, nucleic acids may be extracted from prokaryotic or eukaryotic cells, such as adherent or non-adherent eukaryotic cells. Nucleic acids are variously extracted from, for example, primary or immortalized rodent, porcine, feline, canine, bovine, equine, primate, or human cell lines. Nucleic acids may be extracted from any of a variety of different cell, organ, or tissue types (e.g., white blood cells, red blood cells, platelets, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, or small intestine). Nucleic acids may be extracted from normal or healthy cells. Alternatively or in combination, acids are extracted from diseased cells, such as cancerous cells, or from pathogenic cells that are infecting a host. Some nucleic acids may be extracted from a distinct subset of cell types, e.g., immune cells (such as T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, and/or macrophages, or any combination thereof), undifferentiated human stem cells, human stem cells that have been induced to differentiate, rare cells (e.g., circulating tumor cells (CTCs), circulating epithelial cells, circulating endothelial cells, circulating endometrial cells, bone marrow cells, progenitor cells, foam cells, mesenchymal cells, or trophoblasts). Other cells are contemplated and consistent with the disclosure herein.

Nucleic acids may optionally be attached to one or more non-nucleotide moieties such as labels and other small molecules, large molecules (such as proteins, lipids, sugars, etc.), and solid or semi-solid supports, for example through covalent or non-covalent linkages with either the 5' or 3' end of the nucleic acid. Labels include any moiety that is detectable using any of a variety of detection methods known to those of skill in the art, and thus renders the attached oligonucleotide or nucleic acid similarly detectable. Some labels, e.g., fluorophores, emit electromagnetic radiation that is optically detectable or visible. Alternatively or in combination, some labels comprise a mass tag that renders the labeled oligonucleotide or nucleic acid visible in mass spectral data, or a redox tag that renders the labeled oligonucleotide or nucleic acid detectable by amperometry or voltammetry. Some labels comprise a magnetic tag that facilitates separation and/or purification of the labeled oligonucleotide or nucleic acid. The nucleotide or polynucleotide is often not attached to a label, and the presence of the oligonucleotide or nucleic acid is directly detected.

Flow cell devices configured for sequencing: In some instances, one or more flow cell devices according to the present disclosure may be configured for nucleic acid sequencing applications, e.g., wherein two or more interior flow cell device surfaces comprise hydrophilic polymer coatings that further comprise one or more capture oligonucleotides, e.g., adapter/primer oligonucleotides, or any other oligonucleotides as disclosed herein. In some instances, the hydrophilic, polymer-coated surfaces of the disclosed flow cell devices may comprise a plurality of oligonucleotides tethered thereto that have been selected for use in sequencing a eukaryotic genome. In some instances, the hydrophilic, polymer-coated surfaces of the disclosed flow cell devices may comprise a plurality of oligonucleotides tethered thereto that have been selected for use in sequencing a prokaryotic genome or portion thereof. In some instances, the hydrophilic, polymer-coated surfaces of the disclosed flow cell devices may comprise a plurality of oligonucleotides tethered thereto that have been selected for use in sequencing a viral genome or portion thereof. In some instances, the hydrophilic, polymer-coated surfaces of the disclosed flow cell devices may comprise a plurality of oligonucleotides tethered thereto that have been selected for use in sequencing a transcriptome.

In some instances, a flow cell device of the present disclosure may comprise a first surface in an orientation generally facing the interior of the flow channel, a second surface in an orientation generally facing the interior of the flow channel and further generally facing or parallel to the first surface, a third surface generally facing the interior of a second flow channel, and a fourth surface, generally facing the interior of the second flow channel and generally opposed to or parallel to the third surface; wherein said second and third surfaces may be located on or attached to opposite sides of a generally planar substrate which may be a reflective, transparent, or translucent substrate. In some instances, an imaging surface or imaging surfaces within a flow cell may be located within the center of a flow cell or within or as part of a division between two subunits or subdivisions of a flow cell, wherein said flow cell may comprise a top surface and a bottom surface, one or both of which may be transparent to such detection mode as may be utilized; and wherein a surface comprising oligonucleotides adapters/primers tethered to one or more polymer coatings may be placed or interposed within the lumen of the flow cell. In some instances, the top and/or bottom surfaces do not include attached oligonucleotide adapters/primers. In some instances, said top and/or bottom surfaces do comprise attached oligonucleotide adapters/primers. In some instances, either said top or said bottom surface may comprise attached oligonucleotide adapters/primers. A surface or surfaces placed or interposed within the lumen of a flow cell may be located on or attached to one side, to an opposite side, or to both sides of a generally planar substrate which may be a reflective, transparent, or translucent substrate.

In general, at least one layer of the one or more layers of low nonspecific binding coating on the flow cell device surfaces may comprise functional groups for covalently or non-covalently attaching oligonucleotide molecules, e.g., adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one third layer may be distributed at a plurality of depths throughout the layer.

In some instances, the oligonucleotide adapter or primer molecules are covalently coupled to the polymer in solution, e.g., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

In some instances, the oligonucleotide adapter or primer molecules may be coupled to the one or more layers of hydrophilic polymer using any of a variety of suitable conjugation chemistries known to those of skill in the art. For example, the oligonucleotide adapter or primer sequences may comprise moieties that are reactive with amine groups, carboxyl groups, thiol groups, and the like. Examples of suitable amine-reactive conjugation chemistries that may be used include, but are not limited to, reactions involving isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester groups. Examples of suitable carboxyl-reactive conjugation chemistries include, but are not limited to, reactions involving carbodiimide compounds, e.g., water soluble EDC (1-ethyl-3-(3-dimethylaminopropyl)carbodiimide HCL). Examples of suitable sulfydryl-reactive conjugation chemistries include maleimides, haloacetyls and pyridyl disulfides.

One or more types of oligonucleotide molecules may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered oligonucleotide adapter and/or primer sequences may range in length from about 10 nucleotides to about 100 nucleotides. In some instances, the tethered oligonucleotide adapter and/or primer sequences may be at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

In some instances, the number of coating layers and/or the material composition of each layer is chosen so as to adjust the resultant surface density of oligonucleotide adapters/primers (or other attached molecules) on the coated interior flow cell surfaces. In some instances, the surface density of oligonucleotide adapters/primers may range from about 1,000 primer molecules per $\mu m^2$ to about 1,000,000 primer molecules per $\mu m^2$. In some instances, the surface density of oligonucleotide primers may be at least 1,000, at least 10,000, at least 100,000, or at least 1,000,000 molecules per $\mu m^2$. In some instances, the surface density of oligonucleotide primers may be at most 1,000,000, at most 100,000, at most 10,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. Those of skill in the art will recognize that the surface density of primer molecules may have any value within this range, e.g., about 455,000 molecules per $\mu m^2$. In some instances, the surface properties of the capillary or channel lumen coating, including the surface density of tethered oligonucleotide primers, may be adjusted to improve or optimize, e.g., solid-phase nucleic acid hybridization specificity and efficiency, and/or solid-phase nucleic acid amplification rate, specificity, and efficiency.

In some instances, the tethered adapter or primer sequences may comprise modifications designed to facilitate the specificity and efficiency of nucleic acid amplification as performed on the low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (e.g., a nucleotide that has neither a purine nor a pyrimidine base), or a lesion site which can be bypassed by the helicase.

Nucleic acid hybridization: In some instances, the hydrophilic, polymer coated flow cell device surfaces disclosed herein may provide advantages when used alone or in combination with improved buffer formulations for performing solid-phase nucleic acid hybridization and/or solid-phase nucleic acid amplification reactions as part of genotyping or nucleic acid sequencing applications. In some instances, the polymer-coated flow cell devices disclosed herein may provide advantages in terms of improved nucleic acid hybridization rate and specificity, and improved nucleic acid amplification rates and specificity that may be achieved through one or more of the following additional aspects of the present disclosure: (i) primer design (e.g., sequence and/or modifications), (ii) control of tethered primer density on the solid support, (iii) the surface composition of the solid support, (iv) the surface polymer density of the solid support, (v) the use of improved hybridization conditions before and during amplification, and/or (vi) the use of improved amplification formulations that decrease non-specific primer amplification or increase template amplification efficiency.

In some instances, it may be desirable to vary the surface density of tethered oligonucleotide adapters or primers on the coated flow cell surfaces and/or the spacing of the tethered adapters or primers away from the coated flow cell surface (e.g., by varying the length of a linker molecule used to tether the adapter or primers to the surface) in order to "tune" the support for optimal performance when, e.g., using a given amplification method. In some instances, adjusting the surface density of tethered oligonucleotide adapters or primers may impact the level of specific and/or non-specific amplification observed on the surface in a manner that varies according to the amplification method selected. In some instances, the surface density of tethered oligonucleotide adapters or primers may be varied by adjusting the ratio of molecular components used to create the support surface. For example, in the case that an oligonucleotide primer—PEG conjugate is used to create the final layer of a low-binding support, the ratio of the oligonucleotide primer—PEG conjugate to a non-conjugated PEG molecule may be varied. The resulting surface density of tethered primer molecules may then be estimated or measured using any of a variety of techniques known to those of skill in the art. Examples include, but are not limited to, the use of radio-isotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the use of the disclosed hydrophilic, polymer-coated flow cell devices, either alone or in combination with improved or optimized buffer formulations, may yield relative hybridization rates that range from about 2× to about 20× faster than that for a conventional hybridization protocol. In some instances, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, at least 20×, at least 25×, at least 30×, or at least 40× that for a conventional hybridization protocol.

In some instances, the use of the disclosed hydrophilic, polymer-coated flow cell devices, either alone or in combination with improved or optimized buffer formulations, may yield total hybridization reaction times (e.g., the time required to reach 90%, 95%, 98%, or 99% completion of the hybridization reaction) of less than 60 minutes, 50 minutes, 40 minutes, 30 minutes, 20 minutes, 15 minutes, 10 minutes, or 5 minutes for any of these completion metrics.

In some instances, the use of the disclosed hydrophilic, polymer-coated flow cell devices, either alone or in combination with improved or optimized buffer formulations, may yield improved hybridization specificity compared to that for a conventional hybridization protocol. In some instances, the hybridization specificity that may be achieved is better than 1 base mismatch in 10 hybridization events, 1 base mismatch in 20 hybridization events, 1 base mismatch in 30 hybridization events, 1 base mismatch in 40 hybridization events, 1 base mismatch in 50 hybridization events, 1 base mismatch in 75 hybridization events, 1 base mismatch in 100 hybridization events, 1 base mismatch in 200 hybridization events, 1 base mismatch in 300 hybridization events, 1 base mismatch in 400 hybridization events, 1 base mismatch in 500 hybridization events, 1 base mismatch in 600 hybridization events, 1 base mismatch in 700 hybridization events, 1 base mismatch in 800 hybridization events, 1 base mismatch in 900 hybridization events, 1 base mismatch in 1,000 hybridization events, 1 base mismatch in 2,000 hybridization events, 1 base mismatch in 3,000 hybridization events, 1 base mismatch in 4,000 hybridization events, 1 base mismatch in 5,000 hybridization events, 1 base mismatch in 6,000 hybridization events, 1 base mismatch in 7,000 hybridization events, 1 base mismatch in 8,000 hybridization events, 1 base mismatch in 9,000 hybridization events, or 1 base mismatch in 10,000 hybridization events.

In some instances, the use of the disclosed hydrophilic, polymer-coated flow cell devices, either alone or in combination with improved or optimized buffer formulations, may yield improved hybridization efficiency (e.g., the fraction of available oligonucleotide primers on the support surface that are successfully hybridized with target oligonucleotide sequences) compared to that for a conventional hybridization protocol. In some instances, the hybridization efficiency that may be achieved is better than 50%, 60%, 70%, 80%, 85%, 90%, 95%, 98%, or 99% for any of the input target oligonucleotide concentrations specified below and in any of the hybridization reaction times specified above. In some instances, e.g., wherein the hybridization efficiency is less than 100%, the resulting surface density of target nucleic acid sequences hybridized to the support surface may be less than the surface density of oligonucleotide adapter or primer sequences on the surface.

In some instances, use of the disclosed hydrophilic, polymer-coated flow cell devices for nucleic acid hybridization (or nucleic acid amplification) applications using conventional hybridization (or amplification) protocols, or improved or optimized hybridization (or amplification) protocols, may lead to a reduced requirement for the input concentration of target (or sample) nucleic acid molecules contacted with the support surface. For example, in some instances, the target (or sample) nucleic acid molecules may be contacted with the support surface at a concentration ranging from about 10 μM to about 1 μM (e.g., prior to annealing or amplification). In some instances, the target (or sample) nucleic acid molecules may be administered at a concentration of at least 10 μM, at least 20 μM, at least 30 μM, at least 40 μM, at least 50 μM, at least 100 μM, at least 200 μM, at least 300 μM, at least 400 μM, at least 500 μM, at least 600 μM, at least 700 μM, at least 800 μM, at least 900 μM, at least 1 nM, at least 10 nM, at least 20 nM, at least 30 nM, at least 40 nM, at least 50 nM, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, or at least 1 μM. In some instances, the target (or sample) nucleic acid molecules may be administered at a concentration of at most 1 μM, at most 900 nM, at most 800 nm, at most 700 nM, at most 600 nM, at most 500 nM, at most 400 nM, at most 300 nM, at most 200 nM, at most 100 nM, at most 90 nM, at most 80 nM, at most 70 nM, at most 60 nM, at most 50 nM, at most 40 nM, at most 30 nM, at most 20 nM, at most 10 nM, at most 1 nM, at most 900 μM, at most 800 μM, at most 700 μM, at most 600 μM, at most 500 μM, at most 400 μM, at most 300 μM, at most 200 μM, at most 100 μM, at most 90 μM, at most 80 μM, at most 70 μM, at most 60 μM, at most 50 μM, at most 40 μM, at most 30 μM, at most 20 μM, or at most 10 μM. Any of the lower and upper values described in this paragraph may be combined to form a range included within the present disclosure, for example, in some instances the target (or sample) nucleic acid molecules may be administered at a concentration ranging from about 90 µM to about 200 nM. Those of skill in the art will recognize that the target (or sample) nucleic acid molecules may be administered at a concentration having any value within this range, e.g., about 855 nM.

In some instances, the use of the disclosed hydrophilic, polymer-coated flow cell devices, either alone or in combination with improved or optimized hybridization buffer formulations, may result in a surface density of hybridized target (or sample) oligonucleotide molecules (e.g., prior to performing any subsequent solid-phase or clonal amplification reaction) ranging from about from about 0.0001 target oligonucleotide molecules per µm$^2$ to about 1,000,000 target oligonucleotide molecules per µm$^2$. In some instances, the surface density of hybridized target oligonucleotide molecules may be at least 0.0001, at least 0.0005, at least 0.001, at least 0.005, at least 0.01, at least 0.05, at least 0.1, at least 0.5, at least 1, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per µm$^2$. In some instances, the surface density of hybridized target oligonucleotide molecules may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, at most 100, at most 90, at most 80, at most 70, at most 60, at most 50, at most 40, at most 30, at most 20, at most 10, at most 5, at most 1, at most 0.5, at most 0.1, at most 0.05, at most 0.01, at most 0.005, at most 0.001, at most 0.0005, or at most 0.0001 molecules per µm$^2$. Any of the lower and upper values described in this paragraph may be combined to form a range included within the present disclosure, for example, in some instances the surface density of hybridized target oligonucleotide molecules may range from about 3,000 molecules per µm$^2$ to about 20,000 molecules per µm$^2$. Those of skill in the art will recognize that the surface density of hybridized target oligonucleotide molecules may have any value within this range, e.g., about 2,700 molecules per µm$^2$.

Stated differently, in some instances the use of the disclosed low-binding supports alone or in combination with improved or optimized hybridization buffer formulations may result in a surface density of hybridized target (or sample) oligonucleotide molecules (e.g., prior to performing any subsequent solid-phase or clonal amplification reaction) ranging from about 100 hybridized target oligonucleotide molecules per mm$^2$ to about $1 \times 10^{12}$ hybridized target oligonucleotide molecules per mm$^2$. In some instances, the surface density of hybridized target oligonucleotide molecules may be at least 100, at least 500, at least 1,000, at least 4,000, at least 5,000, at least 6,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per mm$^2$. In some instances, the surface density of hybridized target oligonucleotide molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm$^2$. Any of the lower and upper values described in this paragraph may be combined to form a range included within the present disclosure, for example, in some instances the surface density of hybridized target oligonucleotide molecules may range from about 5,000 molecules per mm$^2$ to about 50,000 molecules per mm$^2$. Those of skill in the art will recognize that the surface density of hybridized target oligonucleotide molecules may have any value within this range, e.g., about 50,700 molecules per mm$^2$.

In some instances, the target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 0.6 kb in length, at least 0.7 kb in length, at least 0.8 kb in length, at least 0.9 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, at least 20 kb in length, at least 30 kb in length, or at least 40 kb in length, or any intermediate value spanned by the range described herein, e.g., at least 0.85 kb in length.

In some instances, the target (or sample) oligonucleotide molecules (or nucleic acid molecules) may comprise single-stranded or double-stranded, multimeric nucleic acid molecules (e.g., concatemers) further comprising repeats of a regularly occurring monomer unit. In some instances, the single-stranded or double-stranded, multimeric nucleic acid molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, at least 30 kb in length, or at least 40 kb in length, or any intermediate value spanned by the range described herein, e.g., about 2.45 kb in length.

In some instances, the target (or sample) oligonucleotide molecules (or nucleic acid molecules) may comprise single-stranded or double-stranded multimeric nucleic acid molecules (e.g., concatemers) comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 17. Thus, in some instances, the surface density of hybridized target sequences in terms of the number of copies of a target sequence per unit area of the support surface may exceed the surface density of oligonucleotide primers even if the hybridization efficiency is less than 100%.

Nucleic acid surface amplification (NASA): As used herein, the phrase "nucleic acid surface amplification" (NASA) is used interchangeably with the phrase "solid-phase nucleic acid amplification" (or simply "solid-phase amplification"). In some aspects of the present disclosure, nucleic acid amplification formulations are described which, in combination with the disclosed hydrophilic, polymer-coated flow cell devices, provide for improved amplification rates, amplification specificity, and amplification efficiency. As used herein, specific amplification refers to amplification of template library oligonucleotide strands that have been tethered to the solid support either covalently or non-covalently. As used herein, non-specific amplification refers to amplification of primer-dimers or other non-template nucleic acids. As used herein, amplification efficiency is a measure of the percentage of tethered oligonucleotides on the support surface that are successfully amplified during a given amplification cycle or amplification reaction. Nucleic acid amplification performed on surfaces disclosed herein may obtain amplification efficiencies of at least 50%, 60%, 70%, 80%, 90%, 95%, or greater than 95%, such as 98% or 99%.

Any of a variety of thermal cycling or isothermal nucleic acid amplification schemes may be used with the disclosed low-binding supports. Examples of nucleic acid amplification methods that may be utilized with the disclosed low-binding supports include, but are not limited to, polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, or single-stranded binding (SSB) protein-dependent amplification.

In some instances, improvements in amplification rate, amplification specificity, and amplification efficiency may be achieved using the disclosed hydrophilic, polymer-coated flow cell devices, either alone or in combination with formulations of the amplification reaction components. In addition to inclusion of nucleotides, one or more polymerases, helicases, single-stranded binding proteins, etc. (or any combination thereof), the amplification reaction mixture may be adjusted in a variety of ways to achieve improved performance including, but are not limited to, choice of buffer type, buffer pH, organic solvent mixtures, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

The use of the disclosed hydrophilic, polymer-coated flow cell devices, alone or in combination with improved or optimized amplification reaction formulations, may yield increased amplification rates compared to those obtained using conventional supports and amplification protocols. In some instances, the relative amplification rates that may be achieved may be at least 2×, at least 3×, at least 4×, at least 5×, at least 6×, at least 7×, at least 8×, at least 9×, at least 10×, at least 12×, at least 14×, at least 16×, at least 18×, or at least 20× that for use of conventional supports and amplification protocols for any of the amplification methods described above.

In some instances, the use of the disclosed hydrophilic, polymer-coated flow cell devices, alone or in combination with improved or optimized buffer formulations, may yield total amplification reaction times (e.g., the time required to reach 90%, 95%, 98%, or 99% completion of the amplification reaction) of less than 180 mins, 120 mins, 90 min, 60 minutes, 50 minutes, 40 minutes, 30 minutes, 20 minutes, 15 minutes, 10 minutes, 5 minutes, 3 minutes, 1 minute, 50 s, 40 s, 30 s, 20 s, or 10 s for any of these completion metrics.

In some instances, the use of the disclosed low-binding supports alone or in combination with improved or optimized amplification buffer formulations may enable faster amplification reaction times (e.g., the times required to reach 90%, 95%, 98%, or 99% completion of the amplification reaction) of no more than 60 minutes, 50 minutes, 40 minutes, 30 minutes, 20 minutes, or 10 minutes. Similarly, use of the disclosed low-binding supports alone or in combination with improved or optimized buffer formulations may enable amplification reactions to be completed in some cases in no more than 2, 3, 4, 5, 6, 7, 8, 9, 10, 15, or no more than 30 cycles.

In some instances, the use of the disclosed hydrophilic, polymer-coated flow cell devices, alone or in combination with improved or optimized amplification reaction formulations, may yield increased specific amplification and/or decreased non-specific amplification compared to that obtained using conventional supports and amplification protocols. In some instances, the resulting ratio of specific amplification-to-non-specific amplification that may be achieved is at least 4:1 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1,000:1.

In some instances, the use of the disclosed hydrophilic, polymer-coated flow cell devices, alone or in combination with improved or optimized amplification reaction formulations, may yield increased amplification efficiency compared to that obtained using conventional supports and amplification protocols. In some instances, the amplification efficiency that may be achieved is better than 50%, 60%, 70% 80%, 85%, 90%, 95%, 98%, or 99% in any of the amplification reaction times specified above.

In some instances, the clonally-amplified target (or sample) oligonucleotide molecules (or nucleic acid molecules) hybridized to the oligonucleotide adapter or primer molecules attached to the hydrophilic, polymer-coated flow cell device surfaces may range in length from about 0.02 kilobases (kb) to about 20 kb or from about 0.1 kilobases (kb) to about 20 kb. In some instances, the clonally-amplified target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., at least 0.85 kb in length.

In some instances, the clonally-amplified target (or sample) oligonucleotide molecules (or nucleic acid molecules) may comprise single-stranded or double-stranded, multimeric nucleic acid molecules (e.g., concatemers) further comprising repeats of a regularly occurring monomer unit. In some instances, the clonally-amplified single-stranded or double-stranded, multimeric nucleic acid molecules may be at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., about 2.45 kb in length.

In some instances, the clonally-amplified target (or sample) oligonucleotide molecules (or nucleic acid molecules) may comprise single-stranded or double-stranded multimeric nucleic acid (e.g., concatemers) molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 12. Thus, in some instances, the surface density of clonally-amplified target sequences in terms of the number of copies of a target sequence per unit area of the support surface may exceed the surface density of oligonucleotide primers even if the hybridization and/or amplification efficiencies are less than 100%.

In some instances, the use of the disclosed hydrophilic, polymer-coated flow cell devices, alone or in combination with improved or optimized amplification reaction formulations, may yield increased clonal copy number compared to that obtained using conventional supports and amplification protocols. In some instances, e.g., wherein the clonally-amplified target (or sample) oligonucleotide molecules comprise concatenated, multimeric repeats of a monomeric target sequence, the clonal copy number may be substantially smaller than compared to that obtained using conventional supports and amplification protocols. Thus, in some instances, the clonal copy number may range from about 1 molecule to about 100,000 molecules (e.g., target sequence molecules) per amplified colony. In some instances, the clonal copy number may be at least 1, at least 5, at least 10, at least 50, at least 100, at least 500, at least 1,000, at least 2,000, at least 3,000, at least 4,000, at least 5,000, at least 6,000, at least 7,000, at least 8,000, at least 9,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, or at least 100,000 molecules per amplified colony. In some instances, the clonal copy number may be at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,000, at most 8,000, at most 7,000, at most 6,000, at most 5,000, at most 4,000, at most 3,000, at most 2,000, at most 1,000, at most 500, at most 100, at most 50, at most 10, at most 5, or at most 1 molecule per amplified colony. Any of the lower and upper values described in this paragraph may be combined to form a range included within the present disclosure, for example, in some instances the clonal copy number may range from about 2,000 molecules to about 9,000 molecules. Those of skill in the art will recognize that the clonal copy number may have any value within this range, e.g., about 2,220 molecules in some instances, or about 2 molecules in others.

As noted above, in some instances the amplified target (or sample) oligonucleotide molecules (or nucleic acid molecules) may comprise concatenated, multimeric repeats of a monomeric target sequence. In some instances, the amplified target (or sample) oligonucleotide molecules (or nucleic acid molecules) may comprise a plurality of molecules each of which comprises a single monomeric target sequence. Thus, the use of the disclosed hydrophilic, polymer-coated flow cell devices, alone or in combination with improved or optimized amplification reaction formulations, may result in a surface density of target sequence copies that ranges from about 100 target sequence copies per mm$^2$ to about $1\times10^{12}$ target sequence copies per mm$^2$. In some instances, the surface density of target sequence copies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, at least $1\times10^{11}$, at least $5\times10^{11}$, or at least $1\times10^{12}$ of clonally amplified target sequence molecules per mm$^2$. In some instances, the surface density of target sequence copies may be at most $1\times10^{12}$, at most $5\times10^{11}$, at most $1\times10^{11}$, at most $5\times10^{10}$, at most $1\times10^{10}$, at most $5\times10^9$, at most $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 target sequence copies per mm$^2$. Any of the lower and upper values described in this paragraph may be combined to form a range included within the present disclosure, for example, in some instances the surface density of target sequence copies may range from about 1,000 target sequence copies per mm$^2$ to about 65,000 target sequence copies mm$^2$. Those of skill in the art will recognize that the surface density of target sequence copies may have any value within this range, e.g., about 49,600 target sequence copies per mm$^2$.

In some instances, the use of the disclosed low-binding supports alone or in combination with improved or optimized amplification buffer formulations may result in a surface density of clonally-amplified target (or sample) oligonucleotide molecules (or clusters) ranging from about from about 100 molecules per mm$^2$ to about $1\times10^{12}$ colonies per mm$^2$. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1\times10^7$, at least $5\times10^7$, at least $1\times10^8$, at least $5\times10^8$, at least $1\times10^9$, at least $5\times10^9$, at least $1\times10^{10}$, at least $5\times10^{10}$, at least $1\times10^{11}$, at least $5\times10^{11}$, or at least $1\times10^{12}$ molecules per mm$^2$. In some instances, the surface density of clonally-amplified molecules may be at most $1\times10^{12}$, at most $5\times10^{11}$, at most $1\times10^{11}$, at most $5\times10^{10}$, at most $1\times10^{10}$, at most $5\times10^9$, at most $1\times10^9$, at most $5\times10^8$, at most $1\times10^8$, at most $5\times10^7$, at most $1\times10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm$^2$. Any of the lower and upper values described in this paragraph may be combined to form a range included within the present disclosure, for example, in some instances the surface density of clonally-amplified molecules may range from about 5,000 molecules per mm$^2$ to about 50,000 molecules per mm$^2$. Those of skill in the art will recognize that the surface density of clonally-amplified colonies may have any value within this range, e.g., about 48,800 molecules per mm$^2$.

In some instances. the use of the disclosed hydrophilic, polymer-coated flow cell devices, alone or in combination with improved or optimized amplification reaction formulations, may yield signal from the amplified and labeled nucleic acid populations (e.g., a fluorescence signal) that has a coefficient of variance of no greater than 50%, such as 50%, 40%, 30%, 20%, 15%, 10%, 5%, or less than 5%.

Similarly, in some instances the use of the disclosed hydrophilic, polymer-coated flow cell devices, alone or in combination with improved or optimized amplification reaction formulations, may yield signal from the amplified and non-labeled nucleic acid populations that has a coefficient of variance of no greater than 50%, such as 50%, 40%, 30%, 20%, 10%, 5%, or less than 5%.

Fluorescence imaging of hydrophilic, polymer-coated flow cell device surfaces: The disclosed hydrophilic, polymer-coated flow cell devices comprising, e.g., clonal clusters of labeled target nucleic acid molecules disposed thereon may be used in any of a variety of nucleic acid analysis applications, e.g., nucleic acid base discrimination, nucleic acid base classification, nucleic acid base calling, nucleic acid detection applications, nucleic acid sequencing applications, and nucleic acid-based (genetic and genomic) diagnostic applications. In many of these applications, fluorescence imaging techniques may be used to monitor hybridization, amplification, and/or sequencing reactions performed on the low-binding supports. Fluorescence imaging may be performed using any of the optical imaging modules disclosed herein, as well as a variety of fluorophores, fluorescence imaging techniques, and other fluorescence imaging instruments known to those of skill in the art.

In some instances, the performance of nucleic acid hybridization and/or amplification reactions using the disclosed hydrophilic, polymer-coated flow cell devices and reaction buffer formulations may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). As noted above, while signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times can be reduced or minimized). At high CNR, the imaging time required to reach accurate signal discrimination (and thus accurate base-calling in the case of sequencing applications) can be drastically reduced even with moderate improvements in CNR.

In most ensemble-based sequencing approaches, the background term is typically measured as the signal associated with 'interstitial' regions. In addition to "interstitial" background ($B_{inter}$), "intrastitial" background ($B_{intra}$) exists within the discrete regions occupied by amplified DNA colonies. The combination of these two background signal terms dictates the achievable CNR in the image, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the foreground signal from the ROI, and the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (e.g., (S)-$B_{inter}$ in the FOV) yields a discernable feature that can be classified. In some instances, the intrastitial background ($B_{intra}$) can contribute a confounding fluorescence signal that is not specific to the target of interest but is present in the same ROI, thus making it far more difficult to average and subtract.

The implementation of nucleic acid amplification on the hydrophilic, polymer-coated substrate surfaces of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low nonspecific binding support surfaces, optionally used in combination with improved hybridization and/or amplification reaction buffer formulations, may lead to improvements in CNR by a factor of 2, 5, 10, 100, 200, 500, or 1000-fold over those achieved using conventional supports and hybridization, amplification, and/or sequencing protocols. Although described here in the context of using fluorescence imaging as the read-out or detection mode, the same principles apply to the use of the disclosed low nonspecific binding supports and nucleic acid hybridization and amplification formulations for other detection modes as well, including both optical and non-optical detection modes.

Alternative sequencing biochemistries: In addition to the sequencing-by-nucleotide incorporation approach described above, the disclosed flow cell devices and optical imaging systems are compatible with other emerging nucleic acid sequencing biochemistries as well. Examples include the "sequencing-by-nucleotide binding" approach described in U.S. Patent No. 10, 655, 176 B2, and the "sequencing-by-avidity" approach described in U.S. Pat. No. 10,768,173 B2.

In some embodiments, the "sequencing-by-nucleotide binding" approach, as currently being developed by Omniome, Inc. (San Diego, CA) is based on performing repetitive cycles of detecting a stabilized complex that forms at each position along the template (e.g. a ternary complex that includes the primed template (tethered to a sample support structure), a polymerase, and a cognate nucleotide for the position), under conditions that prevent covalent incorporation of the cognate nucleotide into the primer, and then extending the primer to allow detection of the next position along the template. In the sequencing-by-binding approach, detection of the nucleotide at each position of the template occurs prior to extension of the primer to the next position. Generally, the methodology is used to distinguish the four different nucleotide types that can be present at positions along a nucleic acid template by uniquely labelling each type of ternary complex (e.g. different types of ternary complexes differing in the type of nucleotide it contains) or by separately delivering the reagents to form each type of ternary complex. In some instances, the labeling may comprise fluorescence labeling of, e.g., the cognate nucleotide or the polymerase that participate in the ternary complex. The approach is thus compatible with the disclosed flow cell devices and imaging systems.

In some embodiments, the "sequencing-by-avidity" approach, as currently being developed by Element Biosciences, Inc. (San Diego, CA) relies on the increased avidity (or "functional affinity") derived from forming a complex comprising a plurality of individual non-covalent binding interactions. In some embodiments, sequencing-by-avidity comprises the detection of a multivalent binding complex formed between a fluorescently-labeled nucleotide conjugate, a polymerase, and a plurality of primed target nucleic acid molecules tethered to a sample support structure, which allows the detection/base-calling step to be separated from the nucleotide incorporation step. In some embodiments, fluorescence imaging is used to detect the bound complex and thereby determine the identity of the N+1 nucleotide in the target nucleic acid sequence (where the primer extension strand is N nucleotides in length). Following the imaging step, the multivalent binding complex is disrupted and washed away, the correct blocked nucleotide is incorporated into the primer extension strand, and the cycle is repeated, in some embodiments.

In some instances, a nucleotide conjugate of the present disclosure may comprise a plurality of nucleotide moieties or nucleotide analog moieties conjugated to a polymer core, e.g., through the 5' end of the nucleotide, either directly or via a linker. By way of non-limiting example, the nucleotide moieties may include ribonucleotide moieties, ribonucleotide analog moieties, deoxyribonucleotide moieties, deoxyribonucleotide analog moieties, or any combination thereof. In some instances, the nucleotides or nucleotide analogs may comprise deoxyadenosine, deoxyguanosine, thymidine, deoxyuridine, deoxycytidine, adenosine, guanosine, 5-methyl-uridine, and/or cytidine. In some instances, the nucleotide or nucleotide analog moieties may comprise a nucleotide that has been modified to inhibit elongation during a polymerase reaction or a sequencing reaction, such as wherein the at least one nucleotide or nucleotide analog is a nucleotide that lacks a 3' hydroxyl group; a nucleotide that has been modified to contain a blocking group at the 3' position; and/or a nucleotide that has been modified with a 3'-O-azido group, a 3'-O-azidomethyl group, a 3'-O-alkyl hydroxylamino group, a 3'-phosphorothioate group, a 3'-O-malonyl group, or a 3'-O-benzyl group.

In some instances, the polymer core may comprise a linear or branched polymer, e.g., linear or branched polyethylene glycol (PEG), polypropylene glycol, polyvinyl alcohol, polylactic acid, polyglycolic acid, poly-glycine, polyvinyl acetate, a dextran, a protein, or other such polymers, or copolymers incorporating any two or more of the foregoing, or incorporating other polymers as are known in the art. In some instances, the polymer is a PEG. In some instances, the polymer is a branched PEG. In some instances, a branched polymer may comprise 2, 3, 4, 5, 6, 7, 8, 9, 10, 11, 12, 13, 14, 15, 16 or more branches or arms, or 2, 4, 8, 16, 32, 64, or more, branches or arms. In some instances, the branches or arms may radiate from a central moiety.

In some instances, the nucleotide conjugate may further comprise one or more detectable labels, e.g., one, two, three, four, five, six, seven, eight, nine, ten, fifteen, twenty, or more than twenty detectable labels. In some instances, the one or more detectable labels may comprise one or more fluorophores (e.g., cyanine dye 3 (Cy®3), cyanine dye 5 (Cy®5), etc.), one or more quantum dots, a fluorescence resonance energy transfer (FRET) donor, and/or a FRET acceptor.

In some instances, the nucleotide conjugate may further comprise a binding moiety attached to each branch of the polymer core or to a subset of branches. Examples of suitable binding moieties include, but are not limited to, biotin, avidin, streptavidin, or the like, polyhistidine domains, complementary paired nucleic acid domains, G-quartet forming nucleic acid domains, calmodulin, maltose-binding protein, cellulase, maltose, sucrose, glutathione-S-transferase, glutathione, 0-6-methylguanine-DNA methyltransferase, benzylguanine and derivatives thereof, benzylcysteine and derivatives thereof, an antibody, an epitope, a protein A, or a protein G. The binding moiety may be any interactive molecule or fragment thereof known in the art to bind to or facilitate interactions between proteins, between proteins and ligands, between proteins and nucleic acids, between nucleic acids, or between small molecule interaction domains or moieties.

As noted above, in the sequencing-by-avidity approach a multivalent binding complex is formed between, e.g., a fluorescently-labeled nucleotide conjugate, a polymerase, and a plurality of primed target nucleic acid molecules tethered to a sample support structure (e.g., a flow cell surface) when the nucleotide moieties of the nucleotide conjugate are complementary to a nucleotide residue of the target sequence. The stability of the multivalent binding complex thus formed allows the detection/base-calling step in a sequencing reaction cycle to be separated from the nucleotide incorporation step.

The stability of the multivalent binding complex—a ternary complex formed between two or more nucleotide moieties of the nucleotide conjugate, two or more polymerase molecules, and two or more primed target nucleic acid sequences—is evidenced by the prolonged persistence times of the complex. For example, in some instances, said multivalent binding complexes (ternary complexes) may have a persistence time of less than 0.5 seconds, less than 1 second, greater than 1 second, greater than 2 seconds, greater than 3 seconds, greater than 4 seconds, greater than 5 seconds, greater than 10 seconds, greater than 15 seconds, greater than 20 seconds, greater than 30 seconds, greater than 60 seconds, greater than 120 seconds, greater than 360 seconds, greater than 720 seconds, greater than 1,440 seconds, greater than 3,600 seconds, or more, or for a time within a range defined by any two or more of these values.

The use of nucleotide conjugates to form a multivalent binding complex with the polymerase and primed target nucleic acid results in an effective local concentration of the nucleotide that is increased many fold over the average nucleotide concentration that can be achieved using single unconjugated or untethered nucleotides, which in turn both enhances the stability of the complex and increases signal intensity following wash steps. The high signal intensity persists throughout the binding, washing, and imaging steps, and contributes to shorter image acquisition times. Following the imaging step, the multivalent binding complex can be destabilized, e.g., by changing the ionic composition, ionic strength, and/or the pH of the buffer, and washed away. A primer extension reaction may then be performed to extend the complementary strand by one base.

Nucleic acid sequencing system performance: In some instances, the disclosed nucleic acid sequencing systems, comprising one or more of the disclosed flow cell devices used in combination with one or more of the disclosed optical imaging systems, and optionally utilizing one of the emerging sequencing biochemistries such as the "sequencing-by-trapping" (or "sequencing-by-avidity") approach described above, may provide improved nucleic acid sequencing performance in terms of, e.g., reduced sample input requirements, reduced image acquisition cycle time, reduced sequencing reaction cycle time, reduced sequencing run time, improved base-calling accuracy, reduced reagent consumption and cost, higher sequencing throughput, and reduced sequencing cost.

Nucleic acid sample input (pM): In some instances, the sample input requirements for the disclosed system may be significantly reduced due to the improved hybridization and amplification efficiencies that may be attained, and the high CNR images that may be acquired for base-calling, using the disclosed hydrophilic, polymer coated flow cell devices and imaging systems. In some instances, the nucleic acid sample input requirement for the disclosed systems may range from about 1 pM to about 10,000 pM. In some instances, the nucleic acid sample input requirement may be at least 1 pM, at least 2 pM, at least 5 pM, at least 10 pM, at least 20 pM, at least 50 pM, at least 100 pM, at least 200 pM, at least 500 pM, at least 1,000 pM, at least 2,000 pM, at least 5,000 pM, at least 10,000 pM. In some instances, the nucleic acid sample input requirement for the disclosed systems may be at most 10,000 pM, at most 5,000 pM, at most 2,000 pM, at most 1,000 pM, at most 500 pM, at most 200 pM, at most 100 pM, at most 50 pM, at most 20 pM, at most 10 pM, at most 5 pM, at most 2 pM, or at most 1 pM. Any of the lower and upper values described in this paragraph may be combined to form a range included within the present disclosure, for example, in some instances the nucleic acid sample input requirement for the disclosed systems may range from about 5 pM to about 500 pM. Those of skill in the art will recognize that the nucleic acid sample input requirement may have any value within this range, e.g., about 132 pM. In one example, a nucleic acid sample input of about 100 pM is sufficient to generate signals for reliable base-calling.

Nucleic acid sample input (nanograms): In some instances, the nucleic acid sample input requirement for the disclosed systems may range from about 0.05 nanograms to about 1,000 nanograms. In some instances, the nucleic acid sample input requirement may be at least 0.05 nanograms, at least 0.1 nanograms, at least 0.2 nanograms, at least 0.4 nanograms, at least 0.6 nanograms, at least 0.8 nanograms, at least 1.0 nanograms, at least 2 nanograms, at least 4 nanograms, at least 6 nanograms, at least 8 nanograms, at least 10 nanograms, at least 20 nanograms, at least 40 nanograms, at least 60 nanograms, at least 80 nanograms, at least 100 nanograms, at least 200 nanograms, at least 400 nanograms, at least 600 nanograms, at least 800 nanograms, or at least 1,000 nanograms. In some instances, the nucleic acid sample input requirement may be at most 1,000 nanograms, at most 800 nanograms, at most 600 nanograms, at most 400 nanograms, at most 200 nanograms, at most 100 nanograms, at most 80 nanograms, at most 60 nanograms, at most 40 nanograms, at most 20 nanograms, at most 10 nanograms, at most 8 nanograms, at most 6 nanograms, at most 4 nanograms, at most 2 nanograms, at most 1 nanograms, at most 0.8 nanograms, at most 0.6 nanograms, at most 0.4 nanograms, at most 0.2 nanograms, at most 0.1 nanograms, or at most 0.05 nanograms. Any of the lower and upper values described in this paragraph may be combined to form a range included within the present disclosure, for example, in some instances the nucleic acid sample input requirement for the disclosed systems may range from about 0.6 nanograms to about 400 nanograms. Those of skill in the art will recognize that the nucleic acid sample input requirement may have any value within this range, e.g., about 2.65 nanograms.

FOV images required to tile flow cell: In some instances, the field-of-view (FOV) of the disclosed optical imaging module is sufficiently large that a multi-channel (or multi-lane) flow cell (e.g., the fluid channel portions thereof) of the present disclosure may be imaged by tiling from about 10 FOV images (or "frames") to about 1,000 FOV images (or "frames"). In some instances, an image of the entire multi-channel flow cell may require tiling at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1,000 FOV images (or "frames"). In some instances, an image of the entire multi-channel flow cell may require tiling at most 1,000, at most 950, at most 900, at most 850, at most 800, at most 750, at most 700, at most 650, at most 600, at most 550, at most 500, at most 450, at most 400, at most 350, at most 300, at most 250, at most 200, at most 150, at most 100, at most 90, at most 80, at most 80, at most 70, at most 60, at most 50, at most 40, at most 30, at most 20, or at most 10 FOV images (or "frames"). Any of the lower and upper values described in this paragraph may be combined to form a range included within the present disclosure, for example, in some instances an image of the entire multi-channel flow cell may require tiling from about 30 to about 100 FOV images. Those of skill in the art will recognize that in some instances the number of required FOV images may have any value within this range, e.g., about 54 FOV images.

Imaging cycle time: In some instances, the combination of large FOV, image sensor response sensitivity, and/or fast FOV translation times enables shortened imaging cycle times (e.g., the time required to acquire a sufficient number of FOV images to tile the entire multichannel flow cell (or the fluid channel portions thereof). In some instances, the imaging cycle time may range from about 10 seconds to about 10 minutes. In some instances, the imaging cycle time may be at least 10 seconds at least 20 seconds, at least 30 seconds, at least 40 seconds, at least 50 seconds, at least 1 minute, at least 2 minutes, at least 3 minutes, at least 4 minutes, at least 5 minutes, at least 6 minutes, at least 7 minutes, at least 8 minutes, at least 9 minutes, or at least 10 minutes. In some instances, the imaging cycle time may be at most 10 minutes, at most 9 minutes, at most 8 minutes, at most 7 minutes, at most 6 minutes, at most 5 minutes, at most 4 minutes, at most 3 minutes, at most 2 minutes, at most 1 minute, at most 50 second, at most 40 second, at most 30 seconds, at most 20 seconds, or at most 10 seconds. Any of the lower and upper values described in this paragraph may be combined to form a range included within the present disclosure, for example, in some instances the imaging cycle time may range from about 20 seconds to about 1 minute. Those of skill in the art will recognize that in some instances the imaging cycle time may have any value within this range, e.g., about 57 seconds.

Sequencing cycle time: In some instances, shortened sequencing reaction steps, e.g., due to reduced wash time requirements for the disclosed hydrophilic, polymer-coated flow cells, may result in shortened overall sequencing cycle times. In some instances, the sequencing cycle times for the disclosed systems may range from about 1 minute to about 60 minutes. In some instances, the sequencing cycle time may be at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, or at least 60 minutes. In some instances, the sequencing reaction cycle time may be at most 60 minutes, at most 55 minutes, at most 50 minutes, at most 45 minutes, at most 40 minutes, at most 35 minutes, at most 30 minutes, at most 25 minutes, at most 20 minutes, at most 15 minutes, at most 10 minutes, at most 9 minutes, at most 8 minutes, at most 7 minutes, at most 6 minutes, at most 5 minutes, at most 4 minutes, at most 3 minutes, at most 2 minutes, or at most 1 minutes. Any of the lower and upper values described in this paragraph may be combined to form a range included within the present disclosure, for example, in some instances the sequencing cycle time may range from about 2 minutes to about 15 minutes. Those of skill in the art will recognize that in some instances the sequencing cycle time may have any value within this range, e.g., about 1 minute, 12 seconds.

Sequencing read length: In some instances, the enhanced CNR images that may be achieved using the disclosed hydrophilic, polymer-coated flow cell devices in combination with the disclosed imaging systems, and in some cases, the use of milder sequencing biochemistries, may enable longer sequencing read lengths for the disclosed systems. In some instances, the maximum (single read) read length may range from about 50 bp to about 500 bp. In some instances, the maximum (single read) read length may be at least 50 bp, at least 100 bp, at least 150 bp, at least 200 bp, at least 250 bp, at least 300 bp, at least 350 bp, at least 400 bp, at least 450 bp, or at least 500 bp. In some instances, the maximum (single read) read length is at most 500 bp, at most 450 bp, at most 400 bp, at most 350 bp, at most 300 bp, at most 250 bp, at most 200 bp, at most 150 bp, at most 100 bp, or at most 50 bp. Any of the lower and upper values described in this paragraph may be combined to form a range included within the present disclosure, for example, in some instances the maximum (single read) read length may range from about 100 bp to about 450 bp. Those of skill in the art will recognize that in some instances the maximum (single read) read length may have any value within this range, e.g., about 380 bp.

Sequencing run time: In some instances, the sequencing run time for the disclosed nucleic acid sequencing systems may range from about 8 hours to about 20 hours. In some instances, the sequencing run time is at least 8 hours, at least 9 hours, at least 10 hours, at least 12 hours, at least 14 hours, at least 16 hours, at least 18 hours, or at least 20 hours. In some instances, the sequencing run time is at most 20 hours, at most 18 hours, at most 16 hours, at most 14 hours, at most 12 hours, at most 10 hours, at most 9 hours, or at most 8 hours. Any of the lower and upper values described in this paragraph may be combined to form a range included within the present disclosure, for example, in some instances the sequencing run time may range from about 10 hours to about 16 hours. Those of skill in the art will recognize that in some instances the sequencing run time may have any value within this range, e.g., about 7 hours, 35 minutes.

Average base-calling accuracy: In some instances, the disclosed nucleic acid sequencing systems may provide an average base-calling accuracy of at least 80%, at least 85%, at least 90%, at least 92%, at least 94%, at least 96%, at least 98%, at least 99%, at least 99.5%, at least 99.8%, or at least 99.9% correct over the course of a sequencing run. In some instances, the disclosed nucleic acid sequencing systems may provide an average base-calling accuracy of at least 80%, at least 85%, at least 90%, at least 92%, at least 94%, at least 96%, at least 98%, at least 99%, at least 99.5%, at least 99.8%, or at least 99.9% correct per every 1,000 bases, 10,0000 bases, 25,000 bases, 50,000 bases, 75,000 bases, or 100,000 bases called.

Average Q-score: In some instances, the quality or accuracy of a sequencing run may be assessed by calculating a Phred quality score (also referred to as a quality score or "Q-score"), which indicates the probability that a given base is called incorrectly by the sequencing system. For example, in some instances base calling accuracy for a specific sequencing chemistry and/or sequencing system may be assessed for a large empirical data set derived from performing sequencing runs on a library of known nucleic acid sequences. The Q-score may then be calculated according to the equation:

$$Q = -10 \log_{10} P$$

where P is the base calling error probability. A Q-score of 30, for example, indicates a probability of making a base calling error of 1 in every 1000 bases called (or a base calling accuracy of 99.9%).

In some instances, the disclosed nucleic acid sequencing systems may provide a more accurate base readout. In some instances, for example, the disclosed nucleic acid sequencing systems may provide a Q-score for base-calling accuracy over a sequencing run that ranges from about 20 to about 50. In some instances, the average Q-score for the run may be at least 20, at least 25, at least 30, at least 35, at least 40, at least 45, or at least 50. Those of skill in the art will recognize that the average Q-score may have any value within this range, e.g., about 32.

Q-score vs. % nucleotides identified: In some instances, the disclosed nucleic acid sequencing systems may provide a Q-score of greater than 20 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 25 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 30 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 35 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 40 for at least 50%, at least 60%, at least 70%, at least 80%, at least 85%, at least 90%, at least 95%, at least 98%, or at least 99% of the terminal (or N+1) nucleotides identified. In some instances, the disclosed nucleic acid sequencing systems may provide a Q-score of greater than 45 for at least 50%, at least 60%, at least 70%, at least 80%, at least 85%, at least 90%, at least 95%, at least 98%, or at least 99% of the terminal (or N+1) nucleotides identified. In some instances, the disclosed compositions and methods for nucleic acid sequencing may provide a Q-score of greater than 50 for at least 50%, at least 60%, at least 70%, at least 80%, at least 85%, at least 90%, at least 95%, at least 98%, or at least 99% of the terminal (or N+1) nucleotides identified.

Reagent consumption: In some instances, the disclosed nucleic acid sequencing systems may have lower reagent consumption rates and costs due to, e.g., the use of the disclosed flow cell devices and fluidic systems that minimize fluid channel volumes and dead volumes. In some instances, the disclosed nucleic acid sequencing systems may thus require an average of at least 5% less, at least 10% less, at least 15% less, at least 20% less, at least 25% less, at least 30% less, at least 35% less, at least 40% less, at least 45% less, or at least 50% less reagent by volume per Gbase sequenced that that consumed by an Illumina MiSeq sequencer.

Sequencing throughput: In some instances, the disclosed nucleic acid sequencing systems may provide a sequencing throughput ranging from about 50 Gbase/run to about 200 Gbase/run. In some instances, the sequencing throughput may be at least 50 Gbase/run, at least 75 Gbase/run, at least 100 Gbase/run, at least 125 Gbase/run, at least 150 Gbase/run, at least 175 Gbase/run, or at least 200 Gbase/run. In some instances, the sequencing throughput may be at most 200 Gbase/run, at most 175 Gbase/run, at most 150 Gbase/run, at most 125 Gbase/run, at most 100 Gbase/run, at most 75 Gbase/run, or at most 50 Gbase/run. Any of the lower and upper values described in this paragraph may be combined to form a range included within the present disclosure, for example, in some instances the sequencing throughput may range from about 75 Gbase/run to about 150 Gbase/run. Those of skill in the art will recognize that in some instances the sequencing throughput may have any value within this range, e.g., about 119 Gbase/run.

Sequencing cost: In some instances, the disclosed nucleic acid sequencing systems may provide nucleic acid sequencing at a cost ranging from about $5 per Gbase to about $30 per Gbase. In some instances, the sequencing cost may be at least $5 per Gbase, at least $10 per Gbase, at least $15 per Gbase, at least $20 per Gbase, at least $25 per Gbase, or at least $30 per Gbase. In some instances, the sequencing cost may be at most $30 per Gbase, at most $25 per Gbase, at most $20 per Gbase, at most $15 per Gbase, at most $10 per Gbase, or at most $30 per Gbase. Any of the lower and upper values described in this paragraph may be combined to form a range included within the present disclosure, for example, in some instances the sequencing cost may range from about $10 per Gbase to about $15 per Gbase. Those of skill in the art will recognize that in some instances the sequencing cost may have any value within this range, e.g., about $7.25 per Gbase.

FURTHER EMBODIMENTS

Disclosed herein are imaging systems configured to image a first interior surface and a second interior surface of a flow cell, the imaging systems comprising: a) an objective lens; b) at least one image sensor; and c) at least one tube lens disposed in an optical path between the objective lens and the at least one image sensor; wherein said optical system has a numerical aperture (NA) of less than 0.6 and a field-of-view (FOV) of greater than 1.0 mm$^2$; and wherein the at least one tube lens is configured to correct imaging performance such that images of the first interior surface of the flow cell and the second interior surface of the flow cell have substantially the same optical resolution.

In some embodiments, the flow cell has a wall thickness of at least 700 µm and a fluid-filled gap between the first interior surface and the second interior surface of at least 50 µm. In some embodiments, the images of the first interior surface and the second interior surface are acquired without moving an optical compensator into an optical path between said objective lens and said at least one image sensor. In some embodiments, the imaging system has a numerical aperture (NA) of less than 0.6. In some embodiments, the imaging system has a numerical aperture (NA) of greater than 0.3. In some embodiments, the imaging system has a field-of-view (FOV) of greater than 1.5 mm$^2$. In some embodiments, the optical resolution of images of the first interior surface and the second interior surface are diffraction-limited across the entire field-of-view (FOV). In some embodiments, the at least one tube lens comprises, in order, an asymmetric convex-convex lens, a convex-plano lens, an asymmetric concave-concave lens, and an asymmetric convex-concave lens. In some embodiments, the imaging system comprises two or more tube lenses which are designed to provide optimal imaging performance for the first interior surface and the second interior surface at two or more fluorescence wavelengths. In some embodiments, the imaging system further comprises a focusing mechanism configured to refocus the optical system between acquiring images of the first interior surface and the second interior surface. In some embodiments, the imaging system is configured to image two or more fields-of-view on at least one of the first interior surface or the second interior surface. In some embodiments, the first interior surface and second interior surface of the flow cell are coated with a hydrophilic coating layer, and wherein said hydrophilic coating layer further comprises labeled nucleic acid colonies disposed thereon at a surface density of >10,000 nucleic acid colonies/mm$^2$. In some embodiments, an image of the first interior surface or second interior surface acquired using the imaging system shows a contrast to noise ratio (CNR) of at least 5 when the nucleic acid colonies are labeled with cyanine dye 3 (Cy®3), the imaging system comprises a dichroic mirror and bandpass filter set optimized for Cy®3 emission, and the image is acquired under non-signal saturating conditions while the surface is immersed in 25 mM ACES, pH 7.4 buffer. In some embodiments, said imaging system comprises 1, 2, 3, or 4 imaging channels configured to detect nucleic acid colonies disposed on at least one of said two distinct surfaces that have been labeled with 1, 2, 3, or 4 distinct detectable labels. In some embodiments, the imaging system is used to monitor a sequencing-by-avidity, sequencing-by-nucleotide base-pairing, sequencing-by-nucleotide binding, or sequencing-by-nucleotide incorporation reaction on at least one of the first interior surface and the second interior surface and detect a bound or incorporated nucleotide base. In some embodiments, the imaging system is used to perform nucleic acid sequencing. In some embodiments, the imaging system is used to determine a genotype of a sample, wherein determining the genotype of the sample comprises preparing a nucleic acid molecule extracted from the sample for sequencing, and then sequencing the nucleic acid molecule. In some embodiments, the at least one image sensor comprises pixels having a pixel dimension chosen such that a spatial sampling frequency for the imaging system is at least twice an optical resolution of the imaging system. In some embodiments, a combination of the objective lens and the at least one tube lens is configured to optimize a modulation transfer function in the spatial frequency range from 700 cycles per mm to 1100 cycles per mm in the sample plane. In some embodiments, the at least one tube lens is designed to correct modulation transfer function (MTF) at one or more specified spatial frequencies, defocus, spherical aberration, chromatic aberration, coma, astigmatism, field curvature, image distortion, image contrast-to-noise ratio (CNR), or any combination thereof, for a combination of the objective lens and the at least one tube lens.

Also disclosed herein are methods of sequencing a nucleic acid molecule, the methods comprising: a) imaging a first surface and an axially-displaced second surface using an optical system which comprises an objective lens and at least one image sensor, wherein said optical system has a numerical aperture (NA) of less than 0.6 and a field-of-view (FOV) of greater than 1.0 mm$^2$, and wherein images of the first surface and the axially-displaced second surface having substantially the same optical resolution are acquired without moving an optical compensator into an optical path between said objective lens and said at least one image sensor; and b) detecting a fluorescently-labeled composition comprising the nucleic acid molecule, or a complement thereof, disposed on the first surface or the axially-displaced second surface to determine an identity of a nucleotide in the nucleic acid molecule.

In some embodiments, a focusing mechanism is utilized to refocus the optical system between acquiring images of the first surface and the axially-displaced second surface. In some embodiments, the method further comprises imaging two or more fields-of-view on at least one of the first surface or axially-displaced second surface. In some embodiments, the first surface and the axially-displaced second surface comprise two surfaces of a flow cell. In some embodiments, said two surfaces of the flow cell are coated with a hydrophilic coating layer. In some embodiments, said hydrophilic coating layer further comprises labeled nucleic acid colonies disposed thereon at a surface density of >10,000 nucleic acid colonies/mm$^2$. In some embodiments, an image of a surface of said two surfaces acquired using said optical system shows a contrast to noise ratio (CNR) of at least 5 when the nucleic acid colonies are labeled with cyanine dye 3 (Cy®3), the optical system comprises a dichroic mirror and bandpass filter set optimized for Cy®3 emission, and the image is acquired under non-signal saturating conditions while the surface is immersed in 25 mM ACES, pH 7.4 buffer. In some embodiments, said optical system comprises 1, 2, 3, or 4 imaging channels configured to detect nucleic acid colonies disposed on at least one of the first surface and the axially-displaced second surface that have been labeled with 1, 2, 3, or 4 distinct detectable labels. In some embodiments, the at least one image sensor comprises pixels having a pixel dimension chosen such that a spatial sampling frequency for the optical system is at least twice an optical resolution of the optical system. In some embodiments, the optical system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 µm and a gap between the first interior surface and the second interior surface of at least 50 µm. In some embodiments, the at least one tube lens comprises, in order, an asymmetric convex-convex lens, a convex-plano lens, an asymmetric concave-concave lens, and an asymmetric convex-concave lens. In some embodiments, the optical system comprises two or more tube lenses which are designed to provide optimal imaging performance at two or more fluorescence wavelengths. In some embodiments, a combination of objective lens and tube lens is configured to optimize a modulation transfer function in the mid to high spatial frequency range. In some embodiments, the imaging performance metric comprises a measurement of modulation transfer function (MTF) at one or more specified spatial frequencies, defocus, spherical aberration, chromatic aberration, coma, astigmatism, field curvature, image distortion, image contrast-to-noise ratio (CNR), or any combination thereof. In some embodiments, the optical resolution of images of the first surface and axially-displaced second surface are diffraction-limited across the entire field-of-view (FOV). In some embodiments, the sequencing of the nucleic acid molecule further comprises performing a sequencing-by-avidity, sequencing-by-nucleotide base-pairing, sequencing-by-nucleotide binding, or sequencing-by-nucleotide incorporation reaction on at least one of the first surface and axially-displaced second surface and detecting a bound or incorporated nucleotide base. In some embodiments, the method further comprises determining a genotype of a sample, wherein determining the genotype of the sample comprises preparing said nucleic acid molecule for sequencing, and then sequencing said nucleic acid molecule.

Disclosed herein are imaging systems configured to image two distinct, axially-displaced surfaces, the imaging systems comprising an objective lens and at least one image sensor, wherein said imaging system has a numerical aperture (NA) of less than 0.6 and a field-of-view (FOV) of greater than 1.0 mm2, and wherein said imaging system is capable of acquiring images of the two distinct, axially-displaced surfaces that have substantially the same optical resolution without moving an optical compensator into an optical path between said objective lens and said at least one image sensor.

In some embodiments, the imaging system has a numerical aperture of greater than 0.3. In some embodiments, the imaging system further comprises a focusing mechanism used to refocus the optical system between acquiring images of the two distinct, axially-displaced surfaces. In some embodiments, the imaging system is configured to image two or more fields-of-view on at least one of said two distinct, axially-displaced surfaces. In some embodiments, said two distinct, axially-displaced surfaces comprise two surfaces of a flow cell. In some embodiments, said two distinct surfaces of the flow cell are coated with a hydrophilic coating layer, and wherein said hydrophilic coating layer further comprises labeled nucleic acid colonies disposed thereon at a surface density of >10,000 nucleic acid colonies/mm$^2$. In some embodiments, said imaging system comprises 1, 2, 3, or 4 imaging channels configured to detect nucleic acid colonies disposed on at least one of said two distinct surfaces that have been labeled with 1, 2, 3, or 4 distinct detectable labels. In some embodiments, the at least one image sensor comprises pixels having a pixel dimension chosen such that a spatial sampling frequency for the imaging system is at least twice an optical resolution of the imaging system. In some embodiments, the imaging system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 µm and a gap between the first interior surface and the second interior surface of at least 50 µm. In some embodiments, the imaging system comprises two or more tube lenses which are designed to provide optimal imaging performance at two or more fluorescence wavelengths. In some embodiments, the optical resolution of images of the two distinct, axially-displaced surfaces are diffraction-limited across the entire field-of-view (FOV).

Disclosed herein are methods of sequencing a nucleic acid molecule, the method comprising: a) imaging a first surface and an axially-displaced second surface using a compensation-free optical system which comprises an objective lens and at least one image sensor, wherein said optical system has a numerical aperture (NA) of less than 0.6 and a field-of-view (FOV) of greater than 1.0 mm$^2$; b) processing the images of the first surface and the axially-displaced second surface to correct for optical aberration such that the images of the first surface and the axially-displaced second surface have substantially the same optical resolution; and c) detecting a fluorescently-labeled composition comprising the nucleic acid molecule, or a complement thereof, disposed on the first surface or the axially-displaced second surface to determine an identity of a nucleotide in the nucleic acid molecule.

In some embodiments, the images of the first surface and the axially-displaced second surface are acquired without moving an optical compensator into an optical path between said objective lens and said at least one image sensor. In some embodiments, the images of the first surface and the axially-displaced second surface are acquired by just refocusing the optical system. In some embodiments, the method further comprises imaging two or more fields-of-view on at least one of the first surface or axially-displaced second surface. In some embodiments, the first surface and the axially-displaced second surface comprise two surfaces of a flow cell. In some embodiments, said two surfaces of the flow cell are coated with a hydrophilic coating layer. In some embodiments, said hydrophilic coating layer further comprises labeled nucleic acid colonies disposed thereon at a surface density of >10,000 nucleic acid colonies/mm$^2$. In some embodiments, an image of a surface of said two surfaces acquired using said optical system shows a contrast to noise ratio (CNR) of at least 5 when the nucleic acid colonies are labeled with cyanine dye 3 (Cy®3), the optical system comprises a dichroic mirror and bandpass filter set optimized for Cy®3 emission, and the image is acquired under non-signal saturating conditions while the surface is immersed in 25 mM ACES, pH 7.4 buffer. In some embodiments, said optical system comprises 1, 2, 3, or 4 imaging channels configured to detect nucleic acid colonies disposed on at least one of the first surface and the axially-displaced second surface that have been labeled with 1, 2, 3, or 4 distinct detectable labels. In some embodiments, at least one image sensor comprises pixels having a pixel dimension chosen such that a spatial sampling frequency for the optical system is at least twice an optical resolution of the optical system. In some embodiments, the optical system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 µm and a gap between the first interior surface and the second interior surface of at least 50 µm. In some embodiments, the at least one tube lens comprises, in order, an asymmetric convex-convex lens, a convex-plano lens, an asymmetric concave-concave lens, and an asymmetric convex-concave lens. In some embodiments, the optical system comprises two or more tube lenses which are designed to provide optimal imaging performance at two or more fluorescence wavelengths. In some embodiments, a combination of objective lens and tube lens is configured to optimize a modulation transfer function in the mid to high spatial frequency range. In some embodiments, the imaging performance metric comprises a measurement of modulation transfer function (MTF) at one or more specified spatial frequencies, defocus, spherical aberration, chromatic aberration, coma, astigmatism, field curvature, image distortion, image contrast-to-noise ratio (CNR), or any combination thereof. In some embodiments, the optical resolution of images of the first surface and axially-displaced second surface are diffraction-limited across the entire field-of-view (FOV). In some embodiments, the sequencing of the nucleic acid molecule further comprises performing a sequencing-by-avidity, sequencing-by-nucleotide binding, or sequencing-by-nucleotide incorporation reaction on at least one of the first surface and axially-displaced second surface and detecting a bound or incorporated nucleotide base. In some embodiments, the method further comprises determining a genotype of a sample, wherein determining the genotype of the sample comprises preparing said nucleic acid molecule for sequencing, and then sequencing said nucleic acid molecule.

Disclosed herein are systems for sequencing a nucleic acid molecule comprising: a) an optical system comprising an objective lens and at least one image sensor, wherein said optical system has a numerical aperture (NA) of less than 0.6 and a field-of-view (FOV) of greater than 1.0 mm$^2$, and is configured to acquire images of a first surface and an axially-displaced second surface; and b) a processor programmed to: i) process images of the first surface and the axially-displaced second surface to correct for optical aberration such that the images of the first surface and the axially-displaced second surface have substantially the same optical resolution; and ii) detect a fluorescently-labeled composition comprising the nucleic acid molecule, or a complement thereof, disposed on the first surface or the axially-displaced second surface to determine an identity of a nucleotide in the nucleic acid molecule.

In some embodiments, the images of the first surface and the axially-displaced second surface are acquired without moving an optical compensator into an optical path between said objective lens and said at least one image sensor. In some embodiments, the images of the first surface and the axially-displaced second surface are acquired by just refocusing the optical system.

In some embodiments, the imaging system has a numerical aperture of greater than 0.3. In some embodiments, the first surface and axially-displaced second surface comprise two surfaces of a flow cell. In some embodiments, said two surfaces of the flow cell are coated with a hydrophilic coating layer, and wherein said hydrophilic coating layer further comprises labeled nucleic acid colonies disposed thereon at a surface density of >10,000 nucleic acid colonies/mm$^2$. In some embodiments, said optical system comprises 1, 2, 3, or 4 imaging channels configured to detect nucleic acid colonies disposed on at least one of the first surface or axially-displaced second surface that have been labeled with 1, 2, 3, or 4 distinct detectable labels. In some embodiments, the at least one image sensor comprises pixels having a pixel dimension chosen such that a spatial sampling frequency for the optical system is at least twice an optical resolution of the optical system. In some embodiments, the system comprises at least one tube lens positioned between the objective lens and the at least one image sensor, and wherein the at least one tube lens is configured to correct an imaging performance metric for imaging a first interior surface of a flow cell and a second interior surface of the flow cell. In some embodiments, the flow cell has a wall thickness of at least 700 µm and a gap between the first interior surface and the second interior surface of at least 50 µm. In some embodiments, the optical system comprises two or more tube lenses which are designed to provide optimal imaging performance at two or more fluorescence wavelengths.

Disclosed herein are fluorescence imaging systems comprising: a) at least one light source configured to provide excitation light within one or more specified wavelength ranges; b) an objective lens configured to collect fluorescence arising from within a specified field-of-view of a sample plane upon exposure of the sample plane to the excitation light, wherein a numerical aperture of the objective lens is at least 0.3, wherein a working distance of the objective lens is at least 700 µm, and wherein the field-of-view has an area of at least 2 mm$^2$; and c) at least one image sensor, wherein the fluorescence collected by the objective lens is imaged onto the image sensor, and wherein a pixel dimension for the image sensor is chosen such that a spatial sampling frequency for the fluorescence imaging system is at least twice an optical resolution of the fluorescence imaging system.

In some embodiments, the numerical aperture is at least 0.75. In some embodiments, the numerical aperture is at least 1.0. In some embodiments, the working distance is at least 850 µm. In some embodiments, the working distance is at least 1,000 µm. In some embodiments, the field-of-view has an area of at least 2.5 mm$^2$. In some embodiments, the field-of-view has an area of at least 3 mm$^2$. In some embodiments, the spatial sampling frequency is at least 2.5 times the optical resolution of the fluorescence imaging system. In some embodiments, the spatial sampling frequency is at least 3 times the optical resolution of the fluorescence imaging system. In some embodiments, the system further comprises an X-Y-Z translation stage such that the system is configured to acquire a series of two or more fluorescence images in an automated fashion, wherein each image of the series is acquired for a different field-of-view. In some embodiments, a position of the sample plane is simultaneously adjusted in an X direction, a Y direction, and a Z direction to match the position of an objective lens focal plane in between acquiring images for different fields-of-view. In some embodiments, the time required for the simultaneous adjustments in the X direction, Y direction, and Z direction is less than 0.4 seconds. In some embodiments, the system further comprises an autofocus mechanism configured to adjust the focal plane position prior to acquiring an image of a different field-of-view if an error signal indicates that a difference in the position of the focal plane and the sample plane in the Z direction is greater than a specified error threshold. In some embodiments, the specified error threshold is 100 nm. In some embodiments, the specified error threshold is 50 nm. In some embodiments, the system comprises three or more image sensors, and wherein the system is configured to image fluorescence in each of three or more wavelength ranges onto a different image sensor. In some embodiments, a difference in the position of a focal plane for each of the three or more image sensors and the sample plane is less than 100 nm. In some embodiments, a difference in the position of a focal plane for each of the three or more image sensors and the sample plane is less than 50 nm. In some embodiments, the total time required to reposition the sample plane, adjust focus, and acquire an image is less than 0.4 seconds per field-of-view. In some embodiments, the total time required to reposition the sample plane, adjust focus, and acquire an image is less than 0.3 seconds per field-of-view.

Also discloser herein are fluorescence imaging systems for dual-side imaging of a flow cell comprising: a) an objective lens configured to collect fluorescence arising from within a specified field-of-view of a sample plane within the flow cell; b) at least one tube lens positioned between the objective lens and at least one image sensor, wherein the at least one tube lens is configured to correct an imaging performance metric for a combination of the objective lens, the at least one tube lens, and the at least one image sensor when imaging an interior surface of the flow cell, and wherein the flow cell has a wall thickness of at least 700 µm and a gap between an upper interior surface and a lower interior surface of at least 50 µm; wherein the imaging performance metric is substantially the same for imaging the upper interior surface or the lower interior surface of the flow cell without moving an optical compensator into or out of an optical path between the flow cell and the at least one image sensor, without moving one or more optical elements of the tube lens along the optical path, and without moving one or more optical elements of the tube lens into or out of the optical path.

In some embodiments, the objective lens is a commercially-available microscope objective. In some embodiments, the commercially-available microscope objective has a numerical aperture of at least 0.3. In some embodiments, the objective lens has a working distance of at least 700 µm. In some embodiments, the objective lens is corrected to compensate for a cover slip thickness (or flow cell wall thickness) of 0.17 mm. In some embodiments, the fluorescence imaging system further comprising an electro-optical phase plate positioned adjacent to the objective lens and between the objective lens and the tube lens, wherein the electro-optical phase plate provides correction for optical aberrations caused by a fluid filling the gap between the upper interior surface and the lower interior surface of the flow cell. In some embodiments, the at least one tube lens is a compound lens comprising three or more optical components. In some embodiments, the at least one tube lens is a compound lens comprising four optical components. In some embodiments, the four optical components comprise, in order, a first asymmetric convex-convex lens, a second convex-plano lens, a third asymmetric concave-concave lens, and a fourth asymmetric convex-concave lens. In some embodiments, the at least one tube lens is configured to correct an imaging performance metric for a combination of the objective lens, the at least one tube lens, and the at least one image sensor when imaging an interior surface of a flow cell having a wall thickness of at least 1 mm. In some embodiments, the at least one tube lens is configured to correct an imaging performance metric for a combination of the objective lens, the at least one tube lens, and the at least one image sensor when imaging an interior surface of a flow cell having a gap of at least 100 µm. In some embodiments, the at least one tube lens is configured to correct an imaging performance metric for a combination of the objective lens, the at least one tube lens, and the at least one image sensor when imaging an interior surface of a flow cell having a gap of at least 200 µm. In some embodiments, the system comprises a single objective lens, two tube lenses, and two image sensors, and each of the two tube lenses is designed to provide optimal imaging performance at a different fluorescence wavelength. In some embodiments, the system comprises a single objective lens, three tube lenses, and three image sensors, and each of the three tube lenses is designed to provide optimal imaging performance at a different fluorescence wavelength. In some embodiments, the system comprises a single objective lens, four tube lenses, and four image sensors, and each of the four tube lenses is designed to provide optimal imaging performance at a different fluorescence wavelength. In some embodiments, the design of the objective lens or the at least one tube lens is configured to optimize the modulation transfer function in the mid to high spatial frequency range. In some embodiments, the imaging performance metric comprises a measurement of modulation transfer function (MTF) at one or more specified spatial frequencies, defocus, spherical aberration, chromatic aberration, coma, astigmatism, field curvature, image distortion, contrast-to-noise ratio (CNR), or any combination thereof. In some embodiments, the difference in the imaging performance metric for imaging the upper interior surface and the lower interior surface of the flow cell is less than 10%. In some embodiments, the difference in imaging performance metric for imaging the upper interior surface and the lower interior surface of the flow cell is less than 5%. In some embodiments, the use of the at least one tube lens provides for an at least equivalent or better improvement in the imaging performance metric for dual-side imaging compared to that for a conventional system comprising an objective lens, a motion-actuated compensator, and an image sensor. In some embodiments, the use of the at least one tube lens provides for an at least 10% improvement in the imaging performance metric for dual-side imaging compared to that for a conventional system comprising an objective lens, a motion-actuated compensator, and an image sensor.

Disclosed herein are illumination systems for use in imaging-based solid-phase genotyping and sequencing applications, the illumination system comprising: a) a light source; and b) a liquid light-guide configured to collect light emitted by the light source and deliver it to a specified field-of-illumination on a support surface comprising tethered biological macromolecules.

In some embodiments, the illumination system further comprises a condenser lens. In some embodiments, the specified field-of-illumination has an area of at least 2 mm$^2$. In some embodiments, the light delivered to the specified field-of-illumination is of uniform intensity across a specified field-of-view for an imaging system used to acquire images of the support surface. In some embodiments, the specified field-of-view has an area of at least 2 mm². In some embodiments, the light delivered to the specified field-of-illumination is of uniform intensity across the specified field-of-view when a coefficient of variation (CV) for light intensity is less than 10%. In some embodiments, the light delivered to the specified field-of-illumination is of uniform intensity across the specified field-of-view when a coefficient of variation (CV) for light intensity is less than 5%. In some embodiments, the light delivered to the specified field-of-illumination has a speckle contrast value of less than 0.1. In some embodiments, the light delivered to the specified field-of-illumination has a speckle contrast value of less than 0.05.

In another aspect, the present disclosure provides a system. The system may comprise a curved substrate. The curved substrate may comprise at least one binding moiety configured to bind to an analyte. The system may comprise an optical system comprising a light source. The light source may be configured to direct light from the light source to the curved substrate. The light may be configured to probe a presence or absence of the analyte bound to the curved surface.

The analyte may comprise an analyte as described elsewhere herein. For example, the analyte may comprise a nucleic acid. In another example, the analyte can comprise a polypeptide. The analyte may comprise a plurality of analytes. For example, the analyte can comprise a plurality of nucleic acids. The binding moiety may be selected based on the analyte. For example, the binding moiety can be selected to have binding affinity for the predetermined analyte. For example, an at least partially complementary nucleic acid can be used as a binding moiety for a nucleic acid analyte.

The curved substrate may be at least a portion of a flow cell. The curved substrate may be a component of a flow cell. For example, the curved substrate can be a portion of a curved wall of the flow cell. In another example, the curved substrate can be disposed within a flow cell. For example, the curved substrate can be disposed on a removable chip placed in the flow cell. The system may comprise a flow cell, and the flow cell may comprise the curved substrate. The curved substrate may comprise a capillary of a flow cell. For example, the curved substrate can be an interior wall of the capillary. The curved substrate may be disposed on a side of the capillary closest to the optical system. For example, for an optical system disposed above the capillary, the curved substrate can be on a top side of the capillary. The curved substrate may be disposed on an opposite side of the capillary from the optical system. For example, for an optical system disposed above the capillary, the curved substrate can be disposed on the bottom of the capillary.

In some cases, the curved substrate can comprise a glass. The glass may be an oxide (e.g., a silicon oxide) with at least partial transparency to the wavelength of the light. The curved substrate may comprise a polymer. Examples of polymers include, but are not limited to, alkyl polymers (e.g., polyethylene, polypropylene, etc.), fluoropolymers (e.g., Teflon-AF (Dupont), Cytop® (Asahi Glass, Japan)), aromatic polymers (e.g., polyxylenes (Parylene, Kisco, Calif), polystyrene, polymethmethylacrytate), another polymer disclosed elsewhere herein, or the like, or any combination thereof. In some cases, the curved substrate comprises a glass and a polymer. For example, a glass pane can be inset into a polymer flow cell. In another example, the curved substrate can comprise a polymer coated glass.

The light source may be a light source as described elsewhere herein. The light source may comprise a laser (e.g., a diode laser, a gas laser, etc.). The light source may comprise a light emitting diode (LED). The light source may comprise an incandescent light source (e.g., a halogen lamp, a filament lamp, etc.). The light source may be configured to provide a light such as an excitation light described elsewhere herein. For example, the light source can be configured to provide light with a wavelength of about 500 nanometers (nm) to about 540 nm, about 620 nm to about 650 nm, about 460 nm to about 500 nm, or any combination thereof. The light source may be a broadband light source (e.g., a light source configured to produce light with a plurality of wavelengths). The light source may be a narrow band light source (e.g., a light source configured to provide a single or a few narrow wavelength bands).

In some cases, the system can comprise a second curved substrate. For example, the system can comprise a plurality of curved substrates in optical communication with at least one light source. The second curved substrate may not be attached to the curved substrate. For example, the second curved substrate can be a curved portion of a different flow cell from the flow cell of the first substrate. The second curved substrate may be a part of a same element of the system. For example, the second curved substrate and the curved substrate can be different parts of a substantially cylindrical component of a flow cell (e.g., a capillary). For example, the curved substrate and the second curved substrate can be opposite sides of a substantially cylindrical flow cell. In this example, the curved substrate and the second curved substrate can be shown in the dotted ovals of FIGS. 54A-54B. The second curved substrate may comprise at least one second binding moiety configured to bind to a second analyte. The second binding moiety may be of a same type as the binding moiety. For example, nucleic acids can be used as both the binding moiety and the second binding moiety. The second binding moiety may be of a different type from the binding moiety. For example, the binding moiety can be a nucleic acid while the second binding moiety can be an antigen.

In some cases, the system is configured to probe the curved substrate in an epifluorescent configuration. The epifluorescent configuration may comprise probing light on a same side of a substrate as the light is introduced on. For example, the system can be configured to use a same objective to collect the light after interaction with the substrate as to deliver the light to the substrate. In some cases, the system is configured to probe the curved substrate in a transmissive configuration. The transmissive configuration may comprise probing light on an opposite side of a substrate as the light is introduced on. For example, a transmissive configuration can probe the transmission and/or absorption of a sample by detecting the light transmitted through the sample. FIG. 54A shows an example of a transmissive configuration, where an imaging sensor is disposed opposite from a light source. The light source and the imaging sensor may be disposed directly opposite from one another. The light source and the imaging sensor can be disposed at an angle from one another.

To address the curved substrate 5301 and the second curved substrate 5302, the system may comprise a focal shifting assembly configured to move a focal field between the curved substrate and the second curved substrate. An example of this shifting can be seen in FIGS. 53A-53B, where an imaging volume 4915 (e.g., a focal field) can be translated between curved substrates through use of a focal shifting assembly. In some cases, the focal field can be shifted horizontally (e.g., in a plane perpendicular to the optical axis).

The focal shifting assembly may comprise at least one movable lens. For example, a lens can be movable with respect to the reset of the system to adjust a focal field of the system. In this example, the movement of the lens can redirect the light moving through the lens to translate the focal field. The lens may be movable along the optical (e.g., z) axis. The lens may be movable out of the optical axis (e.g., in an xy plane). The lens may be movable in three dimensions. The lens may be disposed within a lens barrel. For example, the lens can be placed in a lens barrel such as that of FIG. 51.

In some cases, the focal shifting assembly can comprise at least one movable prism. The movable prism may be configured to shift a light beam traveling through the movable prism by refraction. For example, a movable prism can refract an incident light beam, and by moving the prism with respect to other optical elements (e.g., prisms, lenses, gratings), the overall path of the light beam can be moved, thereby shifting a focal field. In some cases, the focal shifting assembly can comprise a plurality of prisms. At least one prism of the plurality of prisms can be movable. Each prism of the plurality of prisms may be movable. For example, two movable prisms can be used to achieve a fine control over the movement of the light through the prisms, which can result in fine control over the movement of the focal field.

The optical system may be movable with respect to the curved substrate. For example, the optical system can be translated with respect to the curved substrate. The optical system may be translatable in three dimensions with respect to the curved substrate. For example, the optical system can be scanned across the curved substrate. The optical system may be rotatable around the curved substrate. The optical system may be rotatable with a same curvature as the curved substrate. For example, the optical system may be rotatable such that the curved substrate is kept at a same distance throughout the rotation. An example of a rotatable optical system can be seen in FIGS. 52A-52B.

The optical system may be configured to image a plurality of binding moieties. The optical system may be configured to image an area of the curved substrate comprising a plurality of binding moieties. For example, a plurality of binding moieties can be arranged on the substrate such that they are present in a field of view of the optical system. The optical system may be configured to image at least about 5, 10, 15, 20, 25, 30, 35, 40, 45, 50, 55, 60, 65, 70, 75, 80, 85, 90, 95, 100, 150, 200, 250, 500, 1,000, or more binding moieties at a same or substantially same time. The optical system may be configured to image at most about 1,000, 500, 250, 200, 150, 100, 95, 90, 85, 80, 75, 70, 65, 60, 55, 50, 45, 40, 35, 30, 25, 20, 15, 10, 5, or fewer binding moieties at a same or substantially same time. The plurality of binding moieties may comprise binding moieties of a same type. For example, each binding moiety of the plurality of binding moieties may be a nucleic acid binding moiety. The plurality of binding moieties may comprise a plurality of different types of binding moieties. For example, the plurality of binding moieties can comprise nucleic acids and proteins.

The curved substrate may have a deviation from flatness. The deviation from flatness may be a measure of the extent of curvature of the curved substrate. For example, a curved substrate with a deviation from flatness of 1 millimeter can have a deviation of 1 millimeter from a flat plane of the substrate. The curved substrate can have a deviation from flatness of at least about 1, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1,000, 1,500, 2,000, 2,500, 5,000, 10,000, or more micrometers. The curved substrate can have a deviation from flatness of at most about 10,000, 5,000, 2,500, 2,000, 1,500, 1,000, 950, 900, 850, 800, 750, 700, 650, 600, 550, 500, 450, 400, 350, 300, 250, 200, 150, 100, 95, 90, 85, 80, 75, 70, 65, 60, 55, 50, 45, 40, 35, 30, 25, 20, 15, 10, 5, 1, or fewer micrometers. The curved substrate may have a deviation from flatness as defined by any two of the proceeding values. For example, the curved substrate can have a deviation from flatness of about 100 to about 500 micrometers. The curved substrate may have a deviation from flatness greater than a focal depth of the optical system. For example, for an optical system with a focal depth of 10 micrometers, the curved substrate may have a deviation from flatness of 500 micrometers. Having a curvature larger than the focal depth of the optical system may permit selective imaging of portions of the curved substrate. For example, light originating outside of the focal depth can be discarded by the optical system. Thus, a plurality of analytes can be imaged from different regions of the curved substrate without moving the substrate or the optical system. Further, by moving the optical system with respect to the curved substrate, a larger number of analytes can be analyzed.

The system may comprise a plurality of sub-optical systems. The plurality of sub-optical systems may or may not be parallel to one another, adjacent to one another, or a combination thereof. The plurality of sub-optical systems may be configured to image at least partially different regions of the curved substrate. For example, the plurality of sub-optical system can be disposed radially around the curved substrate (e.g., as shown in FIG. 52). The plurality of sub-optical systems can be configured with a focal shifting assembly as described elsewhere herein. The use of the sub-optical systems with the focal shifting assembly can enable detection over an entire cylindrical curved substrate without encircling the cylindrical substrate in sub-optical assemblies. For example, sub-optical assemblies can be disposed on one half of the cylindrical curved substrate, and the other side of the cylindrical curved substrate can be addressable using a focal shifting assembly within the sub-optical assembly. Each sub-optical system of the plurality of sub optical systems can be individually disposed perpendicular to a plurality of tangents of the curved substrate. For example, the three sub-optical assemblies of FIG. 52 can be disposed perpendicular to three different tangents of the curved substrate.

The system may comprise a stage. The curved substrate may be disposed on the stage. For example, the curved substrate can be attached to the stage. The stage may be configured to support and/or move the curved substrate within the system. The stage may comprise one or more of a tilt stage (e.g., a stage configured to tilt the curved substrate in one, two, or three dimensions), a rotation stage (e.g., a stage configured to rotate the curved substrate in one, two, or three dimensions), a translation stage (e.g., a stage configured to translate the curved substrate in one, two, or three dimensions), or the like.

The curved substrate may comprise a hydrophilic polymer coupled thereto. The hydrophilic polymer may be as described elsewhere herein. The hydrophilic polymer may reduce a surface tension of a sample in contact with the curved substrate. For example, coupling the hydrophilic polymer to the curved substrate may permit analytes to move closer to the curved substrate than in an absence of the hydrophilic polymer. The at least one binding moiety may be coupled to the hydrophilic polymer. For example, the at least one binding moiety may be bound to the hydrophilic polymer. In this example, a reactive moiety in the hydrophilic polymer can be reacted with a reactive moiety in the binding moiety.

The system can have a numerical aperture as described elsewhere herein (e.g., the numerical aperture of an objective lens and/or an optical imaging module). The system may comprise an imaging sensor as described elsewhere herein. For example, the imaging sensor can be configured to collect the light subsequent to the directing of the light to the curved substrate. In some cases, the system comprises a heater configured to heat the substrate. The heater may be a heater as described elsewhere herein. For example, the heater can be an integrated heater. In another example, the heater can be an infrared heater.

In another embodiment, the present disclosure provides a system. The system may comprise a curved substrate. The system may comprise an optical system comprising a light source. The light source may be configured to direct light from the light source to the curved substrate.

In another embodiment, the present disclosure provides a system. The system may comprise a substrate. The system may comprise an optical system. The optical system may be configured to image an area of the substrate of at least about 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or more square millimeters ($mm^2$). The optical system may be configured to image an area of the substrate of at most about 50, 45, 40, 35, 30, 25, 20, 15, 10, 9.5, 9, 8.5, 8, 7.5, 7, 6.5, 6, 5.5, 5, 4.5, 4, 3.5, 3, 2.5, 2, 1.5, 1, 0.5, or fewer $mm^2$. The optical system may be configured to image an area of the substrate in a range as defined by any two of the proceeding values. For example, the optical system can be configured to image an area of the substrate of about 4.5 to about 5.5 $mm^2$. The substrate may be as described elsewhere herein. The optical system may be as described elsewhere herein.

The optical system may be configured to simultaneously image the area. For example, the optical system can be configured such that the entire area of the substrate within a field of view of the optical system. In this example, the entire field of view can be imaged at a same time. The optical system may be configured to image the area substantially simultaneously. For example, the optical system can be configured to image a first region and a second region of the area at a substantially same time.

The optical system may comprise a plurality of sub-optical systems. The plurality of sub-optical systems may be as described elsewhere herein. For example, the plurality of sub-optical systems can be parallel and adjacent to one another. The plurality of sub-optical systems may be configured to image the area of the substrate in parallel. For example, the plurality of sub-optical systems can be oriented adjacent to one another and configured to each image at least a portion of the area of the substrate. In this example, the plurality of sub-optical systems can each generate a sub-image, and the plurality of sub-images can be combined to form an image of the entire area.

The optical system may comprise a light source configured to provide a light beam and a lens. The lens may be configured to focus the light beam from the light source onto a focal region of the substrate comprising the area. The light source may be as described elsewhere herein. The lens may comprise a lens as described elsewhere herein. The lens may have an area of at least about 10, 50, 100, 200, 300, 400, 500, 600, 700, 800, 900, 1,000, 1,500, 2,000, 2,500, 3,000, 3,500, 4,000, 4,500, 5,000, 10,000, or more $mm^2$. The lens may have an area of at most about 10,000, 5,000, 4,500, 4,000, 3,500, 3,000, 2,500, 2,000, 1,500, 1,000, 900, 800, 700, 600, 500, 400, 300, 200, 100, 50, 10, or fewer $mm^2$. The lens may be a large-format lens (e.g., a lens configured for use over a large area). A homogeneity of the light beam over the focal regions can be at least about 5, 10, 15, 20, 25, 30, 35, 40, 45, 50, 55, 60, 65, 70, 75, 80, 85, 90, 95, 96, 97, 98, 99, 99.9, or more percent. A homogeneity of the light beam over the focal regions can be at most about 99.9, 98, 97, 96, 95, 90, 85, 80, 75, 70, 65, 60, 55, 50, 45, 40, 35, 30, 25, 20, 15, 10, 5, or less percent. A homogeneity of the light beam over the focal regions can be in a range as defined by any two of the proceeding values. The homogeneity may be a measure of the consistency of one or more properties of the light beam (e.g., power, wavelength, flux, etc.) over the focal region. The homogeneity may be in two dimensions or three dimensions. The homogeneity may be affected by the elements of the optical system. For example, inhomogeneity can be increased when defects are present in the lens.

The substrate may be as described elsewhere herein. For example, the substrate may be a curved substrate. For example, the substrate can be disposed as a cylinder. The substrate may be at least a portion of a capillary flow cell as described elsewhere herein. The substrate may have a deviation from flatness as described elsewhere herein.

The system may comprise a stage as described elsewhere herein, and the substrate may be disposed on the stage. For example, the stage can comprise a tilt stage, a rotation stage, a translation stage, or the like, or any combination thereof. The system may have a numerical aperture as described elsewhere herein. For example, the system can have a numerical aperture of at most about 0.6. The system may comprise a heater as described elsewhere herein. For example, the heater can be an integrated heater. The substrate may comprise a hydrophilic polymer coupled thereto as described elsewhere herein.

The optical system may be configured to image the area of the substrate with a resolution of at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 60, 70, 80, 90, 100, 150, 200, 250, 500, or more micrometers. The optical system may be configured to image the area of the substrate with a resolution of at most about 500, 250, 200, 150, 100, 90, 80, 70, 60, 50, 45, 40, 35, 30, 25, 20, 15, 10, 9.5, 9, 8.5, 8, 7.5, 7, 6.5, 6, 5.5, 5, 4.5, 4, 3.5, 3, 2.5, 2, 1.5, 1, 0.9, 0.8, 0.7, 0.6, 0.5, 0.4, 0.3, 0.2, 0.1, or less micrometers. The optical system may be configured to image the area of the substrate with a resolution in a range as defined by any two of the proceeding values.

The system may comprise an imaging sensor configured to collect the light subsequent to the directing to the substrate. The imaging sensor may be as described elsewhere herein. For example, the imaging sensor can be a camera. The imaging sensor may be configured to provide a color image of the light. For example, the imaging sensor can be configured to record information on the color of the light subsequent to the directing to the substrate. The imaging sensor may be configured to not record a color image of the light. For example, the imaging sensor can record the intensity of the light, but not the wavelength.

Computer Systems

Figure 63:
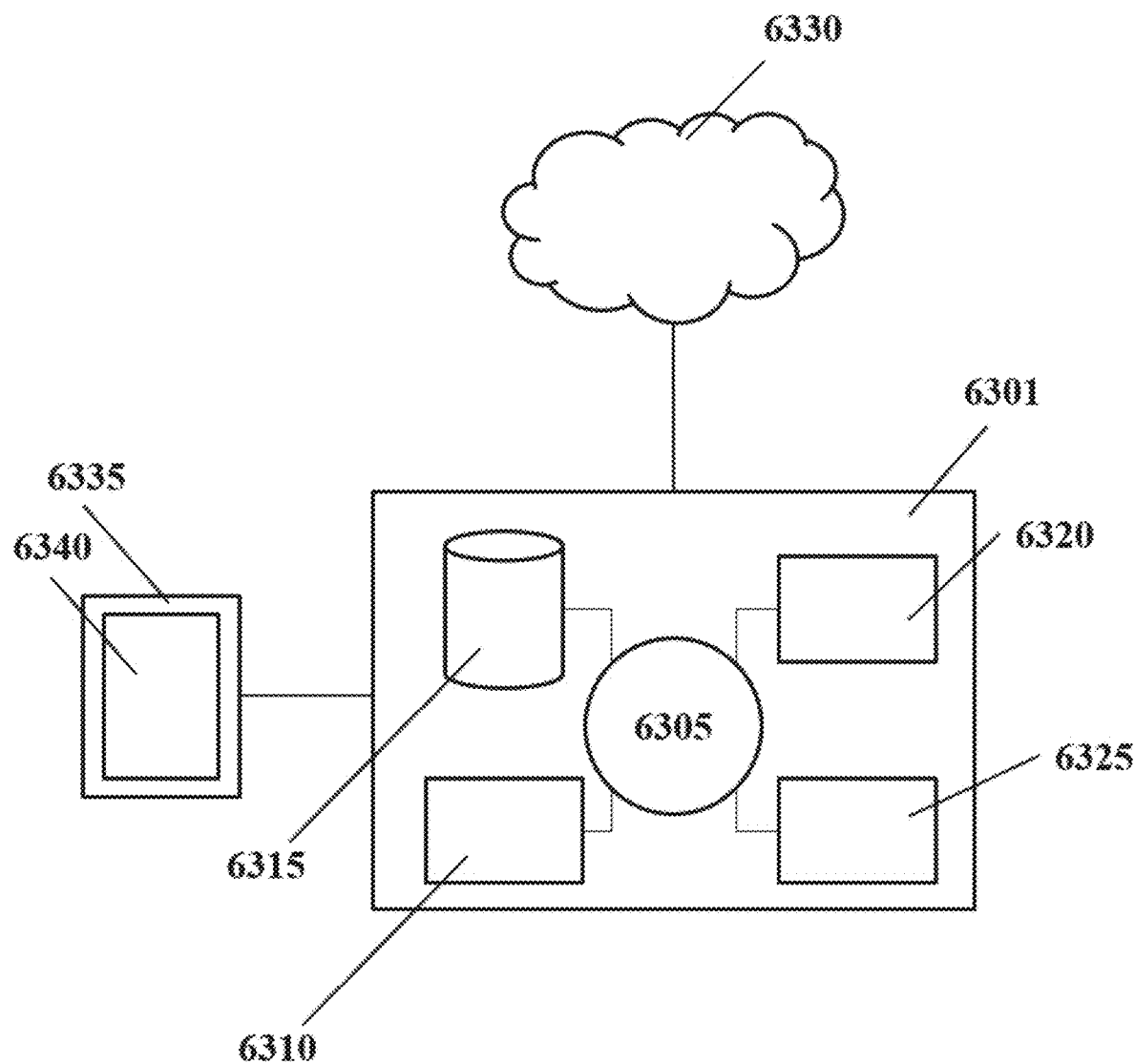
FIG. 63 shows a computer system that is programmed or otherwise configured to implement methods provided herein.

The present disclosure provides computer systems that are programmed to implement methods of the disclosure. FIG. 63 shows a computer system 6301 that is programmed or otherwise configured to image surfaces. The computer system 6301 can regulate various aspects of the present disclosure. The computer system 6301 can be an electronic device of a user or a computer system that is remotely located with respect to the electronic device. The electronic device can be a mobile electronic device.

The computer system 6301 includes a central processing unit (CPU, also "processor" and "computer processor" herein) 6305, which can be a single core or multi core processor, or a plurality of processors for parallel processing. The computer system 6301 also includes memory or memory location 6310 (e.g., random-access memory, read-only memory, flash memory), electronic storage unit 6315 (e.g., hard disk), communication interface 6320 (e.g., network adapter) for communicating with one or more other systems, and peripheral devices 6325, such as cache, other memory, data storage and/or electronic display adapters. The memory 6310, storage unit 6315, interface 6320 and peripheral devices 6325 are in communication with the CPU 6305 through a communication bus (solid lines), such as a motherboard. The storage unit 6315 can be a data storage unit (or data repository) for storing data. The computer system 6301 can be operatively coupled to a computer network ("network") 6330 with the aid of the communication interface 6320. The network 6330 can be the Internet, an internet and/or extranet, or an intranet and/or extranet that is in communication with the Internet. The network 6330 in some cases is a telecommunication and/or data network. The network 6330 can include one or more computer servers, which can enable distributed computing, such as cloud computing. The network 6330, in some cases with the aid of the computer system 6301, can implement a peer-to-peer network, which may enable devices coupled to the computer system 6301 to behave as a client or a server.

The CPU 6305 can execute a sequence of machine-readable instructions, which can be embodied in a program or software. The instructions may be stored in a memory location, such as the memory 6310. The instructions can be directed to the CPU 6305, which can subsequently program or otherwise configure the CPU 6305 to implement methods of the present disclosure. Examples of operations performed by the CPU 6305 can include fetch, decode, execute, and writeback. In some cases, instead of CPU 6305, a graphics processing unit (GPU), field-programmable gate array (FPGA), or an array comprising one or more CPUs, GPUs, FPGAs, or any combination thereof may be used.

The CPU 6305 can be part of a circuit, such as an integrated circuit. One or more other components of the system 6301 can be included in the circuit. In some cases, the circuit is an application specific integrated circuit (ASIC).

The storage unit 6315 can store files, such as drivers, libraries and saved programs. The storage unit 6315 can store user data, e.g., user preferences and user programs. The computer system 6301 in some cases can include one or more additional data storage units that are external to the computer system 6301, such as located on a remote server that is in communication with the computer system 6301 through an intranet or the Internet.

The computer system 6301 can communicate with one or more remote computer systems through the network 6330. For instance, the computer system 6301 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 6301 via the network 6330.

Methods as described herein can be implemented by way of machine (e.g., computer processor) executable code stored on an electronic storage location of the computer system 6301, such as, for example, on the memory 6310 or electronic storage unit 6315. The machine executable or machine readable code can be provided in the form of software. During use, the code can be executed by the processor 6305. In some cases, the code can be retrieved from the storage unit 6315 and stored on the memory 6310 for ready access by the processor 6305. In some situations, the electronic storage unit 6315 can be precluded, and machine-executable instructions are stored on memory 6310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 6301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 6301 can include or be in communication with an electronic display 6335 that comprises a user interface (UI) 6340 for providing, for example, a control interface for an optical system. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 6305. The algorithm can, for example, control an optical system.

NUMBERED EMBODIMENTS

1. A system for sequencing nucleic acid molecules comprising:
   a) a flow cell with an interior surface comprising a plurality of primed target nucleic acid sequences coupled thereto, wherein a primed target nucleic acid sequence of the plurality of primed target nucleic acid sequences has a polymerase bound thereto;
   b) a fluid flow controller configured to control sequential and iterative delivery of a reagent to the interior surface of the flow cell;
   c) an imaging module comprising:
      i) a structured illumination system; and
      ii) an image acquisition system configured to acquire images of the interior surface of the flow cell; and
   d) a processor, wherein the processor is programed to instruct the system to iteratively perform a method comprising:
      i) contacting the plurality of primed target nucleic acid sequences coupled to the interior surface of the flow cell with a nucleotide composition to form a transient binding complex between the plurality of primed target nucleic acid sequences and a plurality of nucleotide moieties when a nucleotide moiety of the nucleotide composition is complementary to a nucleotide of the primed target nucleic acid sequence; and
      ii) imaging the interior surface of the flow cell to detect the transient binding complex and thereby determine an identity of the nucleotide of the primed target nucleic acid sequence.

2. The system of embodiment 1, wherein the structured illumination system comprises an optical system designed to project a plurality of periodic patterns of light on the interior surface of the flow cell, and wherein a relative orientation or phase shift of the plurality of the periodic patterns of light is adjustable.

3. The system of embodiment 1, wherein the structured illumination system comprises a first optical arm comprising a first light emitter to emit light and a first beam splitter to split the light emitted by the first light emitter into a first plurality of fringes and to project the first plurality of fringes on the interior surface of the flow cell.

4. The system of embodiment 3, wherein the structured illumination system further comprises a second optical arm comprising a second light emitter to emit light and a second beam splitter to split the light emitted by the second light emitter into a second plurality of fringes and to project the second plurality of fringes on the interior surface of the flow cell.

5. The system of embodiment 4, wherein the structured illumination system further comprises an optical element to combine an optical path of the first arm and the second arm.

6. The system of embodiment 4 or embodiment 5, wherein the first beam splitter comprises a first transmissive diffraction grating and the second beam splitter comprises a second transmissive diffraction grating.

7. The system of embodiment 4 or embodiment 5, wherein the first and second light emitters emit unpolarized light, and wherein the first and second transmissive diffraction gratings are to diffract unpolarized light emitted by a respective one of the first and second light emitters.

8. The system of embodiment 6 or embodiment 7, wherein the optical element to combine an optical path of the first plurality of fringes and the second plurality of fringes comprises a mirror with holes, with the mirror arranged to reflect light diffracted by the first transmissive diffraction grating and with the holes arranged to pass through at least first orders of light diffracted by the second transmissive diffraction grating.

9. The system of embodiment 8, further comprising: one or more optical elements to phase shift the first plurality of fringes and the second plurality of fringes.

10. The system of embodiment 9, wherein the one or more optical elements to phase shift the first plurality of fringes and the second plurality of fringes comprise a first rotating optical window to phase shift the first plurality of fringes and a second rotating optical window to phase shift the second plurality of optical fringes.

11. The system of embodiment 9 or embodiment 10, wherein the one or more optical elements to phase shift the first plurality of fringes and the second plurality of fringes comprise a first linear motion stage to translate the first diffraction grating and a second linear motion stage to translate the second diffraction grating.

12. The system of any one of embodiments 9 to 11, wherein the one or more optical elements to phase shift the first plurality of fringes and the second plurality of fringes comprise a single rotating optical window, wherein the single rotating optical window is positioned after the mirror with holes in an optical path to the sample.

13. The system of embodiment 12, wherein an axis of rotation of the single rotating optical window is offset by about 45 degrees from an optical axis of each of the gratings.

14. The system of any one of embodiments 9 to 13, wherein the first plurality of fringes is angularly offset from the second plurality of fringes on the sample plane by about 90 degrees.

15. The system of embodiment 14, wherein the sample comprises a plurality of features regularly patterned in a rectangular array or hexagonal array.

16. The system of any one of embodiments 9 to 15, further comprising: an objective lens to project each of the first plurality of fringes and the second plurality of fringes on the sample.

17. The system of any one of embodiments 9 to 16, further comprising: one or more optical beam blockers for blocking zero orders of light emitted by each of the first and second diffraction gratings.

18. The system of embodiment 17, wherein the one or more optical beam blockers comprise a Bragg grating.

19. The system of any one of embodiments 6 to 18, wherein the optical element to combine an optical path of the first arm and the second arm comprises a polarizing beam splitter, wherein the first diffraction grating diffracts vertically polarized light and wherein the second diffraction grating diffracts horizontally polarized light.

20. The system of any one of embodiments 4 to 19, wherein the first and second beam splitters each comprise a beam splitter cube or plate.

21. The system of any one of embodiments 3 to 20, wherein the first beam splitter comprises a first reflective diffraction grating and the second beam splitter comprises a second reflective diffraction grating.

22. The system of any one of embodiments 1 to 21, wherein the structured illumination system comprises a multiple beam splitter slide comprising a plurality of beam splitters mounted on a linear translation stage such that the plurality of beam splitters has fixed orientations with respect to the system's optical axis.

23. The system of embodiment 22, wherein the plurality of beam splitters comprises a plurality of diffraction gratings.

24. The system of embodiment 23, wherein the plurality of diffraction gratings comprises two different diffraction gratings.

25. The system of any one of embodiments 1 to 24, wherein the structured illumination system comprises a fixed two-dimensional diffraction grating used in combination with a spatial filter wheel to project one-dimensional diffraction patterns on the interior surface of the flow cell.

26. The system of any one of embodiments 1 to 25, wherein the image acquisition system comprises a custom tube lens which, in combination with an objective lens, enables imaging of a first interior flow cell surface and a second interior flow cell surface with substantially the same image resolution.

27. The system of any one of embodiments 1 to 26, wherein the nucleotide composition comprises a conjugated polymer-nucleotide composition.

28. The system of embodiment 27, wherein the conjugated polymer-nucleotide composition comprises a plurality of nucleotide moieties conjugated to a polymer core.

29. The system of embodiment 28, wherein the plurality of nucleotide moieties comprises nucleotides, nucleotide analogs, or any combination thereof.

30. The system of embodiment 28 or embodiment 29, wherein the plurality of nucleotide moieties comprises a plurality of identical nucleotide moieties.

31. The system of any one of embodiments 1 to 30, wherein prior to forming the transient binding complex the nucleotide composition lacks a polymerase.

32. A method for sequencing nucleic acid molecules comprising:
   a) providing a plurality of primed target nucleic acid sequences tethered to a surface, wherein a primed target nucleic acid sequence of the plurality of primed target nucleic acid sequences has a polymerase bound thereto;
   b) contacting the plurality of primed target nucleic acid sequences with a nucleotide composition to form a transient binding complex between the plurality of primed target nucleic acid sequences and a plurality of nucleotide moieties when a nucleotide moiety of the nucleotide composition is complementary to a nucleotide of the primed target nucleic acid sequence; and
   c) detecting the transient binding complex to determine the identity of the nucleotide of the primed target nucleic acid sequence, wherein the detecting comprises:
      i) illuminating the surface with light provided by a structured illumination system under a first set of illumination conditions to project a first plurality of fringes oriented in a specific direction on the surface;
      ii) capturing a first plurality of phase images of the surface, wherein during capture of the first plurality of images, the positions of the first plurality of fringes are shifted on the surface;
      iii) illuminating the surface with light provided by the structured illumination system under a second set of illumination conditions to project a second plurality of fringes on the surface, wherein the second plurality of fringes are angularly offset from the first plurality of fringes on the surface; and
      iv) capturing a second plurality of phase images of the surface illuminated with the second plurality of fringes, wherein during capture of the second plurality of fringes, the positions of the second plurality of fringes are shifted on the surface.

33. The method of embodiment 32, wherein the structured illumination system comprises a first optical arm comprising a first light emitter to emit light and a first diffraction grating to diffract light emitted by the first light emitter to project the first plurality of fringes oriented in a specific direction on the surface.

34. The method of embodiment 33, wherein the structured illumination system comprises a second optical arm comprising a second light emitter to emit light and a second diffraction grating to diffract light emitted by the second light emitter to project the second plurality of fringes that are angularly offset from the first plurality of fringes on the surface.

35. The method of any one of embodiments 32 to 34, wherein the structured illumination system comprises a multiple beam splitter slide comprising a plurality of beam splitters mounted on a linear translation stage such that the plurality of beam splitters have fixed orientations with respect to the system's optical axis, and wherein the first set of illumination conditions corresponds to a first position of the linear translation stage and the second set of illumination conditions corresponds to a second position of the linear translation stage.

36. The method of embodiment 35, wherein the plurality of beam splitters comprises a plurality of diffraction gratings.

37. The method of embodiment 36, wherein the plurality of diffraction gratings comprises two diffraction gratings.

38. The method of any one of embodiments 32 to 37, wherein the structured illumination system comprises a fixed two-dimensional diffraction grating used in combination with a spatial filter wheel to project one-dimensional diffraction patterns on the surface, and wherein the first set of illumination conditions corresponds to a first position of the spatial filter wheel and the second set of illumination conditions corresponds to a second position of the spatial filter wheel.

39. The method of any one of embodiments 34 to 38, wherein the first diffraction grating and the second diffraction grating are transmissive diffraction gratings, wherein the structured illumination system comprises a mirror with holes to reflect light diffracted by the first diffraction grating and to pass through at least first orders of light diffracted by the second diffraction grating.

40. The method of any one of embodiments 32 to 39, further comprising: using at least the first plurality of captured phase images and the second plurality of captured phased images to computationally reconstruct one or more images having higher resolution than each of the first and second pluralities of captured phased images.

41. The method of embodiment 40, wherein the first plurality of fringes is angularly offset from the second plurality of fringes on the surface by about 90 degrees.

42. The method of any one of embodiments 32 to 41, wherein the surface comprises a plurality of features regularly patterned in a rectangular array or hexagonal array.

43. The method of any one of embodiments 32 to 42, wherein the first plurality of fringes and the second plurality of fringes are phase shifted by rotating a single optical window positioned in an optical path between the surface and each of the first and second diffraction gratings, wherein an axis of rotation of the single rotating optical window is offset from an optical axis of each of the diffraction gratings.

44. The method of any one of embodiments 34 to 43, wherein the first optical arm is turned off and the second optical arm of the structured illumination system is turned on after capturing the first plurality of phase images.

45. The method of any one of embodiments 34 to 44, wherein the first diffraction grating and the second diffraction grating are mechanically fixed during image capture.

46. The method of any one of embodiments 32 to 45, wherein the nucleotide composition comprises a conjugated polymer-nucleotide composition.

47. The method of embodiment 46, wherein the conjugated polymer-nucleotide composition comprises a plurality of nucleotide moieties conjugated to a polymer core.

48. The method of embodiment 47, wherein the plurality of nucleotide moieties comprises nucleotides, nucleotide analogs, or any combination thereof.

49. The method of embodiment 47 or embodiment 48, wherein the plurality of nucleotide moieties comprises a plurality of identical nucleotide moieties.

50. The method of any one of embodiments 32 to 49, wherein the method is used to determine the identity of an N+1 or terminal nucleotide of a primer strand of the primed target nucleic acid sequence.

51. The method of any one of embodiments 32 to 50, wherein prior to forming the transient binding complex the nucleotide composition lacks a polymerase.

52. A detection apparatus, comprising
a) a read-head assembly comprising a plurality of microfluorometers,
   wherein the plurality of microfluorometers are held in fixed positions relative to each other to form a multiplexed read-head,
   wherein at least one of a first subset of the plurality of microfluorometers is configured to acquire a wide-field image of a different area of a first sample plane, and
   wherein at least one of a second subset of the plurality of microfluorometers is configured to acquire a wide-field image of a different area of a second sample plane.

53. The detection apparatus of embodiment 52, further comprising a translation stage configured to move the read-head assembly in at least one direction parallel to the first and second sample planes.

54. The detection apparatus of embodiment 52 or embodiment 53, further comprising a sample stage configured to hold a flow cell comprising first and second interior surfaces such that the first interior surface is held at the first sample plane, and the second interior surface is held at the second sample plane.

55. The detection apparatus of any one of embodiments 52 to 54, wherein at least one microfluorimeter of the plurality of microfluorimeters is configured to acquire wide-field images having a field-of-view of at least 1 mm.

56. The detection apparatus of any one of embodiments 52 to 55, wherein at least one microfluorimeter of the plurality of microfluorimeters is configured to acquire wide-field images having a field-of-view of at least 1.5 mm.

57. The detection apparatus of any one of embodiments 52 to 56, wherein at least one of the microfluorometers further comprises a dedicated autofocus mechanism.

58. The detection apparatus of embodiment 57, wherein the autofocus mechanism for a first microfluorometer is configured to integrate data from an autofocus mechanism for a second microfluorometer, whereby the autofocus mechanisms for the first microfluorometer alters a focus of the first microfluorometer based on a focus position of the first microfluorometer and a focus position of the second microfluorometer.

59. The detection apparatus of any one of embodiments 52 to 58, wherein an individual microfluorometer further comprises an objective, abeam splitter and a detector, wherein the beam splitter is positioned to direct excitation radiation from an excitation radiation source to the objective and to direct emission radiation from the objective to the detector.

60. The detection apparatus of embodiment 59, wherein at least one individual microfluorometer further comprises an individual excitation radiation source.

61. The detection apparatus of embodiment 59 or embodiment 60, wherein the excitation radiation source directs the excitation radiation to the objectives of two or more individual microfluorometers of the plurality such that the two or more individual microfluorometers share the excitation radiation source.

62. The detection apparatus of any one of embodiments 59 to 61, wherein two or more individual microfluorometers of the plurality further comprise or share at least two excitation radiation sources.

63. The detection apparatus of any one of embodiments 59 to 62, wherein the objectives of the individual microfluorometers of the plurality have a numerical aperture between 0.2 and 0.5.

64. The detection apparatus of any one of embodiments 52 to 63, wherein the microfluorometers of the plurality are configured to acquire images at a resolution sufficient to distinguish features that are less than 50 microns apart.

65. The detection apparatus of any one of embodiments 52 to 64, wherein the microfluorometers of the plurality are configured to have a depth-of-field that is less than the separation distance between the first and second interior surfaces of the flow cell.

66. The detection apparatus of any one of embodiments 52 to 65, wherein the first subset of the plurality of microfluorometers is configured to acquire wide-field images at a first fluorescence emission wavelength and the second subset of the plurality of microfluorometers is configured to acquire wide field images at a second fluorescence emission wavelength.

67. A method for determining an identity of a nucleotide in a target nucleic acid sequence comprising:

a) providing a plurality of primed target nucleic acid sequences, wherein a primed target nucleic acid sequence of the plurality of primed target nucleic acid sequences has a polymerase bound thereto;
b) contacting the plurality of primed target nucleic acid sequences with a nucleotide composition to form a transient binding complex between the plurality of primed target nucleic acid sequences and a plurality of nucleotide moieties when a nucleotide moiety of the nucleotide composition is complementary to a nucleotide of the primed target nucleic acid sequence; and
c) detecting the transient binding complex to determine the identity of the nucleotide of the primed target nucleic acid sequence, wherein the detecting comprises:
translating a multiplexed read-head in at least one direction parallel to a surface on which the plurality of primed target nucleic acid sequences is tethered, wherein the multiplexed read-head comprises a plurality of microfluorometers held in fixed positions relative to each other, and
wherein at least one microfluorometer of the plurality of microfluorometers is configured to acquire a wide-field image of a different area of the surface than other microfluorometers of the plurality.

68. The method of embodiment 67, wherein the nucleotide composition comprises a conjugated polymer-nucleotide composition.

69. The method of embodiment 68, wherein the conjugated polymer-nucleotide composition comprises a plurality of nucleotide moieties conjugated to a polymer core.

70. The method of embodiment 69, wherein the plurality of nucleotide moieties comprises nucleotides, nucleotide analogs, or any combination thereof.

71. The method of embodiment 69 or embodiment 70, wherein the plurality of nucleotide moieties comprises a plurality of identical nucleotide moieties.

72. The method of any one of embodiments 67 to 71, wherein the method is used to determine the identity of an N+1 or terminal nucleotide of a primer strand of the primed target nucleic acid sequence.

73. The method of any one of embodiments 67 to 72, wherein prior to forming the transient binding complex the nucleotide composition lacks a polymerase.

74. The method of any one of embodiments 67 to 73, wherein the plurality of primed target nucleic acid sequences is tethered to a first interior surface and a second interior surface of a flow cell, and wherein a first subset of the plurality of microfluorometers is configured to acquire wide-field images of different areas of the first interior surface of the flow cell, and a second subset of the plurality of microfluorometers is configured to acquire wide-field images of different areas of the second interior surface of the flow cell.

75. A system for sequencing nucleic acid molecules comprising:
a) a flow cell having at least one interior surface comprising a plurality of primed target nucleic acid sequences coupled thereto, wherein a primed target nucleic acid sequence of the plurality of primed target nucleic acid sequences has a polymerase bound thereto;
b) a fluid flow controller configured to control sequential and iterative delivery of a reagent to the at least one interior surface of the flow cell;
c) an imaging module configured to image the at least one interior surface of the flow cell, wherein the imaging module comprises:
a multiplexed read-head assembly comprising a plurality of microfluorometers held in fixed positions relative to each other,
wherein at least one microfluorometer of the plurality of microfluorometers is configured to acquire a wide-field image of a different area of the at least one surface than other microfluorometers of the plurality; and
d) a processor, wherein the processor is programed to instruct the system to iteratively perform a method comprising:
i) contacting the plurality of primed target nucleic acid sequences coupled to the at least one interior surface of the flow cell with a nucleotide composition to form a transient binding complex between the plurality of primed target nucleic acid sequences and a plurality of nucleotide moieties when a nucleotide moiety of the nucleotide composition is complementary to a nucleotide of the primed target nucleic acid sequence; and
ii) imaging the at least one interior surface of the flow cell using the multiplexed read-head to detect the transient binding complex and thereby determine the identity of the nucleotide of the primed target nucleic acid sequence.

76. The system of embodiment 75, wherein the nucleotide composition comprises a conjugated polymer-nucleotide composition.

77. The system of embodiment 76, wherein the conjugated polymer-nucleotide composition comprises a plurality of nucleotide moieties conjugated to a polymer core.

78. The system of embodiment 77, wherein the plurality of nucleotide moieties comprises nucleotides, nucleotide analogs, or any combination thereof.

79. The system of embodiment 77 or embodiment 78, wherein the plurality of nucleotide moieties comprises a plurality of identical nucleotide moieties.

80. The system of any one of embodiments 75 to 79, wherein the method is used to determine the identity of an N+1 or terminal nucleotide of a primer strand of the primed target nucleic acid sequence.

81. The system of any one of embodiments 75 to 80, wherein prior to forming the transient binding complex the nucleotide composition lacks a polymerase.

82. The method of any one of embodiments 75 to 81, wherein the plurality of primed target nucleic acid sequences is tethered to a first interior surface and a second interior surface of the flow cell, and wherein a first subset of the plurality of microfluorometers is configured to acquire wide-field images of different areas of the first interior surface of the flow cell, and a second subset of the plurality of microfluorometers is configured to acquire wide-field images of different areas of the second interior surface of the flow cell.

83. The system of any one of embodiments 75 to 82, further comprising a translation stage configured to move the multiplexed read-head assembly in at least one direction parallel to the first and second sample planes.

84. The system of any one of embodiments 75 to 83, wherein at least one microfluorometer of the plurality of microfluorometers is configured to acquire wide-field images having a field-of-view of at least 1 mm.

85. The system of any one of embodiments 75 to 84, wherein at least one microfluorometer of the plurality of microfluorometers is configured to acquire wide-field images having a field-of-view of at least 1.5 mm.

86. The system of any one of embodiments 74 to 85, wherein at least one of the microfluorometers further comprises a dedicated autofocus mechanism.

87. The system of embodiment 86, wherein the autofocus mechanism for a first microfluorometer is configured to integrate data from an autofocus mechanism for a second microfluorometer, whereby the autofocus mechanisms for the first microfluorometer alters a focus of the first microfluorometer based on a focus position of the first microfluorometer and a focus position of the second microfluorometer.

88. The system of any one of embodiments 75 to 87, wherein an individual microfluorometer of the plurality further comprises an objective, a beam splitter and a detector, wherein the beam splitter is positioned to direct excitation radiation from an excitation radiation source to the objective and to direct emission radiation from the objective to the detector.

89. The system of embodiment 88, wherein at least one individual microfluorometer further comprises an individual excitation radiation source.

90. The system of embodiment 89, wherein the excitation radiation source directs the excitation radiation to the objectives of two or more individual microfluorometers of the plurality such that the two or more individual microfluorometers share the excitation radiation source.

91. The system of any one of embodiments 88 to 90, wherein two or more individual microfluorometers of the plurality further comprise or share at least two excitation radiation sources.

92. The system of any one of embodiments 88 to 91, wherein the objectives of the individual microfluorometers of the plurality have a numerical aperture between 0.2 and 0.5.

93. The system of any one of embodiments 75 to 92, wherein the microfluorometers of the plurality are configured to acquire images at a resolution sufficient to distinguish features that are less than 50 microns apart.

94. The system of any one of embodiments 82 to 93, wherein the microfluorometers of the plurality are configured to have a depth-of-field that is less than the separation distance between the first and second interior surfaces of the flow cell.

95. The system of any one of embodiments 82 to 94, wherein the first subset of the plurality of microfluorometers is configured to acquire wide-field images at a first fluorescence emission wavelength and the second subset of the plurality of microfluorometers is configured to acquire wide field images at a second fluorescence emission wavelength.

96. A method of sequencing a nucleic acid molecule, the method comprising:
 a) providing flow cell comprising a surface; wherein the surface comprises:
  i) a substrate;
  ii) at least one hydrophilic polymer coating layer;
  iii) a plurality of oligonucleotide molecules attached to at least one hydrophilic polymer coating layer; and
  iv) at least one discrete region of said surface that comprises a plurality of clonally-amplified, sample nucleic acid molecules immobilized to said plurality of attached oligonucleotide molecules, wherein said plurality of immobilized clonally amplified sample nucleic acid molecules are present at distance less than $\lambda/(2*NA)$, wherein $\lambda$ is the center wavelength of an excitation energy source and NA is the numerical aperture of an imaging system.
 b) applying a stochastic photo-switching chemistry to said plurality of clonally amplified sample nucleic acid molecules at the same time to cause said plurality of clonally amplified sample nucleic acid molecules to fluoresce in on and off events in up to four different colors by stochastic photo-switching; and
 c) detecting said on and off events in a color channel for each color in real-time as the on and off events are occurring for said plurality of clonally amplified sample nucleic acid molecules to determine an identify of a nucleotide of said clonally amplified sample nucleic acid molecule.

97. The method of embodiment 96, wherein concentrations of reagents for said stochastic photo switching are sufficient such that the probability that an on event for a given nucleotide for a given clonally amplified sample nucleic acid molecule of said plurality of clonally amplified sample nucleic acid molecules will occur at the same time as an on event for a given nucleotide of a clonally amplified sample nucleic acid molecule adjacent to said given clonally amplified sample nucleic acid molecule is less than about 0.5%.

98. The method of embodiment 96, further comprising, controlling a rate at which said on and off events occur to control a probability that an on event for a given nucleotide for a given clonally amplified sample nucleic acid molecule will occur at the same time as an on event for a nucleotide of a clonally amplified sample nucleic acid molecule adjacent to said given clonally amplified sample nucleic acid molecule.

99. The method of embodiment 98, wherein controlling said rate at which said on and off events occur comprises adjusting concentrations of nucleotides and enzymes in said stochastic photo-switching chemistry.

100. The method of embodiment 96, further comprising, determining whether an illumination intensity of a detection event in a color channel is greater than a predetermined threshold.

101. The method of embodiment 96, further comprising, determining whether a spot size of a detection event in a color channel is greater than a predetermined threshold.

102. The method of embodiment 96, wherein said at least one hydrophilic polymer coating layer comprises PEG.

103. The method of embodiment 96, wherein detecting comprises acquiring an image of said surface, wherein said image exhibits a contrast to noise ratio (CNR) of at least 40.

104. The method of embodiment 96, wherein detecting comprises acquiring an image of said surface, wherein said image exhibits a contrast to noise ratio (CNR) of at least 60.

105. The method of embodiment 96, wherein said substrate comprises glass.

106. The method of embodiment 96, wherein said substrate comprises plastic.

107. The method of embodiment 96, wherein said surface is positioned on the interior of a flow channel.

108. The method of embodiment 96, wherein said at least one hydrophilic polymer layer comprises a branched hydrophilic polymer having at least 8 branches.

109. The method of embodiment 96, wherein a background fluorescence intensity measured at a region of said surface that is laterally-displaced from said at least one discrete region is no more than 2× of the intensity measured at said at least one discrete region prior to said clonal amplification.

110. The method of embodiment 96, wherein said sample nucleic acid molecules comprise single-stranded multimeric nucleic acid molecules comprising repeats of a regularly occurring monomer unit.

111. The method of embodiment 110, wherein said single-stranded multimeric nucleic acid molecules are at least 10 kb in length.

112. The method of embodiment 110, further comprising double-stranded monomeric copies of the regularly occurring monomer unit.

113. The method of embodiment 96, wherein said surface comprises a first layer comprising a monolayer of polymer molecules tethered to a surface of said substrate; a second layer comprising polymer molecules tethered to said polymer molecules of said first layer; and a third layer comprising polymer molecules tethered to said polymer molecules of said second layer, wherein at least on layer comprises branched polymer molecules.

114. The method of embodiment 113, wherein said third layer further comprises oligonucleotides tethered to said polymer molecules of said third layer.

115. The method of embodiment 114, wherein said oligonucleotides tethered to said polymer molecules of said third layer are distributed at a plurality of depths throughout said third layer.

116. The method of embodiment 113, further comprising a fourth layer comprising branched polymer molecules tethered to said polymer molecules of said third layer, and a fifth layer comprising polymer molecules tethered to said branched polymer molecules of said fourth layer.

117. The method of embodiment 116, wherein said polymer molecules of said fifth layer further comprise oligonucleotides tethered to said polymer molecules of said fifth layer.

118. The method of embodiment 117, wherein said oligonucleotides tethered to said polymer molecules of said fifth layer are distributed at a plurality of depths throughout said fifth layer.

119. The method of embodiment 96, wherein said at least one hydrophilic polymer coating layer, comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxyethyl methacrylate) (PHEMA), poly(oligo(ethylene glycol) methyl ether methacrylate) (POEGMA), polyglutamic acid (PGA), poly-lysine, poly-glucoside, streptavidin, and dextran.

120. An optical system, comprising:
a plurality of imaging sensors;
a plurality of light sources;
a flow cell disposed in an optical path between said plurality of imaging sensors and said plurality of light sources; and
a multi-band notch filter disposed in said optical path between said flow cell and said plurality of imaging sensors.

121. The optical system of embodiment 120, wherein said flow cell comprises one or more interior surfaces having a hydrophilic polymer layer coupled thereto.

122. The optical system of embodiment 121, wherein said flow cell further comprises a plurality of biological polymers coupled to said hydrophilic polymer layer.

123. The optical system of embodiment 121, wherein said hydrophilic polymer layer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxyethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof.

124. The optical system of embodiment 120, further comprising a pixel shifter.

125. The optical system of embodiment 120, wherein the multi-band notch filter comprises a tri-band notch filter.

126. The optical system of embodiment 120, further comprising an imaging optic disposed in said optical path between said multi-band notch filter and said flow cell.

127. The optical system of embodiment 120, wherein the imaging optic has a reduction comprising 1×.

128. The optical system of embodiment 120, wherein the optical system has a reduction of 1×.

129. The optical system of embodiment 120, wherein the optical system has a field-of-view (FOV) comprising greater than 1 mm$^2$.

130. The optical system of embodiment 120, wherein said optical system has a numerical aperture (NA) comprising less than 0.6.

131. The optical system of embodiment 130, wherein said NA comprises about 0.25.

132. The optical system of embodiment 129, wherein said plurality of imaging sensors is configured to capture said FOV.

133. The optical system of embodiment 120, wherein said plurality of light sources comprises:
a first light source configured to emit light in a first wavelength range;
a second light source configured to emit light in a second wavelength range; and
a third light source configured to emit light in a third wavelength range, wherein said first wavelength range, said second wavelength range, and said third wavelength range are different wavelength ranges.

134. The optical system of embodiment 133, wherein a first fluorophore excited by said first wavelength range of said first light source is different than a second fluorophore excited by said second wavelength range of said second light source.

135. The optical system of embodiment 120, wherein:
a first fluorophore excited by said first wavelength range of said first light source is different than a second fluorophore excited by said second wavelength range of said second light source; and
said second fluorophore excited by said second wavelength range of said second light source is different than a third fluorophore excited by said third wavelength range of said third light source.

136. The optical system of embodiment 135, wherein said third fluorophore excited by said third wavelength range of said third light source is different than said first fluorophore excited by said first wavelength range of said first light source.

137. The optical system of embodiment 133, wherein said first wavelength range of said first light source comprises between about 500 to about 540 nanometers (nm).

138. The optical system of embodiment 133, wherein said second wavelength range of said second light source comprises between about 620 to about 640 nm.

139. The optical system of embodiment 133, wherein said third wavelength range of the third light source comprises between about 460 to about 500 nm.

140. The optical system of embodiment 120, wherein said flow cell comprises an interior surface comprising a plurality of discrete regions, wherein (i) a first discrete region of said plurality of discrete regions comprises a first set of nucleic acid molecules coupled to said interior surface at said first discrete region, and (ii) a second discrete region of said plurality of discrete regions comprises a second set of said nucleic acid molecules coupled to said interior surface at said second discrete region, wherein said first set of said nucleic acid molecules is different than said second set of said nucleic acid molecules.

141. The optical system of embodiment 140, wherein said first set of said nucleic acid molecules comprises a first fluorophore coupled thereto, and said second set of said nucleic acid molecules comprises a second fluorophore coupled thereto, wherein said first fluorophore is different than said second fluorophore.

142. The optical system of embodiment 141, wherein a third discrete region of said plurality of discrete regions comprises a third set of said nucleic acid molecules coupled to said interior surface at said third discrete region, and wherein said third set of said nucleic acid molecules is different than said first set and said second set of said nucleic acid molecules.

143. The optical system of embodiment 142, wherein said third set of said nucleic acid molecules comprises a third fluorophore coupled thereto, wherein said third fluorophore is different than second first fluorophore and said second fluorophore.

144. The optical system of embodiment 24, wherein a fourth set of said nucleic acid molecules coupled to said interior surface at said fourth discrete region, wherein said fourth set of nucleic acid molecules comprise said first fluorophore and said third fluorophore, wherein said first fluorophore and said third fluorophore are detectably distinct.

145. The optical system of embodiment 120, wherein said plurality of light sources comprises a light emitting diode (LED) light source.

146. The optical system of embodiment 120, further comprising a second multi-band notch filter.

147. The optical system of embodiment 120, wherein said optical system does not comprise:
 (a) a dichroic;
 (b) a tube lens;
 (c) a corrective optical element configured to move in and out of said optical path between said flow cell and said plurality of imaging sensors;
 (d) an autofocus element;
 (e) a laser; or
 (f) any combination of (a) to (e).

148. The optical system of embodiment 120, wherein said flow cell comprises a curved substrate.

149. The optical system of embodiment 120, wherein said optical system comprises a pixel shifter.

150. The optical system of embodiment 149, wherein said pixel shifter comprises a plurality of prisms.

151. The optical system of embodiment 149, wherein said pixel shifter comprises a movable lens.

152. A method of imaging a biological polymer, said method comprising:
 (a) providing an optical system comprising:
  (i) a plurality of light sources comprising a first light source having a first wavelength range and a second light source having a second wavelength range, wherein said first wavelength range is different from said second wavelength range; and
  (ii) a plurality of imaging sensors comprising a first imaging sensor configured to image one or more biological polymers disposed in an optical path between said plurality of light sources and said plurality of imaging sensors in presence of said first wavelength emitted by said first light source, and a second imaging sensor configured to image said one or more biological polymers in presence of said second waving emitted by said second light source;
 (b) bringing said one or more biological polymers into contact with a plurality of fluorophores under conditions sufficient to cause a first biological polymer of said one or more biological polymers to bind with a first fluorophore of said plurality of fluorophores and a second biological polymer of said one or more biological polymers to bind with a second fluorophore of said plurality of fluorophores, wherein said first fluorophore is different than said second fluorophore;
 (c) imaging said first biological polymer with said optical system, wherein said imaging comprises (i) illuminating said first biological polymer with said first light source, thereby exciting said first fluorophore, and (ii) acquiring a first image of said first biological polymer with said first imaging sensor; and
 (d) imaging said second polymer with said optical system, wherein said imaging comprises (i) illuminating said second biological polymer with said second light source, thereby exciting said second fluorophore, and (ii) acquiring a second image of said second biological polymer with said second imaging sensor.

153. The method of embodiment 152, wherein said first biological polymer is identical to said second biological polymer.

154. The method of embodiment 152, further comprising: imaging a third biological polymer of said one or more biological polymers comprising (i) illuminating said third biological polymer using a third light source of said plurality of light sources, wherein said third light source emits a third wavelength range exciting a third fluorophore of said plurality of fluorophores, and (ii) acquiring a third image of said third biological polymer with a second imaging sensor of said plurality of imaging sensors.

155. The method of embodiment 152, further comprising combining said first image and said second image into a composite image.

156. The method of embodiment 155, further comprising identifying a unit of said first biological polymer bound by said first fluorophore comprising analyzing a first region of interest (ROI) of said composite image to detect a first signal emitted by said first fluorophore.

157. The method of embodiment 155, further comprising identifying a unit of said second biological polymer bound by said second fluorophore comprising analyzing a second ROI of said composite image to detect a second signal emitted by said second fluorophore.

158. The method of embodiment 155, further comprising:
 (e) identifying a first unit of said first biological polymer bound by said first fluorophore comprising analyzing a first ROI of said composite image to detect a first signal emitted by said first fluorophore; and
 (f) identifying a second unit of said second biological polymer bound by said second fluorophore comprising analyzing a second ROI of said composite image to detect a second signal emitted by said first fluorophore.

159. The method of embodiment 154, further comprising combining said first image, said second image, and said third image into a composite image.

160. The method of embodiment 159, further comprising identifying a third unit of said third biological polymer bound by said third fluorophore comprising analyzing a third ROI of said composite image to detect a third signal emitted by said third fluorophore.

161. The method of embodiment 154, further comprising:
(e) identifying a first unit of said first biological polymer bound by said first fluorophore comprising analyzing a first region of interest (ROI) of said composite image to detect a first signal emitted by said first fluorophore;
(f) identifying a second unit of said second biological polymer bound by said second fluorophore comprising analyzing a second ROI of said composite image to detect a second signal emitted by said first fluorophore; and
(g) identifying a third unit of said third biological polymer bound by said third fluorophore comprising analyzing a third ROI of said composite image to detect a third signal emitted by said third fluorophore.

162. The method of any one of embodiments 152-161, wherein said one or more biological polymers comprise one or more nucleic acid molecules, polypeptides, proteins, or a combination thereof.

163. The method of embodiment 152, wherein said one or more biological polymers is coupled to a surface of a hydrophilic polymer layer.

164. The method of embodiment 152, wherein said one or more biological polymers is coupled to an interior surface of a flow cell.

165. The method of embodiment 163, wherein said hydrophilic polymer layer is coupled to an interior surface of a flow cell.

166. The method of embodiment 152, further comprising moving said first image sensor to a new location following imaging said first biological polymer in (c) with a pixel shifter of said optical system.

167. The method of embodiment 152, further comprising rejecting a wavelength range with one or more tri-band notch filters of said optical system, wherein said tri-band notch filters are disposed in said optical path in between said plurality of imaging sensors and said one or more biological polymers.

168. The method of embodiment 152, wherein said optical system has a reduction of 1×.

169. The method of embodiment 152, wherein said optical system has a field-of-view (FOV) of greater than 4 mm$^2$.

170. The method of embodiment 152, wherein said optical system has a numerical aperture (NA) of less than 0.6.

171. The method of embodiment 166, wherein said NA is 0.25.

172. The method of embodiment 165, further comprising capturing said FOV with said plurality of imaging sensors.

173. The method of embodiment 152, wherein said methods does not comprise:
(a) imaging with a dichroic;
(b) using a tube lens;
(c) using a corrective optical element configured to move in and out of said optical path between said flow cell and said plurality of imaging sensors;
(d) autofocusing;
(e) using a laser; or
(f) any combination of (a) to (e).

174. The method of embodiment 152, wherein said imaging in each of (c) and (d) is performed in 0.1 seconds or less.

175. The method of embodiment 28, wherein said imaging in (c) and imaging in (d) are performed in 0.2 seconds or less.

176. The method of embodiment 154, wherein said imaging in each of (c) to (e) is performed in 0.1 second or less.

177. The method of embodiment 30, wherein said imaging in (c), imaging in (d), and imaging in (e) are performed in 0.3 seconds or less.

178. The method of embodiment 152, wherein said illuminating in (c) is performed before illuminating in (d).

179. The method of embodiment 154, wherein said illuminating in (c) to (e) is performed sequentially.

180. The method of embodiment 152, wherein said illuminating (c) comprises pulsing said first light source on and off, and said illuminating in (d) comprises pulsing said second light source on and off.

181. The method of embodiment 180, wherein said pulsing said first light source on and off is performed at a different time than said pulsing said second light source on and off.

182. The method of embodiment 155 or 159, further comprising applying an error-correction algorithm to said composite image to reduce systematic bias.

183. The method of embodiment 152, wherein said one or more biological polymers comprises one or more nucleic acid sequences.

184. The method of embodiment 152, further comprising repeating (c) to (d) to identify said one or more nucleic acid sequences.

181. A system, comprising:
a flow cell; and
an optical system comprising:
a plurality of light sources configured to direct a first light to said flow cell;
a multi-band notch filter configured to (i) receive a second light from said flow cell and (ii) transmit a third light, wherein said third light is different than said second light; and
a plurality of imaging sensors configured to receive said third light from said multi-band notch filter.

182. The system of embodiment 181, wherein said flow cell comprises one or more interior surfaces having a hydrophilic polymer layer coupled thereto.

183. The system of embodiment 182, wherein said flow cell further comprises a plurality of biological polymers coupled to said hydrophilic polymer layer.

184. The system of embodiment 182, wherein said hydrophilic polymer layer comprises polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof.

185. The system of embodiment 181, wherein said optical system further comprises a pixel shifter.

186. The system of embodiment 181, wherein the multi-band notch filter comprises a tri-band notch filter.

187. The system of embodiment 181, wherein said optical system further comprises an imaging optic disposed in said optical path between said multi-band notch filter and said flow cell.

188. The system of embodiment 187, wherein the imaging optic has a reduction comprising 1×.

189. The system of embodiment 181, wherein the optical system has a field-of-view (FOV) comprising greater than 1 mm² 190. The system of embodiment 181, wherein said optical system has a numerical aperture (NA) comprising less than 0.6.

191. The system of embodiment 190, wherein said NA comprises about 0.25.

192. The system of embodiment 181, wherein said plurality of imaging sensors is configured to capture said FOV.

193. The system of embodiment 181, wherein said plurality of light sources comprises:
- a first light source configured to emit light in a first wavelength range;
- a second light source configured to emit light in a second wavelength range; and
- a third light source configured to emit light in a third wavelength range, wherein said first wavelength range, said second wavelength range, and said third wavelength range are different wavelength ranges.

194. The system of embodiment 193, wherein a first fluorophore excited by said first wavelength range of said first light source is different than a second fluorophore excited by said second wavelength range of said second light source.

195. The system of embodiment 193, wherein:
- a first fluorophore excited by said first wavelength range of said first light source is different than a second fluorophore excited by said second wavelength range of said second light source; and
- said second fluorophore excited by said second wavelength range of said second light source is different than a third fluorophore excited by said third wavelength range of said third light source.

196. The system of embodiment 195, wherein said third fluorophore excited by said third wavelength range of said third light source is different than said first fluorophore excited by said first wavelength range of said first light source.

197. The system of embodiment 193, wherein said first wavelength range of said first light source comprises between about 500 to about 540 nanometers (nm).

198. The system of embodiment 193, wherein said second wavelength range of said second light source comprises between about 620 to about 640 nm.

199. The system of embodiment 193, wherein said third wavelength range of the third light source comprises between about 460 to about 500 nm.

200. The system of embodiment 181, wherein said flow cell comprises an interior surface comprising a plurality of discrete regions, wherein (i) a first discrete region of said plurality of discrete regions comprises a first set of nucleic acid molecules coupled to said interior surface at said first discrete region, and (ii) a second discrete region of said plurality of discrete regions comprises a second set of said nucleic acid molecules coupled to said interior surface at said second discrete region, wherein said first set of said nucleic acid molecules is different than said second set of said nucleic acid molecules.

201. The system of embodiment 200, wherein said first set of said nucleic acid molecules comprises a first fluorophore coupled thereto, and said second set of said nucleic acid molecules comprises a second fluorophore coupled thereto, wherein said first fluorophore is different than said second fluorophore.

202. The system of embodiment 201, wherein a third discrete region of said plurality of discrete regions comprises a third set of said nucleic acid molecules coupled to said interior surface at said third discrete region, and wherein said third set of said nucleic acid molecules is different than said first set and said second set of said nucleic acid molecules.

203. The system of embodiment 202, wherein said third set of said nucleic acid molecules comprises a third fluorophore coupled thereto, wherein said third fluorophore is different than second first fluorophore and said second fluorophore.

204. The system of embodiment 203, wherein a fourth discrete region of said plurality of discrete regions comprises a fourth set of nucleic acid molecules coupled to said interior surface at said forth discrete region, and wherein said fourth set of nucleic acid molecules comprise said first fluorophore and said third fluorophore, wherein said first fluorophore is different than said third fluorophore.

205. The system of embodiment 181, wherein said flow cell comprises a curved substrate.

206. The system of embodiment 181, wherein said optical system comprises a pixel shifter, and optionally wherein said pixel shifter comprises a plurality of prisms or a movable lens.

207. The system of embodiment 181, wherein said optical system does not comprise:
(a) a dichroic;
(b) a tube lens;
(c) a corrective optical element configured to move in and out of said optical path between said flow cell and said plurality of imaging sensors;
(d) an autofocus element;
(e) a laser; or
(f) any combination of (a) to (e).

208. The system of embodiment 181, wherein said flow cell is disposed between said plurality of light sources and said plurality of imaging sensors.

209. A method, comprising:
(a) providing an optical system comprising (i) a plurality of light sources, (ii) a multi-band notch filter, and (iii) a plurality of imaging sensors;
(b) using said plurality of light sources to direct a first light to a flow cell;
(c) subsequent to (b), using said multi-band notch filter to (i) receive a second light from said flow cell and (ii) transmit a third light, wherein said third light is different than said second light; and
(d) using said plurality of imaging sensors to receive said third light from said multi-band notch filter.

210. The method of embodiment 209, wherein said flow cell comprises one or more interior surfaces having a hydrophilic polymer layer coupled thereto.

211. The method of embodiment 209, wherein said flow cell further comprises one or more biological polymers coupled to said hydrophilic polymer layer.

212. The method of embodiment 211, further comprising:
(e) bringing said one or more biological polymers into contact with a plurality of fluorophores under conditions sufficient to cause a first biological polymer of said one or more biological polymers to bind with a first fluorophore of said plurality of fluorophores; and
(f) imaging said first biological polymer with said optical system, wherein said imaging comprises (i) illuminating said first biological polymer with said first light, thereby exciting said first fluorophore and emitting said second light, (ii) filtering said second light with said multi-band notch filter, and (iii) acquiring a first image of said first biological polymer with a first imaging sensor of said plurality of imaging sensors.

213. The method of embodiment 212, further comprising:
(g) bringing said one or more biological polymers into contact with said plurality of fluorophores under conditions sufficient to cause a second biological polymer of said one or more biological polymers to bind with a second fluorophore of said plurality of fluorophores, wherein said first fluorophore is different than said second fluorophore; and
(h) imaging said second biological polymer with said optical system, wherein said imaging comprises (i) illuminating said second biological polymer with a fourth light, thereby exciting said second fluorophore and emitting a fifth light, (ii) filtering said fifth light with said multi-band notch filter, and (iii) acquiring a second image of said second biological polymer with a second imaging sensor of said plurality of imaging sensors.

214. The method of embodiment 213, further comprising combining said first image and said second image into a composite image.

215. The method of embodiment 214, further comprising identifying a unit of said first biological polymer bound by said first fluorophore comprising analyzing a first region of interest (ROI) of said composite image to detect a first signal emitted by said first fluorophore.

216. The method of embodiment 214, further comprising identifying a unit of said second biological polymer bound by said second fluorophore comprising analyzing a second ROI of said composite image to detect a second signal emitted by said second fluorophore.

217. The method of embodiment 214, further comprising:
(e) identifying a first unit of said first biological polymer bound by said first fluorophore comprising analyzing a first ROI of said composite image to detect a first signal emitted by said first fluorophore; and
(f) identifying a second unit of said second biological polymer bound by said second fluorophore comprising analyzing a second ROI of said composite image to detect a second signal emitted by said first fluorophore.

218. The method of any one of embodiments 211-217, wherein said one or more biological polymers comprise one or more nucleic acid molecules, polypeptides, proteins, or a combination thereof.

219. The method of embodiment 212, further comprising moving said first imaging sensor of said plurality of imaging sensors to anew location following imaging said first biological polymer in (f) with a pixel shifter of said optical system.

220. The method of embodiment 209, further comprising rejecting an undesired wavelength range with a tri-band notch filter of said optical system, wherein said tri-band notch filter is disposed in said optical path in between said plurality of imaging sensors and said flow cell.

221. The method of embodiment 209, wherein said optical system has a reduction of 1×.

222. The method of embodiment 209, wherein said optical system has a field-of-view (FOV) of greater than 4 mm².

223. The method of embodiment 209, wherein said optical system has a numerical aperture (NA) of less than 0.6.

224. The method of embodiment 223, wherein said NA is 0.25.

225. The method of embodiment 224, further comprising capturing said FOV with said plurality of imaging sensors.

226. The method of embodiment 209, wherein said methods does not comprise:
(a) imaging with a dichroic;
(b) using a tube lens;
(c) using a corrective optical element configured to move in and out of said optical path between said flow cell and said plurality of imaging sensors;
(d) autofocusing;
(e) using a laser; or
(f) any combination of (a) to (e).

227. The method of embodiment 209, wherein performing (b) to (f) is performed in 0.1 seconds or less.

228. The method of embodiment 227, wherein performing (b) to (h) is performed in 0.2 seconds or less.

229. The method of embodiment 227, wherein said imaging in (f) is performed before said imaging in (h).

230. The method of embodiment 209, wherein said using said plurality of said light sources to direct said first light to said flow cell of (b) comprises pulsing said first light on and off in 0.1 seconds or less.

231. The method of embodiment 209, further comprising applying an error-correction algorithm to said composite image to reduce systematic bias.

232. The method of embodiment 209, wherein said one or more biological polymers comprises one or more nucleic acid sequences.

233. The method of embodiment 209, wherein said one or more biological polymers comprises one or more nucleic acid sequences, and said method further comprises repeating (a) to (f) to identify a nucleic acid base type in said one or more nucleic acid sequences.

234. A system, comprising:
a curved surface; and
an optical system comprising a light source, wherein said light source is configured to direct light from said light source to said curved surface.

235. A system, comprising:
a surface; and
an optical system, wherein said optical system is configured to image an area of said surface of at least about 5 square millimeters (mm²).

236. The system of embodiment 235, wherein said optical system is configured to simultaneously image said area.

237. The system of embodiment 235, wherein said optical system comprises a plurality of sub-optical systems.

238. The system of embodiment 238, wherein the plurality of sub-optical systems are configured to image said area of said surface in parallel.

239. The system of embodiment 235, wherein said optical system comprises a light source configured to provide a light beam and a lens, wherein said lens is configured to focus said light beam from said light source onto a focal region of said surface comprising said area.

240. The system of embodiment 239, wherein a homogeneity of said light beam over said focal region is at least about 90%.

241. The system of embodiment 239, wherein said area of said surface is disposed as a hollow cylinder.

242. The system of embodiment 235, wherein said surface is at least a portion of a capillary flow cell.

243. The system of embodiment 242, wherein said capillary flow cell comprises a solid core.

244. The system of embodiment 235, further comprising a stage, wherein said surface is disposed on said stage.

245. The system of embodiment 244, wherein said stage comprises a tilt stage, a rotation stage, a translation stage, or any combination thereof.

246. The system of embodiment 235, wherein said surface comprises a hydrophilic polymer coupled thereto.

247. The system of embodiment 246, wherein said at least one binding moiety is coupled to said hydrophilic polymer.

248. The system of embodiment 246, wherein said hydrophilic polymer comprises polyethylene glycol (PEG), poly (vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, or dextran, or any combination thereof.

249. The system of embodiment 235, wherein said system has a numerical aperture of at most about 0.6.

250. The system of embodiment 249, wherein said numerical aperture is at most about 0.25.

251. The system of embodiment 235, further comprising an imaging sensor configured to collect said light subsequent to said directing to said surface.

252. The system of embodiment 235, further comprising a heater configured to heat said surface.

253. The system of embodiment 252, wherein said heater is an integrated heater.

254. The system of embodiment 252, wherein said heater is an infrared heater.

255. The system of embodiment 235, wherein said surface is a curved surface.

256. The system of embodiment 255, wherein said curved surface has a deviation from flatness of 25 micrometers (μm).

257. The system of embodiment 256, wherein said curved surface has a deviation from flatness greater than a focal depth of said optical system.

258. The system of embodiment 235, wherein said optical system is configured to image said area of said surface with a resolution of about 1 μm or less.

259. A method, comprising:
(a) providing a system comprising a flow cell and a light source, wherein said flow cell is functionalized with a first capture probe on a side of said flow cell, wherein said first capture probe is coupled to an analyte, and wherein said analyte is coupled to a nucleotide conjugate comprising a core, a plurality of nucleotide moieties coupled thereto, and one or more detectable labels coupled to said core;
(b) illuminating, using said light source, said first side of said flow cell, wherein said illuminating comprises directing light from said light source through a first focusing element and a second focusing element, wherein said first focusing element moves relative to said second focusing element within a housing without moving said housing relative to an optical path; and
(c) detecting an optical signal from said first side of said flow cell of said flow cell.

260. The method of embodiment 259, further comprising a second capture probe on a second side of said flow cell, wherein said first side and said second side are disposed opposite one another, wherein said second capture probe has a binding affinity for said one or more analytes, and wherein said illuminating comprises directing said light towards said second side of said flow cell, and wherein said optical signal additionally is generated from said second side of said flow cell.

261. The method of embodiment 259, wherein imaging said first side and said second side is performed with a movement of said first focusing element.

262. The method of embodiment 259, wherein said one or more analytes are one or more nucleic acid molecules.

263. The method of embodiment 262, wherein said nucleotide conjugate comprises a plurality of nucleic acid molecules.

264. The method of embodiment 259, further comprising directing a solution comprising one or more analytes through said flow cell and in contact with said first capture probe 265. A system, comprising:
a flow cell comprising a first capture probe on a first wall of said flow cell;
a plurality of analytes, wherein a first analyte of said plurality of analytes is bound to said first capture probe;
a plurality of multivalent molecules, wherein at least a first nucleotide conjugate comprising a core, a plurality of nucleotide moieties coupled thereto, and one or more detectable labels coupled to said core is configured to be bound to said first analyte; and
an optical system comprising a light source, wherein said optical system is configured to direct light from said light source to said flow cell to detect a signal associated with said first nucleotide conjugate, wherein said signal is detected at least in part with use of a first focusing element and a second focusing element, wherein said first focusing element is configured to move relative to said second focusing element within a housing without moving said housing relative to an optical path.

266. The system of embodiment 265, wherein said analyte comprises a nucleic acid molecule.

267. The system of embodiment 265, wherein said signal from said first wall and said second wall is detected without moving said flow cell relative to said optical system.

268. The system of embodiment 265, wherein said flow cell comprises a second capture probe on a second wall of said flow cell, wherein said first wall and said second wall are disposed on opposite sides of said flow cell.

269. The system of embodiment 268, wherein a second analyte of said plurality of analytes is bound to said second capture probe.

270. The system of embodiment 269, further comprising a second a nucleotide conjugate comprising a core, a plurality of nucleotide moieties coupled thereto, and one or more detectable labels coupled to said core configured to bind to said second analyte.

271. The system of embodiment 270, wherein said optical system is configured to detect a signal associated with said second nucleotide conjugate.

272. A method, comprising:
(a) providing a system comprising a flow cell comprising a non-flat surface and a light source configured to illuminate said flow cell, wherein said flow cell is functionalized with a first capture probe on a first side of said flow cell;
(b) directing a solution comprising one or more analytes, wherein said first capture probe;
(c) directing a solution comprising a nucleotide conjugate comprising a core, a plurality of nucleotide moieties coupled thereto, and one or more detectable labels coupled to said core configured to bind to at least a portion of said one or more analytes;
(d) illuminating, using said light source, said first side of said flow cell; and
(e) detecting an optical signal from said first side of said flow cell of said flow cell.

273. The method of embodiment 272, further comprising a second capture probe on a second side of said flow cell, wherein said first side and said second side are disposed opposite one another, wherein said second capture probe has a binding affinity for said one or more analytes, and wherein said illuminating comprises directing said light towards said second side of said flow cell, and wherein said optical signal additionally is generated from said second side of said flow cell.

274. The method of embodiment 272, wherein said non-flat surface is a circular surface, and wherein said circular surface comprises said first side and said second side.

275. The method of embodiment 272, wherein said one or more analytes are one or more nucleic acid molecules.

276. The method of embodiment 275, wherein said nucleotide conjugate comprises a plurality of nucleic acid molecules.

277. A system, comprising:
a flow cell comprising a non-flat surface and a first capture probe on a first wall of said flow cell;
a plurality of analytes, wherein a first analyte of said plurality of analytes is bound to said first capture probe;
a plurality of multivalent molecules, wherein at least a first nucleotide conjugate comprising a core, a plurality of nucleotide moieties coupled thereto, and one or more detectable labels coupled to said core is configured to be bound to said first analyte; and
an optical system comprising a light source, wherein said optical system is configured to direct light from said light source to said flow cell to detect a signal associated with said first nucleotide conjugate.

278. The system of embodiment 277, wherein said flow cell is circular, and wherein said first wall and said second wall are at least a portion of said circular flow cell.

279. The system of embodiment 277, wherein said analyte comprises a nucleic acid molecule.

280. The system of embodiment 277, wherein said flow cell comprises a second capture probe on a second wall of said flow cell, wherein said first wall and said second wall are disposed on opposite sides of said flow cell.

281. The system of embodiment 277, wherein a second analyte of said plurality of analytes is bound to said second capture probe.

282. The system of embodiment 281, further comprising a second a nucleotide conjugate comprising a core, a plurality of nucleotide moieties coupled thereto, and one or more detectable labels coupled to said core configured to bind to said second analyte.

283. The system of embodiment 282, wherein said optical system is configured to detect a signal associated with said second nucleotide conjugate

EXAMPLES

These examples are provided for illustrative purposes only and not to limit the scope of the claims provided herein.

Example 1—Design Specifications for a Fluorescence Imaging Module for Genomics Applications A non-limiting example of design specifications for a fluorescence imaging module of the present disclosure is provided in Table 2.

TABLE 2

Examples of design specifications for a fluorescence imaging module for genomics applications.

| Design Parameter | Specification |
|---|---|
| Numerical aperture | ≥0.3 |
| Image quality | Diffraction limited |
| Field-of-view (FOV) | >2.0 mm$^2$ |
| Image plane curvature | Best focal plane within 100 nm for >90% of the FOV, within 150 nm for 99% of the FOV, and within 200 nm for the entire FOV |
| Image distortion | <0.5% across the FOV |
| Magnification | 2× to 20× |
| Camera pixel size at sample plane | ≥2 × optical system modulation transfer function (MTF) limit |
| Coverslip thickness | >700 μm |
| Number of fluorescence imaging channels | ≥3 |
| Chromatic focal plane difference at camera between all imaging channels | ≤100 nm equivalent at sample plane |
| Number of AF channels | 1 |
| Imaging time | ≤2 seconds per FOV |
| Autofocus | Single step autofocus with error correction |
| Autofocus accuracy | <100 nm |
| Scanning stage step and settle time | <0.4 seconds |
| Channel-specific optimized tube lens | 1 per imaging channel |
| Illumination optical path | Liquid light guide with underfilled entrance aperture |

Example 2—Fabrication of Glass Microfluidic Flow Cell Devices

Figure 36A:
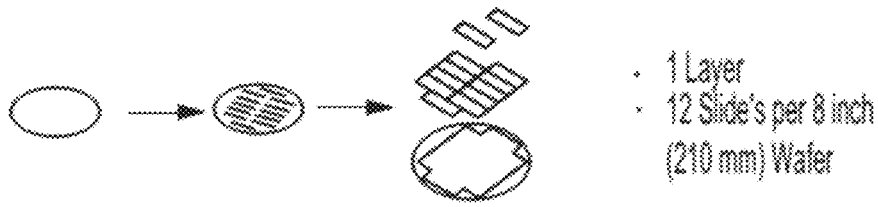
FIGS. 36A-36C illustrates non-limiting examples of flow cell device fabrication.
Figure 36B:
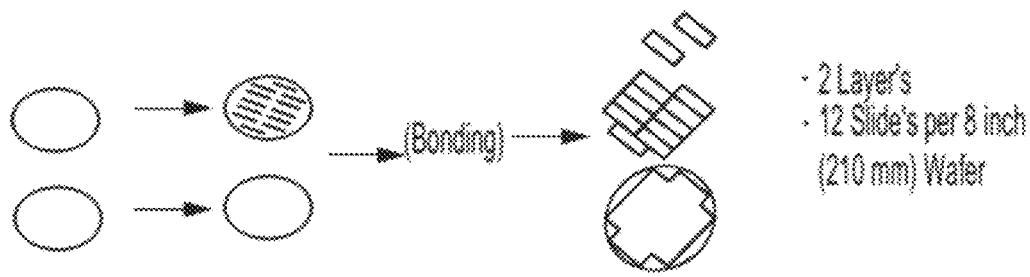
Figure 36C:
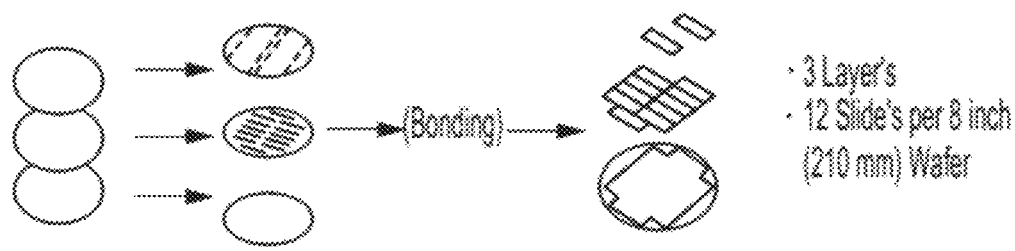

Wafer-scale fabrication of microfluidic devices for use as flow cells can be constructed from, for example, one, two, or three layers of glass, e.g., borosilicate glass, fused-silica glass, or quartz, using one of the processed illustrated in FIGS. 36A-36C and a processing technique such as focused femtosecond laser photoablation and/or laser glass bonding.

In FIG. 36A, a first wafer is processed with a laser (e.g., that produces femtosecond laser radiation) to ablate the wafer material and provide a patterned surface. The patterned wafer surface may comprise a plurality of microfluidic devices (e.g., 12 devices per 210 mm diameter wafer), each of which may comprise a plurality of fluid channels. The processed wafer may then be diced to create individual microfluidic chips comprising open fluid channels that may optionally be subsequently sealed, e.g., by sealing with a film or by clamping the device to another support surface.

In FIG. 36B, a first wafer is processed to create a patterned surface which may then be placed in contact with and bonded to a second wafer to seal the fluid channels. Depending on the materials used, e.g., glass wafers, silicon wafers, etc., the bonding may be performed using, e.g., a thermal bonding process, an anodic bonding process, a laser glass bonding process, etc. The second wafer covers and/or seals the grooves, indentations, and/or apertures on the wafer having the patterned surface to form fluid channels and/or fluid chambers (e.g., the interior portion) of the device at the interface of the two wafer components. The bonded structure may then be diced into individual microfluidic chips, e.g., 12 microfluidic chips per 210 mm diameter wafer.

In FIG. 36C, the first wafer is processed to create a pattern of fluid channels that are cut or etched through the full thickness of the wafer (e.g., open on either surface of the wafer). The first wafer is then sandwiched between and bonded to a second wafer on one side and a third wafer on the other side. Depending on the materials used, e.g., glass wafers, silicon wafers, etc., the bonding may be performed using, e.g., a thermal bonding process, an anodic bonding process, a laser glass bonding process, etc. The second and third wafers cover and/or seal the grooves, indentations, and/or apertures in the first wafer to form fluid channels and/or fluid chambers (e.g. the interior portions) of the device. The bonded structure may then be diced into individual microfluidic chips, e.g., 12 microfluidic chips per 210 mm diameter wafer.

Example 3—Coating Flow Cell Surfaces with a Hydrophilic Polymer Coating

Glass flow cell devices were coated by washing prepared glass channels with KOH, followed by rinsing with ethanol and then silanization for 30 minutes at 65° C. Fluid channel surfaces were activated with EDC-NHS for 30 min., followed by grafting of oligonucleotide primers by incubation of the activated surface with 5 µm primer for 20 min., and then passivation with 30 µm of an amino-terminated polyethylene glycol (PEG-NH2).

Multilayer surfaces are made following the approach described above, where following the PEG-NH2 passivation step, a multi-armed PEG-NHS is flowed through the fluid channels, followed by another addition of the PEG-NH2, optionally followed by another incubation with PEG-NHS, and optionally followed by another incubation with multi-armed PEG-NH2. For these surfaces, the primer may be grafted at any step, and especially following the last addition of multi-armed PEG-NH2.

Example 4—Flow Cell Devices for Nucleic Acid Sequencing

Figure 37A:
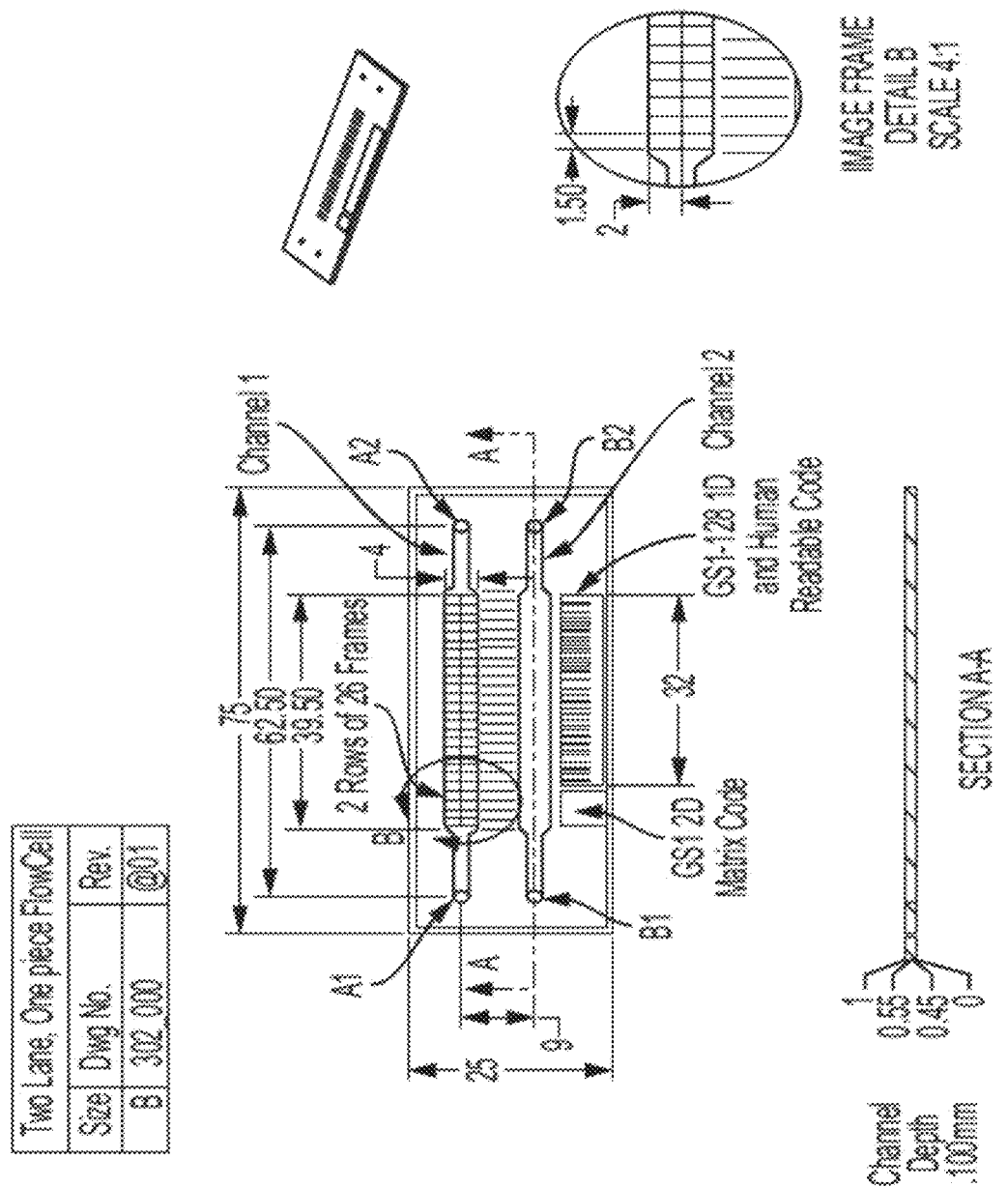
FIGS. 37A-37C illustrates non-limiting examples of glass flow cell designs.

FIG. 37A illustrates a non-limiting example of a one-piece glass microfluidic chip/flow cell design. In this design, fluid channels and inlet/outlet holes may be fabricated using, e.g., focused femtosecond laser radiation. There are two fluid channels ("lanes") in the flow cell device, and each fluid channel comprises, e.g., 2 rows of 26 frames each (e.g., where a "frame" is the image area equivalent to the field-of-view for a corresponding imaging module) each, such that tiling 2×26=52 images suffices to image an entire fluid channel. The fluid channel can have, e.g., a depth of about 100 µm. Fluid channel 1 has an inlet hole A1 and an outlet hole A2, and fluid channel 2 has an inlet hole B1 and an outlet hole B2. The flow cell device may also comprise a 1D linear, human-readable and/or machine-readable barcode, and optionally a 2D matrix barcode.

Figure 37B:
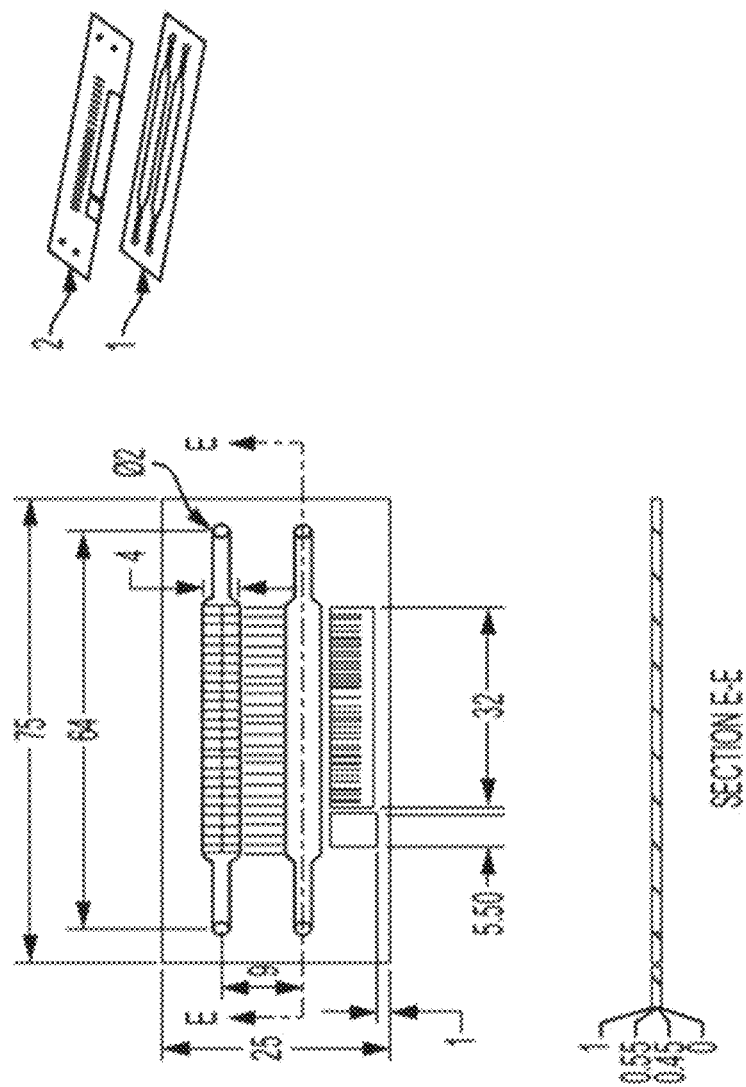

FIG. 37B illustrates a non-limiting example of a two-piece glass microfluidic chip/flow cell design. In this design, fluid channels and inlet/outlet holes may be fabricated using, e.g., focused femtosecond laser photoablation or photolithography and chemical etching processes. The 2 pieces can be bonded together using any of a variety of techniques as described above. The inlet and outlet holes may be positioned on the top layer of the structure and oriented in such a way that they are in fluid communication with at least one of the fluid channels and/or fluid chambers formed in the interior portion of the device. There are two fluid channels in the flow cell device, and as with the device illustrated in FIG. 37A, each fluid channel comprises, e.g., 2 rows with 26 frames in each row. The fluid channels can have, e.g., a depth of about 100 µm. Fluid channel 1 has an inlet hole A1 and an outlet hole A2, and fluid channel 2 has an inlet hole B1 and an outlet hole B2. The flow cell device may also comprise a 1D linear, human-readable and/or machine-readable barcode, and optionally a 2D matrix barcode.

Figure 37C:
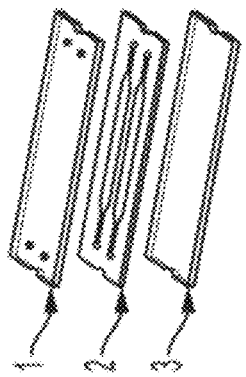
Figure 37C:
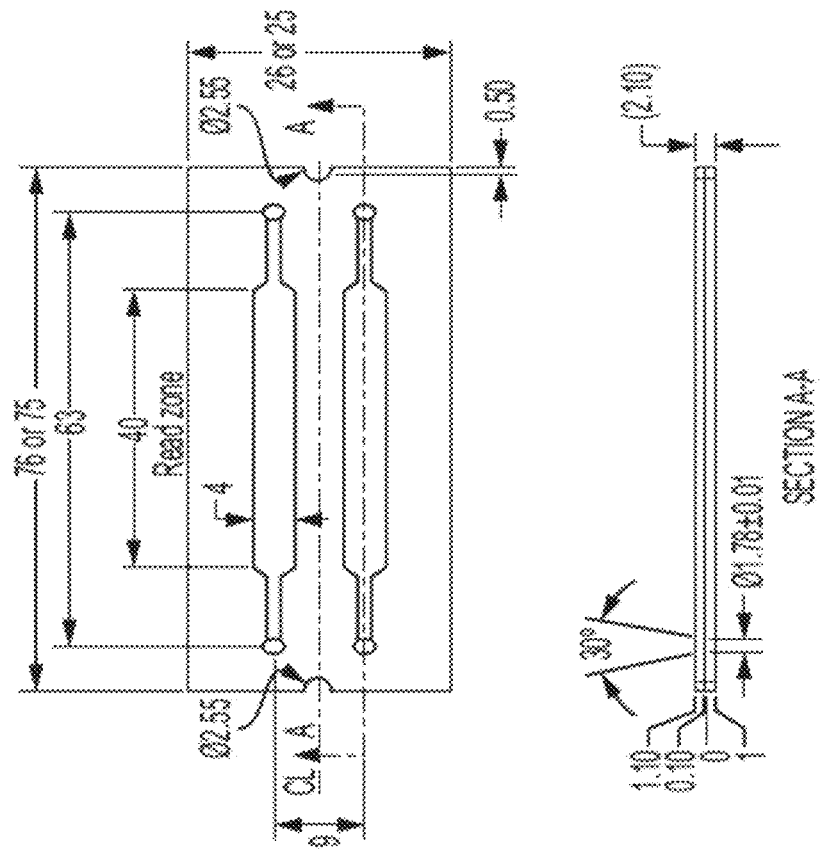

FIG. 37C illustrates a non-limiting example of a three-piece glass microfluidic chip/flow cell design. In this design, fluid channels and inlet/outlet holes may be fabricated using, e.g., focused femtosecond laser photoablation or photolithography and chemical etching processes. The 3 pieces can be bonded together using any of a variety of techniques as described above. The first wafer (comprising a through-pattern of fluid channels or fluid chambers) can be sandwiched between and bonded to a second wafer on one side and a third wafer on the other side. The inlet and outlet holes may be positioned on the top layer of the structure and oriented in a way such that they are in fluid communication with at least one of the fluid channels and/or fluid chambers formed in the interior portion of the device. There are two fluid channels in the flow cell device, and as with the devices illustrated in FIGS. 37A and 37B, each fluid channel has 2 rows with 26 frames in each row. The fluid channel can have a depth of, e.g., about 100 µm. Fluid channel 1 has an inlet hole A1 and an outlet hole A2, and fluid channel 2 has an inlet hole B1 and an outlet hole B2. The flow cell device may also comprise a 1D linear, human-readable and/or machine-readable barcode, and optionally a 2D matrix barcode.

Example 5—Imaging of Nucleic Acid Clusters in a Capillary Flow Cell

Nucleic acid clusters were established within a capillary and subjected to fluorescence imaging. A flow device having a capillary tube was used for the test. An example of the resulting cluster images is presented in FIG. 38. The figure demonstrated that nucleic acid clusters formed by amplification within the lumen of a capillary flow cell device as disclosed herein can be reliably formed and visualized.

Example 6—Plastic Sample Support Structures

In some instances, the disclosed sample support structures may be fabricated from a polymer. Examples of materials from which the sample support structure, e.g., a capillary flow cell device, may be fabricated include, but are not limited to, polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), or any combination thereof. Various compositions comprising both glass and plastic substrates are also contemplated.

Modification of a polymer surface for the surface coating purposes disclosed herein involves making surfaces reactive with other chemical groups (—R), including amines. When prepared on an appropriate substrate, these reactive surfaces can be stored long term at room temperature, for example, for at least 3 months or more in some instances. Such surfaces can be further grafted with R-PEG and R-primer oligomer for on-surface amplification of nucleic acids, as described elsewhere herein. Plastic surfaces, such as cyclic olefin polymer (COP), may be modified using any of a variety of methods known in the art. For example, they can be treated with Ti:Sapphire laser ablation, UV-mediated ethylene glycol methacrylate photografting, plasma treatment, or mechanical agitation (e.g., sand blasting, or polishing, etc.) to create hydrophilic surfaces that can remain reactive for months towards a variety of chemical groups, such as amines. These groups may then allow conjugation of passivation polymers such as PEG, or biomolecules such as DNA or proteins, without loss of biochemical activity. For example, attachment of DNA primer oligomers allows DNA amplification on a passivated plastic surface while reducing or minimizing the non-specific adsorption of proteins, fluorophore molecules, or other hydrophobic molecules.

Additionally, in some instances, surface modification can be combined with, e.g., laser printing or UV masking, to create patterned surfaces. This allows patterned attachment of DNA oligomers, proteins, or other moieties, providing for surface-based enzymatic activity, binding, detection, or processing. For example, DNA oligomers may be used to amplify DNA only within patterned features, or to capture amplified long DNA concatemers in a patterned fashion. In some embodiments, enzyme islands may be generated in the patterned areas that are capable of reacting with solution-based substrates. Because plastic surfaces are especially amenable to these processing modes, in some embodiments as contemplated herein, plastic sample support surfaces or flow cell devices may be recognized as being particularly advantageous.

Furthermore, plastic can be injection molded, embossed, stamped, or 3D printed to form any shape, including microfluidic devices, much more easily than glass substrates, and thus can be used to create surfaces for the binding and analysis of biological samples in multiple configurations, e.g., sample-to-result microfluidic chips for biomarker detection or DNA sequencing.

Specific and localized DNA amplification on modified plastic surfaces can be performed to produce nucleic acid spots with an ultra-high contrast to noise ratio and very low background when probed with fluorescent labels.

Hydrophilized and amine-reactive cyclic olefin polymer surface with amine-primer and amine-PEG can be prepared and has been demonstrated to support rolling circle amplification. When probed with fluorophore labeled primers, or when labeled dNTPs were added to the hybridized primers by a polymerase, bright spots of DNA amplicons were observed that exhibited signal to noise ratios greater than 100 with backgrounds that are extremely low, indicating highly specific amplification, and ultra-low levels of non-specific protein and hydrophobic fluorophore binding, which are hallmarks of the high accuracy detection required for systems such as fluorescence-based DNA sequencers.

Example 7—Example of the Use of a Structured Illumination Imaging System for Sequencing A structured illumination imaging system 4100 such as the non-limiting example illustrated in FIG. 41 may be used in combination with a flow cell 4187 comprising a low non-specific binding surface to perform nucleic acid sequencing. Target nucleic acid sequences are hybridized to adapter/primer sequences attached to the low non-specific binding surface 4188 on the interior of the flow cell 4187 at high surface density and clonally amplified using hybridization and amplification buffers that are specially formulated for said surface to enhance specific hybridization and amplification rates.

The flow cell 4187 is mounted in the structured illumination imaging system 4100, and a sequencing reaction cycle comprising the use of, e.g., the nucleotide conjugate chemistry described above and the workflow illustrated in FIG. 40 is initiated. The fluorescently labeled nucleotide conjugate is introduced into the flow cell 4187 and contacted with the surface 4188 to form multivalent binding complexes if the nucleotide moiety of the nucleotide conjugate is complementary to a nucleotide of the target sequence. Excess, unbound nucleotide conjugate is then rinsed away.

For each detection step, a series of images of surface 4188 are captured using different orientations of a diffraction grating, e.g., 4130A, in at least one branch of an illumination optical path and at several different positions of an optical phase modulator, e.g., 4140A, to project illumination light fringe patterns onto the surface 4188. Following image acquisition, the series of images are processed using an image reconstruction algorithm to generate a higher resolution image than that achievable using diffraction-limited optics alone. The process may be repeated for several positions on surface 4188 to create a tiled image of the interior flow cell surface. Optionally, the focal plane may be adjusted, and the process may be repeated to generate higher resolution images of a second interior flow cell surface 4189.

The combination of high contrast-to-noise ratio images (achieved using the disclosed low-binding surfaces with multiply-labeled nucleotide conjugate sequencing chemistry) and efficient processing of a relatively small number of images acquired using a structured illumination imaging system to image flow cell surfaces at super-resolution (thus enabling the use of higher surface densities of target sequence clusters) may contribute to higher overall sequencing throughput.

Example 8—Example of Using a Multiplexed Read-Head for Dual Surface Imaging

A multiplexed read-head such as that illustrated schematically in FIGS. 44A and 44B is designed to perform dual surface imaging. The read-head comprises a plurality of microfluorometers which are assembled so that they are held in a fixed position relative to one another and may be scanned in a direction horizontal to a pair of opposed interior flow cell surfaces to acquire images of a swath of each surface. As illustrated in FIG. 44A, a first subset of the plurality of microfluorometers is configured to acquire images of a first interior flow cell surface, and a second subset of the plurality of microfluorometers is configured to acquire images of a second interior flow cell surface that faces the first interior surface and is separated from it by the thickness of an intervening fluid channel. In some cases, the horizontal direction can be parallel to the flow cell. In some cases, a vertical direction can be perpendicular or orthogonal to the flow cell.

A flow cell comprising a low non-specific binding surface coating is used to perform nucleic acid sequencing. Target nucleic acid sequences are hybridized to adapter/primer sequences attached to the low non-specific binding surfaces on the interior of the flow cell and clonally amplified using hybridization and amplification buffers that are specially formulated for said surfaces to enhance specific hybridization and amplification rates.

The flow cell is mounted in an imaging system comprising the multiplexed read-head, and a sequencing reaction cycle comprising the use of, e.g., the nucleotide conjugate chemistry described above and the workflow illustrated in FIG. 40 is initiated. The fluorescently labeled nucleotide conjugate is introduced into the flow cell and contacted with the interior surfaces to form multivalent binding complexes if the nucleotide moiety of the nucleotide conjugate is complementary to a nucleotide of the target sequence. Excess, unbound nucleotide conjugate is then rinsed away.

For each detection step, the multiplexed read-head is scanned in at least one direction parallel to the interior surfaces of the flow cell (or the flow cell may be scanned relative to the multiplexed read-head) and images of both the first and second interior flow cell surfaces are acquired simultaneously, as illustrated in FIG. 44B, while an autofocus mechanism maintains the proper working distance between the objectives of the multiplexed read-head and at least one of the interior flow cell surfaces.

The ability to image both flow cell surfaces simultaneously using a single-pass scan of the flow cell (depending on the design of the read-head) may provide significant improvements in sequencing throughput.

Example 9—Example of Using an Optical System

The purpose of this example is to demonstrate sequencing of a nucleic acid sequence using an optical system as described herein. Such an optical system provides additional advantages and utility for nucleic acid sequencing applications due to reduced optical components, less moving parts and higher throughput.

In this example, a sample 4515 is delivered to a hydrophobic pad 4516 of a flow cell 4521 by a liquid handling system 4514 as shown in FIG. 45. The sample 4515 is drawn into an interior channel 4517 of the flow cell 4521 by a vacuum pump 4518. Nucleic acid sequences present in the sample react with primers attached to walls of the interior channel 4517 of the flow cell 4521. The nucleic acid sequences of the sample are then amplified and washed. After amplification and washing, a solution containing: (1) DAPI modified nucleotide conjugate complementary to A nucleotides; (2) FITC modified nucleotide conjugate complementary to G nucleotides; (3) TRITC modified nucleotide conjugate complementary to C nucleotides; and (4) a fourth nucleotide conjugate modified with both DAPI and TRITC that is complementary toward T nucleotides is introduced to the flow cell 4521 and allowed to react with the primed nucleic acid sequence. The sample in the flow cell 4521 is then illuminated by a 0.1 second pulse of UV-blue light via a first LED light source 4522 thus exciting the DAPI fluorophore. In synchronization with the UV-blue light pulse, the imaging sensors acquire a first image capturing emission of light given off by any DAPI modified nucleotide conjugate bound specifically to the sample. Only light emitted by DAPI fluorescence emission is collected by the imaging sensors because the UV-blue excitation light emitted by the first light source is negligible past 405 nm. This light is blocked by a tri-band bandpass filter (Edmund Scientific stock #87-236) with multi-band center wavelengths at 432 nm, 517 nm and 615 nm. For this filter, bandwidths are 36® 432 nm, 23® 517 nm and 61®615 nm. Next, the sample is pulsed with 0.1 seconds of green light via a second LED light source 4523, capable of exciting the FITC fluorophore. In synchronization with the green light pulse, a second image is acquired capturing emission of light given off by FITC modified nucleotide conjugate bound specifically to the sample. The sample can then be pulsed with 0.1 seconds of red light via a third LED light source 4524 thus exciting the TRITC fluorophore. In synchronization with the red light pulse, a third image is acquired capturing emission of light given off by any TRITC modified nucleotide conjugate bound specifically to the sample. In this example, excitation filters are used for each LED light source to minimize fluorescence channel cross-talk, or bleed-through of the excitation light into the emission bandpasses (notches) of the tri-band bandpass filter.

In this example, the base calling process, shown schematically 4602, in FIG. 46 is as follows. The first image of the cycle is analyzed for regions of interest (ROI) showing strong fluorescence signal. ROI's showing strong fluorescence signal in the first image indicate nucleic acid amplicons with either A or T at the open position prior to exposure to the nucleotide conjugates for the following reason. Capture of the first image was synchronized with sample illumination by UV-blue light, thus exciting DAPI. Since the nucleotide conjugates complementary toward A where labeled with DAPI and nucleotide conjugates complementary toward T were labeled with both DAPI and TRITC, ROI's of the first image showing strong fluorescence indicate either an A or T. Next, the second image of the cycle is analyzed for ROI's showing strong fluorescence signal. Since nucleotide conjugates complementary toward G were labeled with FITC and since capture of the second image was synchronized with the green pulse capable of exciting FTIC, ROI's in the second image showing strong fluorescent signal indicate G. Next, the third image of the cycle is analyzed for ROI's showing strong fluorescence signal. These ROI's indicate nucleic acid amplicons with either C or T present at the open position prior to exposure to the nucleotide conjugates. This is because in synchronization with the capture of the third image, the sample is illuminated with red light, thus exciting TRITC. Nucleotide conjugates complementary to C are labeled with TRITC and nucleotide conjugates complementary toward T are labeled with both DAPI and TRITC. ROI's with strong fluorescence signal observed in both the first and third image indicate a T nucleotide at the open position prior to exposure to the nucleotide conjugates. Identification of ROI's containing T's then allows for identification ROI's containing of A and C. The sequencing and imaging cycle is repeated until the entire nucleic acid sequence has been identified.

Example 10—Example of Using a Super Resolution Enhanced Optical System

The purpose of this example is to demonstrate sequencing of a nucleic acid sequence using a super resolution enhanced optical system as described herein. Such a system provides additional advantages and utility for nucleic acid sequencing applications due to reduced optical components, less moving parts and higher throughput, while providing for super high resolution readout.

In this example, a sample is delivered to capillary flow cell 5201 as shown in FIGS. 53A and B. Sample sites 4902 comprising nucleic acid sequences present in the sample react with primers attached to walls of the interior channel of the capillary flow cell 5201. The nucleic acid sequences of the sample are then amplified and washed. After amplification and washing, a solution containing (1) DAPI modified nucleotide conjugate complementary to A nucleotides; (2) FITC modified nucleotide conjugate complementary to G nucleotides; (3) TRITC modified nucleotide conjugate complementary to C nucleotides; and (4) a fourth nucleotide conjugate modified with both DAPI and TRITC that is complementary toward T nucleotides is introduced to the capillary flow cell 5201 and allowed to react with the primed nucleic acid sequence. The sample in the capillary flow cell 5201 is then illuminated by a 0.1 second pulse of UV-blue light via a first LED light source of the light source 4901 thus exciting the DAPI fluorophore. In synchronization with the UV-blue light pulse, the imaging sensors acquire a first image capturing emission of light given off by any DAPI modified nucleotide conjugate bound specifically to the sample. Only light emitted by DAPI fluorescence emission is collected by the imaging sensors because the UV-blue excitation light emitted by the first light source is negligible past 405 nm. This light is blocked by a tri-band band stop filter 4910. Next, the sample is pulsed with 0.1 seconds of green light via a second LED light source of the light source 4902, capable of exciting the FITC fluorophore. In synchronization with the green light pulse, a second image is acquired capturing emission of light given off by FITC modified nucleotide conjugate bound specifically to the sample. The sample is pulsed with 0.1 seconds of red light via a third LED light source of the light source 4901 thus exciting the TRITC fluorophore. In synchronization with the red light pulse, a third image is acquired capturing emission of light given off by any TRITC modified nucleotide conjugate bound specifically to the sample. In this example, excitation filters are used for each LED light source to minimize fluorescence channel cross-talk, or bleed-through of the excitation light that may not be stopped by the notches, or band stops of the tri-band band stop filter 4910.

A wedge block 4916 can be included in each optical subsystem 4914 in order to image the entire inner surface of the capillary flow cell 5201. As shown in FIG. 54A when the top-wedge piece 4907 is aligned with the bottom wedge piece 4906 the optical subsystems 4916 acquire images on the far side of the inner surface of the capillary flow cell. As shown in FIG. 54B when the top-wedge piece 4907 is moved out of alignment to increase the optical pathlength 4913 the optical subsystems 4916 acquire images on the front interior surface of the capillary flow cell 5201.

The optical system in this example is capable of super resolution imaging, wherein at least one sample site comprising clonally-amplified, sample nucleic acid molecules immobilized to a plurality of attached oligonucleotide molecules, wherein said plurality of immobilized clonally amplified sample nucleic acid molecules are present at distance less than $\lambda/(2*NA)$, wherein k is the center wavelength of an excitation energy source and NA is the numerical aperture of an imaging system. A stochastic photo-switching chemistry is then applied to said clonally amplified sample nucleic acid molecules at the same time to cause said plurality of clonally amplified sample nucleic acid molecules to fluoresce in on and off events in up to four different colors by stochastic photo-switching; and on and off events are detected in a color channel for each color in real-time as the on and off events are occurring for said plurality of clonally amplified sample nucleic acid molecules to determine an identify of a nucleotide of said clonally amplified sample nucleic acid molecule.

In this example, the base calling process, shown schematically 4602, in FIG. 46 is as follows. The first image of the cycle is analyzed for regions of interest (ROI) showing strong fluorescence signal. ROI's showing strong fluorescence signal in the first image indicate nucleic acid amplicons with either A or T at the open position prior to exposure to the nucleotide conjugates for the following reason. Capture of the first image was synchronized with sample illumination by UV-blue light, thus exciting DAPI. Since the nucleotide conjugates complementary toward A where labeled with DAPI and nucleotide conjugates complementary toward T were labeled with both DAPI and TRITC, ROI's of the first image showing strong fluorescence indicate either an A or T. Next, the second image of the cycle is analyzed for ROI's showing strong fluorescence signal. Since nucleotide conjugates complementary toward G were labeled with FITC and since capture of the second image was synchronized with the green pulse capable of exciting FTIC, ROI's in the second image showing strong fluorescent signal indicate G. Next, the third image of the cycle is analyzed for ROI's showing strong fluorescence signal. These ROI's indicate nucleic acid amplicons with either C or T present at the open position prior to exposure to the nucleotide conjugates. This is because in synchronization with the capture of the third image, the sample is illuminated with red light, thus exciting TRITC. Nucleotide conjugates complementary to C are labeled with TRITC and nucleotide conjugates complementary toward T are labeled with both DAPI and TRITC. ROI's with strong fluorescence signal observed in both the first and third image indicate a T nucleotide at the open position prior to exposure to the nucleotide conjugates. Identification of ROI's containing T's then allows for identification ROI's containing of A and C. The sequencing and imaging cycle is repeated until the entire nucleic acid sequence has been identified.

Example 11—Preparation of Nucleotide-Arms

In a 1.5 mL Eppendorf tube, 320 uL of biotin-5k PEG-SVA (from Laysan Bio) was mixed with 33% DMF to produce a concentration of 25 mM of the Biotin-5k PEG-SVA. In a separate tube, add 440 uL buffer (0.2 M NaHCO$_3$Na$_2$CO$_3$ pH 9) and 200 uL of dGTP-PA-NH$_2$ (10 mM stock, from MyChem), the tube was centrifuged. The dissolved biotin-5k PEG SVA was added to the second tube and incubated at room temperature for 1 hour. The reaction was purified via ion exchange chromatography.

The nucleotide-arm comprising an azido group was synthesized as follows. The FMOC N3 linker was obtained from a commercial source. An NHS ester synthesis reaction was conducted by mixing together one equivalent of the N3 linker, one equivalent of disuccinimidyl carbonate (DSC), one equivalent of 4-dimethylaminopyridine (DMAP), with anhydrous N,N-dimethylformamide (DMF), at room temperature for 1 hour. The conjugation to propargyl-amine dNTPs was conducted by reacting three equivalents of the NHS-ester solution with one equivalent of propargyl-dATP, with reaction buffer, at room temperature, for 1 hour.

Example 12—Preparation of Streptavidin Core

Ten mg of streptavidin (Anaspec, catalog No. AS-72177) was dissolved in 525 uL of freshly-prepared 1×PBS buffer (pH 8), and centrifuged for 5 minutes at 14,000 rcf at 4° C. to aggregate the protein. The concentration of the mixture was analyzed via Nanodrop at absorption 280 nm, with ε=179200 M-1 cm-1 for the tetramer (assuming MW=56, 000). The mixture was diluted 1:10 with water.

The fluorophore NHS ester was prepared as a 25 mM stock in DMSO. In a 5 mL Eppendorf tube, DMSO and modified 1×PBS buffer (pH8 with 0.01% Tween) and streptavidin was added. The fluorophore was added slowly, and incubated in the dark at room temperature for 7 hours. The reaction was quenched by adding 100 uL of 1M glycine (pH 9). The mixture was centrifuged for 5 minutes at 14,000 rcf at 4° C., and any precipitate was discarded. Unreacted fluorophore was removed using an Amicon Ultra-15 filter.

Example 13—Preparation of Multivalent Molecules

One type of multivalent molecule was prepared by reacting propargylamine dNTPs with Biotin-PEG-NHS. This aqueous reaction was driven to completion and purified to produce a biotin-PEG-dNTP species. In separate reactions, several different PEG lengths were used, corresponding to average molecular weights varying from 1K Da to 20K Da. The Biotin-PEG-dNTP species were mixed with either freshly prepared or commercially-sourced dye-labeled streptavidin (SA) using a Dye: SA ratio of approximately 3-5:1. Mixing of biotin-PEG-dNTP with dye-labeled streptavidin was conducted in the presence of excess biotin-PEG-dNTP to ensure saturation of the biotin binding sites on each streptavidin tetramer. Complete complexes were purified away from excess biotin-PEG-dNTP by size exclusion chromatography. Each type of multivalent nucleotide having either dATP, dGTP, dCTP or dTTP nucleotide units was conjugated and purified separately, then mixed together to create a four base mixture for nucleotide binding, nucleotide incorporation and nucleic acid sequencing reactions.

Another type of multivalent molecules was prepared in a single pot by reacting multi-arm PEG NHS with excess dye-NH$_2$ and propargylamine dNTPs. Various multi-arm PEG NHS variants were used ranging from 4-16 arms and ranging in molecular weight from 5K Da to 40K Da. After reacting, excess small molecule dye and dNTP were removed by size exclusion chromatography. Each type of multivalent nucleotide having either dATP, dGTP, dCTP or dTTP nucleotide units was conjugated and purified separately, then mixed together to create a four base mixture for nucleotide binding, nucleotide incorporation and nucleic acid sequencing reactions.

The single pot method is described herein. In a 2 mL Eppendorf tube, mixed 914.1 uL of water, 150 uL of acetonitrile, 112.5 uL of TEAB, 51.6 uL of the biotinylated nucleotide-arms, and 271.7 uL of the labeled streptavidin core. The mixture was incubated for 15 minutes at room temperature in the dark. Unreacted biotinylated nucleotide-arms were removed with Amicon Ultra-4.

Example 14—Trapping Assays on Plates

Trapping assays were conducted to determine the capability of a nucleotide unit (as part of a multivalent molecule) to bind a complexed polymerase. The trapping assays were conducted under conditions that permit binding of the nucleotide unit to the complexed polymerase but without incorporation. The complexed polymerase included a polymerase bound to a nucleic acid template molecule which is hybridized to a primer.

Wells of 394-well plates were coated with PEG-silane. Single-stranded polonies of template molecules (clonally-amplified) were prepared in the wells. A sequencing primer was hybridized to the polonies.

Trapping assay using nucleotides having a 3' azido-blocked moiety: The wells were pre-washed once with 20 mM TRIS pH 8.8, 10 mM (NH$_4$)$_2$SO$_4$, 10 mM KCl, 10 mM MgSO$_4$. Azido-blocked nucleotides were incorporated in 20 mM TRIS pH 8.8, 10 mM (NH$_4$)$_2$SO$_4$, 10 mM KCl, 10 mM MgSO$_4$, 5 uM dNTP-N3, 600 nM a polymerase at 55° C. for 5 minutes. The wells were washed six times with 50 mM TRIS pH 8.0, 1 mM EDTA pH 7.5, 750 mM NaCl, 0.02% Tween-20.

Trapping assay using multivalent molecules: The wells were washed once with 10 mM TRIS pH 8.0, 0.5 mM EDTA, 50 mM NaCl. Trap reactions were performed by adding 10 mM TRIS pH 8.0, 2 M Betaine, 1% Triton X-100, 0.48 uM polymerase, 10 mM CaCl$_2$), 0.5 mM EDTA, 100 mM NaCl, 20-160 nM fluorescently-labeled multivalent molecules, for 45 seconds at 45° C. The wells were washed 5 times with 10 mM TRIS pH 8.0, 2 M betaine, 10 mM CaCl$_2$), 100 nM NaCl, 0.5 mM EDTA, 1% Triton X-100.

The trapping assay using the multivalent molecules were suitable for forming a plurality of avidity complexes on concatemer template molecules (e.g., polonies). For example, the trapping assays comprise: (a) binding a first nucleic acid primer, a first polymerase, and a first multivalent molecule to a first portion of a concatemer template molecule thereby forming a first binding complex, wherein a first nucleotide unit of the first multivalent molecule binds to the first polymerase; and (b) binding a second nucleic acid primer, a second polymerase, and the first multivalent molecule to a second portion of the same concatemer template molecule thereby forming a second binding complex, wherein a second nucleotide unit of the first multivalent molecule binds to the second polymerase, wherein the first and second binding complexes which include the same multivalent molecule forms a first avidity complex.

The surfaces were imaged using epifluorescence and the signal intensity was determined using the $90^{th}$ percentile. The data is shown in FIGS. 55 and 56.

Figure 55:
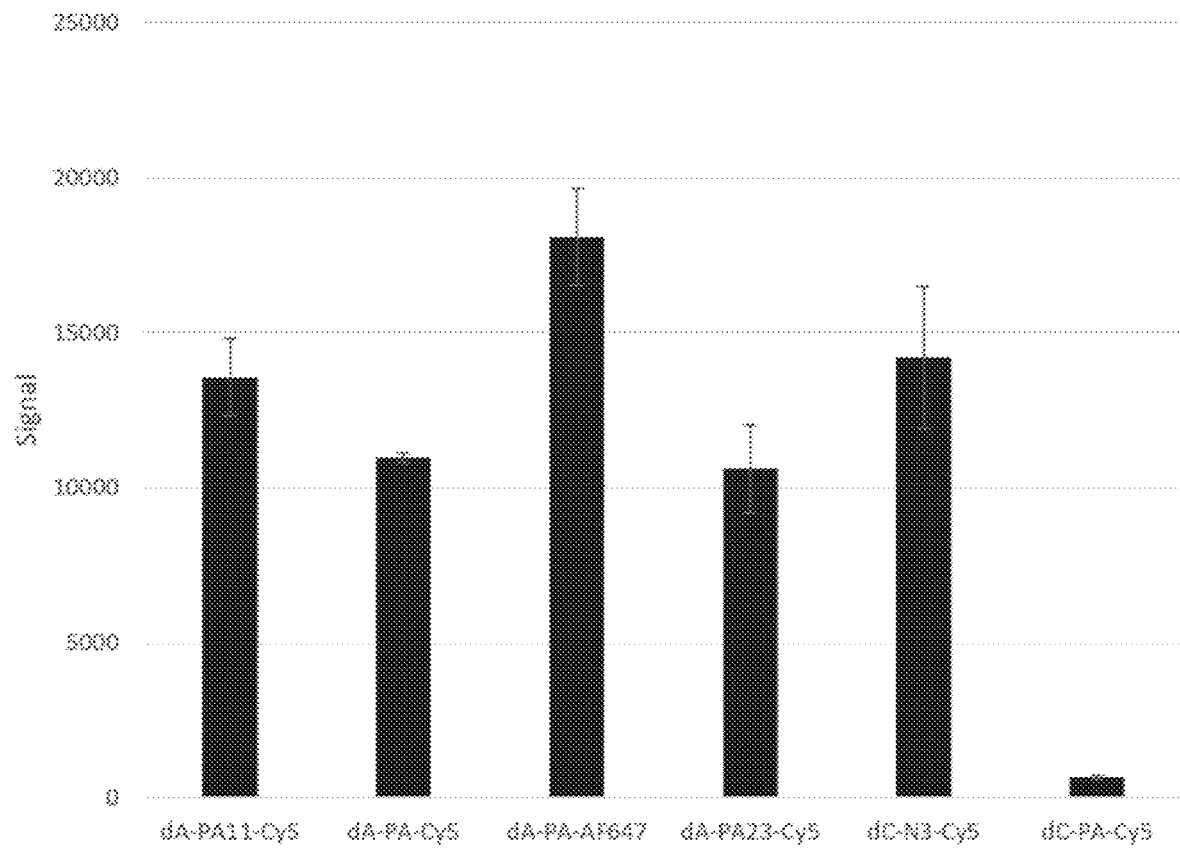
FIG. 55 is a bar graph showing the results of a trapping assay conducted by reacting various fluorescently-labeled multivalent molecules with a corresponding correct DNA template.

The data in FIG. 55 shows that dA multivalent molecules (dATP nucleotide unit) produce optimal signals using PA, PA11, or PA23 linkers. The dC multivalent molecules (dCTP nucleotide units) produce an optimal signal when carrying the N3 linker. It is notable that multivalent molecules carrying the PA linker produces an optimal signal when linked to a dA (dATP) nucleotide unit, however multivalent molecules carrying the same linker and Cy®5 dye combination fails to produce an optimal signal when linked to a dC (dCTP) nucleotide unit.

Figure 56:
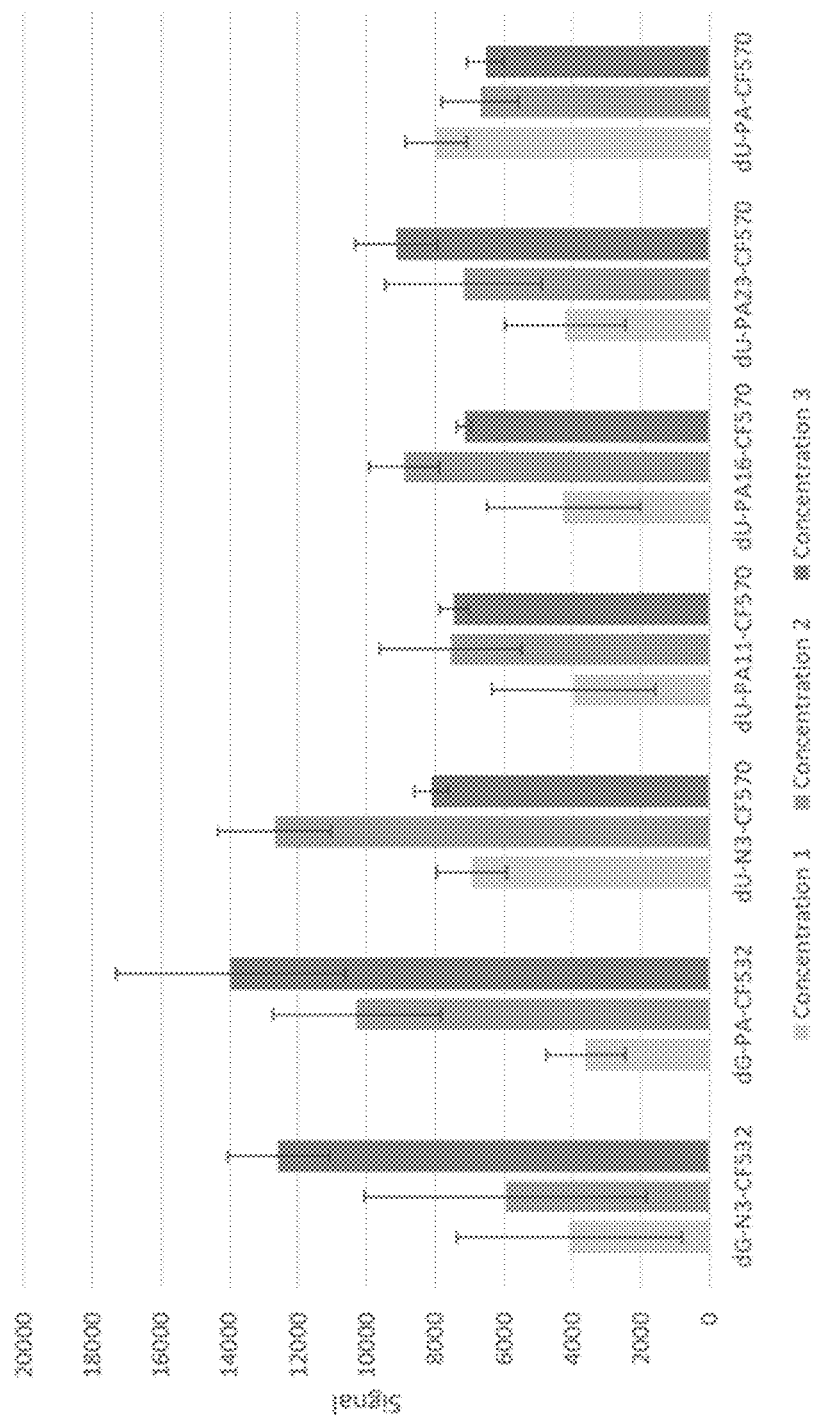
FIG. 56 is a bar graph showing the results of a trapping assay in which increasing concentrations of various fluorescently-labeled multivalent molecules were reacted with corresponding correct DNA templates.

The data in FIG. 56 show that signal intensity varied as a function of linker and concentration.

Example 15—Trapping Assays on Flow Cells

Trapping assays were conducted to determine the capability of a nucleotide unit (as part of a multivalent molecule) to bind a complexed polymerase. The trapping assays were conducted under conditions that permit binding of the nucleotide unit to the complexed polymerase but without incorporation. A complexed polymerase includes a polymerase bound to a nucleic acid template molecule which is hybridized to a primer.

Fluorescently-labeled multivalent molecules carrying Linker-6 were prepared. Labeled multivalent molecules carrying the N3-Linker, Linker-8 or 11-atom Linker (sometimes called 'PA' Linker) were also prepared. The multivalent molecules were labeled with fluorophores CF®680, CF®532, CF®570 or AF®647.

Mixes of multivalent molecules carrying two different color fluorophores were prepared. One mix contained 20 nM or 80 nM of each of dCTP-CF®680 and dUTP-CF®532 multivalent molecules. Another mix contained 20 nM or 80 nM of each of dATP-AF®647 and dGTP-CF®570 multivalent molecules. Each of these mixes were prepared for multivalent molecules having a different linker: N3-Linker; Linker-6 (A-linker); Linker-8 (mAMBA-linker); or 11 atom Linker (also called PA Linker). For example, a first mix contained 20 nM of dCTP-CF®680 and dUTP-CF®532 multivalent molecules carrying N3-Linkers. A second mix contained 20 nM of dCTP-CF®680 and dUTP-CF®532 multivalent molecules carrying Linker-6. Twelve different mixes were prepared. Each mix also contained 0.1 uM sequencing polymerase, 5 mM strontium acetate, a buffering compound, EDTA, a salt, detergent and viscosity additives. The strontium acetate was included in the mixes to promote binding of the nucleotide units of the multivalent molecules to the complexed polymerases without incorporation. Individual complexed polymerases included a polymerase bound to a template molecule which was hybridized to a primer.

Single-stranded concatemer template molecules were immobilized on a flow cell. The template molecules were hybridized with sequencing primers. The flow cell was loaded into a sequencing apparatus configured to deliver laser excitation to the flow cell and obtain fluorescent images from the flow cell.

Repeat cycles of binding reactions were conducted. Each binding cycle included the following general method: flowing a multivalent mix and incubation; washing; imaging; and washing. The flow cell was pre-washed, then flowed with a mix of labeled multivalent molecules and incubated for a different length of time (e.g., 2-180 seconds). The flow cell was washed.

The flow cell was imaged using epifluorescence of a red and green channel, and the signal intensity was determined using the $90^{th}$ percentile. The flow cell was washed. The binding cycles were repeated 62 times for the mixes containing dATP-AF®647 and dGTP-CF®570 multivalent molecules, and 71 times for the mixes containing dCTP-CF®680 and dUTP-CF®532 multivalent molecules.

The trapping assay using the multivalent molecules were suitable for forming a plurality of avidity complexes on concatemer template molecules (e.g., polonies). For example, the trapping assays comprise: (a) binding a first nucleic acid primer, a first polymerase, and a first multivalent molecule to a first portion of a concatemer template molecule thereby forming a first binding complex, wherein a first nucleotide unit of the first multivalent molecule binds to the first polymerase; and (b) binding a second nucleic acid primer, a second polymerase, and the first multivalent molecule to a second portion of the same concatemer template molecule thereby forming a second binding complex, wherein a second nucleotide unit of the first multivalent molecule binds to the second polymerase, wherein the first and second binding complexes which include the same multivalent molecule forms a first avidity complex.

Figure 57:
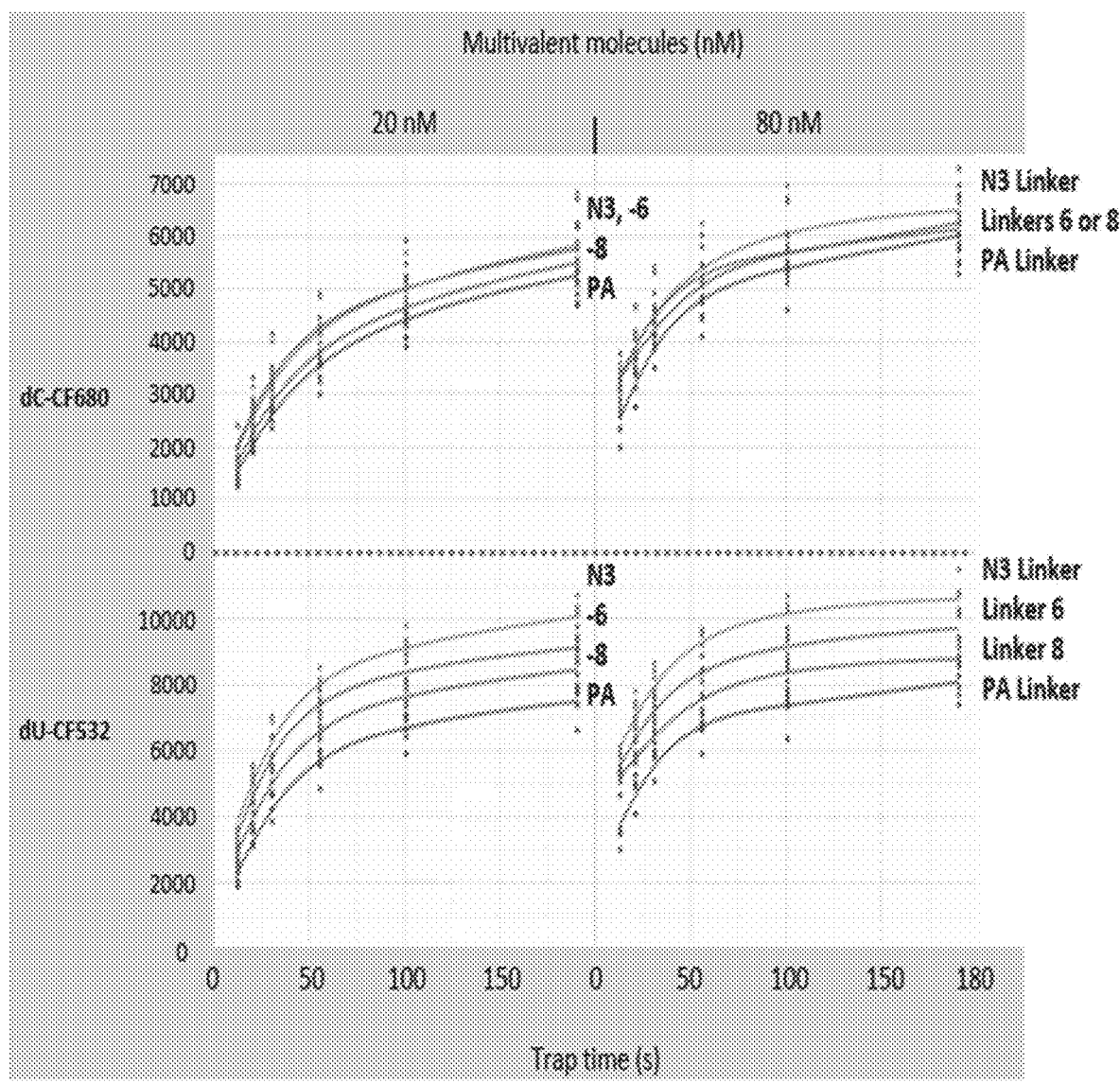
FIG. 57 presents four graphs showing the results of a trapping assay comparing the signal intensity of fluorescently-labeled multivalent molecules carrying nucleotide arms comprising either an N3-Linker, Linker-6, Linker-8 or propargyl Linker. The multivalent molecules were labeled with CF®680 or CF®532 fluorophores. Two different concentrations of multivalent molecules were tested (20 and 80 nM). The graphs show trap time in seconds (x-axis) and P90 signal intensity (y-axis).
Figure 58:
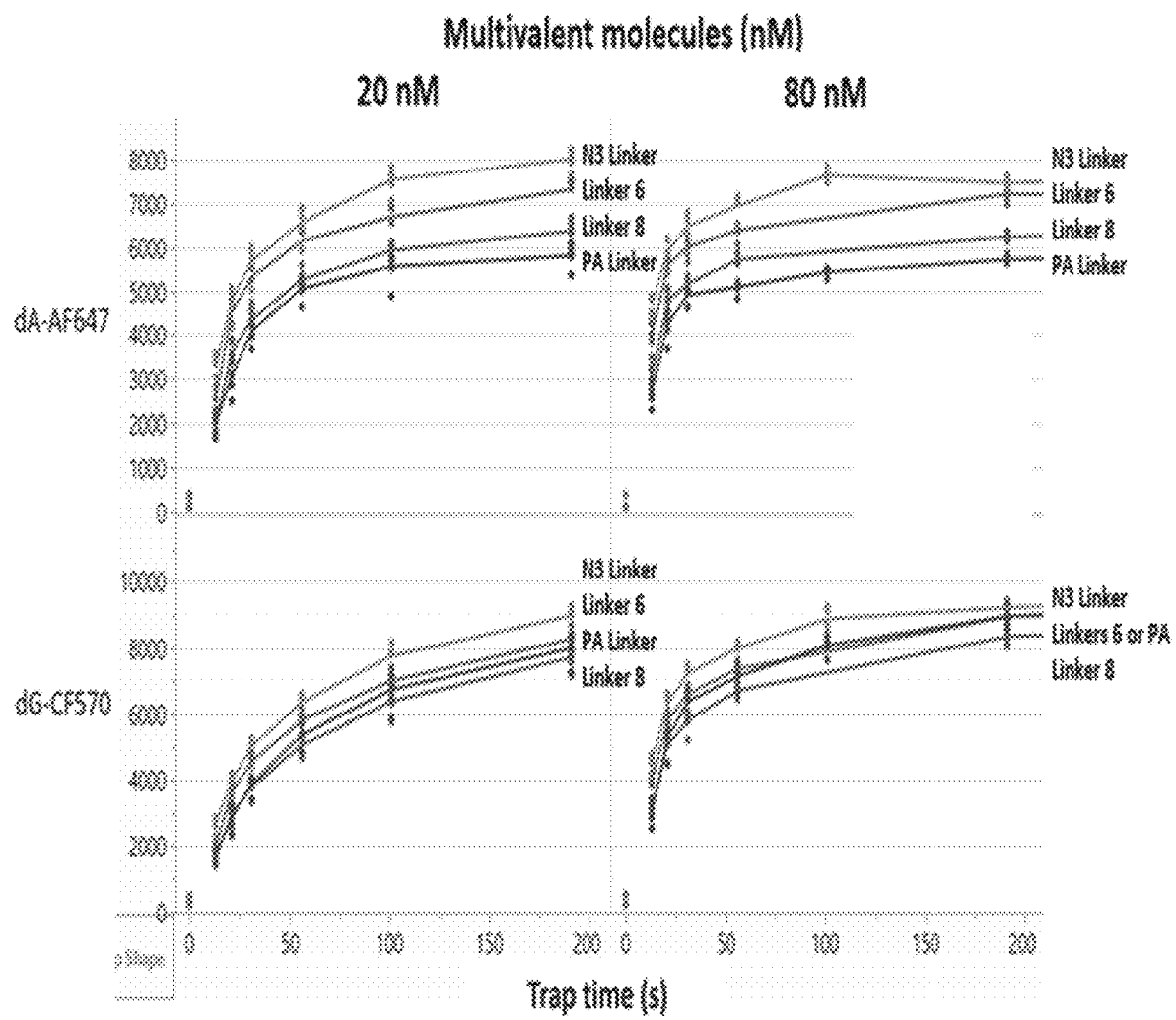
FIG. 58 presents four graphs showing the results of a trapping assay comparing the signal intensity of fluorescently-labeled multivalent molecules carrying nucleotide arms comprising either an N3-Linker, Linker-6, Linker-8 or propargyl Linker. The multivalent molecules were labeled with AF®647 or CF®570 fluorophores. Two different concentrations of multivalent molecules were tested (20 and 80 nM). The graphs show trap time in seconds (x-axis) and P90 signal intensity (y-axis).

In FIGS. 57 and 58, the data for N3-Linker molecules are in green, Linker-molecules are in blue, Linker-8 molecules are in red, and 11 atom Linker molecules are in purple.

The data in FIG. 57 generally shows that multivalent molecules at a concentration of 20 nM or 80 nM, and having dCTP or dUTP nucleotide units, and labeled with CF®680 or CF®532, the N3-Linker generated the highest signal intensities at all binding times tested, the Linker-6 molecules generated the next highest signal intensities, Linker-8 molecules generated lower signal intensities, and the 11 atom Linker molecules generated the lowest signal intensities.

The data in FIG. 58 generally shows that multivalent molecules at a concentration of 20 nM or 80 nM, and having dATP nucleotide units, and labeled with AF®647, the N3-Linker generated the highest signal intensities at all binding times tested, the Linker-6 molecules generated the next highest signal intensities, Linker-8 molecules generated lower signal intensities, and the 11 atom Linker molecules generated the lowest signal intensities.

The data in FIG. 58 generally shows that multivalent molecules at a concentration of 20 nM or 80 nM, and having dGTP nucleotide units, and labeled with CF®570, the N3-Linker generated the highest signal intensities at all binding times tested, and the Linker-8 molecules generated the lowest signal intensities. The Linker-6 and 11 atom Linker molecules generated similar signal intensities that were lower than the intensities of the N3-Linker molecules and higher than the Linker-8 molecules.

The data in FIGS. 57 and 58 indicate that signal intensities generated by labeled multivalent molecules binding to complexed polymerases may be impacted by the linker structure, the nucleotide unit, the fluorophore dye, or a combination thereof.

Example 16—Real-Time Imaging of Trapping on a Microscope

Real-time trapping assays were conducted to determine the binding kinetics of a nucleotide unit (as part of a multivalent molecule) to bind a complexed polymerase. The real-time trapping assays were conducted under conditions that permit binding of the nucleotide unit to the complexed polymerase but without incorporation. The complexed polymerase included a polymerase bound to a nucleic acid template molecule which is hybridized to a primer.

A trap mix with quencher was prepared, which included: Tris HCl (pH 8.8), EDTA (pH 7.5), NaCl, Triton X-100, strontium acetate, sucrose, and a combination of reagents that can act as singlet oxygen quenchers. Sequencing polymerase was added to the trap/quencher mix to generate a trap/quencher/enzyme mix. The trap/quencher/enzyme mix was split into twelve separate aliquots, and each aliquot was mixed with one type of multivalent molecule at a concentration of 2.5 nM, 7.5 nM or 15 nM (e.g., the multivalent molecules included nucleotide units dATP, dGTP, dCTP or dUTP) to generate twelve separate enzyme/multivalent molecule mixes. The multivalent molecules in each of the twelve separate mixes were labeled with either a red or green fluorophore. Different enzyme/multivalent molecule mixes were prepared to test and compare multivalent molecules carrying a different linker, including Linker 6, 10, 11, 12, 13, 14, 15 or 16.

Figure 59:
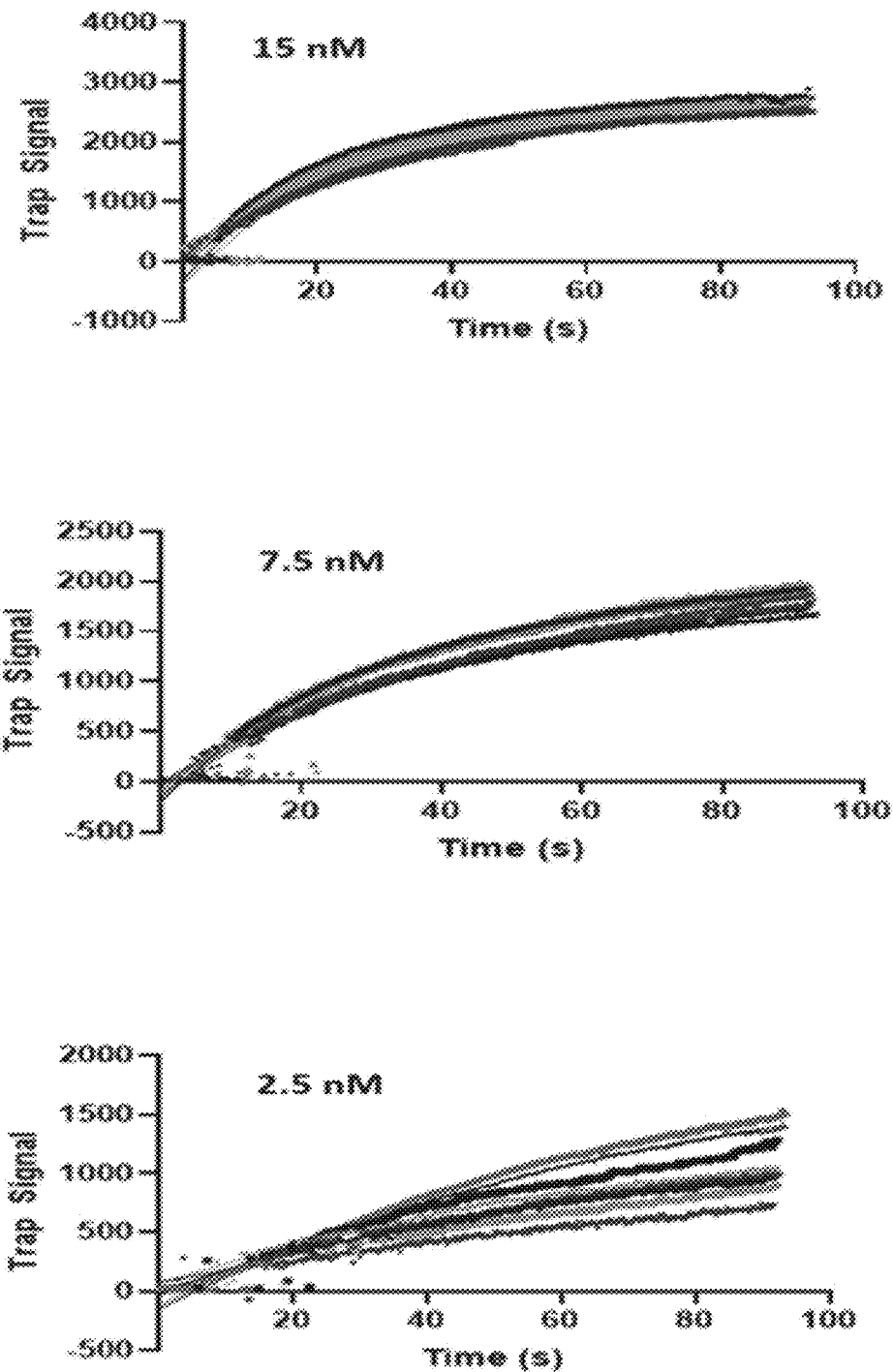
FIG. 59 presents three graphs showing the results of real-time imaging trapping kinetics assays comparing signal intensity of fluorescently-labeled multivalent molecules carrying nucleotide arms comprising one of Linkers 6 or 10-16. Three different concentrations of the multivalent molecules were tested (15, 7.5 and 2.5 nM). The graphs show trap time in second (x-axis) and signal intensity (y-axis).
Figure 60:
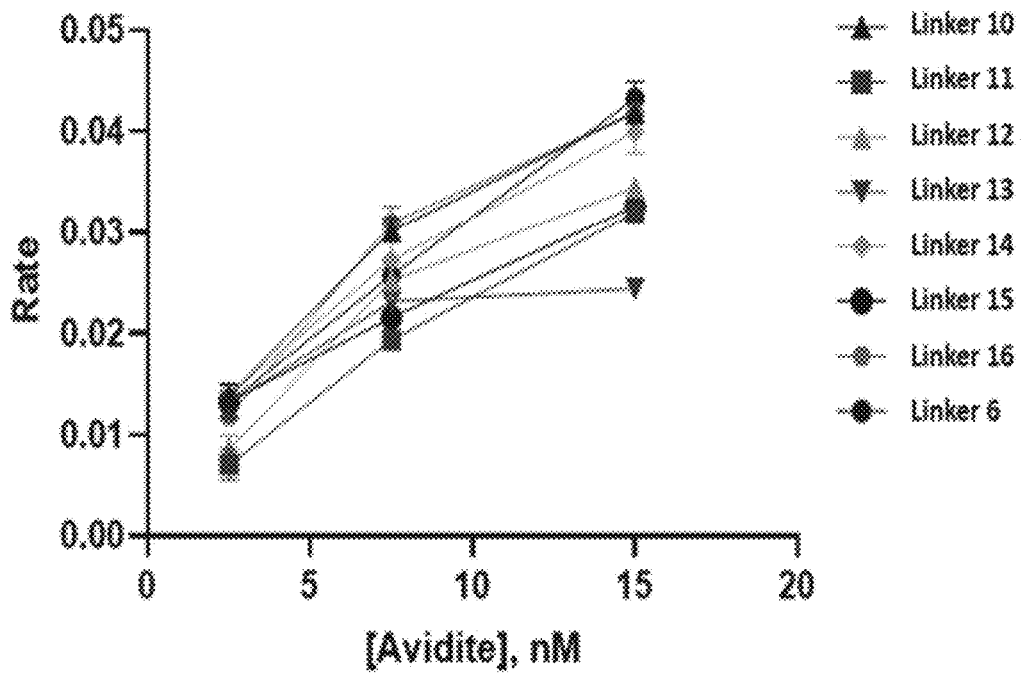
FIG. 60 is a graph showing the results of a binding kinetic study of fluorescently-labeled multivalent molecules carrying nucleotide arms comprising one of Linkers 6 or 10-16. The graph shows multivalent molecule concentration (x-axis, nM) and rate (y-axis). The legend shown in FIG. 14 is also applicable to FIG. 13.
Figure 61:
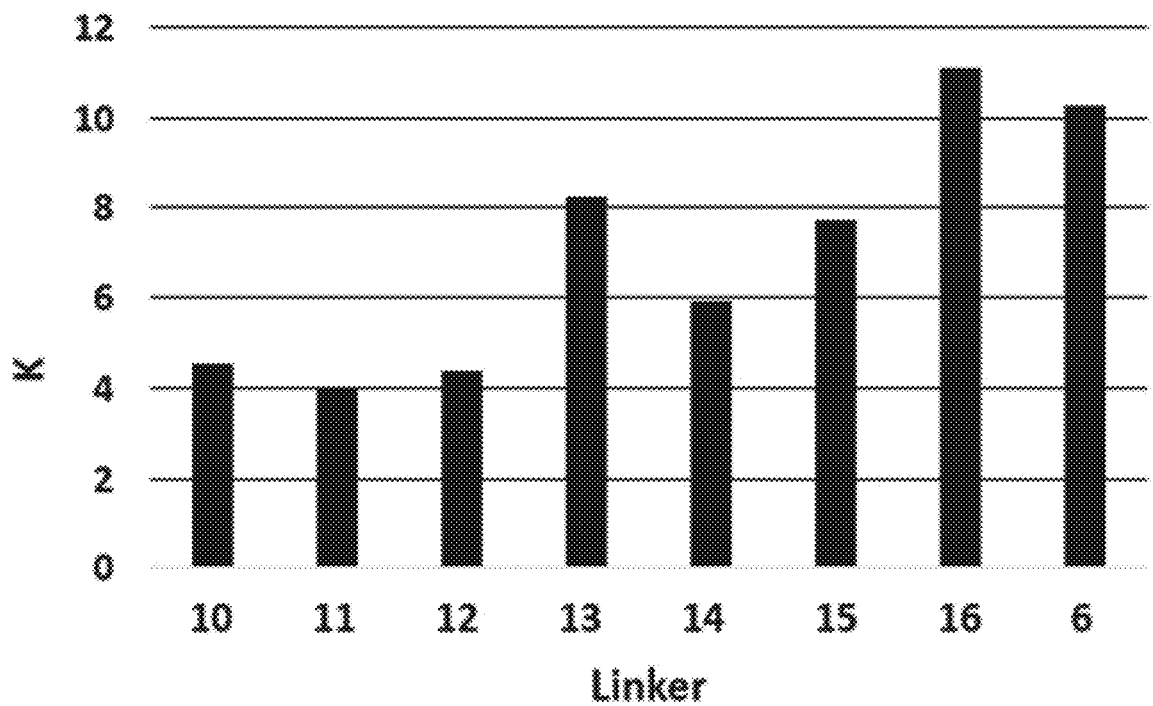
FIG. 61 is a bar graph showing the binding constant (K) determined for fluorescently-labeled multivalent molecules carrying nucleotide arms comprising one of Linkers 6 or 10-16.

A flow cell having immobilized concatemer template molecules was prepared. The flow cell was loaded into a sequencing apparatus configured to deliver laser excitation to the flow cell and obtain fluorescent images from the flow cell (e.g., a flow cell as described elsewhere herein, a flow cell coupled to a microscope as described elsewhere herein, etc.). The enzyme/multivalent molecule mixes were flowed onto the flow cell. Images were obtained for 0.25 second exposure time (e.g., 400 images were obtained for 100 seconds). The signal intensities of the images were plotted and fitted to a single-phase exponential curve to determine the K value, and upper and lower limits. The results are shown in FIGS. 59, 60 and 61. The legend shown in FIG. 60 is also applicable to the date in FIG. 59.

Example 17—Sequencing by Avidity System

Figure 62:
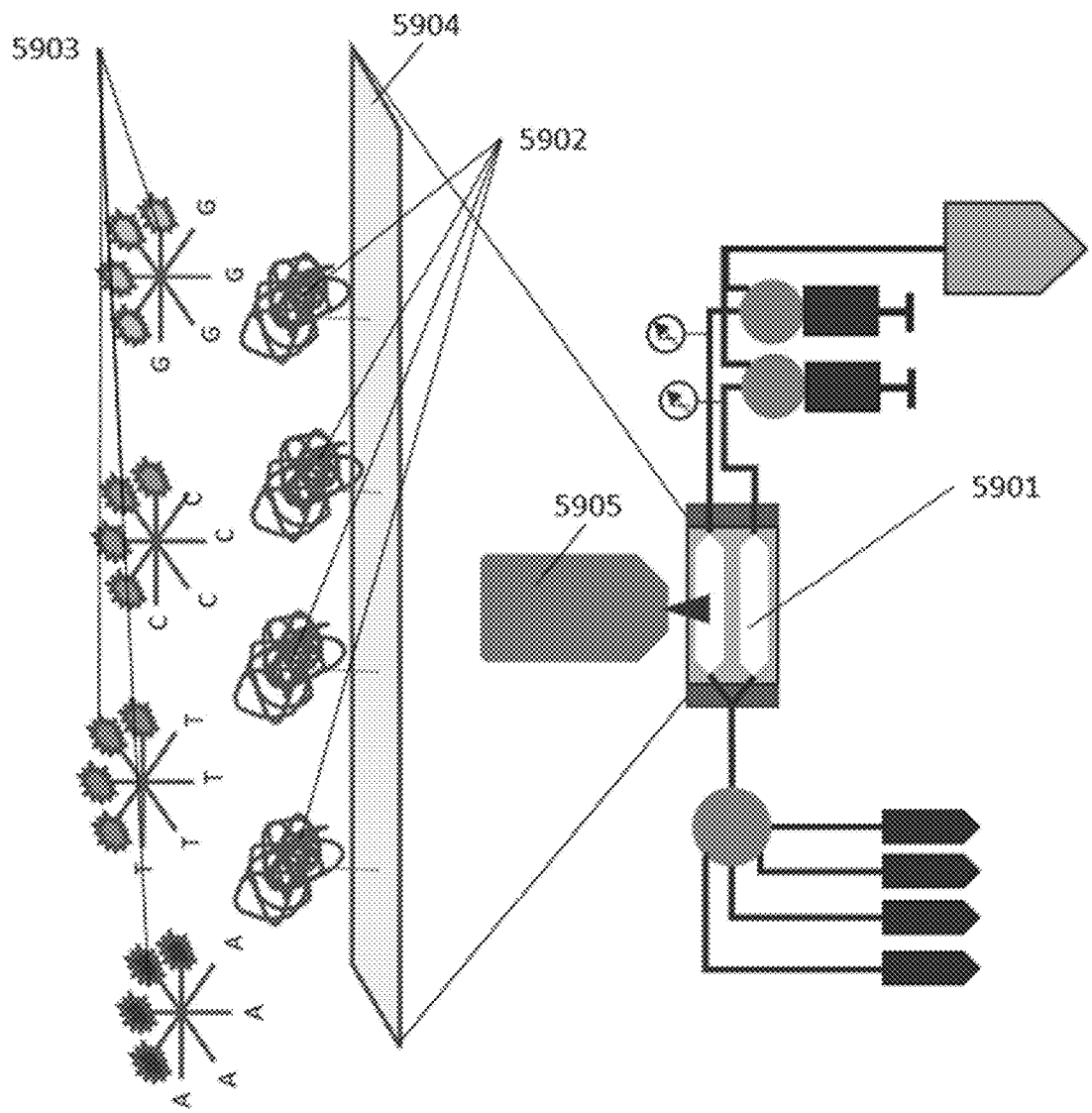
FIG. 62 generally shows an example of a combined sequencing by avidity system, according to some embodiments.

FIG. 62 generally shows an example of a combined sequencing by avidity system, according to some embodiments. A system can comprise a flow cell 5901. The flow cell can be as described elsewhere herein (e.g., a flow cell of Example 16). The flow cell can be configured with a plurality of immobilized concatemer template molecules 5902 on a substrate 5904 as described elsewhere herein. The template molecules can be configured to form a concatemer template molecule (e.g., polony) to which the multivalent molecules 5903 can be configured to bind. The multivalent molecules may be as described elsewhere herein. The system may comprise an optical system 5905. The optical system may be as described elsewhere herein. For example, the optical system can be configured with a light source, filter, and sensor as described elsewhere herein. Additional elements may also be present in the system (e.g., reagent storage, fluidic systems, pumps, etc.). In some cases, the system can be configured as described elsewhere herein to implement the methods described elsewhere herein.

Example 18—Sequencing Using Multivalent Molecules

A two-stage sequencing reaction was conducted on a flow cell having a plurality of concatemer template molecules immobilized thereon.

The first-stage sequencing reaction was conducted by hybridizing a plurality of soluble sequencing primer(s) to the immobilized concatemers to form immobilized primer-concatemer duplexes. A plurality of a first sequencing polymerase was flowed onto the flow cell (e.g., contacting the immobilized primer-concatemer duplexes) and incubated under a condition suitable to bind the sequencing polymerase to the duplexes to form complexed polymerases. A mixture of fluorescently labeled multivalent molecules (e.g., at a concentration of about 20-100 nM) was flowed onto the flow cell in the presence of a buffer that included a non-catalytic cation (e.g., strontium, barium, calcium, or combination thereof) and incubated under conditions suitable to bind complementary nucleotide units of the multivalent molecules to the complexed polymerases to form avidity complexes without polymerase-catalyzed incorporation of the nucleotide units. The complexed polymerases were washed. An image was obtained of the fluorescently labeled multivalent molecules that remained bound to the complexed polymerases. The first sequencing polymerases and multivalent molecules were removed, while retaining the sequencing primers hybridized to the immobilized concatemers (retained duplexes), by washing with a buffer comprising a detergent.

The first stage sequencing reaction was suitable for forming a plurality of avidity complexes on concatemer template molecules (e.g., polonies). For example, the first stage sequencing reaction comprises: (a) binding a first nucleic acid primer, a first polymerase, and a first multivalent molecule to a first portion of a concatemer template molecule thereby forming a first binding complex, wherein a first nucleotide unit of the first multivalent molecule binds to the first polymerase; and (b) binding a second nucleic acid primer, a second polymerase, and the first multivalent molecule to a second portion of the same concatemer template molecule thereby forming a second binding complex, wherein a second nucleotide unit of the first multivalent molecule binds to the second polymerase, wherein the first and second binding complexes which include the same multivalent molecule forms a first avidity complex.

The second-stage sequencing reaction was conducted by contacting the retained duplexes with a plurality of second sequencing polymerases to form complexed polymerases. A mixture of fluorescently labeled nucleotide analogs (e.g., 3'O-methylazido nucleotides) (e.g., about 1-5 uM) was added to the complexed polymerases in the presence of a buffer that included a catalytic cation (e.g., magnesium, manganese, or a combination of magnesium and manganese) and incubated under conditions suitable to bind complementary nucleotides to the complexed polymerases and promote polymerase-catalyzed incorporation of the nucleotides to generate a nascent extended sequencing primer. The complexed polymerases were washed. An image was obtained of the incorporated fluorescently labeled nucleotide analogs as a part of the complexed polymerases. The incorporated fluorescently labeled nucleotide analogs were reacted with a cleaving reagent that removes the 3' O-methylazido group and generates an extendible 3'OH group.

In an alternative second stage sequencing reaction, a mixture of non-labeled nucleotide analogs (e.g., 3'O-methylazido nucleotides) (e.g., about 1-5 uM) was added to the complexed polymerases in the presence of a buffer that included a catalytic cation (e.g., magnesium, manganese, or a combination of magnesium and manganese) and incubated under conditions suitable to bind complementary nucleotides to the complexed polymerases and promote polymerase-catalyzed incorporation of the nucleotides to generate a nascent extended sequencing primer. The complexed polymerases were washed. No image was obtained. The incorporated non-labeled nucleotide analogs were reacted with a cleaving reagent that removes the 3' O-methylazido group and generates an extendible 3'OH group.

The second sequencing polymerases were removed, while retaining the nascent extended sequencing primers hybridized to the concatemers (retained duplexes), by washing with a buffer comprising a detergent. Recurring sequencing reactions were conducted by performing multiple cycles of first-stage and second-stage sequencing reactions to generate extended forward sequencing primer strands.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

What is claimed is:
1. A method, comprising:
 (a) providing a system comprising:
  (i) a flow cell comprising a sample,
  (ii) a light source,
  (iii) a detector comprising a plurality of pixels, and
  (iv) a pixel shifter disposed in an optical path from the flow cell to the detector;
 (b) illuminating the sample using the light source, wherein the illuminating generates a signal light corresponding to an identity of a portion of the sample;
 (c) shifting the signal light across the plurality of pixels using the pixel shifter; and
 (d) detecting, using the plurality of pixels, the signal light from the sample to generate data related to the identity of the portion of the sample.

2. The method of claim 1, wherein the sample is a nucleic acid sample.

3. The method of claim 2, wherein the portion of the nucleic acid sample comprises a nucleotide or a nucleic acid sequence, and further comprising using the data to identify the nucleotide or the nucleic acid sequence of the nucleic acid sample.

4. The method of claim 3, wherein the nucleic acid sequence or the nucleotide of the nucleic acid sample is identified, at least in part, by:
(i) contacting a labeled molecule to the nucleic acid sample, wherein the labeled molecule binds to the nucleic acid sample;
(ii) illuminating the labeled molecule bound to the nucleic acid sample using the light source, thereby generating light from the labeled molecule;
(iii) detecting, using the plurality of pixels, the light from the labeled molecule to generate the data, wherein the data corresponds to the light from the labeled molecule; and
(iv) processing the data to determine the identity of the portion of the nucleic acid sample bound to the labeled molecule.

5. The method of claim 4, further comprising (v) removing the labeled molecule from the nucleic acid sample.

6. The method of claim 5, further comprising (vi) repeating (i)-(v) for an additional labeled molecule that binds to another portion of the nucleic acid sample.

7. The method of claim 2, further comprising binding one or more labels to the nucleic acid sample, wherein the one or more labels are configured to absorb the light from the light source and emit the signal light.

8. The method of claim 1, wherein the flow cell comprises a plurality of interior surfaces.

9. The method of claim 8, wherein the illuminating in (b) comprises illuminating at least two interior surfaces of the plurality of interior surfaces, and the detecting in (d) comprises detecting the signal light from the at least two interior surfaces of the plurality of interior surfaces.

10. The method of claim 8, wherein the sample is coupled to at least one interior surface of the plurality of interior surfaces.

11. The method of claim 10, wherein at least a portion of the sample is coupled to each interior surface of the plurality of interior surfaces.

12. The method of claim 1, further comprising using a plurality of detectors comprising the detector to each detect a portion of the signal light from a plurality of portions of the signal light, wherein each portion of the plurality of portions of the signal light comprises a different wavelength from another portion of the plurality of portions of the signal light.

13. The method of claim 12, further comprising using a plurality of pixel shifters comprising the pixel shifter to shift the plurality of portions of the signal light over each detector of the plurality of detectors.

14. The method of claim 12, further comprising using a plurality of focusing elements disposed in an optical path of the signal light to focus the signal light onto the plurality of detectors.

15. The method of claim 1, further comprising a plurality of light sources comprising the light source, wherein each light source of the plurality of light sources is used to illuminate the sample using a different wavelength of light from another light source of a plurality of light sources.

16. The method of claim 1, wherein the signal light is a fluorescent signal light.

17. The method of claim 1, wherein the flow cell comprises a curved surface with the sample coupled thereto.

18. The method of claim 1, wherein the system has a numerical aperture (NA) of less than about 0.6.

19. The method of claim 1, wherein the system has a field of view (FOV) of at least about 1 square millimeter ($mm^2$).

20. The method of claim 1, wherein the detector comprises a charge coupled device (CCD) detector.

* * * * *